US011732029B2

(12) United States Patent
Hubbell et al.

(10) Patent No.: US 11,732,029 B2
(45) Date of Patent: Aug. 22, 2023

(54) METHODS AND COMPOSITIONS FOR THE TREATMENT OF WOUNDS

(71) Applicants: The University of Chicago, Chicago, IL (US); Imperial College Innovations Limited, London (GB)

(72) Inventors: Jeffrey A. Hubbell, Chicago, IL (US); Anna M. Randi, London (GB); Jun Ishihara, Chicago, IL (US); Ako Ishihara, Chicago, IL (US); Priscilla Briquez, Chicago, IL (US); Richard Starke, London (GB)

(73) Assignees: The University Chicago, Chicago, IL (US); Imperial College Innovations Limited, London (GB)

( * ) Notice: Subject to any disclaimer, the term of this patent is extended or adjusted under 35 U.S.C. 154(b) by 252 days.

(21) Appl. No.: 15/733,085

(22) PCT Filed: Nov. 13, 2018

(86) PCT No.: PCT/US2018/060760
§ 371 (c)(1),
(2) Date: May 13, 2020

(87) PCT Pub. No.: WO2019/094938
PCT Pub. Date: May 16, 2019

(65) Prior Publication Data
US 2021/0040179 A1 Feb. 11, 2021

Related U.S. Application Data

(60) Provisional application No. 62/585,101, filed on Nov. 13, 2017, provisional application No. 62/758,845, filed on Nov. 12, 2018.

(51) Int. Cl.
*A61K 38/00* (2006.01)
*C07K 5/00* (2006.01)
(Continued)

(52) U.S. Cl.
CPC ............ *C07K 14/78* (2013.01); *A61K 9/0024* (2013.01); *A61K 9/7007* (2013.01); *A61K 38/00* (2013.01);
(Continued)

(58) Field of Classification Search
None
See application file for complete search history.

(56) References Cited

U.S. PATENT DOCUMENTS 9,260,507 B2   2/2016   Rousselle
2002/0151489 A1   10/2002   Gravereaux et al.
(Continued)

FOREIGN PATENT DOCUMENTS

WO   WO 2002/058723   8/2002
WO   WO-2006025646 A1 *   3/2006   ............. C07K 14/78
(Continued)

OTHER PUBLICATIONS

"Implant", Merriam Webster, available online at www.merriam-webster.com/dictionary/implant, 7 pages (accessed on Sep. 7, 2022) (Year: 2022).*
(Continued)

*Primary Examiner* — Thea D'Ambrosio
(74) *Attorney, Agent, or Firm* — Norton Rose Fulbright US LLP

(57) ABSTRACT

The methods and compositions described herein address the need in the art by providing peptides and polypeptides comprising a growth factor binding domain. In some embodiments, the peptides have an amino acid sequence that is at least 80% identical to one of SEQ ID NOS:1-7, 13-15, 49-50, or 66-70, or a fragment thereof; wherein the peptide is less than 300 amino acids in length.

16 Claims, 31 Drawing Sheets

Specification includes a Sequence Listing.

(51) Int. Cl.
| | | |
|---|---|---|
| C07K 7/00 | (2006.01) | |
| C07K 16/00 | (2006.01) | |
| C07K 17/00 | (2006.01) | |
| C07K 14/00 | (2006.01) | |
| A61K 38/17 | (2006.01) | |
| A61K 38/18 | (2006.01) | |
| C07K 14/475 | (2006.01) | |
| A61P 17/02 | (2006.01) | |
| A61K 38/16 | (2006.01) | |
| C07K 14/78 | (2006.01) | |
| A61L 27/22 | (2006.01) | |
| C07K 16/18 | (2006.01) | |
| A61K 9/00 | (2006.01) | |
| A61K 9/70 | (2006.01) | |
| C07K 14/705 | (2006.01) | |
| A61K 47/64 | (2017.01) | |
| C07K 14/81 | (2006.01) | |
| A61K 47/69 | (2017.01) | |
| A61K 38/39 | (2006.01) | |

(52) U.S. Cl.
CPC .............. *A61K 38/18* (2013.01); *A61K 38/39* (2013.01); *A61K 47/6435* (2017.08); *A61K 47/6903* (2017.08); *A61L 27/22* (2013.01); *A61P 17/02* (2018.01); *C07K 14/475* (2013.01); *C07K 14/70546* (2013.01); *C07K 14/8121* (2013.01); *C07K 16/18* (2013.01); *A61L 2300/412* (2013.01); *C07K 2317/55* (2013.01); *C07K 2319/70* (2013.01)

(56) References Cited

U.S. PATENT DOCUMENTS

| | | |
|---|---|---|
| 2004/0086489 A1 | 5/2004 | Schall et al. |
| 2008/0233125 A1 | 9/2008 | Peter |
| 2013/0251752 A1 | 9/2013 | Antonia et al. |
| 2014/0127193 A1 | 5/2014 | Nixon et al. |

FOREIGN PATENT DOCUMENTS

| | | |
|---|---|---|
| WO | WO 2015/168379 | 11/2015 |
| WO | WO 2016/102374 | 6/2016 |
| WO | WO 2017/190074 | 11/2017 |
| WO | WO 2018/195386 | 10/2018 |

OTHER PUBLICATIONS

Schense et al., Bioconjugate Chem. 10:75-81 (1999) (Year: 1999).*
"List of cancer types." Wikipedia, May 22, 2020, https://en/wikipedia.org/wiki/List_of_cancer_types.
"What is Cancer?" National Cancer Institute, May 22, 2020, https://www.cancer.gov/about-cancer/understanding/what-is-cancer.
Bhagawati et al., "Biofunctionalization of Hydrogels for Engineering the Cellular Microenvironment." *Micro- and Nanoengineering of the Cell Surface*, 2014, 315-348.
Briquez et al., "Extracellular Matrix-Inspired Growth Factor Delivery Systems for Skin Wound Healing." *Adv Wound Care (New Rochelle)* 2015, 4(8), 479-489.
Card, et al., "Emerging Roles of Lymphatic Endothelium in Regulating Adaptive Immunity," *The Journal of Clinical Investigation*, 124; 943-952, 2014.
Cheng, et al. "Serum Vascular Endothelial Growth Factor (VEGF-C) as a Diagnostic and Prognostic Marker in Patients with Ovarian Cancer," PLOS One, 2013, 8(2):e55309.
Dadras, et al. "Tumor Lymphangiogenesis a Novel Prognostic Indicator for Cutaneous Melanoma Metastasis and Survival," American Journal of Pathology, 2003, 162(6):1951-1960.
Dobrzycka, et al. "Serum levels of VEGF and VEGF-C in patients with endometrial cancer," Eur. Cytokine Netw, 2011, 22(1):45-51.
Ehrbar et al., "Cell-demanded liberation of VEGF from fibrin implants induces local and controlled blood vessel Growth." *Circ. Res.* 2004, 94, 1124-1132.
Fankhauser, et al. "Tumor lymphangiogenesis promotes T cell infiltration and potentiates immunotherapy in melanoma," Science Translational Medicine, 2017, 9:eaal4712.
Hirosue et al., "Steady Antigen Scavenging, Cross-Presentation, and CD8+ T Cell Priming: A New Role for Lymphatic Endothelial Cells" *Journal of Immunology*, 2014, 192:5002-5011.
Hubbell et al., "Materials engineering for immunomodulation," *Nature*, 2009, 462:449-460.
International Search Report and Written Opinion issued in Corresponding PCT Application No. PCT/US2018/060760, dated May 28, 2019.
International Search Report Issued in Corresponding PCT Application No. PCT/US2017/030242, dated Jul. 13, 2017.
Ishihara et al., "Laminin heparin-binding peptides bind to several growth factors and enhance diabetic wound healing" *Nature Communications* 2018, 9(1), 14 pages.
Jiang, et al. "Serum vascular endothelial growth factor-C levels predict lymph node metastasis and prognosis of patients with gallbladder cancer," Oncology Letters, 2018, 16:6065-6070.
Kim et al., "Extracorporeal shock wave therapy combined with Vascular Endothelial Growth Factor-C Hydrogel for lymphangiogenesis" *J. Vasc. Res.* 2013, 50, 124-133.
Laporte et al., "Tenascin C Promiscuously Binds Growth Factors via Its Fifth Fibronectin Type 111-Like Domain" *PLOS One* 2013, 8(4), e62076, 9 pages.
Liang, et al. "Elevated VEGF concentrations in ascites and serum predict adverse prognosis in ovarian cancer," Scandinavian Journal of Clinical and Laboratory Investigation, 2013, 73:309-314.
Lund, et al., "VEGF-C Promotes Immune Tolerance in B16 Melanomas and Cross Presentation of Tumor Antigen by Lymph Node Lymphatics," *Cell Reports*, 1(3); 191-199,2012.
Martino et al., "Extracellular matrix and growth factor engineering for controlled angiogenesis in regenerative medicine" *Frontiers In Bioengineering and Biotechnology* 2015, 3, 8 pages.
Martino et al., "Heparin-binding domain of fibrin(ogen) binds growth factors and promotes tissue repair when incorporated within a synthetic matrix" *PNAS* 2013, 110(12), 4563-4568.
Martino, et al., "Growth Factors Engineered for Super-Affinity to the Extracellular Matrix Enhance Tissue Healing," *Science*, 343(6173); 885-888, 2014.
Martino, MM. & JA Hubbell, "The 12th-14th type III repeats of fibronectin function as a highly promiscuous growth factor-binding domain." *The FASEB Journal* 2010, 24(12), 4711-4721.
Mitchell et al., "Engineering growth factors for regenerative medicine applications" *Acta Biomaterialia* 2016, 30, 1-12.
Moon et al., "Engineering nano- and microparticles to tune immunity," *Advanced Materials*, 2012, 24:3724-3746.
Schense et al., "Cross-Linking Exogenous Bifunctional Peptides-into Fibrin Gels with Factor XIIIa" *Bioconjugate Chemistry* 1999, 10, 75-81.
Zisch et al., "Covalently conjugated VEGF-fibrin matrices for endothelialization," *Journal of Controlled Release*, 2001, 72:101-113.

* cited by examiner

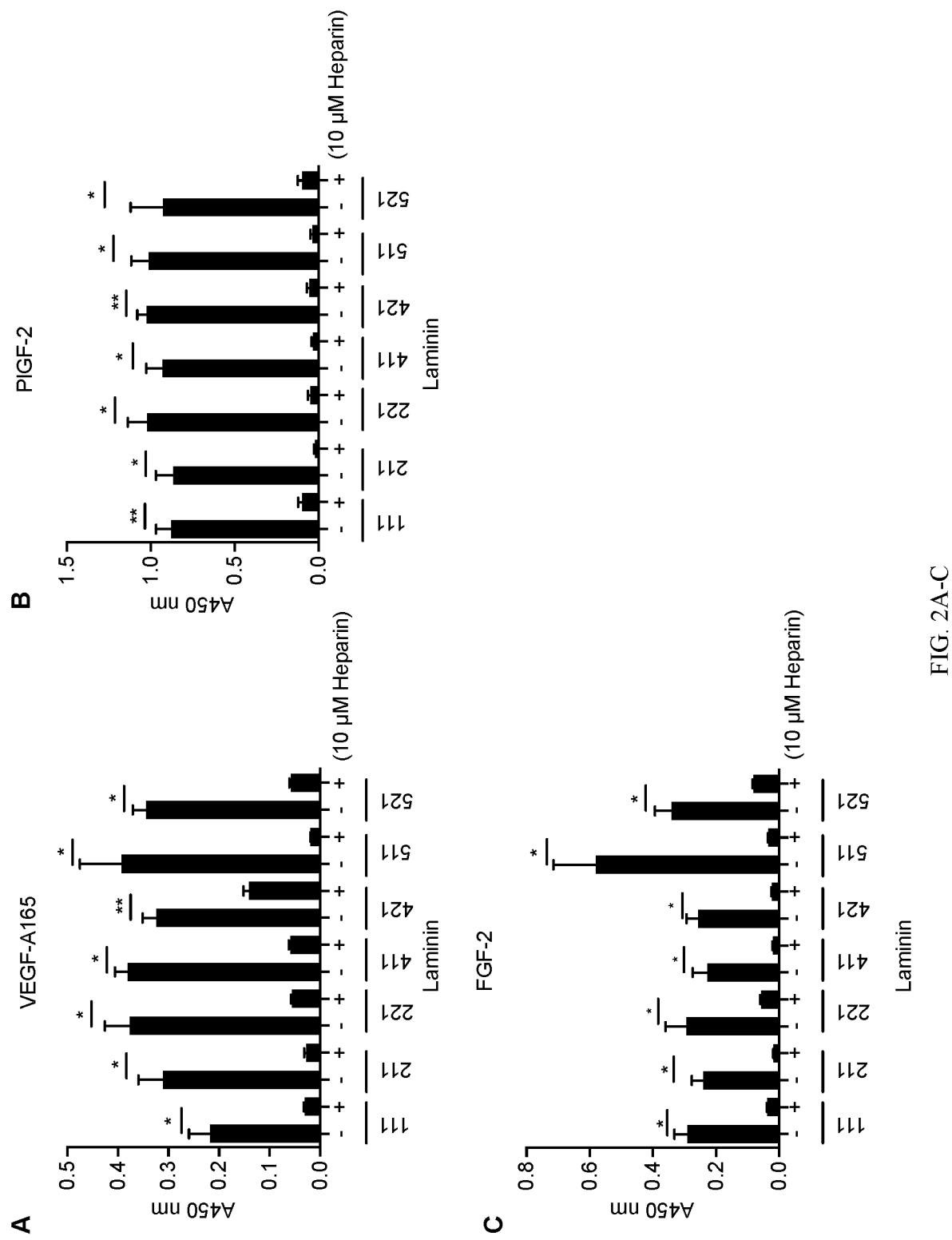
FIG. 2A-C

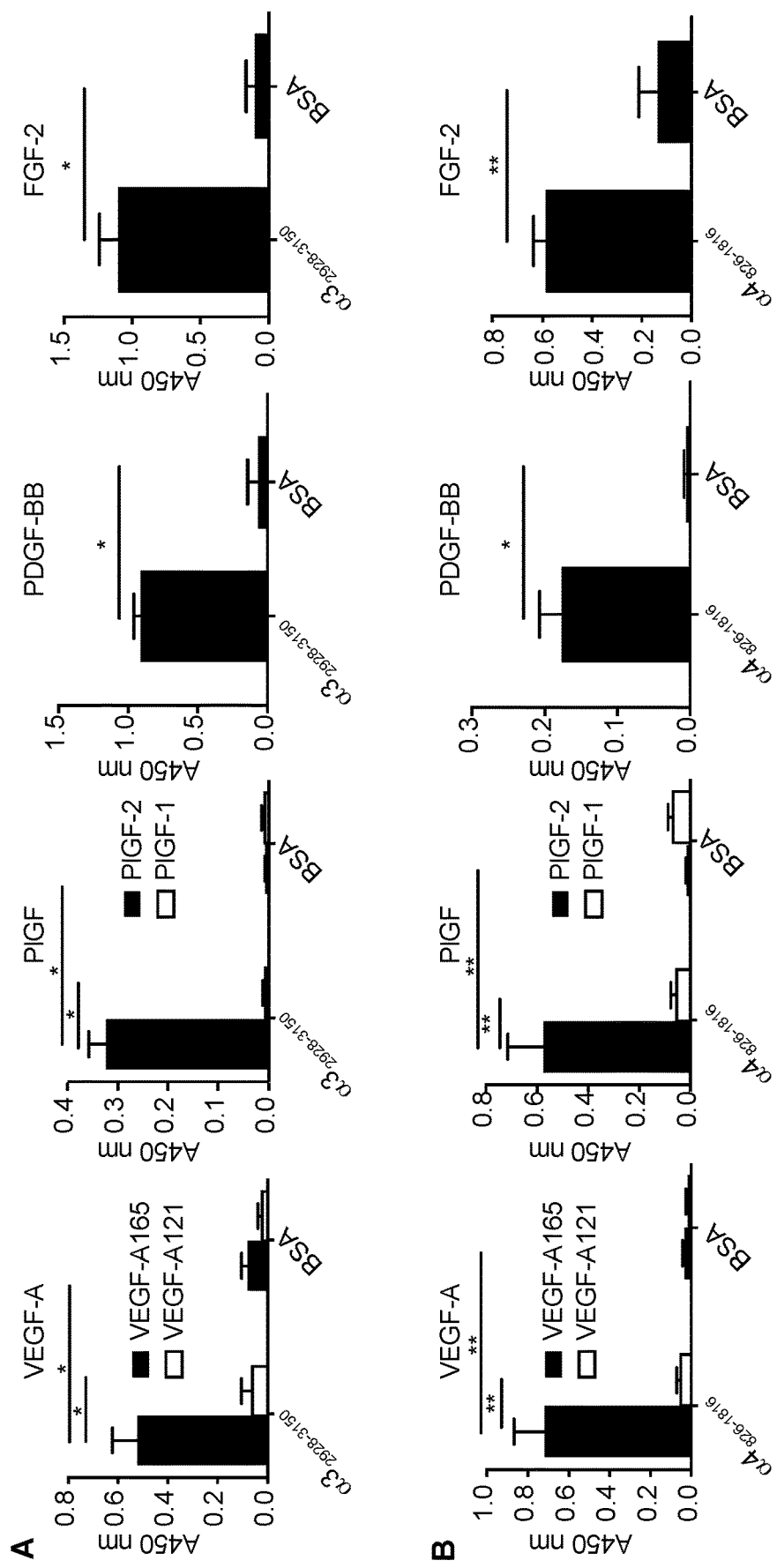
FIG. 3A-B

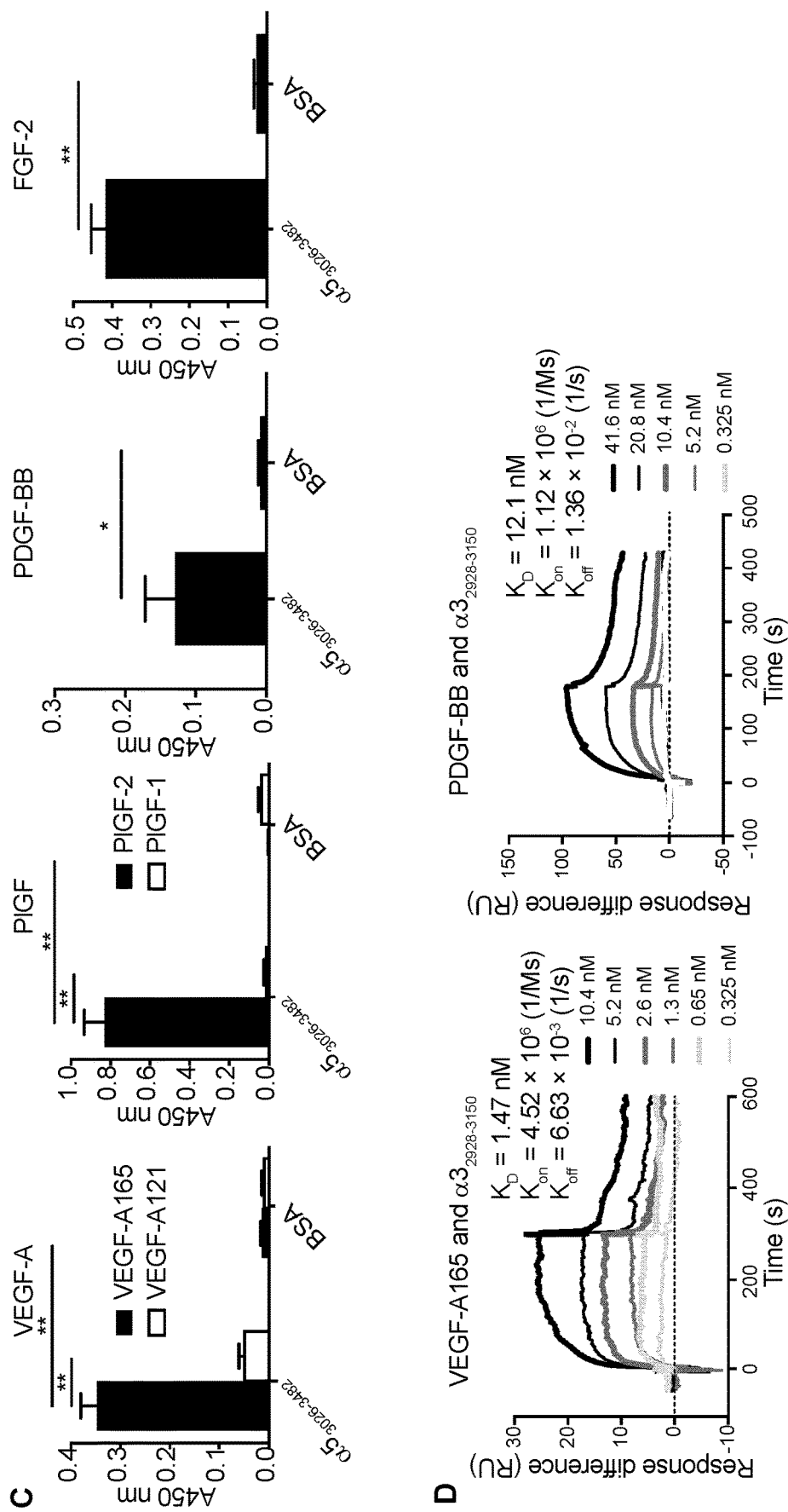
FIG. 3C-D

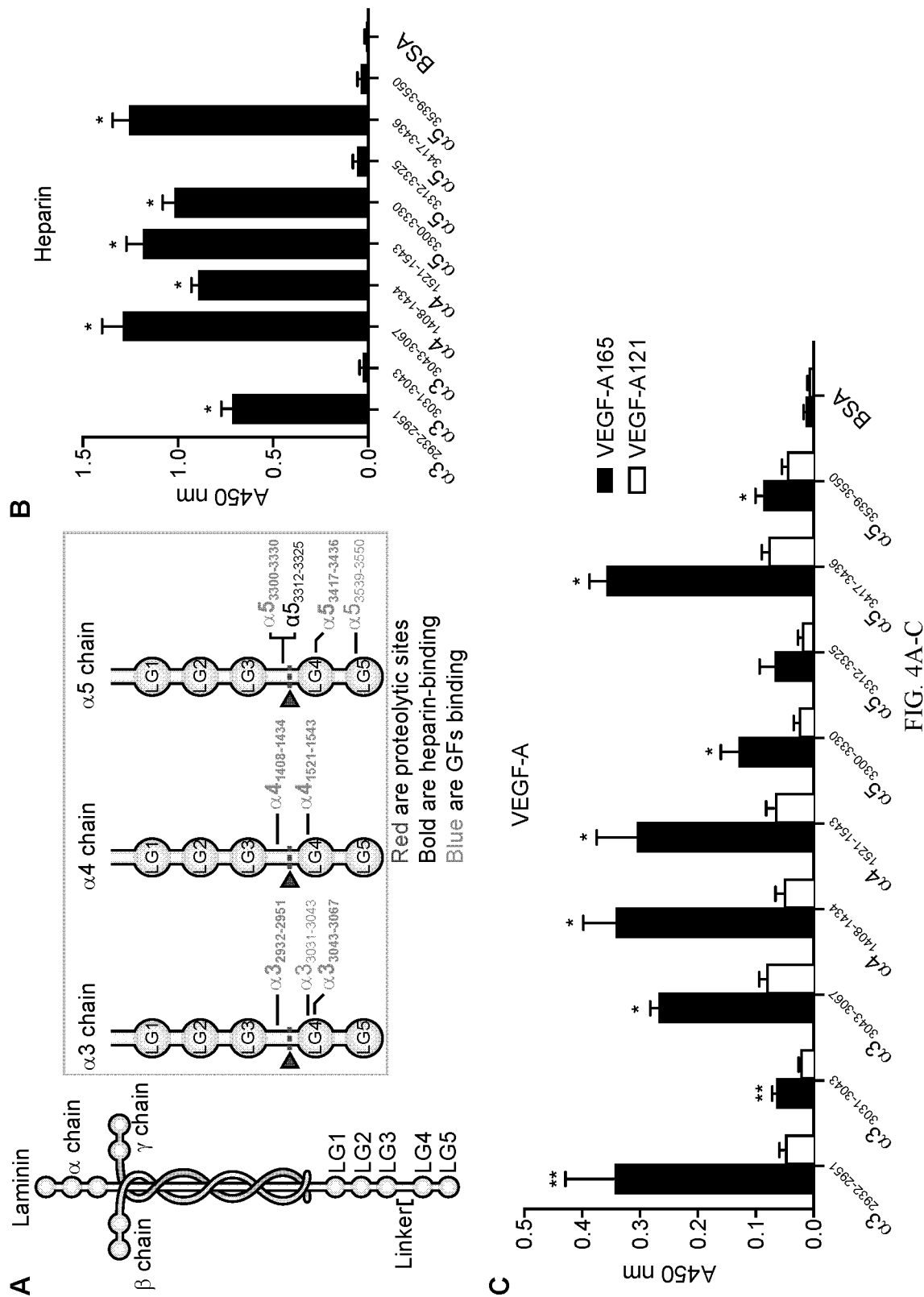
FIG. 4A-C

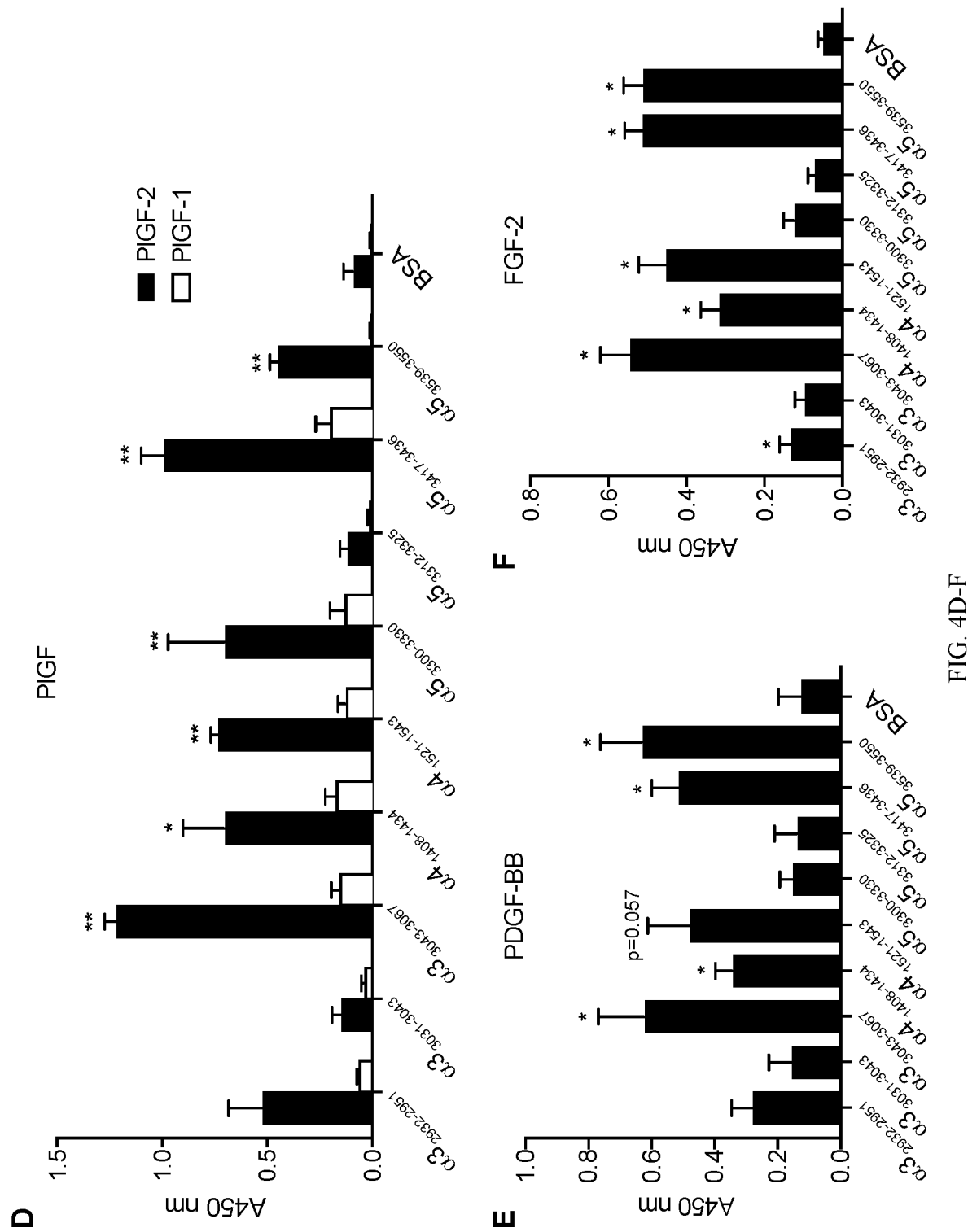
FIG. 4D-F

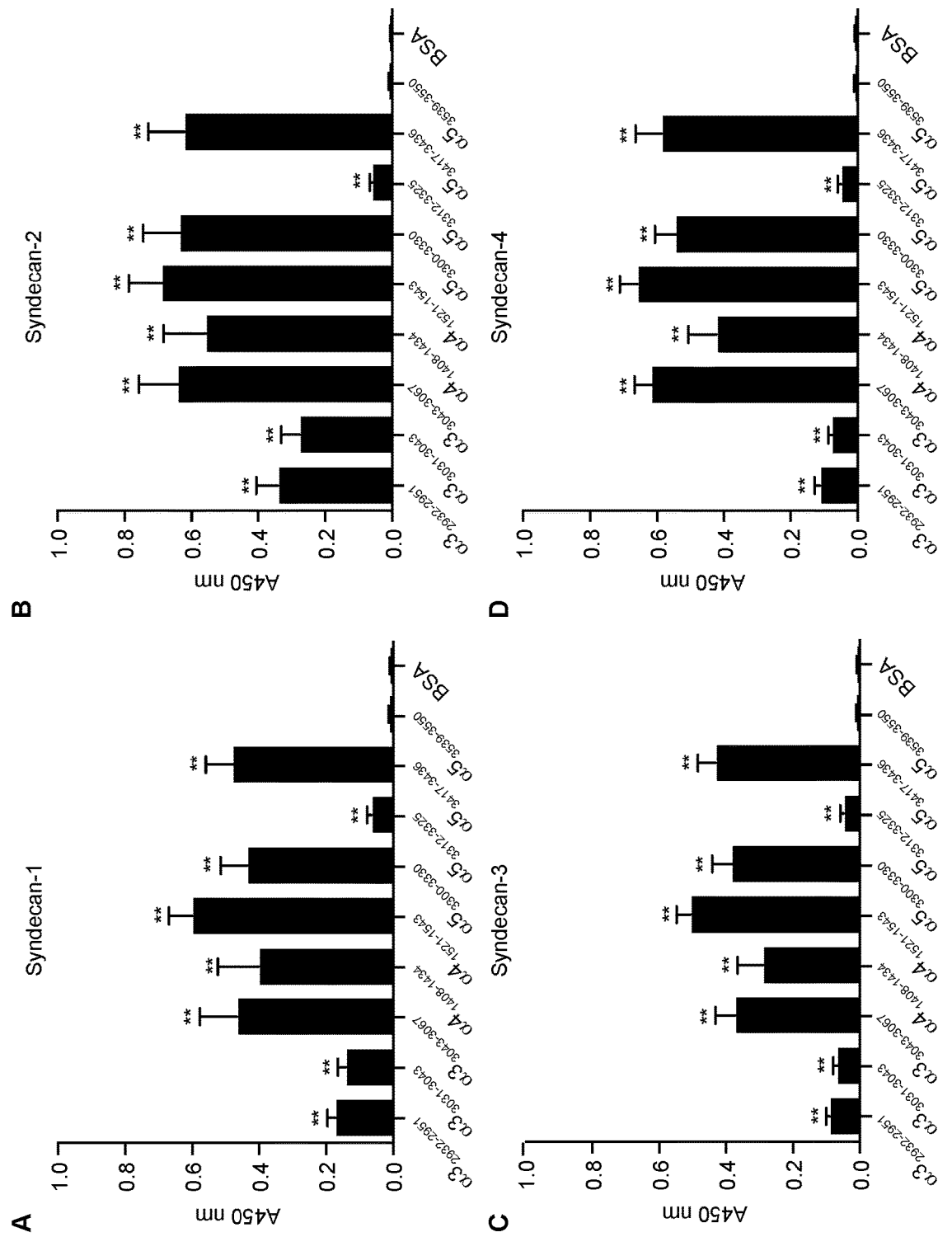
FIG. 5A-D

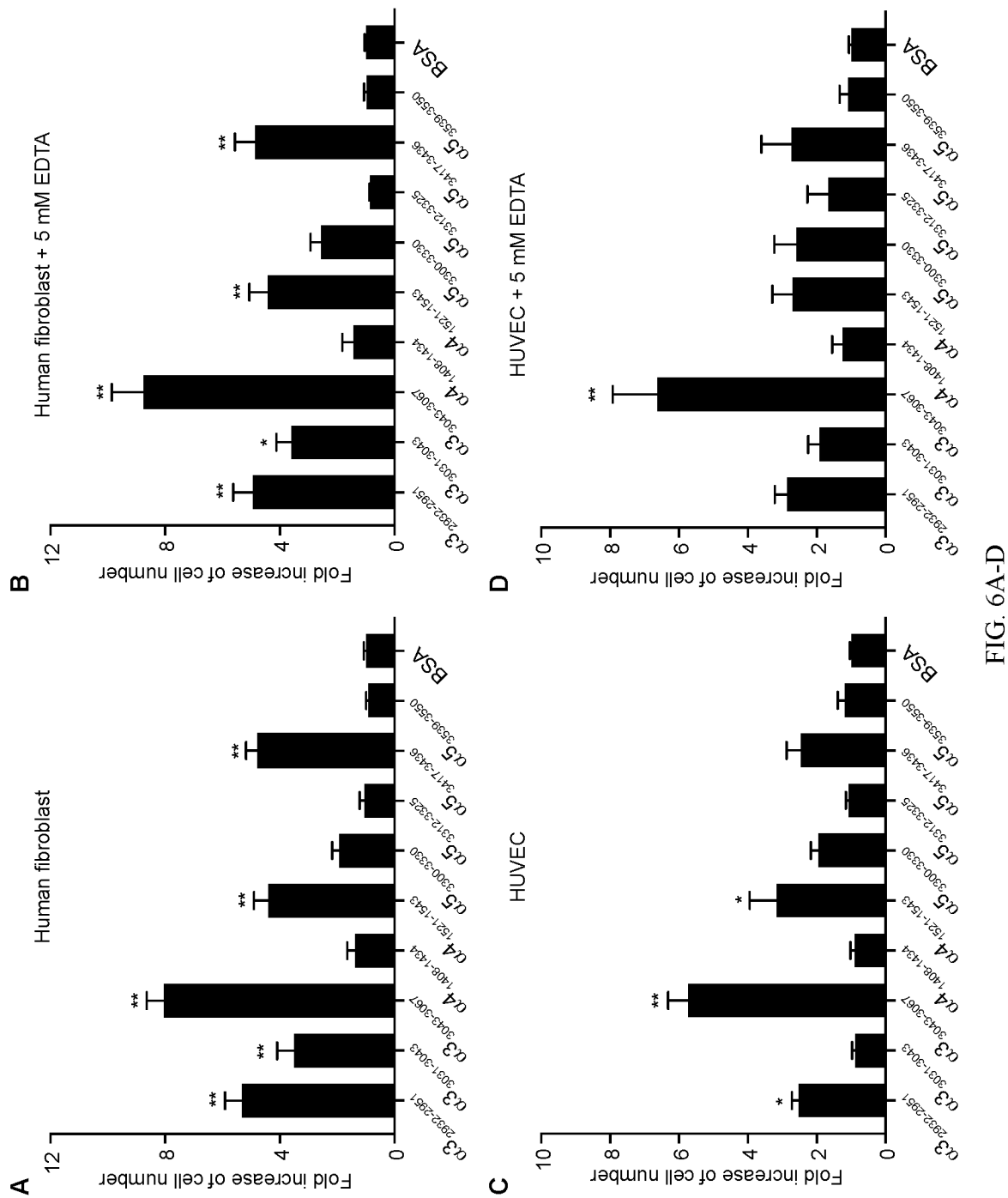
FIG. 6A-D

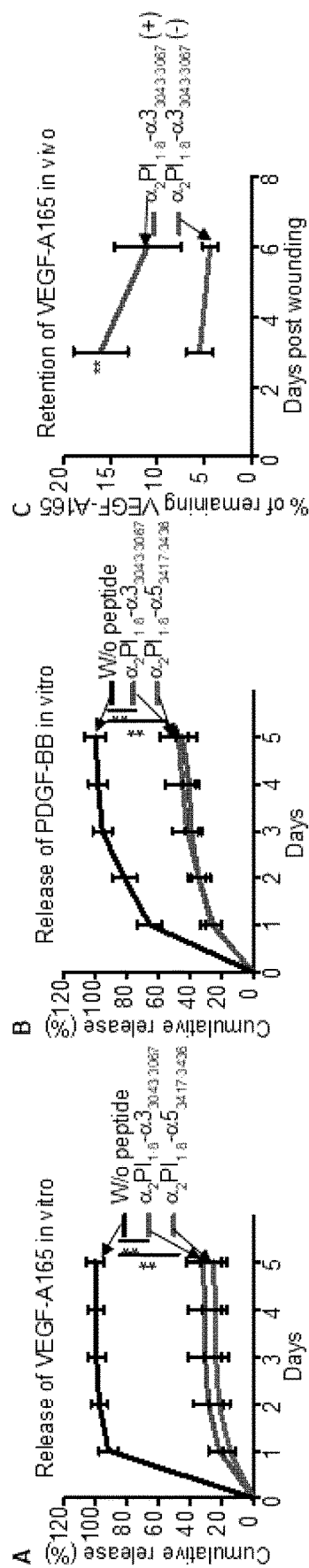
FIG. 7A-C

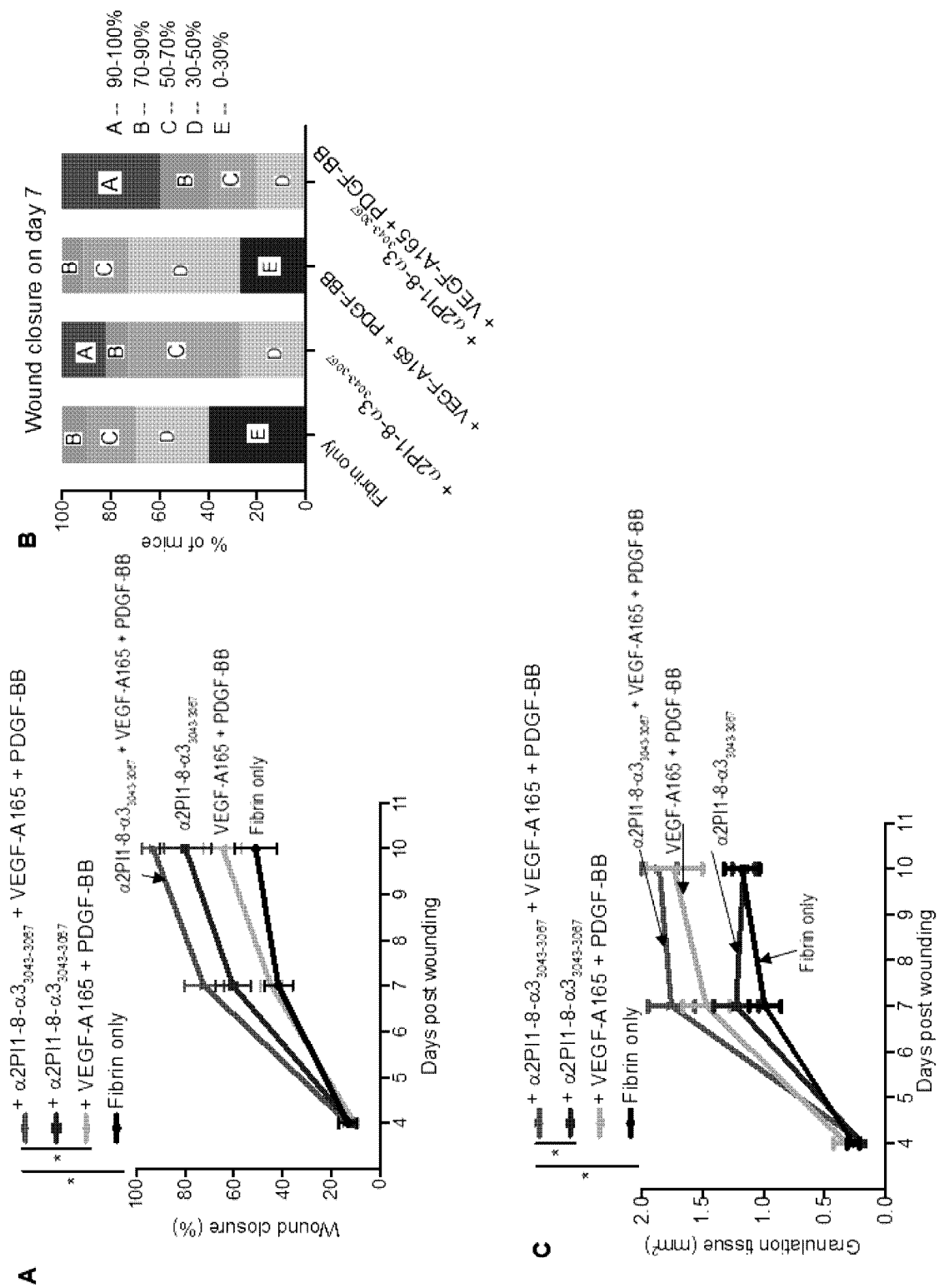
FIG. 8A-C

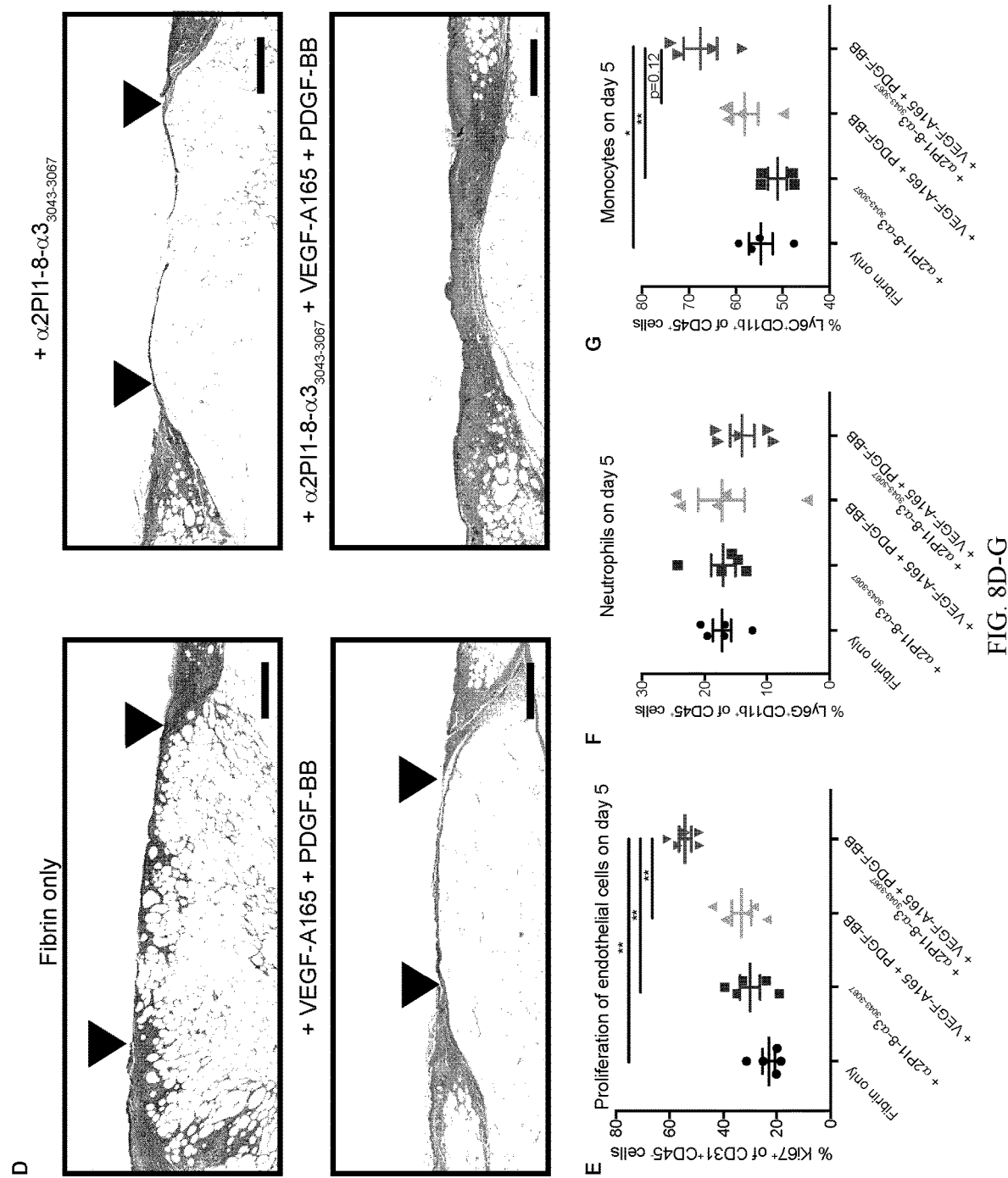
FIG. 8D-G

Wound on day 0
Wound on day 7
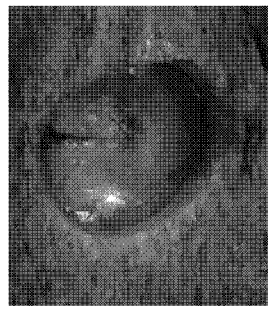
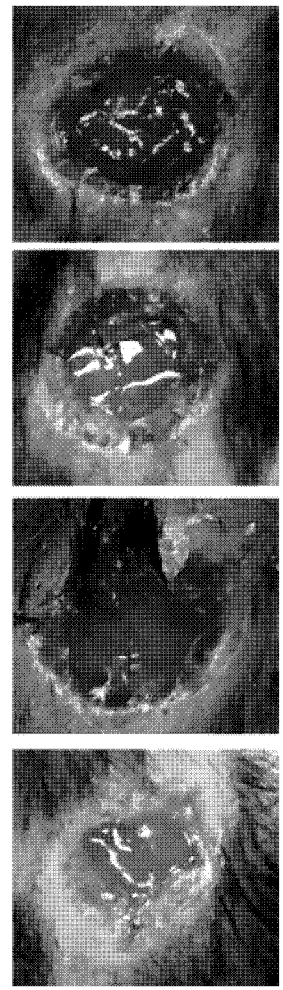
Fibrin only
+ α2PI1-8-α3$_{3043-3067}$
+ VEGF-A165 + PDGF-BB
+ α2PI1-8-α3$_{3043-3067}$
+ VEGF-A165 + PDGF-BB
FIG. 11

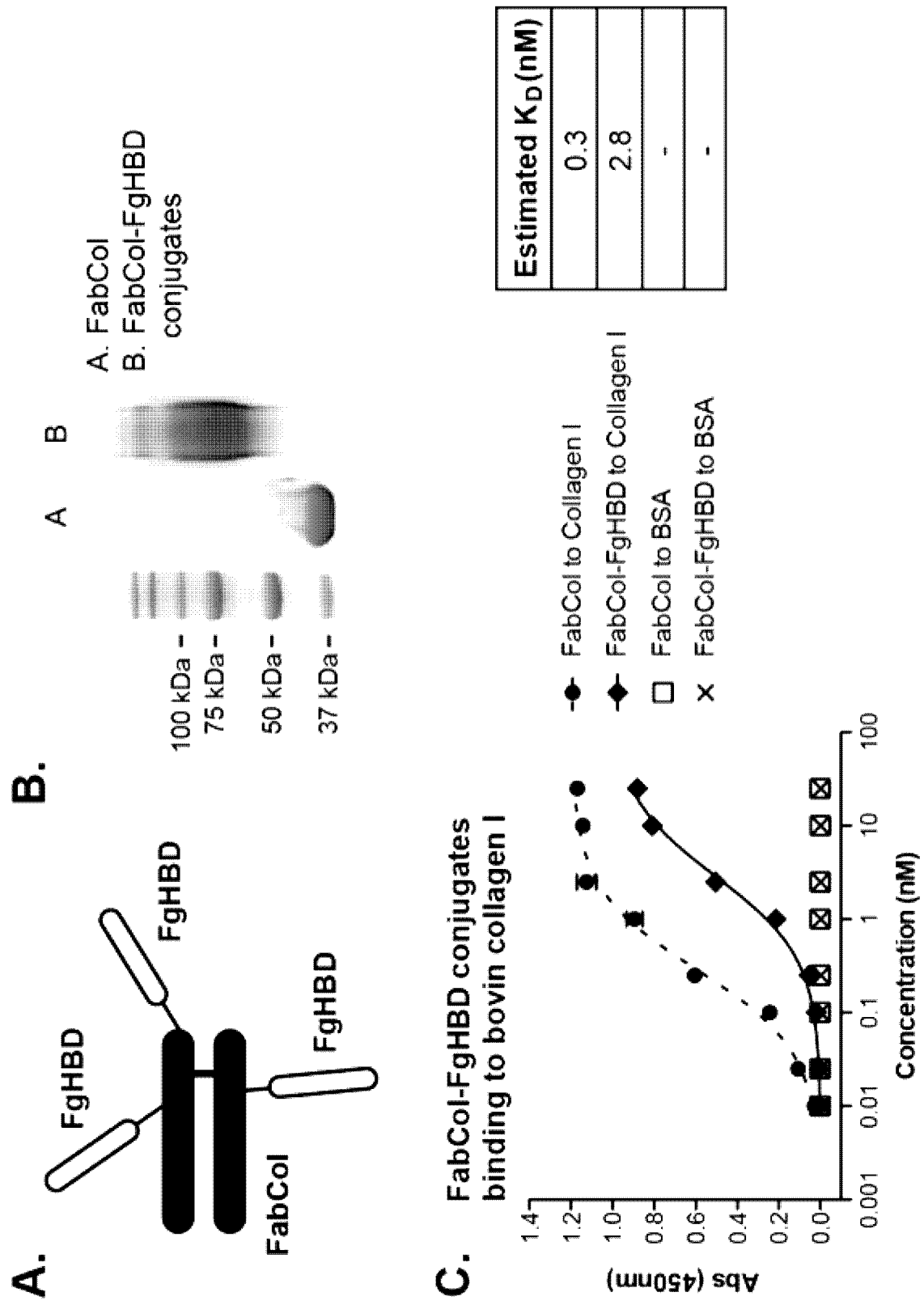
FIG. 13A-C

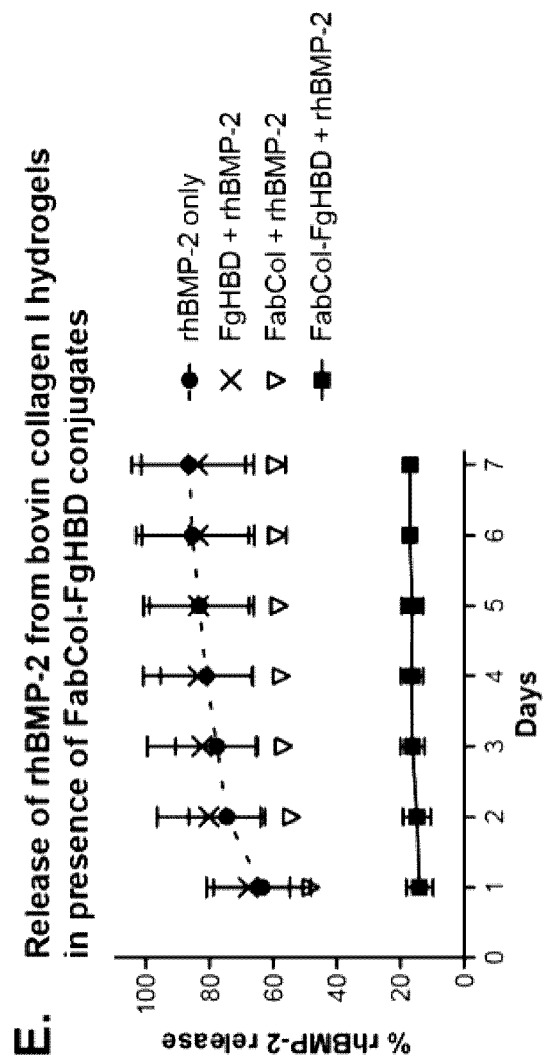
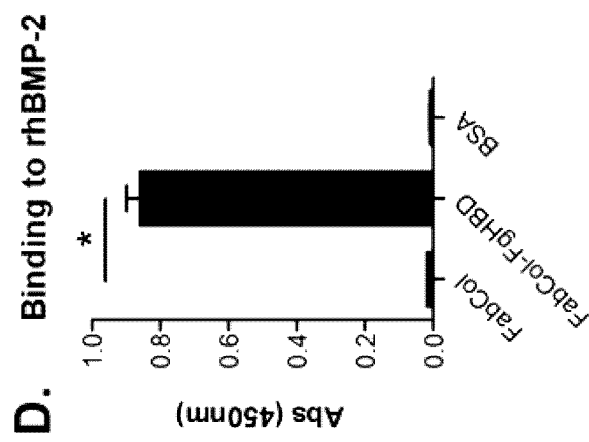
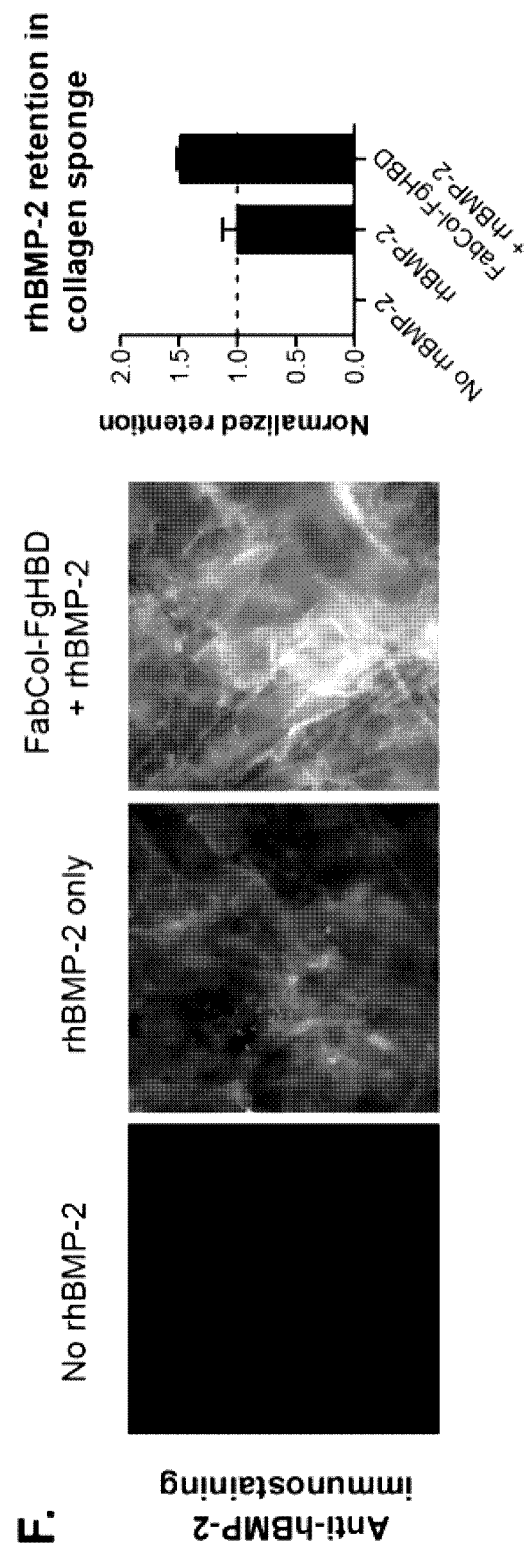
FIG. 13D-F

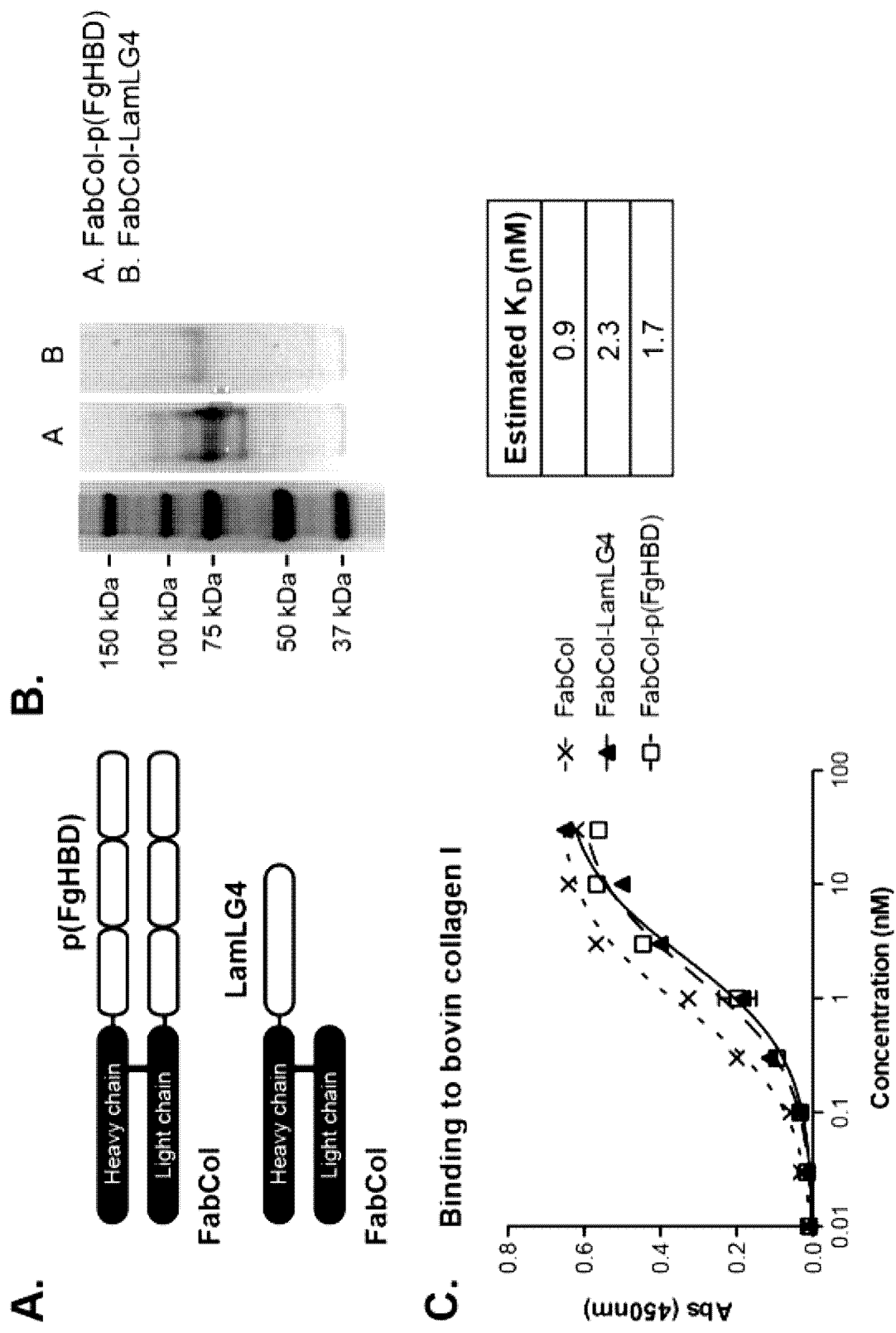
FIG. 14A-C

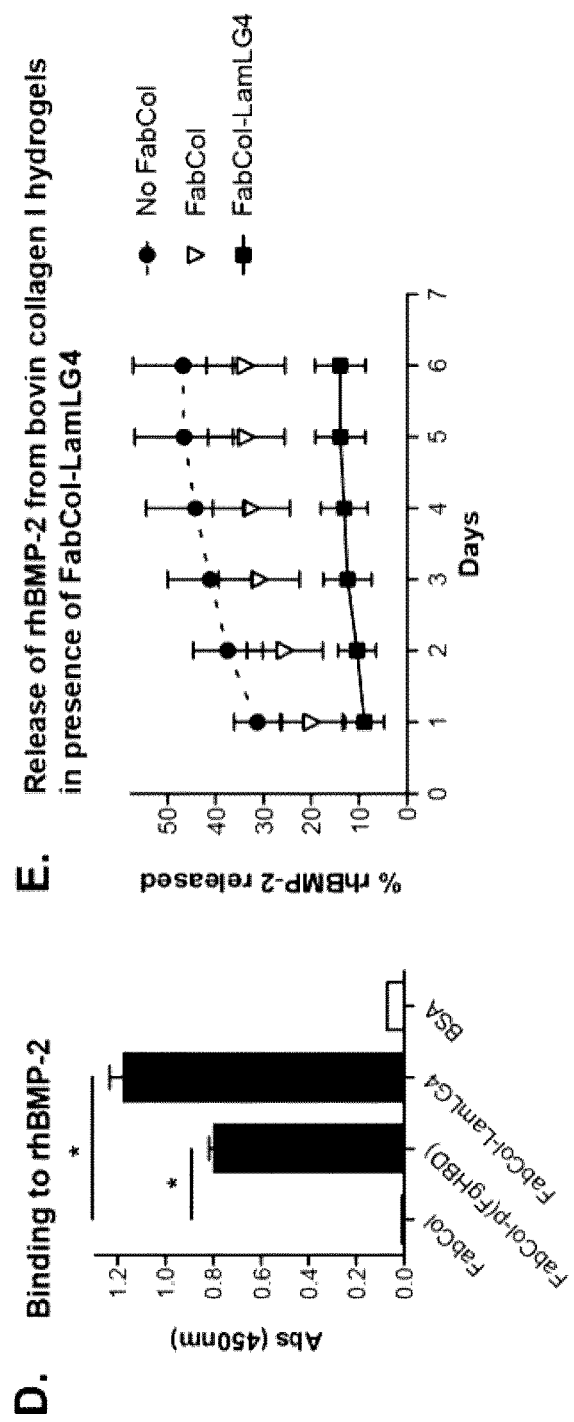
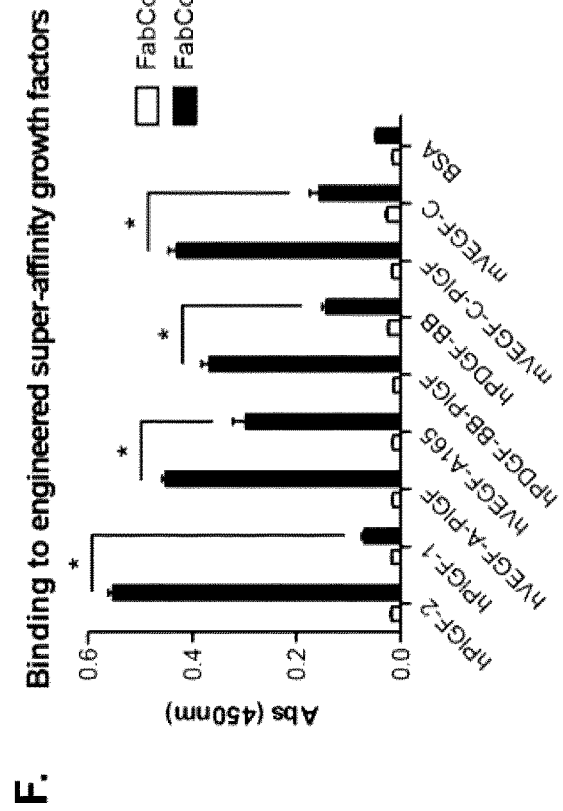
FIG. 14D-F

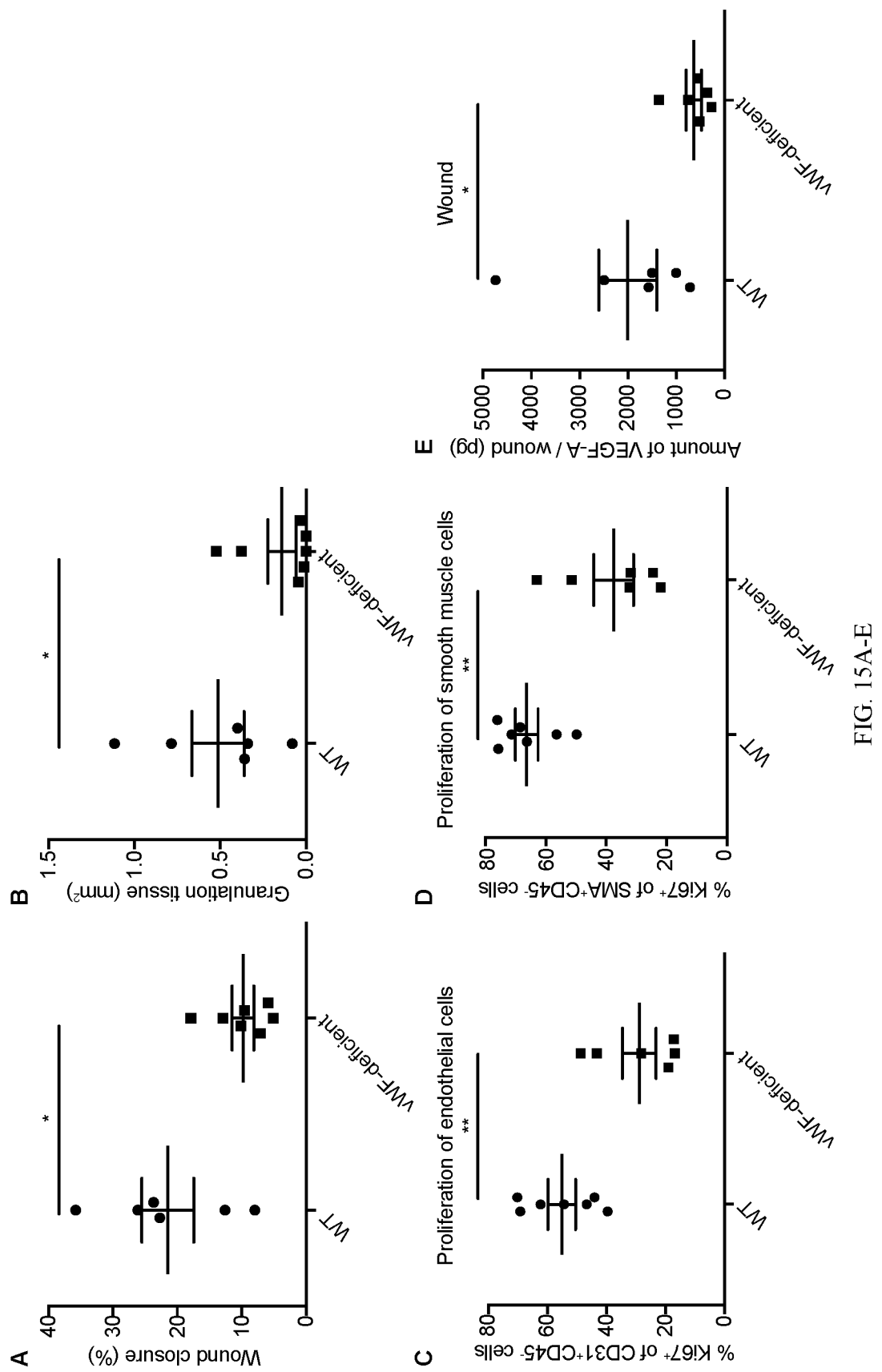
FIG. 15A-E

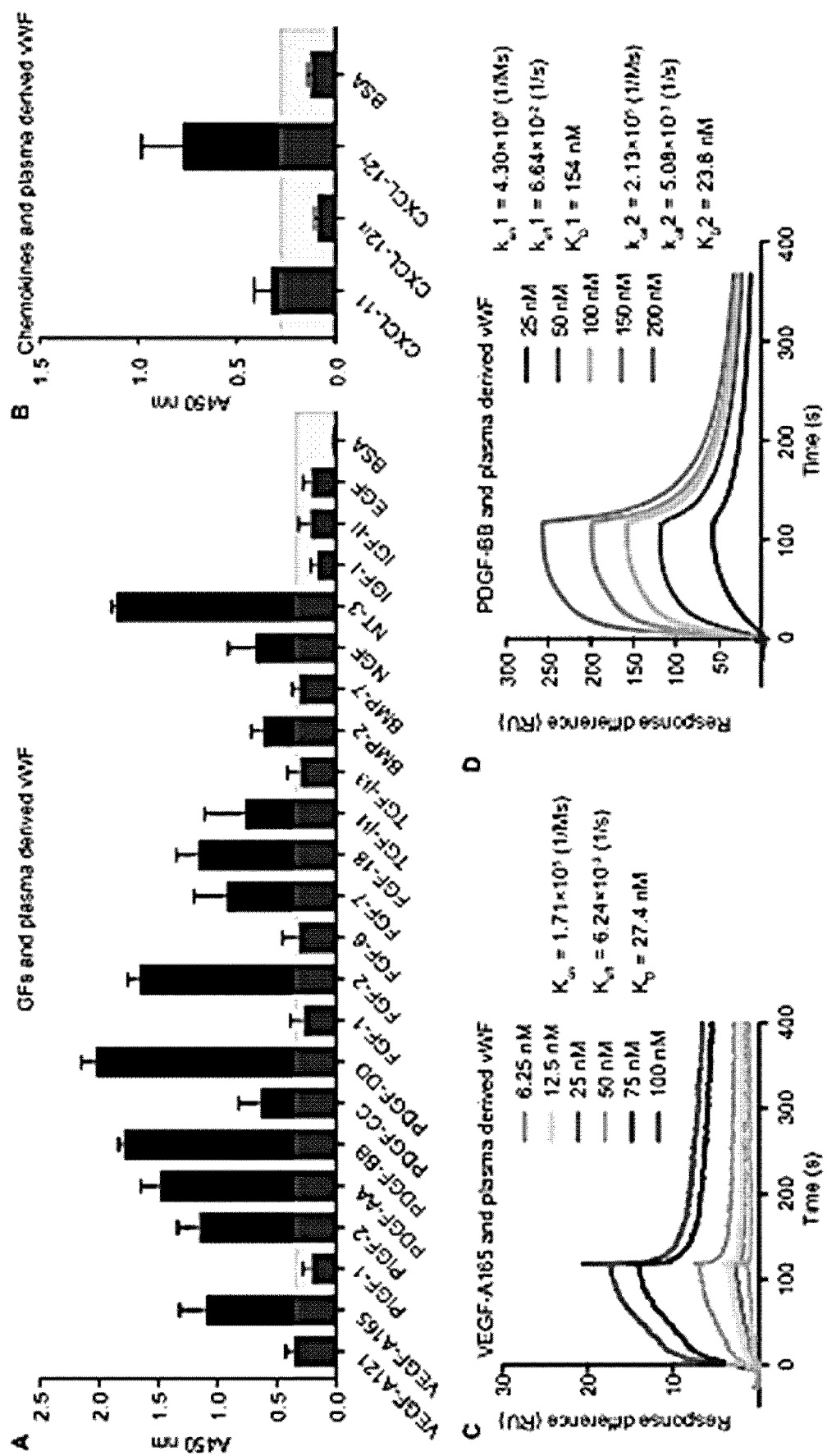
FIG. 16A-D

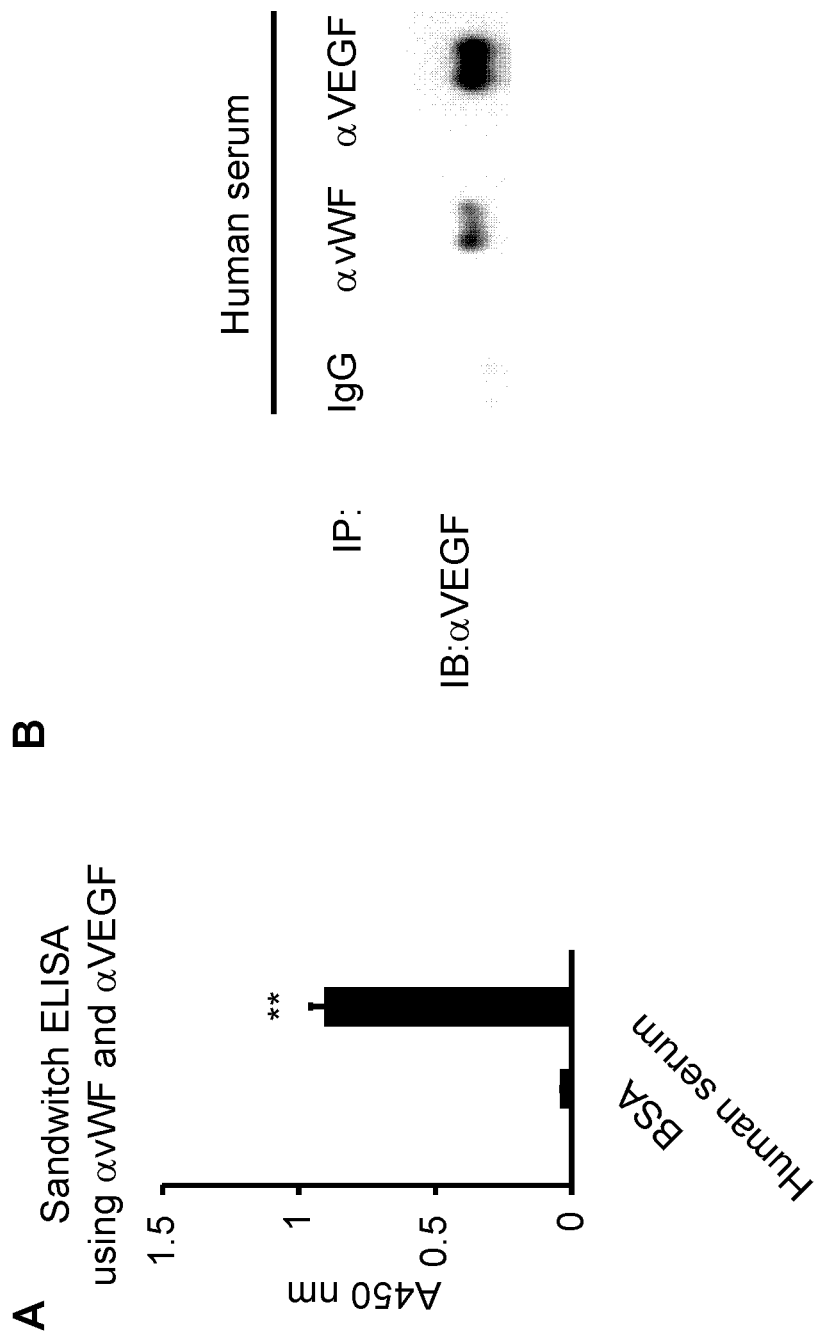
FIG. 17A-B

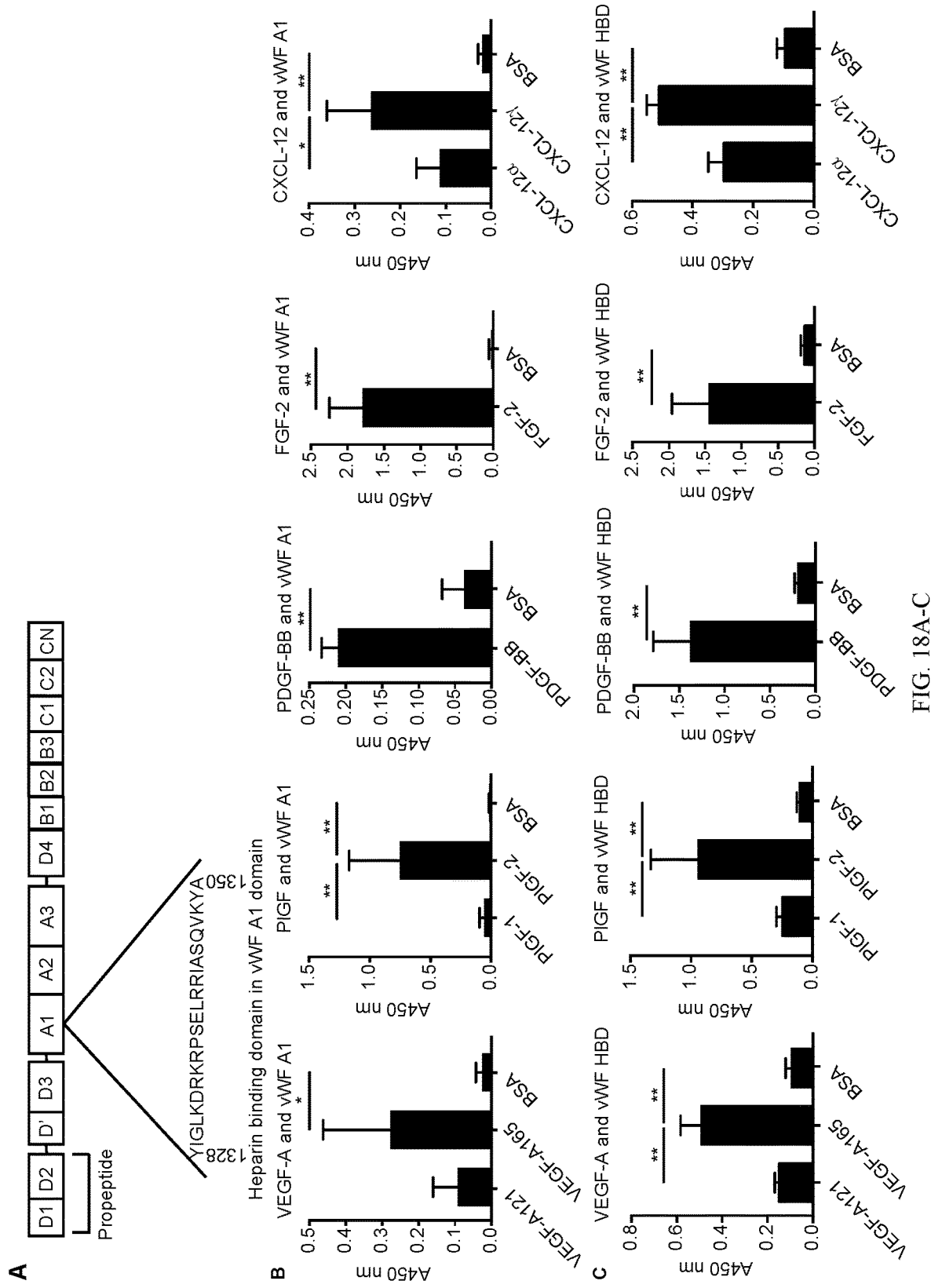
FIG. 18A-C

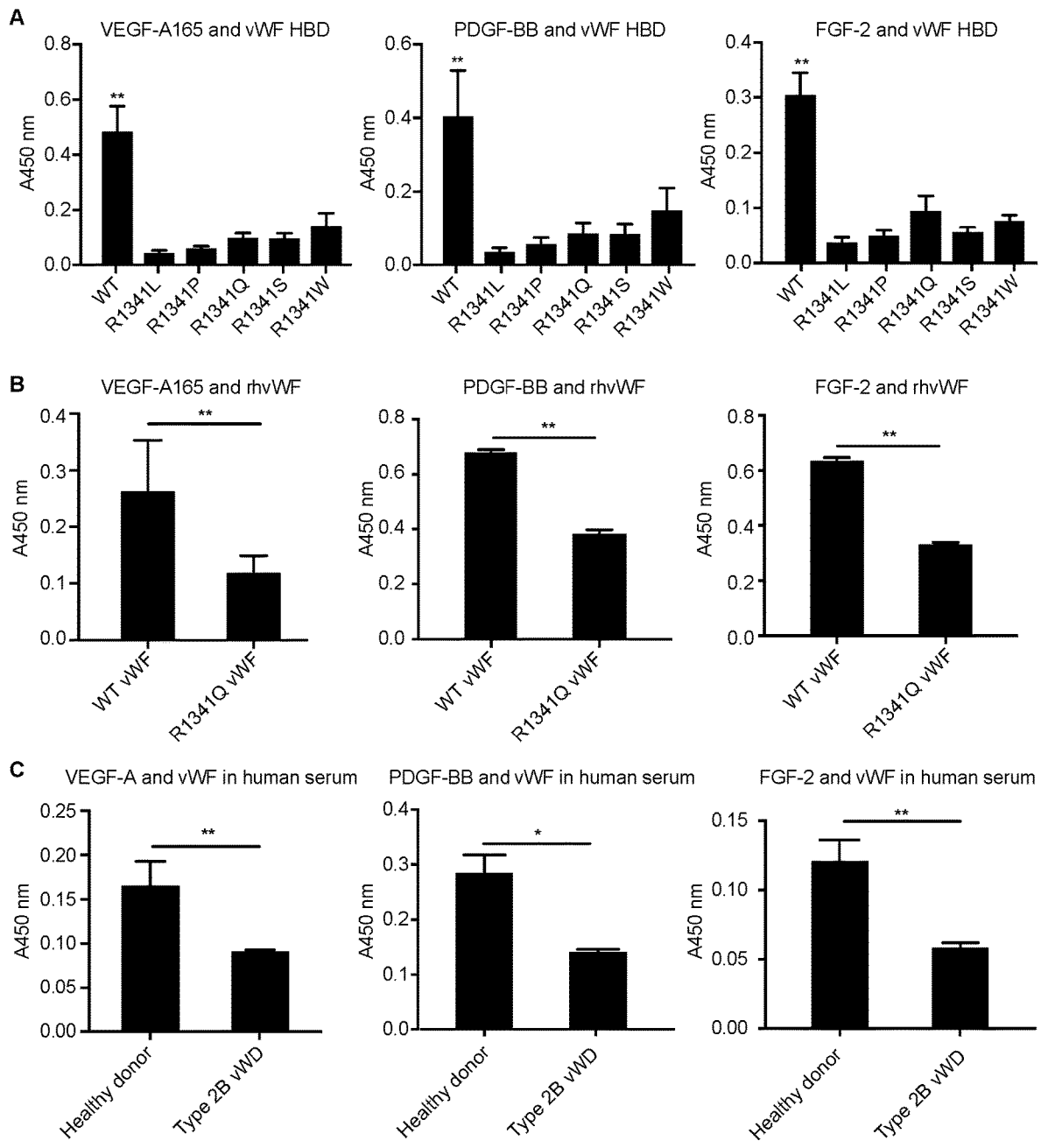
FIG. 19A-C

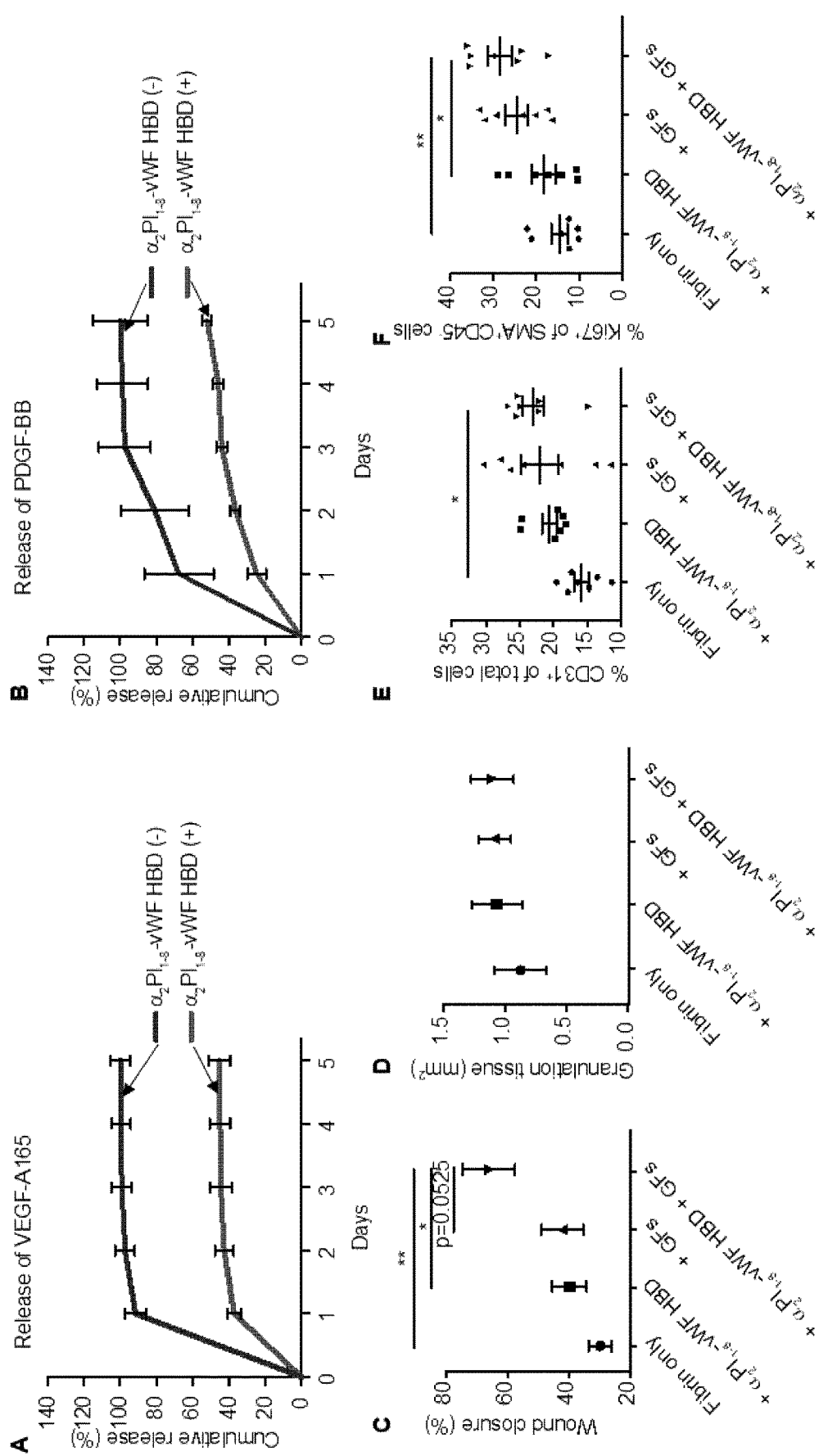
FIG. 20A-F

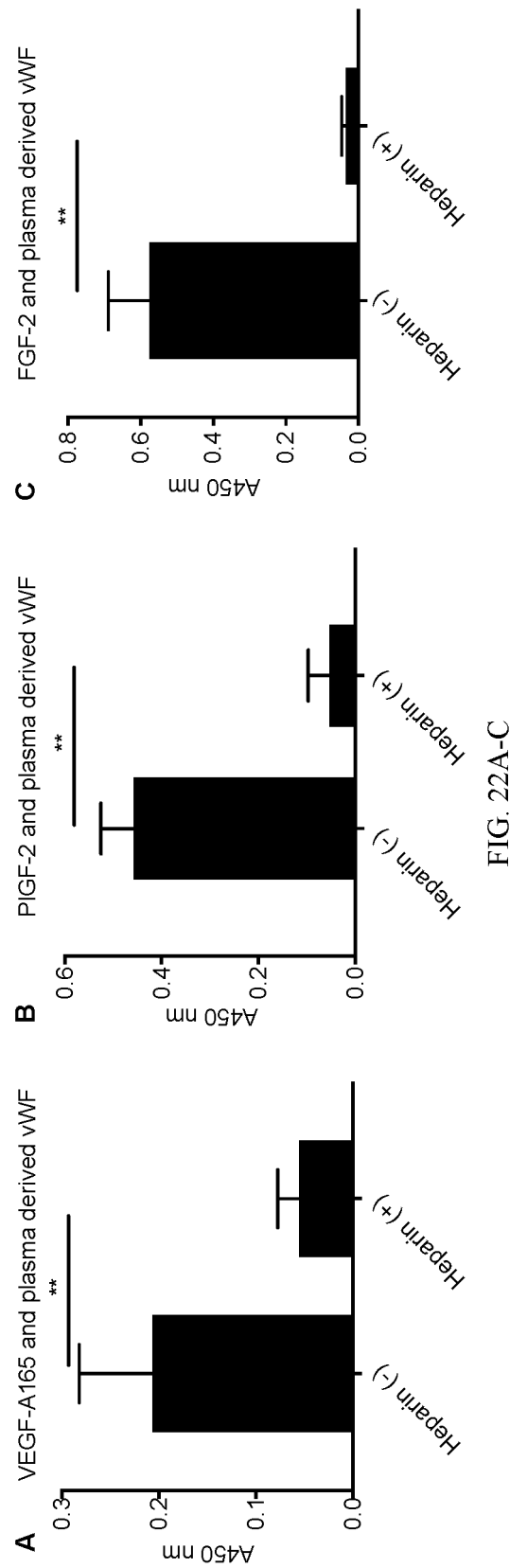
FIG. 22A-C

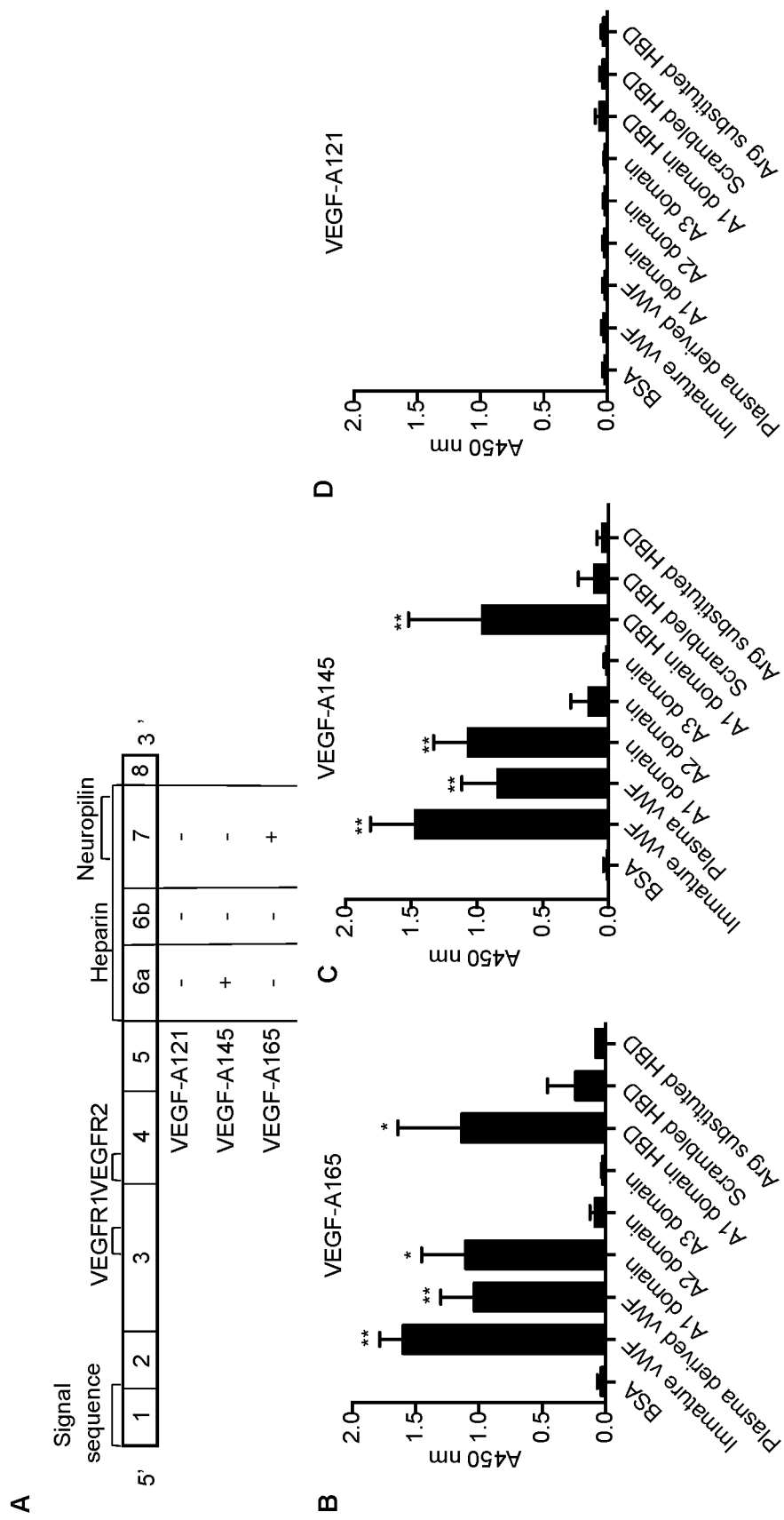
FIG. 23A-D

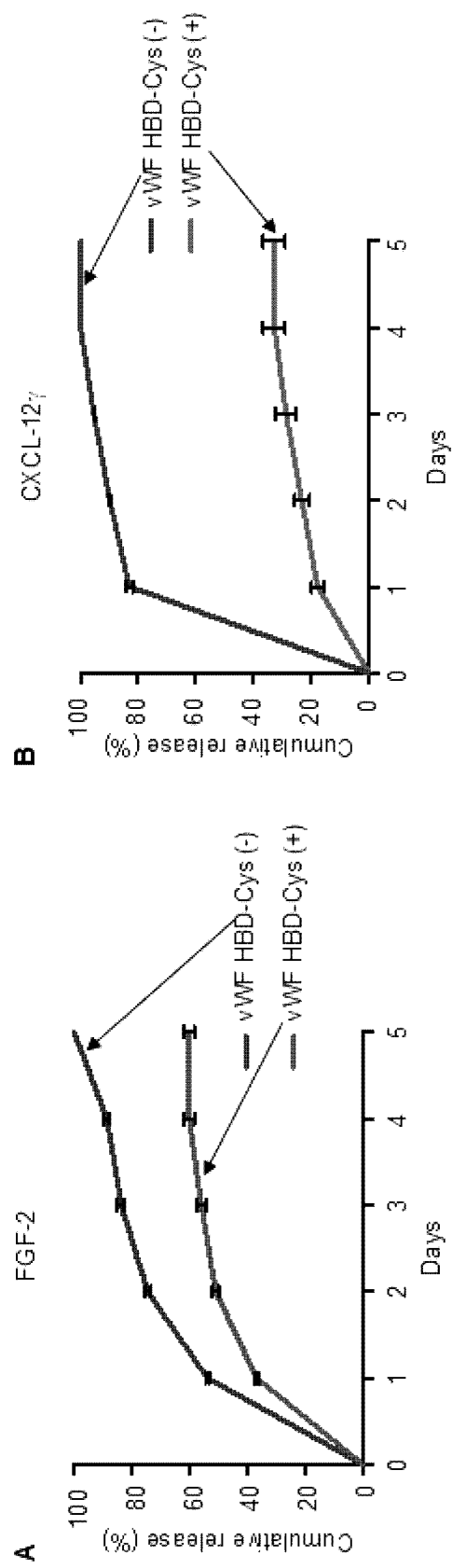
FIG. 24A-B

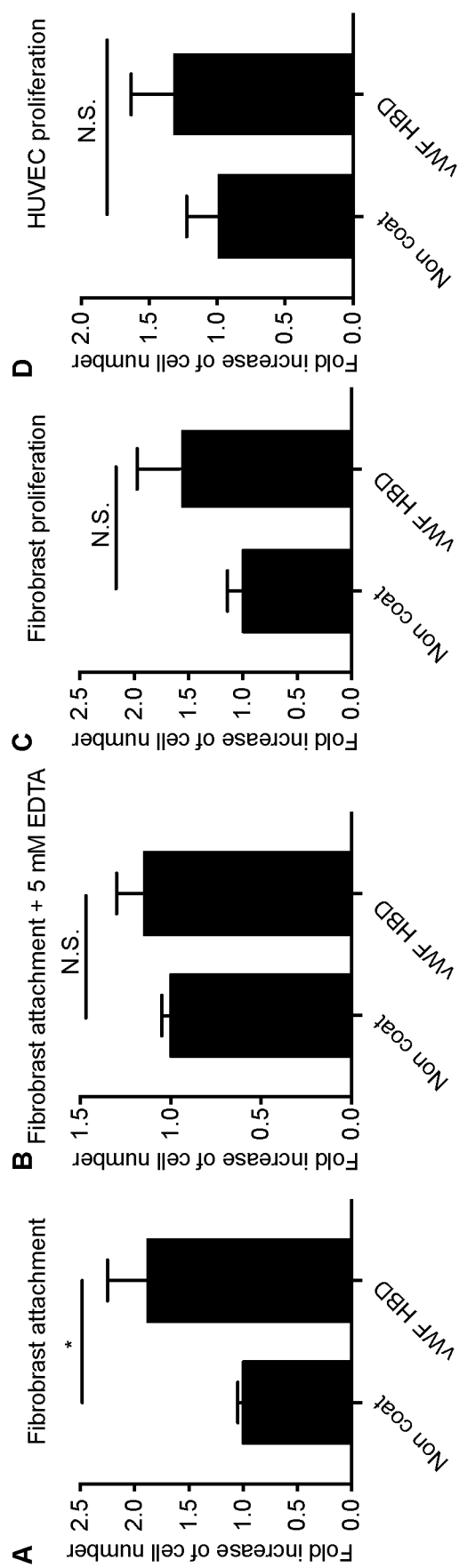
FIG. 25A-D

METHODS AND COMPOSITIONS FOR THE TREATMENT OF WOUNDS

CROSS-REFERENCE TO RELATED APPLICATIONS

This application is a national phase application under 35 U.S.C. § 371 of International Application No. PCT/US2018/060760 filed Nov. 13, 2018, which claims the benefit of priority of U.S. Provisional Patent Application No. 62/585,101 filed Nov. 13, 2017, and U.S. Provisional Patent Application No. 62/758,845 filed Nov. 12, 2018. The entire contents of each of the above-referenced disclosures are specifically incorporated herein by reference without disclaimer.

STATEMENT OF GOVERNMENT SUPPORT

The invention was made with government support under DK108215 awarded by the National Institutes of Health. The government has certain rights in the invention.

BACKGROUND

Field of the Invention

The invention generally relates to the field of medicine. More particularly, it concerns compositions and methods involving peptides providing for the delivery and/or in vivo recruitment of growth factors.

Background

GFs are considered as crucial molecules in regenerative medicine, including the treatment of chronic diabetic ulcers as well as the treatment of non-regenerating bone defect (chronic non-union fractures, critical bone defects). However, GFs have had only modest effects in the clinic to date (Fonder, M. A. et al. *Journal of the American Academy of Dermatology* 58, 185-206, (2008) and Falanga, V. *Lancet* (London, England) 366, 1736-1743, (2005)). For example, recombinant human VEGF-A has not been approved for clinical use by the U.S. Food and Drug Administration (FDA) due to a negative result in phase II clinical trials (Whittam, A. J. et al. *Advances in wound care* 5, 79-88 (2016)). PDGF-BB (Regranex in the clinic) has shown clinical efficacy, but safety issues such as cancer risk have been flagged, potentially due to high dosing (Marti-Carvajal, A. J. et al. The Cochrane database of systematic reviews, Cd008548, (2015) and Papanas, D. & Maltezos, E. Drug safety 33, 455-461 (2010)). As another example, the bone morphogenetic protein-2 (BMP-2) was delivered through collagen sponges in InFUSE® Bone Graft (Medtronic) at supraphysiological doses, and led to serious side effects as ectopic bone growth, increased cancer risk and nerve injuries. Therefore, engineering GF delivery approaches for regenerative medicine, including for wound healing and bone repair, to enhance efficacy and reduce GF doses and side effects is crucial. Due to the challenges of delivering growth factors, there is a need in the art for more advanced growth factor delivery and/or in vivo treatments.

SUMMARY OF INVENTION

The methods and compositions described herein address the need in the art by providing peptides and polypeptides comprising a growth factor binding domain that are useful in tissue regeneration, wound healing, and the treatment of certain disorders. In some embodiments, the peptides have an amino acid sequence that is at least 80% identical to one of SEQ ID NOS:1-7, 13-15, 49-50, or 66-70, or a fragment thereof wherein the peptide is less than 300 amino acids in length.

In some embodiments, the peptides have an amino acid sequence that is at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% identical (or any derivable range therein) to one of SEQ ID NOS:1-7, 13-15, 49-50, or 66-70, or a fragment thereof.

In some embodiments, the peptide is less than 300, 275, 250, 225, 200, 190, 180, 170, 160, 150, 140, 130, 120, 110, 100, 90, 80, 70, 60, 50, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, or 8 amino acids in length (or any derivable range therein).

In some embodiments, the peptide is attached to a transglutaminase-reactive peptide. In some embodiments, the transglutaminase-reactive peptide is attached to the amino or carboxy end of the growth factor binding domain peptide. In some embodiments, the transglutaminase-reactive peptide is from the α2-plasmin inhibitor. In some embodiments, the transglutaminase-reactive peptide comprises an amino acid sequence that is at least 80% identical to SEQ ID NO:12 or a fragment thereof. In some embodiments, the transglutaminase-reactive peptide comprises an amino acid sequence that is at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% identical (or any derivable range therein) to SEQ ID NO:12 or a fragment thereof.

In some embodiments, the peptide comprises an amino acid sequence that is at least 80% identical to SEQ ID NO:8, 16-13, or a fragment thereof. In some embodiments, the peptide comprises an amino acid sequence that is at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% identical (or any derivable range therein) to SEQ ID NO:8, 16-13, or a fragment thereof.

In some embodiments, the peptide comprises an amino acid sequence that is at least 80% identical to SEQ ID NO:49 or 50, or a fragment thereof. In some embodiments, the peptide comprises an amino acid sequence that is at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% identical (or any derivable range therein) to SEQ ID NO:49 or 50. In some embodiments, the peptide comprises a positively charged residue at position 14 of SEQ ID NO:49 or 50. In some embodiments, the positively charged residue comprises lysine, arginine, or histidine. In some embodiments, the peptide is unsubstituted at position 14 of SEQ ID NO:49 or 50. In some embodiments, the positively charged residues are unsubstituted or substituted with another positively charged residue. In some embodiments, the arginine residues are unsubstituted.

In some embodiments, the peptide is linked to one or more additional peptides, wherein each additional peptide has an amino acid sequence that is at least 80% identical to one of SEQ ID NOS:1-7, 13-15, 49-50, or 66-70, or a fragment thereof. In some embodiments, at least 2, 3, 4, 5, 6, or 7 peptides are linked together, wherein each linked peptide has an amino acid sequence that is at least 80% identical to one of SEQ ID NOS:1-7, 13-15, 49-50, or 66-70, or a fragment thereof. In some embodiments, the peptides are separated by one or more linkers. In some embodiments, the linker comprises SEQ ID NO:60, wherein x=1, 2, 3, 4, 5, or 6 or comprises SEQ ID NO:61. In some embodiments, the linker(s) comprises a flexible linker. In some embodiments, the flexible linker comprises glycine and serine amino acid residues.

In some embodiments, the peptide is attached to a collagen binding peptide. In some embodiments, the collagen binding peptide comprises the A3 domain of von Willebrand Factor (vWF A3) or fragment thereof, or a peptide with at least 80% identity to vWF A3 or fragment thereof. In some embodiments, the collagen binding peptide comprises a peptide having an amino acid sequence of SEQ ID NO:47 or a fragment thereof, or a peptide with at least 80% identity to SEQ ID NO:47 or fragment thereof. In some embodiments, the collagen binding peptide comprises a peptide with at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% sequence identity (or any derivable range therein) to SEQ ID NO:47 or fragment thereof. In some embodiments, the collagen binding peptide comprises a decorin polypeptide or fragment thereof, or a peptide with at least 80% identity to a decorin polypeptide or fragment thereof. In some embodiments, the collagen binding peptide comprises a peptide having an amino acid sequence of SEQ ID NO:48 or a fragment thereof, or a peptide with at least 80% identity to SEQ ID NO:48 or fragment thereof. In some embodiments, the collagen binding peptide comprises a peptide with at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% sequence identity (or any derivable range therein) to SEQ ID NO:48 or fragment thereof.

In some embodiments, the collagen binding peptide comprises one or more complementarity determining regions (CDRs) from an anti-collagen antibody. In some embodiments, the collagen binding peptide comprises a CDR1, CDR2, and/or CDR3 from a light chain variable region of an anti-collagen antibody. In some embodiments, the collagen binding peptide comprises a CDR1, CDR2, and CDR3 from a light chain variable region of an anti-collagen antibody. In some embodiments, the collagen binding peptide comprises a CDR1, CDR2, and/or CDR3 from a heavy chain variable region of an anti-collagen antibody. In some embodiments, the collagen binding peptide comprises a CDR1, CDR2, and CDR3 from a heavy chain variable region of an anti-collagen antibody. In some embodiments, the collagen binding peptide comprises a heavy or light chain variable region from an anti-collagen antibody. In some embodiments, the collagen binding peptide comprises a collagen-binding fragment from an anti-collagen antibody or a collagen-binding fragment derived from an anti-collagen antibody. In some embodiments, the collagen binding peptide comprises an anti-collagen antibody, or a Fab, scFv, nanobody, minibody, or unibody from an anti-collagen antibody or derived from an anti-collagen antibody. In some embodiments, the collagen binding peptide is humanized or chimeric. In some embodiments, the collagen binding peptide comprises human constant regions or a human framework. In some embodiments, the collagen binding peptide is chemically conjugated to the peptide. In some embodiments, there is a linker between the collagen binding peptide and the peptide comprising a growth factor binding domain. In some embodiments, the linker comprises SEQ ID NO:60, wherein x=1, 2, 3, 4, 5, or 6 or comprises SEQ ID NO:61. In some embodiments, the linker(s) comprises a flexible linker. In some embodiments, the flexible linker comprises glycine and serine amino acid residues. In some embodiments, the peptide is attached to the carboxy terminus of the collagen binding peptide. In some embodiments, the peptide is attached to the amino terminus of the collagen binding peptide.

In some embodiments, the collagen-binding domain is derived from variable regions of an anti-collagen antibody. In some embodiments, the collagen-binding domain comprises one or both of a heavy chain variable region and a light chain variable region of a collagen-binding antibody. Examples include single-chain variable fragments (scFv), antigen-binding fragments (Fab), and third-generation (3G) molecules such as nanobodies, minibodies, and unibodies.

In some embodiments, the peptide is chemically synthesized. In some embodiments, the peptide comprises a methionine as the amino-terminal amino acid. In some embodiments, the methionine is immediately adjacent to the first amino acid of one of SEQ ID NOS:1-7, 13-15, 49-50, or 66-70. In some embodiments, the amino terminal methionine is immediately adjacent to one of the peptide embodiments of the disclosure.

In some embodiments, the peptide is attached to a cell adhesion moiety. In some embodiments, the cell adhesion moiety comprises a ligand for a glycoprotein or a cell surface receptor. In some embodiments, the cell adhesion moiety comprises an integrin-binding peptide.

In some embodiments, the peptide is attached to a tag. In some embodiments, the tag comprises a purification tag, a signaling sequence, a post-translational modifier, or a targeting moiety. In some embodiments, the peptide is attached to a tag described herein. In some embodiments, the peptide is conjugated to a functional moiety. In some embodiments, the functional moiety comprises an antibody, an enzyme, a fluorescent compound, an imaging agent, or a therapeutic agent. In some embodiments, the functional moiety comprises a gadolinium chelation moiety. In some embodiments, the peptide is attached to a functional moiety described herein. In some embodiments, the tag and/or functional moiety is at the carboxy or amino terminus of the peptide.

In some embodiments, the peptide comprises two or more growth factor binding domains, wherein each growth factor binding domain has an amino acid sequence that is at least 80% identical to one of SEQ ID NOS:1-7, 13-15, 49-50, or 66-70. In some embodiments, the peptide comprises two or more growth factor binding domains, wherein each growth factor binding domain has an amino acid sequence that is at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% identical (or any derivable range therein) to one of SEQ ID NOS:1-7, 13-15, 49-50, or 66-70.

In some embodiments, the peptide comprises one or more substitutions relative to SEQ ID NOS:1-7, 13-15, 49-50, or 66-70. For example, the peptide may comprise at least, at most, or exactly 1, 2, 3, 4, 5, 6, 7, 8, 9, 10, 11, 12, 13, 14, or 15 (or any derivable range therein) substitutions at position(s) 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, and/or 200. In some embodiments, the one or more substitutions are conservative substitutions. In further embodiments, the one or more substitutions are non-conservative. In other embodiments, the one or more substitutions are a mix of conservative and non-conservative substitutions.

Further aspects of the disclosure relate to a molecular complex comprising any of the peptide embodiments described herein and one or more growth factors or cytokines are bound to the peptide. In some embodiments, the growth factors are bound by non-covalent interactions with the peptide. In some embodiments, the growth factors comprise one or more of VEGF, PlGF, PDGF, FGF, and BMP. In some embodiments, the growth factor comprises one or more of VEGF-A 165, PlGF2, PDGF-BB, PDGF-CC, FGF-2, and BMP-2. In some embodiments, the molecular complex comprises one or more growth factors or cytokines described herein. In some embodiments, the growth factor is linked to an ECM-binding domain. In some embodiments, the ECM-binding domain is from PlGF or from PlGF2. In some embodiments, the ECM-binding domain is linked to the peptide through a peptide bond. Further examples of ECM binding domains are described in WO2014006082A1.

Further aspects of the disclosure relate to a composition comprising any of the peptide or molecular complex embodiments described herein. In some embodiments, the composition further comprises one or more growth factors. In some embodiments, the growth factors comprise one or more of VEGF, PlGF, PDGF, FGF and BMP. In some embodiments, the growth factor comprises one or more of VEGF-A 165, PlGF2, PDGF-BB, FGF-2 and BMP-2. In some embodiments, the composition comprises one or more growth factors or cytokines described herein.

Further aspects of the disclosure relate to a biomaterial scaffold comprising any of the peptide or molecular complex embodiments described herein. In some embodiments, the scaffold comprises fibrin. In some embodiments, the peptide is covalently linked to the fibrin. In some embodiments, the covalent linkage is through the α2 plasmin inhibitor peptide ($\alpha_2PI_{1-8}$). In some embodiments, the scaffold comprises one or more of collagen, heparin, ceramic, a synthetic polymer, proteoglycans alginate-based substrates, chitosan, hyaluronic acid and/or methylcellulose substrates. In some embodiments, the biomaterial comprises less than 50 mg of exogenous growth factors. The term exogenous refers to materials, such as growth factors, that are added outside the body and do not include any of those materials that may be present in the body and associate with the scaffold or peptide in vivo. The exogenous components may be polypeptides and proteins that have been recombinantly or chemically produced.

In some embodiments, the dose of a growth factor is adminstered according to a dosage amount and schedule described herein.

In some embodiments, with respect to PDGF or specifically PDGF-BB or PDGF-CC, the dosage may be at most, at least, or exactly 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, or 4.5 (or any derivable range therein) μg/kg body weight. In some embodiments, with respect to PDGF or specifically PDGF-BB, the dosage may be at least, at most, or exactly 1, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495 or 500 mg, μg, or ng/dose (or any derivable range therein). In some embodiments, with respect to PDGF or specifically PDGF-BB, the dosage may be at most, at least, or exactly 1, 2, 3, 4, 5, 6, 7, 8, 9, 10, 11, 12, 13, 14, 15, 16, 17, 18, 19, or 20 μg/cm2 wound or tissue area (or any derivable range therein). The administration may be repeated daily or every 2, 3, 4, 5 6, or 7 days (or any derivable range therein for at least, at most, or exactly 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days or 1 2, 3, 4, 5, 6, 7, 8, 9, or 10 weeks (or any derivable range therein). In some embodiments, the dose refers to a total prescribed dose that is to be administered over a period of time.

In some embodiments, with respect to VEGF or specifically VEGF-A or VEGF-A 165, the dosage may be at most, at least, or exactly 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.75, 2, 2.25, 2.5, 2.75, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 52, 54, 55, 56, 58, 60, 62, 64, 66, 68, 70, 72, 75, or 100 mg, μg, or ng/dose (or any derivable range therein). In some embodiments, with respect to VEGF or specifically VEGF-A or VEGF-A 165, the dosage may be at most, at least, or exactly 100, 125, 150, 175, 200, 225, 250, 275, 300, 325, 350, 375, 400, 425, 450, 475, 500, 525, 550, 575, 600, 625, 650, 670, 675, 700, 725, 750, 775, or 800 μg/cm2 wound or tissue area (or any derivable range therein). The administration may be repeated daily or every 2, 3, 4, 5 6, or 7 days (or any derivable range therein for at least, at most, or exactly 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days or 1 2, 3, 4, 5, 6, 7, 8, 9, or 10 weeks (or any derivable range therein). In some embodiments, the dose refers to a total prescribed dose that is to be administered over a period of time.

In some embodiments, with respect to FGF or specifically FGF-2, the dosage may be at most, at least, or exactly 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, or 4.5 (or any derivable range therein) μg/kg body weight. In some embodiments, with respect to FGF or specifically FGF-2, the dosage may be at least, at most, or exactly 1, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495 or 500 mg, μg, or ng/dose (or any derivable range therein). In some embodiments, with respect to FGF or specifically FGF-2, the dosage may be at most, at least, or exactly 1, 2, 3, 4, 5, 6, 7, 8, 9, 10, 11, 12, 13, 14, 15, 16, 17, 18, 19, or 20 μg/cm2 wound or tissue area (or any derivable range therein). The administration may be repeated daily or every 2, 3, 4, 5 6, or 7 days (or any derivable range therein for at least, at most, or exactly 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days or 1 2, 3, 4, 5, 6, 7, 8, 9, or 10 weeks (or any derivable range therein). In some embodiments, the dose refers to a total prescribed dose that is to be administered over a period of time.

In some embodiments, with respect to PlGF or specifically PlGF2, the dosage may be at most, at least, or exactly 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, or 4.5 (or any derivable range therein) μg/kg body weight. In some embodiments, with respect to PlGF or specifically PlGF2, the dosage may be at least, at most, or exactly 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495 or 500 mg, μg, or ng/dose (or any derivable range therein). In some embodiments, with respect to PlGF or specifically PlGF2, the dosage may be at most, at least, or exactly 1, 2, 3, 4, 5, 6, 7, 8, 9, 10, 11, 12, 13, 14, 15, 16, 17, 18, 19, or 20 μg/cm2 wound or tissue area (or any derivable range therein). The administration may be repeated daily or every 2, 3, 4, 5 6, or 7 days (or any derivable range therein for at least, at most, or exactly 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days or 1 2, 3, 4, 5, 6, 7, 8, 9, or 10 weeks (or any derivable range therein). In some embodiments, the dose refers to a total prescribed dose that is to be administered over a period of time.

In some embodiments, with respect to BMP or specifically BMP-2, the dosage may be at most, at least, or exactly 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, or 4.5 (or any derivable range therein) μg/kg body weight. In some embodiments, with respect to BMP or specifically BMP-2, the dosage may be at least, at most, or exactly 1, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495 or 500 mg, μg, or ng/dose (or any derivable range therein). In some embodiments, with respect to BMP or specifically BMP-2, the dosage may be at most, at least, or exactly 1, 2, 3, 4, 5, 6, 7, 8, 9, 10, 11, 12, 13, 14, 15, 16, 17, 18, 19, or 20 μg/cm2 wound or tissue area (or any derivable range therein). The administration may be repeated daily or every 2, 3, 4, 5 6, or 7 days (or any derivable range therein for at least, at most, or exactly 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days or 1 2, 3, 4, 5, 6, 7, 8, 9, or 10 weeks (or any derivable range therein). In some embodiments, the dose refers to a total prescribed dose that is to be administered over a period of time.

In some embodiments, externally added VEGF-A165 is in an amount of less than 20 μg, less than 10 μg, less than 1 μg, less than 500 ng, less than 400 ng, less than 300 ng, less than 200 ng, less than 100 ng, or less than 1 ng. In some embodiments, externally added PDGF-BB is in an amount of less than 10 μg, less than 1 μg, less than 500 ng, less than 400 ng, less than 300 ng, less than 200 ng, less than 100 ng, or less than 1 ng.

In some embodiments, the biomaterial scaffold or implant is one that retains at least 80% of exogenously added growth factors for at least 3 days. In some embodiments, the biomaterial scaffold or implant is one that retains at least 50, 60, 70, 75, 80, 85, 90, 91, 92, 93, 94, 95, 96, 97, 98, 99, or 100% (or any derivable range therein) of exogenously added growth factors for at least 1, 2, 3, 4, 5, 6, 7, 8, 9, or 10 days (or any derivable range therein).

Further aspects of the disclosure relate to an implant comprising any one of the peptide, molecular complex, composition, or biomaterial embodiments described herein. In some embodiment, the implant comprises a medical device, a stent, or a vascular graft.

Further aspects relate to a method for regenerating tissue in a subject, the method comprising administering a peptide, molecular complex, composition, biomaterial scaffold, or implant embodiment of the disclosure to the subject.

Further aspects relate to a method for facilitating wound or tissue healing in a subject, the method comprising administering a peptide, molecular complex, composition, biomaterial scaffold, or implant embodiment of the disclosure to the subject.

Yet further aspects relate to a method for treating angiodysplasia and/or von mucosal/cutaneous bleeding in a subject, the method comprising administering a biomaterial scaffold, composition, or implant of the disclosure to the subject. Yet further aspects relate to a method for treating von Willebrand disease (VWD) in a subject, the method comprising administering a biomaterial scaffold, composition, or implant of the disclosure to the subject. In some embodiments, von Willebrand disease comprises acquired von Willebrand disease (AVWD). In some embodiments, von Willebrand disease comprises congenital von Willebrand disease (AVWD). In some embodiments, VWD comprises type 1 VWD. In some embodiments, VWD comprises type 2 VWD. In some embodiments, VWD comprises type 3 VWD. In some embodiments, VWD comprises type 2A VWD. In some embodiments, VWD comprises type 2B VWD. In some embodiments, the method is for treating GI bleeding associated with angiodysplasia. In some embodiments, the subject is one that has reduced high molecular weight multimers (HMWM) of the vWF protein.

Yet further aspects of the disclosure relate to the treatment of diabetic ulcers in a subject, the method comprising administering a biomaterial scaffold, composition, or implant of the disclosure to the subject.

In some embodiments, the peptide, molecular complex, composition, biomaterial scaffold, or implant is administered locally to a specific tissue or wound. In some embodiments, the subject has or has been diagnosed with a deficiency in wound healing. In some embodiments, the subject has diabetes. In some embodiments, the wound comprises a diabetic ulcer. In some embodiments, the tissue comprises bone. In some embodiments, the tissue is one disclosed herein. In some embodiments, the biomaterial scaffold or implant is administered locally to bone or a location adjacent thereto. In some embodiments, the percentage of wound closure after seven days of administration is at least 60%. In some embodiments, the percentage of wound closure after 1, 2, 3, 4, 5, 6, 7, 8, 9, 10, 11, 12, 13, 14, 15, 16, 17, 18, 19, or 20 days (or any derivable range therein) of administration is at least 40, 45, 50, 55, 60, 65, 70, 75, 80, 85, 90, 95, 96, 97, 98, or 99%, or any derivable range therein. In some embodiments, the amount of granulation of the tissue after seven days of administration is at least 1 mm$^2$. In some embodiments, the amount of granulation of the tissue after 1, 2, 3, 4, 5, 6, 7, 8, 9, 10, 11, 12, 13, 14, 15, 16, 17, 18, 19, or 20 days (or any derivable range therein) of administration is at least 0.5, 0.6, 0.7, 0.8, 0.9, 1.0, 1.1, 1.2, 1.3, 1.4, 1.5, 1.6, 1.8, 1.9, or 2 mm$^2$, or any derivable range therein.

In some embodiments, the subject has and/or has been diagnosed with von Willebrand disease (VWD). In some embodiments, VWD comprises type 1 VWD. In some embodiments, VWD comprises severe type 1 VWD. In some embodiments, VWD comprises type 2 VWD. In some embodiments, VWD comprises type 3 VWD. In some embodiments, VWD comprises type 2A VWD. In some embodiments, VWD comprises type 2B VWD. In some embodiments, the subject has and/or has been diagnosed with acquired von Willebrand disease (AVWD). In some embodiments, the subject has and/or has been diagnosed with congenital von Willebrand disease. In some embodiments, the subject is deficient for the vWF protein. In some embodiments, the subject has been determined to be deficient for the vWF protein. In some embodiments, the subject has and/or has been determined to have a mutant vWF protein. In some embodiments, the subject has been identified with having blood vessel abnormalities. In some embodiments, the subject has and/or has been determined to have a mutation in the A1 domain of vWF. In some embodiments, the subject has a mutant vWF with increased affinity for GPIbα. In some embodiments, the subject has been shown to have one or more of spontaneous platelet aggregation, loss of active high molecular weight vWF multimers, thrombocytopenia and/or bleeding. In some embodiments, the subject has been determined to have mutations in exon 28 of the vWF gene. In some embodiments, the subject has been determined to have a R1341 substitution or deletion in the vWF protein, or a mutation in the vWF gene which results in a R1341 substitution or deletion in the vWF protein. In some embodiments, the subject is determined to have a R1341 substitution, wherein the arginine is substituted with Leu, Pro, Gln, Trp, or Ser. In some embodiments, the subject has been diagnosed with angiodysplasia. In some embodiments, the subject has been determined to have GI bleeding. In some embodiments, the subject is one that has reduced high molecular weight multimers (HMWM) of the vWF protein.

In some embodiments, the patient has been previously treated for a condition or indication described herein. In some embodiments, the subject was resistant to the previous treatment. In some embodiments, the patient has been diagnosed with and/or is susceptible to a condition or indication described herein. In some embodiments, the method further comprises administration of an additional therapy, such as, for example, additional therapies described herein.

The terms "protein", "polypeptide" and "peptide" are used interchangeably herein when referring to a gene product or synthetic amino acid polymer.

The terms "subject," "mammal," and "patient" are used interchangeably. In some embodiments, the subject being treated is a mammal. In some embodiments, the subject is a human. In some embodiments, the subject is a mouse, rat, rabbit, dog, donkey, sheep, goat, pig, or a laboratory test animal such as fruit fly, zebrafish, etc.

It is contemplated that the methods and compositions include exclusion of any of the embodiments described herein.

The terms "a" and "an" are defined as one or more unless this disclosure explicitly requires otherwise.

The term "substantially" is defined as being largely but not necessarily wholly what is specified (and include wholly what is specified) as understood by one of ordinary skill in the art. In any disclosed embodiment, the term "substantially" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, the methods and systems of the present invention that "comprises," "has," "includes" or "contains" one or more elements possesses those one or more elements, but is not limited to possessing only those one or more elements. Likewise, an element of a method or system of the present invention that "comprises," "has," "includes" or "contains" one or more features possesses those one or more features, but is not limited to possessing only those one or more features.

The feature or features of one embodiment may be applied to other embodiments, even though not described or illustrated, unless expressly prohibited by this disclosure or the nature of the embodiments.

Any method or system of the present invention can consist of or consist essentially of—rather than comprise/include/contain/have—any of the described elements and/or features and/or steps. Thus, in any of the claims, the term "consisting of" or "consisting essentially of" can be substituted for any of the open-ended linking verbs recited above, in order to change the scope of a given claim from what it would otherwise be using the open-ended linking verb. A composition "consisting essentially of" the recited elements excludes any further active ingredients but does not exclude pharmaceutical excipients, buffers, structural components, etc.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 2A-C. Excess heparin inhibits GF-laminin binding. Inhibition of GF-binding to laminin (−111, −211, −221, −411, −421, −511, and −521) by excess heparin. ELISA plates were coated with 10 μg/mL laminin and further incubated with a 1 μg/mL (A) VEGF-A165, (B) PlGF-2, or (C) FGF-2 solution in the absence or presence of excess (10 μM) heparin. Bound GFs were detected using a specific antibody for each GF (n=4, mean±SEM). Statistical analyses were done using the Mann-Whitney U test by comparing the signals with and without heparin. *p<0.05, **p<0.01.

FIGS. 3A-D. GFs bind to recombinant LG domain protein derived from laminin α3, α4 and α5 chains. Affinity of GFs against recombinant laminin LG domains. ELISA plates were coated with 1 μg/mL (A) α3$_{2928-3150}$, (B) α4$_{826-1816}$, or (C) α5$_{3026-3482}$ and further incubated with 1 μg/mL of VEGF-A165, VEGF-A121, PlGF-2, PlGF-1, PDGF-BB, or FGF-2 solution. Bound GFs were detected using a specific antibody for each GF (n=4, mean±SEM). Statistical analyses were done using the Mann-Whitney U test by comparing the signals obtained from the laminin domain- and the BSA-coated wells. *p<0.05, **p<0.01. (D) Affinities ($K_D$ values are shown) of laminin α3$_{2928-3150}$ against VEGF-A165 and PDGF-BB were measured by SPR. A SPR chip was functionalized with the laminin α3$_{2928-3150}$ recombinant protein (~1000 RU), and each GF was flowed over the chip at indicated concentrations. Curves represent the specific responses (in RU) to laminin. Experimental curves were fitted with Langmuir binding kinetics. Binding kinetics values [dissociation constants ($K_D$) and rate constants ($K_{on}$ and $K_{off}$)] determined from the fitted curves are shown.

FIGS. 4A-F. GFs bind to chemically synthesized laminin HBD peptides derived from the LG domain of laminin α3, α4, and α5 chains. (A) The location of laminin-derived peptides in the LG domain of laminin α3, α4, and α5 chains. (B-F) Affinity of heparin and GFs against chemically synthesized peptides derived from the LG domain of laminin α3, α4, and α5 chains. ELISA plates were coated with 10 μg/mL laminin peptide and further incubated with (B) biotinylated heparin, (C) VEGF-A165 and VEGF-A121, (D) PlGF-2 and PlGF-1, (E) PDGF-BB, or (F) FGF-2. Concentrations were 1 μg/mL for GFs and 10 μg/mL for heparin. Bound heparin was detected with streptavidin, and bound GFs with a specific antibody for each GF (n=4, mean±SEM). Statistical analyses were done using the Mann-Whitney U test by comparing the signals obtained from the laminin peptide- and the BSA-coated wells. *p<0.05, **p<0.01.

FIGS. 5A-D. Chemically synthesized peptides derived from the LG domain of laminin α3, α4 and α5 chains bind to syndecans. Affinity of syndecans to chemically synthesized peptides derived from the laminin α3, α4 and α5 LG domains. ELISA plates were coated with 10 μg/mL laminin peptide and further incubated with 1 μg/mL of (A) syndecan-1, (B) syndecan-2, (C) syndecan-3, or (D) syndecan-4. Bound syndecans were detected using an antibody against histidine-tag on the recombinant syndecans (n=8, mean±SEM). Statistical analyses were done using the Mann-Whitney U test by comparing the signals obtained from the laminin peptide- and the BSA-coated wells. *p<0.05, **p<0.01.

FIGS. 6A-D. Laminin HBD peptides promote fibroblast and endothelial cell adhesion in vitro. (A, B) 3000 cells/well human lung fibroblasts were cultured (A) without or (B) with 5 mM EDTA in FGM-2 culture media containing 1% FBS. (C, D) 3000 cells/well HUVEC were cultured (C) without or (D) with 5 mM EDTA in EBM-2 culture media containing 100 ng/ml VEGF-A165 and 1% FBS. Cells were plated on 1 μg/mL laminin peptide pre-coated non-tissue culture treated plates and incubated for 30 min at 37° C. After plate washes, cell numbers were quantified using a CyQUANT assay (n=10, mean±SEM). The signals obtained from BSA-coated wells are normalized to 1, and relative fold increases of cell numbers were calculated. Statistical analyses were done using ANOVA with Tukey's test. Kruskal-Wallis test followed by Dunn's multiple comparison was used in (B, C). *p<0.05, **p<0.01.

FIGS. 7A-C. GF retention in fibrin matrices is enhanced by incorporating laminin HBD peptide. (A,B) GF retention in fibrin matrix. α$_2$PI$_{1-8}$-α3$_{3043-3067}$ or α$_2$PI$_{1-8}$-α5$_{3417-3436}$ peptide-functionalized fibrin matrices were made in the presence of VEGF-A165 or PDGF-BB, and incubated in 8 volumes of physiological buffer for 5 days. The buffer was changed each day, and released GFs were quantified daily. Graphs show the cumulative release of (A) VEGF-A165 or (B) PDGF-BB over 5 days (n=4; mean±SEM). All data points for laminin HBD peptides were statistically significant compared to controls without laminin HBD peptide (p<0.01, Mann-Whitney U test). (C) Fibrin matrices containing VEGF-A165 (200 ng/wound) with or without α$_2$PI$_{1-8}$-α3$_{3043-3067}$ peptide were placed on the full-thickness back-skin wounds in db/db diabetic mice. After 3 and 6 days, retention of VEGF-A165 after 3 and 6 days in the fibrin matrix and the tissue surrounding the wound (2 mm beyond the wound margin) were quantified. n≥4 per time point, mean±SEM. Student's t-test; **p<0.01.

FIGS. 8A-G. Delivering GFs within laminin HBD peptide-functionalized fibrin matrices enhances skin wound healing in db/db diabetic mice. Full-thickness back-skin wounds were treated with combined VEGF-A165 (100 ng/wound) and PDGF-BB (50 ng/wound). Four groups were tested: fibrin only, fibrin functionalized with α$_2$PI$_{1-8}$-α3$_{3043-3067}$ peptide, fibrin containing admixed GFs, and fibrin functionalized with α$_2$PI$_{1-8}$-α3$_{3043-3067}$ peptide containing GFs. After 4, 7, and 10 days, (A-B) wound closure and (C) granulation tissue area were evaluated by histology (means±SEM, day 4: n=6, day 7: fibrin only and α$_2$PI$_{1-8}$-α3$_{3043-3067}$ peptide+GFs, n=10; other treatment groups, n=11, day 10: α$_2$PI$_{1-8}$-α3$_{3043-3067}$ peptide, n=8, α$_2$PI$_{1-8}$-α3$_{3043-3067}$ peptide+GFs, n=9, other treatment groups, n=7). (B) The proportions of the mice were categorized by the degree of healing after day 7 of wound treatment. (D) Wound histology (hematoxylin and eosin staining) at day 7. Red arrows indicate tips of the epithelium tongue. The granulation tissue (pink-violet) is characterized by a large number of granulocytes with nuclei that stain in dark-violet or black. Muscle under the wounds is stained in red. Fat tissue appears as transparent bubbles. Scale bar=800 μm. (E-G) 5 days after the wound treatment, (E) proliferation of CD31$^+$CD45$^+$ endothelial cells is assessed by Ki67$^+$ marker, and (F) the frequency of Ly6G$^+$CD11b$^+$ neutrophils within CD45$^+$ cells and (G) the frequency of Ly6C$^+$CD11b$^+$ monocytes within CD45$^+$ cells were determined using flow cytometry (means±SEM). *P<0.05, **P<0.01, ANOVA with Tukey's test.

μg/mL for GFs. Bound GF was detected with a specific antibody for each GF (n=4, mean±SEM). Statistical analyses were done using one-way ANOVA. *p<0.05, **p<0.01. Sequence of the peptides are described in Table 2.

Figure 10:
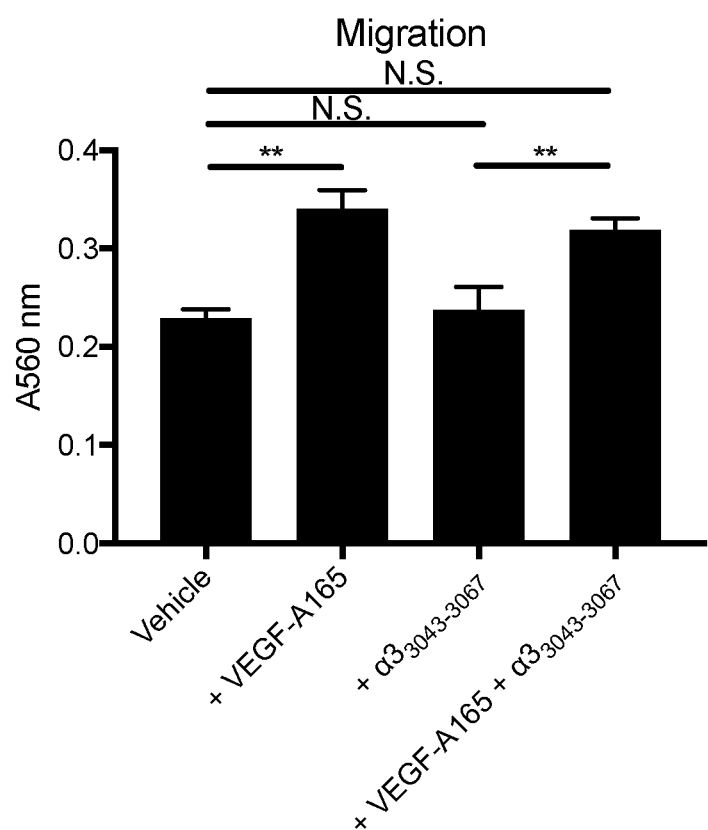

FIG. 10. Laminin HBD peptide did not enhance the migration of endothelial cells in vitro. $4 \times 10^4$ HUVEC cells were added to the transwell upper parts. Solutions containing 30 ng/mL of VEGF-A165 preincubated with or without 0.1 μM of $\alpha 3_{3043\text{-}3067}$ peptide were added to the bottom side of the transwell. The signals of the cells that passed through a migration transwell after 6 hr of incubation were measured. (means±SEM, n=4). Statistical analyses were done using one-way ANOVA. **P<0.01

FIG. 11. Photos of the wounds. Full-thickness back-skin wounds were treated with combined VEGF-A165 (100 ng/wound) and PDGF-BB (50 ng/wound). Four groups were tested: fibrin only, fibrin functionalized with $\alpha_2 PI_{1\text{-}8}$-$\alpha 3_{3043\text{-}3067}$ peptide, fibrin containing admixed GFs, and fibrin functionalized with $\alpha_2 PI_{1\text{-}8}$-$\alpha 3_{3043\text{-}3067}$ peptide containing GFs. Representative pictures of wounds after 0 and 7 days are presented.

Figure 12:
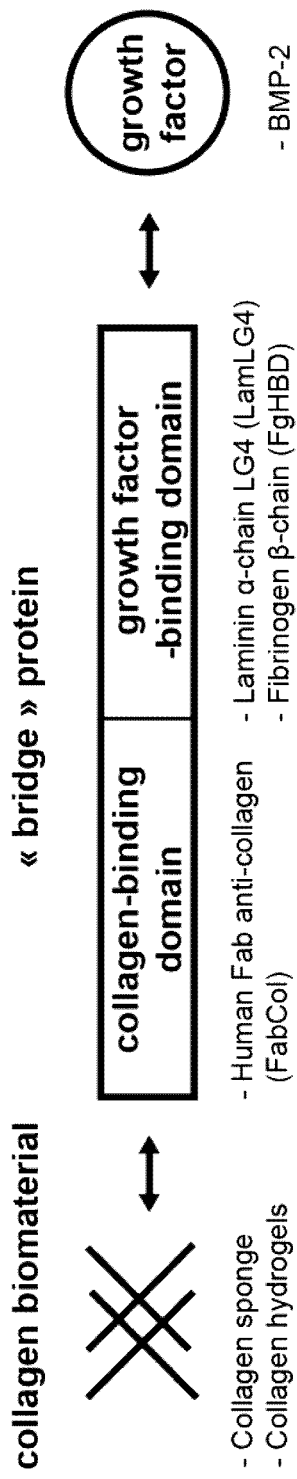

FIG. 12. Bipartite «bridge» proteins composed of a growth factor-binding domain linked to a collagen I-binding domain.

FIGS. 13A-F. Conjugation of a collagen-binding domain FabCol to a growth factor-binding domain FgHBD.

FIGS. 14A-F. Engineering recombinant fusion protein linking a collagen-binding domain FabCol to LamLG4 or FgHBD growth factor-binding domains to sequester rhBMP-2 into collagen biomaterials.

FIGS. 15A-E. vWF-deficient mouse shows impaired wound healing through poor angiogenesis. Full-thickness back-skin wounds were made in wild-type (WT) and vWF-deficient mice. After 5 d, (A) wound closure and (B) granulation tissue area were evaluated by histomorphometry. (means±SEM). Proliferation of (C) CD31+CD45− endothelial cells and (D) SMA+CD45− SMCs assessed by Ki67+ marker determined using flow cytometry (means±SEM). (E) The amounts of VEGF-A in the wounds were quantified by ELISA. *p<0.05, **p<0.01, ANOVA with Tukey's test.

FIGS. 16A-D. Human plasma-derived vWF binds promiscuously to GFs with high affinity. vWF binding to (A) GFs and (B) chemokines were measured by ELISA. A450 nm represents absorbance at 450 nm. Signals from VEGF-A121 served as a baseline, and bovine serum albumin (BSA) served as a negative control (n=4, mean±SD). Affinity (KD values are shown) of vWF against (C) VEGF-A165 and (D) PDGF-BB was measured by SPR. SPR chips were functionalized with vWF (~2000 RU), and VEGF-A165 or PDGF-BB was flowed over the chips at indicated concentrations. Curves represent the specific responses (in resonance units (RU)) to vWF obtained. Experimental curves were fitted with (C) 1:1 Langmuir fit model and (D) heterogeneous ligand-parallel reactions binding. Binding kinetics values [dissociation constants (KD) and rate constants (kon and koff)] determined from the fitted curves are shown.

FIGS. 17A-B. vWF binds to VEGF-A in human serum. (A) ELISA plates were coated with 10 μg/mL anti-human vWF monoclonal antibody and further incubated with human serum. Bound VEGF-A was detected using a specific antibody for VEGF-A (n=3, mean±SD). (B) Human serum was subjected to immunoprecipitation with anti-human vWF monoclonal antibody or anti-human VEGF-A monoclonal antibody. Western blotting was performed with collected proteins using anti-human VEGF-A antibody. Representative image of 3 human serum. Statistical analyses were done using Student's t-test. **p<0.01.

FIGS. 18A-C. The HBD within the A1 domain of vWF mediates GF binding. (A) The location of the A1 domain and HBD within vWF. FIG. 18A discloses SEQ ID NO: 50. (B-C) Affinity of VEGF-A, PlGF, PDGF-BB, FGF-2, or CXCL-12 against (B) recombinant vWF A1 domain protein or (C) vWF A1 HBD peptide. ELISA plates were coated with 10 μg/mL recombinant vWF A1 domain protein or 10 μg/mL vWF A1 HBD peptide and further incubated with a 1 μg/mL VEGF-A, PlGF, PDGF-BB, FGF-2, or CXCL-12 solution. Bound GFs were detected using a specific antibody for each GF (n=4, mean±SD). Statistical analyses were done using ANOVA with Tukey's test or Student's t-test. *p<0.05, **p<0.01.

FIGS. 19A-C. R1341 mutations observed in vWD type 2B patients impaired vWF-GF binding. (A) Binding of VEGF-A165, PDGF-BB, and FGF-2 to vWF A1 HBDs with R1341 substitutions. (n=4, mean±SD). (B) Binding of VEGF-A165, PDGF-BB, and FGF-2 to recombinant human (rh)vWF with R1341Q substitution. (n=4, mean±SD). (C) Binding of VEGF-A165, PDGF-BB, and FGF-2 to vWF in healthy donor or type 2B vWD patient serum (n=3, mean+SD). Statistical comparisons were carried out using (A) ANOVA with Tukey's test compared with BSA control and (B-C) Student's t-test **p<0.01.

FIGS. 20A-F. Delivering GFs within vWF HBD-functionalized fibrin matrices enhance skin wound healing in diabetic mice. (A-B) GF retention in fibrin matrix. Graph showing the cumulative release of (A) VEGF-A165 or (B) PDGF-BB over 5 d (n=4; mean±SEM). Full-thickness back-skin wounds were treated with combined 100 ng of VEGF-A165 and 50 ng of PDGF-BB. Four groups were tested: fibrin only, fibrin functionalized with $\square_2 PI_{1\text{-}8}$-vWF HBD only, fibrin containing GFs only, and fibrin functionalized with $\square_2 PI_{1\text{-}8}$-vWF HBD containing GFs. (C) After 7 d, wound closure and (D) granulation tissue area were evaluated by histomorphometry. (means±SEM, n=11-13 per treatment group). (E-F) 5 d after the wound treatment, (E) the frequency of $CD31^+CD45^-$ endothelial cells within total alive cells and (F) proliferation of $SMA^+CD45^-$ SMC assessed by $Ki67^+$ marker were determined using flow cytometry (means±SEM). *p<0.05, **p<0.01, ANOVA with Tukey's test.

Figure 21:
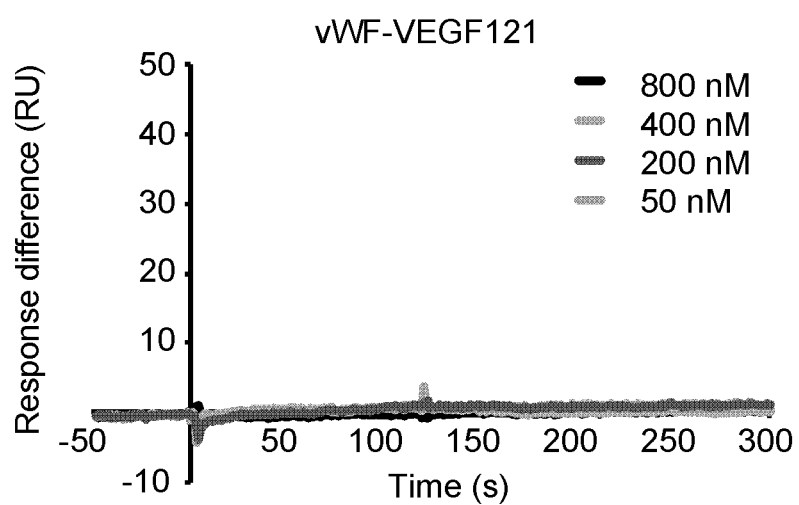

FIG. 21. No binding was observed between VEGF-A121 and vWF. Affinity of VEGF-A121 for vWF, estimated by SPR. SPR chips were functionalized with plasma derived vWF, and VEGF-A121 was flowed over the chips at various concentrations (50-800 nM). Curves represent the responses (in RU) to vWF obtained.

FIGS. 22A-C. Excess heparin inhibits GF binding to vWF. Inhibition of GF binding to vWF by excess heparin. ELISA plates were coated with 10 μg/mL vWF and further incubated with a 1 μg/mL (A) VEGF-A165, (B) PlGF-2, or (C) FGF-2 solution containing 10 μM heparin. Bound GFs were detected using a specific antibody for each GF (n=4, mean±SD).

FIGS. 23A-D. vWF A1 HBD binds to VEGF-A145 and VEGF-A165. (A) Diagram of exon sequence of VEGF-A showing inclusion (+) or exclusion (−) of heparin binding domain exons for the different VEGF-A isoforms. (B-D) Binding of (B) VEGF-A165, (C) VEGF-A145, or (D) VEGF-A121 to vWF domains. ELISA plates were coated with 50 nM vWF domains and further incubated with recombinant human VEGF-A121, VEGF-A145 or VEGF-A165 (1 μg/mL, each). Bound VEGF-A was detected using a specific antibody for VEGF-A (n=4, mean±SD). Statistical comparisons were done using ANOVA with Tukey's test compared with BSA control. **p<0.01.

FIGS. 24A-B. The vWF A1 HBD retains GFs when incorporated into synthetic matrices. Retention of GFs in PEG-based synthetic matrix functionalized with C-terminus Cys added vWF HBD peptide using a Michael addition reaction. The graph shows the cumulative release of (A) FGF-2 or (B) CXCL-12γ over 5 d. (n=3; mean±SEM). All data points for vWF HBD were statistically significant compared to controls without vWF HBD (p<0.01, Student's t-test)

FIGS. 25A-D. Fibroblast attachment and proliferation on the vWF HBD peptide coated plate in vitro. Cell adhesion assays. 3000 cells/well human lung fibroblasts were cultured (A) without or (B) with 5 mM EDTA in FGM-2 culture media. Cells were plated on 1 µg/mL vWF HBD pre-coated non-tissue culture treated plates and incubated for 30 min at 37° C. After plate washes, cell numbers were quantified using a CyQUANT assay (n=4, mean±SD). (C) 1000 cells/well human lung fibroblasts or (D) 1000 cells/well human umbilical vein endothelial cells (HUVEC) were cultured on 1 µg/mL vWF HBD pre-coated 96-well tissue culture plates. Cell numbers were quantified after 72 hrs using a CyQUANT assay (n=4, mean±SD). The signals obtained from non-coated wells are normalized to 1, and relative fold increase of cell numbers were calculated. Statistical comparisons were carried out by Student's t-test. *p<0.05, N.S.=not significant.

DETAILED DESCRIPTION

Lamin and von Willebrand (vWF) peptides that bind certain growth factors are useful in would healing and tissue repair.

Laminins have been reported as crucial molecules for adhesion of various cell types, both in vitro and in vivo, thus serving as a cell scaffold protein. The inventors found that multiple isoforms of laminin promiscuously bind several growth factors (GFs) from the VEGF/PDGF, FGF, BMP, and NT families, in addition to HB-EGF and CXCL12γ, through their heparin binding domains (HBDs). By engineering a fibrin matrix displaying the laminin peptide, the inventors have demonstrated that the laminin peptide linked to fibrin matrix promotes wound closure when applied to skin wounds in the db/db mouse, as a model of delayed wound healing, when applied with VEGF-A165 and PDGF-BB. In addition to showing a GF-modulating function for laminin, an important tissue repair protein, the examples also show that both GF- and cell-binding character promotes tissue repair when incorporated within fibrin matrix, which may be clinically useful. In addition, the inventors have demonstrated that the laminin HBD peptide can be fused or conjugated to collagen-binding domain to allow retention of GFs into collagen-based biomaterials. The inventors showed this art focusing on the sequestration of BMP-2 into collagen hydrogels and sponges for application in bone regeneration.

von Willebrand factor is a large plasma glycoprotein synthesized by endothelial cells and megakaryocytes. It is best known for its role in hemostasis, where it mediates platelet adhesion to the subendothelium at sites of endothelial damage and acts as a carrier to coagulation factor VIII. In patients with von Willebrand disease (vWD), the most common inherited bleeding disorder caused by defects in or deficiency of vWF, blood vessel abnormalities have been identified. In a subset of patients, vascular malformations in the gastrointestinal tract (i.e. angiodysplasia) can cause severe, intractable bleeding. vWF is comprised of a number of subunits, made up of conserved modular domains in the order D1-D2-D'-D3-A1-A2-A3-D4-B1-B2-B3-C1-C2. Mature vWF is formed after proteolysis of the vWF propeptide, i.e. the D1 and D2 domains. The A1 domain contains the binding site for platelet glycoprotein glycoprotein Ibα (GPIbα and also binds heparin and types I and III collagen. This disclosure describes the use of vWF as a growth factor reservoir for the enhancement of angiogenesis and wound healing.

I. GROWTH FACTOR BINDING PEPTIDES AND POLYPEPTIDES

Embodiments of the disclosure relate to laminin peptides and von Willebrand factor peptides that bind to growth factors.

Laminins are major basement membrane extracellular matrix (ECM) proteins for which at least 16 isoforms exist. Five α (LAMA1-5), three β (LAMB1-3), and three γ (LAMC1-3) chains have been identified. Laminin's structure is a heterotrimer comprising an α, a β, and a γ chain that assemble into a cross shape.

A common hallmark of the laminin α chain structure is the presence of five laminin-type G domain (LG) modules arranged at the C-terminus in a tandem array. LG modules consist of 180-200 amino acids, and all the laminin α chains contain five LG domains (LG1-5). The laminin LG modules bind to heparin sulfate, perlecan and fibulin-1, as well as cellular receptors including α6β1, α7β1 and α6β4 integrins and syndecan. The laminin α3, α4, and α5 chains are processed in vivo in tissue through cleavage by proteases such as plasmin and elastase at the linker between the LG3 and LG4 domains.

A. Exemplary Growth Factor Binding Peptides and Polypeptides

In some embodiments, the growth factor binding domain comprises a heparin binding domain (HBD). In some embodiments, the growth factor binding domain is from a laminin polypeptide. In some embodiments, the growth factor binding domain is from a vWF polypeptide. In some embodiments, the growth factor binding domain is not a heparin binding domain and/or does not bind to heparin. In some embodiments, the growth factor binding domain comprises a peptide from LAMA1. In some embodiments, the growth factor binding domain comprises a peptide from LAMA2. In some embodiments, the growth factor binding domain comprises a peptide from LAMA3. In some embodiments, the growth factor binding domain comprises a peptide from LAMA4. In some embodiments, the growth factor binding domain comprises a peptide from LAMA5. In some embodiments, the growth factor binding domain comprises a peptide from LAMB1. In some embodiments, the growth factor binding domain comprises a peptide from LAMB2. In some embodiments, the growth factor binding domain comprises a peptide from LAMB3. In some embodiments, the growth factor binding domain comprises a peptide from LAMB4. In some embodiments, the growth factor binding domain comprises a peptide from LAMC1. In some embodiments, the growth factor binding domain comprises a peptide from LAMC2. In some embodiments, the growth factor binding domain comprises a peptide from LAMC3. Exemplary laminin polypeptides are shown below:

| Human Laminin | Sequence |
|---|---|
| Laminin subunit alpha-1 precursor (LAMA1); SEQ ID NO: 25 | MRGGVLLVLLLCVAAQCRQRGLFPAILNLASNAHISTNATCGEKGPE<br>MFCKLVEHVPGRPVRNPQCRICDGNSANPRERHPISHAIDGTNNWWQ<br>SPSIQNGREYHWVTITLDLRQVFQVAYVIIKAANAPRPGNWILERSLDG<br>TTFSPWQYYAVSDSECLSRYNITPRRGPPTYRADDEVICTSYYSRLVPL<br>EHGEIHTSLINGRPSADDLSPKLLEFTSARYIRLRLQRIRTLNADLMTLS<br>HREPKELDPIVTRRYYYSIKDISVGGMCICYGHASSCPWDETTKKLQC<br>QCEHNTCGESCNRCCPGYHQQPWRPGTVSSGNTCEACNCHNKAKDC<br>YYDESVAKQKKSLNTAGQFRGGGVCINCLQNTMGINCETCIDGYYRP<br>HKVSPYEDEPCRPCNCDPVGSLSSVCIKDDLHSDLHNGKQPGQCPCKE<br>GYTGEKCDRCQLGYKDYPTCVSCGCNPVGSASDEPCTGPCVCKENVE<br>GKACDRCKPGFYNLKEKNPRGCSECFCFGVSDVCSSLSWPVGQVNSM<br>SGWLVTDLISPRKIPSQQDALGGRHQVSINNTAVMQRLAPKYYWAAP<br>EAYLGNKLTAFGGFLKYTVSYDIPVETVDSNLMSHADVIIKGNGLTLS<br>TQAEGLSLQPYEEYLNVVRLVPENFQDFHSKRQ1DRDQLMTVLANVT<br>HLLIRANYNSAKMALYRLESVSLDIASSNAIDLVVAADVEHCECPQGY<br>TGTSCESCLSGYYRVDGILFGGICQPCECHGHAAECNVHGVCIACAHN<br>TTGVHCEQCLPGFYGEPSRGTPGDCQPCACPLTIASNNFSPTCHLNDGD<br>EVVCDWCAPGYSGAWCERCADGYYGNPTVPGESCVPCDCSGNVDPS<br>EAGHCDSVTGECLKCLGNTDGAHCERCADGFYGDAVTAKNCRACEC<br>HVKGSHSAVCHLETGLCDCKPNVTGQQCDQCLHGYYGLDSGHGCRP<br>CNCSVAGSVSDGCTDEGQCHCVPGVAGKRCDRCAHGFYAYQDGSCT<br>PCDCPHTQNTCDPETGECVCPPHTQGVKCEECEDGHWGYDAEVGCQ<br>ACNCSLVGSTHHRCDVVTGHCQCKSKFGGRACDQCSLGYRDFPDCVP<br>CDCDLRGTSGDACNLEQGLCGCVEETGACPCKENVFGPQCNECREGT<br>FALRADNPLGCSPCFCSGLSHLCSELEDYVRTPVTLGSDQPLLRVVSQS<br>NLRGTTEGVYYQAPDFLLDAATVRQHIRAEPFYWRLPQQFQGDQLMA<br>YGGKLKYSVAFYSLDGVGTSNFEPQVLIKGGRIRKQVIYMDAPAPENG<br>VRQEQEVAMRENFWKYFNSVSEKPVTREDFMSVLSDIEYILIKASYGQ<br>GLQQSRISDISMEVGRKAEKLHPEEEVASLLENCVCPPGTVGFSCQDC<br>APGYHRGKLPAGSDRGPRPLVAPCVPCSCNNHSDTCDPNTGKCLNCG<br>DNTAGDHCDVCTSGYYGKVTGSASDCALCACPHSPPASFSPTCVLEG<br>DHDFRCDACLLGYEGKHCERCSSSYYGNPQTPGGSCQKCDCNPHGSV<br>HGDCDRTSGQCVCRLGASGLRCDECEPRHILMETDCVSCDDECVGVL<br>LNDLDEIGDAVLSLNLTGIIPVPYGILSNLENTTKYLQESLLKENMQKD<br>LGKIKLEGVAEETDNLQKKLTRMLASTQKVNRATERIFKESQDLAIAIE<br>RLQMSITEIMEKTTLNQTLDEDFLLPNSTLQNMQQNGTSLLEIMQIRF<br>TQLHQNATLELKAAEDLLSQIQENYQKPLEELEVLKEAASHVLSKHNN<br>ELKAAEALVREAEAKMQESNHLLLMVNANLREFSDKKLHVQEEQNL<br>TSELIVQGRGLIDAAAAQTDAVQDALEHLEDHQDKLLLWSAKIRHHID<br>DLVMHMSQRNAVDLVYRAEDHAAEFQRLADVLYSGLENIRNVSLNA<br>TSAAYVHYNIQSLIEESEELARDAHRTVTETSLLSESLVSNGKAAVQRS<br>SRFLKEGNNLSRKLPGIALELSELRNKTNRFQENAVEITRQTNESLLILR<br>AIPKGIRDKGAKTKELATSASQSAVSTLRDVAGLSQELLNTSASLSRVN<br>TTLRETHQLLQDSTMATLLAGRKVKDVEIQANLLFDRLKPLKMLEEN<br>LSRNLSEIKLLISQARKQAASIKVAVSADRDCIRAYQPQISSTNYNTLTL<br>NVKTQEPDNLLFYLGSSTASDFLAVEMRRGRVAFLWDLGSGSTRLEFP<br>DEPIDDNRWHSIHVAREGNIGSLSVKEMSSNQKSPTKTSKSPGTANVLD<br>VNNSTLMFVGGLGGQIKKSPAVKVTHFKGCLGEAFLNGKSIGLWNYIE<br>REGKCRGCFGSSQNEDPSEHFDGSGYSVVEKSLPATVTQIIMLENTESP<br>NGLLLYLGSYGTKDFLSIELFRGRVKVMTDLGSGPITLLTDRRYNNGT<br>WYKIAFQRNRKQGVLAVIDAYNTSNKETKQGETPGASSDLNRLDKDPI<br>YVGGLPRSRVVRRGVTTKSFVGCIKNLEISRSTFDLLRNSYGVRKGCLL<br>EPIRSVSFLKGGYIELPPKSLSPESEWLVTFATTNSSGIILAALGGDVEKR<br>GDREEAHVPFFSVMLIGGNIEVHVNPGDGTGLRKALLHAPTGTCSDGQ<br>AHSISLVRNRRIITVQLDENNPVEMKLGTLVESRTINVSNLYVGGIPEGE<br>GTSLLTMRRSEHGCIKNLIENLELLDENSAVGHEQVDLDTCWLSERPK<br>LAPDAEDSKLLPEPRAFPEQCVVDAALEYVPGAHQEGLTQNSHEILPEN<br>QSAVRKKLSVELSIRTFASSGLIYYMAHQNQADYAVLQLHGGRLHFM<br>FDLGKGRTKVSHPALLSDGKWHTVKTDYVKRKGFITVDGRESPMVTV<br>VGDGTMLDVEGLFYLGGLPSQYQARKIGNITHSIPACIGDVTVNSKQL<br>DKDSPVSAFTVNRCYAVAQEGTYFDGSGYAALVKEGYKVQSDVNITL<br>EFRTSSQNGVLLGISTAKVDAIGLELVDGKVLFHVNNGAGRITAAYEP<br>KTATVLCDGKWHTLQANKSKHRITLIVDGNAVGAESPHTQSTSVDTN<br>NPIYVGGYPAGVKQKCLRSQTSFRGCLRKLALIKSPQVQSEDESRAFEL<br>HGVFLHSCPGTES |
| laminin subunit alpha-2 isoform a precursor (LAMA2-isoform a); SEQ ID NO: 26 | MPGAAGVLLLLLLSGGLGGVQAQRPQQQRQSQAHQQRGLFPAVLNL<br>ASNALITTNATCGEKGPEMYCKLVEHVPGQPVRNPQCRICNQNSSNPN<br>QRHPITNAIDGKNTWWQSPSIKNGIEYHYVTITLDLQQVFQIAYVIVKA<br>ANSPRPGNWILERSLDDVEYKPWQYHAVTDTECLTYNIYPRTGPPSY<br>AKDDEVICTSFYSKIHPLENGEIHISLINGRPSADDPSPELLEFTSARYIRL<br>RFQRIRTLNADLMMFAHKDPREIDPIVTRRYYYSVKDISVGGMCICYG<br>HARACPLDPATNKSRECECEHNTCGDSCDQCCPGFHQKPWRAGTPLTK<br>TECEACNCHGKAEECYYDENVARRNLSLNIRGKYIGGGVCINCTQNT<br>AGINCETCTDGFFRPKGVSPNYPRPCQPCHCDPIGSLNEVCVKDEKHA<br>RRGLAPGSCHCKTGFGGVSCDRCARGYTGYPDCKACNCSGLGSKNED<br>PCFGPCICKENVEGGDCSRCKSGFFNLQEDNWKGCDECFCSGVSNRCQ<br>SSYWTYGKIQDMSGWYLTDLPGRIRVAPQQDDLSPQQISISNAEARQ |

| Human Laminin | Sequence |
|---|---|
| | ALPHSYYWSAPAPYLGNKLPAVGGQLTFTISYDLEEEEEDTERVLQLM<br>IILEGNDLSISTAQDEVYLHPSEEHTNVLLLKEESFTIHGTHFPVRRKEF<br>MTVLANLKRVLLQITYSFGMDAIFRLSSVNLESAVSYPTDGSIAAAVE<br>VCQCPPGYTGSSCESCWPRHRRVNGTIFGGICEPCQCFGHAESCDDVT<br>GECLNCKDHTGGPYCDKCLPGFYGEPTKGTSEDCQPCACPLNIPSNNF<br>SPTCHLDRSLGLICDGCPVGYTGPRCERCAEGYFGQPSVPGGSCQPCQ<br>CNDNLDFSIPGSCDSLSGSCLICKPGTTGRYCELCADGYFGDAVDAKN<br>CQPCRCNAGGSFSEVCHSQTGQCECRANVQGQRCDKCKAGTFGLQSA<br>RGCVPCNCNSFGSKSFDCEESGQCWCQPGVTGKKCDRCAHGYFNFQE<br>GGCTACECSHLGNNCDPKTGRCICPPNTIGEKCSKCAPNTWGHSITTG<br>CKACNCSTVGSLDFQCNVNTGQCNCHPKFSGAKCTECSRGHWNYPRC<br>NLCDCFLPGTDATTCDSETKKCSCSDQTGQCTCKVNVEGIHCDRCRPG<br>KFGLDAKNPLGCSSCYCFGTTTQCSEAKGLIRTWVTLKAEQTILPLVD<br>EALQHTTTKGIVFQHPEIVAHMDLMREDLHLEPFYWKLPEQFEGKKL<br>MAYGGKLKYAIYFEAREETGFSTYNPQVIIRGGTPTHARIIVRHMAAPL<br>IGQLTRHEIEMTEKEWKYYGDDPRVHRTVTREDFLDILYDIHYILIKAT<br>YGNFMRQSRISEISMEVAEQGRGTTMTPPADLIEKCDCPLGYSGLSCEA<br>CLPGFYRLRSQPGGRTPGPTLGTCVPCQCNGHSSLCDPETSICQNCQHH<br>TAGDFCERCALGYYGIVKGLPNDCQQCACPLISSSNNFSPSCVAEGLD<br>DYRCTACPRGYEGQYCERCAPGYTGSPGNPGGSCQECECDPYGSLPVP<br>CDPVTGFCTCRPGATGRKCDGCKHWAREGWECVFCGDECTGLLLG<br>DLARLEQMVMSINLTGPLPAPYKMLYGLENIVITQELKHLLSPQRAPER<br>LIQLAEGNLNTLVTEMNELLTRATKVTADGEQTGQDAERTNTRAKSL<br>GEFIKELARDAEAVNEKAIKLNETLGTRDEAFERNLEGLQKEIDQMIKE<br>LRRKNLETQKEIAEDELVAAEALLKKVKKLFGESRGENEEMEKDLRE<br>KLADYKNKVDDAWDLLREATDKIREANRLFAVNQKNMTALEKKKEA<br>VESGKRQIENTLKEGNDILDEANRLADEINSIIDYVEDIQTKLPPMSEEL<br>NDKIDDLSQEIKDRKLAEKVSQAESHAAQLNDSSAVLDGILDEAKNISF<br>NATAAFKAYSNIKDYIDEAEKVAKEAKDLAHEATKLATGPRGLLKED<br>AKGCLQKSFRILNEAKKLANDVKENEDHLNGLKTRIENADARNGDLL<br>RTLNDTLGKLSAIPNDTAAKLQAVKDKARQANDTAKDVLAQITELHQ<br>NLDGLKKNYNKLADSVAKTNAVVKDPSKNKIIADADATVKNLEQEA<br>DRLIDKLKPIKELEDNLKKNISEIKELINQARKQANSIKVSVSSGGDCIR<br>TYKPEIKKGSYNNIVVNVKTAVADNLLFYLGSAKFIDFLAIEMRKGKV<br>SFLWDVGSGVGRVEYPDLTIDDSYWYRIVASRTGRNGTISVRALDGPK<br>ASIVPSTHHSTSPPGYTILDVDANAMLFVGGLTGKLKKADAVRVITFT<br>GCMGETYFDNKPIGLWNFREKEGDCKGCTVSPQVEDSEGTIQFDGEG<br>YALVSRPIRWYPNISTVMFKFRTFSSSALLMYLATRDLRDFMSVELTD<br>GHIKVSYDLGSGMASVVSNQNHNDGKWKSFTLSRIQKQANISIVDIDT<br>NQEENIATSSSGNNFGLDLKADDKIYFGGLPTLRNLSMKARPEVNLKK<br>YSGCLKDIEISRTPYNILSSPDYVGVTKGCSLENVYTVSFPKPGFVELSP<br>VPIDVGTEINLSFSTKNESGIILLGSGGTPAPPRRKRRQTGQAYYVILLN<br>RGRLEVHLSTGARTMRKIVIRPEPNLFHDGREHSVHVERTRGIFTVQV<br>DENRRYMQNLTVEQPIEVKKLFVGGAPPEFQPSPLRNIPPFEGCIWNLV<br>INSVPMDFARPVSFKNADIGRCAHQKLREDEDGAAPAEIVIQPEPVPTP<br>AFPTPTPVLTHGPCAAESEPALLIGSKQFGLSRNSHIAIAFDDTKVKNRL<br>TIELEVRTEAESGLLFYMARINHADFATVQLRNGLPYFSYDLGSGDTH<br>TMIPTKINDGQWHKIKIMRSKQEGILYVDGASNRTISPKKADILDVVG<br>MLYVGGLPINYTTRRIGPVTYSIDGCVRNLHMAEAPADLEQPTSSFHV<br>GTCFANAQRGTYFDGTGFAKAVGGFKVGLDLLVEFEFRTTTTTGVLL<br>GISSQKMDGMGIEMIDEKLMFHVDNGAGRFTAVYDAGVPGHLCDGQ<br>WHKVTANKIKHRIELTVDGNQVEAQSPNPASTSADTNDPVFVGGFPD<br>DLKQFGLTTSIPFRGCIRSLKLTKGTGKPLEVNFAKALELRGVQPVSCP<br>AN |
| laminin<br>subunit<br>alpha-2<br>isoform b<br>precursor<br>(LAMA2-<br>isoform b);<br>SEQ ID<br>NO: 27 | MPGAAGVLLLLLLSGGLGGVQAQRPQQQRQSQAHQQRGLFPAVLNL<br>ASNALITTNATCGEKGPEMYCKLVEHVPGQPVRNPQCRICNQNSSNPN<br>QRHPITNAIDGKNTWWQSPSIKNGIEYHYVTITLDLQQVFQIAYVIVKA<br>ANSPRPGNWILERSLDDVEYKPWQYHAVTDTECLTLYNIYPRTGPPSY<br>AKDDEVICTSFYSKIHPLENGEIHISLINGRPSADDPSPELLEFTSARYIRL<br>RFQRIRTLNADLMMFAHKDPREIDPIVTRRYYYSVKDISVGGMCICYG<br>HARACPLDPATNKSRCECEHNTCGDSCDQCCPGFHQKPWRAGTFLTK<br>TECEACNCHGKAEECYYDENVARRNLSLNIRGKYIGGGVCINCTQNT<br>AGINCETCTDGFFRPKGVSPNYPRPCQPCHCDPIGSLNEVCVKDEKHA<br>RRGLAPGSCHCKTGFGGVSCDRCARGYTGYPDCKACNCSGLGSKNED<br>PCFGPCICKENVEGGDCSRCKSGFFNLQEDNWKGCDECFCSGVSNRCQ<br>SSYWTYGKIQDMSGWYLTDLPGRIRVAPQQDDLDSPQQISISNAEARQ<br>ALPHSYYWSAPAPYLGNKLPAVGGQLTFTISYDLEEEEEDTERVLQLM<br>IILEGNDLSISTAQDEVYLHPSEEHTNVLLLKEESFTIHGTHFPVRRKEF<br>MTVLANLKRVLLQITYSFGMDAIFRLSSVNLESAVSYPTDGSIAAAVE<br>VCQCPPGYTGSSCESCWPRHRRVNGTIFGGICEPCQCFGHAESCDDVT<br>GECLNCKDHTGGPYCDKCLPGFYGEPTKGTSEDCQPCACPLNIPSNNF<br>SPTCHLDRSLGLICDGCPVGYTGPRCERCAEGYFGQPSVPGGSCQPCQ<br>CNDNLDFSIPGSCDSLSGSCLICKPGTTGRYCELCADGYFGDAVDAKN<br>CQPCRCNAGGSFSEVCHSQTGQCECRANVQGQRCDKCKAGTFGLQSA<br>RGCVPCNCNSFGSKSFDCEESGQCWCQPGVTGKKCDRCAHGYFNFQE |

| Human Laminin | Sequence |
|---|---|
| | GGCTACECSHLGNNCDPKTGRCICPPNTIGEKCSKCAPNTWGHSITTG CKACNCSTVGSLDFQCNVNTGQCNCHPKFSGAKCTECSRGHWNYPRC NLCDCFLPGTDATTCDSETKKCSCSDQTGQCTCKVNVEGIHCDRCRPG KFGLDAKNPLGCSSCYCFGTTTQCSEAKGLIRTWVTLKAEQTILPLVD EALQHTTTKGIVFQHPEIVAHMDLMREDLHLEPFYWKLPEQFEGKKL MAYGGKLKYAIYFEAREETGFSTYNPQVIIRGGTPTHARIIVRHMAAPL IGQLTRHEIEMTEKEWKYYGDDPRVHRTVTREDFLDILYDIHYILIKAT YGNFMRQSRISEISMEVAEQGRGTTMTPPADLIEKCDCPLGYSGLSCEA CLPGFYRLSQPGGRTPGPTLGTCVPCQCNGHSSLCDPETSICQNCQHH TAGDFCERCALGYYGIVKGLPNDCQQCACPLISSSNNFSPSCVAEGLD DYRCTACPRGYEGQYCERCAPGYTGSPGNPGGSCQECECDPYGSLPVP CDPVTGFCTCRPGATGRKCDGCKHWAREGWECVFCGDECTGLLLG DLARLEQMVMSINLTGPLPAPYKMLYGLENMTQELKHLLSPQRAPER LIQLAEGNLNTLVTEMNELLTRATKVTADGEQTGQDAERTNTRAKSL GEFIKELARDAEAVNEKAIKLNETLGTRDEAFERNLEGLQKEIDQMIKE LRRKNLETQKEIAEDELVAAEALLKKVKKLFGESRGENEEMEKDLRE KLADYKNKVDDAWDLLREATDKIREANRLFAVNQKNMTALEKKKEA VESGKRQIENTLKEGNDILDEANRLADEINSIIDYVEDIQTKLPPMSEEL NDKIDDLSQEIKDRKLAEKVSQAESHAAQLNDSSAVLDGILDEAKNISF NATAAFKAYSNIKDYIDEAEKVAKEAKDLAHEATKLATGPRGLLKED AKGCLQKSFRILNEAKKLANDVKENEDHLNGLKTRIENADARNGDLL RTLNDTLGKLSAIPNDTAAKLQAVKDKARQANDTAKDVLAQITELHQ NLDGLKKNYNKLADSVAKTNAVVKDPSKNKIIADADATVKNLEQEA DRLIDKLKPIKELEDNLKKNISEIKELINQARKQANSIKVSVSSGGDCIR TYKPEIKKGSYNNIVVNVKTAVADNLLFYLGSAKFIDFLAIEMRKGKV SFLWDVGSGVGRVEYPDLTIDDSYWYRIVASRTGRNGTISVRALDGPK ASIVPSTHHSTSPPGYTILDVDANAMLFVGGLTGKLKKADAVRVITFT GCMGETYFDNKPIGLWNFREKEGDCKGCTVSPQVIEDSEGTIQFDGEG YALVSRPIRWYPNISTVMEKERTFSSSALLMYLATRDLRDFMSVELTD GHIKVSYDLGSGMASVVSNQNHNDGKWKSFTLSRIQKQANISIVDIDT NQEENIATSSSGNNFGLDLKADDKIYFGGLPTLRNLRPEVNLKKYSGC LKDIEISRTPYNILSSPDYVGVTKGCSLENVYTVSFPKPGEVELSPVID VGTEINLSFSTKNESGIILLGSGGTPAPPRRKRRQTGQAYYVILLNRGRL EVHLSTGARTMRKIVIRPEPNLFHDGREHSVHVERTRGIFTVQVDENR RYMQNLTVEQPIEVKKLFVGGAPPEFQPSPLRNIPPFEGCIWNLVINSVP MDFARPVSFKNADIGRCAHQKLREDEDGAAPAEIVIQPEPVPTPAFPTP TPVLTHGPCAAESEPALLIGSKQFGLSRNSHIAIAFDDTKVKNRLTIELE VRTEAESGLLFYMARINHADFATVQLRNGLPYFSYDLGSGDTHTMIPT KINDGQWHKIKIMRSKQEGILYVDGASNRTISPKKADILDVVGMLYVG GLPINYTTRRIGPVTYSIDGCVRNLHMAEAPADLEQPTSSFHVGTCFAN AQRGTYFDGTGFAKAVGGEKVGLDLLVEFEERTTTTTGVLLGISSQKM DGMGIEMIDEKLMFHVDNGAGRFTAVYDAGVPGHLCDGQWHKVTA NKIKHRIELTVDGNQVEAQSPNPASTSADTNDPVFVGGFPDDLKQFGL TTSIPERGCIRSLKLTKGTGKPLEVNFAKALELRGVQPVSCPAN |
| laminin subunit alpha-3 isoform 1 precursor (LAMA3-isoform 1); SEQ ID NO: 28 | MAAAARPRGRALGPVLPPTPLLLLVLRVLPACGATARDPGAAAGLSL HPTYFNLAEAARIWATATCGERGPGEGRPQPELYCKLVGGPTAPGSGH TIQGQFCDYCNSEDPRKAHPVTNAIDGSERWWQSPPLSSGTQYNRVNL TLDLGQLFHVAYILIKFANSPRPDLWVLERSVDFGSTYSPWQYFAHSK VDCLKEFGREANMAVTRDDDVLCVTEYSRIVPLENGEVVVSLINGRPG AKNFTFSHTLREFTKATNIRLRFLRTNTLLGHLISKAQRDPTVTRRYYY SIKDISIGGQCVCNGHAEVCNINNPEKLFRCECQHHTCGETCDRCCTGY NQRRWRPAAWEQSHECEACNCHGHASNCYYDPDVERQQASLNTQGI YAGGGVCINCQHNTAGVNCEQCAKGYYRPYGVPVDAPDGCIPCSCDP EHADGCEQGSGRCHCKPNFHGDNCEKCAIGYYNFPPFCLRIPIFPVSTPS SEDPVAGDIKGCDCNLEGVLPEICDAHGRCLCRPGVEGPRCDTCRSGF YSFPICQACWCSALGSYQMPCSSVTGQCECRPGVTGQRCDRCLSGAY DFPHCQGSSSACDPAGTINSNLGYCQCKLHVEGPTCSRCKLLYWNLD KENPSGCSECKCHKAGTVSGTGECRQGDGDCHCKSHVGGDSCDTCED GYFALEKSNYFGCQGCQCDIGGALSSMCSGPSGVCQCREHVGKVCQ RPENNYYFPDLHHMKYEIEDGSTPNGRDLRFGFDPLAFPEFSWRGYAQ MTSVQNDVRITLNVGKSSGSLFRVILRYVNPGTEAVSGHITIYPSWGAA QSKEIIFLPSKEPAFVTVPGNGFADPFSITPGIWVACIKAEGVLLDYLVL LPRDYYEASVLQLPVTEPCAYAGPPQENCLLYQHLPVTRFPCTLACEA RHFLLDGEPRPVAVRQPTPAHPVMVDLSGREVELHLRLRIPQVGHYVV VVEYSTEAAQLFVVDVNVKSSGSVLAGQVNIYSCNYSVLCRSAVIDH MSRIAMYELLADADIQLKGHMARFLLHQVCIIPIEEFSAEYVRPQVHCI ASYGRFVNQSATCVSLAHETPPTALILDVLSGRPFPHLPQQSSPSVDVL PGVTLKAPQNQVTLRGRVPHLGRYVFVIHFYQAAHPTFPAQVSVDGG WPRAGSFHASFCPHVLGCRDQVIAEGQIEFDISEPEVAATVKVPEGKSL VLVRVLVVPAENYDYQILHKKSMDKSLEFITNCGKNSFYLDPQTASRF CKNSARSLVAFYHKGALPCEHPTGATGPHCSPEGGQCPCQPNVIGRQ CTRCATGHYGPPRCKPCSCGRRLCEEMTGQCRCPPRTVRPQCECETH SFSFHPMAGCEGCNCSRRGTIEAAMPECDRDSGQCRCKPRITGRQCDR CASGFYRFPECVPCNCNRDGTEPGVCDPGTGACLCKENVEGTECNVC REGSFHLDPANLKGCTSCFCFGVNNQCHSSHKRRTKFVDMLGWHLET |

| Human Laminin | Sequence |
|---|---|
| | ADRVDIPVSFNPGSNSMVADLQELPATIHSASWVAPTSYLGDKVSSYG<br>GYLTYQAKSFGLPGDMVLLEKKPDVQLTGQHMSIIYEETNTPRPDRLH<br>HGRVHVVEGNFRHASSRAPVSREELMTVLSRLADVRIQGLYFTETQRL<br>TLSEVGLEEASDTGSGRIALAVEICACPPAYAGDSCQGCSPGYYRDHK<br>GLYTGRCVPCNCNGHSNQCQDGSGICVNCQHNTAGEHCERCQEGYY<br>GNAVHGSCRACPCPHTNSFATGCVVNGGDVRCSCKAGYTGTQCERC<br>APGYFGNPQKFGGSCQPCSCNSNGQLGSCHPLTGDCINQEPKDSSPAE<br>ECDDCDSCVMTLLNDLATMGEQLRLVKSQLQGLSASAGLLEQMRHM<br>ETQAKDLRNQLLNYRSAISNHGSKIEGLERELTDLNQEFETLQEKAQV<br>NSRKAQTLNNNVNRATQSAKELDVKIKNVIRNVHILLKQISGTDGEGN<br>NVPSGDFSREWAEAQRMMRELRNRNFGKHLREAEADKRESQLLLNRI<br>RTWQKTHQGENNGLANSIRDSLNEYEAKLSDLRARLQEAAAQAKQA<br>NGLNQENERALGAIQRQVKEINSLQSDFTKYLTTADSSLLQTNIALQL<br>MEKSQKEYEKLAASLNEARQELSDKVRELSRSAGKTSLVEEAEKHAR<br>SLQELAKQLEEIKRNASGDELVRCAVDAATAYENILNAIKAAEDAANR<br>AASASESALQTVIKEDLPRKAKTLSSNSDKLLNEAKMTQKKLKQEVSP<br>ALNNLQQTLNIVTVQKEVIDTNLTTLRDGLHGIQRGDIDAMISSAKSM<br>VRKANDITDEVLDGLNPIQTDVERIKDTYGRTQNEDFKKALTDADNSV<br>NKLTNKLPDLWRKIESINQQLLPLGNISDNMDRIRELIQQARDAASKVA<br>VPMRFNGKSGVEVRLPNDLEDLKGYTSLSLFLQRPNSRENGGTENMF<br>VMYLGNKDASRDYIGMAVVDGQLTCVYNLGDREAELQVDQILTKSE<br>TKEAVMDRVKFQRIYQFARLNYTKGATSSKPETPGVYDMDGRNSNTL<br>LNLDPENVFYVGGYPPDFKLPSRLSFPPYKGCIELDDLNENVLSLYNF<br>KKTFNLNTTEVEPCRRRKEESDKNYFEGTGYARVPTQPHAPIPTFGQTI<br>QTTVDRGLLFFAENGDRFISLNIEDGKLMVRYKLNSELPKERGVGDAI<br>NNGRDHSIQIKIGKLQKRMWINVDVQNTIIDGEVFDFSTYYLGGIPIAIR<br>ERFNISTPAFRGCMKNLKKTSGVVRLNDTVGVTKKCSEDWKLVRSAS<br>FSRGGQLSFTDLGLPPTDHLQASFGFQTFQPSGILLDHQTWTRNLQVTL<br>EDGYIELSTSDSGGPIFKSPQTYMDGLLHYVSVISDNSGLRLLIDDQLLR<br>NSKRLKHISSSRQSLRLGGSNFEGCISNVFVQRLSLSPEVLDLTSNSLKR<br>DVSLGGCSLNKPPFLMLLKGSTRFNKTKTFRINQLLQDTPVASPRSVK<br>VWQDACSPLPKTQANHGALQFGDIPTSHLLFKLPQELLKPRSQFAVDM<br>QTTSSRGLVFHTGTKNSFMALYLSKGRLVFALGTDGKKLRIKSKEKCN<br>DGKWHTVVFGHDGEKGRLVVDGLRAREGSLPGNSTISIRAPVYLGSPP<br>SGKPKSLPTNSFVGCLKNFQLDSKPLYTPSSSFGVSSCLGGPLEKGIYFS<br>EEGGHVVLAHSVLLGPEFKLVFSIRPRSLTGILIHIGSQPGKHLCVYLEA<br>GKVTASMDSGAGGTSTSVTPKQSLCDGQWHSVAVTIKQHILHLELDT<br>DSSYTAGQIPFPPASTQEPLHLGGAPANLTTLRIPVWKSFFGCLRNIHV<br>NHIPVPVTEALEVQGPVSLNGCPDQ |
| laminin<br>subunit<br>alpha-3<br>isoform 2<br>precursor<br>(LAMA3-<br>isoform 2);<br>SEQ ID<br>NO: 29 | MPPAVRRSACSMGWLWIFGAALGQCLGYSSQQQRVPFLQPPGQSQLQ<br>ASYVEFRPSQGCSPGYYRDHKGLYTGRCVPCNCNGHSNQCQDGSGIC<br>VNCQHNTAGEHCERCQEGYYGNAVHGSCRACPCPHTNSFATGCVVN<br>GGDVRCSCKAGYTGTQCERCAPGYFGNPQKFGGSCQPCSCNSNGQLG<br>SCHPLTGDCINQEPKDSSPAEECDDCDSCVMTLLNDLATMGEQLRLVK<br>SQLQGLSASAGLLEQMRHMETQAKDLRNQLLNYRSAISNHGSKIEGLE<br>RELTDLNQEFETLQEKAQVNSRKAQTLNNNVNRATQSAKELDVKIKN<br>VIRNVHILLKQISGTDGEGNNVPSGDFSREWAEAQRMMRELRNRNFG<br>KHLREAEADKRESQLLLNRIRTWQKTHQGENNGLANSIRDSLNEYEA<br>KLSDLRARLQEAAAQAKQANGLNQENERALGAIQRQVKEINSLQSDF<br>TKYLTTADSSLLQTNIALQLMEKSQKEYEKLAASLNEARQELSDKVRE<br>LSRSAGKTSLVEEAEKHARSLQELAKQLEEIKRNASGDELVRCAVDAA<br>TAYENILNAIKAAEDAANRAASASESALQTVIKEDLPRKAKTLSSNSD<br>KLLNEAKMTQKKLKQEVSPALNNLQQTLNIVTVQKEVIDTNLTTLRD<br>GLHGIQRGDIDANTISSAKSMVRKANDITDEVLDGLNPIQTDVERIKDTY<br>GRTQNEDFKKALTDADNSVNKLTNKLPDLWRKIESINQQLLPLGNISD<br>NMDRIRELIQQARDAASKVAVPMRFNGKSGVEVRLPNDLEDLKGYTS<br>LSLFLQRPNSRENGGTENMFVMYLGNKDASRDYIGMAVVDGQLTCV<br>YNLGDREAELQVDQILTKSETKEAVMDRVKFQRIYQFARLNYTKGAT<br>SSKPETPGVYDMDGRNSNTLLNLDPENVFYVGGYPPDFKLPSRLSFP<br>PYKGCIELDDLNENVLSLYNFKKTFNLNTTEVEPCRRRKEESDKNYFE<br>GTGYARVPTQPHAPIPTFGQTIQTTVDRGLLFFAENGDRFISLNIEDGKL<br>MVRYKLNSELPKERGVGDAINNGRDHSIQIKIGKLQKRMWINVDVQN<br>TIIDGEVFDFSTYYLGGIPIAIRERFNISTPAFRGCMKNLKKTSGVVRLN<br>DTVGVTKKCSEDWKLVRSASFSRGGQLSFTDLGLPPTDHLQASFGFQT<br>FQPSGILLDHQTWTRNLQVTLEDGYIELSTSDSGGPIFKSPQTYMDGLL<br>HYVSVISDNSGLRLLIDDQLLRNSKRLKHISSSRQSLRLGGSNFEGCISN<br>VFVQRLSLSPEVLDLTSNSLKRDVSLGGCSLNKPPFLMLLKGSTRFNKT<br>KTFRINQLLQDTPVASPRSVKVWQDACSPLPKTQANHGALQFGDIPTS<br>HLLFKLPQELLKPRSQFAVDMQTTSSRGLVFHTGTKNSFMALYLSKGR<br>LVFALGTDGKKLRIKSKEKCNDGKWHTVVFGHDGEKGRLVVDGLRA<br>REGSLPGNSTISIRAPVYLGSPPSGKPKSLPTNSFVGCLKNFQLDSKPLY<br>TPSSSFGVSSCLGGPLEKGIYFSEEGGHVVLAHSVLLGPEFKLVFSIRPR<br>SLTGILIHIGSQPGKHLCVYLEAGKVTASMDSGAGGTSTSVTPKQSLCD<br>GQWHSVAVTIKQHILHLELDTDSSYTAGQIPFPPASTQEPLHLGGAPAN<br>LTTLRIPVWKSFFGCLRNIHVNHIPVPVTEALEVQGPVSLNGCPDQ |

| Human Laminin | Sequence |
|---|---|
| laminin subunit alpha-3 isoform 3 precursor (LAMA3-isoform 3); SEQ ID NO: 30 | MAAAARPRGRALGPVLPPTPLLLLVLRVLPACGATARDPGAAAGLSL<br>HPTYFNLAEAARIWATATCGERGPGEGRPQPELYCKLVGGPTAPGSGH<br>TIQGQPFCDYCNSEDPRKAHPVTNAIDGSERWWQSPPLSSGTQYNRVNL<br>TLDLGQLFHVAYILIKFANSPRPDLWVLERSVDFGSTYSPWQYFAHSK<br>VDCLKEFGREANMAVTRDDDVLCVTEYSRIVPLENGEVVVSLINGRPG<br>AKNFTFSHTLREFTKATNIRLRFLRTNTLLGHLISKAQRDPTVTRRYYY<br>SIKDISIGGQCVCNGHAEVCNINNPEKLFRCECQHHTCGETCDRCCTGY<br>NQRRWRPAAWEQSHECEACNCHGHASNCYYDPDVERQQASLNTQGI<br>YAGGGVCINCQHNTAGVNCEQCAKGYYRPYGVPVDAPDGCIPCSCDP<br>EHADGCEQGSGRCHCKPNFHGDNCEKCAIGYYNFPFCLRIPIFPVSTPS<br>SEDPVAGDIKGCDCNLEGVLPEICDAHGRCLCRPGVEGPRCDTCRSGF<br>YSFPICQACWCSALGSYQMPCSSVTGQCECRPGVTGQRCDRCLSGAY<br>DFPHCQGSSSACDPAGTINSNLGYCQCKLHVEGPTCSRCKLLYWNLD<br>KENPSGCSECKCHKAGTVSGTGECRQGDGDCHCKSHVGGDSCDTCED<br>GYFALEKSNYFGCQGCQCDIGGALSSMCSGPSGVCQCREHVVGKVCQ<br>RPENNYYFPDLHHMKYEIEDGSTPNGRDLRFGFDPLAFPEFSWRGYAQ<br>MTSVQNDVRITLNVGKSSGSLFRVILRYVNPGTEAVSGHITIYPSWGAA<br>QSKEIIFLPSKEPAFVTVPGNGFADPFSITPGIWVACIKAEGVLLDYLVL<br>LPRDYYEASVLQLPVTEPCAYAGPPQENCLLYQHLPVTRFPCTLACEA<br>RHFLLDGEPRPVAVRQPTPAHPVMVDLSGREVELHLRLRIPQVGHYVV<br>VVEYSTEAAQLFVVDVNVKSSGSVLAGQVNIYSCNYSVLCRSAVIDH<br>MSRIAMYELLADADIQLKGHMARFLLHQVCIIPIEEFSAEYVRPQVHCI<br>ASYGRFVNQSATCVSLAHETPPTALILDVLSGRPFPHLPQQSSPSVDVL<br>PGVTLKAPQNQVTLRGRVPHLGRYVFVIHFYQAAHPTFPAQVSVDGG<br>WPRAGSFHASFCPHVLGCRDQVIAEGQIEFDISEPEVAATVKVPEGKSL<br>VLVRVLVVPAENYDYQILHKKSMDKSLEFITNCGKNSFYLDPQTASRF<br>CKNSARSLVAFYHKGALPCECHPTGATGPHCSPEGGQCPCQPNVIGRQ<br>CTRCATGHYGFPRCKPCSCGRRLCEEMTGQCRCPPRTVRPQCEVCETH<br>SFSFHPMAGCEGCNCSRRGTIEAAMPECDRDSGCRCKPRITGRQCDR<br>CASGFYRFPECVPCNCNRDGTEPGVCDPGTGACLCKENVEGTECNVC<br>REGSFHLDPANLKGCTSCFCFGVNNQCHSSHKRRTKFVDMLGWHLET<br>ADRVDIPVSFNPGSNSMVADLQELPATIHSASWVAPTSYLGDKVSSYG<br>GYLTYQAKSFGLPGDMVLLEKKPDVQLTGQHMSIIYEETNTPRPDRLH<br>HGRVHVVEGNFRHASSRAPVSREELMTVLSRLADVRIQGLYFTETQRL<br>TLSEVGLEEASDTGSGRIALAVEICACPPAYAGDSCQGCSPGYYRDHK<br>GLYTGRCVPCNCNGHSNQCQDGSGICVNCQHNTAGEHCERCQEGYY<br>GNAVHGSCRACPCPHTNSFATGCVVNGGDVRCSCKAGYTGTQCERC<br>APGYFGNPQKFGGSCQPCSCNSNGQLGSCHPLTGDCINQEPKDSSPAE<br>ECDDCDSCVMTLLNDLATMGEQLRLVKSQLQGLSASAGLLEQMRHM<br>ETQAKDLRNQLLNYRSAISNHGSKIEGLERELTDLNQEFETLQEKAQV<br>NSRKAQTLNNNVNRATQSAKELDVKIKNVIRNVHMLNRIRTWQKTHQ<br>GENNGLANSIRDSLNEYEAKLSDLRARLQEAAAQAKQANGLNQENER<br>ALGAIQRQVKEINSLQSDFTKYLTTADSSLLQTNIALQLMEKSQKEYEK<br>LAASLNEARQELSDKVRELSRSAGKTSLVEEAEKHARSLQELAKQLEE<br>IKRNASGDELVRCAVDAATAYENILNAIKAAEDAANRAASASESALQT<br>VIKEDLPRKAKTLSSNSDKLLNEAKMTQKKLKQEVSPALNNLQQTLNI<br>VTVQKEVIDTNLTTLRDGLHGIQRGDIDAMISSAKSMVRKANDITDEV<br>LDGLNPIQTDVERIKDTYGRTQNEDFKKALTDADNSVNKLTNKLPDL<br>WRKIESINQQLLPLGNISDNMDRIRELIQQARDAASKVAVPMRENGKS<br>GVEVRLPNDLEDLKGYTSLSLFLQRPNSRENGGTENMFVMYLGNKDA<br>SRDYIGMAVVDGQLTCVYNLGDREAELQVDQILTKSETKEAVMDRV<br>KFQRIYQFARLNYTKGATSSKPETPGVYDMDGRNSNTLLNLDPENVVF<br>YVGGYPPDFKLPSRLSFPPYKGCIELDDLNENVLSLYNFKKTFNLNTTE<br>VEPCRRRKEESDKNYFEGTGYARVPTQPHAPIPTFGQTIQTTVDRGLLF<br>FAENGDRFISLNIEDGKLMVRYKLNSELPKERGVGDAINNGRDHSIQIK<br>IGKLQKRMWINVDVQNTIIDGEVEDFSTYYLGGIPIAIRERFNISTPAFR<br>GCMKNLKKTSGVVRLNDTVGVTKKCSEDWKLVRSASFSRGGQLSFT<br>DLGLPPTDHLQASFGFQTFQPSGILLDHQTWTRNLQVTLEDGYIELSTS<br>DSGGPIFKSPQTYMDGLLHYVSVISDNSGLRLLIDDQLLRNSKRLKHIS<br>SSRQSLRLGGSNFEGCISNVFVQRLSLSPEVLDLTSNSLKRDVSLGGCS<br>LNKPPFLMLLKGSTRFNKTKTFRINQLLQDTPVASPRSVKVWQDACSP<br>LPKTQANHGALQFGDIPTSHLLFKLPQELLKPRSQFAVDMQTTSSRGL<br>VFHTGTKNSFMALYLSKGRLVFALGTDGKKLRIKSKEKCNDGKWHTV<br>VFGHDGEKGRLVVDGLRAREGSLPGNSTISIRAPVYLGSPPSGKPKSLP<br>TNSFVGCLKNFQLDSKPLYTPSSSFGVSSCLGGPLEKGIYFSEEGGHVV<br>LAHSVLLGPEFKLVFSIRPRSLTGILIHIGSQPGKHLCVYLEAGKVTASM<br>DSGAGGTSTSVTPKQSLCDGQWHSVAVTIKQHILHLELDTDSSYTAGQ<br>IPFPPASTQEPLHLGGAPANLTTRIPVWKSFFGCLRNIHVNHIPVPVTE<br>ALEVQGPVSLNGCPDQ |
| laminin subunit alpha-3 isoform 4 precursor | MPPAVRRSACSMGWLWIFGAALGQCLGYSSQQQRVPFLQPPGQSQLQ<br>ASYVEFRPSQGCSPGYYRDHKGLYTGRCVPCNCNGHSNQCQDGSGIC<br>VNCQHNTAGEHCERCQEGYYGNAVHGSCRACPCPHTNSFATGCVVN<br>GGDVRCSCKAGYTGTQCERCAPGYFGNPQKFGGSCQPCSCNSNGQLG<br>SCHPLTGDCINQEPKDSSPAEECDDCDSCVMTLLNDLATMGEQLRLVK |

| Human Laminin | Sequence |
|---|---|
| (LAMA3-isoform 4); SEQ ID NO: 31 | SQLQGLSASAGLLEQMRHMETQAKDLRNQLLNYRSAISNHGSKIEGLE RELTDLNQEFETLQEKAQVNSRKAQTLNNNVNRATQSAKELDVKIKN VIRNVHMLNRIRTWQKTHQGENNGLANSIRDSLNEYEAKLSDLRARL QEAAAQAKQANGLNQENERALGAIQRQVKEINSLQSDFTKYLTTADS SLLQTNIALQLMEKSQKEYEKLAASLNEARQELSDKVRELSRSAGKTS LVEEAEKHARSLQELAKQLEEIKRNASGDELVRCAVDAATAYENILNA IKAAEDAANRAASASESALQTVIKEDLPRKAKTLSSNSDKLLNEAKMT QKKLKQEVSPALNNLQQTLNIVTVQKEVIDTNLTTLRDGLHGIQRGDI DAMISSAKSMVRKANDITDEVLDGLNPIQTDVERIKDTYGRTQNEDFK KALTDADNSVNKLTNKLPDLWRKIESINQQLLPLGNISDNMDRIRELIQ QARDAASKVAVPMRFNGKSGVEVRLPNDLEDLKGYTSLSLFLQRPNS RENGGTENNIFVMYLGNKDASRDYIGMAVVDGQLTCVYNLGDREAEL QVDQILTKSETKEAVMDRVKFQRIYQFARLNYTKGATSSKPETPGVYD MDGRNSNTLLNLDPENVVFYVGGYPPDFKLPSRLSFPPYKGCIELDDL NENVLSLYNFKKTFNLNTTEVEPCRRRKEESDKNYFEGTGYARVPTQP HAPIPTFGQTIQTTVDRGLLFFAENGDRFISLNIEDGKLMVRYKLNSELP KERGVGDAINNGRDHSIQIKIGKLQKRMWINVDVQNTIIDGEVFDFSTY YLGGIPIAIRERFNISTPAFRGCMKNLKKTSGVVRLNDTVGVTKKCSED WKLVRSASFSRGGQLSFTDLGLPPTDHLQASFGFQTFQPSGILLDHQT WTRNLQVTLEDGYIELSTSDSGGPIFKSPQTYMDGLLHYVSVISDNSGL RLLIDDQLLRNSKRLKHISSSRQSLRLGGSNFEGCISNVFVQRLSLSPEV LDLTSNSLKRDVSLGGCSLNKPPFLMLLKGSTRFNKTKTFRINQLLQDT PVASPRSVKVWQDACSPLPKTQANHGALQFGDIPTSHLLFKLPQELLK PRSQFAVDMQTTSSRGLVFHTGTKNSFMALYLSKGRLVFALGTDGKK LRIKSKEKCNDGKWHTVVFGHDGEKGRLVVDGLRAREGSLPGNSTISI RAPVYLGSPPSGKPKSLPTNSFVGCLKNFQLDSKPLYTPSSSFGVSSCL GGPLEKGIYFSEEGGHVVLAHSVLLGPEFKLVFSIRPRSLTGILIHIGSQP GKHLCVYLEAGKVTASMDSGAGGTSTSVTPKQSLCDGQWHSVAVTIK QHILHLELDTDSSYTAGQIPFPPASTQEPLHLGGAPANLTTLRIPVWKSF FGCLRNIFIVNHIPVPVTEALEVQGPVSLNGCPDQ |
| laminin subunit alpha-3 isoform 5 precursor (LAMA3-isoform 5); SEQ ID NO: 32 | MAAAARPRGRALGPVLPPTPLLLLVLRVLPACGATARDPGAAAGLSL HPTYFNLAEAARIWATATCGERGPGEGRPQPELYCKLVGGPTAPGSGH TIQGQFCDYCNSEDPRKAHPVTNAIDGSERWWQSPPLSSGTQYNRVNL TLDLGQLFHVAYILIKFANSPRPDLWVLERSVDFGSTYSPWQYFAHSK VDCLKEFGREANMAVTRDDDVLCVTEYSRIVPLENGEVVVSLINGRPG AKNFTFSHTLREFTKATNIRLRFLRTNTLLGHLISKAQRDPTVTRRYYY SIKDISIGGQCVCNGHAEVCNINNPEKLFRCECQHHTCGETCDRCCTGY NQRRWRPAAWEQSHECEACNCHGHASNCYYDPDVERQQASLNTQGI YAGGGVCINCQHNTAGVNCEQCAKGYYRPYGVPVDAPDGCIRKFHF KLVYLSLCVLPQRSHQANFGSVNNFLHALSLQSISCARYVTSVTYTVS LNFGFIACKWK |
| laminin subunit alpha-4 isoform 1 precursor (LAMA4-isoform 1); SEQ ID NO: 33 | MALSSAWRSVLPLWLLWSAACSRAASGDDNAFPFDIEGSSAVGRQDP PETSEPRVALGRLPPAAEKCNAGFFHTLSGECVPCDCNGNSNECLDGS GYCVHCQRNTTGEHCEKCLDGYIGDSIRGAPQFCQPCPCPLPHLANFA ESCYRKNGAVRCICNENYAGPNCERCAPGYYGNPLLIGSTCKKCDCSG NSDPNLIFEDCDEVTGQCRNCLRNTTGFKCERCAPGYYGDARIAKNCA VCNCGGGPCDSVTGECLEEGFEPPTGMDCPTISCDKCVWDLTDDLRL AALSIEEGKSGVLSVSSGAAAHRHVNEINATIYLLKTKLSERENQYALR KIQINNAENTMKSLLSDVEELVEKENQASRKGQLVQKESMDTINHASQ LVEQAHDMRDKIQEINNKMLYYGEEHELSPKEISEKLVLAQKMLEEIR SRQPFFTQRELVDEEADEAYELLSQAESWQRLHNETRTLFPVVLEQLD DYNAKLSDLQEALDQALNYVRDAEDMNRATAARQRDHEKQQERVR EQMEVVNMSLSTSADSLTTPRLTLSELDDIIKNASGIYAEIDGAKSELQ VKLSNLSNLSHDLVQEAIDHAQDLQQEANELSRKLHSSDMNGLVQKA LDASNVYENIVNYVSEANETAEFALNTTDRIYDAVSGIDTQIIYHKDES ENLLNQARELQAKAESSSDEAVADTSRRVGGALARKSALKTRLSDAV KQLQAAERGDAQQRLGQSRLITEEANRTTMEVQQATAPMANNLTNW SQNLQHFDSSAYNTAVNSARDAVRNLTEVVPQLLDQLRTVEQKRPAS NVSASIQRIRELIAQTRSVASKIQVSMMFDGQSAVEVHSRTSMDDLKA FTSLSLSYMKPPVKRPELTETADQFILYLGSKNAKKEYMGLAIKNDNLV YVYNLGTKDVEIPLDSKPVSSWPAYFSIVKIERVGKHGKVFLTVPSLSS TAEEKFIKKGEFSGDDSLLDLDPEDTVFYVGGVPSNFKLPTSLNLPGFV GCLELATLNNDVISLYNFKHIYNMDPSTSVPCARDKLAFTQSRAASYF FDGSGYAVVRDITRRGKFGQVTRFDIEVRTPADNGLILLMVNGSMFFR LEMRNGYLHVFYDFGFSGGPVHLEDTLKKAQINDAKYHEISIIYHNDK KMILVVDRRHVKSMDNEKMKIPFTDIYIGGAPPEILQSRALRAHLPLDI NFRGCMKGFQFKKDFNLLEQTETLGVGYGCPEDSLISRRAYFNGQSF IASIQKISFFDGFEGGFNFRTLQPNGLLFYYASGSDVFSISLDNGTVIMD VKGIKVQSVDKQYNDGLSHFVISSVSPTRYELIVDKSRVGSKNPTKGKI EQTQASEKKFYFGGSPISAQYANFTGCISNAYFTRVDRDVEVEDFQRY TEKVHTSLYECPIESSPLFLLHKKGKNLSKPKASQNKKGGKSKDAPSW DPVALKLPERNTPRNSHCHLSNSPRAIEHAYQYGGTANSRQEFEHLKG DFGAKSQFSIRLRTRSSHGMIFYVSDQEENDFMTLFLAHGRLVYMPNV GHKKLKIRSQEKYNDGLWHDVIFIRERSSGRLVIDGLRVLEESLPPTEA |

| Human Laminin | Sequence |
|---|---|
| | TWKIKGPIYLGGVAPGKAVKNVQINSIYSFSGCLSNLQLNGASITSASQ<br>TFSVTPCFEGPMETGTYFSTEGGYVVLDESFNIGLKFEIAFEVRPRSSSG<br>TLVHGHSVNGEYLNVHMKNGQVIVKVNNGIRDFSTSVTPKQSLCDGR<br>WHRITVIRDSNVVQLDVDSEVNHVVGPLNPKPIDHREPVFVGGVPESL<br>LTPRLAPSKPFTGCIRHFVIDGHPVSFSKAALVSGAVSINSCPAA |
| laminin<br>subunit<br>alpha-4<br>isoform 2<br>precursor<br>(LAMA4-<br>isoform 2);<br>SEQ ID<br>NO: 34 | MALSSAWRSVLPLWLLWSAACSRAASGDDNAFPFDIEGSSAVGRQDP<br>PETSEPRVALGRLPPAAEKCNAGFFHTLSGECVPCDCNGNSNECLDGS<br>GYCVHCQRNTTGEHCEKCLDGYIGDSIRGAPQFCQPCPCPLPHLANFA<br>ESCYRKNGAVRCICNENYAGPNCERCAPGYYGNPLLIGSTCKKCDCSG<br>NSDPNLIFEDCDEVTGQCRNCLRNTTGFKCERCAPGYYGDARIAKNCA<br>VCNCGGGPCDSVTGECLEEGFEPPTGCDKCVWDLTDDLRLAALSIEEG<br>KSGVLSVSSGAAAHRHVNEINATIYLLKTKLSERENQYALRKIQINNAE<br>NTMKSLLSDVEELVEKENQASRKGQLVQKESMDTINHASQLVEQAHD<br>MRDKIQEINNKMLYYGEEHELSPKEISEKLVLAQKMLEEIRSRQPFFTQ<br>RELVDEEADEAYELLSQAESWQRLHNETRTLFPVVLEQLDDYNAKLS<br>DLQEALDQALNYVRDAEDMNRATAARQRDHEKQQERVREQMEVVN<br>MSLSTSADSLTTPRLTLSELDDIIKNASGIYAEIDGAKSELQVKLSNLSN<br>LSHDLVQEAIDHAQDLQQEANELSRKLHSSDMNGLVQKALDASNVYE<br>NIVNYVSEANETAEFALNTTDRIYDAVSGIDTQIIYHKDESENLLNQAR<br>ELQAKAESSSSDEAVADTSRRVGGALARKSALKTRLSDAVKQLQAAER<br>GDAQQRLGQSRLITEEANRTTMEVQQATAPMANNLTNWSQNLQHFD<br>SSAYNTAVNSARDAVRNLTEVVPQLLDQLRTVEQKRPASNVSASIQRI<br>RELIAQTRSVASKIQVSMMFDGQSAVEVHSRTSMDDLKAFTSLSLYM<br>KPPVKRPELTETADQFILYLGSKNAKKEYMGLAIKNDNLVYVYNLGT<br>KDVEIPLDSKPVSSWPAYFSIVKIERVGKHGKVFLTVPSLSSTAEEKFIK<br>KGEFSGDDSLLDLDPEDTVFYVGGVPSNFKLPTSLNLPGFVGCLELATL<br>NNDVISLYNFKHIYNMDPSTSVPCARDKLAFTQSRAASYFFDGSGYAV<br>VRDITRRGKFGQVTRFDIEVRTPADNGLILLMVNGSMFFRLEMRNGYL<br>HVFYDFGFSGGPVHLEDTLKKAQINDAKYHEISIIYHNDKKMILVVDR<br>RHVKSMDNEKMKIPPFTDIYIGGAPPEILQSRALRAHLPLDINFRGCMKG<br>FQFQKKDFNLLEQTETLGVGYGCPEDSLISRRAYFNGQSFIASIQKISFF<br>DGFEGGFNFRTLQPNGLLFYYASGSDVFSISLDNGTVIMDVKGIKVQS<br>VDKQYNDGLSHFVISSVSPTRYELIVDKSRVGSKNPTKGKIEQTQASEK<br>KFYFGGSPISAQYANFTGCISNAYFTRVDRDVEVEDFQRYTEKVHTSL<br>YECPIESSPLFLLHKKGKNLSKPKASQNKKGGKSKDAPSWDPVALKLP<br>ERNTPRNSHCHLSNSPRAIEHAYQYGGTANSRQEFEHLKGDFGAKSQF<br>SIRLRTRSSHGMIFYVSDQEENDFMTLFLAHGRLVYMFNVGHKKLKIR<br>SQEKYNDGLWHDVIFIRERSSGRLVIDGLRVLEESLPPTEATWKIKGPI<br>YLGGVAPGKAVKNVQINSIYSFSGCLSNLQLNGASITSASQTFSVTPCF<br>EGPMETGTYFSTEGGYVVLDESFNIGLKFEIAFEVRPRSSSGTLVHGHS<br>VNGEYLNVHMKNGQVIVKVNNGIRDFSTSVTPKQSLCDGRWHRITVI<br>RDSNVVQLDVDSEVNHVVGPLNPKPIDHREPVFVGGVPESLLTPRLAP<br>SKPFTGCIRHFVIDGHPVSFSKAALVSGAVSINSCPAA |
| laminin<br>subunit<br>alpha-4<br>isoform 3<br>precursor<br>(LAMA4-<br>isoform 3);<br>SEQ ID<br>NO: 35 | MALSSAWRSVLPLWLLWSAACSRAASGDDNAFPFDIEGSSAVGRQDP<br>PETSEPRVALGRLPPAAEVQCPCHCHPAGAPAPPRAVPHSSFSLSPPLSS<br>PQCLESFTWARSVRKLEIKSFPL |
| laminin<br>subunit<br>alpha-5<br>precursor<br>(LAMA5);<br>SEQ ID<br>NO: 36 | MAKRLCAGSALCVRGPRGPAPLLLVGLALLGAARAREEAGGGFSLHP<br>PYFNLAEGARIAASATCGEEAPARGSPRPTEDLYCKLVGGPVAGGDPN<br>QTIRGQYCDICTAANSNKAHPASNAIDGTERWWQSPPLSRGLEYNEVN<br>VTLDLGQVFHVAYVLIKFANSPRPDLWVLERSMDFGRTYQPWQFFAS<br>SKRDCLERFGPQTLERITRDDAAICTTEYSRIVPLENGEIVVSLVNGRPG<br>AMNFSYSPLLREFTKATNVRLRFLRTNTLLGHLMGKALRDPTVTRRY<br>YYSIKDISIGGRCVCHGHADACDAKDPTDPFRLQCTCQHNTCGGTCDR<br>CCPGFNQQPWKPATANSANECQSCNCYGHATDCYYDPEVDRRRASQ<br>SLDGTYQGGGVCIDCQHHTTGVNCERCLPGFYRSPNHPLDSPHVCRRC<br>NCESDFTDGTCEDLTGRCYCRPNFSGERCDVCAEGFTGFPSCYPTPSSS<br>NDTREQVLPAGQIVNCDCSAAGTQGNACRKDPRVGRCLCKPNFQGTH<br>CELCAPGFYGPGCQPCQCSSPGVADDRCDPDTGQCRCRVGFEGATCD<br>RCAPGYFHFPLCQLCGCSPAGTLPEGCDEAGRCLCQPEFAGPHCDRCR<br>PGYHGFPNCQACTCDPRGALDQLCGAGGLCRCRPGYTGTACQECSPG<br>FHGFPSCVPCHCSAEGSLHAACDPRSGQCSCRPRVTGLRCDTCVPGSP<br>NFPYCEAGSCHPAGLAPVDPALPEAQVPCMCRAHVEGPSCDRCKPGF<br>WGLSPSNPEGCTRCSCDLRGTLGGVAECQPGTGQCFCKPHVCGQACA<br>SCKDGEEGLDQADYFGCRSCRCDIGGALGQSCEPRTGVCRCRPNTQGP<br>TCSEPARDHYLPDLHHLRLELEEAATPEGHAVRFGFNPLEFENFSWRG<br>YAQMAPVQPRIVARLNLTSPDLFWLVFRYVNRGAMSVSGRVSVREEG<br>RSATCANCTAQSQPVAFPPSTEPAFITVPQRGEGEPEVLNPGTWALRVE |

| Human Laminin | Sequence |
|---|---|
| | AEGVLLDYVVLLPSAYYEAALLQLRVTEACTYRPSAQQSGDNCLLYT |
| | HLPLDGFPSAAGLEALCRQDNSLPRPCPTEQLSPSHPPLITCTGSDVDV |
| | QLQVAVPQPGRYALVVEYANEDARQEVGVAVHTPQRAPQQGLLSLH |
| | PCLYSTLCRGTARDTQDHLAVFHLDSEASVRLTAEQARFFLHGVTLVP |
| | IEEESPEFVEPRVSCISSHGAFGPNSAACLPSRFPKPPQPIILRDCQVIPLP |
| | PGLPLTHAQDLTPAMSPAGPRPRPPTAVDPDAEPTLLREPQATVVFTTH |
| | VPTLGRYAELLHGYQPAEIPTEPVEVLINAGRVWQGHANASFCPHGYG |
| | CRTLVVCEGQALLDVTHSELTVTVRVPKGRWLWLDYVLVVPENVYS |
| | FGYLREEPLDKSYDFISHCAAQGYHISPSSSSLFCRNAAASLSLFYNNG |
| | ARPCGCHEVGATGPTCEPFGGQCPCHAHVIGRDCSRCATGYWGFPNC |
| | RPCDCGARLCDELTGQCICPPRTIPPDCLLCQPQTFGCHPLVGCEECNC |
| | SGPGIQELTDPTCDTDSGQCKCRPNVTGRRCDTCSPGFHGYPRCRPCD |
| | CHEAGTAPGVCDPLTGQCYCKENVQGPKCDQCSLGTFSLDAANPKGC |
| | TRCFCFGATERCRSSSYTRQEFVDMEGWVLLSTDRQVVPHERQPGTE |
| | MLRADLRHVPEAVPEAFPELYWQAPPSYLGDRVSSYGGTLRYELHSE |
| | TQRGDVFVPMESRPDVVLQGNQMSITFLEPAYPTPGHVHRGQLQLVE |
| | GNFRHTETRNTVSREELMMVLASLEQLQIRALFSQISSAVFLRRVALEV |
| | ASPAGQGALASNVELCLCPASYRGDSCQECAPGFYRDVKGLFLGRCV |
| | PCQCHGHSDRCLPGSGVCVDCQHNTEGAHCERCQAGFVSSRDDPSAP |
| | CVSCPCPLSVPSNNFAEGCVLRGGRTQCLCKPGYAGASCERCAPGFFG |
| | NPLVLGSSCQPCDCSGNGDPNLLFSDCDPLTGACRGCLRHTTGPRCEIC |
| | APGFYGNALLPGNCTRCDCTPCGTEACDPHSGHCLCKAGVTGRRCDR |
| | CQEGHFGEDGCGGCRPCACGPAAEGSECHPQSGQCHCRPGTMGPQCR |
| | ECAPGYWGLPEQGCRRCQCPGGRCDPHTGRCNCPPGLSGERCDTCSQ |
| | QHQVPVPGGPVGHSIHCEVCDHCVVLLLDDLERAGALLPAIHEQLRGI |
| | NASSMAWARLHRLNASIADLQSQLRSPLGPRHETAQQLEVLEQQSTSL |
| | GQDARRLGGQAVGTRDQASQLLAGTEATLGHAKTLLAAIRAVDRTLS |
| | ELMSQTGHLGLANASAPSGEQLLRTLAEVERLLWEMRARDLGAPQAA |
| | AEAELAAAQRLLARVQEQLSSLWEENQALATQTRDRLAQHEAGLMD |
| | LREALNRAVDATREAQELNSRNQERLEEALQRKQELSRDNATLQATL |
| | HAARDTLASVFRLLHSLDQAKEELERLAASLDGARTPLLQRMQTFSPA |
| | GSKLRLVEAAEAHAQQLGQLALNLSSIILDVNQDRLTQRAIEASNAYS |
| | RILQAVQAAEDAAGQALQQADHTWATVVRQGLVDRAQQLLANSTAL |
| | EEAMLQEQQRLGLVWAALQGARTQLRDVRAKKDQLEAHIQAAQAM |
| | LAMDTDETSKKIAHAKAVAAEAQDTATRVQSQLQAMQENVERWQG |
| | QYEGLRGQDLGQAVLDAGHSVSTLEKTLPQLLAKLSILENRGVHNASL |
| | ALSASIGRVRELIAQARGAASKVKVPMKFNGRSGVQLRTPRDLADLA |
| | AYTALKFYLQGPEPEPGQGTEDRFVMYMGSRQATGDYMGVSLRDKK |
| | VHHWVYQLGEAGPAVLSIDEDIGEQFAAVSLDRTLQFGHMSVTVERQM |
| | IQETKGDTVAPGAEGLLNLRPDDFVFYVGGYPSTFTPPPLLRFPGYRGC |
| | IEMDTLNEEVVSLYNEERTEQLDTAVDRPCARSKSTGDPWLTDGSYLD |
| | GTGEARISEDSQISTTKREEQELRLVSYSGVLEELKQQSQFLCLAVQEGS |
| | LVLLYDFGAGLKKAVPLQPPPPLTSASKAIQVFLLGGSRKRVLVRVER |
| | ATVYSVEQDNDLELADAYYLGGVPPDQLPPSLRRLFPTGGSVRGCVK |
| | GIKALGKYVDLKRLNTTGVSAGCTADLLVGRAMTFHGHGFLRLALSN |
| | VAPLTGNVYSGFGFHSAQDSALLYYRASPDGLCQVSLQQGRVSLQLL |
| | RTEVKTQAGFADGAPHYVAFYSNATGVWLYVDDQLQQMKPHRGPPP |
| | ELQPQPEGPPRLLLGGLPESGTIYNFSGCISNVFVQRLLGPQRVFDLQQ |
| | NLGSVNVSTGCAPALQAQTPGLGPRGLQATARKASRRSRQPARHPAC |
| | MLPPHLRTTRDSYQFGGSLSSHLEFVGILARHRNWPSLSMHVLPRSSR |
| | GLLLFTARLRPGSPSLALFLSNGHFVAQMEGLGTRLRAQSRQRSRPGR |
| | WHKVSVRWEKNRILLVTDGARAWSQEGPHRQHQGAEHPQPHTLFVG |
| | GLPASSHSSKLPVTVGFSGCVKRLRLHGRPLGAPTRMAGVTPCILGPLE |
| | AGLFFPGSGGVITLDLPGATLPDVGLELEVRPLAVTGLIFHLGQARTPP |
| | YLQLQVTEKQVLLRADDGAGEFSTSVTRPSVLCDGQWHRLAVMKSG |
| | NVLRLEVDAQSNHTVGPLLAAAAGAPAPLYLGGLPEPMAVQPWPPAY |
| | CGCMRRLAVNRSPVAMTRSVEVHGAVGASGCPAA |
| laminin subunit beta-1 precursor (LAMB1); SEQ ID NO: 37 | MGLLQLLAFSFLALCRARVRAQEPEFSYGCAEGSCYPATGDLLIGRAQ |
| | KLSVTSTCGLHKPEPYCIVSHLQEDKKCFICNSQDPYHETLNPDSHLIE |
| | NVVTTFAPNRLKIWWQSENGVENVTIQLDLEAEFHFTHLIMTFKTFRP |
| | AAMLIERSSDFGKTWGVYRYFAYDCEASFPGISTGPMKKVDDIICDSR |
| | YSDIEPSTEGEVIFRALDPAFKIEDPYSPRIQNLLKITNLRIKFVKLHTLG |
| | DNLLDSRMEIREKYYYAVYDMVVRGNCFCYGHASECAPVDGFNEEV |
| | EGMVHGHCMCRHNTKGLNCELCMDFYHDLPWRPAEGRNSNACKKC |
| | NCNEHSISCHFDMAVYLATGNVSGGVCDDCQHNTMGRNCEQCKPFY |
| | YQHPERDIRDPNFCERCTCDPAGSQNEGICDSYTDFSTGLIAGQCRCKL |
| | NVEGEHCDVCKEGFYDLSSEDPFGCKSCACNPLGTIPGGNPCDSETGH |
| | CYCKRLVTGQHCDQCLPEHWGLSNDLDGCRPCDCDLGGALNNSCFA |
| | ESGQCSCRPHMIGRQCNEVEPGYYFATLDHYLYEAEEANLGPGVSIVE |
| | RQYIQDRIPSWTGAGFVRVPEGAYLEFFIDNIPYSMEYDILIRYEPQLPD |
| | HWEKAVITVQRPGRIPTSSRCGNTIPDDDNQVVSLSPGSRYVVLPRPVC |
| | FEKGTNYTVRLELPQYTSSDSDVESPYTLIDSLVLMPYCKSLDIFTVGG |
| | SGDGVVTNSAWETFQRYRCLENSRSVVKTPMTDVCRNIIFSISALLHQT |
| | GLACECDPQGSLSSVCDPNGGQCQCRPNVVGRTCNRCAPGTFGFGPS |
| | GCKPCECHLQGSVNAFCNPVTGQCHCFQGVYARQCDRCLPGHWGFPS |

| Human Laminin | Sequence |
|---|---|
| | CQPCQCNGHADDCDPVTGECLNCQDYTMGHNCERCLAGYYGDPIIGS GDHCRPCPCPDGPDSGRQFARSCYQDPVTLQLACVCDPGYIGSRCDDC ASGYFGNPSEVGGSCQPCQCHNNIDTTDPEACDKETGRCLKCLYHTEG EHCQFCRFGYYGDALQQDCRKCVCNYLGTVQEHCNGSDCQCDKATG QCLCLPNVIGQNCDRCAPNTWQLASGTGCDPCNCNAAHSFGPSCNEF TGQCQCMPGFGGRTCSECQELFWGDPDVECRACDCDPRGIETPQCDQ STGQCVCVEGVEGPRCDKCTRGYSGVFPDCTPCHQCFALWDVIIAELT NRTHRFLEKAKALKISGVIGPYRETVDSVERKVSEIKDILAQSPAAEPL KNIGNLFEEAEKLIKDVTEMMAQVEVKLSDTTSQSNSTAKELDSLQTE AESLDNTVKELAEQLEFIKNSDIRGALDSITKYFQMSLEAEERVNASTT EPNSTVEQSALMRDRVEDVMMERESQFKEKQEEQARLLDELAGKLQS LDLSAAAEMTCGTPPGASCSETECGGPNCRTDEGERKCGGPGCGGLV TVAHNAWQKAMDLDQDVLSALAEVEQLSKMVSEAKLRADEAKQSA EDILLKTNATKEKMDKSNEELRNLIKQIRNFLTQDSADLDSIEAVANEV LKMEMPSTPQQLQNLTEDIRERVESLSQVEVILQHSAADIARAEMLLEE AKRASKSATDVKVTADMVKEALEEAEKAQVAAEKAIKQADEDIQGT QNLLTSHESETAASEETLFNASQRISELERNVEELKRKAAQNSGEAEYIE KVVYTVKQSAEDVKKTLDGELDEKYKKVENLIAKKTEESADARRKAE MLQNEAKTLLAQANSKLQLLKDLERKYEDNQRYLEDKAQELARLEG EVRSLLKDISQKVAVYSTCL |
| laminin subunit beta-2 precursor (LAMB2); SEQ ID NO: 38 | MELTSRERGRGQPLPWELRLGLLLSVLAATLAQAPAPDVPGCSRGSCY PATGDLLVGRADRLTASSTCGLNGPQPYCIVSHLQDEKKCFLCDSRRP FSARDNPHSHRIQNVVTSFAPQRRAAWWQSENGIPAVTIQLDLEAEFH FTHLIMTFKTFRPAAMLVERSADFGRTWHVYRYFSYDCGADFPGVPL APPRHWDDVVCESRYSEIEPSTEGEVIYRVLDPAIPIPDPYSSRIQNLLKI TNLRVNLTRLHTLGDNLLDPRREIREKYYYALYELVVRGNCFCYGHA SECACAPAPGAPAHAEGMVHGACICKHNTRGLNCEQCQDFYRDLPWRPA EDGHSHACRKCECHGHTHSCHFDMAVYLASGNVSGGVCDGCQHNTA GRHCELCRPFFYRDPTKDLRDPAVCRSCDCDPMGSQDGGRCDSHDDP ALGLVSGQCRCKEHVVGTRCQQCRDGFFGLSISDRLGCRRCQCNARG TVPGSTPCDPNSGSCYCKRLVTGRGCDRCLPGHWGLSHDLLGCRPCD CDVGGALDPQCDEGTGQCHCRQHMVGRRCEQVQPGYFRPFLDHLIW EAEDTRGQVLDVVERLVTPGETPSWTGSGFVRLQEGQTLEFLVASVPK AMDYDLLLRLEPQVPEQWAELELIVQRPGPVPAHSLCGHLVPKDDRIQ GTLQPHARYLIFPNPVCLEPGISYKLHLKLVRTGGSAQPETPYSGPGLLI DSLVLLPRVLVLEMFSGGDAAALERQATFERYQCHEEGLVPSKTSPSE ACAPLLISLSTLIYNGALPCQCNPQGSLSSECNPHGGQCLCKPGVVGRR CDLCAPGYYGFGPTGCQACQCSHEGALSSLCEKTSGQCLCRTGAFGLR CDRCQRGQWGFPSCRPCVCNGHADECNTHTGACLGCRDHTGGEHCE RCIAGFHGDPRLPYGGQCRPCPCPEGPGSQRHFATSCHQDEYSQQIVC HCRAGYTGLRCEACAPGHFGDPSRPGGRCQLCECSGNIDPMDPDACD PHTGQCLRCLHHTEGPHCAHCKPGFHGQAARQSCHRCTCNLLGTNPQ QCPSPDQCHCDPSSGQCPCLPNVQGPSCDRCAPNFWNLTSGHGCQPCA CHPSRARGPTCNEFTGQCHCRAGFGGRTCSECQELHWGDPGLQCHAC DCDSRGIDTPQCHRFTGHCSCRPGVSGVRCDQCARGFSGIFPACHPCH ACFGDWDRVVQDLAARTQRLEQRAQELQQTGVLGAFESSFWHMQEK LGIVQGIVGARNTSAASTAQLVEATEELRREIGEATEHLTQLEADLTDV QDENFNANHALSGLERDRLALNLTLRQLDQHLDLLKHSNFLGAYDSIR HAHSQSAEAERRANTSALAVPSPVSNSASARHRTEALMDAQKEDFNS KHMANQRALGKLSAHTHTLSLTDINELVCGAPGDAPCATSPCGGAGC RDEDGQPRCGGLSCNGAAATADLALGRARHTQAELQRALAEGGSILS RVAETRRQASEAQQRAQAALDKANASRGQVEQANQELQELIQSVKDF LNQEGADPDSIEMVATRVLELSIPASAEQIQHLAGAIAERVRSLADVDA ILARTVGDVRRAEQLLQDARRARSWAEDEKQKAETVQAALEEAQRA QGIAQGAIRGAVADTRDTEQTLYQVQERMAGAERALSSAGERARQLD ALLEALKLKRAGNSLAASTAEETAGSAQGRAQEAEQLLRGPLGDQYQ TVKALAERKAQGVLAAQARAEQLRDEARDLLQAAQDKLQRLQELEG TYEENERALESKAAQLDGLEARMRSVLQAINLQVQIYNTCQ |
| laminin subunit beta-3 precursor (LAMB3); SEQ ID NO: 39 | MRPFFLLCFALPGLLHAQQACSRGACYPPVGDLLVGRTRFLRASSTCG LTKPETYCTQYGEWQMKCCKCDSRQPHNYYSHRVENVASSSGPMRW WQSQNDVNPVSLQLDLDRRFQLQEVMMEFQGPMPAGMLIERSSDFG KTWRVYQYLAADCTSTFPRVRQGRPQSWQDVRCQSLPQRPNARLNG GKVQLNLMDLVSGIPATQSQKIQEVGEITNLRVNFTRLAPVPQRGYHP PSAYYAVSQLRLQGSCFCHGHADRCAPKPGASAGPSTAVQVHDVCVC QHNTAGPNCERCAPFYNNRPWRPAEGQDAHECQRCDCNGHSETCHF DPAVFAASQGAYGGVCDNCRDHTEGKNCERCQLHYFRNRRPGASIQE TCISCECDPDGAVPGAPCDPVTGQCVCKEHVQGERCDLCKPGFTGLTY ANPQGCHRCDCNILGSRRDMPCDEESGRCLCLPNVVGPKCDQCAPYH WKLASGQGCEPCACDPHNSLSPQCNQFTGQCPCREGFGGLMCSAAAI RQCPDRTYGDVATGCRACDCFRGTEGPGCDKASGRCLCRPGLTGPR CDQCQRGYCNRYPVCVACHPCFQTYDADLREQALRFGRLRNATASL WSGPGLEDRGLASRILDAKSKIEQIRAVLSSPAVTEQEVAQVASAILSL RRTLQGLQLDLPLEEETLSLPRDLESLDRSFNGLLTMYQRKREQFEKIS SADPSGAFRMLSTAYEQSAQAAQQVSDSSRLLDQLRDSRREAERLVR |

| Human Laminin | Sequence |
| --- | --- |
| | QAGGGGGTGSPKLVALRLEMSSLPDLTPTFNKLCGNSRQMACTPISCP GELCPQDNGTACGSRCRGVLPRAGGAFLMAGQVAEQLRGFNAQLQR TRQMIRAAEESASQIQSSAQRLETQVSASRSQMEEDVRRTRLLIQQVR DFLTDPDTDAATIQEVSEAVLALWLPTDSATVLQKMNEIQAIAARLPN VDLVLSQTKQDIARARRLQAEAEEARSRAHAVEGQVEDVVGNLRQGT VALQEAQDTMQGTSRSLRLIQDRVAEVQQVLRPAEKLVTSMTKQLGD FWTRMEELRHQARQQGAEAVQAQQLAEGASEQALSAQEGFERIKQK YAELKDRLGQSSMLGEQGARIQSVKTEAEELFGETMEMMDRMKDME LELLRGSQAIMLRSADLTGLEKRVEQIRDHINGRVLYYATCK |
| laminin subunit beta-4 isoform 1 precursor (LAMB4-isoform 1); SEQ ID NO: 40 | MQFQLTLFLHLGWLSYSKAQDDCNRGACHPTTGDLLVGRNTQLMAS STCGLSRAQKYCILSYLEGEQKCFICDSRFPYDPYDQPNSHTIENVIVSF EPDREKKWWQSENGLDHVSIRLDLEALFRFSHLILTFKTFRPAAMLVE RSTDYGHNWKVFKYFAKDCATSFPNITSGQAQGVGDIVCDSKYSDIEP STGGEVVLKVLDPSFEIENPYSPYIQDLVTLTNLRINFTKLHTLGDALLG RRQNDSLDKYYYALYEMIVRGSCFCNGHASECRPMQKMRGDVFSPPG MVHGQCVCQHNTDGPNCERCKDFFQDAPWRPAADLQDNACRSCSCN SHSSRCHFDMTTYLASGGLSGGVCEDCQHNTEGQHCDRCRPLFYRDP LKTISDPYACIPCECDPDGTISGGICVSHSDPALGSVAGQCLCKENVEG AKCDQCKPNHYGLSATDPLGCQPCDCNPLGSLPFLTCDVDTGQCLCLS YVTGAHCEECTVGYWGLGNHLHGCSPCDCDIGGAYSNVCSPKNGQC ECRPHVTGRSCSEPAPGYFFAPLNFYLYEAEEATTLQGLAPLGSETFGQ SPAVHVVLGEPVPGNPVTWTGPGFARVLPGAGLRFAVNNIPFPVDFTI AIHYETQSAADWTVQIVVNPPGGSEHCIPKTLQSKPQSFALPAATRIML LPTPICLEPDVQYSIDVYFSQPLQGESHAHSHVLVDSLGLIPQINSLENF CSKQDLDEYQLHNCVEIASAMGPQVLPGACERLIISMSAKLHDGAVAC KCHPQGSVGSSCSRLGGQCQCKPLVVGRCCDRCSTGSYDLGHHGCHP CHCHPQGSKDTVCDQVTGQCPCHGEVSGRRCDRCLAGYFGFPSCHPC PCNRFAELCDPETGSCFNCGGFTTGRNCERCIDGYYGNPSSGQPCRPCL CPDDPSSNQYFAHSCYQNLWSSDVICNCLQGYTGTQCGECSTGFYGNP RISGAPCQPCACNNNIDVTDPESCSRVTGECLRCLHNTQGANCQLCKP GHYGSALNQTCRRCSCHASGVSPMECPPGGGACLCDPVTGACPCLPN VTGLACDRCADGYWNLVPGRGCQSCDCDPRTSQSSHCDQLTGQCPC KLGYGGKRCSECQENYYGDPPGRCIPCDCNRAGTQKPICDPDTGMCR CREGVSGQRCDRCARGHSQEFPTCLQCHLCFDQWDHTISSLSKAVQG LMRLAANMEDKRETLPVCEADFKDLRGNVSEIERILKHPVFPSGKFLK VKDYHDSVRRQIMQLNEQLKAVYEFQDLKDTIERAKNEADLLLEDLQ EEIDLQSSVLNASIADSSENIKKYYHISSSAEKKINETSSTINTSANTRND LLTILDLTLTSKGNLSLERLKQIKIPDIQILNEKVCGDPGNVPCVPLPCGG ALCTGRKGHRKCRGPGCHGSLTLSTNALQKAQEAKSIIRNLDKQVRGL KNQIESISEQAEVSKNNALQLREKLGNIRNQSDSEEENINLFIKKVKNFL LEENVPPEDIEKVANGVLDIHLPIPSQNLTDELVKIQKHMQLCEDYRTD ENRLNEEADGAQKLLVKAKAAEKAANILLNLDKTLNQLQQAQITQGR ANSTITQLTANITKIKKNVLQAENQTREMKSELELAKQRSGLEDGLSLL QTKLQRHQDHAVNAKVQAESAQHQAGSLEKEFVELKKQYAILQRKTS TTGLTKETLGKVKQLKDAAEKLAGDTEAKIRRITDLERKIQDLNLSRQ AKADQLRILEDQVVAIKNEIVEQEKKYARCYS |
| laminin subunit beta-4 isoform 2 precursor (LAMB4-isoform 2); SEQ ID NO: 41 | MQFQLTLFLHLGWLSYSKAQDDCNRGACHPTTGDLLVGRNTQLMAS STCGLSRAQKYCILSYLEGEQKCFICDSRFPYDPYDQPNSHTIENVIVSF EPDREKKWWQSENGLDHVSIRLDLEALFRFSHLILTFKTFRPAAMLVE RSTDYGHNWKVFKYFAKDCATSFPNITSGQAQGVGDIVCDSKYSDIEP STGGEVVLKVLDPSFEIENPYSPYIQDLVTLTNLRINFTKLHTLGDALLG RRQNDSLDKYYYALYEMIVRGSCFCNGHASECRPMQKMRGDVFSPPG MVHGQCVCQHNTDGPNCERCKDFFQDAPWRPAADLQDNACRSCSCN SHSSRCHFDMTTYLASGGLSGGVCEDCQHNTEGQHCDRCRPLFYRDP LKTISDPYACIPCECDPDGTISGGICVSHSDPALGSVAGQCLCKENVEG AKCDQCKPNHYGLSATDPLGCQPCDCNPLGSLPFLTCDVDTGQCLCLS YVTGAHCEECTVGYWGLGNHLHGCSPCDCDIGGAYSNVCSPKNGQC ECRPHVTGRSCSEPAPGYFFAPLNFYLYEAEEATTLQGLAPLGSETFGQ SPAVHVVLGEPVPGNPVTWTGPGFARVLPGAGLRFAVNNIPFPVDFTI AIHYETQSAADWTVQIVVNPPGGSEHCIPKTLQSKPQSFALPAATRIML LPTPICLEPDVQYSIDVYFSQPLQGESHAHSHVLVDSLGLIPQINSLENF CSKQDLDEYQLHNCVEIASAMGPQVLPGACERLIISMSAKLHDGAVAC KCHPQGSVGSSCSRLGGQCQCKPLVVGRCCDRCSTGSYDLGHHGCHP CHCHPQGSKDTVCDQVTGQCPCHGEVSGRRCDRCLAGYFGFPSCHPC PCNRFAELCDPETGSCFNCGGFTTGRNCERCIDGYYGNPSSGQPCRPCL CPDDPSSNQYFAHSCYQNLWSSDVICNCLQGYTGTQCGECSTGFYGNP RISGAPCQPCACNNNIDVTDPESCSRVTGECLRCLHNTQGANCQLCKP GHYGSALNQTCRRCSCHASGVSPMECPPGGGACLCDPVTGACPCLPN VTGLACDRCADGYWNLVPGRGCQSCDCDPRTSQSSHCDQARYFKAY |
| laminin subunit beta-4 isoform 3 precursor | MQFQLTLFLHLGWLSYSKAQDDCNRGACHPTTGDLLVGRNTQLMAS STCGLSRAQKYCILSYLEGEQKCFICDSRFPYDPYDQPNSHTIENVIVSF EPDREKKWWQSENGLDHVSIRLDLEALFRFSHLILTFKTFRPAAMLVE RSTDYGHNWKVFKYFAKDCATSFPNITSGQAQGVGDIVCDSKYSDIEP |

| Human Laminin | Sequence |
|---|---|
| (LAMB4-isoform 3); SEQ ID NO: 42 | STGGEVVLKVLDPSFEIENPYSPYIQDLVTLTNLRINFTKLHTLGDALLG RRQNDSLDKYYYALYEMIVRGSCFCNGHASECRPMQKMRGDVFSPPG MVHGQCVCQHNTDGPNCERCKDFFQDAPWRPAADLQDNACRSCSCN SHSSRCHFDMTTYLASGGLSGGVCEDCQHNTEGQHCDRCRPLFYRDP LKTISDPYACIPCECDPDGTISGGICVSHSDPALGSVAGQCLCKENVEG AKCDQCKPNHYGLSATDPLGCQPCDCNPLGSLPFLTCDVDTGQCLCLS YVTGAHCEECTVGYWGLGNHLHGCSPCDCDIGGAYSNVCSPKNGQC ECRPHVTGRSCSEPAPGYFFAPLNFYLYEAEEATTLQGLAPLGSETFGQ SPAVHVVLGEPVPGNPVTWTGPGFARVLPGAGLRFAVNNIPFPVDFTI AIHYETQSAADWTVQIVVNPPGGSEHCIPKTLQSKPQSFALPAATRIML LPTPICLEPDVQYSIDVYFSQPLQGESHAHSHVLVDSAAVQWHNLGSL QPPPPECKQFSCFSFPSSWDYREIPPPHLANFCIFSRDGVSPHWPGWSQT PDLR |
| laminin subunit gamma-1 precursor (LAMC1); SEQ ID NO: 43 | MRGSHRAAPALRPRGRLWPVLAVLAAAAAAGCAQAAMDECTDEGG RPQRCMPEFVNAAFNVTVVATNTCGTPPEEYCVQTGVTGVTKSCHLC DAGQPHLQHGAAFLTDYNNQADTTWWQSQTMLAGVQYPSSINLTLH LGKAFDITYVRLKFHTSRPESFAIYKRTREDGPWIPYQYYSGSCENTYS KANRGFIRTGGDEQQALCTDEFSDISPLTGGNVAFSTLEGRPSAYNFDN SPVLQEWVTATDIRVTLNRLNTFGDEVFNDPKVLKSYYYAISDFAVGG RCKCNGHASECMKNEFDKLVCNCKHNTYGVDCEKCLPFFNDRPWRR ATAESASECLPCDCNGRSQECYFDPELYRSTGHGGHCTNCQDNTDGA HCERCRENFFRLGNNEACSSCHCSPVGSLSTQCDSYGRCSCKPGVMGD KCDRCQPGFHSLTEAGCRPCSCDPSGSIDECNIETGRCVCKDNVEGFNC ERCKPGFFNLESSNPRGCTPCFCFGHSSVCTNAVGYSVYSISSTFQIDED GWRAEQRDGSEASLEWSSERQDIAVISDSYFPRYFIAPAKFLGKQVLSY GQNLSFSFRVDRRDTRLSAEDLVLEGAGLRVSVPLIAQGNSYPSETTV KYVFRLHEATDYPWRPALTPFEFQKLLNNLTSIKIRGTYSERSAGYLDD VTLASARPGPGVPATWVESCTCPVGYGGQFCEMCLSGYRRETPNLGP YSPCVLCACNGHSETCDPETGVCNCRDNTAGPHCEKCSDGYYGDSTA GTSSDCQPCPCPGGSSCAVVPKTKEVVCTNCPTGTTGKRCELCDDGYF GDPLGRNGPVRLCRLCQCSDNIDPNAVGNCNRLTGECLKCIYNTAGFY CDRCKDGFFGNPLAPNPADKCKACNCNLYGTMKQQSSCNPVTGQCE CLPHVTGQDCGACDPGFYNLQSGQGCERCDCHALGSTNGQCDIRTGQ CECQPGITGQHCERCEVNHFGFGPEGCKPCDCHPEGSLSLQCKDDGRC ECREGFVGNRCDQCEENYFYNRSWPGCQECPACYRLVKDKVADHRV KLQEELESLIANLGTGDEMVTDQAFEDRLKEAEREVMDLLREAQDVKD VDQNLMDRLQRVNNTLSSQISRLQNIRNTIEETGNLAEQARAHVENTE RLIEIASRELEKAKVAAANVSVTQPESTGDPNNMTLLAEEARKLAERH KQEADDIVRVAKTANDTSTEAYNLLLRTLAGENQTAFEIEELNRKYEQ AKNISQDLEKQAARVHEEAKRAGDKAVEIYASVAQLSPLDSETLENEA NNIKMEAENLEQLIDQKLKDYEDLREDMRGKELEVKNLLEKGKTEQQ TADQLLARADAAKALAEEAAKKGRDTLQEANDILNNLKDFDRRVND NKTAAEEALRKIPAINQTITEANEKTREAQQALGSAAADATEAKNKAH EAERIASAVQKNATSTKAEAERTFAEVTDLDNEVNNMLKQLQEAAEKE LKRKQDDADQDMMMAGMASQAAQEAEINARKAKNSVTSLLSIINDL LEQLGQLDTVDLNKLNEIEGTLNKAKDEMKVSDLDRKVSDLENEAKK QEAAIMDYNRDIEEIMKDIRNLEDIRKTLPSGCFNTPSIEKP |
| laminin subunit gamma-2 isoform a precursor (LAMC2-isoform a); SEQ ID NO: 44 | MPALWLGCCLCFSLLLPAARATSRREVCDCNGKSRQCIFDRELHRQTG NGFRCLNCNDNTDGIHCEKCKNGFYRHRERDRCLPCNCNSKGSLSAR CDNSGRCSCKPGVTGARCDRCLPGFHMLTDAGCTQDQRLLDSKCDCD PAGIAGPCDAGRCVCKPAVTGERCDRCRSGYYNLDGGNPEGCTQCFC YGHSASCRSSAEYSVHKITSTFHQDVDGWKAVQRNGSPAKLQWSQRH QDVFSSAQRLDPVYFVAPAKFLGNQQVSYGQSLSFDYRVDRGGRHPS AHDVILEGAGLRITAPLMPLGKTLPCGLTKTYTFRLNEHPSNNWSPQLS YFEYRRLLRNLTALRIRATYGEYSTGYIDNVTLISARPVSGAPAPWVEQ CICPVGYKGQFCQDCASGYKRDSARLGPFGTCIPCNCQGGGACDPDTG DCYSGDENPDIECADCP1GFYNDPHDPRSCKPCPCHNGFSCSVMPETEE VVCNNCPPGVTGARCELCADGYFGDPFGEHGPVRPCQPCQCNNNVDP SASGNCDRLTGRCLKCIHNTAGIYCDQCKAGYFGDPLAPNPADKCRA CNCNPMGSEPVGCRSDGTCVCKPGFGGPNCEHGAFSCPACYNQVKIQ MDQFMQQLQRMEALISKAQGGDGVVPDTELEGRMQQAEQALQDILR DAQISEGASRSLGLQLAKVRSQENSYQSRLDDLKMTVERVRALGSQY QNRVRDTHRLITQMQLSLAESEASLGNTNIPASDHYVGPNGFKSLAQE ATRLAESHVESASNMEQLTRETEDYSKQALSLVRKALHEGVGSGSGSP DGAVVQGLVEKLEKTKSLAQQLTREATQAEIEADRSYQHSLRLLDSVS RLQGVSDQSFQVEEAKRIKQKADSLSSLVTRHMDEFKRTQKNLGNWK EEAQQLLQNGKSGREKSDQLLSRANLAKSRAQEALSMGNATFYEVESI LKNLREFDLQVDNRKAEAEEAMKRLSYISQKVSDASDKTQQAERALG SAAADAQRAKNGAGEALEISSEIEQEIGSLNLEANVTGALAMEKGL ASLKSEMREVEGELERKELEFDTNMDAVQMVITEAQKVDTRAKNAG VTIQDTLNTLDGLLHLMDQPLSVDEEGLVLLEQKLSRAKTQINSQLRP MMSELEERARQQRGHLHLLETSIDGILADVKNLENIRDNLPPGCYNTQ ALEQQ |

| Human Laminin | Sequence |
|---|---|
| laminin subunit gamma-2 isoform b precursor (LAMC2-isoform b); SEQ ID NO: 45 | MPALWLGCCLCFSLLLPAARATSRREVCDCNGKSRQCIFDRELHRQTG NGFRCLNCNDNTDGIHCEKCKNGFYRHRERDRCLPCNCNSKGSLSAR CDNSGRCSCKPGVTGARCDRCLPGFHMLTDAGCTQDQRLLDSKCDCD PAGIAGPCDAGRCVCKPAVTGERCDRCRSGYYNLDGGNPEGCTQCFC YGHSASCRSSAEYSVHKITSTFHQDVDGWKAVQRNGSPAKLQWSQRH QDVFSSAQRLDPVYFVAPAKFLGNQQVSYGQSLSFDYRVDRGGRHPS AHDVILEGAGLRITAPLMPLGKTLPCGLTKTYTFRLNEHPSNNWSPQLS YFEYRRLLRNLTALRIRATYGEYSTGYIDNVTLISARPVSGAPAPWVEQ CICPVGYKGQFCQDCASGYKRDSARLGPFGTCIPCNCQGGGACDPDTG DCYSGDENPDIECADCPlGFYNDPHDPRSCKPCPCHNGFSCSVMPETEE VVCNNCPPGVTGARCELCADGYFGDPFGEHGPVRPCQPCQCNNNVDP SASGNCDRLTGRCLKCIHNTAGIYCDQCKAGYFGDPLAPNPADKCRA CNCNPMGSEPVGCRSDGTCVCKPGFGGPNCEHGAFSCPACYNQVKIQ MDQFMQQLQRMEALISKAQGGDGVVPDTELEGRMQQAEQALQDILR DAQISEGASRSLGLQLAKVRSQENSYQSRLDDLKMTVERVRALGSQY QNRVRDTHRLITQMQLSLAESEASLGNTNIPASDHYVGPNGFKSLAQE ATRLAESHVESASNMEQLTRETEDYSKQALSLVRKALHEGVGSGSGSP DGAVVQGLVEKLEKTKSLAQQLTREATQAEIEADRSYQHSLRLLDSVS RLQGVSDQSFQVEEAKRIKQKADSLSSLVTRHMDEFKRTQKNLGNWK EEAQQLLQNGKSGREKSDQLLSRANLAKSRAQEALSMGNATFYEVESI LKNLREFDLQVDNRKAEAEEAMKRLSYISQKVSDASDKTQQAERALG SAAADAQRAKNGAGEALEISSEIEQEIGSLNLEANVTADGALAMEKGL ASLKSEMREVEGELERKELEFDTNMDAVQMVITEAQKVDTRAKNAG VTIQDTLNTLDGLLHLMGM |
| laminin subunit gamma-3 precursor (LAMC3); SEQ ID NO: 46 | MAAAALLLGLALLAPRAAGAGMGACYDGAGRPQRCLPVFENAAFGR LAQASHTCGSPPEDFCPHVGAAGAGAHCQRCDAADPQRHEINASYLT DFHSQDESTWWQSPSMAFGVQYPTSVNITLRLGKAYEITYVRLKFHTS RPESFAIYKRSRADGPWEPYQFYSASCQKTYGRPEGQYLRPGEDERVA FCTSEFSDISPLSGGNVAFSTLEGRPSAYNFEESPGLQEWVTSTELLISL DRLNTFGDDIFKDPKVLQSYYYAVSDFSVGGRCKCNGHASECGPDVA GQLACRCQHNTTGTDCERCLPFFQDRPWARGTAEAAHECLPCNCSGR SEECTFDRELFRSTGHGGRCHHCRDHTAGPHCERCQENFYHWDPRMP CQPCDCQSAGSLHLQCDDTGTCACKPTVTGWKCDRCLPGFHSLSEGG CRPCTCNPAGSLDTCDPRSGRCPCKENVEGNLCDRCRPGTFNLQPHNP AGCSSCFCYGHSKVCASTAQFQVHHILSDFHQGAEGWWARSVGGSEH PPQWSPNGVLLSPEDEEELTAPEKFLGDQRFSYGQPLILTFRVPPGDSPL PVQLRLEGTGLALSLRHSSLSGPQDAGHPREVELRFHLQETSEDVAPPL PPFHFQRLLANLTSLRLRVSPGPSPAGPVFLTEVRLTSARPGLSPPASW VEICSCPTGYTGQFCESCAPGYKREMPQGGPYASCVPCTCNQHGTCDP NTGICVCSHHTEGPSCERCLPGFYGNPFAGQADDCQPCPCPGQSACTTI PESREVVCTHCPPGQRGRRCEVCDDGFFGDPLGLFGHPQPCHQCQCSG NVDPNAVGNCDPLSGHCLRCLHNTTGDHCEHCQEGFYGSALAPRPAD KCMPCSCHPQGSVSEQMPCDPVTGQCSCLPHVTARDCSRCYPGFFDL QPGRGCRSCKCHPLGSQEDQCHPKTGQCTCRPGVTGQACDRCQLGFF GFSIKGCRACRCSPLGAASAQCHENGTCVCRPGFEGYKCDRCHDNFFL TADGTHCQQCPSCYALVKEEAAKLKARLTLTEGWLQGSDCGSPWGPL DILLGEAPRGDVYQGHEILLPGAREAFLEQMMSLEGAVKAAREQLQRL NKGARCAQAGSQKTCTQLADLEAVLESSEEEILHAAAILASLEIPQEGP SQPTKWSHLATEARALARSHRDTATKIAATAWRALLASNTSYALLWN LLEGRVALETQRDLEDRYQEVQAAQKALRTAVAEVLPEAESVLATVQ QVGADTAPYLALLASPGALPQKSRAEDLGLKAKALEKTVASWQHMA TEAARTLQTAAQATLRQTEPLTKLHQEARAALTQASSSVQAATVTVM GARTLLADLEGMKLQFPRPKDQAALQRKADSVSDRLLADTRKKTKQ AERMLGNAAPLSSSAKKKGREAEVLAKDSAKLAKALLRERKQAHRR ASRLTSQTQATLQQASQQVLASEARRQELEEAERVGAGLSEMEQQIRE SRISLEKDIETLSELLARLGSLDTHQAPAQALNETQWALERLRLQLGSP GSLQRKLSLLEQESQQQELQIQGFESDLAEIRADKQNLEAILHSLPENC ASWQ |

Further exemplary peptides useful in the methods and compositions of the disclosure include:

| SEQ ID NO: | Name (location) length | Peptide sequence |
|---|---|---|
| 1 | α3 $_{3043-3067}$ (LG4) 25 aa. | RLVFALGTDGKKLRIKSKEKCNDGK |
| 9 | α3 $_{3031-3043}$ (LG4) 13 aa. | KNSFMALYLSKGR |
| 2 | α3 $_{2932-2951}$ (Linker) 20 aa. | PPFLMLLKGSTRFNKTKTFR |
| 3 | α4 $_{1521-1543}$ (LG4) 23 aa. | TLFLAHGRLVYMFNVGHKKLKIR |
| 4 | α4 $_{1408-1434}$ (Linker) 27 aa. | PLFLLHKKGKNLSKPKASQNKKGGKSK |
| 5 | α5 $_{3539-3550}$ (LG5) 12 aa. | TLPDVGLELEVR |
| 6 | α5 $_{3417-3436}$ (LG4) 20 aa. | RQRSRPGRWHKVSVRWEKNR |
| 10 | α5 $_{3312-3325}$ (Linker) 14 aa. | ARKASRRSRQPARH |
| 7 | α5 $_{3300-3330}$ (Linker) 31 aa. | TPGLGPRGLQATARKASRRSRQPARHPACML |
| 8 | α2PI $_{1-8}$- α3 $_{3043-3067}$ 33 aa. | NQEQVSPLRLVFALGTDGKKLRIKSKEKCNDGK |
| 11 | α2PI $_{1-8}$- α5 $_{3312-3325}$ 22 aa. | NQEQVSPLARKASRRSRQPARH |
| 12 | α2PI $_{1-8}$ | NQEQVSPL |
| 49 | vWF A1 | YIGLKDRKRPSELRRIASQVKYAC |

In some embodiments, the compositions and methods comprise a peptide from a LG4 domain or fragment thereof. Exemplary LG4 domains are shown below:

| SEQ ID NO: | Name | Sequence |
|---|---|---|
| 13 | LAMA3_Human, LG4 domain aa2986-aa3150 (UniprotKB database Q16787) | ALQFGDIPTSHLLFKLPQELLKPRSQFAVDMQT TSSRGLVFHTGTKNSFMALYLSKGRLVFALGTD GKKLRIKSKEKCNDGKWHTVVFGHDGEKGRLVV DGLRAREGSLPGNSTISIRAPVYLGSPPSGKPK SLPTNSFVGCLKNFQLDSKPLYTPSSSFGVSSC |
| 14 | LAMA4_Human, LG4 domain aa1469-aa1640 | AYQYGGTANSRQEFEHLKGDFGAKSQFSIRLRT RSSHGMIFYVSDQEENDFMTLFLAHGRLVYMFN VGHKKLKIRSQEKYNDGLWHDVIFIRERSSGRL VIDGLRVLEESLPPTEATWKIKGPIYLGGVAPG KAVKNVQINSIYSFSGCLSNLQLNGASITSASQ TFSVTPC |
| | (UniprotKB database Q16363) | |
| 15 | LAMA5_Human, LG4 domain aa3340-aa3513 (UniprotKB database O15230) | SYQFGGSLSSHLEFVGILARHRNWPSLSMHVLP RSSRGLLLFTARLRPGSPSLALFLSNGHFVAQM EGLGTRLRAQSRQRSRPGRWHKVSVRWEKNRIL LVTDGARAWSQEGPHRQHQGAEHPQPHTLFVGG LPASSHSSKLPVTVGFSGCVKRLRLHGRPLGAP TRMAGVTPC |

In some embodiments, the compositions and methods include an engineered Laminin peptide comprising a factor XIIIa transglutaminase substrate domain from the α$_2$-plasmin inhibitor. Such exemplary peptides are described below:

| SEQ ID NO. | Name | Sequence |
|---|---|---|
| 16 | Human α2PI $_{1-8}$- LAMA3_ LG4 $_{2986-3150}$ | NQEQVSPLGGSGALQFGDIPTSHLLFKLP QELLKPRSQFAVDMQTTSSRGLVFHTGTK NSFMALYLSKGRLVFALGTDGKKLRIKSK EKCNDGKWHTVVFGHDGEKGRLVVDGLRA REGSLPGNSTISIRAPVYLGSPPSGKPKS LPTNSFVGCLKNFQLDSKPLYTPSSSFGV SSC |
| 17 | Human α2PI $_{1-8}$- LAMA4_ LG4 $_{1469-1640}$ | NQEQVSPLGGSGAYQYGGTANSRQEFEHL KGDFGAKSQFSIRLRTRSSHGMIFYVSDQ EENDFMTLFLAHGRLVYMFNVGHKKLKIR SQEKYNDGLWHDVIFIRERSSGRLVIDGL RVLEESLPPTEATWKIKGPIYLGGVAPGK AVKNVQINSIYSFSGCLSNLQLNGASITS ASQTFSVTPC |
| 18 | Human α2PI $_{1-8}$- LAMA5_ LG4 $_{3340-3513}$ | NQEQVSPLGGSGSYQFGGSLSSHLEFVGI LARHRNWPSLSMHVLPRSSRGLLLFTARL RPGSPSLALFLSNGHFVAQMEGLGTRLRA QSRQRSRPGRWHKVSVRWEKNRILLVTDG ARAWSQEGPHRQHQGAEHPQPHTLFVGGL PASSHSSKLPVTVGFSGCVKRLRLHGRPL GAPTRMAGVTPC |

In some embodiments, the compositions and methods comprise peptides comprising a collagen binding peptide. Exemplary collagen binding peptides are shown below.

| SEQ ID NO. | Name | Sequence |
|---|---|---|
| 47 | vWF A3 domain | CSQPLDVILLLDGSSSFPASYFDEMKSFAKAFISKA NIGPRLTQVSVLQYGSITTIDVPWNVVPEKAHLLS LVDVMQREGGPSQIGDALGFAVRYLTSEMHGAR PGASKAVVILVTDVSVDSVDAAADAARSNRVTV FPIGIGDRYDAAQLRILAGPAGDSNVVKLQRIEDL PTMVTLGNSFLHKLCSGFVRICTG |
| 48 | Decorin | CGPFQQRGLFDFMLEDEASGIGPEVPDDRDFEPSL GPVCPFRCQCHLRVVQCSDLGLDKVPKDLPPDTT LLDLQNNKITEIKDGDFKNLKNLHALILVNNKISK VSPGAFTPLVKLERLYLSKNQLKELPEKMPKTLQ ELRAHENEITKVRKVTFNGLNQMIVIELGTNPLKS SGIENGAFQGMKKLSYIRIADTNITSIPQGLPPSLTE LHLDGNKISRVDAASLKGLNNLAKLGLSFNSISAV |

| SEQ ID NO. | Name | Sequence |
|---|---|---|
| | | DNGSLANTPHLRELHLDNNKLTRVPGGLAEHKYI QVVYLHNNNISVVGSSDFCPPGHNTKKASYSGVS LFSNPVQYWEIQPSTFRCVYVRSAIQLGNYK |

The growth factor-binding peptide may be a peptide with 75, 76, 77, 78, 79, 80, 81, 82, 83, 84, 85, 86, 87, 88, 89, 90, 91, 92, 93, 94, 95, 96, 97, 98, 99, or 100% identity (or any derivable range therein) to a peptide of the disclosure, such as peptides, proteins, or polypeptides defined by any one of SEQ ID NOS:1-50. The peptide or polypeptide may have one or more conservative or non-conservative substitutions. Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

Embodiments of the disclosure include a peptide/polypeptide that is at least, at most, or exactly 75, 76, 77, 78, 79, 80, 81, 82, 83, 84, 85, 86, 87, 88, 89, 90, 91, 92, 93, 94, 95, 96, 97, 98, 99, or 100% identical (or any derivable range therein) to a peptide or polypeptide/polypeptide that has at least, at most, or exactly 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more contiguous amino acids, or any range derivable therein to a peptide/polypeptide that starts at position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, or 450 of any one of SEQ ID NOS:1-50.

The polypeptides or peptides described herein may include 1, 2, 3, 4, 5, 6, 7, 8, 9, 10, 11, 12, 13, 14, 15, or more (or any derivable range therein) variant amino acids within at least, or at most 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more contiguous amino acids, or any range derivable therein, of a peptide or polypeptide of the disclosure, such as peptides, proteins, or polypeptides defined by any one of SEQ ID NOS:1-50.

A polypeptide segment as described herein may include 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more contiguous amino acids, or any range derivable therein of a peptide or polypeptide of the disclosure, such as peptides, proteins, or polypeptides defined by any one of SEQ ID NOS:1-50.

The polypeptides or peptides described herein may be of a fixed length of at least, at most, or exactly 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more amino acids (or any derivable range therein) or a peptide or polypeptide of the disclosure, such as peptides, proteins, or polypeptides defined by any one of SEQ ID NOS:1-50.

A linker sequence may be included in the peptide construction. For example, a linker having at least, at most, or exactly 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids (or any derivable range therein) may separate a peptide of the disclosure, such as peptides, proteins, or polypeptides defined by any one of SEQ ID NOS:1-50, to an attached moiety, such as a transglutaminase-reactive peptide, a collagen binding peptide, cell adhesion moiety, tag, or functional moiety. In some embodiments, the linker comprises a glycine serine linker. In some embodiments, the linker comprises (GSGG)$_x$ (SEQ ID NO:60), wherein x=1-6. In some embodiments, x=2. In some embodiments, x=1, 2, 3, 4, 5, or 6 (or any derivable range therein) In some embodiments, the linker comprises GSGGGSGG (SEQ ID NO:61).

B. Exemplary Attachments to the Growth Factor Binding Peptides/Polypeptides

Embodiments include a growth factor binding peptide attached to moieties such as a functional moiety. In some embodiments, the functional moiety may be a therapeutic agent, marker, cell adhesion molecule, antigen, protein, protein drug, or cytokine. In some embodiments, the growth factor binding peptide is attached to a second growth factor binding peptide. In some embodiments, the growth factor binding peptide is attached to a chemical moiety, such as a marker or fluorescent marker. The fusion comprises the peptides conjugated directly or indirectly to each other. The peptides may be directly conjugated to each other or indirectly through a linker. The linker may be a peptide, a polymer, an aptamer, a nucleic acid, or a particle. The particle may be, e.g., a microparticle, a nanoparticle, a polymersome, a liposome, or a micelle. The polymer may be, e.g., natural, synthetic, linear, or branched. A fusion protein that comprises the first peptide and the second peptide is an example of a molecular fusion of the peptides, with the fusion protein comprising the peptides directly joined to each other or with intervening linker sequences and/or further sequences at one or both ends. The conjugation to the linker may be through covalent bonds. Methods include preparing a molecular fusion or a composition comprising the molecular fusion, including such a composition in a pharmaceutically acceptable form.

Embodiments include a molecular fusion of a polypeptide that comprises a growth factor binding peptide and a transglutaminase (TG)-reactive peptide. An embodiment of a TG-reactive peptide is a peptide that comprises residues 1-8 of alpha 2-plasmin inhibitor (NQEQVSPL) (SEQ ID NO:12). In some embodiments, the TG-reactive peptide is at the amino terminus of the growth factor binding peptide. In some embodiments, the TG-reactive peptide is at the carboxy terminus of the growth factor binding peptide. Embodiments include such a polypeptide being a recombinant fusion polypeptide. The molecular fusion may be further comprising a cell adhesion moiety having a specific binding affinity for a cell adhesion molecule. Various cell adhesion moieties are known, for instance, wherein the cell adhesion moiety comprises a ligand for a glycoprotein or a cell surface receptor. Or the cell adhesion moiety may comprise a ligand with specific binding to the cell adhesion molecule and the cell adhesion molecule is a cell surface receptor chosen from the group consisting of an integrin, and a cadherin. Or the cell adhesion moiety may comprise an integrin-binding peptide such as Tenascin III3, an RGD sequence.

In some aspects, the peptide or polypeptide of the disclosure is attached to a tag. The tag may be a purification tag, a signaling sequence, a detectable marker, a post-translational modifier, or a targeting moiety. In some embodiments, the peptide or polypeptide is attached to a functional moiety such as an enzyme, a fluorescent compound, or a therapeutic agent. Detectable markers include, for example, a radioactive atom, a chromophore, a fluorophore, or the like. Other examples of tags or functional moieties include enzymes, radioisotopes, fluorochromes, chemiluminescent compounds, dyes, and proteins. Examples of luminescent labels that produce signals include, but are not limited to bioluminescence and chemiluminescence. Detectable luminescence response generally comprises a change in, or an occurrence of, a luminescence signal. Suitable methods and luminophores for luminescently labeling assay components are known in the art and described for example in Haugland, Richard P. (1996) Handbook of Fluorescent Probes and Research Chemicals (6.sup.th ed.). Examples of luminescent probes include, but are not limited to, aequorin and luciferases. Examples of suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, and Texas Red. Other suitable optical dyes are described in the Haugland, Richard P. (1996) Handbook of Fluorescent Probes and Research Chemicals (6.sup.th ed.). In another aspect, the fluorescent label is functionalized to facilitate covalent attachment to a cellular component present in or on the surface of the cell or tissue such as a cell surface marker. Suitable functional groups, including, but not are limited to, isothiocyanate groups, amino groups, haloacetyl groups, maleimides, succinimidyl esters, and sulfonyl halides, all of which may be used to attach the fluorescent label to a second molecule. The choice of the functional group of the fluorescent label will depend on the site of attachment to either a linker, the agent, the marker, or the second labeling agent. Attachment of a tag or functional moiety may be either directly to the cellular component or compound or alternatively, can by via a linker. Suitable binding pairs for use in indirectly linking the fluorescent label to the intermediate include, but are not limited to, antigens/antibodies, e.g., rhodamine/anti-rhodamine, biotin/avidin and biotin/strepavidin.

In some embodiments, the functional moiety comprises an imaging agent. Exemplary imaging agents include gadolinium, iodine, barium, or a radio pharmaceutical such as calcium-47, carbon-11, carbon-14, chromium-51, cobalt-57, cobalt-58, erbium-169, fluorine-18, gallium-67, gallium-68, hydrogen-3, indium-111, iodine-123, iodine-125, iodine-131, iron-59, krypton-81m, nitrogen-13, oxygen-15, phosphorus-32, radium-223, rubidium-82, samarium-153, selenium-75, sodium-22, sodium-24, strontium-89, technetium-99m, thallium-201, xenon-133, and yttrium-90.

The term molecular fusion, or the term conjugated, refers to direct or indirect association by chemical bonds, including covalent, electrostatic ionic, or charge-charge. In some embodiments, the conjugation is through a peptide bond. The conjugation creates a unit that is sustained by chemical bonding. Direct conjugation refers to chemical bonding to the agent, with or without intermediate linkers or chemical groups. Indirect conjugation refers to chemical linkage to a carrier. The carrier may largely encapsulate the agent, e.g., a polymersome, a liposome or micelle or some types of nanoparticles, or have the agent on its surface, e.g., a metallic nanoparticle or bead, or both, e.g., a particle that includes some of the agent in its interior as well as on its exterior. The carrier may also encapsulate an antigen for immunotolerance. For instance a polymersome, liposome, or a particle may be made that encapsulates the antigen. The term encapsulate means to cover entirely, effectively without any portion being exposed, for instance, a polymersome may be made that encapsulates an antigen or an agent.

Conjugation may be accomplished by covalent bonding of the peptide to another molecule, with or without use of a linker. The formation of such conjugates is within the skill of artisans and various techniques are known for accomplishing the conjugation, with the choice of the particular technique being guided by the materials to be conjugated. The addition of amino acids to the polypeptide (C- or N-terminal) which contain ionizable side chains, i.e. aspartic acid, glutamic acid, lysine, arginine, cysteine, histidine, or tyrosine, and are not contained in the active portion of the polypeptide sequence, serve in their unprotonated state as a potent nucleophile to engage in various bioconjugation reactions with reactive groups attached to polymers, i.e. homo- or hetero-bi-functional PEG (e.g., Lutolf and Hubbell, Biomacromolecules 2003; 4:713-22, Hermanson, Bioconjugate Techniques, London. Academic Press Ltd; 1996).

In some embodiments, a soluble polymer linker is used, and may be administered to a patient in a pharmaceutically acceptable form. Or a drug may be encapsulated in polymerosomes or vesicles or covalently attached to the peptide ligand.

The molecular fusion may comprise a particle. The growth factor binding peptide may be attached to the particle. An antigen, agent, or other substance may be in or on the particle. Examples of nanoparticles, micelles, and other particles are found at, e.g., US 2008/0031899, US 2010/0055189, US 2010/0003338, which applications are hereby incorporated by reference herein for all purposes, including combining the same with a ligand as set forth herein; in the case of conflict, however, the instant specification controls.

Nanoparticles may be prepared as collections of particles having an average diameter of between about 10 nm and about 200 nm, including all ranges and values between the explicitly articulated bounds, e.g., from about 20 to about 200, and from about 20 to about 40, to about 70, or to about 100 nm, depending on the polydispersity which is yielded by the preparative method. Various nanoparticle systems can be utilized, such as those formed from copolymers of poly(ethylene glycol) and poly(lactic acid), those formed from copolymers of poly(ethylene oxide) and poly(beta-amino ester), and those formed from proteins such as serum albumin. Other nanoparticle systems are known to those skilled in these arts. See also Devalapally et al., Cancer Chemother Pharmacol., Jul. 25, 2006; Langer et al., International Journal of Pharmaceutics, 257:169-180 (2003); and Tobio et al., Pharmaceutical Research, 15(2):270-275 (1998).

Larger particles of more than about 200 nm average diameter incorporating the growth factor binding peptides may also be prepared, with these particles being termed microparticles herein since they begin to approach the micron scale and fall approximately within the limit of optical resolution. For instance, certain techniques for making microparticles are set forth in U.S. Pat. Nos. 5,227,165, 6,022,564, 6,090,925, and 6,224,794.

Functionalization of nanoparticles to employ targeting capability requires association of the targeting polypeptide with the particle, e.g., by covalent binding using a bioconjugation technique, with choice of a particular technique being guided by the particle or nanoparticle, or other construct, that the polypeptide is to be joined to. In general, many bioconjugation techniques for attaching peptides to other materials are well known and the most suitable technique may be chosen for a particular material. For instance, additional amino acids may be attached to the polypeptide sequences, such as a cysteine in the case of attaching the polypeptide to thiol-reactive molecules.

The molecular fusion may comprise a polymer. The polymer may be branched or linear.

The molecular fusion may comprise a dendrimer. In general, soluble hydrophilic biocompatible polymers may be used so that the conjugate is soluble and is bioavailable after introduction into the patient. Examples of soluble polymers are polyvinyl alcohols, polyethylene imines, and polyethylene glycols (a term including polyethylene oxides) having a molecular weight of at least 100, 400, or between 100 and 400,000 (with all ranges and values between these explicit values being contemplated). Solubility in this context refers to a solubility in water or physiological saline of at least 1 gram per liter. Domains of biodegradable polymers may also be used, e.g., polylactic acid, polyglycolic acid, copolymers of polylactic and polyglycolic acid, polycaprolactones, polyhydroxy butyric acid, polyorthoesters, polyacetals, polydihydropyrans, and polycyanoacylates.

II. NUCLEIC ACIDS

In certain embodiments, the current disclosure concerns recombinant polynucleotides encoding the proteins, polypeptides, and peptides of the disclosure.

As used in this application, the term "polynucleotide" refers to a nucleic acid molecule that either is recombinant or has been isolated free of total genomic nucleic acid. Included within the term "polynucleotide" are oligonucleotides (nucleic acids of 100 residues or less in length), recombinant vectors, including, for example, plasmids, cosmids, phage, viruses, and the like. Polynucleotides include, in certain aspects, regulatory sequences, isolated substantially away from their naturally occurring genes or protein encoding sequences. Polynucleotides may be single-stranded (coding or antisense) or double-stranded, and may be RNA, DNA (genomic, cDNA or synthetic), analogs thereof, or a combination thereof. Additional coding or non-coding sequences may, but need not, be present within a polynucleotide.

In this respect, the term "gene," "polynucleotide," or "nucleic acid" is used to refer to a nucleic acid that encodes a protein, polypeptide, or peptide (including any sequences required for proper transcription, post-translational modification, or localization). As will be understood by those in the art, this term encompasses genomic sequences, expression cassettes, cDNA sequences, and smaller engineered nucleic acid segments that express, or may be adapted to express, proteins, polypeptides, domains, peptides, fusion proteins, and mutants. A nucleic acid encoding all or part of a polypeptide may contain a contiguous nucleic acid sequence of: 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1095, 1100, 1500, 2000, 2500, 3000, 3500, 4000, 4500, 5000, 5500, 6000, 6500, 7000, 7500, 8000, 9000, 10000, or more nucleotides, nucleosides, or base pairs, including all values and ranges there between, of a polynucleotide encoding one or more amino acid sequence described or referenced herein. It also is contemplated that a particular polypeptide may be encoded by nucleic acids containing variations having slightly different nucleic acid sequences but, nonetheless, encode the same or substantially similar protein.

In particular embodiments, the invention concerns isolated nucleic acid segments and recombinant vectors incorporating nucleic acid sequences that encode a polypeptide or peptide of the disclosure. The term "recombinant" may be used in conjunction with a polynucleotide or polypeptide and generally refers to a polypeptide or polynucleotide produced and/or manipulated in vitro or that is a replication product of such a molecule.

In other embodiments, the invention concerns isolated nucleic acid segments and recombinant vectors incorporating nucleic acid sequences that encode a polypeptide or peptide of the disclosure.

The nucleic acid segments used in the current disclosure can be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant nucleic acid protocol. In some cases, a nucleic acid sequence may encode a polypeptide sequence with additional heterologous coding sequences, for example to allow for purification of the polypeptide, transport, secretion, post-translational modification, or for therapeutic benefits such as targeting or efficacy. As discussed above, a tag or other heterologous polypeptide may be added to the modified polypeptide-encoding sequence, wherein "heterologous" refers to a polypeptide that is not the same as the modified polypeptide.

In certain embodiments, the current disclosure provides polynucleotide variants having substantial identity to the sequences disclosed herein; those comprising at least 70%, 75%, 80%, 85%, 90%, 95%, 96%, 97%, 98%, or 99% or higher sequence identity, including all values and ranges there between, compared to a polynucleotide sequence of this disclosure using the methods described herein (e.g., BLAST analysis using standard parameters).

The disclosure also contemplates the use of polynucleotides which are complementary to all the above described polynucleotides.

A. Vectors

Polypeptides of the disclosure may be encoded by a nucleic acid molecule comprised in a vector. The term "vector" is used to refer to a carrier nucleic acid molecule into which a heterologous nucleic acid sequence can be inserted for introduction into a cell where it can be replicated and expressed. A nucleic acid sequence can be "heterologous," which means that it is in a context foreign to the cell in which the vector is being introduced or to the nucleic acid in which is incorporated, which includes a sequence homologous to a sequence in the cell or nucleic acid but in a position within the host cell or nucleic acid where it is ordinarily not found. Vectors include DNAs, RNAs, plasmids, cosmids, viruses (bacteriophage, animal viruses, and plant viruses), and artificial chromosomes (e.g., YACs). One of skill in the art would be well equipped to construct a vector through standard recombinant techniques (for example Sambrook et al., 2001; Ausubel et al., 1996, both incorporated herein by reference). In addition to encoding a polypeptide of the disclosure, the vector can encode other polypeptide sequences such as a one or more other bacterial peptide, a tag, or an immunogenicity enhancing peptide. Useful vectors encoding such fusion proteins include pIN vectors (Inouye et al., 1985), vectors encoding a stretch of histidines, and pGEX vectors, for use in generating glutathione S-transferase (GST) soluble fusion proteins for later purification and separation or cleavage. In some embodiments, the vector comprises pSeqTag-A or pcDNA3.1.

The term "expression vector" refers to a vector containing a nucleic acid sequence coding for at least part of a gene product capable of being transcribed. In some cases, RNA molecules are then translated into a protein, polypeptide, or peptide. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described herein.

B. Promoters and Enhancers

A "promoter" is a control sequence. The promoter is typically a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and expression of that sequence. A promoter may or may not be used in conjunction with an "enhancer," which refers to a cis-acting regulatory sequence involved in the transcriptional activation of a nucleic acid sequence.

Naturally, it may be important to employ a promoter and/or enhancer that effectively directs the expression of the DNA segment in the cell type or organism chosen for expression. Those of skill in the art of molecular biology generally know the use of promoters, enhancers, and cell type combinations for protein expression (see Sambrook et al., 2001, incorporated herein by reference). The promoters employed may be constitutive, tissue-specific, or inducible and in certain embodiments may direct high level expression of the introduced DNA segment under specified conditions, such as large-scale production of recombinant proteins or peptides.

Various elements/promoters may be employed in the context of the present invention to regulate the expression of a gene. Examples of such inducible elements, which are regions of a nucleic acid sequence that can be activated in response to a specific stimulus, include but are not limited to Immunoglobulin Heavy Chain (Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990), Immunoglobulin Light Chain (Queen et al., 1983; Picard et al., 1984), T Cell Receptor (Luria et al., 1987; Winoto et al., 1989; Redondo et al.; 1990), HLA DQ α and/or DQ β (Sullivan et al., 1987), β Interferon (Goodbourn et al., 1986; Fujita et al., 1987; Goodbourn et al., 1988), Interleukin-2 (Greene et al., 1989), Interleukin-2 Receptor (Greene et al., 1989; Lin et al., 1990), MHC Class II 5 (Koch et al., 1989), MHC Class II HLA-DRα (Sherman et al., 1989), β-Actin (Kawamoto et al., 1988; Ng et al.; 1989), Muscle Creatine Kinase (MCK) (Jaynes et al., 1988; Horlick et al., 1989; Johnson et al., 1989), Prealbumin (Transthyretin) (Costa et al., 1988), Elastase I (Ornitz et al., 1987), Metallothionein (MTII) (Karin et al., 1987; Culotta et al., 1989), Collagenase (Pinkert et al., 1987; Angel et al., 1987), Albumin (Pinkert et al., 1987; Tronche et al., 1989, 1990), α-Fetoprotein (Godbout et al., 1988; Campere et al., 1989), γ-Globin (Bodine et al., 1987; Perez-Stable et al., 1990), β-Globin (Trudel et al., 1987), c-fos (Cohen et al., 1987), c-Ha-Ras (Triesman, 1986; Deschamps et al., 1985), Insulin (Edlund et al., 1985), Neural Cell Adhesion Molecule (NCAM) (Hirsh et al., 1990), α1-Antitrypain (Latimer et al., 1990), H2B (TH2B) Histone (Hwang et al., 1990), Mouse and/or Type I Collagen (Ripe et al., 1989), Glucose-Regulated Proteins (GRP94 and GRP78) (Chang et al., 1989), Rat Growth Hormone (Larsen et al., 1986), Human Serum Amyloid A (SAA) (Edbrooke et al., 1989), Troponin I (TN I) (Yutzey et al., 1989), Platelet-Derived Growth Factor (PDGF) (Pech et al., 1989), Duchenne Muscular Dystrophy (Klamut et al., 1990), SV40 (Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988), Polyoma (Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell et al., 1988), Retroviruses (Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989), Papilloma Virus (Campo et al., 1983; Lusky et al., 1983; Spandidos and Wilkie, 1983; Spalholz et al., 1985; Lusky et al., 1986; Cripe et al., 1987; Gloss et al., 1987; Hirochika et al., 1987; Stephens et al., 1987), Hepatitis B Virus (Bulla et al., 1986; Jameel et al., 1986; Shaul et al., 1987; Spandau et al., 1988; Vannice et al., 1988), Human Immunodeficiency Virus (Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989), Cytomegalovirus (CMV) IE (Weber et al., 1984; Boshart et al., 1985; Foecking et al., 1986), Gibbon Ape Leukemia Virus (Holbrook et al., 1987; Quinn et al., 1989).

Inducible elements include, but are not limited to MT II—Phorbol Ester (TFA)/Heavy metals (Palmiter et al., 1982; Haslinger et al., 1985; Searle et al., 1985; Stuart et al., 1985; Imagawa et al., 1987, Karin et al., 1987; Angel et al., 1987b; McNeall et al., 1989); MMTV (mouse mammary tumor virus)—Glucocorticoids (Huang et al., 1981; Lee et al., 1981; Majors et al., 1983; Chandler et al., 1983; Lee et al., 1984; Ponta et al., 1985; Sakai et al., 1988); β-Interferon—poly(rI)x/poly(rc) (Tavernier et al., 1983); Adenovirus 5 E2—E1A (Imperiale et al., 1984); Collagenase—Phorbol Ester (TPA) (Angel et al., 1987a); Stromelysin—Phorbol Ester (TPA) (Angel et al., 1987b); SV40—Phorbol Ester (TPA) (Angel et al., 1987b); Murine MX Gene—Interferon, Newcastle Disease Virus (Hug et al., 1988); GRP78 Gene—A23187 (Resendez et al., 1988); α-2-Macroglobulin—IL-6 (Kunz et al., 1989); Vimentin—Serum (Rittling et al., 1989); MEW Class I Gene H-2κb—Interferon (Blanar et al., 1989); HSP70—E1A/SV40 Large T Antigen (Taylor et al., 1989, 1990a, 1990b); Proliferin—Phorbol Ester/TPA (Mordacq et al., 1989); Tumor Necrosis Factor—PMA (Hensel et al., 1989); and Thyroid Stimulating Hormone α Gene—Thyroid Hormone (Chatterjee et al., 1989).

The particular promoter that is employed to control the expression of peptide or protein encoding polynucleotide of the invention is not believed to be critical, so long as it is capable of expressing the polynucleotide in a targeted cell, preferably a bacterial cell. Where a human cell is targeted, it is preferable to position the polynucleotide coding region adjacent to and under the control of a promoter that is capable of being expressed in a human cell. Generally speaking, such a promoter might include either a bacterial, human or viral promoter.

C. Initiation Signals and Internal Ribosome Binding Sites (IRES)

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988; Macejak and Sarnow, 1991). IRES elements can be linked to heterologous open reading frames. Multiple open reading frames can be transcribed together, each separated by an IRES, creating polycistronic messages. Multiple genes can be efficiently expressed using a single promoter/enhancer to transcribe a single message (see U.S. Pat. Nos. 5,925,565 and 5,935,819, herein incorporated by reference).

D. Selectable and Screenable Markers

In certain embodiments of the invention, cells containing a nucleic acid construct of the current disclosure may be identified in vitro or in vivo by encoding a screenable or selectable marker in the expression vector. When transcribed and translated, a marker confers an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker. As an alternative, 2A peptides could be used to introduce ribosomal skips to enable expression of multiple polypeptidic or protein sequences.

E. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector or expressing a heterologous gene encoded by a vector. A host cell can, and has been, used as a recipient for vectors or viruses. A host cell may be "transfected" or "transformed," which refers to a process by which exogenous nucleic acid, such as a recombinant protein-encoding sequence, is transferred or introduced into the host cell. A transformed cell includes the primary subject cell and its progeny.

Host cells may be derived from prokaryotes or eukaryotes, including bacteria, yeast cells, insect cells, and mammalian cells for replication of the vector or expression of part or all of the nucleic acid sequence(s). Numerous cell lines and cultures are available for use as a host cell, and they can be obtained through the American Type Culture Collection (ATCC), which is an organization that serves as an archive for living cultures and genetic materials (www.atcc.org).

F. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

In addition to the disclosed expression systems of the invention, other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

III. COMPOSITIONS

In some embodiments, pharmaceutical compositions are administered to a subject. Different aspects involve administering an effective amount of a composition to a subject. In some embodiments, a composition comprising a peptide of the disclosure may be administered to the subject or patient to treat wounds or facilitate wound, tissue, or bone repair. Additionally, such compositions can be administered in combination with an additional therapy.

A. Carriers and Excipients

Pharmaceutically acceptable carriers or excipients may be used to deliver embodiments as described herein. Excipient refers to an inert substance used as a diluent or vehicle for a therapeutic agent. Pharmaceutically acceptable carriers are used, in general, with a compound (eg. peptide of the disclosure) so as to make the compound useful for a therapy or as a product. In general, for any substance, a carrier is a material that is combined with the substance for delivery to an animal. Conventional pharmaceutical carriers, aqueous, powder or oily bases, thickeners and the like may be necessary or desirable. In some cases the carrier is essential for delivery, e.g., to solubilize an insoluble compound for liquid delivery; a buffer for control of the pH of the substance to preserve its activity; or a diluent to prevent loss of the substance in the storage vessel. In other cases, however, the carrier is for convenience, e.g., a liquid for more convenient administration. Pharmaceutically acceptable salts of the compounds described herein may be synthesized according to methods known to those skilled in the arts. Thus a pharmaceutically acceptable compositions are highly purified to be free of contaminants, are sterile, biocompatible and not toxic, and further may include a carrier, salt, or excipient suited to administration to a patient. In the case of water as the carrier, the water is highly purified and processed to be free of contaminants, e.g., endotoxins.

The compounds described herein may be administered in admixture with suitable pharmaceutical diluents, excipients, extenders, or carriers (termed herein as a pharmaceutically acceptable carrier, or a carrier) suitably selected with respect to the intended form of administration and as consistent with conventional pharmaceutical practices. Thus the deliverable compound may be made in a form suitable for oral, rectal, topical, intravenous injection, intra-articular injection, intradermal, intramuscular, and/or parenteral administration. Carriers include solids or liquids, and the type of carrier is chosen based on the type of administration being used. Suitable binders, lubricants, disintegrating agents, coloring agents, flavoring agents, flow-inducing agents, and melting agents may be included as carriers, e.g., for pills. For instance, an active component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. The compounds can be administered orally in solid dosage forms, such as capsules, tablets, and powders, or in liquid dosage forms, such as elixirs, syrups, and suspensions. The active compounds can also be administered parentally, in sterile liquid dosage forms. Buffers for achieving a physiological pH or osmolarity may also be used.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. The term "pharmaceutically acceptable carrier," means a pharmaceutically acceptable material, composition or vehicle, such as a liquid or solid filler, diluent, excipient, solvent or encapsulating material, involved in carrying or transporting a chemical agent.

As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. Pharmaceutically acceptable salts include the conventional non-toxic salts or the quaternary ammonium salts of the parent compound formed, for example, from non-toxic inorganic or organic acids. The pharmaceutically acceptable salts can be synthesized from the parent compound which contains a basic or acidic moiety by conventional chemical methods.

B. Dosage

Some variation in dosage will necessarily occur depending on the condition of the subject. The person responsible for administration will, in any event, determine the appropriate dose for the individual subject. An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the effects desired. Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition.

Upon formulation, solutions will be administered in a manner compatible with the dosage formulation and in such amount as is therapeutically or prophylactically effective. The formulations are easily administered in a variety of dosage forms, such as the type of injectable solutions described above.

Typically, for a human adult (weighing approximately 70 kilograms), from about 0.1 mg to about 3000 mg (including all values and ranges there between), or from about 5 mg to about 1000 mg (including all values and ranges there between), or from about 10 mg to about 100 mg (including all values and ranges there between), of a compound are administered. It is understood that these dosage ranges are by way of example only, and that administration can be adjusted depending on the factors known to the skilled artisan.

In certain embodiments, a subject is administered about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000 milligrams (mg) or micrograms (mcg) or µg/kg or micrograms/kg/minute or mg/kg/min or micrograms/kg/hour or mg/kg/hour, or any range derivable therein of an agent of the disclosure (e.g. growth factor, cytokine, peptide, polypeptide, functional moiety, etc. . . . ).

A dose may be administered on an as needed basis or every 1, 2, 3, 4, 5, 6, 7, 8, 9, 10, 11, 12, 18, or 24 hours (or any range derivable therein) or 1, 2, 3, 4, 5, 6, 7, 8, 9, or times per day (or any range derivable therein). A dose may be first administered before or after signs of a condition. In some embodiments, the patient is administered a first dose of a regimen 1, 2, 3, 4, 5, 6, 7, 8, 9, 10, 11, 12 hours (or any range derivable therein) or 1, 2, 3, 4, or 5 days after the patient experiences or exhibits signs or symptoms of the condition (or any range derivable therein). The patient may be treated for 1, 2, 3, 4, 5, 6, 7, 8, 9, 10 or more days (or any range derivable therein) or until symptoms of the condition have disappeared or been reduced or after 6, 12, 18, or 24 hours or 1, 2, 3, 4, or 5 days after symptoms of an infection have disappeared or been reduced.

C. Growth Factors and Cytokines

Certain embodiments of the disclosure relate to compositions, molecular complexes, biomaterials, and implants comprising growth factors and cytokines. Exemplary non-limiting growth factors and cytokines include mammalian proteins such as ANG-1, ANG-2, EGF, EPO, NGF, FGF-2, FGF-4, FGF-6, FGF-7, FGF-10, FGF-17, FGF-18, TGF-α, TGF-β, TGF-β1, TGF-β2, TGF-β3, NGF, NT-3, BDNF, PlGF-1, PlGF-2, PlGF-3, BMP-2, BMP-7, BMP-9 PDGF-AA, PDGF-AB, PDGF-BB, PDGF-DD, VEGF-A165, VEGF-A121, VEGF-B, VEGF-C, VEGF-D, IGF-1, IGF-BP3, IGF-BP5, HGF, EGF, HB-EGF, CXCL12, or CXCL11. In some embodiments, the growth factor or cytokine is a mammalian growth factor or cytokine. In some embodiments, the growth factor or cytokine is a human, mouse, pig, monkey, horse, goat, rabbit, sheep or rat growth factor or cytokine. In some embodiments, one or more of ANG-1, ANG-2, EGF, EPO, NGF, FGF-2, FGF-4, FGF-6, FGF-7, FGF-10, FGF-17, FGF-18, TGF-α, TGF-β, TGF-β1, TGF-β2, NT-3, BDNF, PlGF-1, PlGF-2, PlGF-3, BMP-2, BMP-7, PDGF-AA, PDGF-AB, PDGF-BB, PDGF-DD, VEGF-A165, VEGF-A121, VEGF-B, VEGF-C, IGF-1, IGF-BP3, IGF-BP5, or HGF are specifically excluded from the compositions, molecular complexes, scaffolds, implants, or matrices described herein. In some embodiments, at least, at most, or exactly, 1, 2, 3, 4, 5, 6, 7, 8, 9, 10, 15, 20, 25, or 30 (or any derivable range therein) of ANG-1, ANG-2, EGF, EPO, NGF, FGF-2, FGF-4, FGF-6, FGF-7, FGF-10, FGF-17, FGF-18, TGF-α, TGF-β, TGF-β1, TGF-β2, NT-3, BDNF, PlGF-1, PlGF-2, PlGF-3, BMP-2, BMP-7, PDGF-AA, PDGF-AB, PDGF-BB, PDGF-DD, VEGF-A165, VEGF-A121, VEGF-B, VEGF-C, IGF-1, IGF-BP3, IGF-BP5, or HGF is included in the embodiments of the disclosure

IV. BIOMATERIAL SCAFFOLD AND IMPLANTS

Certain embodiments of the disclosure relate to biomaterial scaffolds or matrix comprising the peptide or polypeptides of the disclosure. The term matrix refers to a three-dimensional structure, including a block, gel, sheet, or film; it is a term used in contrast to a soluble or fluid material. The scaffolds have to withstand mechanical loads, contain suitable degradation kinetics, and present bioactive molecules. Scaffolds function as a fusion of cell carrier and drug delivery device for the purpose of tissue engineering. To mimic the natural microenvironment for cells in order to induce tissue repair and regeneration, synthetic materials can be modified with ECM fragments. ECM fragments described herein may be designed to form a molecular fusion with a transglutaminase (TG) peptide at the N or C terminus. In some embodiments, the TG-reactive peptide consists of residues 1-8 of the protein alpha2 plasmin inhibitor ($\alpha_2PI_{1-8}$, NQEQVSPL (SEQ ID NO:12)). Factor XIIIa can therefore be used as a transglutaminase to catalyze the reaction between the glutamines of this sequence (NQEQVSPL (SEQ ID NO: 12)) and the lysines of different biomaterials. The coagulation enzyme, factor XIIIa, will covalently bind the free amine group of the lysines (Lys) to the gamma-carboxamid group of glutamine (Gln), resulting in bonds that exhibit high resistance to proteolytic degradation. For example, natural fibrin hydrogels are cross-linked by this mechanism and TG-TNC III1-5 can therefore be cross-linked inside the gel (Schense and Hubbell, 1999).

Modification of synthetic hydrogels is possible by engineering counter-substrates for transglutaminases, such as lysines inside poly ethylene glycol (PEG-Lys) hydrogels. PEG is modified with lysines by chemically cross-linking a lysine containing peptide that includes The SH group of the cysteine functions as nucleophile (Mikael donor) in a Mikael type addition, with VS functioning as Michael acceptor (Lutolf, Lauer-Fields, et al., 2003). This technology has been used to make TG-PEG gels, which are cross-linked by two multi-arm PEG-peptide conjugates, PEG-Lys and PEG-Gln, in the presence of factor XIII, which allows for incorporation of other proteins containing a TG substrate (Ehrbar, Rizzi, et al., 2007). Alternatively, chemical crosslinking through cysteine residues may be used to attach proteins, peptides, and polypeptides to polymeric compositions and gels.

The peptide, polypeptides, compositions, and molecular complexes of the disclosure can be further immobilized into biomaterial matrices, forming additional embodiments. The peptides and polypeptides can be fused to a transglutaminase substrate that can covalently bind to natural protein biomaterials such as fibrin or to synthetic biomaterials engineered to comprise counter-substrates for transglutaminases.

Biomaterial scaffolds useful in the embodiments of the disclosure may comprise ceramics, synthetic polymers, and/or natural polymers. Ceramic scaffolds include, for example, hydroxyapatite (HA) and tri-calcium phosphate (TCP). Ceramic scaffolds are typically characterized by high mechanical stiffness (Young's modulus), very low elasticity, and a hard brittle surface. Examples of synthetic polymers include polystyrene, poly-1-lactic acid (PLLA), polyglycolic acid (PGA) and poly-dl-lactic-co-glycolic acid (PLGA). Exemplary natural polymers include collagen, proteoglycans, alginate-based substrates, and chitosan. Natural polymers are biologically active and typically promote excellent cell adhesion and growth. Furthermore, they are also biodegradable and so allow host cells, over time, to produce their own extracellular matrix and replace the degraded scaffold. In some embodiments, the biomaterial scaffold may comprise different components such as ceramics and natural or synthetic polymers.

According to a further aspect of the present invention, the biomaterial scaffold or implant comprises synthetic cartilage, bone, ligament, tendon, meniscus, periodontal tissue, dentine, enamel, intervertebral disc, annulus fibrosus, or nucleus pulposus implant, graft, substitute, scaffold, filler, coating or cement.

The biomaterial or implants may further comprise cells. The cells may be stem or progenitor cells, differentiated cells, terminally differentiated cells, or combinations thereof. The cells may be totipotent, pluripotent or unipotent stem cells, or induced pluripotent stem cells. The cells may be human embryonic stem cells, derived via a technology which does not necessitate the destruction of the human embryo, for example via an established cell line. Mesenchymal stem cells (also referred to as marrow stromal cells, multipotent stromal cells, or MSCs) are pluripotent stem cells which can differentiate into a variety of cell types including osteoblasts, tenocytes, chondrocytes, myocytes, adipocytes. These cell types have the ability to generate bone, tendon, ligament, cartilage, muscle, and fat. The cells may be MSCs or any cell within the MSC lineage. Progenitor cells can go through several rounds of cell division before terminally differentiating into a mature cells, and the cells may be these intermediary cells. The cells may be selected from the group consisting of: MSCs (marrow stromal cells, mesenchymal stem cells, multipotent stromal cells), chondrocytes, fibrochondrocytes, osteocytes, osteoblasts, osteoclasts, synoviocytes, adipocytes, bone marrow cells, mesenchymal cells, stromal cells, genetically transformed cells, or combinations thereof. The cells may be autologous or heterologous.

In some embodiments, the biomaterial scaffold comprises fibrin. Other materials may also be engineered to include peptides of the disclosure. Such materials are described in U.S. Pat. Nos. 7,241,730, 6,331,422, 6,607,740, 6,723,344, US Pub 2007/0202178, US Pub 2007/0264227, which are hereby incorporated herein by reference for all purposes.

In some embodiments, the biomaterial scaffold comprises collagen. Collagen scaffolds are described in, for example, US Publications: 2017/0182212, 20170173216, 20160199538, and 20150367030, which are hereby incorporated herein by reference for all purposes.

V. THERAPEUTIC METHODS

After damage, tissue repair or regeneration is the result of a spatio-temporal coordination of cell fate processes that are controlled by a multitude of cell-signaling events coming from the extracellular microenvironment and recruited cells at the site of injury (Gurtner, Werner, et al., 2008). To site few, tissue healing processes such as angiogenesis (Herbert and Stainier, 2011), stem cells homing (Karp and Leng Teo, 2009), or inflammation (Eming, Hammerschmidt, et al., 2009) are all tightly coordinated and controlled by a cascade of cell-signaling events. Angiogenesis, the formation of new blood vessels, is crucial to provide oxygen and nutrients to the regenerating tissue. Various approaches have been made with a goal of providing amenable and tissue-specific matrices to control cell processes, such as adhesion, migration, proliferation, differentiation (Lutolf and Hubbell, 2005; Atala, 2008; Huebsch and Mooney, 2009). A goal is to provide matrices to contain signals that directly act on tissue-damaged cells, attract regeneration-competent cells, block regeneration-suppressing signals, and guide cell fate. Powerful molecules to control these processes are secreted cell-signaling molecules such as morphogens (Affolter and Basler, 2007), cytokines (Vilcek and Feldmann, 2004), and growth factors (Cross and Dexter, 1991).

The embodiments of the disclosure may facilitate these processes and can be used to assist in the healing of normal wounds, including those resulting from accidents, surgery or failure of healing of a surgical wound (e.g., a dehiscent wound). Certain aspects of the disclosure will accelerate wound healing, reduce scarring and ultimately promote repair, regeneration and restoration of structure and function in all tissues.

The embodiments of the disclosure can be used to treat external wounds caused by, but not limited to scrapes, cuts, lacerated wounds, bite wounds, bullet wounds, stab wounds, burn wounds, sun burns, chemical burns, surgical wounds, bed sores, radiation injuries, all kinds of acute and chronic wounds, wounds or lesions created by cosmetic skin procedures and also ameliorate the effects of skin aging. The embodiments of the disclosure may accelerate wound healing in all kinds of external wounds and improve the cosmetic appearance of wounded areas, and skin subject to aging and disease. In certain embodiments, the composition, peptide, polypeptide, implant, molecular complex, scaffold, or matrix of the disclosure may be provided directly, as a pre-treatment, as a pre-conditioning, coincident with injury, pre-injury, or post-injury. The composition be used to treat internal injury caused by, but not limited to, disease, surgery, gunshots, stabbing, accidents, infarcts, ischemic injuries, to organs and tissues including but not limited to heart, bone, brain, spinal cord, retina, peripheral nerves and other tissues and organs commonly subject to acute and chronic injury, disease, congenital and developmental malformation and aging processes. Injury to internal organs causes a fibrotic response, which leads to loss of structure and function in organ systems.

In certain aspects, regenerative processes aided by the compositions peptides, polypeptides, implants, molecular complexes scaffolds, or matrices of the disclosure may include, but are not limited to internal and external injury, regeneration of tissues, organs, or other body parts, healing and restoration of function following vascular occlusion and ischemia, brain stroke, myocardial infarction, spinal cord damage, brain damage, peripheral nerve damage, ocular damage (e.g., to corneal tissue), bone damage and other insults to tissues causing destruction, damage or otherwise resulting from, but not limited to, injury, surgery, cancer, congenital and developmental malformation, and diseases causing progressive loss of tissue structure and function, including but not limited to diabetes, bacterial, viral and prion-associated diseases, Alzheimer's disease, Parkinson's disease, AIDs and other genetically determined, environmentally determined or idiopathic disease processes causing loss of tissue/organ/body part structure and function. In addition, the compositions described herein can be administered with drugs or other compounds promoting tissue and cellular regeneration including, but not limited to, trophic factors in processes including, but not limited to, brain, retina, spinal cord and peripheral nervous system regeneration (e.g., NGFs, FGFs, Neurtrophins, Neuregulins, Endothelins, GDNFs, BDNF. BMPs, TGFs, Wnts), as well as pre-conditioning factors or stimuli e.g., hypoxia, norepinephrine, bradykinin, anesthetics, nitrate, ethanol, Alda-1, ALDH2 antagonists, PKC-epsilon agonists, exogenous ligands that activate opioid receptors (DPDPE, deltorphin II, methadone, SNC-80, BW373U86, DPI-287, DPI-3290)

delivered in a prospective pre-treatment prior to a surgery of other procedure disrupting tissue in a subject.

Embodiments of the disclosure further include the use of the peptides, compositions, polypeptides, implants, molecular complexes, scaffolds, or matrices of the disclosure to aid in the healing of pathological wounds, such as through use of a contractile toroid for assisting the closure of slow healing wounds e.g., diabetic wounds. Diabetic wounds are examples of difficult to heal wound can include, for example, a wound that is often characterized by slower than normal re-epithelialization/closure inflammatory phase and delayed formation and remodeling of extracellular matrix.

The present disclosure can also assist in the healing of chronic wounds or wounds that do not heal. Wounds that have not healed within three months, for example, are said to be chronic. Chronic wounds include, diabetic, diabetic foot, ischemic, venous, venous stasis, arterial, pressure, vasculitic, infectious, decubitis, burn, trauma-induced, gangrenous and mixed ulcers. Chronic wounds include, wounds that are characterized by and/or chronic inflammation, deficient and overprofuse granulation tissue differentiation and failure of re-epithelialization and wound closure and longer repair times. Chronic wounds can include ocular ulcers, including corneal ulcers. Use of the disclosed embodiments in would healing and tissue regeneration would include in humans and agricultural, sports and pet animals.

VI. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Figure 1A:
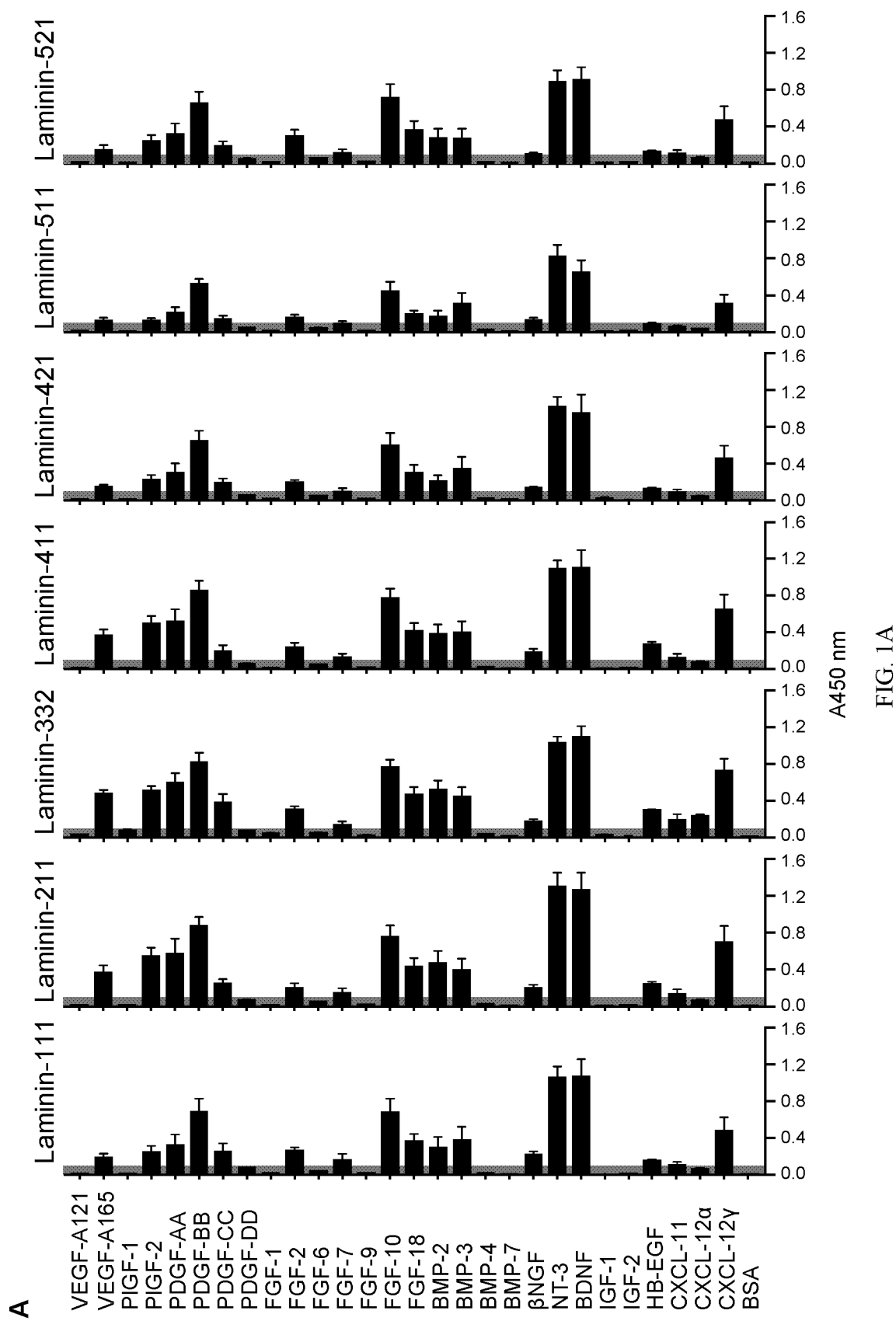
FIGS. 1A-B. Multiple isoforms of laminin bind promiscuously to GFs and chemokines with high affinities. (A) Binding of multiple isoforms of full-length laminin (−111, −211, −332, −411, −421, −511, and −521) to GFs and CXCL chemokines were measured by ELISA. A450 nm represents absorbance at 450 nm. BSA-coated wells served as negative controls (n=4, mean±SEM). Signals greater than 0.1 (grey box) are considered to be significant. (B) Affinities ($K_D$ values are shown) of full-length laminin against VEGF-A165, PlGF-2 and PDGF-BB were measured by SPR. A SPR chip was functionalized with laminin-521 (~2000 RU), and each GF was flowed over the chip at indicated concentrations. Curves represent the specific responses (in RU) to laminin obtained. Experimental curves were fitted with Langmuir binding kinetics. Binding kinetics values [dissociation constants ($K_D$) and rate constants ($K_{on}$ and $K_{off}$)] determined from the fitted curves are shown.

Example 1—Laminin Heparin-Binding Peptides Bind to Several Growth Factors and Enhance Diabetic Wound Healing 1. Results a. Multiple GFs Bind to Multiple Isoforms of Laminin The inventors first examined the capacity of a variety of full-length laminin isoforms (−111, −211, −332, −411, −421, −511, and −521) to bind GFs from the VEGF/PDGF, FGF, BMP, NT, IGF, EGF and CXCL chemokine families, for which the inventors have previously observed binding to other ECM proteins, including fibronectin, vitronectin, tenascin-C, osteopontin, and fibrinogen, as well as that reportedly modulate wound-healing. Binding of laminin to absorbed GFs was detected using an antibody against laminin, and signals greater than 0.1 were considered to be indicative of a binding event. Overall, it was found that multiple GFs strongly bound to all tested laminin isoforms (FIG. 1A). Specifically, from the VEGF/PDGF family, VEGF-A165, PlGF-2, PDGF-AA, PDGF-BB, and PDGF-CC bound to all isoforms of laminin, in contrast to VEGF-A121, PlGF-1, and PDGF-DD which did not show binding. From the FGF family, the inventors observed that FGF-2, FGF-7, FGF-10, and FGF-18 bound to all laminin isoforms, whereas FGF-1, FGF-6, and FGF-9 did not. Among the BMPs, BMP-2 and BMP-3 showed binding to laminins, but not BMP-4 and BMP-7. NT-3 and BDNF showed strong binding towards all tested laminin isoforms, while βNGF bound only weakly. Neither IGF-1 nor IGF-2 displayed significant binding to laminins. In addition, HB-EGF weakly bound to laminins. As to the tested chemokines, CXCL-12γ bound to all laminin isoforms, whereas CXCL-11 and CXCL-12α bound weakly to laminin-332 but not to the other isoforms.

Figure 1B:
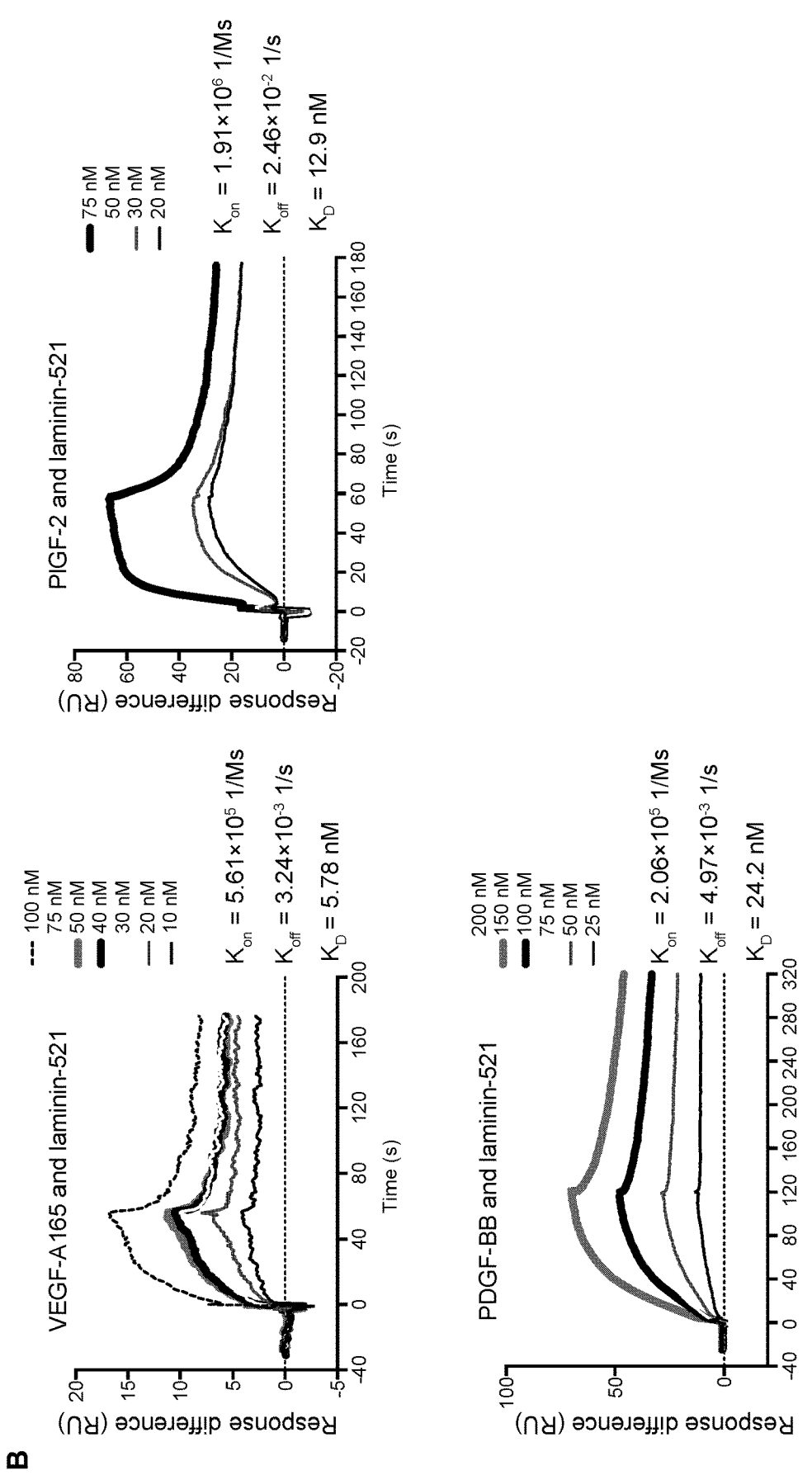

Next, the inventors measured the affinities between laminin-521, as an example, and VEGF-A165, PlGF-2, and PDGF-BB using surface plasmon resonance (SPR). SPR chips were functionalized with laminin-521, and growth factors were flowed over the surface. The obtained binding curves were fitted with Langmuir binding kinetics to calculate specific dissociation constants ($K_D$) (FIG. 1B). $K_D$ values were 5.8 nM for VEGF-A165, 12.9 nM for PlGF-2, and 24.2 nM for PDGF-BB. The nM range of $K_D$ values demonstrated the strong binding affinities of laminin-521 to the selected GFs.

b. GFs Bind to the HBDs of Laminin

Because the GFs that bound to laminins have also been previously reported to bind to other ECM glycoproteins through HBDs, it was hypothesized that HBDs of laminins might be responsible for the interactions between GFs and laminin. To address this hypothesis, ELISA assays were repeated for VEGF-A165, PlGF-2 or FGF-2 in the presence of heparin added in excess (10 μM). As a result, the inventors observed that excess heparin inhibited GF binding to laminin (FIG. 2A-C), supporting that laminin HBDs mediated interactions with GFs. To further confirm this, the inventors tested direct GF binding to the LG domains from human laminin α3, α4 and α5, within which HBDs of laminin were localized. It was found that VEGF-A165, PlGF-2, PDGF-BB, and FGF-2 bound to laminin LG domains $α3_{2928-3150}$, $α4_{826-1816}$ and $α5_{3026-3482}$, in contrast to VEGF-A121 and PlGF-1 which did not show any binding (FIG. 3A-C), as tested by ELISA. The binding affinities between $α3_{2928-3150}$ and VEGF-A165 or PDGF-BB were then measured by SPR, and $K_D$ values were 1.2 nM for VEGF-A165, and 10.2 nM for PDGF-BB (FIG. 3D). These data again demonstrated the strong affinities of the laminin LG domain to the tested GFs.

The inventors next examined the binding of GFs to chemically synthesized laminin LG domain peptides, the sequences of which are all derived from human laminin sequences (Table 1, FIG. 4A). These peptides are putative HBDs; they were determined based on previous reports with mouse or human HBD sequences, or are positively charged sequences located within the linker domain between the LG3 and LG4 domains in laminin α3, α4 and α5 chains. Of 9 tested peptides, 6 bound to heparin (i.e. HBDs), namely $α3_{2932-2951}$, $α3_{3043-3067}$, $α4_{1408-1434}$, $α4_{1521-1543}$, $α5_{3300-3330}$, and $α5_{3417-3436}$ among which $α3_{2932-2951}$, $α4_{1408-1434}$, and $α5_{3300-3330}$ are derived from the LG3-LG4 linker. Interestingly, $α5_{3312-3325}$, which is a subdomain of $α5_{3300-3330}$, did not bind to heparin.

Figure 9:
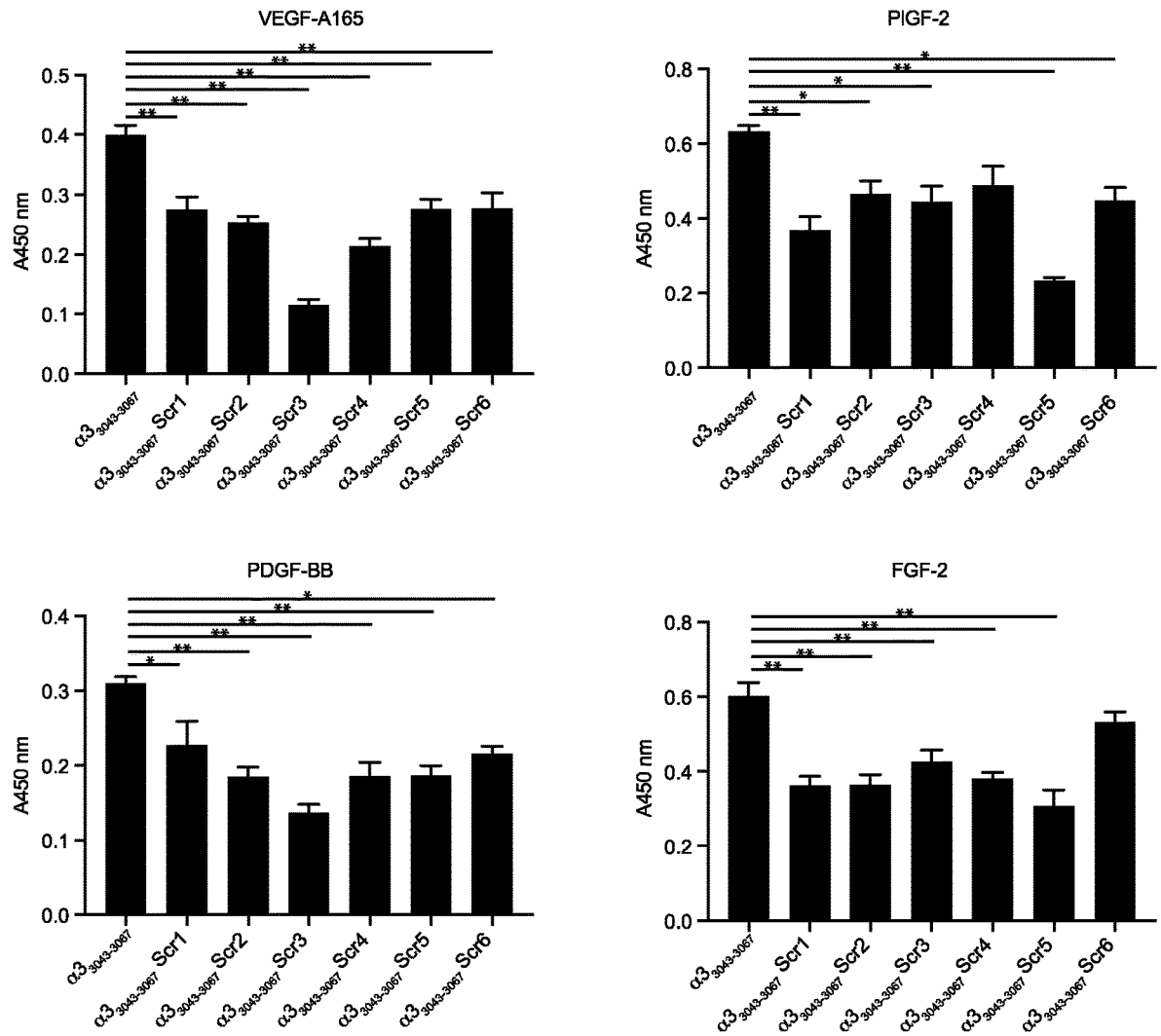
FIG. 9. Scrambling the sequence of laminin HBD peptide decreases the GF binding capacity. Affinity of GFs against chemically synthesized peptides that are scrambled (Scr) the sequence of α3$_{3043-3062}$. ELISA plates were coated with 10 μg/mL laminin peptide and further incubated with VEGF-A165, PlGF-2, PDGF-BB, or FGF-2. Concentrations were 1

Finally, the affinities of VEGF-A, PlGF, PDGF-BB, and FGF-2 to these peptides were examined (FIG. 4B-F). The inventors observed that all heparin-binding peptides showed significant binding to some GFs. Indeed, $α3_{3043-3067}$, $α4_{1408-1434}$, and $α5_{3417-3436}$ bound to VEGF-A165, PlGF-2, PDGF-BB, and FGF-2. $α4_{1521-1543}$ showed similar results except for the binding to PDGF-BB, which was not statistically significant. $α3_{2932-2951}$ and $α5_{3300-3330}$ preferentially bound to VEGF-A165 and FGF-2, and VEGF-A165 and PlGF-2 respectively. As to the non-heparin-binding peptides, $α5_{3312-3325}$ did not show particular binding to any tested GF. Interestingly, $\alpha 5_{3539\text{-}3550}$, which did not show binding to heparin, significantly bound to all tested GFs, and $\alpha 3_{3031\text{-}3043}$ bound to VEGF-A165. None of the tested laminin-derived peptides bound to VEGF-A121 nor to PlGF-1, consistent with the results obtained in FIG. 1 and FIG. 3. To examine sequence specificity of this binding to GFs, the inventors produced a scrambled sequence $\alpha 3_{3043\text{-}3067}$ peptide (FIG. 9); scrambling the sequence of $\alpha 3_{3043\text{-}3067}$ decreased the binding signals between $\alpha 3_{3043\text{-}3067}$ and VEGF-A165, PlGF-2, PDGF-BB, and FGF-2, compared to its native form. Taken together, these data suggest that GFs bind to the HBDs of laminin, located in the LG3-LG4 linker or in LG4-LG5 domains.

c. Laminin HBD Peptides Promote Adhesion of Multiple Types of Cells

Because the laminin HBDs have been reported to bind to syndecan, a key cell surface adhesion molecule, the inventors tested syndecan binding to the synthesized laminin-derived peptides (FIG. 5A-D). $\alpha 3_{3043\text{-}3067}$, $\alpha 4_{1521\text{-}1543}$, $\alpha 4_{1408\text{-}1434}$, $\alpha 5_{3417\text{-}3436}$, and $\alpha 5_{3300\text{-}3330}$ showed significant binding to all isoforms of recombinant syndecans, i.e. syndecan 1-4. $\alpha 3_{2932\text{-}2951}$, $\alpha 3_{3031\text{-}3043}$, and $\alpha 5_{3312\text{-}3325}$ showed weak binding to the tested syndecans, while $\alpha 5_{3539\text{-}3550}$ did not show binding to any syndecan isoform. Because laminin-derived peptides that interact with syndecans may further promote cell adhesion by providing binding substrates, the inventors tested fibroblasts and HUVEC adhesion to plates coated with these peptides. The inventors observed enhancement of fibroblast attachment on $\alpha 3_{2932\text{-}2951}$, $\alpha 3_{3031\text{-}3043}$, $\alpha 3_{3043\text{-}3067}$, $\alpha 4_{1521\text{-}1543}$ and $\alpha 5_{3417\text{-}3436}$-coated surfaces (FIG. 6A). Fibroblast binding was observed even in the presence of EDTA, consistent with syndecan function (FIG. 6B). Of these peptides, $\alpha 3_{2932\text{-}2951}$, $\alpha 3_{3043\text{-}3067}$, and $\alpha 4_{1521\text{-}1543}$ also promoted HUVEC attachment (FIG. 6C), even in the presence of EDTA in the case of $\alpha 3_{3043\text{-}3067}$ (FIG. 6D). Interestingly, peptides that promoted both fibroblast and HUVEC adhesion in vitro through syndecan binding were those that the inventors previously found to be laminin HBDs (FIG. 4A). VEGF-A165 increases the degree of migration of HUVEC cells in vitro (FIG. 10). However, both in the presence and absence of VEGF-A165, $\alpha 3_{3043\text{-}3067}$ did not increase the degree of cell migration.

d. Retention of VEGF-A165 and PDGF-BB in Fibrin Matrix is Increased by the Incorporation of Laminin HBD Peptides The inventors then sought to determine whether laminin HBD peptides, which showed binding to GFs, were able to improve the retention of VEGF-A165 and PDGF-BB within fibrin matrix. VEGF-A165 and PDGF-BB are both crucial factors for angiogenesis. These GFs are known to be quickly released from fibrin matrices upon delivery, which limits their wound healing efficacy in vivo. For this purpose, the inventors selected $\alpha 3_{3043\text{-}3067}$ and $\alpha 5_{3417\text{-}3436}$ laminin HBD peptides, and fused them to a transglutaminase-reactive sequence from the $\alpha_2$-plasmin inhibitor to allow their covalent incorporation by factor XIIIa into fibrin matrices during polymerization. GF release from fibrin matrices containing $\alpha_2 PI_{1\text{-}8}\text{-}\alpha 3_{3043\text{-}3067}$, $\alpha_2 PI_{1\text{-}8}\text{-}\alpha 5_{3417\text{-}3436}$ or no laminin-derived peptide were then monitored daily and quantified by ELISA (FIG. 7A, B). As expected, the inventors observed that VEGF-A165 and PDGF-BB were quickly released from the fibrin matrix (>85% released after 24 h). However, incorporation of either $\alpha_2 PI_{1\text{-}8}\text{-}\alpha 3_{3043\text{-}3067}$ or $\alpha_2 PI_{1\text{-}8}\text{-}\alpha 5_{3417\text{-}3436}$ allowed significant retention of VEGF-A165 and PDGF-BB into matrices, which were respectively released after 5 days, for VEGF-A165 ($\alpha_2 PI_{1\text{-}8}\text{-}\alpha 3_{3043\text{-}3067}$: 25%, $\alpha_2 PI_{1\text{-}8}\text{-}\alpha 5_{3417\text{-}3436}$: 31%) and for PDGF-BB ($\alpha_2 PI_{1\text{-}8}\text{-}\alpha 3_{3043\text{-}3067}$: 45%, $\alpha_2 PI_{1\text{-}8}\text{-}\alpha 5_{3417\text{-}3436}$: 47%). This data highlights the key biological role of laminin in sequestering GFs into ECM, and demonstrates the potential of laminin HBD peptides to control GF delivery from fibrin biomaterials (FIG. 7A, B). The inventors next evaluated the effect of $\alpha_2 PI_{1\text{-}8}\text{-}\alpha 3_{3043\text{-}3067}$ on GF retention in diabetic wounds in the type 2 diabetic db/db mouse in vivo (FIG. 7C). Incorporation of $\alpha_2 PI_{1\text{-}8}\text{-}\alpha 3_{3043\text{-}3067}$ into fibrin matrices significantly enhanced the amount of VEGF-A165 remaining in the wounds 3 days after treatment, showing that incorporation of $\alpha_2 PI_{1\text{-}8}\text{-}\alpha 3_{3043\text{-}3067}$ prolongs retention of GFs in vivo.

e. Laminin HBD-Functionalized Fibrin Matrices Potentiate GFs and Promote Wound Healing In Vivo Although the etiology of non-healing wounds is multifaceted in diabetes, the progression to a non-healing phenotype is related to poor blood vessel formation. Thus, induction of mature blood vessels is a crucial step for diabetic wound-healing. Previous studies have reported a synergistic effect between angiogenesis inducers VEGF-A165 and PDGF-BB in wound healing, more precisely topical application of VEGF-A165 improves wound closure and PDGF-BB promotes the amount of granulation tissue in the type 2 diabetic db/db mouse. The inventors further evaluated whether fibrin matrices engineered with laminin-HBD peptides could enhance skin repair in a model of delayed wound healing, by controlling the release of VEGF-A165 and PDGF-BB in vivo. VEGF-A165 (100 ng/wound) and PDGF-BB (50 ng/wound) were co-delivered from fibrin matrix onto full-thickness back-skin wounds in db/db mice, which provides a well-established and clinically-relevant model of impaired wound healing. Here, the inventors particularly functionalized fibrin with the laminin peptide $\alpha 3_{3043\text{-}3067}$, since it bound to GFs and syndecans, and promoted fibroblast and endothelial cells adhesion in vitro (FIG. 4-6). Four groups were tested: fibrin only, fibrin functionalized with $\alpha_2 PI_{1\text{-}8}\text{-}\alpha 3_{3043\text{-}3067}$, fibrin containing GFs, and fibrin functionalized with $\alpha_2 PI_{1\text{-}8}\text{-}\alpha 3_{3043\text{-}3067}$ and containing GFs. Wound histology was analyzed after 4, 7 and 10 days, considering that wounds are normally fully closed after 15 days when treated with fibrin matrix. As a result, wounds that received fibrin matrices containing GFs or $\alpha_2 PI_{1\text{-}8}\text{-}\alpha 3_{3043\text{-}3067}$ peptide only did not differ from wounds treated with fibrin alone on day 7, neither in amount of granulation tissue nor in extent of wound closure (FIG. 8A-C). In contrast, the co-delivery of VEGF-A165 and PDGF-BB in fibrin functionalized with $\alpha_2 PI_{1\text{-}8}\text{-}\alpha 3_{3043\text{-}3067}$ led to a significantly faster wound closure after 7 days, as well as a significant increase in granulation tissue formation (FIG. 8A-C). GFs alone improved the amount of granulation tissue but not wound closure on day 10, suggesting that $\alpha_2 PI_{1\text{-}8}\text{-}\alpha 3_{3043\text{-}3067}$ peptide speeds the wound healing process by these GFs. Representative wound morphology for all four treatments is presented in FIG. 8D. Clear differences in granulation tissue thickness and extent of re-epithelialization can be visualized when GFs were delivered within the $\alpha_2 PI_{1\text{-}8}\text{-}\alpha 3_{3043\text{-}3067}$ peptide-functionalized fibrin matrix compared to the other conditions.

Angiogenesis is a crucial step of wound-healing in diabetic wounds, and both VEGF-A165 and PDGF-BB are angiogenesis inducers. The inventors next examined endothelial cell proliferation (FIG. 8E). Co-delivery of VEGF-A165 and PDGF-BB in fibrin functionalized with $\alpha_2 PI_{1\text{-}8}\text{-}\alpha 3_{3043\text{-}3067}$ led to a significantly increased frequency of Ki67$^+$, a proliferation marker, within CD31$^+$ CD45$^-$ endothelial cells compared to other treatment groups on day 5. This is consistent with the increase in granulation tissue observed on day 7 as a result of delivery of GFs in fibrin functionalized with $\alpha_2 PI_{1-8}$-$\alpha 3_{3043-3067}$ (FIG. 8C).

Immune cells play crucial role in wound-healing regulation. The inventors next examined the immune cell population in the wound in each treatment group. Delivery of GFs in fibrin functionalized with $\alpha_2 PI_{1-8}$-$\alpha 3_{3043-3067}$ slightly decreased the frequency of neutrophils within CD45$^+$ cells compared to other treatment groups. On the other hand, delivery of GFs in fibrin functionalized with $\alpha_2 PI_{1-8}$-$\alpha 3_{3043-3067}$ increased the frequency of monocytes within CD45$^+$ cells compared to other treatment groups. Among immune cells, neutrophils migrate first into wounds and then monocytes appear[43,44]. Therefore, this set of data suggests that delivery of GFs in fibrin functionalized with $\alpha_2 PI_{1-8}$-$\alpha 3_{3043-3067}$ promotes wound healing immunologically as well. Inclusion of $\alpha_2 PI_{1-8}$-$\alpha 3_{3043-3067}$ improved the GF delivery capacity of fibrin in vivo, resulting in an accelerated wound healing.

2. Discussion

It was unexpectedly found that GF binding to laminin does not seem to be limited to HBDs, as a few non-heparin binding peptides also bound to some GFs, notably $\alpha 3_{3031-3043}$ and $\alpha 5_{3539-3550}$. These peptides are human alignments of reported mouse HBD peptides, called A3G75 and A5G94 respectively. Thus, the mechanism of GF-binding to laminin still remains incompletely clarified and may be resolved by further crystallography studies of GF-laminin complex.

Physiologically, proteolytic cleavage of LG4 and LG5 domains is crucial for the deposition of laminin in the native ECM. Upon tissue injury, laminin is overexpressed, and LG4-LG5 domains accumulate in wounds, wherein they promote tissue healing mechanisms. In this study, the inventors characterized laminin-derived peptides that are located just before the proteolytic cleavage site, in the linker between the LG3 and LG4 domains, or within the LG4-LG5 domains (Table. 2, FIG. 4A). On one side, the inventors discovered 3 novel heparin-, GF- and syndecan-binding peptides within the LG3-LG4 linker regions of $\alpha 3$, $\alpha 4$, and $\alpha 5$ chains, namely $\alpha 3_{2932-2951}$, $\alpha 4_{1408-1434}$, and $\alpha 5_{3300-3330}$, identifiable through their highly cationic sequences (FIG. 4). Since $\alpha 3$, $\alpha 4$ and $\alpha 5$ chains are known to be predominantly present in their processed form (i.e. lacking LG4-LG5) in mature, unwounded skin, it is likely that these peptides are exposed in vivo under homeostatic conditions, thus providing both GF ligands and cell adhesion sites in basement membranes. Interestingly, laminin $\alpha 1$ chain, which is not proteolytically processed, and $\alpha 2$ chain do not contain such cationic sequences in the LG3-LG4 linker region, which might reflect functional differences between $\alpha$ chain isoforms. On the other side, the inventors identified 5 peptides in the LG4 and LG5 domains of $\alpha 3$, $\alpha 4$ and $\alpha 5$ chains that displayed specific binding to GFs, in particular to VEGF-A165. Among them, $\alpha 3_{3043-3067}$, $\alpha 5_{3539-3550}$, and $\alpha 5_{3417-3436}$ additionally bound to PDGF-BB, FGF-2 and PlGF-2 with high affinities (FIG. 4). These growth factors are well-known as key regulators of the wound healing cascade, and are particularly involved in wound angiogenesis. Therefore, it is proposed that the reported positive effects of LG4-LG5 domains during wound healing might be related to promiscuous interactions with GFs, in addition to binding to syndecans and release of laminin-derived pro-angiogenic peptides.

In this study, the inventors identified 5 laminin HBDs that are able to bind to both GFs and syndecan cell-surface receptors (FIGS. 4 and 5), among which $\alpha 3_{3043-3067}$, $\alpha 4_{1521-1543}$ and $\alpha 5_{3417-3446}$ further promoted cell attachment (FIG. 6). Although syndecans are not known to directly activate major signaling pathways, they support cell adhesion and integrin signaling. Moreover, direct binding of laminin peptides from LG domains to integrins has also been reported; for example, the integrin $\alpha 3\beta 1$ binds to $\alpha 3_{2932-2943}$. Nevertheless, in the assays, EDTA did not abolish cell adhesion, suggesting that initial cell attachment was mediated by syndecans rather than integrins (the binding of which is Ca$^{2+}$-dependent). Consequently, and considering the short length of the laminin HBD peptides, it is unlikely that laminin HBD peptides can enhance GF signaling via synergy with integrins. It is believed that GF binding properties, more than cell adhesion properties, of laminin HBDs in fibrin matrices substantially contribute to the promotion of wound healing.

Although GFs are promising drugs for tissue regeneration, their uncontrolled delivery upon application on wounded tissue has limited their clinical efficacy and safety to date. For example, recombinant human VEGF-A has not been approved for clinical use by the U.S. Food and Drug Administration (FDA) due to a negative result in phase II clinical trials. PDGF-BB (Regranex in the clinic) has shown clinical efficacy, but safety issues such as cancer risk have been flagged, potentially due to high dosing. Because 20 µg per wound of VEGF-A165 applied topically for five consecutive days were known to promote wound healing in the db/db mouse and 10 µg per wound of PDGF-BB did not significantly enhance wound healing, the inventors treated full-thickness back-skin wounds with a roughly 40- to 250-fold lower dose of GFs (combination of 100 ng VEGF-A165 and 50 ng of PDGF-BB) delivered once in a fibrin matrix. Thus, controlling GF delivery to improve efficacy and dose reduction seems essential in future GF-based therapies and could be achieved by use of biomaterials matrices.

Here, the inventors showed that covalent incorporation of an engineered GF-binding domain derived from laminin, $\alpha_2 PI_{1-8}$-$\alpha 3_{3043-3067}$, into fibrin matrix significantly enhanced the effect of VEGF-A165 and PDGF-BB on skin wound healing, by highly increasing GF retention into fibrin both in vitro and in vivo (FIG. 8). In contrast, wounds treated with fibrin matrix containing GFs only, in which PDGF-BB and VEGF-A165 were not specifically retained in the fibrin matrices, had no detectable effect on wound healing at the tested dose (FIG. 8). Wounds treated with fibrin matrix containing $\alpha_2 PI_{1-8}$-$\alpha 3_{3043-3067}$ only promoted wound-closure slightly. This might be the result of trapping endogenous GFs. Considering the importance of angiogenesis in diabetic wounds and the inventors' observation of increased Ki67$^+$ within CD31$^+$CD45$^-$ endothelial cells, the healing process induced by fibrin matrix containing $\alpha_2 PI_{1-8}$-$\alpha 3_{3043-3067}$ and GFs was driven by enhanced angiogenesis in the wounds. Improved angiogenesis, which sustains the newly formed granulation tissue, resulted from effective sequestration of VEGF-A165 and PDGF-BB (FIG. 7). Granulation tissue morphogenesis translated to improved morphogenesis at the level of the dermal epithelium, as reflected by faster wound closure.

One advantage of using the laminin HBD peptide for wound healing, is production simplicity: the laminin HBD peptide is short enough to be chemically synthesized in large scale, rather than requiring recombinant expression. Furthermore, the inventors showed that a laminin HBD can functionalize fibrin matrix in both aspects as a GF reservoir and an adhesion-promoting cell scaffold (FIGS. 6 and 7).

In conclusion, the inventors found that multiple isoforms of laminin promiscuously bind GFs from the VEGF/PDGF, FGF, BMP, and NT families, in addition to HB-EGF and CXCL12γ, through their HBDs. By engineering a fibrin matrix displaying the α3$_{3043-3067}$ laminin HBD, as a demonstrative example, the inventors have shown that the laminin HBD peptide promotes skin wound closure in the db/db mouse, as a model of delayed wound healing, when associated with VEGF-A165 and PDGF-BB. In addition to highlighting a GF-modulating function for laminin, an important tissue homeostasis and repair protein, the inventors show that both GF- and cell-binding characters of a laminin HBD can promote tissue repair when incorporated within fibrin matrix, which may be clinically useful.

3. Tables

TABLE 1

The sequences of laminin-derived peptides.

| Name (location) length | Peptide sequence |
|---|---|
| α3$_{2932-2951}$ (Linker) 20 aa. | PPFLMLLKGSTRFNKTKTFR (SEQ ID NO: 2) |
| α3$_{3031-3043}$ (LG4) 13 aa. | KNSFMALYLSKGR (SEQ ID NO: 9) |
| α3$_{3043-3067}$ (LG4) 25 aa. | RLVFALGTDGKKLRIKSKEKCNDGK (SEQ ID NO: 1) |
| α4$_{1408-1434}$ (Linker) 27 aa. | PLFLLHKKGKNLSKPKASQNKKGGKSK (SEQ ID NO: 4) |
| α4$_{1521-1543}$ (LG4) 23 aa. | TLFLAHGRLVYMFNVGHKKLKIR (SEQ ID NO: 3) |
| α5$_{3300-3330}$ (Linker) 31 aa. | TPGLGPRGLQATARKASRRSRQPARHPACML (SEQ ID NO: 7) |
| α5$_{3312-3325}$ (Linker) 14 aa. | ARKASRRSRQPARH (SEQ ID NO: 10) |
| α5$_{3417-3436}$ (LG4) 20 aa. | RQRSRPGRWHKVSVRWEKNR (SEQ ID NO: 6) |
| α5$_{3539-3550}$ (LG5) 12 aa. | TLPDVGLELEVR (SEQ ID NO: 5) |
| α3$_{3043-3067}$ Scr1 25 aa. | RLVKALKTDKFLGRIGSEKCNDKGK (SEQ ID NO: 74) |
| α3$_{3043-3067}$ Scr2 25 aa. | RKTDALELVFLKKGGIGSKKCNDKR (SEQ ID NO: 75) |
| α3$_{3043-3067}$ Scr3 25 aa. | CRKKKRKKKALLLGIGDFNSEVTDG (SEQ ID NO: 76) |
| α3$_{3043-3067}$ Scr4 25 aa. | KKRKLVALTDFLGICGSENDGRKKK (SEQ ID NO: 77) |
| α3$_{3043-3067}$ Scr5 25 aa. | LVRAKLTDKFLGKRIGSKECNKDKG (SEQ ID NO: 78) |
| α3$_{3043-3067}$ Scr6 25 aa. | ALLLGIGRDFNKKKRKKKSEVTDGC (SEQ ID NO: 79) |
| a2PI1-8-α3$_{3043-3067}$ 33 aa. | NQEQVSPLRLVFALGTDGKKLRIKSKEKCNDGK (SEQ ID NO: 8) |
| a2PI1-8-α5$_{3312-3325}$ 22 aa. | NQEQVSPLARKASRRSRQPARH (SEQ ID NO: 11) |

TABLE 2

Summary of laminin-derived peptide interactions.

| Laminin-derived peptides | Interaction with | | | Cell adhesion | |
|---|---|---|---|---|---|
| | Heparin | GFs | Syndecans | Fibroblasts | HUVECs |
| α3$_{2932-2951}$ | ++ | + | + | + | + |
| α3$_{3031-3043}$ | | + | + | + | |
| α3$_{3043-3067}$ | ++ | ++ | ++ | ++ | ++ |
| α4$_{1408-1434}$ | ++ | ++ | ++ | | |
| α4$_{1521-1543}$ | ++ | + | ++ | + | + |
| α5$_{3300-3330}$ | ++ | + | ++ | | |
| α5$_{3312-3325}$ | | + | | | |
| α5$_{3417-3436}$ | ++ | ++ | ++ | + | |
| α5$_{3539-3550}$ | | + | | | |

++ indicates high affinities, + indicates medium/low affinities. The laminin-derived peptide tested in vivo is highlighted in bold.

4. Materials and Methods a. Growth Factors and Chemokines

All growth factors (GFs) and chemokines were purchased in their mature forms, highly pure (>95% pure), carrier-free, and lyophilized[1]. Vascular endothelial growth factor (VEGF)-A121, VEGF-A165, placental growth factor (PlGF)-1, PlGF-2, platelet-derived growth factor (PDGF)-AA, PDGF-BB, PDGF-CC, PDGF-DD, fibroblast growth factor (FGF)-1, FGF-2, FGF-6, FGF-7, FGF-9, FGF-10, FGF-18, bone morphogenetic protein (BMP)-2, BMP-3, BMP-4, BMP-7, β-nerve growth factor (NGF), neurotrophin (NT)-3, brain-derived neurotrophic factor (BDNF), insulin-like growth factor (IGF)-1, IGF-2, heparin-binding epidermal growth factor (HB-EGF), C—X—C motif ligand (CXCL)-11, and CXCL-12α were purchased from Pepro-Tech. CXCL-12γ was purchased from R&D systems. Except for PDGF-DD and BMP-7, which were produced in eukaryotic cells, all GFs were produced in *Escherichia coli* and thus were not glycosylated. All GFs were reconstituted and stored according to the provider's instructions to regain full activity and prevent loss of protein.

b. Detection of Laminin Binding to Recombinant GFs

ELISA tests were performed as previously reported. In brief, ELISA plates (med-binding, Greiner Bio-One) were coated with 50 nM GFs at 37° C. for more than 2 hrs. After blocking with 2% BSA solution containing PBS and 0.05% Tween 20 (PBS-T), 10 nM recombinant human laminin isoforms (−111, −211, −332, −411, −421, −511, and −521) (>95% purity tested by SDS-PAGE, BioLamina) were added. Bound laminin was detected with rabbit anti-human laminin γ1 chain antibody (1:1000 dilution, Assay biotech) or rabbit anti-human laminin α3 chain antibody (1:1000 dilution, Assay biotech). After incubation with biotinylated anti-rabbit antibody for 60 min at room temperature (RT), HRP conjugated streptavidin (Jackson ImmunoResearch) was added. After 60 min of incubation at RT, 50 μL TMB substrate (Sigma-Aldrich) was added. The reactions were stopped by adding 25 μL of 2N H$_2$SO$_4$. Subsequently, the absorbance at 450 nm was measured with a reference of 570 nm.

c. Production and Purification of Recombinant Laminin α3$_{2928-3150}$ Protein

Protein production and purification were performed as described previously[1]. The sequence encoding for human laminin alpha 3 LG domain Ser2928-Cys3150 (linker domain and LG4 domain) was synthesized and subcloned into the mammalian expression vector pcDNA3.1(+) by Genscript. A sequence encoding for 6 His (SEQ ID NO: 80) was added at the N-terminus for further purification of the recombinant protein. Suspension-adapted HEK-293F cells were routinely maintained in serum-free FreeStyle 293 Expression Medium (Gibco). On the day of transfection, cells were inoculated into fresh medium at a density of $1\times10^6$ cells/mL. 1 µg/mL plasmid DNA, 2 µg/mL linear 25 kDa polyethylenimine (Polysciences), and OptiPRO SFM media (4% final concentration, Thermo Fisher) were sequentially added. The culture flask was agitated by orbital shaking at 135 rpm at 37° C. in the presence of 5% $CO_2$. 6 days after transfection, the cell culture medium was collected by centrifugation and filtered through a 0.22 µm filter. Culture media was loaded into a HisTrap HP 5 mL column (GE Healthcare), using an ÁKTA pure 25 (GE Healthcare). After washing of the column with wash buffer (20 mM imidazole, 20 mM $NaH_2PO_4$, 0.5 M NaCl, pH 7.4), protein was eluted with a gradient of 500 mM imidazole (in 20 mM $NaH_2PO_4$, 0.5 M NaCl, pH 7.4). The elusion solution was further purified with size exclusion chromatography using a HiLoad Superdex 200PG column (GE healthcare). All purification steps were carried out at 4° C. The expression of laminin LG domain was determined by western blotting using anti-His tag antibody (BioLegend) and the proteins were verified as >90% pure by SDS-PAGE.

d. Surface Plasmon Resonance (SPR)

SPR analysis was performed as described previously[2]. In brief, measurements were made with a Biacore 3000 SPR system (GE Healthcare). Laminin-521 or laminin $\alpha3_{2928-3150}$ was immobilized via amine coupling on a C1 chip (GE Healthcare) for ~2000 or ~1000 resonance units (RU), respectively, according to the manufacturer's instructions. VEGF-A165, PDGF-BB, or PlGF-2 was flowed at increasing concentrations in the running buffer at 20 µL/min. The sensor chip was regenerated with 50 mM NaOH for every cycle. Specific bindings of GFs to laminin were calculated by comparison to a non-functionalized channel used as a reference. Experimental results were fitted with Langmuir binding kinetics using BIAevaluation software (GE Healthcare).

e. Inhibition of Laminin-GF Binding by Heparin

ELISA plates (med-binding) were coated with 10 µg/mL laminin isoforms (–111, –211, –221, –411, –421, –511, and –521) in PBS for 2 hrs at 37° C. Then, wells were blocked with 2% BSA-containing PBS-T and further incubated with 1 µg/mL each of VEGF-A165, PlGF-2, or FGF-2 for 60 min at RT with 10 µM heparin. Next, the wells were incubated with biotinylated anti-VEGF, anti-PlGF, or anti-FGF-2 antibodies (R&D Systems). The antibodies were detected by streptavidin-HRP (R&D Systems). Signals were revealed and measured as described above.

f. Detection of GF Binding to Recombinant Laminin LG Domain Protein and the Synthesized Laminin HBD Peptides ELISA tests were performed as described above. In brief, ELISA plates were coated with 1 µg/mL of laminin alpha 3 LG domain recombinant protein, laminin alpha 4 LG domain recombinant protein (R&D systems), laminin alpha 5 LG domain recombinant protein (LD BioPharma), or laminin peptide (sequences are described in Table 1, chemically synthesized by Genscript) in PBS for 2 hrs at 37° C. 1 µg/mL of BSA served as non-binding protein control. After blocking with 2% BSA PBS-0.05% Tween 20 (PBS-T) solution, 1 µg/mL of the recombinant human proteins (VEGF-A121, VEGF-A165, PlGF-1, PlGF-2, PDGF-BB or FGF-2) or 10 µg/mL of biotinylated heparin (Sigma-Aldrich) were added. Bound GF was detected with biotinylated antibodies for human VEGF, PlGF, PDGF-BB, or FGF-2 (R&D Systems). The antibodies were detected by streptavidin-HRP (R&D Systems). Signals were revealed and measured as described above.

g. Detection of Recombinant Syndecan Binding to the Synthesized Laminin HBD Peptides ELISA tests were performed as described above. In brief, ELISA plates were coated with 1 µg/mL laminin peptide (sequences are described in Table 1, chemically synthesized by Genscript) in PBS for 2 hrs at 37° C. 1 µg/mL of BSA served as non-binding protein control. After blocking with 2% BSA PBS-T solution, 1 µg/mL of the recombinant human syndecan-1, syndecan-2, syndecan-3, syndecan-4 (all syndecan proteins are histidine-tagged; SinoBiological) were added. Bound GF was detected with anti-histidine tag antibody (1:1000 dilution, BioLegend). Signals were revealed and measured as described above.

h. Cell Adhesion Assay 96-well plates (non-tissue culture treated, Greiner Bio-one) were pre-coated with 1 µg/mL with laminin HBD peptides in PBS for 2 hrs at 37° C., followed by blocking with 2% BSA PBS for 1 h at RT. Cell adhesion assays were performed using human lung fibroblasts (Lonza) in FGM-2 medium (Lonza) or human umbilical vein endothelial cells (HUVEC; Lonza) in EGM-2 medium (Lonza) supplemented with 1% fetal bovine serum (FBS) and 100 µg/mL VEGF-A165, with or without 5 mM EDTA (Sigma-Aldrich). Cells were plated at 3000 cells/well on laminin peptide pre-coated plates and incubated for 30 min at 37° C., 5% $CO_2$. Then, the medium was removed, and wells were quickly washed three times with PBS. Cell numbers were quantified using a CyQUANT assay, according to the manufacturer's instructions (Invitrogen). All cell lines were checked for mycoplasma contamination and used in passages from 5 to 8.

i. Migration Assay

A migration assay was performed as described previously[3]. A QCM 24-Well Colorimetric Cell Migration Assay kit was used to perform migration assay. Both sides of inserts were coated with 0.1 µM of bovine collagen I (C4243, Sigma-Aldrich) for 1 hr at 37° C. Then, the inserts were washed with water, dried in a laminar flow cabinet and disposed on 24-well cell culture plate covers. Solutions containing 30 ng/mL of VEGF-A165 preincubated with or without 0.1 µM of $\alpha3_{3043-3067}$ peptide in medium (MCDB-131, 0.05% BSA) were added to the bottom side of the transwell (500 µL/well). Directly thereafter, HUVEC cells in medium containing 0.05% BSA (300 µL/transwell, $4\times10^4$ cells/transwell) were added to the transwell upper parts. After 6 hr, migrated cells were stained and absorbance at 560 nm was measured according to the manufacturer's instructions.

j. Release of GF from Fibrin Matrix

Fibrin matrices were generated with human fibrinogen (VWF and fibronectin depleted, Enzyme Research Laboratories) as described previously[1]. In brief, fibrin matrices were generated with 8 mg/mL fibrinogen, 2 U/mL human thrombin (Sigma-Aldrich), 4 U/mL factor XIIIa (Fibrogammin; Behring), 5 mM calcium chloride (Sigma-Aldrich), 2 µM $\alpha_2PI_{1-8}$-laminin peptide (sequences are described in Table 1, chemically synthesized by Genscript), and 500 ng/mL recombinant human VEGF-A165 or PDGF-BB. Thus, the peptides were incorporated into the 3D fibrin matrix through enzymatic coupling, via the coagulation transglutaminase factor XIIIa, of the $\alpha_2PI_{1-8}$ peptide sequence (NQEQVSPL (SEQ ID NO: 12)) fused to the laminin peptide. Fibrin matrix was polymerized at 37° C. for 1 hr and transferred into 24-well Ultra Low Cluster plates (Corning) containing 500 µL of buffer (20 mM Tris-HCl, 150 mM NaCl, and 0.1% BSA; pH 7.4). A control well that served as a 100% released control contained only the GF in 500 µL of buffer. Every 24 hrs, buffers were removed, stored at −20° C., and replaced with fresh buffer. For the 100% released control well, 20 μL of buffer was removed each day and stored at −20° C. After 5 days, the cumulative release of GF was quantified by ELISA (DuoSet; R&D Systems), using the 100% released control as a reference.

k. Retention of VEGF-A165 at the Wound Site

Retention assays were performed as previously reported[1]. Briefly, C57BLKS/J-m/Lepr db (db/db) mice ages 10 to 11 wks were used. Their backs were shaved and four full-thickness punch-biopsy wounds (6 mm in diameter) were created in each mouse. Directly after, fibrin matrices [80 μL total, fibrinogen (10 mg/mL), 2 U/mL human thrombin, 4 U/mL factor XIII, 5 mM calcium chloride, 2 μM $\alpha_2PI_{1-8}$-$\alpha3_{3043-3067}$, 200 ng of recombinant human VEGF-A165] were polymerized on the wounds. To avoid drying of the matrices, the wounds were covered with non-adhering dressing (Adaptic, Johnson & Johnson), and then with adhesive film dressing (Hydrofilm, Hartmann). After 3 or 6 days, mice were sacrificed. The wounds were punched again, in order to recover the fibrinous matrices. Moreover, the tissue surrounding the wounds (2 mm beyond the wound margin) was removed. The tissue was transferred in 0.9 mL of tissue T-PER Tissue Protein Extraction Reagent (Thermo Scientific) containing 1 mg/mL of collagenase IV (Sigma-Aldrich), and homogenized with a tissue homogenizer. The tissue lysate was incubated 1 hr at 37° C. and 100 μL of a 5 M NaCl solution containing protease inhibitors (1 tablet of protease inhibitor cocktail for 10 mL) was added to the lysate. The samples were centrifuged at 10000×g for 5 min, and the supernatants were stored at −80° C. Recombinant human VEGF-A165 remaining in the fibrinous matrix and in the tissue surrounding the wound were quantified by ELISA (DuoSet, R&D Systems), using 200 ng of recombinant human VEGF-A165 as 100%.

l. Mouse Skin Chronic Wound Healing Model

Skin wound healing assays were performed as previously reported[1]. Briefly, C57BLKS/J-m/Lepr db (db/db) male mice were 10 to 12 wks old at the start of the experiments. Their backs were shaved and four full-thickness punch biopsy wounds (6 mm in diameter) were created in each mouse. Directly after, fibrin matrices [80 μL total, fibrinogen (10 mg/mL), 2 U/mL human thrombin, 4 U/mL factor XIII, 5 mM calcium chloride, 2 μM $\alpha_2PI_{1-8}$-$\alpha3_{3043-3067}$, 100 ng of VEGF-A165, and 50 ng of PDGF-BB] were polymerized on the wounds. The wounds were covered with adhesive film dressing. Mice were single-caged after the wound surgery. After 4, 7, 10 days, mice were euthanized and the skin wounds were carefully harvested for histological analysis.

m. Histomorphometric Analysis of Wound Tissue Sections

Histomorphometric analyses were performed as previously reported[1]. Briefly, an area of 8 mm in diameter, which includes the complete epithelial margins, was excised. Wounds were cut in the center into two and embedded into paraffin. Histological analysis was performed on 5 μm serial sections. Images were captured with an EVOS FL Auto microscope (Life Technologies). The extent of re-epithelialization and granulation tissue formation was measured by histomorphometric analysis of tissue sections (H&E stain) using ImageJ software (NIH). For analysis of re-epithelialization, the distance that the epithelium had traveled across the wound was measured; the muscle edges of the panniculus carnosus were used as indicator for the initial wound edges; and re-epithelialization was calculated as the percentage of the distance of edges of the panniculus carnosus muscle. For granulation tissue quantification, the area covered by a highly cellular tissue was determined.

n. Flow Cytometric Analysis of the Wounds

Skin wounds were treated with fibrin matrices as described above. After 5 days, the wounded skins were removed as described above, cut into small pieces (<0.5 mm²) and transferred to 1 mL of an enzyme solution (collagenase D (1 mg/mL)) and agitated for 1 hr at 37° C. Then, the cells from digested wounds were re-suspended in PBS, passed through a cell strainer and centrifuged. Then, cells were stained for 15 min in 100 μL of FACS buffer containing antibodies: anti-CD31 (MEC13.3, BD Biosciences), anti-Ki67 (B56, BD Biosciences), anti-CD45 (30-F11), anti-Ly6G (1A8), anti-Ly6C (HK1.4), and anti-CD11b (M1/70). All antibodies were purchased from BioLegend if not otherwise described. Fixable live/dead cell discrimination was performed using Fixable Viability Dye eFluor 455 (eBioscience) according to the manufacturer's instructions. Intracellular staining was performed using the Intracellular Staining Permeabilization Wash Buffer according to manufacturer's instructions (BioLegend). Cells were analyzed using a Fortessa (BD Biosciences) flow cytometer and analyzed using FlowJo software (FlowJo, LLC).

o. Statistical Analysis

Statistical methods were not used to predetermine necessary sample size, but sample sizes were chosen based on estimates from pilot experiments and previously published results such that appropriate statistical tests could yield significant results. Statistically significant differences between experimental groups were determined by one-way ANOVA followed by Tukey's HSD post hoc test with Prism software (v7, GraphPad). Variance between groups was found to be similar by the Brown-Forsythe test. For non-parametric data, the Kruskal-Wallis test followed by Dunn's multiple comparison test was used. For ELISA data, the two-tailed Mann-Whitney U test was used. For the animal studies, experiments were not performed in a blinded fashion. Mice were randomized into treatment groups within a cage immediately before the wound surgery and treated in the same way. All animal experiments were performed with approval from the Veterinary Authority of the Institutional Animal Care and Use Committee of the University of Chicago. GF-laminin binding ELISA assays were repeated 4 times. Wound healing assays were repeated 3 times. The P values less than 0.05 are considered to be significantly different. The P values less than 0.05 and 0.01 indicate symbols * and **, respectively.

Example 2—Use of Recombinant Laminin A-Chain LG4 Domain for Controlled Delivery of Growth Factor/Chemokines from Biomaterials Controlling the release kinetic of therapeutic proteins, such as growth factors (GFs) and chemokines, is essential to fully exploit their biological effects. In regenerative medicine, for example, GFs that are rapidly release from an injured site showed very modest clinical efficacy, thus implying their use at supra-physiological doses. As a consequence of such high non-physiological dosing, several GF-based therapies received safety warnings due to serious side effects directly related to the GF activity (e.g. ectopic tissue growth, tumor development). In this context, it has been demonstrated that engineering the slow-release of therapeutic proteins from biomaterials significantly increase their biological effects at reduced doses.

The inventors showed that LG4 domains located in the α-chain of the different laminin isoforms strongly bind to multiple GFs and chemokines. In this example, the use of these high affinity and promiscuous interactions between the laminin α-chain LG4 domains and GFs/chemokines to control GFs/chemokines delivery from biomaterials is described. Indeed, the incorporation of the LG4 domains in biomaterials can substantially increase retention of GF/chemokines, by providing high-affinity binding substrates.

Experimental design: Here, the incorporation of recombinant laminin LG4 domains into biomaterials through enzymatic cross-linking within the biomaterial is exemplified. More precisely, the LG4 domain of α3, α4 or α5-chain isoforms of laminin can be incorporated into fibrin-containing biomaterials through enzymatic crosslinking by the factor XIIIa during fibrin polymerization.

Other incorporation methods may include direct chemical conjugation of recombinant laminin LG4 to the biomaterial, or fusion of LG4 domains to protein sequences displaying strong but non-covalent binding to the biomaterial.

Methods: In this approach, the DNA sequence encoding for the transglutaminase substrate domain of the $\alpha_2$-plasmin inhibitor, named $\alpha_2PI_{1-8}$ (amino acid sequence: NQEQVSPL (SEQ ID NO: 12)), followed by the DNA sequence of a short GGSG linker (SEQ ID NO: 81), can be fused to the 5'-end of the DNA sequence encoding for a LG4 domain of laminin α3, α4 or α5-chains; so that the end construct will be $\alpha_2PI_{1-8}$-GGSG (SEQ ID NO: 81)-LG4 (see sequences below).

Modified recombinant LG4 domains sequences can be then inserted into a DNA plasmid suitable for protein production. For production in mammalian cells, plasmids generally contain a Kozak sequence, a start codon and a signal sequence for protein secretion (e.g. IgGκ signal sequence), downstream of a strong ubiquitous promotor (e.g. CMV). The termination of the protein is achieved by a stop codon added at the C-terminus of the DNA sequence. An additional tag, such as a 6× histidine-tag (SEQ ID NO: 80), can be added at the N-terminus of the recombinant protein (i.e. after the signal sequence) or at its C-terminus (i.e. before the stop codon), to further facilitate protein purification. Following this design, recombinant LG4 domains will be produced by transient transfection of HEK293F cells over 7 days, and directly purified from the cell supernatant by affinity chromatography (e.g. to the histidine tag, to heparin) and/or physicochemical-based chromatography (e.g. size exclusion or ion-exchange chromatography). Final purity and identity of the recombinant laminin LG4 domain will be confirmed by SDS-PAGE and western blot analyses.

Results: Recombinant LG4 domains fused to the $\alpha_2PI_{1-8}$ domain can be first assessed for their ability to remain incorporated into fibrin matrix. This is commonly achieved by performing release assays; after incorporation, the amount of recombinant LG4 domain released from fibrin matrix can be daily quantified either by ELISA or by fluorescence measurements, considering that LG4 domains could be fluorescently-labeled prior to incorporation.

As soon as the functionality of the $\alpha_2PI_{1-8}$ domain as a substrate for crosslinking into fibrin can be established, the retention of GF/chemokines into fibrin containing laminin LG4 domains (versus fibrin alone) can be evaluated by ELISA-based release assays. Upon confirmation of successful GF/chemokines retention into fibrin by the recombinant laminin LG4 domains, fibrin matrices containing LG4 domains can be further characterized as a GF/chemokines delivery system in vivo, similarly to what was done in Example 1 with the $\alpha_2PI_{1-8}$-fused LG4-derived peptides.

Interpretation: This molecular engineering of LG4 domains of α3, α4 and α5-chains of human laminin illustrates the use of recombinant LG4 domain as an additive to biomaterials, to enhance pharmacokinetic properties of biomaterials in delivering of GF/chemokines. Particularly in this example, the fusion of LG4 domains with the transglutaminase substrate sequence from $\alpha_2$-plasmin inhibitor could leverage the GF/chemokines delivery properties of fibrin. Fusion of recombinant LG4 domains to other peptidic domains able to be sequestered into natural or synthetic biomaterials could be similarly envisioned.

1. Native Human Sequences of Laminin α-Chain Isoforms

LAMA3 Human, LG4 domain aa2986-aa3150 (UniprotKB database Q16787):
(SEQ ID NO: 13)
ALQFGDIPTSHLLFKLPQELLKPRSQFAVDMQTTSSRGLVFHTGTKNSFM

ALYLSKGRLVFALGTDGKKLRIKSKEKCNDGKWHTVVFGHDGEKGRLVVD

GLRAREGSLPGNSTISIRAPVYLGSPPSGKPKSLPTNSFVGCLKNFQLDS

KPLYTPSSSFGVSSC

NCBI-CCDS database (CCDS11880.1):
(SEQ ID NO: 19)
GCCCTCCAGTTTGGGGACATTCCCACCAGCCACTTGCTATTCAAGCTTCC

TCAGGAGCTGCTGAAACCCAGGTCACAGTTTGCTGTGGACATGCAGACAA

CATCCTCCAGAGGACTGGTGTTTCACACGGGCACTAAGAACTCCTTTATG

GCTCTTTATCTTTCAAAAGGACGTCTGGTCTTTGCACTGGGGACAGATGG

GAAAAAATTGAGGATCAAAAGCAAGGAGAAATGCAATGATGGGAAATGGC

ACACGGTGGTGTTTGGCCATGATGGGAAAAGGGCGCTTGGTTGTGGAT

GGACTGAGGGCCCGGGAGGGAAGTTTGCCTGGAAACTCCACCATCAGCAT

CAGAGCGCCAGTTTACCTGGGATCACCTCCATCAGGGAAACCAAAGAGCC

TCCCCACAAACAGCTTTGTGGGATGCCTGAAGAACTTTCAGCTGGATTCA

AAACCCTTGTATACCCCTTCTTCAAGCTTCGGGGTGTCTTCCTGC.

LAMA4_Human, LG4 domain aa1469-aa1640 (UniprotKB database Q16363):
(SEQ ID NO: 14)
AYQYGGTANSRQEFEHLKGDFGAKSQFSIRLRTRSSHGMIFYVSDQEEND

FMTLFLAHGRLVYMFNVGHKKLKIRSQEKYNDGLWHDVIFIRERSSGRLV

IDGLRVLEESLPPTEATWKIKGPIYLGGVAPGKAVKNVQINSIYSFSGCL

SNLQLNGASITSASQTFSVTPC.

NCBI-CCDS database (CCDS34514.1):
(SEQ ID NO: 20)
GCCTATCAATATGGAGGAACAGCCAACAGCCGCCAAGAGTTTGAACACTT

AAAAGGAGATTTTGGTGCCAAATCTCAGTTTTCCATTCGTCTGAGAACTC

GTTCCTCCCATGGCATGATCTTCTATGTCTCAGATCAAGAAGAGAATGAC

TTCATGACTCTATTTTTGGCCCATGGCCGCTTGGTTTACATGTTTAATGT

TGGTCACAAAAAACTGAAGATTAGAAGCCAGGAGAAATACAATGATGGCC

TGTGGCATGATGTGATATTTATTCGAGAAAGGAGCAGTGGCCGACTGGTA

ATTGATGGTCTCCGAGTCCTAGAAGAAAGTCTTCCTCCTACTGAAGCTAC

CTGGAAAATCAAGGGTCCCATTTATTTGGGAGGTGTGGCTCCTGGAAAGG

CTGTGAAAAATGTTCAGATTAACTCCATCTACAGTTTTAGTGGCTGTCTC

```
AGCAATCTCCAGCTCAATGGGGCCTCCATCACCTCTGCTTCTCAGACATT

CAGTGTGACCCCTTGC

LAMA5_Human, LG4 domain aa3340-aa3513 (UniprotKB
database O15230):
                                        (SEQ ID NO: 15)
SYQFGGSLSSHLEFVGILARHRNWPSLSMHVLPRSSRGLLLFTARLRPGS

PSLALFLSNGHFVAQMEGLGTRLRAQSRQRSRPGRWHKVSVRWEKNRILL

VTDGARAWSQEGPHRQHQGAEHPQPHTLFVGGLPASSHSSKLPVTVGFSG

CVKRLRLHGRPLGAPTRMAGVTPC

NCBI-CCDS database (CCDS33502.1):
                                        (SEQ ID NO: 21)
TCCTACCAGTTTGGGGGTTCCCTGTCCAGTCACCTGGAGTTTGTGGGCAT

CCTGGCCCGACATAGGAACTGGCCCAGTCTCTCCATGCACGTCCTCCCGC

GAAGCTCCCGAGGCCTCCTCCTCTTCACTGCCCGTCTGAGGCCCGGCAGC

CCCTCCCTGGCGCTCTTCCTGAGCAATGGCCACTTCGTTGCACAGATGGA

AGGCCTCGGGACTCGGCTCCGCGCCCAGAGCCGCCAGCGCTCCCGGCCTG

GCCGCTGGCACAAGGTCTCCGTGCGCTGGGAGAAGAACCGGATCCTGCTG

GTGACGGACGGGGCCCGGGCCTGGAGCCAGGAGGGGCCGCACCGGCAGCA

CCAGGGGGCAGAGCACCCCCAGCCCCACACCCTCTTTGTGGGCGGCCTCC

CGGCCAGCAGCCACAGCTCCAAACTTCCGGTGACCGTCGGGTTCAGCGGC

TGTGTGAAGAGACTGAGGCTGCACGGGAGGCCCCTGGGGGCCCCCACACG

GATGGCAGGGGTCACACCCTGC
```

2. Engineered Human Sequences of Laminin α-Chain Isoforms

Sequence design: The factor XIIIa transglutaminase substrate domain from the α₂-plasmin inhibitor (NQEQVSPL—SEQ ID NO:12) was added at the N-terminus of laminin LG4 domains, and separated from the LG4 domain by a short linker GGSG (SEQ ID NO: 81). The α2-plasmin inhibitor domain (NQEQVSPL—SEQ ID NO:12) could have been alternatively added to the C-terminus of LG4 domains (sequences not shown).

```
Human α2PI₁₋₈-LAMA3_LG4₂₉₈₆₋₃₁₅₀:
                                        (SEQ ID NO: 16)
NQEQVSPLGGSGALQFGDIPTSHLLFKLPQELLKPRSQFAVDMQTTSSRG

LVFHTGTKNSFMALYLSKGRLVFALGTDGKKLRIKSKEKCNDGKWHTVVF

GHDGEKGRLVVDGLRAREGSLPGNSTISIRAPVYLGSPPSGKPKSLPTNS

FVGCLKNFQLDSKPLYTPSSSFGVSSC.

Possible DNA sequence of human
α2PI₁₋₈-LAMA3_LG4₂₉₈₆₋₃₁₅₀:
                                        (SEQ ID NO: 22)
AACCAGGAGCAGGTGTCCCCACTTGGTGGATCCGGCGCCCTCCAGTTTGG

GGACATTCCCACCAGCCACTTGCTATTCAAGCTTCCTCAGGAGCTGCTGA

AACCCAGGTCACAGTTTGCTGTGGACATGCAGACAACATCCTCCAGAGGA

CTGGTGTTTCACACGGGCACTAAGAACTCCTTTATGGCTCTTTATCTTTC

AAAAGGACGTCTGGTCTTTGCACTGGGGACAGATGGGAAAAAATTGAGGA

TCAAAAGCAAGGAGAAATGCAATGATGGGAAATGGCACACGGTGGTGTTT

GGCCATGATGGGGAAAAGGGGCGCTTGGTTGTGGATGGACTGAGGGCCCG

GGAGGGAAGTTTGCCTGGAAACTCCACCATCAGCATCAGAGCGCCAGTTT

ACCTGGGATCACCTCCATCAGGGAAACCAAAGAGCCTCCCCACAAACAGC

TTTGTGGGATGCCTGAAGAACTTTCAGCTGGATTCAAAACCCTTGTATAC

CCCTTCTTCAAGCTTCGGGGTGTCTTCCTGC.

Human α2PI₁₋₈-LAMA4_LG4₁₄₆₉₋₁₆₄₀:
                                        (SEQ ID NO: 17)
NQEQVSPLGGSGAYQYGGTANSRQEFEHLKGDFGAKSQFSIRLRTRSSHG

MIFYVSDQEENDFMTLFLAHGRLVYMFNVGHKKLKIRSQEKYNDGLWHDV

IFIRERSSGRLVIDGLRVLEESLPPTEATWKIKGPIYLGGVAPGKAVKNV

QINSIYSFSGCLSNLQLNGASITSASQTFSVTPC.

Possible DNA sequence of human
α2PI₁₋₈-LAMA4_LG4₁₄₆₉₋₁₆₄₀:
                                        (SEQ ID NO: 23)
AACCAGGAGCAGGTGTCCCCACTTGGTGGATCCGGCGCCTATCAATATGG

AGGAACAGCCAACAGCCGCCAAGAGTTTGAACACTTAAAAGGAGATTTTG

GTGCCAAATCTCAGTTTTCCATTCGTCTGAGAACTCGTTCCTCCCATGGC

ATGATCTTCTATGTCTCAGATCAAGAAGAGAATGACTTCATGACTCTATT

TTTGGCCCATGGCCGCTTGGTTTACATGTTTAATGTTGGTCACAAAAAAC

TGAAGATTAGAAGCCAGGAGAAATACAATGATGGCCTGTGGCATGATGTG

ATATTTATTCGAGAAAGGAGCAGTGGCCGACTGGTAATTGATGGTCTCCG

AGTCCTAGAAGAAAGTCTTCCTCCTACTGAAGCTACCTGGAAAATCAAGG

GTCCCATTTATTTGGGAGGTGTGGCTCCTGGAAAGGCTGTGAAAAATGTT

CAGATTAACTCCATCTACAGTTTTAGTGGCTGTCTCAGCAATCTCCAGCT

CAATGGGGCCTCCATCACCTCTGCTTCTCAGACATTCAGTGTGACCCCTT

GC

Human α2PI₁₋₈-LAMA5_LG4₃₃₄₀₋₃₅₁₃:
                                        (SEQ ID NO: 18)
NQEQVSPLGGSGSYQFGGSLSSHLEFVGILARHRNWPSLSMHVLPRSSRG

LLLFTARLRPGSPSLALFLSNGHFVAQMEGLGTRLRAQSRQRSRPGRWHK

VSVRWEKNRILLVTDGARAWSQEGPHRQHQGAEHPQPHTLFVGGLPASSH

SSKLPVTVGFSGCVKRLRLHGRPLGAPTRMAGVTPC.

Possible DNA sequence of human
α2PI₁₋₈-LAMA5_LG4₃₃₄₀₋₃₅₁₃:
                                        (SEQ ID NO: 24)
AACCAGGAGCAGGTGTCCCCACTTGGTGGATCCGGCTCCTACCAGTTTGG

GGGTTCCCTGTCCAGTCACCTGGAGTTTGTGGGCATCCTGGCCCGACATA

GGAACTGGCCCAGTCTCTCCATGCACGTCCTCCCGCGAAGCTCCCGAGGC

CTCCTCCTCTTCACTGCCCGTCTGAGGCCCGGCAGCCCCTCCCTGGCGCT

CTTCCTGAGCAATGGCCACTTCGTTGCACAGATGGAAGGCCTCGGGACTC

GGCTCCGCGCCCAGAGCCGCCAGCGCTCCCGGCCTGGCCGCTGGCACAAG

GTCTCCGTGCGCTGGGAGAAGAACCGGATCCTGCTGGTGACGGACGGGGC

CCGGGCCTGGAGCCAGGAGGGGCCGCACCGGCAGCACCAGGGGGCAGAGC

ACCCCCAGCCCCACACCCTCTTTGTGGGCGGCCTCCCGGCCAGCAGCCAC
```

-continued

```
AGCTCCAAACTTCCGGTGACCGTCGGGTTCAGCGGCTGTGTGAAGAGACT

GAGGCTGCACGGGAGGCCCCTGGGGGCCCCCACACGGATGGCAGGGGTCA

CACCCTGC.
```

Example 3—Use of Recombinant Laminin α-Chain LG4 Domain (or Other ECM Protein-Derived Growth Factor-Binding Domain) for Controlled Release of the Bone Morphogenetic Protein from Collagen Biomaterials Collagen biomaterials are widely used in regenerative medicine, serving as a biocompatible supporting scaffold to promote cell activities during tissue regeneration, and to modulate the release of drugs (e.g. growth factors) upon implantation. As an example, the clinical product InFUSE® Bone Graft (Medtronic) is composed of a bovine Type I collagen sponge laden with the bone morphogenetic protein-2 (BMP-2), a well-known growth factor promoting bone regeneration. In the clinic, delivery of supraphysiological doses of BMP-2 (order of milligrams) into patients raised serious side effects, including ectopic bone formation, nerve injuries and increased cancer risk. Consequently, engineering delivery systems to control the release of BMP-2, as well as other growth factors, from collagen biomaterials constitutes a strong matter of interest for therapeutic use of growth factors. Here, the inventors exemplified the use of the laminin α-chain LG4 domain (LamLG4) and the fibrinogen β-chain heparin-binding domain (FgHBD) (Martino et al., *PNAS*, 2012), as growth factor-binding domains, to control the retention of BMP-2 into collagen biomaterials, and subsequently slow down their release.

1. Protein Designs

The inventors have engineered bipartite «bridge» proteins composed of a growth factor-binding domain linked to a collagen I-binding domain, which are able to retain BMP-2 into collagen biomaterials via non-covalent interactions (FIG. 12). The growth factors binding domains, namely LamLG4 or FgHBD, display strong affinity to BMP-2, and the collagen I-binding domain display strong affinity to collagen biomaterials, more particularly to bovine type I collagen hydrogels and sponges. In this example, the collagen-binding domain is made of a human antigen-binding fragment Fab from an anti-collagen I antibody (here named FabCol) patented elsewhere (WO 2016016269 A1).

2. Materials and Methods a. DNA Sequences Preparation

The sequences of the variable regions of FabCol were taken from the patent WO 2016016269A1 (clone C11) and synthesized by Genscript (USA), before being incorporated into a plasmid containing human Fab constant regions. Both recombinant light chain and heavy chain were placed under the control of CMV promoters. LamLG4 and p(FgHBD) sequences were synthesized by Genscript. To prepare the FabCol-LamLG4 recombinant fusion protein DNA sequence, LamLG4 domain was placed at the C-terminus of the FabCol heavy chain, and separated from it by an 8 amino acids glycine-serine linker. As to the FabCol-p(FgHBD) fusion protein, 3 copies of the FgHBD domain were inserted at the C-termini of both the light and the heavy chains of FabCol, each copy linked to another by a 8 amino acids glycine-serine linker.

b. Protein Production of FabCol, FabCol-LamLG4, FabCol-p(FgHBD)

DNA plasmids of FabCol, FabCol-LamLG4 and FabCol-p(FgHBD) were prepared using NucleoBond Xtra maxiprep kits (Macherey-Nagel, USA). Plasmids were then transfected into human embryonic kidney cells (HEK293-F) using polyethyleneimine-mediated transfection and 1.5 mg plasmid per L of culture. The cells were cultured in suspension for 7 days in Freestyle 293 medium (ThermoFisher Scientific, USA). The culture supernatant was then collected and purified using HiTrap Mab Select column and an Akta PureM25 fast protein liquid chromatography FPLC systems (GE Healthcare Life Sciences, USA) according to the manufacturer instructions. FabCol-LamLG4 and FabCol-p(FgHBD) recombinant fusion proteins were further purified using HiTrap Heparin HP columns (GE Healthcare). Proteins were then dialyzed in phosphate saline buffer (PBS; pH 7.4), sterile-filtered and stored at −80° C.

c. Chemical Conjugation of FgHBD to FabCol

FgHBD peptide (>95% pure) was synthesized by Genscript (USA). FgHBD was chemically conjugated to FabCol using sulfo-SMCC crosslinker (ThermoFisher Scientific). One mg of FabCol was incubated with 30-fold molar excess of the sulfo-SMCC in PBS at room temperature for 1 h, agter what the excess crosslinker was removed using Zeba Spin desalting columns, 7K MWCO (ThermoFisher Scientific). FgHBD peptide was then added to the FabCol at 30-fold molar excess, and the mixture was incubated for 1 h at room temperature. Unconjugated peptides were then removed using an Amicon 30 kDa centrifugal filters by diluting FabCol-p(FgHBD) conjugates into PBS and re-concentrating them, in repeated cycles. The removal of unconjugated FgHBD was assessed by SDS-PAGE gel chromatography. The conjugates were kept at 4° C. for maximum 2 weeks prior to experimentation.

d. SDS-PAGE Analyses

SDS-PAGE was used to assess size of the different FabCol variants. Protein samples were diluted in Laemmli buffer and loaded on MiniProtean TGX precast gels (gradient 4-20%; BioRad, Hercules Calif., USA). Electrophoresis was run in Tris-Glycine-SDS buffer at 130 V for 1 h. Proteins were visualized using SimplyBlue SafeStain staining (ThermoFisher scientific).

e. Binding Assay to Bovine Type I Collagen

ELISA plates (NUNC MaxiSorp, ThermoFisher Scientific) were coated overnight with 10 µg/mL of bovine type I collagen (PureCol, Advanced BioMatrix, San Diego Calif., USA) at room temperature. The plate was further blocked using 2% bovine serum albumine (BSA) for 2 h at room temperature. Then, appropriate amount of the FabCol-FgHBD conjugates, FabCol-LamLG4 or FabCol-p(FgHBD) recombinant proteins were diluted in PBS-0.05% Tween (PBST)+0.1% BSA to reach concentrations ranging from 0.01 nM to 30 nM, and were incubated for 1 h at room temperature. The plate was washed thrice in PBST, and an horseradish peroxidase-conjugated anti-human Fab antibody (Jackson ImmunoResearch) was used to detect bound FabCol variants. The plate was revealed using TMB substrate solution, and stop with 1 M H2SO4. Absorbance at 450 nm was read using a Jackson ImmunoResearch, and corrected using the absorbance at 570 nm. Curve fits and dissociation constant KD were computed using Prism (GraphPad Software Inc., USA).

f. Binding Assay to rhBMP-2

ELISA plates (NUNC MaxiSorp) were coated with 50 nM of recombinant human BMP-2 (CHO produced, R&D Systems, Minneapolis Minn., USA) overnight at room temperature. The plate was then blocked using 2% BSA for 2 h at room temperature, after which the plate was washed in PBST and incubated with 50 nM of the FabCol-FgHBD conjugates, FabCol-LamLG4 or FabCol-p(FgHBD) recombinant proteins diluted in PBS-0.05% Tween (PBST)+0.1% BSA. Bound FabCol variants were detected and revealed as described above.

g. Binding Assay to Engineered Super-Affinity Growth Factors

Engineered super-affinity growth factors and mouse wild-type VEGF-C were produced as described in Martino et al., Science, 2014. Other wild-type recombinant human growth factors were purchased from R&D Systems or Peprotech (Rocky Hill N.J., USA). Growth factors were coated on medium-binding plates (Greiner) at a concentration of 100 nM for 1 h at 37° C. Plates were then blocked with 2% BSA in PBS for 2 h at room temperature. Then, the FabCol variants (100 nM) were diluted in 1% BSA and incubated in the wells for 1 h at room temperature. The plate was washed four times in PB ST and an HRP-anti-human Fab antibody was used to detect bound FabCol variants. Plate absorbance was read as described above.

h. Release from Collagen Matrix

Collagen hydrogels of 150 µL were prepared using Pure-Col bovine type I collagen (Advanced BioMatrix). FabCol variants (120 nM) and rhBMP-2 (500 ng/mL) were mixed with collagen (2.4 mg/mL) and 1× Minimum Essential Medium (MEM), used as a pH indicator. Under agitation, the pH was neutralized by adding 1 M NaOH, after what the mixture was directly plated into a 48-well plate, previously blocked overnight with 2% BSA in PBS. Gels were then polymerized for 1 h at 37° C. Release buffer (1 mL; Tris 20 mM, NaCl 150 mM, 0.1% BSA, 1% Penicillin-Streptomycin) was then added to the wells, and the gels were gently detached from the plate. The release buffer was collected and refreshed daily, and stored at −20° C. until analysis. A well that contained only BMP-2 served as a 100% released control. The amount of released rhBMP-2 was quantified using human BMP-2 DuoSet ELISA kit (R&D Systems), according to the manufacturer's instructions.

i. Immunohistochemistry Assessment of rhBMP-2 Retention into Collagen Sponge

Recombinant human BMP-2 (0.1 mg/mL in PBS) mixed with the FabCol variants at a 1:1 molar ratio was dripped onto collagen sponges (7 µL; Integra LifeSciences, Plainsboro Township N.J., USA), and further incubated 15 min at room temperature. Sponges were washed twice for 2.5 h in 10 mL of PBS containing 2% Fetal Bovine Serum (FBS). Sponges were then fixed in 2% paraformaldehyde (PFA) for 30 min. Sponges were again washed in PBS-2% FBS, and stained using a biotinylated anti-hBMP-2 (R&D Systems) and a streptavidin-AF594 using standard staining procedures. Sponges were imaged using a Leica DMi8 microscope (Leica, Wetzlar, Germany) and analysed using Fiji software (ImageJ, National Institute of Health, USA).

3. Results:

a. Conjugation of a Collagen-Binding Domain FabCol to a Growth Factor-Binding Domain FgHBD In this example, fibrinogen-derived domain FgHBD is used as the growth factor binding domain. The laminin-derived growth factor binding domains, such as LamLG4 may also be used. To engineer a bridge protein able to link growth factors into collagen biomaterials, FgHBD was chemically conjugated to FabCol using a sulfo-SMCC linker (FIG. 13A). Conjugation was confirmed by SDS-PAGE analysis, which revealed a shift of about 35 kDa in size between the non-conjugated FabCol and the FabCol-FgHBD conjugates. Such a size difference suggests that multiple copies of the FgHBD peptides were conjugated to the FabCol (FIG. 13B). After conjugation, the binding of FabCol-FgHBD conjugates to bovine type I collagen was preserved, although the affinity was reduced compared to non-conjugated FabCol. The dissociation constant $K_D$ of FabCol-FgHBD conjugates to collagen I was determined by ELISA to be of high affinity, around 2.8 nM (FIG. 13C). In addition, FabCol-FgHBD conjugates strongly bound to rhBMP-2, whereas FabCol only did not (FIG. 13D).

b. FabCol-FgHBD Conjugates Increased Retention of rhBMP-2 into Collagen Biomaterials When incorporated into collagen hydrogels, FabCol-FgHBD strikingly increased the retention of rhBMP-2 (FIG. 13E); indeed, only 20% of rhBMP-2 was released after 7 days, in contrast to 80% for the gels containing rhBMP-2 only or in presence of FgHBD peptides, and 50% for the gels containing FabCol. In collagen sponges, increased sequestration in presence of FabCol-FgHBD, added at a 1:1 molar ratio with rhBMP-2, was visualized by immunohistochemistry (FIG. 13F). Under the tested experimental conditions, rhBMP-2 showed some retention into collagen sponge, yet the presence of FabCol-FgHBD conjugates substantially increased this retention.

c. Engineering Recombinant Fusion Protein Linking a Collagen-Binding Domain FabCol to LamLG4 or FgHBD Growth Factor-Binding Domains to Sequester rhBMP-2 into Collagen Biomaterials Two recombinant fusion proteins were made to bridge growth factors, particularly rhBMP-2, to collagen biomaterials (FIG. 14A). In a first design, 3 sequential repeats of FgHBD domain separated by glycine-serine linkers were fused to both C-termini of the FabCol light and heavy chains. In a second design, the LamLG4 domain was fused to the C-terminus of the FabCol heavy chain. Both fusion proteins were successfully produced in HEK293 cells and purified using protein A and heparin affinity, confirming the presence of FabCol and the growth factor-binding domains on the fusion proteins. Indeed, both FgHBD and LamLG4 were shown to bind to heparin (Ishihara et al., Nature Communications 2018; Martino et al., PNAS 2013). Purified proteins were analysed by SDS-PAGE, which revealed the presence of multiple bands around 75 kDa for the FabCol-p(FgHBD) variant, which theoretical size is 80 kDa. In contrast, FabCol-LamLG4 variant appeared as a single band around 80 kDa while its theoretical size is 71 kDa (FIG. 14B). Importantly, strong affinity of FabCol-p(FgHBD) and FabCol-LamLG4 to bovine type I collagen was observed by ELISA, with $K_{DS}$ around 1.7 nM and 2.3 nM respectively (FIG. 14C). Similarly, both variants strongly bound to rhBMP-2, with FabCol-LamLG4 being superior to FabCol-p(FgHBD) (FIG. 14D). Finally, release tests showed that rhBMP-2 sequestration into type I collagen is substantially increased in presence of FabCol-LamLG4 (FIG. 14E).

d. Combining FabCol-LamLG4 Bridge Protein Technology with the Engineering of Super-Affinity ECM-Binding Growth Factors to Further Enhance Growth Factors Delivery Interestingly, the inventors further assessed the affinity of FabCol-LamLG4 to other growth factors and growth factors engineered for super-affinity to the ECM (Martino et al. Science, 2014, WO2014006082A1). Super-affinity growth factors were engineered as fusion of wild-type growth factors with an ECM-binding domain derived from the placental growth factor-2, which allow their strong retention within physiological ECMs, mostly through interactions with glycoproteins (e.g. fibronectin, vitronectin, tenascin) and glycosaminoglycans (e.g. heparan-sulfates GAGs). Because LamLG4 is derived from laminin, a well-known ECM protein of the basement matrix, PlGF-2 engineered growth factors are expected to exhibit higher affinities to FabCol-LamLG4 than the wild-type growth factors. Indeed, one can appreciate in FIG. 14F that the binding of FabCol-LamLG4 to PlGF-2-engineered growth factors was significantly higher than the one to non-engineered wild-type growth factors. This results would suggests that retention of growth factors into collagen biomaterials in presence of FabCol-LamLG4 might be further increased by the engineering of the growth factor using the PlGF-2-derived ECM-binding domain, and so that these two technologies could rationally be used in combination.

4. Sequences:

```
FabCol light chain with the human Fab constant
region:
                                  (SEQ ID NO: 62)
EIVLTQSPGTLSLSPGERATLSCRASQSVSSSYLAWYQQKPGQAPRLLIY

GASSRATGIPDRFSGSGSGTDFTLTISRLEPEDFAVYYCQQAIGFPQTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

Anti-Collagen light chain variable region:
                                  (SEQ ID NO: 63)
EIVLTQSPGTLSLSPGERATLSCRASQSVSSSYLAWYQQKPGQAPRLLIY

GASSRATGIPDRFSGSGSGTDFTLTISRLEPEDFAVYYCQQAIGFPQTFG

QGTKVEIK

FabCol heavy chain with the human Fab constant
region:
                                  (SEQ ID NO: 64)
EVQLLESGGGLVQPGGSLRLSCAASGFTFSSYAMSWVRQAPGKGLEQVSA

ISGSGGSTYYADSVKGRFTISRDNSKNTLYLQMNSLRAEDTAVYYCAKTL

AAFDYWGQGTLVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKRVEPKSCGS
Anti-Collagen heavy chain variable region:
                                  (SEQ ID NO: 65)
EVQLLESGGGLVQPGGSLRLSCAASGFTFSSYAMSWVRQAPGKGLEQVSA

ISGSGGSTYYADSVKGRFTISRDNSKNTLYLQMNSLRAEDTAVYYCAKTL

AAFDYWGQGTLVTV

FgHBD (used for conjugation):
                                  (SEQ ID NO: 66)
GCGGSLRPAPPPISGGGYRARPAKAAATQKKVERKAPDA In some embodiments, the FgHBD comprises:
                                  (SEQ ID NO: 67)
SLRPAPPPISGGGYRARPAKAAATQKKVERKAPDA FabCol-LamLG4 heavy chain with the human Fab
constant region (LamLG4 is displayed in italic):
                                  (SEQ ID NO: 71)
EVQLLESGGGLVQPGGSLRLSCAASGFTFSSYAMSWVRQAPGKGLEQVSA

ISGSGGSTYYADSVKGRFTISRDNSKNTLYLQMNSLRAEDTAVYYCAKTL

AAFDYWGQGTLVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKRVEPKSCGSGGGSGG*SLNKPPFLMLLKGSTRFNKT*

*KTFRINQLLQDTPVASPRSVKVWQDACSPLPKTQANH*

*GALQFGDIPTSHLLFKLPQELLKPRSQFAVDMQTTSSRGL*

*VFHTGTKNSFMALYLSKGRLVFALGTDGKKLRIKSKEK*

*CNDGKWHTVVFGHDGEKGRLVVDGLRAREGSLPG*

*NSTISIRAPVYLGSPPSGKPKSLPTNSFVGCLKNFQLDSKPL*

*YTPSSSFGVSSCTG*.

LamLG4:
                                  (SEQ ID NO: 68)
SLNKPPFLMLLKGSTRFNKTKTFRINQLLQDTPVASPRSVKVWQDACSPL

PKTQANHGALQFGDIPTSHLLFKLPQELLKPRSQFAVDMQTTSSRGLVFH

TGTKNSFMALYLSKGRLVFALGTDGKKLRIKSKEKCNDGKWHTVVFGHDG

EKGRLVVDGLRAREGSLPGNSTISIRAPVYLGSPPSGKPKSLPTNSFVGC

LKNFQLDSKPLYTPSSSFGVSSCTG.

FabCol-p(FgHBD) light chain with the human Fab
constant region (the 3 repeats of p(FgHBD) are
displayed in italic):
                                  (SEQ ID NO: 72)
EIVLTQSPGTLSLSPGERATLSCRASQSVSSSYLAWYQQKPGQAPRLLIY

GASSRATGIPDRFSGSGSGTDFTLTISRLEPEDFAVYYCQQAIGFPQTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGECGAGGGSGG*GHRPLDK*

*KREEAPSLRPAPPPISGGGYRARPAKAAATQKKVERKA*

*PDAGGGSGGGSGGGHRPLDKKREEAPSLRPAPPPISGGG*

*YRARPAKAAATQKKVERKAPDAGGGSGGGSGGGHRPL*

*DKKREEAPSLRPAPPPISGGGYRARPAKAAATQKK*

*VERKAPDAGGGT*.

Three repeats of p(FgHBD):
                                  (SEQ ID NO: 69)
GHRPLDKKREEAPSLRPAPPPISGGGYRARPAKAAATQKKVERKAPDAGG

GSGGGSGGGHRPLDKKREEAPSLRPAPPPISGGGYRARPAKAAATQKKVE

RKAPDAGGGSGGGSGGGHRPLDKKREEAPSLRPAPPPISGGGYRARPAKA

AATQKKVERKAPDAGGGT
or
                                  (SEQ ID NO: 70)
GHRPLDKKREEAPSLRPAPPPISGGGYRARPAKAAATQKKVERKAPDAGG

GSGGGSGGGHRPLDKKREEAPSLRPAPPPISGGGYRARPAKAAATQKKVE

RKAPDAGGGSGGGSGGGHRPLDKKREEAPSLRPAPPPISGGGYRARPAKA

AATQKKVERKAPDAGGTG

FabCol-p(FgHBD) heavy chain with the human Fab
constant region (the 3 repeats of p(FgHBD) are
displayed in italic):
                                  (SEQ ID NO: 73)
EVQLLESGGGLVQPGGSLRLSCAASGFTFSSYAMSWVRQAPGKGLEQVSA

ISGSGGSTYYADSVKGRFTISRDNSKNTLYLQMNSLRAEDTAVYYCAKTL

AAFDYWGQGTLVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKRVEPKSCGSGGGSGG*GHRPLDKKREEAPSLRPAPPPI*
```

-continued

SGGGYRARPAKAAATQKKVERKAPDAGGGSGGGSG

GGHRPLDKKREEAPSLRPAPPPISGGGYRARPAKAA

ATQKKVERKAPDAGGGSGGGSGGGHRPLDKKREEAPSLR

PAPPPISGGGYRARPAKAAATQKKVERKAPDAGGTG.

Example 4: A Peptide from Von Willebrand Factor that Functions as a Growth Factor Reservoir to Promote Wound Healing During wound healing, the distribution, availability and signaling of growth factors (GFs) are orchestrated by their binding to extracellular components in the wound microenvironment and provisional matrix. The hemostatic protein von Willebrand factor (vWF) regulates angiogenesis; its deficiency or dysfunction is associated with vascular malformations. This example shows that vWF deficiency delays wound healing accompanied by decreased angiogenesis and decreased amounts of vascular endothelial growth factor-A (VEGF-A) in the wound. In vitro, vWF binds to several GFs and vWF binds to GFs in human serum. Serum from a type 2B von Willebrand disease (vWD) patient carrying the R1341Q point mutation within the vWF peptide showed reduced vWF-GF associations. Incorporation of the vWF peptide into fibrin matrices enabled sequestration and slow release of incorporated GFs. Treatment of chronic skin wounds with VEGF-A165 and platelet derived growth factor (PDGF)-BB incorporated within vWF peptide-functionalized fibrin matrices accelerated wound healing, with increased angiogenesis and smooth muscle cell proliferation. Therefore, the vWF peptide can function as a GFs reservoir, leading to effective angiogenesis and tissue regeneration.

1. Materials and Methods a. Wound-Healing of vWF-Deficient Mice

Mouse surgical preparation, wounding, splinting, and bandaging was performed as previously described. Briefly, vWF deficient and littermate control mice ages 20 to 24 wk were used. Their backs were shaved and two full-thickness punch biopsy wounds (6 mm in diameter) were created in each mouse. Donut-like silicone disc was used as a splint. The splint was placed on the wound and anchor the splint with 6-0 nylon sutures to ensure positioning. Then, wounds were covered with a adhesive film dressing (Hydrofilm, Hartmann). After 5 d, wounds were collected and used for further analysis. All animal experiments were performed with approval from the Veterinary Authority of the Institutional Animal Care and Use Committee of the University of Chicago and Imperial College London in accordance with the UK Animals (Scientific Procedures) act of 1986.

b. Histomorphometric Analysis of Wound Tissue Sections

Histomorphometric analyses were performed as previously reported. Briefly, an area of 8 mm in diameter, which includes the complete epithelial margins, was excised. Wounds were fixed with 2% PFA and cut in the center into two and embedded into paraffin. Histological analysis was performed on 5 µm serial sections. Images were captured with an EVOS FL Auto microscope (Life Technologies). The extent of re-epithelialization and granulation tissue formation were measured by histomorphometric analysis of tissue sections (H&E staining) using ImageJ software. For analysis of re-epithelialization, the distance that the epithelium had traveled across the wound was measured; the muscle edges of the panniculus carnosus were used as an indicator for the initial wound edges, and re-epithelialization was calculated as the percentage of the distance of edges of the panniculus carnosus muscle. For granulation tissue quantification, the area covered by a highly cellular tissue was determined.

c. Flow Cytometric Analysis of the Wounds

The wounded skins regions were removed, cut into small pieces (<0.5 mm$^2$) and transferred to 1 mL of an enzyme solution (collagenase D (1 mg/mL)) and agitated for 1 hr at 37° C. Then, the cells from digested wounds were re-suspended in PBS, passed through a cell strainer, and centrifuged. Then, cells were stained for 15 min in 100 µL of FACS buffer containing antibodies: anti-CD31 (MEC13.3, BD Biosciences), anti-Ki67 (B56, BD Biosciences), anti-CD45 (30-F11), anti-α-smooth muscle actin (SMA) (R & D systems). Fixable live/dead cell discrimination was performed using Fixable Viability Dye eFluor 455 (eBioscience) according to the manufacturer's instructions. Intracellular staining was performed using the Intracellular Staining Permeabilization Wash Buffer according to manufacturer's instructions (BioLegend). Cells were analyzed using a Fortessa (BD Biosciences) flow cytometer and data was analyzed using FlowJo software (FlowJo, LLC).

d. Quantification of VEGF-A in the Wounds

Wounds were harvested using an 8 mm diameter biopsy punch. The tissue was transferred in 0.9 mL of tissue T-PER Tissue Protein Extraction Reagent (Thermo Scientific) containing 1 mg/mL of collagenase IV (Sigma-Aldrich), and homogenized with a tissue homogenizer. The tissue lysate was incubated 1 hr at 37° C. and 100 µL of a 5 M NaCl solution containing protease inhibitors (1 tablet of protease inhibitor cocktail for 10 mL) added to the lysate. The samples were centrifuged at 10000×g for 5 min, and the supernatants were stored at −80° C. Recombinant human VEGF-A165 in the wound tissue was quantified by ELISA (DuoSet, R&D Systems).

e. Mouse Diabetic Skin Wound Healing Model

Diabetic skin wound healing assays were performed in the mouse as previously reported. Briefly, C57BLKS/J-m/Lepr db (db/db) male mice were 10 to 12 wk old at the start of the experiments. Their backs were shaved and four full-thickness punch biopsy wounds (6 mm in diameter) were created in each mouse. Directly after, fibrin matrices [80 mL total, fibrinogen (10 mg/mL), 2 µM α$_2$PI$_{1-8}$-vWF peptide, 100 ng of VEGF-A165, and 50 ng of PDGF-BB] were polymerized on the wounds; the N-terminal α2 plasmin inhibitor peptide (α$_2$PI$_{1-8}$) is a substrate for factor XIIIa and provides covalent incorporation of the vWF peptide into fibrin during coagulation, as previously reported for other biomolecules. To avoid drying of the matrices, the wounds were covered with adhesive film dressing (Hydrofilm, Hartmann). Mice were single-caged after the wound surgery. After 7 d, mice were sacrificed and the skin wounds were carefully harvested for histological analysis.

f. Statistical Analysis

Statistically significant differences between experimental groups were determined by one-way ANOVA followed by Tukey's HSD post hoc test with Prism software (v7, GraphPad). For single comparisons, a two-tailed Student's t-test was used. The symbols * and ** indicate p values less than 0.05 and 0.01, respectively; N.S., not significant.

2. Results a. vWF Deficiency Results in Delayed Wound Healing by Decreased Angiogenesis The inventors first tested whether endogenous vWF plays a role in dermal wound healing. Full-thickness back-skin wounds were made on vWF-deficient mice and littermate wild-type (WT) controls. After 5 d, wounds were analyzed (FIG. 15). As a result, vWF deficiency significantly delayed wound closure, which was associated with poor granulation tissue formation (FIG. 15A-B). vWF deficiency decreased the proliferation of CD31$^+$ endothelial cells and smooth muscle cells (SMCs), in the wounds, suggesting impaired angiogenesis (FIG. 8C-D). The inventors next tested the amount of VEGF-A, a strong angiogenesis inducer, per wound. ELISA after homogenization of wound tissue samples revealed that vWF deficiency decreased the amount of the VEGF-A in the wounds (FIG. 15E). These results suggest that vWF contributes to skin tissue repair through angiogenesis and GF involvement.

b. vWF Binds to Multiple GFs

The inventors then tested the hypothesis that vWF promiscuously binds to GFs. A panel of GFs from the PDGF/VEGF, FGF, TGFβ/bone morphogenetic protein (BMP), neurotrophin, and chemokine families were selected. VEGF-A121, which did not show significant binding to vWF by surface plasmon resonance (SPR) (FIG. 21), was used as non-binding reference. The results of the binding screening are shown (FIG. 16A-B). As a result, vWF bound to VEGF-A165, placenta growth factor (PlGF)-2, PDGF-AA, PDGF-BB, PDGF-CC, and PDGF-DD, but not to VEGF-A121 or PlGF-1, neither of which bind heparin. From the FGF family, vWF bound to FGF-2, FGF-7, and FGF-18, but not to FGF-1 or FGF-6. Among the transforming growth factor (TGF)β/bone morphogenetic protein (BMP) family, vWF showed strong binding to TGF-β1 and BMP-2, but not to TGF-β3 or BMP-7. Regarding the neurotrophins, both nerve growth factor (β-NGF) and neurotrophin-3 (NT-3) showed relevant binding. Neither insulin-like growth factor-I (IGF-I) nor IGF-II bound to vWF. In addition, epidermal growth factor (EGF) did not show binding to vWF. From the chemokine family, CXCL-11 bound to vWF and CXCL-12α did not, whereas its isoform CXCL-12γ which has an additional HBD in its C-terminus, showed strong binding signal to vWF. These data indicate that vWF binds to multiple heparin binding GFs.

The binding affinity of vWF to VEGF-A165 and PDGF-BB was determined by SPR (FIG. 16C-D). The curves obtained for the specific binding signals were fitted with Langmuir binding kinetics. The binding affinity between VEGF-A165 and vWF was described by a single dissociation constant ($K_D$ value) of 27 nM. PDGF-BB had two estimated binding sites, with the lowest $K_D$ value of 24 nM. The nM range of $K_D$ values demonstrate strong binding affinities of vWF to the tested heparin-binding GFs.

c. vWF Binds to VEGF-A in Human Serum

The inventors next tested the presence of the GF-vWF complex in pooled serum from healthy donors. Both sandwich ELISA and immunoprecipitation followed by Western blotting showed that vWF binds to VEGF-A in two different lots of pooled human serum (FIG. 17A-B). These data suggest that VEGF-A-vWF complexes are present in the circulation.

d. The HBD of vWF A1 Domain Binds to Multiple GFs

The inventors next investigated the domain within vWF responsible for association with GFs. ELISA assays for vWF binding to VEGF-A165, PlGF-2 or FGF-2, were carried out in the presence of excess (10 μM) heparin. Excess heparin inhibited vWF binding to the GFs (FIG. 22), indicating involvement of HBDs. The HBD of vWF is located in the A1 domain (FIG. 18A); thus the inventors evaluated GF binding to the recombinant A1 domain. VEGF-A165, PlGF-2, PDGF-BB, FGF-2 and CXCL-12γ showed strong binding to recombinant A1 domain, as measured by ELISA (FIG. 18B). The inventors next used a chemically synthesized vWF HBD (24-amino acid peptide, Table 1). In these studies, VEGF-A165, PlGF-2, PDGF-BB, FGF-2 and CXCL-12γ showed binding to the vWF HBD, whereas neither VEGF-A121 nor PlGF-1 were able to bind to the vWF HBD, consistent with the results in FIG. 16 (FIG. 18C). These data show that the vWF A1 peptide binds to GFs.

e. vWF Binds to Heparin-Binding VEGF-A Via the HBD within the A1 Domain

The inventors examined the association between multiple recombinant isoforms of VEGF-A and vWF domains (FIG. 23A). VEGF-A165 was found to bind plasma-derived purified vWF as well as immature, pro-peptide-containing recombinant vWF (FIG. 23B). Similarly, VEGF-A145, which also contains VEGF's HBD, bound to vWF (FIG. 23C), whilst VEGF-A121, which lacks a HBD, did not (FIG. 23D). The vWF A1 domain bound to VEGF-A165 and VEGF-A145. However, no binding of the vWF A2 or A3 domains to VEGF-A165 or VEGF-A145 was detected (FIG. 23B-C). The vWF A1 HBD peptide was also able to bind to VEGF-A165 and VEGF-A145, with a similar magnitude. Scrambling of the amino acid sequence of the vWF A1 HBD abolished the binding (FIG. 23B-C), suggesting that the sequence, not just the total charge, is crucial for the association with VEGF-A165 and VEGF-A145. In addition, substitutions of Arg with Ser in the vWF A1 HBD sequence impaired the binding (FIG. 23B-C), indicating that the positively charged residues are essential. These data demonstrate that the HBDs in vWF A1 domain and in VEGF-A are responsible for binding between the two proteins.

f. Type 2B vWD R1341 Mutation Impairs vWF Binding to GF In Vitro and in Human Serum Missense point mutations within the A1 domain of vWF have been reported in patients with type 2B vWD, a subtype where the increased affinity of vWF for GPIbα results in spontaneous platelet aggregation, loss of the most active high molecular weight vWF multimers, thrombocytopenia and bleeding. Type 2B mutations are clustered in exon 28 of the vWF gene, encoding the vWF A1 domain, and some map within the HBD. One such mutation, affecting R1341 within the HBD, has been reported in several patients with type 2B vWD (vWF Variant Database found on the world wide web at vWF.group.shef.ac.uk/), with substitutions to either Leu, Pro, Gln, or Trp. Because Arg in HBDs seems to be crucial for the GF binding (FIG. 23B-C), The inventors next investigated whether this mutation could affect vWF-GF binding. Mutation of R1341 to any of these residues, or Ser, abolished binding between the vWF A1 HBD and GFs (considering VEGF-A165, PDGF-BB, and FGF-2) (FIG. 19A). These data indicate that the R1341 residue is indispensable for binding between vWF A1 HBD and GFs. Crucially, the R1341Q mutation also decreased binding to GFs (i.e. VEGF-A165, PDGF-BB, and FGF-2) to full-length recombinant human vWF, compared to its WT form (FIG. 19B). Moreover, serum from a patient with type 2B vWD carrying the R1341Q mutation displayed decreased vWF binding to GFs (i.e. VEGF-A165, PDGF-BB, and FGF-2), compared to serum from healthy donors (FIG. 19C).

Next, the inventors examined whether vWF HBD peptide is able to improve GF retention within a fibrin matrix, using VEGF-A165 and PDGF-BB, which have been observed to be quickly released from fibrin. Fibrinogen solutions containing GFs and the vWF HBD with integrated factor XIIIa transglutaminase reactive substrate sequence, i.e. $\alpha_2 PI_{1-8}$-vWF HBD, were polymerized to form a fibrin matrix using thrombin and factor XIII. GF release from the matrix was determined by ELISA (FIG. 20A-B). As previously shown, VEGF-A165 and PDGF-BB were quickly released from the unmodified fibrin matrix (>85% released after 1 d). However, by incorporating the $\alpha_2PI_{1-8}$-vWF HBD peptide, VEGF-A165 and PDGF-BB were retained within the fibrin matrices (45% and 52% retention on day 5, respectively). These results demonstrate that the vWF HBD enhances the function of a fibrin matrix as a GF reservoir. The inventors also observed the effect of vWF HBD on slow-release of other GFs (i.e. CXCL-12γ and FGF-2) from a poly ethylene glycol (PEG)-based synthetic matrix, which has no intrinsic affinity for GFs (FIG. 24). These data show that vWF HBD serves as a GFs reservoir in multiple contexts and for multiple factors.

g. α2PI$_{1-8}$-vWF HBD Peptide Functionalized Fibrin Matrix Promotes Chronic Wound Healing In Vivo.

The inventors hypothesized that fibrin matrices functionalized with the vWF HBD peptide could potentiate the effect of GFs due to GF sequestration and resulting slow release from matrices, resulted in enhancing skin wound healing in a delayed wound healing model. A genetic mouse model of type 2 diabetes provides a well-established and clinically relevant experimental system of delayed wound healing, and induction of angiogenesis reportedly promotes wound healing in this model. VEGF-A165 and PDGF-BB, which are crucial angiogenesis inducers and exhibited binding to the vWF HBD, were incorporated within a fibrin matrix. As above, the inventors used the Factor XIIIa-induced coupling of the $\alpha_2PI_{1-8}$ sequence to fibrin with the $\alpha_2PI_{1-8}$-vWF HBD to functionalize the matrix. Four groups of treatment were established: fibrin only, fibrin functionalized with $\alpha_2PI_{1-8}$-vWF HBD, fibrin containing the GFs, and fibrin functionalized with $\alpha_2PI_{1-8}$-vWF HBD containing the GFs. After 7 d, histology of wounded skin was analyzed. The wounds that received fibrin matrices containing only GFs or vWF HBD did not differ from wounds treated with fibrin alone, in either amount of granulation tissue or degree of wound closure (FIG. 20C). In contrast, the combined delivery of VEGF-A165 and PDGF-BB by fibrin functionalized with $\alpha_2PI_{1-8}$-vWF HBD led to significantly faster wound closure due to re-epithelialization. The development of granulation tissue was maintained (FIG. 20D). The inventors next examined endothelial cells in the wounds (FIG. 20E). Co-delivery of VEGF-A165 and PDGF-BB in fibrin functionalized with $\alpha_2PI_{1-8}$-vWF HBD led to a significantly increased frequency of CD31$^+$CD45$^-$ endothelial cells compared to fibrin only group after 5 d of wounding. Co-delivery of VEGF-A165 and PDGF-BB in $\alpha_2PI_{1-8}$-vWF HBD functionalized fibrin significantly increased frequency of Ki67$^+$, a proliferation marker, within SMCs compared to fibrin only and $\alpha_2PI_{1-8}$-vWF HBD functionalized fibrin only treatment groups on day 5 (FIG. 20F). These data show that treatment with $\alpha_2PI_{1-8}$-vWF HBD and GFs incorporated within a fibrin matrix promoted wound healing via angiogenesis by sequestration and slow release of VEGF-A165 and PDGF-BB.

h. vWF HBD does not Affect Endothelial or Fibroblast Proliferation In Vitro.

The inventors next tested functions of the vWF HBD on fibroblast and endothelial cell attachment and proliferation. vWF HBD peptide coating significantly enhanced fibroblast attachment (FIG. 25A); this effect was inhibited by adding 5 mM ethylenediaminetetraacetic acid (EDTA) to the in vitro culture, suggesting that vWF HBD peptide may bind to cation-dependent cell adhesion receptors such as integrins (FIG. 25B). Coating of the vWF HBD peptide on cell culture plates did not significantly affect fibroblast proliferation in the presence of FGF-2, suggesting that the vWF HBD may slightly enhance cell adhesion, but did not induce cell proliferation in concert with at least this GF in vitro (FIG. 25C). Similarly, vWF HBD did not affect endothelial proliferation in vitro (FIG. 25D). These data support that, in the context of wound healing and tissue repair, the vWF HBD acts as a GF reservoir rather than a cell scaffold, promoting effective wound healing and angiogenesis through its binding to the growth factors.

i. Growth Factors and Chemokines

All GFs and chemokines were purchased in their mature forms, highly pure (>95% pure), carrier-free, and lyophilized, as previously reported1. VEGF-A121, VEGF-A165, PlGF-1, PlGF-2, PDGF-AA, PDGF-BB, PDGF-CC, PDGF-DD, FGF-1, FGF-2, FGF-6, FGF-7, FGF-18, TGF-β1, TGF-β3, BMP-2, BMP-7, NGF, NT-3, IGF-I, IGF-II, EGF, CXCL-11, and CXCL-12α were purchased from PeproTech. CXCL-12γ was purchased from R & D Systems. Except for PDGF-DD, TGF-β1, TGF-β3, and BMP-7, which were produced in eukaryotic cells, all GFs were produced in *Escherichia coli* and thus were not glycosylated. All GFs were reconstituted and stored according to the provider's instructions to regain full activity and prevent loss of protein.

j. Detection of vWF Binding to Recombinant GFs

ELISA tests were performed as previously reported1. In brief, ELISA plates (med-binding, Greiner Bio-One) were coated with 50 nM GFs at 37° C. for 2 hrs. After blocking with 2% BSA solution containing PBS-T, 1 µg/mL of plasma-derived vWF (EMD Millipore) was added. Bound vWF was detected with 1 µg/mL of rabbit anti-human vWF antibody (Sino Biological). Then, HRP conjugated goat anti-rabbit antibody (Jackson ImmunoResearch) was added. After 60 min of incubation, 50 µL TMB substrate (Sigma-Aldrich) was added. The reaction was stopped by adding 25 µL of 2N H2SO4. Subsequently, the absorbance at 450 nm was measured and subtracted the absorbance at 570 nm.

k. Surface Plasmon Resonance (SPR)

SPR assays were performed as described previously2. In brief, measurements were made with a Biacore X100 SPR system or Biacore 3000 SPR system (GE Healthcare). Plasma-derived vWF was immobilized via amine coupling on a C1 chip (GE Healthcare) for 2000 resonance units (RU) according to the manufacturer's instructions. Recombinant human VEGF-A165, VEGF-A121, or PDGF-BB was flowed at increasing concentrations in the running buffer at 30 µL/min. The sensor chip was regenerated with glycine at pH 2 for every cycle. Specific binding of GFs to vWF was calculated automatically using the response to a non-functionalized channel as a reference. Binding curves were fitted using BIAevalution software (GE Healthcare). vWF-VEGF-A165 binding results were fitted with Langmuir binding kinetics (1:1 binding with drifting baseline Rmax local). vWF-PDGF-BB binding results were fitted with heterogeneous ligand-parallel reaction.

l. Inhibition of vWF-GF Binding by Heparin

ELISA plates (med-binding) were coated with 10 µg/mL vWF. Then, wells were blocked with 2% BSA-containing PBS-T and further incubated with 1 µg/mL each of VEGF-A, PlGF-2, or FGF-2 for 60 min at room temperature (RT) with 10 µM heparin. Next, the wells were incubated with biotinylated anti-VEGF-A, anti-PlGF, or anti-FGF-2 antibodies (R & D Systems). The antibodies were detected by streptavidin-HRP (R & D Systems). Color development and the absorbance measurement were done as described above.

m. Detection of vWF Binding to VEGF-A by Western Blotting

One mL of human serum was immunoprecipitated with 10 μg of monoclonal rabbit anti-human vWF antibody (Sino-Biological) or control rabbit IgG (EMD Millipore) and 50 μL of protein G-agarose (Thermo Fisher Scientific) overnight at 4° C. The resulting pellet was dissolved in Laemmli buffer and subjected to Western blot analysis. Western blot analysis was performed after SDS-PAGE (4-20% gradient gel, Bio-Rad) and transfer onto MS nitrocellulose membranes (Membrane Solutions). GFs were detected using 1 μg/mL biotinylated antibodies for human VEGF-A (R & D Systems), followed by incubation with HRP conjugated streptavidin (R & D Systems) at 1:200 dilutions. The proteins were detected and visualized with the ECL Plus Western Blotting Detection System (GE Healthcare).

n. Detection of vWF Binding to GFs in Human Serum by ELISA

The study was approved by the ethics committees of the Hammersmith, Queen Charlotte's, and Royal Marsden hospitals; informed consent was obtained from all individuals in accordance with the Declaration of Helsinki. ELISA plates (med-binding) were coated with 10 μg/mL rabbit monoclonal anti-human vWF antibody (clone: 111, SinoBiological). Then, wells were blocked with 2% BSA-containing PBS-T and further incubated with human serum derived from healthy donor (Sigma-Aldrich) or type 2B vWD patient for 60 min at RT. Next, the wells were incubated with biotinylated antibodies for human VEGF-A, PDGF-BB or FGF-2 (R & D Systems). The antibodies were detected by streptavidin-HRP (R & D Systems). Color development and the absorbance measurement were done as described above.

o. Expression of Recombinant vWF

The expression vector pcDNA-full length(FL)-vWF has been previously described3. R1341 residue was mutated to Glutamine (Q) using the QuikChange® XL site-directed mutagenesis kit (Stratagene). The sequences were verified and fragments containing mutations were subcloned into a vector containing full length vWF. Briefly, the 5' XhoI to KpnI fragment was digested from pGEM (XhoI-KpnI) while the 5' KpnI to AgeI fragment from pcDNA3.1-A2-CK vector, those were then cloned into pcDNA 3.1 FL-vWF-KpnI that had been digested with the same enzymes. Recombinant WT and R1341Q vWF were expressed in HEK293T cells as previously described using 10 mM polyethylenimine (PEI) as transfection reagent3. The conditioned medium was collected after 3 days, filtered and if required, concentrated or purified for further analysis. Recombinant vWF was purified using a combination of ion-exchange and heparin-Sepharose affinity chromatography as previously described3,4. Briefly, filtered vWF expression medium was applied to an SK-16 chromatography column (Amersham Pharmacia, UK) previously packed with Fractogel-EMD-TMAE+ (Merck) according to manufacturers instructions. The VWF was then eluted using 20 mM Tris, 500 mM NaCl, pH 7.4 and dialysed into 20 mM Tris, 150 mM NaCl, pH 7.4 and further purified using a HeparinSepharose 6 fast flow column (Amersham Pharmacia, UK). The purity of vWF was assessed by SDS-PAGE gel electrophoresis and concentration determined by vWF-ELISA.

p. Detection of Recombinant GF Binding to the vWF Recombinant Protein and A1 HBD Peptide.

ELISA tests were performed as described above. In brief, ELISA plates were coated with 1 μg/mL of FL-vWF (WT or R1341Q), 1 μg/mL of vWF A1 recombinant protein (U-Protein Express) or 1 μg/mL of vWF A1 HBD peptide (sequence YIGLKDRKRPSELRRIASQVKYA, (SEQ ID NO:50) chemically synthesized by Genscript) at 37° C. overnight. After blocking with 2% BSA solution containing PBS-T, 1 μg/mL of the recombinant human proteins VEGF-A121, VEGF-A165, PlGF-1, PlGF-2, PDGF-BB, FGF-2, CXCL-12α and CXCL-12γ were added. 1 μg/mL of BSA served as non-binding protein control. Bound GF or chemokine was detected with biotinylated antibodies for human VEGF-A, PlGF, PDGF-BB, FGF-2, or CXCL-12 (R & D Systems). The antibodies were detected by streptavidin-HRP (R & D Systems). Color development and the absorbance measurement were done as described above.

q. Detection of vWF Binding to Recombinant VEGF-A Isoforms

ELISA was performed as previously reported1. In brief, ELISA plates (med binding: Greiner Bio-One) were coated with 50 nM BSA (GE Healthcare), pro-peptide containing recombinant vWF (Sino Biological), plasma-derived vWF (EMD Millipore), recombinant human vWF A1 domain (U-Protein Express), recombinant human vWF A2 domain (R & D systems), recombinant human vWF A3 domain (U-Protein Express), vWF A1 HBD peptide or scrambled/mutated HBD peptide (all peptides were synthesized by Genscript). After blocking with 2% BSA solution containing PBS-T, 1 μg/mL of recombinant human VEGF-A121 (PeproTech), recombinant human VEGF-A145 (R & D Systems), or recombinant human VEGF-A165 (PeproTech) was added. Bound VEGF-A was detected with 1 μg/mL of mouse anti-human VEGF-A antibody (clone: 26503, R & D systems). After 60 min of incubation, horseradish peroxidase (HRP) conjugated goat anti-mouse antibody (1:2000 dilution, Dako) was added and incubated for another 60 min. Color development and the absorbance measurement were done as described above.

r. Release of GF from Fibrin Matrix

Fibrin matrices were generated with human fibrinogen as described previously1,5. In brief, fibrin matrices were generated with 8 mg/mL fibrinogen, 2 U/mL human thrombin (Sigma-Aldrich), 4 U/mL factor XIIIa (Fibrogammin; Behring), 5 mM calcium chloride, 2 μM □2PI1-8-vWF HBD peptide (NQEQVSPLYIGLKDRKRPSELRRIASQVKYA (SEQ ID NO:51), chemically synthesized by Genscript), and 500 ng/mL recombinant human VEGF-A165 or PDGF-BB. Fibrin gels were polymerized at 37° C. for 1 hr and transferred into 24-well Ultra Low Cluster plates (Corning) containing 500 μL of buffer (20 mM Tris-HCl, 150 mM NaCl, and 0.1% BSA; pH 7.4). A control well that served as a 100% released control contained only the GF in 500 μL of buffer. Every 24 hr, buffers were removed, stored at −20° C., and replaced with fresh buffer. For the 100% released control well, 20 μL of buffer was removed each day. After 5 d, the cumulative release of GF was quantified by ELISA (DuoSet; R&D Systems), using the 100% released control as a reference.

s. Release of GFs from Fibrin-Mimetic Matrix

Fibrin-mimetic matrices were formed from reactive PEG precursors as previously described6. Matrices (50 μL) were generated in 50 mM Tris buffer (pH 7.6) to obtain 1.75% (wt/vol) PEG, 10 μM vWF HBD-Cys (YIGLKDRKRPSELRRIASQVKYAC (SEQ ID NO:49), chemically synthesized by Genscript), 10 U/mL factor XIIIa, 50 mM CaCl2, 1 μg/mL FGF-2 and 1 μg/mL CXCL-12γ. Fibrin-mimetic gels were polymerized at 37° C. for 1 hr and then transferred into 24-well Ultra Low Cluster plates (Corning) containing 1 mL of buffer (20 mM Tris-HCl, 150 mM NaCl, and 0.1% BSA; pH 7.4). A control well that served as 100% released control contained only the GFs in 1 mL of buffer. Every 24 hr, buffers were removed, stored at −20° C., and replaced with fresh buffer. For the 100% released control well, 20 μL of buffer was removed each day and stored at −20° C. Cumulative release of GF was quantified by ELISA (DuoSet; R&D Systems), using the 100% released control as a reference.

t. Cell Adhesion Assay

Cell adhesion assays were performed using starved human lung fibroblasts (Lonza) in FGM-2 medium (Lonza) with or without 5 mM EDTA. Cells were plated at 3000 cells/well on 1 μg/mL vWF HBD pre-coated 96-well plates (non-tissue culture treated, Greiner Bio-one) and incubated for 30 min at 37° C. Then, the medium was removed, and wells were further washed three times with new FGM-2 medium. Cell numbers were quantified using a CyQUANT assay (Invitrogen).

u. Cell Proliferation Assay with vWF HBD

Cell proliferation assays were performed as previously reported1. Briefly, human lung fibroblasts (Lonza) were cultured using FGM-2 medium (Lonza) (1000 cells/well) or human umbilical vein endothelial cells (HUVEC, Lonza) were cultured using EGM-2 medium (Lonza) (1000 cells/well) on 1 μg/mL vWF HBD pre-coated 96-well plates (Tissue culture treated, Falcon). Cell numbers were quantified after 72 hrs using a CyQUANT assay (Invitrogen).

TABLE 1

THE SEQUENCES OF VWF A1 HBD PEPTIDES.

| SEQ ID NO | Name | Peptide sequence |
|---|---|---|
| 49 | vWF A1 HBD | YIGLKDRKRPSELRRIASQVKYAC |
| 52 | Scrambled HBD | LYCEIARGYSLKRKVPDQIRSRKA |
| 53 | Arg substituted HBD | YIGLKDSKSPSELSSIASQVKYAC |
| 54 | Naïve | YIGLKDRKRPSELRRIASQVKYA |
| 55 | R1341L | YIGLKDRKRPSELLRIASQVKYA |
| 56 | R1341P | YIGLKDRKRPSELPRIASQVKYA |
| 57 | R1341Q | YIGLKDRKRPSELQRIASQVKYA |
| 58 | R1341W | YIGLKDRKRPSELWRIASQVKYA |
| 59 | R1341S | YIGLKDRKRPSELSRIASQVKYA |

Although certain embodiments have been described above with a certain degree of particularity, or with reference to one or more individual embodiments, those skilled in the art could make numerous alterations to the disclosed embodiments without departing from the scope of this invention. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments. Any reference to a patent publication or other publication is a herein a specific incorporation by reference of the disclosure of that publication. The claims are not to be interpreted as including means-plus- or step-plus-function limitations, unless such a limitation is explicitly recited in a given claim using the phrase(s) "means for" or "step for," respectively.

REFERENCES

The following references, to the extent that they provide exemplary procedural or other details supplementary to those set forth herein, are specifically incorporated herein by reference.

1. De Cristofaro, R, Peyvandi, F, Baronciani, L et al. Molecular mapping of the chloride-binding site in von Willebrand factor (VWF): energetics and conformational effects on the VWF/ADAMTS-13 interaction. J Biol Chem. 2006; 281(41):30400-30411.
2. Emsley, J, Cruz, M, Handin, R, Liddington, R. Crystal structure of the von Willebrand Factor A1 domain and implications for the binding of platelet glycoprotein Ib. J Biol Chem. 1998; 273(17):10396-10401.
3. Randi, A M, Laffan, M A. Von Willebrand factor and angiogenesis: basic and applied issues. J Thromb Haemost. 2017; 15(1):13-20.
4. Selvam, S N, Casey, L J, Bowman, M L et al. Abnormal angiogenesis in blood outgrowth endothelial cells derived from von Willebrand disease patients. Blood Coagul Fibrinolysis. 2017; 28(7):521-533.
5. Barg, K, Wiewiorski, M, Anderson, A E et al. Total ankle replacement in patients with von Willebrand disease: mid-term results of 18 procedures. Haemophilia. 2015; 21(5):e389-401.
6. Denis, C V, Andre, P, Saffaripour, S, Wagner, D D. Defect in regulated secretion of P-selectin affects leukocyte recruitment in von Willebrand factor-deficient mice. Proc Natl Acad Sci USA. 2001; 98(7):4072-4077.
7. Jenkins, P V, Pasi, K J, Perkins, S J. Molecular modeling of ligand and mutation sites of the type A domains of human von Willebrand factor and their relevance to von Willebrand's disease. Blood. 1998; 91(6):2032-2044.
8. Morales, L D, Martin, C, Cruz, M A. The interaction of von Willebrand factor-A1 domain with collagen: mutation G1324S (type 2M von Willebrand disease) impairs the conformational change in A1 domain induced by collagen. J Thromb Haemost. 2006; 4(2):417-425.
9. Sobel, M, McNeill, P M, Carlson, P L et al. Heparin inhibition of von Willebrand factor-dependent platelet function in vitro and in vivo. J Clin Invest. 1991; 87(5):1787-1793.
10. Martino, M M, Briquez, P S, Guc, E et al. Growth factors engineered for super-affinity to the extracellular matrix enhance tissue healing. Science. 2014; 343(6173):885-888.
11. Martino, M M, Briquez, P S, Ranga, A, Lutolf, M P, Hubbell, J A. Heparin-binding domain of fibrin (ogen) binds growth factors and promotes tissue repair when incorporated within a synthetic matrix. Proceedings of the National Academy of Sciences. 2013; 110(12):4563-4568.
12. Martino, M M, Hubbell, J A. The 12th-14th type III repeats of fibronectin function as a highly promiscuous growth factor-binding domain. The FASEB Journal. 2010; 24(12):4711-4721.
13. De Laporte, L, Rice, J J, Tortelli, F, Hubbell, J A. Tenascin C promiscuously binds growth factors via its fifth fibronectin type III-like domain. PLoS One. 2013; 8(4):e62076.
14. O'Regan, A, Berman, J S. Osteopontin: a key cytokine in cell-mediated and granulomatous inflammation. Int J Exp Pathol. 2000; 81(6):373-390.
15. Dalton, B A, McFarland, C D, Underwood, P A, Steele, J G. Role of the heparin binding domain of fibronectin in attachment and spreading of human bone-derived cells. J Cell Sci. 1995; 108 (Pt 5)(5):2083-2092.
16. Briquez, P S, Hubbell, J A, Martino, M M. Extracellular Matrix-Inspired Growth Factor Delivery Systems for Skin Wound Healing. Adv Wound Care (New Rochelle). 2015; 4(8):479-489.
17. Mitchell, A C, Briquez, P S, Hubbell, J A, Cochran, J R. Engineering growth factors for regenerative medicine applications. Acta Biomater. 2016; 30:1-12.
18. Martino, M M, Tortelli, F, Mochizuki, M et al. Engineering the growth factor microenvironment with fibronectin domains to promote wound and bone tissue healing. Sci Transl Med. 2011; 3(100):100ra189.
19. Chen, T T, Luque, A, Lee, S, Anderson, S M, Segura, T, Iruela-Arispe, M L. Anchorage of VEGF to the extracellular matrix conveys differential signaling responses to endothelial cells. J Cell Biol. 2010; 188(4):595-609.
20. Lutolf, M P, Weber, F E, Schmoekel, H G et al. Repair of bone defects using synthetic mimetics of collagenous extracellular matrices. Nature biotechnology. 2003; 21(5): 513-518.
21. Dunn, L, Prosser, H C, Tan, J T, Vanags, L Z, Ng, M K, Bursill, C A. Murine model of wound healing. J Vis Exp. 2013(75):e50265.
22. Starke, R D, Ferraro, F, Paschalaki, K E et al. Endothelial von Willebrand factor regulates angiogenesis. Blood. 2011; 117(3):1071-1080.
23. Schense, J C, Hubbell, J A. Cross-linking exogenous bifunctional peptides into fibrin gels with factor XIIIa. Bioconjugate chemistry. 1999; 10(1):75-81.
24. Vempati, P, Popel, A S, Mac Gabhann, F. Extracellular regulation of VEGF: isoforms, proteolysis, and vascular patterning. Cytokine Growth Factor Rev. 2014; 25(1):1-19.
25. Rueda, P, Balabanian, K, Lagane, B, Staropoli, I, Chow, K, Gold, J A. The CXCL12c Chemokine Displays Unprecedented Structural and Functional. 2008.
26. Janowski, M. Functional diversity of SDF-1 splicing variants. Cell Adh Migr. 2009; 3(3):243-249.
27. Fujimura, Y, Titani, K, Holland, L Z et al. A heparin-binding domain of human von Willebrand factor. Characterization and localization to a tryptic fragment extending from amino acid residue Val-449 to Lys-728. J Biol Chem. 1987; 262(4):1734-1739.
28. Nurden, P, Debili, N, Vainchenker, W et al. Impaired megakaryocytopoiesis in type 2B von Willebrand disease with severe thrombocytopenia. Blood. 2006; 108(8): 2587-2595.
29. Tischer, A, Madde, P, Moon-Tasson, L, Auton, M. Misfolding of vWF to pathologically disordered conformations impacts the severity of von Willebrand disease. Biophys J. 2014; 107(5):1185-1195.
30. Wood, N, Standen, G R, Murray, E W et al. Rapid genotype analysis in type 2B von Willebrand's disease using a universal heteroduplex generator. Br J Haematol. 1995; 89(1):152-156.
31. Sullivan, S R, Underwood, R A, Gibran, N S et al. Validation of a model for the study of multiple wounds in the diabetic mouse (db/db). Plast Reconstr Surg. 2004; 113(3):953-960.
32. Krilleke, D, Ng, Y S, Shima, D T. The heparin-binding domain confers diverse functions of VEGF-A in development and disease: a structure-function study. Biochem Soc Trans. 2009; 37(Pt 6):1201-1206.
33. Stalmans, I, Ng, Y S, Rohan, R et al. Arteriolar and venular patterning in retinas of mice selectively expressing VEGF isoforms. J Clin Invest. 2002; 109(3):327-336.
34. Gerhardt, H, Golding, M, Fruttiger, M et al. VEGF guides angiogenic sprouting utilizing endothelial tip cell filopodia. J Cell Biol. 2003; 161(6):1163-1177.
35. Lee, R J, Springer, M L, Blanco-Bose, W E, Shaw, R, Ursell, P C, Blau, H M. VEGF gene delivery to myocardium: deleterious effects of unregulated expression. Circulation. 2000; 102(8): 898-901.
36. Sundberg, C, Nagy, J A, Brown, L F et al. Glomeruloid microvascular proliferation follows adenoviral vascular permeability factor/vascular endothelial growth factor-164 gene delivery. Am J Pathol. 2001; 158(3):1145-1160.
37. Randi, A M, Laffan, M A, Starke, R D. Von Willebrand factor, angiodysplasia and angiogenesis. Mediterr J Hematol Infect Dis. 2013; 5(1):e2013060.
38. Zanetta, L, Marcus, S G, Vasile, J et al. Expression of Von Willebrand factor, an endothelial cell marker, is up-regulated by angiogenesis factors: a potential method for objective assessment of tumor angiogenesis. Int J Cancer. 2000; 85(2):281-288.
39. Fonder, M A, Lazarus, G S, Cowan, D A, Aronson-Cook, B, Kohli, A R, Mamelak, A J. Treating the chronic wound: A practical approach to the care of nonhealing wounds and wound care dressings. J Am Acad Dermatol. 2008; 58(2):185-206.
40. Falanga, V. Wound healing and its impairment in the diabetic foot. Lancet. 2005; 366(9498): 1736-1743.
41. Marti-Carvajal, A J, Gluud, C, Nicola, S et al. Growth factors for treating diabetic foot ulcers. Cochrane Database Syst Rev. 2015(10):CD008548.
42. Galiano, R D, Tepper, O M, Pelo, C R et al. Topical Vascular Endothelial Growth Factor Accelerates Diabetic Wound Healing through Increased Angiogenesis and by Mobilizing and Recruiting Bone Marrow-Derived Cells. The American Journal of Pathology. 2004; 164(6): 1935-1947.
43. Chan, R K, Liu, P H, Pietramaggiori, G, Ibrahim, S I, Hechtman, H B, Orgill, D P. Effect of recombinant platelet-derived growth factor (Regranex) on wound closure in genetically diabetic mice. J Burn Care Res. 2006; 27(2):202-205.
44. Martino, M M, Briquez, P S, Guc, E et al. Growth factors engineered for super-affinity to the extracellular matrix enhance tissue healing. Science. 2014; 343(6173):885-888.
45. Martino, M M, Briquez, P S, Ranga, A, Lutolf, M P, Hubbell, J A. Heparin-binding domain of fibrin (ogen) binds growth factors and promotes tissue repair when incorporated within a synthetic matrix. Proceedings of the National Academy of Sciences. 2013; 110(12):4563-4568.
46. Nowak, A A, Canis, K, Riddell, A, Laffan, M A, McKinnon, T A. O-linked glycosylation of von Willebrand factor modulates the interaction with platelet receptor glycoprotein Ib under static and shear stress conditions. Blood. 2012; 120(1):214-222.
47. McKinnon, T A, Chion, A C, Millington, A J, Lane, D A, Laffan, M A. N-linked glycosylation of VWF modulates its interaction with ADAMTS13. Blood. 2008; 111(6): 3042-3049.
48. Martino, M M, Tortelli, F, Mochizuki, M et al. Engineering the growth factor microenvironment with fibronectin domains to promote wound and bone tissue healing. Sci Transl Med. 2011; 3(100):100ra189.
49. Lutolf, M P, Weber, F E, Schmoekel, H G et al. Repair of bone defects using synthetic mimetics of collagenous extracellular matrices. Nature biotechnology. 2003; 21(5): 513-518.

The invention claimed is:

1. A polypeptide comprising a growth factor binding domain comprising 25-100 contiguous amino acids of SEQ ID NO: 13 and wherein the 25-100 contiguous amino acids include SEQ ID NO: 1, and wherein the polypeptide is attached to a transglutaminase-reactive peptide having the amino acid sequence of SEQ ID NO:12.

2. The polypeptide of claim 1, wherein the polypeptide is linked to one or more additional peptides, wherein each additional polypeptide has an amino acid sequence that is at least 80% identical to one of SEQ ID NOs:1-7, 13-15, 49-50, or 66-70, or a fragment thereof.

3. The polypeptide of claim 2, wherein the polypeptides are separated by one or more linkers.

4. The polypeptide of claim 1, wherein the polypeptide is attached to a collagen binding peptide.

5. The polypeptide of claim 1, wherein the polypeptide is attached to a cell adhesion moiety.

6. The polypeptide of claim 1, wherein the polypeptide is attached to a tag or a functional moiety.

7. The polypeptide of claim 1, wherein the polypeptide comprises the amino acid sequence of SEQ ID NO:8.

8. The polypeptide of claim 1, wherein the growth factor binding domain consists of SEQ ID NO:1.

9. The polypeptide of claim 1, wherein the growth factor binding domain comprising 25-50 contiguous amino acids of SEQ ID NO:13 and wherein the 25-50 contiguous amino acids include SEQ ID NO:1.

10. The polypeptide of claim 1, wherein the growth factor binding domain comprising 25-40 contiguous amino acids of SEQ ID NO:13 and wherein the 25-40 contiguous amino acids include SEQ ID NO:1.

11. A composition comprising the polypeptide of claim 1.

12. A biomaterial scaffold comprising the polypeptide of claim 1.

13. A biomaterial scaffold comprising the polypeptide of claim 1, wherein the polypeptide is covalently linked to fibrin, and wherein the biomaterial scaffold further comprises exogenously added Vascular Endothelial Growth Factor (VEGF) and Platelet-derived Growth Factor (PDGF).

14. An implant comprising the polypeptide of claim 1.

15. A method for regenerating tissue in a subject in need thereof, the method comprising administering to the subject the biomaterial of claim 12.

16. A method for facilitating wound or tissue healing in a subject in need thereof, the method comprising administering the biomaterial of claim 12 to the subject.

* * * * *

UNITED STATES PATENT AND TRADEMARK OFFICE
CERTIFICATE OF CORRECTION

| | |
|---|---|
| PATENT NO. | : 11,732,029 B2 |
| APPLICATION NO. | : 15/733085 |
| DATED | : August 22, 2023 |
| INVENTOR(S) | : Hubbell et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 299 days.

Signed and Sealed this
Twelfth Day of November, 2024

*Katherine Kelly Vidal*

Katherine Kelly Vidal
*Director of the United States Patent and Trademark Office*

SEQUENCE LISTING

<160> NUMBER OF SEQ ID NOS: 81

<210> SEQ ID NO 1
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Arg Leu Val Phe Ala Leu Gly Thr Asp Gly Lys Lys Leu Arg Ile Lys
1               5                   10                  15

Ser Lys Glu Lys Cys Asn Asp Gly Lys
            20                  25

<210> SEQ ID NO 2
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Pro Pro Phe Leu Met Leu Leu Lys Gly Ser Thr Arg Phe Asn Lys Thr
1               5                   10                  15

Lys Thr Phe Arg
            20

<210> SEQ ID NO 3
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Thr Leu Phe Leu Ala His Gly Arg Leu Val Tyr Met Phe Asn Val Gly
1               5                   10                  15

His Lys Lys Leu Lys Ile Arg
            20

<210> SEQ ID NO 4
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Pro Leu Phe Leu Leu His Lys Lys Gly Lys Asn Leu Ser Lys Pro Lys
1               5                   10                  15

Ala Ser Gln Asn Lys Lys Gly Gly Lys Ser Lys
            20                  25

<210> SEQ ID NO 5
<211> LENGTH: 12
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic peptide"

<400> SEQUENCE: 5

Thr Leu Pro Asp Val Gly Leu Glu Leu Glu Val Arg
1               5                   10

<210> SEQ ID NO 6
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Arg Gln Arg Ser Arg Pro Gly Arg Trp His Lys Val Ser Val Arg Trp
1               5                   10                  15

Glu Lys Asn Arg
            20

<210> SEQ ID NO 7
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Thr Pro Gly Leu Gly Pro Arg Gly Leu Gln Ala Thr Ala Arg Lys Ala
1               5                   10                  15

Ser Arg Arg Ser Arg Gln Pro Ala Arg His Pro Ala Cys Met Leu
            20                  25                  30

<210> SEQ ID NO 8
<211> LENGTH: 33
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Asn Gln Glu Gln Val Ser Pro Leu Arg Leu Val Phe Ala Leu Gly Thr
1               5                   10                  15

Asp Gly Lys Lys Leu Arg Ile Lys Ser Lys Glu Lys Cys Asn Asp Gly
            20                  25                  30

Lys

<210> SEQ ID NO 9
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Lys Asn Ser Phe Met Ala Leu Tyr Leu Ser Lys Gly Arg
```

<210> SEQ ID NO 10
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 10

Ala Arg Lys Ala Ser Arg Arg Ser Arg Gln Pro Ala Arg His
1               5                   10

<210> SEQ ID NO 11
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 11

Asn Gln Glu Gln Val Ser Pro Leu Ala Arg Lys Ala Ser Arg Arg Ser
1               5                   10                  15

Arg Gln Pro Ala Arg His
            20

<210> SEQ ID NO 12
<211> LENGTH: 8
<212> TYPE: PRT
<213> ORGANISM: Unknown
<220> FEATURE:
<221> NAME/KEY: source
<223> OTHER INFORMATION: /note="Description of Unknown: Alpha2 plasmin inhibitor sequence"

<400> SEQUENCE: 12

Asn Gln Glu Gln Val Ser Pro Leu
1               5

<210> SEQ ID NO 13
<211> LENGTH: 165
<212> TYPE: PRT
<213> ORGANISM: Homo sapiens

<400> SEQUENCE: 13

Ala Leu Gln Phe Gly Asp Ile Pro Thr Ser His Leu Leu Phe Lys Leu
1               5                   10                  15

Pro Gln Glu Leu Leu Lys Pro Arg Ser Gln Phe Ala Val Asp Met Gln
            20                  25                  30

Thr Thr Ser Ser Arg Gly Leu Val Phe His Thr Gly Thr Lys Asn Ser
        35                  40                  45

Phe Met Ala Leu Tyr Leu Ser Lys Gly Arg Leu Val Phe Ala Leu Gly
    50                  55                  60

Thr Asp Gly Lys Lys Leu Arg Ile Lys Ser Lys Glu Lys Cys Asn Asp
65                  70                  75                  80

Gly Lys Trp His Thr Val Val Phe Gly His Asp Gly Glu Lys Gly Arg
                85                  90                  95

Leu Val Val Asp Gly Leu Arg Ala Arg Glu Gly Ser Leu Pro Gly Asn
            100                 105                 110

```
Ser Thr Ile Ser Ile Arg Ala Pro Val Tyr Leu Gly Ser Pro Pro Ser
            115                 120                 125

Gly Lys Pro Lys Ser Leu Pro Thr Asn Ser Phe Val Gly Cys Leu Lys
    130                 135                 140

Asn Phe Gln Leu Asp Ser Lys Pro Leu Tyr Thr Pro Ser Ser Ser Phe
145                 150                 155                 160

Gly Val Ser Ser Cys
                165

<210> SEQ ID NO 14
<211> LENGTH: 172
<212> TYPE: PRT
<213> ORGANISM: Homo sapiens

<400> SEQUENCE: 14

Ala Tyr Gln Tyr Gly Gly Thr Ala Asn Ser Arg Gln Glu Phe Glu His
1               5                   10                  15

Leu Lys Gly Asp Phe Gly Ala Lys Ser Gln Phe Ser Ile Arg Leu Arg
            20                  25                  30

Thr Arg Ser Ser His Gly Met Ile Phe Tyr Val Ser Asp Gln Glu Glu
        35                  40                  45

Asn Asp Phe Met Thr Leu Phe Leu Ala His Gly Arg Leu Val Tyr Met
50                  55                  60

Phe Asn Val Gly His Lys Lys Leu Lys Ile Arg Ser Gln Glu Lys Tyr
65                  70                  75                  80

Asn Asp Gly Leu Trp His Asp Val Ile Phe Ile Arg Glu Arg Ser Ser
                85                  90                  95

Gly Arg Leu Val Ile Asp Gly Leu Arg Val Leu Glu Glu Ser Leu Pro
            100                 105                 110

Pro Thr Glu Ala Thr Trp Lys Ile Lys Gly Pro Ile Tyr Leu Gly Gly
        115                 120                 125

Val Ala Pro Gly Lys Ala Val Lys Asn Val Gln Ile Asn Ser Ile Tyr
    130                 135                 140

Ser Phe Ser Gly Cys Leu Ser Asn Leu Gln Leu Asn Gly Ala Ser Ile
145                 150                 155                 160

Thr Ser Ala Ser Gln Thr Phe Ser Val Thr Pro Cys
                165                 170

<210> SEQ ID NO 15
<211> LENGTH: 174
<212> TYPE: PRT
<213> ORGANISM: Homo sapiens

<400> SEQUENCE: 15

Ser Tyr Gln Phe Gly Gly Ser Leu Ser Ser His Leu Glu Phe Val Gly
1               5                   10                  15

Ile Leu Ala Arg His Arg Asn Trp Pro Ser Leu Ser Met His Val Leu
            20                  25                  30

Pro Arg Ser Ser Arg Gly Leu Leu Phe Thr Ala Arg Leu Arg Pro
        35                  40                  45

Gly Ser Pro Ser Leu Ala Leu Phe Leu Ser Asn Gly His Phe Val Ala
    50                  55                  60

Gln Met Glu Gly Leu Gly Thr Arg Leu Arg Ala Gln Ser Arg Gln Arg
65                  70                  75                  80

Ser Arg Pro Gly Arg Trp His Lys Val Ser Val Arg Trp Glu Lys Asn
                85                  90                  95
```

```
Arg Ile Leu Leu Val Thr Asp Gly Ala Arg Ala Trp Ser Gln Glu Gly
            100                 105                 110

Pro His Arg Gln His Gln Gly Ala Glu His Pro Gln Pro His Thr Leu
            115                 120                 125

Phe Val Gly Gly Leu Pro Ala Ser Ser His Ser Ser Lys Leu Pro Val
            130                 135                 140

Thr Val Gly Phe Ser Gly Cys Val Lys Arg Leu Arg Leu His Gly Arg
145                 150                 155                 160

Pro Leu Gly Ala Pro Thr Arg Met Ala Gly Val Thr Pro Cys
                165                 170
```

```
<210> SEQ ID NO 16
<211> LENGTH: 177
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Asn Gln Glu Gln Val Ser Pro Leu Gly Gly Ser Gly Ala Leu Gln Phe
1               5                   10                  15

Gly Asp Ile Pro Thr Ser His Leu Leu Phe Lys Leu Pro Gln Glu Leu
            20                  25                  30

Leu Lys Pro Arg Ser Gln Phe Ala Val Asp Met Gln Thr Thr Ser Ser
            35                  40                  45

Arg Gly Leu Val Phe His Thr Gly Thr Lys Asn Ser Phe Met Ala Leu
50                  55                  60

Tyr Leu Ser Lys Gly Arg Leu Val Phe Ala Leu Gly Thr Asp Gly Lys
65                  70                  75                  80

Lys Leu Arg Ile Lys Ser Lys Glu Lys Cys Asn Asp Gly Lys Trp His
            85                  90                  95

Thr Val Val Phe Gly His Asp Gly Glu Lys Gly Arg Leu Val Val Asp
            100                 105                 110

Gly Leu Arg Ala Arg Glu Gly Ser Leu Pro Gly Asn Ser Thr Ile Ser
            115                 120                 125

Ile Arg Ala Pro Val Tyr Leu Gly Ser Pro Pro Ser Gly Lys Pro Lys
            130                 135                 140

Ser Leu Pro Thr Asn Ser Phe Val Gly Cys Leu Lys Asn Phe Gln Leu
145                 150                 155                 160

Asp Ser Lys Pro Leu Tyr Thr Pro Ser Ser Phe Gly Val Ser Ser
                165                 170                 175

Cys
```

```
<210> SEQ ID NO 17
<211> LENGTH: 184
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Asn Gln Glu Gln Val Ser Pro Leu Gly Gly Ser Gly Ala Tyr Gln Tyr
1               5                   10                  15

Gly Gly Thr Ala Asn Ser Arg Gln Glu Phe Glu His Leu Lys Gly Asp
            20                  25                  30
```

```
Phe Gly Ala Lys Ser Gln Phe Ser Ile Arg Leu Arg Thr Arg Ser Ser
        35                  40                  45

His Gly Met Ile Phe Tyr Val Ser Asp Gln Glu Glu Asn Asp Phe Met
        50                  55                  60

Thr Leu Phe Leu Ala His Gly Arg Leu Val Tyr Met Phe Asn Val Gly
65                  70                  75                  80

His Lys Lys Leu Lys Ile Arg Ser Gln Glu Lys Tyr Asn Asp Gly Leu
                85                  90                  95

Trp His Asp Val Ile Phe Ile Arg Glu Arg Ser Ser Gly Arg Leu Val
                100                 105                 110

Ile Asp Gly Leu Arg Val Leu Glu Glu Ser Leu Pro Pro Thr Glu Ala
                115                 120                 125

Thr Trp Lys Ile Lys Gly Pro Ile Tyr Leu Gly Gly Val Ala Pro Gly
            130                 135                 140

Lys Ala Val Lys Asn Val Gln Ile Asn Ser Ile Tyr Ser Phe Ser Gly
145                 150                 155                 160

Cys Leu Ser Asn Leu Gln Leu Asn Gly Ala Ser Ile Thr Ser Ala Ser
                165                 170                 175

Gln Thr Phe Ser Val Thr Pro Cys
            180
```

<210> SEQ ID NO 18
<211> LENGTH: 186
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 18

```
Asn Gln Glu Gln Val Ser Pro Leu Gly Gly Ser Gly Ser Tyr Gln Phe
1               5                   10                  15

Gly Gly Ser Leu Ser Ser His Leu Glu Phe Val Gly Ile Leu Ala Arg
            20                  25                  30

His Arg Asn Trp Pro Ser Leu Ser Met His Val Leu Pro Arg Ser Ser
            35                  40                  45

Arg Gly Leu Leu Leu Phe Thr Ala Arg Leu Arg Pro Gly Ser Pro Ser
        50                  55                  60

Leu Ala Leu Phe Leu Ser Asn Gly His Phe Val Ala Gln Met Glu Gly
65                  70                  75                  80

Leu Gly Thr Arg Leu Arg Ala Gln Ser Arg Gln Arg Ser Arg Pro Gly
                85                  90                  95

Arg Trp His Lys Val Ser Val Arg Trp Glu Lys Asn Arg Ile Leu Leu
                100                 105                 110

Val Thr Asp Gly Ala Arg Ala Trp Ser Gln Glu Gly Pro His Arg Gln
            115                 120                 125

His Gln Gly Ala Glu His Pro Gln Pro His Thr Leu Phe Val Gly Gly
        130                 135                 140

Leu Pro Ala Ser Ser His Ser Ser Lys Leu Pro Val Thr Val Gly Phe
145                 150                 155                 160

Ser Gly Cys Val Lys Arg Leu Arg Leu His Gly Arg Pro Leu Gly Ala
                165                 170                 175

Pro Thr Arg Met Ala Gly Val Thr Pro Cys
            180                 185
```

<210> SEQ ID NO 19
<211> LENGTH: 495
<212> TYPE: DNA
<213> ORGANISM: Homo sapiens

<400> SEQUENCE: 19

```
gccctccagt ttggggacat tcccaccagc cacttgctat tcaagcttcc tcaggagctg      60
ctgaaaccca ggtcacagtt tgctgtggac atgcagacaa catcctccag aggactggtg     120
tttcacacgg gcactaagaa ctcctttatg gctctttatc tttcaaaagg acgtctggtc     180
tttgcactgg ggacagatgg gaaaaaattg aggatcaaaa gcaaggagaa atgcaatgat     240
gggaaatggc acacggtggt gtttggccat gatggggaaa aggggcgctt ggttgtggat     300
ggactgaggg cccgggaggg aagtttgcct ggaaactcca ccatcagcat cagagcgcca     360
gtttacctgg gatcacctcc atcagggaaa ccaaagagcc tccccacaaa cagctttgtg     420
ggatgcctga agaactttca gctggattca aaacccttgt ataccccttc ttcaagcttc     480
ggggtgtctt cctgc                                                      495
```

<210> SEQ ID NO 20
<211> LENGTH: 516
<212> TYPE: DNA
<213> ORGANISM: Homo sapiens

<400> SEQUENCE: 20

```
gcctatcaat atggaggaac agccaacagc cgccaagagt ttgaacactt aaaaggagat      60
tttggtgcca aatctcagtt ttccattcgt ctgagaactc gttcctccca tggcatgatc     120
ttctatgtct cagatcaaga agagaatgac ttcatgactc tattttggc ccatggccgc      180
ttggtttaca tgtttaatgt tggtcacaaa aaactgaaga ttagaagcca ggagaaatac     240
aatgatggcc tgtggcatga tgtgatattt attcgagaaa ggagcagtgg ccgactggta     300
attgatggtc tccgagtcct agaagaaagt cttcctccta ctgaagctac ctggaaaatc     360
aagggtccca tttatttggg aggtgtggct cctggaaagg ctgtgaaaaa tgttcagatt     420
aactccatct acagttttag tggctgtctc agcaatctcc agctcaatgg ggcctccatc     480
acctctgctt ctcagacatt cagtgtgacc ccttgc                               516
```

<210> SEQ ID NO 21
<211> LENGTH: 522
<212> TYPE: DNA
<213> ORGANISM: Homo sapiens

<400> SEQUENCE: 21

```
tcctaccagt ttgggggttc cctgtccagt cacctggagt ttgtgggcat cctggcccga      60
cataggaact ggcccagtct ctccatgcac gtcctcccgc gaagctcccg aggcctcctc     120
ctcttcactg cccgtctgag gccggcagcc cctccctgg cgctcttcct gagcaatggc      180
cacttcgttg cacagatgga aggcctcggg actcggctcc gcgcccagag ccgccagcgc     240
tcccggcctg gccgctggca caaggtctcc gtgcgctggg agaagaaccg gatcctgctg     300
gtgacggacg gggcccgggc ctggagccag gaggggccgc accggcagca caggggggca     360
gagcaccccc agccccacac cctctttgtg ggcggcctcc cggccagcag ccacagctcc     420
aaacttccgg tgaccgtcgg gttcagcggc tgtgtgaaga gactgaggct gcacgggagg     480
cccctggggg cccccacacg gatggcaggg gtcacaccct gc                        522
```

<210> SEQ ID NO 22
<211> LENGTH: 531
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 22

```
aaccaggagc aggtgtcccc acttggtgga tccggcgccc tccagtttgg ggacattccc    60
accagccact tgctattcaa gcttcctcag gagctgctga aacccaggtc acagtttgct   120
gtggacatgc agacaacatc ctccagagga ctggtgtttc acgggcac taagaactcc    180
tttatggctc tttatctttc aaaaggacgt ctggtctttg cactggggac agatgggaaa   240
aaattgagga tcaaaagcaa ggagaaatgc aatgatggga aatggcacac ggtggtgttt   300
ggccatgatg gggaaaaggg gcgcttggtt gtggatggac tgagggcccg ggaggaagt    360
ttgcctggaa actccaccat cagcatcaga gcgccagttt acctgggatc acctccatca   420
gggaaaccaa agagcctccc cacaaacagc tttgtgggat gcctgaagaa ctttcagctg   480
gattcaaaac ccttgtatac cccttcttca agcttcgggg tgtcttcctg c            531
```

<210> SEQ ID NO 23
<211> LENGTH: 552
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 23

```
aaccaggagc aggtgtcccc acttggtgga tccggcgcct atcaatatgg aggaacagcc    60
aacagccgcc aagagtttga acacttaaaa ggagatttg gtgccaaatc tcagttttcc   120
attcgtctga gaactcgttc ctcccatggc atgatcttct atgtctcaga tcaagaagag   180
aatgacttca tgactctatt tttggcccat ggccgcttgg tttacatgtt taatgttggt   240
cacaaaaaac tgaagattag aagccaggag aaatacaatg atggcctgtg gcatgatgtg   300
atatttattc gagaaaggag cagtggccga ctggtaattg atggtctccg agtcctagaa   360
gaaagtcttc ctcctactga agctacctgg aaaatcaagg gtcccattta tttgggaggt   420
gtggctcctg gaaaggctgt gaaaaatgtt cagattaact ccatctacag ttttagtggc   480
tgtctcagca atctccagct caatggggcc tccatcacct gcttctca gacattcagt    540
gtgacccctt gc                                                        552
```

<210> SEQ ID NO 24
<211> LENGTH: 558
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 24

```
aaccaggagc aggtgtcccc acttggtgga tccggctcct accagtttgg gggttccctg    60
tccagtcacc tggagtttgt gggcatcctg gcccgacata ggaactggcc cagtctctcc   120
atgcacgtcc tcccgcgaag ctcccgaggc ctcctcctct tcactgcccg tctgaggccc   180
```

-continued

```
ggcagcccct ccctggcgct cttcctgagc aatggccact tcgttgcaca gatggaaggc      240
ctcgggactc ggctccgcgc ccagagccgc cagcgctccc ggcctggccg ctggcacaag      300
gtctccgtgc gctgggagaa gaaccggatc ctgctggtga cggacggggc ccgggcctgg      360
agccaggagg ggccgcaccg gcagcaccag ggggcagagc accccagcc ccacaccctc       420 tttgtgggcg gcctcccggc cagcagccac agctccaaac ttccggtgac cgtcgggttc      480
agcggctgtg tgaagagact gaggctgcac gggaggcccc tggggccccc cacacggatg      540 gcagggtca caccctgc                                                     558
```

<210> SEQ ID NO 25
<211> LENGTH: 3075
<212> TYPE: PRT
<213> ORGANISM: Homo sapiens

<400> SEQUENCE: 25

```
Met Arg Gly Gly Val Leu Leu Val Leu Leu Cys Val Ala Ala Gln
1               5                   10                  15

Cys Arg Gln Arg Gly Leu Phe Pro Ala Ile Leu Asn Leu Ala Ser Asn
            20                  25                  30

Ala His Ile Ser Thr Asn Ala Thr Cys Gly Glu Lys Gly Pro Glu Met
        35                  40                  45

Phe Cys Lys Leu Val Glu His Val Pro Gly Arg Pro Val Arg Asn Pro
50                  55                  60

Gln Cys Arg Ile Cys Asp Gly Asn Ser Ala Asn Pro Arg Glu Arg His
65                  70                  75                  80

Pro Ile Ser His Ala Ile Asp Gly Thr Asn Asn Trp Trp Gln Ser Pro
                85                  90                  95

Ser Ile Gln Asn Gly Arg Glu Tyr His Trp Val Thr Ile Thr Leu Asp
            100                 105                 110

Leu Arg Gln Val Phe Gln Val Ala Tyr Val Ile Ile Lys Ala Ala Asn
        115                 120                 125

Ala Pro Arg Pro Gly Asn Trp Ile Leu Glu Arg Ser Leu Asp Gly Thr
130                 135                 140

Thr Phe Ser Pro Trp Gln Tyr Tyr Ala Val Ser Asp Ser Glu Cys Leu
145                 150                 155                 160

Ser Arg Tyr Asn Ile Thr Pro Arg Arg Gly Pro Pro Thr Tyr Arg Ala
                165                 170                 175

Asp Asp Glu Val Ile Cys Thr Ser Tyr Tyr Ser Arg Leu Val Pro Leu
            180                 185                 190

Glu His Gly Glu Ile His Thr Ser Leu Ile Asn Gly Arg Pro Ser Ala
        195                 200                 205

Asp Asp Leu Ser Pro Lys Leu Leu Glu Phe Thr Ser Ala Arg Tyr Ile
210                 215                 220

Arg Leu Arg Leu Gln Arg Ile Arg Thr Leu Asn Ala Asp Leu Met Thr
225                 230                 235                 240

Leu Ser His Arg Glu Pro Lys Glu Leu Asp Pro Ile Val Thr Arg Arg
                245                 250                 255

Tyr Tyr Tyr Ser Ile Lys Asp Ile Ser Val Gly Gly Met Cys Ile Cys
            260                 265                 270

Tyr Gly His Ala Ser Ser Cys Pro Trp Asp Glu Thr Thr Lys Lys Leu
        275                 280                 285

Gln Cys Gln Cys Glu His Asn Thr Cys Gly Glu Ser Cys Asn Arg Cys
290                 295                 300
```

-continued

```
Cys Pro Gly Tyr His Gln Gln Pro Trp Arg Pro Gly Thr Val Ser Ser
305                 310                 315                 320
Gly Asn Thr Cys Glu Ala Cys Asn Cys His Asn Lys Ala Lys Asp Cys
                325                 330                 335
Tyr Tyr Asp Glu Ser Val Ala Lys Gln Lys Lys Ser Leu Asn Thr Ala
            340                 345                 350
Gly Gln Phe Arg Gly Gly Val Cys Ile Asn Cys Leu Gln Asn Thr
        355                 360                 365
Met Gly Ile Asn Cys Glu Thr Cys Ile Asp Gly Tyr Tyr Arg Pro His
    370                 375                 380
Lys Val Ser Pro Tyr Glu Asp Glu Pro Cys Arg Pro Cys Asn Cys Asp
385                 390                 395                 400
Pro Val Gly Ser Leu Ser Ser Val Cys Ile Lys Asp Asp Leu His Ser
                405                 410                 415
Asp Leu His Asn Gly Lys Gln Pro Gly Gln Cys Pro Cys Lys Glu Gly
            420                 425                 430
Tyr Thr Gly Glu Lys Cys Asp Arg Cys Gln Leu Gly Tyr Lys Asp Tyr
        435                 440                 445
Pro Thr Cys Val Ser Cys Gly Cys Asn Pro Val Gly Ser Ala Ser Asp
450                 455                 460
Glu Pro Cys Thr Gly Pro Cys Val Cys Lys Glu Asn Val Glu Gly Lys
465                 470                 475                 480
Ala Cys Asp Arg Cys Lys Pro Gly Phe Tyr Asn Leu Lys Glu Lys Asn
                485                 490                 495
Pro Arg Gly Cys Ser Glu Cys Phe Cys Phe Gly Val Ser Asp Val Cys
            500                 505                 510
Ser Ser Leu Ser Trp Pro Val Gly Gln Val Asn Ser Met Ser Gly Trp
        515                 520                 525
Leu Val Thr Asp Leu Ile Ser Pro Arg Lys Ile Pro Ser Gln Gln Asp
530                 535                 540
Ala Leu Gly Gly Arg His Gln Val Ser Ile Asn Asn Thr Ala Val Met
545                 550                 555                 560
Gln Arg Leu Ala Pro Lys Tyr Tyr Trp Ala Ala Pro Glu Ala Tyr Leu
                565                 570                 575
Gly Asn Lys Leu Thr Ala Phe Gly Gly Phe Leu Lys Tyr Thr Val Ser
            580                 585                 590
Tyr Asp Ile Pro Val Glu Thr Val Asp Ser Asn Leu Met Ser His Ala
        595                 600                 605
Asp Val Ile Ile Lys Gly Asn Gly Leu Thr Leu Ser Thr Gln Ala Glu
610                 615                 620
Gly Leu Ser Leu Gln Pro Tyr Glu Glu Tyr Leu Asn Val Val Arg Leu
625                 630                 635                 640
Val Pro Glu Asn Phe Gln Asp Phe His Ser Lys Arg Gln Ile Asp Arg
                645                 650                 655
Asp Gln Leu Met Thr Val Leu Ala Asn Val Thr His Leu Leu Ile Arg
            660                 665                 670
Ala Asn Tyr Asn Ser Ala Lys Met Ala Leu Tyr Arg Leu Glu Ser Val
        675                 680                 685
Ser Leu Asp Ile Ala Ser Ser Asn Ala Ile Asp Leu Val Val Ala Ala
    690                 695                 700
Asp Val Glu His Cys Glu Cys Pro Gln Gly Tyr Thr Gly Thr Ser Cys
705                 710                 715                 720
Glu Ser Cys Leu Ser Gly Tyr Tyr Arg Val Asp Gly Ile Leu Phe Gly
```

```
              725                 730                 735
Gly Ile Cys Gln Pro Cys Glu Cys His Gly His Ala Ala Glu Cys Asn
              740                 745                 750
Val His Gly Val Cys Ile Ala Cys Ala His Asn Thr Thr Gly Val His
              755                 760                 765
Cys Glu Gln Cys Leu Pro Gly Phe Tyr Gly Glu Pro Ser Arg Gly Thr
              770                 775                 780
Pro Gly Asp Cys Gln Pro Cys Ala Cys Pro Leu Thr Ile Ala Ser Asn
785                 790                 795                 800
Asn Phe Ser Pro Thr Cys His Leu Asn Asp Gly Asp Glu Val Val Cys
              805                 810                 815
Asp Trp Cys Ala Pro Gly Tyr Ser Gly Ala Trp Cys Glu Arg Cys Ala
              820                 825                 830
Asp Gly Tyr Tyr Gly Asn Pro Thr Val Pro Gly Glu Ser Cys Val Pro
              835                 840                 845
Cys Asp Cys Ser Gly Asn Val Asp Pro Ser Glu Ala Gly His Cys Asp
              850                 855                 860
Ser Val Thr Gly Glu Cys Leu Lys Cys Leu Gly Asn Thr Asp Gly Ala
865                 870                 875                 880
His Cys Glu Arg Cys Ala Asp Gly Phe Tyr Gly Asp Ala Val Thr Ala
                  885                 890                 895
Lys Asn Cys Arg Ala Cys Glu Cys His Val Lys Gly Ser His Ser Ala
              900                 905                 910
Val Cys His Leu Glu Thr Gly Leu Cys Asp Cys Lys Pro Asn Val Thr
              915                 920                 925
Gly Gln Gln Cys Asp Gln Cys Leu His Gly Tyr Tyr Gly Leu Asp Ser
      930                 935                 940
Gly His Gly Cys Arg Pro Cys Asn Cys Ser Val Ala Gly Ser Val Ser
945                 950                 955                 960
Asp Gly Cys Thr Asp Glu Gly Gln Cys His Cys Val Pro Gly Val Ala
              965                 970                 975
Gly Lys Arg Cys Asp Arg Cys Ala His Gly Phe Tyr Ala Tyr Gln Asp
              980                 985                 990
Gly Ser Cys Thr Pro Cys Asp Cys  Pro His Thr Gln Asn  Thr Cys Asp
          995                 1000                1005
Pro Glu Thr Gly Glu Cys Val  Cys Pro Pro His Thr  Gln Gly Val
      1010                1015                1020
Lys Cys Glu Glu Cys Glu Asp  Gly His Trp Gly Tyr  Asp Ala Glu
      1025                1030                1035
Val Gly Cys Gln Ala Cys Asn  Cys Ser Leu Val Gly  Ser Thr His
      1040                1045                1050
His Arg Cys Asp Val Val Thr  Gly His Cys Gln Cys  Lys Ser Lys
      1055                1060                1065
Phe Gly Gly Arg Ala Cys Asp  Gln Cys Ser Leu Gly  Tyr Arg Asp
      1070                1075                1080
Phe Pro Asp Cys Val Pro Cys  Asp Cys Asp Leu Arg  Gly Thr Ser
      1085                1090                1095
Gly Asp Ala Cys Asn Leu Glu  Gln Gly Leu Cys Gly  Cys Val Glu
      1100                1105                1110
Glu Thr Gly Ala Cys Pro Cys  Lys Glu Asn Val Phe  Gly Pro Gln
      1115                1120                1125
Cys Asn Glu Cys Arg Glu Gly  Thr Phe Ala Leu Arg  Ala Asp Asn
      1130                1135                1140
```

-continued

```
Pro Leu Gly Cys Ser Pro Cys Phe Cys Ser Gly Leu Ser His Leu
    1145                1150                1155

Cys Ser Glu Leu Glu Asp Tyr Val Arg Thr Pro Val Thr Leu Gly
    1160                1165                1170

Ser Asp Gln Pro Leu Leu Arg Val Val Ser Gln Ser Asn Leu Arg
    1175                1180                1185

Gly Thr Thr Glu Gly Val Tyr Tyr Gln Ala Pro Asp Phe Leu Leu
    1190                1195                1200

Asp Ala Ala Thr Val Arg Gln His Ile Arg Ala Glu Pro Phe Tyr
    1205                1210                1215

Trp Arg Leu Pro Gln Gln Phe Gln Gly Asp Gln Leu Met Ala Tyr
    1220                1225                1230

Gly Gly Lys Leu Lys Tyr Ser Val Ala Phe Tyr Ser Leu Asp Gly
    1235                1240                1245

Val Gly Thr Ser Asn Phe Glu Pro Gln Val Leu Ile Lys Gly Gly
    1250                1255                1260

Arg Ile Arg Lys Gln Val Ile Tyr Met Asp Ala Pro Ala Pro Glu
    1265                1270                1275

Asn Gly Val Arg Gln Glu Gln Glu Val Ala Met Arg Glu Asn Phe
    1280                1285                1290

Trp Lys Tyr Phe Asn Ser Val Ser Glu Lys Pro Val Thr Arg Glu
    1295                1300                1305

Asp Phe Met Ser Val Leu Ser Asp Ile Glu Tyr Ile Leu Ile Lys
    1310                1315                1320

Ala Ser Tyr Gly Gln Gly Leu Gln Gln Ser Arg Ile Ser Asp Ile
    1325                1330                1335

Ser Met Glu Val Gly Arg Lys Ala Glu Lys Leu His Pro Glu Glu
    1340                1345                1350

Glu Val Ala Ser Leu Leu Glu Asn Cys Val Cys Pro Pro Gly Thr
    1355                1360                1365

Val Gly Phe Ser Cys Gln Asp Cys Ala Pro Gly Tyr His Arg Gly
    1370                1375                1380

Lys Leu Pro Ala Gly Ser Asp Arg Gly Pro Arg Pro Leu Val Ala
    1385                1390                1395

Pro Cys Val Pro Cys Ser Cys Asn Asn His Ser Asp Thr Cys Asp
    1400                1405                1410

Pro Asn Thr Gly Lys Cys Leu Asn Cys Gly Asp Asn Thr Ala Gly
    1415                1420                1425

Asp His Cys Asp Val Cys Thr Ser Gly Tyr Tyr Gly Lys Val Thr
    1430                1435                1440

Gly Ser Ala Ser Asp Cys Ala Leu Cys Ala Cys Pro His Ser Pro
    1445                1450                1455

Pro Ala Ser Phe Ser Pro Thr Cys Val Leu Glu Gly Asp His Asp
    1460                1465                1470

Phe Arg Cys Asp Ala Cys Leu Leu Gly Tyr Glu Gly Lys His Cys
    1475                1480                1485

Glu Arg Cys Ser Ser Ser Tyr Tyr Gly Asn Pro Gln Thr Pro Gly
    1490                1495                1500

Gly Ser Cys Gln Lys Cys Asp Cys Asn Pro His Gly Ser Val His
    1505                1510                1515

Gly Asp Cys Asp Arg Thr Ser Gly Gln Cys Val Cys Arg Leu Gly
    1520                1525                1530
```

```
Ala Ser Gly Leu Arg Cys Asp Glu Cys Glu Pro Arg His Ile Leu
1535                1540                1545

Met Glu Thr Asp Cys Val Ser Cys Asp Asp Glu Cys Val Gly Val
1550                1555                1560

Leu Leu Asn Asp Leu Asp Glu Ile Gly Asp Ala Val Leu Ser Leu
1565                1570                1575

Asn Leu Thr Gly Ile Ile Pro Val Pro Tyr Gly Ile Leu Ser Asn
1580                1585                1590

Leu Glu Asn Thr Thr Lys Tyr Leu Gln Glu Ser Leu Leu Lys Glu
1595                1600                1605

Asn Met Gln Lys Asp Leu Gly Lys Ile Lys Leu Glu Gly Val Ala
1610                1615                1620

Glu Glu Thr Asp Asn Leu Gln Lys Lys Leu Thr Arg Met Leu Ala
1625                1630                1635

Ser Thr Gln Lys Val Asn Arg Ala Thr Glu Arg Ile Phe Lys Glu
1640                1645                1650

Ser Gln Asp Leu Ala Ile Ala Ile Glu Arg Leu Gln Met Ser Ile
1655                1660                1665

Thr Glu Ile Met Glu Lys Thr Thr Leu Asn Gln Thr Leu Asp Glu
1670                1675                1680

Asp Phe Leu Leu Pro Asn Ser Thr Leu Gln Asn Met Gln Gln Asn
1685                1690                1695

Gly Thr Ser Leu Leu Glu Ile Met Gln Ile Arg Asp Phe Thr Gln
1700                1705                1710

Leu His Gln Asn Ala Thr Leu Glu Leu Lys Ala Ala Glu Asp Leu
1715                1720                1725

Leu Ser Gln Ile Gln Glu Asn Tyr Gln Lys Pro Leu Glu Glu Leu
1730                1735                1740

Glu Val Leu Lys Glu Ala Ala Ser His Val Leu Ser Lys His Asn
1745                1750                1755

Asn Glu Leu Lys Ala Ala Glu Ala Leu Val Arg Glu Ala Glu Ala
1760                1765                1770

Lys Met Gln Glu Ser Asn His Leu Leu Leu Met Val Asn Ala Asn
1775                1780                1785

Leu Arg Glu Phe Ser Asp Lys Lys Leu His Val Gln Glu Glu Gln
1790                1795                1800

Asn Leu Thr Ser Glu Leu Ile Val Gln Gly Arg Gly Leu Ile Asp
1805                1810                1815

Ala Ala Ala Ala Gln Thr Asp Ala Val Gln Asp Ala Leu Glu His
1820                1825                1830

Leu Glu Asp His Gln Asp Lys Leu Leu Leu Trp Ser Ala Lys Ile
1835                1840                1845

Arg His His Ile Asp Asp Leu Val Met His Met Ser Gln Arg Asn
1850                1855                1860

Ala Val Asp Leu Val Tyr Arg Ala Glu Asp His Ala Ala Glu Phe
1865                1870                1875

Gln Arg Leu Ala Asp Val Leu Tyr Ser Gly Leu Glu Asn Ile Arg
1880                1885                1890

Asn Val Ser Leu Asn Ala Thr Ser Ala Ala Tyr Val His Tyr Asn
1895                1900                1905

Ile Gln Ser Leu Ile Glu Glu Ser Glu Glu Leu Ala Arg Asp Ala
1910                1915                1920

His Arg Thr Val Thr Glu Thr Ser Leu Leu Ser Glu Ser Leu Val
```

-continued

```
              1925                1930                1935

Ser  Asn  Gly  Lys  Ala  Ala  Val  Gln  Arg  Ser  Ser  Arg  Phe  Leu  Lys
              1940                1945                1950

Glu  Gly  Asn  Asn  Leu  Ser  Arg  Lys  Leu  Pro  Gly  Ile  Ala  Leu  Glu
              1955                1960                1965

Leu  Ser  Glu  Leu  Arg  Asn  Lys  Thr  Asn  Arg  Phe  Gln  Glu  Asn  Ala
              1970                1975                1980

Val  Glu  Ile  Thr  Arg  Gln  Thr  Asn  Glu  Ser  Leu  Leu  Ile  Leu  Arg
              1985                1990                1995

Ala  Ile  Pro  Lys  Gly  Ile  Arg  Asp  Lys  Gly  Ala  Lys  Thr  Lys  Glu
              2000                2005                2010

Leu  Ala  Thr  Ser  Ala  Ser  Gln  Ser  Ala  Val  Ser  Thr  Leu  Arg  Asp
              2015                2020                2025

Val  Ala  Gly  Leu  Ser  Gln  Glu  Leu  Leu  Asn  Thr  Ser  Ala  Ser  Leu
              2030                2035                2040

Ser  Arg  Val  Asn  Thr  Thr  Leu  Arg  Glu  Thr  His  Gln  Leu  Leu  Gln
              2045                2050                2055

Asp  Ser  Thr  Met  Ala  Thr  Leu  Leu  Ala  Gly  Arg  Lys  Val  Lys  Asp
              2060                2065                2070

Val  Glu  Ile  Gln  Ala  Asn  Leu  Leu  Phe  Asp  Arg  Leu  Lys  Pro  Leu
              2075                2080                2085

Lys  Met  Leu  Glu  Glu  Asn  Leu  Ser  Arg  Asn  Leu  Ser  Glu  Ile  Lys
              2090                2095                2100

Leu  Leu  Ile  Ser  Gln  Ala  Arg  Lys  Gln  Ala  Ala  Ser  Ile  Lys  Val
              2105                2110                2115

Ala  Val  Ser  Ala  Asp  Arg  Asp  Cys  Ile  Arg  Ala  Tyr  Gln  Pro  Gln
              2120                2125                2130

Ile  Ser  Ser  Thr  Asn  Tyr  Asn  Thr  Leu  Thr  Leu  Asn  Val  Lys  Thr
              2135                2140                2145

Gln  Glu  Pro  Asp  Asn  Leu  Leu  Phe  Tyr  Leu  Gly  Ser  Ser  Thr  Ala
              2150                2155                2160

Ser  Asp  Phe  Leu  Ala  Val  Glu  Met  Arg  Arg  Gly  Arg  Val  Ala  Phe
              2165                2170                2175

Leu  Trp  Asp  Leu  Gly  Ser  Gly  Ser  Thr  Arg  Leu  Glu  Phe  Pro  Asp
              2180                2185                2190

Phe  Pro  Ile  Asp  Asp  Asn  Arg  Trp  His  Ser  Ile  His  Val  Ala  Arg
              2195                2200                2205

Phe  Gly  Asn  Ile  Gly  Ser  Leu  Ser  Val  Lys  Glu  Met  Ser  Ser  Asn
              2210                2215                2220

Gln  Lys  Ser  Pro  Thr  Lys  Thr  Ser  Lys  Ser  Pro  Gly  Thr  Ala  Asn
              2225                2230                2235

Val  Leu  Asp  Val  Asn  Asn  Ser  Thr  Leu  Met  Phe  Val  Gly  Gly  Leu
              2240                2245                2250

Gly  Gly  Gln  Ile  Lys  Lys  Ser  Pro  Ala  Val  Lys  Val  Thr  His  Phe
              2255                2260                2265

Lys  Gly  Cys  Leu  Gly  Glu  Ala  Phe  Leu  Asn  Gly  Lys  Ser  Ile  Gly
              2270                2275                2280

Leu  Trp  Asn  Tyr  Ile  Glu  Arg  Glu  Gly  Lys  Cys  Arg  Gly  Cys  Phe
              2285                2290                2295

Gly  Ser  Ser  Gln  Asn  Glu  Asp  Pro  Ser  Phe  His  Phe  Asp  Gly  Ser
              2300                2305                2310

Gly  Tyr  Ser  Val  Val  Glu  Lys  Ser  Leu  Pro  Ala  Thr  Val  Thr  Gln
              2315                2320                2325
```

```
Ile Ile Met Leu Phe Asn Thr Phe Ser Pro Asn Gly Leu Leu Leu
    2330            2335            2340

Tyr Leu Gly Ser Tyr Gly Thr Lys Asp Phe Leu Ser Ile Glu Leu
    2345            2350            2355

Phe Arg Gly Arg Val Lys Val Met Thr Asp Leu Gly Ser Gly Pro
    2360            2365            2370

Ile Thr Leu Leu Thr Asp Arg Arg Tyr Asn Asn Gly Thr Trp Tyr
    2375            2380            2385

Lys Ile Ala Phe Gln Arg Asn Arg Lys Gln Gly Val Leu Ala Val
    2390            2395            2400

Ile Asp Ala Tyr Asn Thr Ser Asn Lys Glu Thr Lys Gln Gly Glu
    2405            2410            2415

Thr Pro Gly Ala Ser Ser Asp Leu Asn Arg Leu Asp Lys Asp Pro
    2420            2425            2430

Ile Tyr Val Gly Gly Leu Pro Arg Ser Arg Val Val Arg Arg Gly
    2435            2440            2445

Val Thr Thr Lys Ser Phe Val Gly Cys Ile Lys Asn Leu Glu Ile
    2450            2455            2460

Ser Arg Ser Thr Phe Asp Leu Leu Arg Asn Ser Tyr Gly Val Arg
    2465            2470            2475

Lys Gly Cys Leu Leu Glu Pro Ile Arg Ser Val Ser Phe Leu Lys
    2480            2485            2490

Gly Gly Tyr Ile Glu Leu Pro Pro Lys Ser Leu Ser Pro Glu Ser
    2495            2500            2505

Glu Trp Leu Val Thr Phe Ala Thr Thr Asn Ser Ser Gly Ile Ile
    2510            2515            2520

Leu Ala Ala Leu Gly Gly Asp Val Glu Lys Arg Gly Asp Arg Glu
    2525            2530            2535

Glu Ala His Val Pro Phe Phe Ser Val Met Leu Ile Gly Gly Asn
    2540            2545            2550

Ile Glu Val His Val Asn Pro Gly Asp Gly Thr Gly Leu Arg Lys
    2555            2560            2565

Ala Leu Leu His Ala Pro Thr Gly Thr Cys Ser Asp Gly Gln Ala
    2570            2575            2580

His Ser Ile Ser Leu Val Arg Asn Arg Arg Ile Ile Thr Val Gln
    2585            2590            2595

Leu Asp Glu Asn Asn Pro Val Glu Met Lys Leu Gly Thr Leu Val
    2600            2605            2610

Glu Ser Arg Thr Ile Asn Val Ser Asn Leu Tyr Val Gly Gly Ile
    2615            2620            2625

Pro Glu Gly Glu Gly Thr Ser Leu Leu Thr Met Arg Arg Ser Phe
    2630            2635            2640

His Gly Cys Ile Lys Asn Leu Ile Phe Asn Leu Glu Leu Leu Asp
    2645            2650            2655

Phe Asn Ser Ala Val Gly His Glu Gln Val Asp Leu Asp Thr Cys
    2660            2665            2670

Trp Leu Ser Glu Arg Pro Lys Leu Ala Pro Asp Ala Glu Asp Ser
    2675            2680            2685

Lys Leu Leu Pro Glu Pro Arg Ala Phe Pro Glu Gln Cys Val Val
    2690            2695            2700

Asp Ala Ala Leu Glu Tyr Val Pro Gly Ala His Gln Phe Gly Leu
    2705            2710            2715
```

```
Thr Gln Asn Ser His Phe Ile Leu Pro Phe Asn Gln Ser Ala Val
2720                2725                2730

Arg Lys Lys Leu Ser Val Glu Leu Ser Ile Arg Thr Phe Ala Ser
2735                2740                2745

Ser Gly Leu Ile Tyr Tyr Met Ala His Gln Asn Gln Ala Asp Tyr
2750                2755                2760

Ala Val Leu Gln Leu His Gly Gly Arg Leu His Phe Met Phe Asp
2765                2770                2775

Leu Gly Lys Gly Arg Thr Lys Val Ser His Pro Ala Leu Leu Ser
2780                2785                2790

Asp Gly Lys Trp His Thr Val Lys Thr Asp Tyr Val Lys Arg Lys
2795                2800                2805

Gly Phe Ile Thr Val Asp Gly Arg Glu Ser Pro Met Val Thr Val
2810                2815                2820

Val Gly Asp Gly Thr Met Leu Asp Val Glu Gly Leu Phe Tyr Leu
2825                2830                2835

Gly Gly Leu Pro Ser Gln Tyr Gln Ala Arg Lys Ile Gly Asn Ile
2840                2845                2850

Thr His Ser Ile Pro Ala Cys Ile Gly Asp Val Thr Val Asn Ser
2855                2860                2865

Lys Gln Leu Asp Lys Asp Ser Pro Val Ser Ala Phe Thr Val Asn
2870                2875                2880

Arg Cys Tyr Ala Val Ala Gln Glu Gly Thr Tyr Phe Asp Gly Ser
2885                2890                2895

Gly Tyr Ala Ala Leu Val Lys Glu Gly Tyr Lys Val Gln Ser Asp
2900                2905                2910

Val Asn Ile Thr Leu Glu Phe Arg Thr Ser Ser Gln Asn Gly Val
2915                2920                2925

Leu Leu Gly Ile Ser Thr Ala Lys Val Asp Ala Ile Gly Leu Glu
2930                2935                2940

Leu Val Asp Gly Lys Val Leu Phe His Val Asn Asn Gly Ala Gly
2945                2950                2955

Arg Ile Thr Ala Ala Tyr Glu Pro Lys Thr Ala Thr Val Leu Cys
2960                2965                2970

Asp Gly Lys Trp His Thr Leu Gln Ala Asn Lys Ser Lys His Arg
2975                2980                2985

Ile Thr Leu Ile Val Asp Gly Asn Ala Val Gly Ala Glu Ser Pro
2990                2995                3000

His Thr Gln Ser Thr Ser Val Asp Thr Asn Asn Pro Ile Tyr Val
3005                3010                3015

Gly Gly Tyr Pro Ala Gly Val Lys Gln Lys Cys Leu Arg Ser Gln
3020                3025                3030

Thr Ser Phe Arg Gly Cys Leu Arg Lys Leu Ala Leu Ile Lys Ser
3035                3040                3045

Pro Gln Val Gln Ser Phe Asp Phe Ser Arg Ala Phe Glu Leu His
3050                3055                3060

Gly Val Phe Leu His Ser Cys Pro Gly Thr Glu Ser
3065                3070                3075

<210> SEQ ID NO 26
<211> LENGTH: 3122
<212> TYPE: PRT
<213> ORGANISM: Homo sapiens

<400> SEQUENCE: 26
```

```
Met Pro Gly Ala Ala Gly Val Leu Leu Leu Leu Leu Ser Gly Gly
1               5                   10                  15

Leu Gly Gly Val Gln Ala Gln Arg Pro Gln Gln Arg Gln Ser Gln
            20                  25                  30

Ala His Gln Gln Arg Gly Leu Phe Pro Ala Val Leu Asn Leu Ala Ser
        35                  40                      45

Asn Ala Leu Ile Thr Thr Asn Ala Thr Cys Gly Glu Lys Gly Pro Glu
    50                  55                  60

Met Tyr Cys Lys Leu Val Glu His Val Pro Gly Gln Pro Val Arg Asn
65                  70                  75                  80

Pro Gln Cys Arg Ile Cys Asn Gln Asn Ser Ser Asn Pro Asn Gln Arg
                85                  90                  95

His Pro Ile Thr Asn Ala Ile Asp Gly Lys Asn Thr Trp Trp Gln Ser
            100                 105                 110

Pro Ser Ile Lys Asn Gly Ile Glu Tyr His Tyr Val Thr Ile Thr Leu
        115                 120                 125

Asp Leu Gln Gln Val Phe Gln Ile Ala Tyr Val Ile Val Lys Ala Ala
    130                 135                 140

Asn Ser Pro Arg Pro Gly Asn Trp Ile Leu Glu Arg Ser Leu Asp Asp
145                 150                 155                 160

Val Glu Tyr Lys Pro Trp Gln Tyr His Ala Val Thr Asp Thr Glu Cys
                165                 170                 175

Leu Thr Leu Tyr Asn Ile Tyr Pro Arg Thr Gly Pro Pro Ser Tyr Ala
            180                 185                 190

Lys Asp Asp Glu Val Ile Cys Thr Ser Phe Tyr Ser Lys Ile His Pro
        195                 200                 205

Leu Glu Asn Gly Glu Ile His Ile Ser Leu Ile Asn Gly Arg Pro Ser
    210                 215                 220

Ala Asp Asp Pro Ser Pro Glu Leu Leu Glu Phe Thr Ser Ala Arg Tyr
225                 230                 235                 240

Ile Arg Leu Arg Phe Gln Arg Ile Arg Thr Leu Asn Ala Asp Leu Met
                245                 250                 255

Met Phe Ala His Lys Asp Pro Arg Glu Ile Asp Pro Ile Val Thr Arg
            260                 265                 270

Arg Tyr Tyr Tyr Ser Val Lys Asp Ile Ser Val Gly Gly Met Cys Ile
        275                 280                 285

Cys Tyr Gly His Ala Arg Ala Cys Pro Leu Asp Pro Ala Thr Asn Lys
    290                 295                 300

Ser Arg Cys Glu Cys Glu His Asn Thr Cys Gly Asp Ser Cys Asp Gln
305                 310                 315                 320

Cys Cys Pro Gly Phe His Gln Lys Pro Trp Arg Ala Gly Thr Phe Leu
                325                 330                 335

Thr Lys Thr Glu Cys Glu Ala Cys Asn Cys His Gly Lys Ala Glu Glu
            340                 345                 350

Cys Tyr Tyr Asp Glu Asn Val Ala Arg Arg Asn Leu Ser Leu Asn Ile
        355                 360                 365

Arg Gly Lys Tyr Ile Gly Gly Val Cys Ile Asn Cys Thr Gln Asn
    370                 375                 380

Thr Ala Gly Ile Asn Cys Glu Thr Cys Thr Asp Gly Phe Phe Arg Pro
385                 390                 395                 400

Lys Gly Val Ser Pro Asn Tyr Pro Arg Pro Cys Gln Pro Cys His Cys
                405                 410                 415
```

```
Asp Pro Ile Gly Ser Leu Asn Glu Val Cys Val Lys Asp Glu Lys His
            420                 425                 430

Ala Arg Arg Gly Leu Ala Pro Gly Ser His Cys Lys Thr Gly Phe
        435                 440                 445

Gly Gly Val Ser Cys Asp Arg Cys Ala Arg Gly Tyr Thr Gly Tyr Pro
    450                 455                 460

Asp Cys Lys Ala Cys Asn Cys Ser Gly Leu Gly Ser Lys Asn Glu Asp
465                 470                 475                 480

Pro Cys Phe Gly Pro Cys Ile Cys Lys Glu Asn Val Glu Gly Gly Asp
                485                 490                 495

Cys Ser Arg Cys Lys Ser Gly Phe Phe Asn Leu Gln Glu Asp Asn Trp
            500                 505                 510

Lys Gly Cys Asp Glu Cys Phe Cys Ser Gly Val Ser Asn Arg Cys Gln
        515                 520                 525

Ser Ser Tyr Trp Thr Tyr Gly Lys Ile Gln Asp Met Ser Gly Trp Tyr
    530                 535                 540

Leu Thr Asp Leu Pro Gly Arg Ile Arg Val Ala Pro Gln Gln Asp Asp
545                 550                 555                 560

Leu Asp Ser Pro Gln Gln Ile Ser Ile Ser Asn Ala Glu Ala Arg Gln
                565                 570                 575

Ala Leu Pro His Ser Tyr Tyr Trp Ser Ala Pro Ala Pro Tyr Leu Gly
            580                 585                 590

Asn Lys Leu Pro Ala Val Gly Gly Gln Leu Thr Phe Thr Ile Ser Tyr
        595                 600                 605

Asp Leu Glu Glu Glu Glu Glu Asp Thr Glu Arg Val Leu Gln Leu Met
    610                 615                 620

Ile Ile Leu Glu Gly Asn Asp Leu Ser Ile Ser Thr Ala Gln Asp Glu
625                 630                 635                 640

Val Tyr Leu His Pro Ser Glu His Thr Asn Val Leu Leu Leu Lys
                645                 650                 655

Glu Glu Ser Phe Thr Ile His Gly Thr His Phe Pro Val Arg Arg Lys
            660                 665                 670

Glu Phe Met Thr Val Leu Ala Asn Leu Lys Arg Val Leu Leu Gln Ile
        675                 680                 685

Thr Tyr Ser Phe Gly Met Asp Ala Ile Phe Arg Leu Ser Ser Val Asn
    690                 695                 700

Leu Glu Ser Ala Val Ser Tyr Pro Thr Asp Gly Ser Ile Ala Ala Ala
705                 710                 715                 720

Val Glu Val Cys Gln Cys Pro Pro Gly Tyr Thr Gly Ser Ser Cys Glu
                725                 730                 735

Ser Cys Trp Pro Arg His Arg Arg Val Asn Gly Thr Ile Phe Gly Gly
            740                 745                 750

Ile Cys Glu Pro Cys Gln Cys Phe Gly His Ala Glu Ser Cys Asp Asp
        755                 760                 765

Val Thr Gly Glu Cys Leu Asn Cys Lys Asp His Thr Gly Gly Pro Tyr
    770                 775                 780

Cys Asp Lys Cys Leu Pro Gly Phe Tyr Gly Glu Pro Thr Lys Gly Thr
785                 790                 795                 800

Ser Glu Asp Cys Gln Pro Cys Ala Cys Pro Leu Asn Ile Pro Ser Asn
                805                 810                 815

Asn Phe Ser Pro Thr Cys His Leu Asp Arg Ser Leu Gly Leu Ile Cys
            820                 825                 830

Asp Gly Cys Pro Val Gly Tyr Thr Gly Pro Arg Cys Glu Arg Cys Ala
```

```
              835                 840                 845
Glu Gly Tyr Phe Gly Gln Pro Ser Val Pro Gly Gly Ser Cys Gln Pro
    850                 855                 860
Cys Gln Cys Asn Asp Asn Leu Asp Phe Ser Ile Pro Gly Ser Cys Asp
865                 870                 875                 880
Ser Leu Ser Gly Ser Cys Leu Ile Cys Lys Pro Gly Thr Thr Gly Arg
                    885                 890                 895
Tyr Cys Glu Leu Cys Ala Asp Gly Tyr Phe Gly Asp Ala Val Asp Ala
                900                 905                 910
Lys Asn Cys Gln Pro Cys Arg Cys Asn Ala Gly Gly Ser Phe Ser Glu
            915                 920                 925
Val Cys His Ser Gln Thr Gly Gln Cys Glu Cys Arg Ala Asn Val Gln
        930                 935                 940
Gly Gln Arg Cys Asp Lys Cys Lys Ala Gly Thr Phe Gly Leu Gln Ser
945                 950                 955                 960
Ala Arg Gly Cys Val Pro Cys Asn Cys Asn Ser Phe Gly Ser Lys Ser
                965                 970                 975
Phe Asp Cys Glu Glu Ser Gly Gln Cys Trp Cys Gln Pro Gly Val Thr
            980                 985                 990
Gly Lys Lys Cys Asp Arg Cys Ala  His Gly Tyr Phe Asn  Phe Gln Glu
        995                 1000                1005
Gly Gly Cys Thr Ala Cys Glu  Cys Ser His Leu Gly  Asn Asn Cys
1010                1015                1020
Asp Pro Lys Thr Gly Arg Cys  Ile Cys Pro Pro Asn  Thr Ile Gly
1025                1030                1035
Glu Lys Cys Ser Lys Cys Ala  Pro Asn Thr Trp Gly  His Ser Ile
1040                1045                1050
Thr Thr Gly Cys Lys Ala Cys  Asn Cys Ser Thr Val  Gly Ser Leu
1055                1060                1065
Asp Phe Gln Cys Asn Val Asn  Thr Gly Gln Cys Asn  Cys His Pro
1070                1075                1080
Lys Phe Ser Gly Ala Lys Cys  Thr Glu Cys Ser Arg  Gly His Trp
1085                1090                1095
Asn Tyr Pro Arg Cys Asn Leu  Cys Asp Cys Phe Leu  Pro Gly Thr
1100                1105                1110
Asp Ala Thr Thr Cys Asp Ser  Glu Thr Lys Lys Cys  Ser Cys Ser
1115                1120                1125
Asp Gln Thr Gly Gln Cys Thr  Cys Lys Val Asn Val  Glu Gly Ile
1130                1135                1140
His Cys Asp Arg Cys Arg Pro  Gly Lys Phe Gly Leu  Asp Ala Lys
1145                1150                1155
Asn Pro Leu Gly Cys Ser Ser  Cys Tyr Cys Phe Gly  Thr Thr Thr
1160                1165                1170
Gln Cys Ser Glu Ala Lys Gly  Leu Ile Arg Thr Trp  Val Thr Leu
1175                1180                1185
Lys Ala Glu Gln Thr Ile Leu  Pro Leu Val Asp Glu  Ala Leu Gln
1190                1195                1200
His Thr Thr Thr Lys Gly Ile  Val Phe Gln His Pro  Glu Ile Val
1205                1210                1215
Ala His Met Asp Leu Met Arg  Glu Asp Leu His Leu  Glu Pro Phe
1220                1225                1230
Tyr Trp Lys Leu Pro Glu Gln  Phe Glu Gly Lys Lys  Leu Met Ala
1235                1240                1245
```

-continued

Tyr Gly Gly Lys Leu Lys Tyr Ala Ile Tyr Phe Glu Ala Arg Glu
1250                1255                1260

Glu Thr Gly Phe Ser Thr Tyr Asn Pro Gln Val Ile Ile Arg Gly
1265                1270                1275

Gly Thr Pro Thr His Ala Arg Ile Ile Val Arg His Met Ala Ala
1280                1285                1290

Pro Leu Ile Gly Gln Leu Thr Arg His Glu Ile Glu Met Thr Glu
1295                1300                1305

Lys Glu Trp Lys Tyr Tyr Gly Asp Pro Arg Val His Arg Thr
1310                1315                1320

Val Thr Arg Glu Asp Phe Leu Asp Ile Leu Tyr Asp Ile His Tyr
1325                1330                1335

Ile Leu Ile Lys Ala Thr Tyr Gly Asn Phe Met Arg Gln Ser Arg
1340                1345                1350

Ile Ser Glu Ile Ser Met Glu Val Ala Glu Gln Gly Arg Gly Thr
1355                1360                1365

Thr Met Thr Pro Pro Ala Asp Leu Ile Glu Lys Cys Asp Cys Pro
1370                1375                1380

Leu Gly Tyr Ser Gly Leu Ser Cys Glu Ala Cys Leu Pro Gly Phe
1385                1390                1395

Tyr Arg Leu Arg Ser Gln Pro Gly Gly Arg Thr Pro Gly Pro Thr
1400                1405                1410

Leu Gly Thr Cys Val Pro Cys Gln Cys Asn Gly His Ser Ser Leu
1415                1420                1425

Cys Asp Pro Glu Thr Ser Ile Cys Gln Asn Cys Gln His His Thr
1430                1435                1440

Ala Gly Asp Phe Cys Glu Arg Cys Ala Leu Gly Tyr Tyr Gly Ile
1445                1450                1455

Val Lys Gly Leu Pro Asn Asp Cys Gln Gln Cys Ala Cys Pro Leu
1460                1465                1470

Ile Ser Ser Ser Asn Asn Phe Ser Pro Ser Cys Val Ala Glu Gly
1475                1480                1485

Leu Asp Asp Tyr Arg Cys Thr Ala Cys Pro Arg Gly Tyr Glu Gly
1490                1495                1500

Gln Tyr Cys Glu Arg Cys Ala Pro Gly Tyr Thr Gly Ser Pro Gly
1505                1510                1515

Asn Pro Gly Gly Ser Cys Gln Glu Cys Glu Cys Asp Pro Tyr Gly
1520                1525                1530

Ser Leu Pro Val Pro Cys Asp Pro Val Thr Gly Phe Cys Thr Cys
1535                1540                1545

Arg Pro Gly Ala Thr Gly Arg Lys Cys Asp Gly Cys Lys His Trp
1550                1555                1560

His Ala Arg Glu Gly Trp Glu Cys Val Phe Cys Gly Asp Glu Cys
1565                1570                1575

Thr Gly Leu Leu Leu Gly Asp Leu Ala Arg Leu Glu Gln Met Val
1580                1585                1590

Met Ser Ile Asn Leu Thr Gly Pro Leu Pro Ala Pro Tyr Lys Met
1595                1600                1605

Leu Tyr Gly Leu Glu Asn Met Thr Gln Glu Leu Lys His Leu Leu
1610                1615                1620

Ser Pro Gln Arg Ala Pro Glu Arg Leu Ile Gln Leu Ala Glu Gly
1625                1630                1635

```
Asn Leu Asn Thr Leu Val Thr Glu Met Asn Glu Leu Leu Thr Arg
    1640            1645                1650
Ala Thr Lys Val Thr Ala Asp Gly Glu Gln Thr Gly Gln Asp Ala
    1655            1660                1665
Glu Arg Thr Asn Thr Arg Ala Lys Ser Leu Gly Glu Phe Ile Lys
    1670            1675                1680
Glu Leu Ala Arg Asp Ala Glu Ala Val Asn Glu Lys Ala Ile Lys
    1685            1690                1695
Leu Asn Glu Thr Leu Gly Thr Arg Asp Glu Ala Phe Glu Arg Asn
    1700            1705                1710
Leu Glu Gly Leu Gln Lys Glu Ile Asp Gln Met Ile Lys Glu Leu
    1715            1720                1725
Arg Arg Lys Asn Leu Glu Thr Gln Lys Glu Ile Ala Glu Asp Glu
    1730            1735                1740
Leu Val Ala Ala Glu Ala Leu Leu Lys Lys Val Lys Lys Leu Phe
    1745            1750                1755
Gly Glu Ser Arg Gly Glu Asn Glu Glu Met Glu Lys Asp Leu Arg
    1760            1765                1770
Glu Lys Leu Ala Asp Tyr Lys Asn Lys Val Asp Asp Ala Trp Asp
    1775            1780                1785
Leu Leu Arg Glu Ala Thr Asp Lys Ile Arg Glu Ala Asn Arg Leu
    1790            1795                1800
Phe Ala Val Asn Gln Lys Asn Met Thr Ala Leu Glu Lys Lys Lys
    1805            1810                1815
Glu Ala Val Glu Ser Gly Lys Arg Gln Ile Glu Asn Thr Leu Lys
    1820            1825                1830
Glu Gly Asn Asp Ile Leu Asp Glu Ala Asn Arg Leu Ala Asp Glu
    1835            1840                1845
Ile Asn Ser Ile Ile Asp Tyr Val Glu Asp Ile Gln Thr Lys Leu
    1850            1855                1860
Pro Pro Met Ser Glu Glu Leu Asn Asp Lys Ile Asp Asp Leu Ser
    1865            1870                1875
Gln Glu Ile Lys Asp Arg Lys Leu Ala Glu Lys Val Ser Gln Ala
    1880            1885                1890
Glu Ser His Ala Ala Gln Leu Asn Asp Ser Ser Ala Val Leu Asp
    1895            1900                1905
Gly Ile Leu Asp Glu Ala Lys Asn Ile Ser Phe Asn Ala Thr Ala
    1910            1915                1920
Ala Phe Lys Ala Tyr Ser Asn Ile Lys Asp Tyr Ile Asp Glu Ala
    1925            1930                1935
Glu Lys Val Ala Lys Glu Ala Lys Asp Leu Ala His Glu Ala Thr
    1940            1945                1950
Lys Leu Ala Thr Gly Pro Arg Gly Leu Leu Lys Glu Asp Ala Lys
    1955            1960                1965
Gly Cys Leu Gln Lys Ser Phe Arg Ile Leu Asn Glu Ala Lys Lys
    1970            1975                1980
Leu Ala Asn Asp Val Lys Glu Asn Glu Asp His Leu Asn Gly Leu
    1985            1990                1995
Lys Thr Arg Ile Glu Asn Ala Asp Ala Arg Asn Gly Asp Leu Leu
    2000            2005                2010
Arg Thr Leu Asn Asp Thr Leu Gly Lys Leu Ser Ala Ile Pro Asn
    2015            2020                2025
Asp Thr Ala Ala Lys Leu Gln Ala Val Lys Asp Lys Ala Arg Gln
```

2030                2035                2040

Ala Asn Asp Thr Ala Lys Asp Val Leu Ala Gln Ile Thr Glu Leu
        2045                2050                2055

His Gln Asn Leu Asp Gly Leu Lys Lys Asn Tyr Asn Lys Leu Ala
        2060                2065                2070

Asp Ser Val Ala Lys Thr Asn Ala Val Val Lys Asp Pro Ser Lys
        2075                2080                2085

Asn Lys Ile Ile Ala Asp Ala Asp Ala Thr Val Lys Asn Leu Glu
        2090                2095                2100

Gln Glu Ala Asp Arg Leu Ile Asp Lys Leu Lys Pro Ile Lys Glu
        2105                2110                2115

Leu Glu Asp Asn Leu Lys Lys Asn Ile Ser Glu Ile Lys Glu Leu
        2120                2125                2130

Ile Asn Gln Ala Arg Lys Gln Ala Asn Ser Ile Lys Val Ser Val
        2135                2140                2145

Ser Ser Gly Gly Asp Cys Ile Arg Thr Tyr Lys Pro Glu Ile Lys
        2150                2155                2160

Lys Gly Ser Tyr Asn Asn Ile Val Val Asn Val Lys Thr Ala Val
        2165                2170                2175

Ala Asp Asn Leu Leu Phe Tyr Leu Gly Ser Ala Lys Phe Ile Asp
        2180                2185                2190

Phe Leu Ala Ile Glu Met Arg Lys Gly Lys Val Ser Phe Leu Trp
        2195                2200                2205

Asp Val Gly Ser Gly Val Gly Arg Val Glu Tyr Pro Asp Leu Thr
        2210                2215                2220

Ile Asp Asp Ser Tyr Trp Tyr Arg Ile Val Ala Ser Arg Thr Gly
        2225                2230                2235

Arg Asn Gly Thr Ile Ser Val Arg Ala Leu Asp Gly Pro Lys Ala
        2240                2245                2250

Ser Ile Val Pro Ser Thr His His Ser Thr Ser Pro Pro Gly Tyr
        2255                2260                2265

Thr Ile Leu Asp Val Asp Ala Asn Ala Met Leu Phe Val Gly Gly
        2270                2275                2280

Leu Thr Gly Lys Leu Lys Lys Ala Asp Ala Val Arg Val Ile Thr
        2285                2290                2295

Phe Thr Gly Cys Met Gly Glu Thr Tyr Phe Asp Asn Lys Pro Ile
        2300                2305                2310

Gly Leu Trp Asn Phe Arg Glu Lys Glu Gly Asp Cys Lys Gly Cys
        2315                2320                2325

Thr Val Ser Pro Gln Val Glu Asp Ser Glu Gly Thr Ile Gln Phe
        2330                2335                2340

Asp Gly Glu Gly Tyr Ala Leu Val Ser Arg Pro Ile Arg Trp Tyr
        2345                2350                2355

Pro Asn Ile Ser Thr Val Met Phe Lys Phe Arg Thr Phe Ser Ser
        2360                2365                2370

Ser Ala Leu Leu Met Tyr Leu Ala Thr Arg Asp Leu Arg Asp Phe
        2375                2380                2385

Met Ser Val Glu Leu Thr Asp Gly His Ile Lys Val Ser Tyr Asp
        2390                2395                2400

Leu Gly Ser Gly Met Ala Ser Val Val Ser Asn Gln Asn His Asn
        2405                2410                2415

Asp Gly Lys Trp Lys Ser Phe Thr Leu Ser Arg Ile Gln Lys Gln
        2420                2425                2430

```
Ala Asn Ile Ser Ile Val Asp Ile Asp Thr Asn Gln Glu Glu Asn
    2435            2440            2445

Ile Ala Thr Ser Ser Ser Gly Asn Asn Phe Gly Leu Asp Leu Lys
    2450            2455            2460

Ala Asp Asp Lys Ile Tyr Phe Gly Gly Leu Pro Thr Leu Arg Asn
    2465            2470            2475

Leu Ser Met Lys Ala Arg Pro Glu Val Asn Leu Lys Lys Tyr Ser
    2480            2485            2490

Gly Cys Leu Lys Asp Ile Glu Ile Ser Arg Thr Pro Tyr Asn Ile
    2495            2500            2505

Leu Ser Ser Pro Asp Tyr Val Gly Val Thr Lys Gly Cys Ser Leu
    2510            2515            2520

Glu Asn Val Tyr Thr Val Ser Phe Pro Lys Pro Gly Phe Val Glu
    2525            2530            2535

Leu Ser Pro Val Pro Ile Asp Val Gly Thr Glu Ile Asn Leu Ser
    2540            2545            2550

Phe Ser Thr Lys Asn Glu Ser Gly Ile Ile Leu Leu Gly Ser Gly
    2555            2560            2565

Gly Thr Pro Ala Pro Arg Arg Lys Arg Arg Gln Thr Gly Gln
    2570            2575            2580

Ala Tyr Tyr Val Ile Leu Leu Asn Arg Gly Arg Leu Glu Val His
    2585            2590            2595

Leu Ser Thr Gly Ala Arg Thr Met Arg Lys Ile Val Ile Arg Pro
    2600            2605            2610

Glu Pro Asn Leu Phe His Asp Gly Arg Glu His Ser Val His Val
    2615            2620            2625

Glu Arg Thr Arg Gly Ile Phe Thr Val Gln Val Asp Glu Asn Arg
    2630            2635            2640

Arg Tyr Met Gln Asn Leu Thr Val Glu Gln Pro Ile Glu Val Lys
    2645            2650            2655

Lys Leu Phe Val Gly Gly Ala Pro Pro Glu Phe Gln Pro Ser Pro
    2660            2665            2670

Leu Arg Asn Ile Pro Pro Phe Glu Gly Cys Ile Trp Asn Leu Val
    2675            2680            2685

Ile Asn Ser Val Pro Met Asp Phe Ala Arg Pro Val Ser Phe Lys
    2690            2695            2700

Asn Ala Asp Ile Gly Arg Cys Ala His Gln Lys Leu Arg Glu Asp
    2705            2710            2715

Glu Asp Gly Ala Ala Pro Ala Glu Ile Val Ile Gln Pro Glu Pro
    2720            2725            2730

Val Pro Thr Pro Ala Phe Pro Thr Pro Thr Pro Val Leu Thr His
    2735            2740            2745

Gly Pro Cys Ala Ala Glu Ser Glu Pro Ala Leu Leu Ile Gly Ser
    2750            2755            2760

Lys Gln Phe Gly Leu Ser Arg Asn Ser His Ile Ala Ile Ala Phe
    2765            2770            2775

Asp Asp Thr Lys Val Lys Asn Arg Leu Thr Ile Glu Leu Glu Val
    2780            2785            2790

Arg Thr Glu Ala Glu Ser Gly Leu Leu Phe Tyr Met Ala Arg Ile
    2795            2800            2805

Asn His Ala Asp Phe Ala Thr Val Gln Leu Arg Asn Gly Leu Pro
    2810            2815            2820
```

```
Tyr Phe Ser Tyr Asp Leu Gly Ser Gly Asp Thr His Thr Met Ile
2825                2830                2835

Pro Thr Lys Ile Asn Asp Gly Gln Trp His Lys Ile Lys Ile Met
2840                2845                2850

Arg Ser Lys Gln Glu Gly Ile Leu Tyr Val Asp Gly Ala Ser Asn
2855                2860                2865

Arg Thr Ile Ser Pro Lys Lys Ala Asp Ile Leu Asp Val Val Gly
2870                2875                2880

Met Leu Tyr Val Gly Gly Leu Pro Ile Asn Tyr Thr Thr Arg Arg
2885                2890                2895

Ile Gly Pro Val Thr Tyr Ser Ile Asp Gly Cys Val Arg Asn Leu
2900                2905                2910

His Met Ala Glu Ala Pro Ala Asp Leu Glu Gln Pro Thr Ser Ser
2915                2920                2925

Phe His Val Gly Thr Cys Phe Ala Asn Ala Gln Arg Gly Thr Tyr
2930                2935                2940

Phe Asp Gly Thr Gly Phe Ala Lys Ala Val Gly Gly Phe Lys Val
2945                2950                2955

Gly Leu Asp Leu Leu Val Glu Phe Glu Phe Arg Thr Thr Thr Thr
2960                2965                2970

Thr Gly Val Leu Leu Gly Ile Ser Ser Gln Lys Met Asp Gly Met
2975                2980                2985

Gly Ile Glu Met Ile Asp Glu Lys Leu Met Phe His Val Asp Asn
2990                2995                3000

Gly Ala Gly Arg Phe Thr Ala Val Tyr Asp Ala Gly Val Pro Gly
3005                3010                3015

His Leu Cys Asp Gly Gln Trp His Lys Val Thr Ala Asn Lys Ile
3020                3025                3030

Lys His Arg Ile Glu Leu Thr Val Asp Gly Asn Gln Val Glu Ala
3035                3040                3045

Gln Ser Pro Asn Pro Ala Ser Thr Ser Ala Asp Thr Asn Asp Pro
3050                3055                3060

Val Phe Val Gly Gly Phe Pro Asp Asp Leu Lys Gln Phe Gly Leu
3065                3070                3075

Thr Thr Ser Ile Pro Phe Arg Gly Cys Ile Arg Ser Leu Lys Leu
3080                3085                3090

Thr Lys Gly Thr Gly Lys Pro Leu Glu Val Asn Phe Ala Lys Ala
3095                3100                3105

Leu Glu Leu Arg Gly Val Gln Pro Val Ser Cys Pro Ala Asn
3110                3115                3120

<210> SEQ ID NO 27
<211> LENGTH: 3118
<212> TYPE: PRT
<213> ORGANISM: Homo sapiens

<400> SEQUENCE: 27

Met Pro Gly Ala Ala Gly Val Leu Leu Leu Leu Leu Ser Gly Gly
1               5               10              15

Leu Gly Gly Val Gln Ala Gln Arg Pro Gln Gln Arg Gln Ser Gln
                20              25              30

Ala His Gln Gln Arg Gly Leu Phe Pro Ala Val Leu Asn Leu Ala Ser
        35              40              45

Asn Ala Leu Ile Thr Thr Asn Ala Thr Cys Gly Glu Lys Gly Pro Glu
        50              55              60
```

```
Met Tyr Cys Lys Leu Val Glu His Val Pro Gly Gln Pro Val Arg Asn
 65                  70                  75                  80

Pro Gln Cys Arg Ile Cys Asn Gln Asn Ser Asn Pro Asn Gln Arg
                 85                  90                  95

His Pro Ile Thr Asn Ala Ile Asp Gly Lys Asn Thr Trp Trp Gln Ser
                100                 105                 110

Pro Ser Ile Lys Asn Gly Ile Glu Tyr His Tyr Val Thr Ile Thr Leu
                115                 120                 125

Asp Leu Gln Gln Val Phe Gln Ile Ala Tyr Val Ile Val Lys Ala Ala
            130                 135                 140

Asn Ser Pro Arg Pro Gly Asn Trp Ile Leu Glu Arg Ser Leu Asp Asp
145                 150                 155                 160

Val Glu Tyr Lys Pro Trp Gln Tyr His Ala Val Thr Asp Thr Glu Cys
                165                 170                 175

Leu Thr Leu Tyr Asn Ile Tyr Pro Arg Thr Gly Pro Pro Ser Tyr Ala
                180                 185                 190

Lys Asp Asp Glu Val Ile Cys Thr Ser Phe Tyr Ser Lys Ile His Pro
            195                 200                 205

Leu Glu Asn Gly Glu Ile His Ile Ser Leu Ile Asn Gly Arg Pro Ser
210                 215                 220

Ala Asp Asp Pro Ser Pro Glu Leu Leu Glu Phe Thr Ser Ala Arg Tyr
225                 230                 235                 240

Ile Arg Leu Arg Phe Gln Arg Ile Arg Thr Leu Asn Ala Asp Leu Met
                245                 250                 255

Met Phe Ala His Lys Asp Pro Arg Glu Ile Asp Pro Ile Val Thr Arg
                260                 265                 270

Arg Tyr Tyr Tyr Ser Val Lys Asp Ile Ser Val Gly Gly Met Cys Ile
                275                 280                 285

Cys Tyr Gly His Ala Arg Ala Cys Pro Leu Asp Pro Ala Thr Asn Lys
            290                 295                 300

Ser Arg Cys Glu Cys Glu His Asn Thr Cys Gly Asp Ser Cys Asp Gln
305                 310                 315                 320

Cys Cys Pro Gly Phe His Gln Lys Pro Trp Arg Ala Gly Thr Phe Leu
                325                 330                 335

Thr Lys Thr Glu Cys Glu Ala Cys Asn Cys His Gly Lys Ala Glu Glu
                340                 345                 350

Cys Tyr Tyr Asp Glu Asn Val Ala Arg Arg Asn Leu Ser Leu Asn Ile
            355                 360                 365

Arg Gly Lys Tyr Ile Gly Gly Val Cys Ile Asn Cys Thr Gln Asn
            370                 375                 380

Thr Ala Gly Ile Asn Cys Glu Thr Cys Thr Asp Gly Phe Phe Arg Pro
385                 390                 395                 400

Lys Gly Val Ser Pro Asn Tyr Pro Arg Pro Cys Gln Pro Cys His Cys
                405                 410                 415

Asp Pro Ile Gly Ser Leu Asn Glu Val Cys Val Lys Asp Glu Lys His
            420                 425                 430

Ala Arg Arg Gly Leu Ala Pro Gly Ser Cys His Cys Lys Thr Gly Phe
            435                 440                 445

Gly Gly Val Ser Cys Asp Arg Cys Ala Arg Gly Tyr Thr Gly Tyr Pro
        450                 455                 460

Asp Cys Lys Ala Cys Asn Cys Ser Gly Leu Gly Ser Lys Asn Glu Asp
465                 470                 475                 480
```

```
Pro Cys Phe Gly Pro Cys Ile Cys Lys Glu Asn Val Glu Gly Gly Asp
                485                 490                 495
Cys Ser Arg Cys Lys Ser Gly Phe Phe Asn Leu Gln Glu Asp Asn Trp
            500                 505                 510
Lys Gly Cys Asp Glu Cys Phe Cys Ser Gly Val Ser Asn Arg Cys Gln
        515                 520                 525
Ser Ser Tyr Trp Thr Tyr Gly Lys Ile Gln Asp Met Ser Gly Trp Tyr
    530                 535                 540
Leu Thr Asp Leu Pro Gly Arg Ile Arg Val Ala Pro Gln Gln Asp Asp
545                 550                 555                 560
Leu Asp Ser Pro Gln Gln Ile Ser Ile Ser Asn Ala Glu Ala Arg Gln
                565                 570                 575
Ala Leu Pro His Ser Tyr Tyr Trp Ser Ala Pro Ala Pro Tyr Leu Gly
            580                 585                 590
Asn Lys Leu Pro Ala Val Gly Gly Gln Leu Thr Phe Thr Ile Ser Tyr
        595                 600                 605
Asp Leu Glu Glu Glu Glu Asp Thr Glu Arg Val Leu Gln Leu Met
    610                 615                 620
Ile Ile Leu Glu Gly Asn Asp Leu Ser Ile Ser Thr Ala Gln Asp Glu
625                 630                 635                 640
Val Tyr Leu His Pro Ser Glu His Thr Asn Val Leu Leu Leu Lys
                645                 650                 655
Glu Glu Ser Phe Thr Ile His Gly Thr His Phe Pro Val Arg Arg Lys
            660                 665                 670
Glu Phe Met Thr Val Leu Ala Asn Leu Lys Arg Val Leu Leu Gln Ile
        675                 680                 685
Thr Tyr Ser Phe Gly Met Asp Ala Ile Phe Arg Leu Ser Ser Val Asn
    690                 695                 700
Leu Glu Ser Ala Val Ser Tyr Pro Thr Asp Gly Ser Ile Ala Ala Ala
705                 710                 715                 720
Val Glu Val Cys Gln Cys Pro Pro Gly Tyr Thr Gly Ser Ser Cys Glu
                725                 730                 735
Ser Cys Trp Pro Arg His Arg Arg Val Asn Gly Thr Ile Phe Gly Gly
            740                 745                 750
Ile Cys Glu Pro Cys Gln Cys Phe Gly His Ala Glu Ser Cys Asp Asp
        755                 760                 765
Val Thr Gly Glu Cys Leu Asn Cys Lys Asp His Thr Gly Gly Pro Tyr
    770                 775                 780
Cys Asp Lys Cys Leu Pro Gly Phe Tyr Gly Glu Pro Thr Lys Gly Thr
785                 790                 795                 800
Ser Glu Asp Cys Gln Pro Cys Ala Cys Pro Leu Asn Ile Pro Ser Asn
                805                 810                 815
Asn Phe Ser Pro Thr Cys His Leu Asp Arg Ser Leu Gly Leu Ile Cys
            820                 825                 830
Asp Gly Cys Pro Val Gly Tyr Thr Gly Pro Arg Cys Glu Arg Cys Ala
        835                 840                 845
Glu Gly Tyr Phe Gly Gln Pro Ser Val Pro Gly Gly Ser Cys Gln Pro
    850                 855                 860
Cys Gln Cys Asn Asp Asn Leu Asp Phe Ser Ile Pro Gly Ser Cys Asp
865                 870                 875                 880
Ser Leu Ser Gly Ser Cys Leu Ile Cys Lys Pro Gly Thr Thr Gly Arg
                885                 890                 895
Tyr Cys Glu Leu Cys Ala Asp Gly Tyr Phe Gly Asp Ala Val Asp Ala
```

-continued

```
                900              905              910
Lys Asn Cys Gln Pro Cys Arg Cys Asn Ala Gly Gly Ser Phe Ser Glu
            915              920              925

Val Cys His Ser Gln Thr Gly Gln Cys Glu Cys Arg Ala Asn Val Gln
        930              935              940

Gly Gln Arg Cys Asp Lys Cys Lys Ala Gly Thr Phe Gly Leu Gln Ser
945              950              955              960

Ala Arg Gly Cys Val Pro Cys Asn Cys Asn Ser Phe Gly Ser Lys Ser
                965              970              975

Phe Asp Cys Glu Glu Ser Gly Gln Cys Trp Cys Gln Pro Gly Val Thr
            980              985              990

Gly Lys Lys Cys Asp Arg Cys Ala His Gly Tyr Phe Asn Phe Gln Glu
        995              1000             1005

Gly Gly Cys Thr Ala Cys Glu Cys Ser His Leu Gly Asn Asn Cys
    1010             1015             1020

Asp Pro Lys Thr Gly Arg Cys Ile Cys Pro Pro Asn Thr Ile Gly
    1025             1030             1035

Glu Lys Cys Ser Lys Cys Ala Pro Asn Thr Trp Gly His Ser Ile
    1040             1045             1050

Thr Thr Gly Cys Lys Ala Cys Asn Cys Ser Thr Val Gly Ser Leu
    1055             1060             1065

Asp Phe Gln Cys Asn Val Asn Thr Gly Gln Cys Asn Cys His Pro
    1070             1075             1080

Lys Phe Ser Gly Ala Lys Cys Thr Glu Cys Ser Arg Gly His Trp
    1085             1090             1095

Asn Tyr Pro Arg Cys Asn Leu Cys Asp Cys Phe Leu Pro Gly Thr
    1100             1105             1110

Asp Ala Thr Thr Cys Asp Ser Glu Thr Lys Lys Cys Ser Cys Ser
    1115             1120             1125

Asp Gln Thr Gly Gln Cys Thr Cys Lys Val Asn Val Glu Gly Ile
    1130             1135             1140

His Cys Asp Arg Cys Arg Pro Gly Lys Phe Gly Leu Asp Ala Lys
    1145             1150             1155

Asn Pro Leu Gly Cys Ser Ser Cys Tyr Cys Phe Gly Thr Thr Thr
    1160             1165             1170

Gln Cys Ser Glu Ala Lys Gly Leu Ile Arg Thr Trp Val Thr Leu
    1175             1180             1185

Lys Ala Glu Gln Thr Ile Leu Pro Leu Val Asp Glu Ala Leu Gln
    1190             1195             1200

His Thr Thr Thr Lys Gly Ile Val Phe Gln His Pro Glu Ile Val
    1205             1210             1215

Ala His Met Asp Leu Met Arg Glu Asp Leu His Leu Glu Pro Phe
    1220             1225             1230

Tyr Trp Lys Leu Pro Glu Gln Phe Glu Gly Lys Lys Leu Met Ala
    1235             1240             1245

Tyr Gly Gly Lys Leu Lys Tyr Ala Ile Tyr Phe Glu Ala Arg Glu
    1250             1255             1260

Glu Thr Gly Phe Ser Thr Tyr Asn Pro Gln Val Ile Ile Arg Gly
    1265             1270             1275

Gly Thr Pro Thr His Ala Arg Ile Ile Val Arg His Met Ala Ala
    1280             1285             1290

Pro Leu Ile Gly Gln Leu Thr Arg His Glu Ile Glu Met Thr Glu
    1295             1300             1305
```

```
Lys Glu Trp Lys Tyr Tyr Gly Asp Asp Pro Arg Val His Arg Thr
        1310                1315                1320

Val Thr Arg Glu Asp Phe Leu Asp Ile Leu Tyr Asp Ile His Tyr
    1325                1330                1335

Ile Leu Ile Lys Ala Thr Tyr Gly Asn Phe Met Arg Gln Ser Arg
    1340                1345                1350

Ile Ser Glu Ile Ser Met Glu Val Ala Glu Gln Gly Arg Gly Thr
    1355                1360                1365

Thr Met Thr Pro Pro Ala Asp Leu Ile Glu Lys Cys Asp Cys Pro
1370                1375                1380

Leu Gly Tyr Ser Gly Leu Ser Cys Glu Ala Cys Leu Pro Gly Phe
    1385                1390                1395

Tyr Arg Leu Arg Ser Gln Pro Gly Gly Arg Thr Pro Gly Pro Thr
    1400                1405                1410

Leu Gly Thr Cys Val Pro Cys Gln Cys Asn Gly His Ser Ser Leu
    1415                1420                1425

Cys Asp Pro Glu Thr Ser Ile Cys Gln Asn Cys Gln His His Thr
    1430                1435                1440

Ala Gly Asp Phe Cys Glu Arg Cys Ala Leu Gly Tyr Tyr Gly Ile
    1445                1450                1455

Val Lys Gly Leu Pro Asn Asp Cys Gln Gln Cys Ala Cys Pro Leu
    1460                1465                1470

Ile Ser Ser Ser Asn Asn Phe Ser Pro Ser Cys Val Ala Glu Gly
    1475                1480                1485

Leu Asp Asp Tyr Arg Cys Thr Ala Cys Pro Arg Gly Tyr Glu Gly
    1490                1495                1500

Gln Tyr Cys Glu Arg Cys Ala Pro Gly Tyr Thr Gly Ser Pro Gly
    1505                1510                1515

Asn Pro Gly Gly Ser Cys Gln Glu Cys Glu Cys Asp Pro Tyr Gly
    1520                1525                1530

Ser Leu Pro Val Pro Cys Asp Pro Val Thr Gly Phe Cys Thr Cys
    1535                1540                1545

Arg Pro Gly Ala Thr Gly Arg Lys Cys Asp Gly Cys Lys His Trp
    1550                1555                1560

His Ala Arg Glu Gly Trp Glu Cys Val Phe Cys Gly Asp Glu Cys
    1565                1570                1575

Thr Gly Leu Leu Leu Gly Asp Leu Ala Arg Leu Glu Gln Met Val
    1580                1585                1590

Met Ser Ile Asn Leu Thr Gly Pro Leu Pro Ala Pro Tyr Lys Met
    1595                1600                1605

Leu Tyr Gly Leu Glu Asn Met Thr Gln Glu Leu Lys His Leu Leu
    1610                1615                1620

Ser Pro Gln Arg Ala Pro Glu Arg Leu Ile Gln Leu Ala Glu Gly
    1625                1630                1635

Asn Leu Asn Thr Leu Val Thr Glu Met Asn Glu Leu Leu Thr Arg
    1640                1645                1650

Ala Thr Lys Val Thr Ala Asp Gly Glu Gln Thr Gly Gln Asp Ala
    1655                1660                1665

Glu Arg Thr Asn Thr Arg Ala Lys Ser Leu Gly Glu Phe Ile Lys
    1670                1675                1680

Glu Leu Ala Arg Asp Ala Glu Ala Val Asn Glu Lys Ala Ile Lys
    1685                1690                1695
```

```
Leu Asn Glu Thr Leu Gly Thr Arg Asp Glu Ala Phe Glu Arg Asn
    1700            1705                1710
Leu Glu Gly Leu Gln Lys Glu Ile Asp Gln Met Ile Lys Glu Leu
    1715            1720                1725
Arg Arg Lys Asn Leu Glu Thr Gln Lys Glu Ile Ala Glu Asp Glu
    1730            1735                1740
Leu Val Ala Ala Glu Ala Leu Leu Lys Lys Val Lys Lys Leu Phe
    1745            1750                1755
Gly Glu Ser Arg Gly Glu Asn Glu Glu Met Glu Lys Asp Leu Arg
    1760            1765                1770
Glu Lys Leu Ala Asp Tyr Lys Asn Lys Val Asp Asp Ala Trp Asp
    1775            1780                1785
Leu Leu Arg Glu Ala Thr Asp Lys Ile Arg Glu Ala Asn Arg Leu
    1790            1795                1800
Phe Ala Val Asn Gln Lys Asn Met Thr Ala Leu Glu Lys Lys Lys
    1805            1810                1815
Glu Ala Val Glu Ser Gly Lys Arg Gln Ile Glu Asn Thr Leu Lys
    1820            1825                1830
Glu Gly Asn Asp Ile Leu Asp Glu Ala Asn Arg Leu Ala Asp Glu
    1835            1840                1845
Ile Asn Ser Ile Ile Asp Tyr Val Glu Asp Ile Gln Thr Lys Leu
    1850            1855                1860
Pro Pro Met Ser Glu Glu Leu Asn Asp Lys Ile Asp Asp Leu Ser
    1865            1870                1875
Gln Glu Ile Lys Asp Arg Lys Leu Ala Glu Lys Val Ser Gln Ala
    1880            1885                1890
Glu Ser His Ala Ala Gln Leu Asn Asp Ser Ser Ala Val Leu Asp
    1895            1900                1905
Gly Ile Leu Asp Glu Ala Lys Asn Ile Ser Phe Asn Ala Thr Ala
    1910            1915                1920
Ala Phe Lys Ala Tyr Ser Asn Ile Lys Asp Tyr Ile Asp Glu Ala
    1925            1930                1935
Glu Lys Val Ala Lys Glu Ala Lys Asp Leu Ala His Glu Ala Thr
    1940            1945                1950
Lys Leu Ala Thr Gly Pro Arg Gly Leu Leu Lys Glu Asp Ala Lys
    1955            1960                1965
Gly Cys Leu Gln Lys Ser Phe Arg Ile Leu Asn Glu Ala Lys Lys
    1970            1975                1980
Leu Ala Asn Asp Val Lys Glu Asn Glu Asp His Leu Asn Gly Leu
    1985            1990                1995
Lys Thr Arg Ile Glu Asn Ala Asp Ala Arg Asn Gly Asp Leu Leu
    2000            2005                2010
Arg Thr Leu Asn Asp Thr Leu Gly Lys Leu Ser Ala Ile Pro Asn
    2015            2020                2025
Asp Thr Ala Ala Lys Leu Gln Ala Val Lys Asp Lys Ala Arg Gln
    2030            2035                2040
Ala Asn Asp Thr Ala Lys Asp Val Leu Ala Gln Ile Thr Glu Leu
    2045            2050                2055
His Gln Asn Leu Asp Gly Leu Lys Lys Asn Tyr Asn Lys Leu Ala
    2060            2065                2070
Asp Ser Val Ala Lys Thr Asn Ala Val Val Lys Asp Pro Ser Lys
    2075            2080                2085
Asn Lys Ile Ile Ala Asp Ala Asp Ala Thr Val Lys Asn Leu Glu
```

```
              2090                2095                2100
Gln Glu Ala Asp Arg Leu Ile Asp Lys Leu Lys Pro Ile Lys Glu
    2105                2110                2115
Leu Glu Asp Asn Leu Lys Lys Asn Ile Ser Glu Ile Lys Glu Leu
    2120                2125                2130
Ile Asn Gln Ala Arg Lys Gln Ala Asn Ser Ile Lys Val Ser Val
    2135                2140                2145
Ser Ser Gly Gly Asp Cys Ile Arg Thr Tyr Lys Pro Glu Ile Lys
    2150                2155                2160
Lys Gly Ser Tyr Asn Asn Ile Val Val Asn Val Lys Thr Ala Val
    2165                2170                2175
Ala Asp Asn Leu Leu Phe Tyr Leu Gly Ser Ala Lys Phe Ile Asp
    2180                2185                2190
Phe Leu Ala Ile Glu Met Arg Lys Gly Lys Val Ser Phe Leu Trp
    2195                2200                2205
Asp Val Gly Ser Gly Val Gly Arg Val Glu Tyr Pro Asp Leu Thr
    2210                2215                2220
Ile Asp Asp Ser Tyr Trp Tyr Arg Ile Val Ala Ser Arg Thr Gly
    2225                2230                2235
Arg Asn Gly Thr Ile Ser Val Arg Ala Leu Asp Gly Pro Lys Ala
    2240                2245                2250
Ser Ile Val Pro Ser Thr His His Ser Thr Ser Pro Pro Gly Tyr
    2255                2260                2265
Thr Ile Leu Asp Val Asp Ala Asn Ala Met Leu Phe Val Gly Gly
    2270                2275                2280
Leu Thr Gly Lys Leu Lys Lys Ala Asp Ala Val Arg Val Ile Thr
    2285                2290                2295
Phe Thr Gly Cys Met Gly Glu Thr Tyr Phe Asp Asn Lys Pro Ile
    2300                2305                2310
Gly Leu Trp Asn Phe Arg Glu Lys Glu Gly Asp Cys Lys Gly Cys
    2315                2320                2325
Thr Val Ser Pro Gln Val Glu Asp Ser Glu Gly Thr Ile Gln Phe
    2330                2335                2340
Asp Gly Glu Gly Tyr Ala Leu Val Ser Arg Pro Ile Arg Trp Tyr
    2345                2350                2355
Pro Asn Ile Ser Thr Val Met Phe Lys Phe Arg Thr Phe Ser Ser
    2360                2365                2370
Ser Ala Leu Leu Met Tyr Leu Ala Thr Arg Asp Leu Arg Asp Phe
    2375                2380                2385
Met Ser Val Glu Leu Thr Asp Gly His Ile Lys Val Ser Tyr Asp
    2390                2395                2400
Leu Gly Ser Gly Met Ala Ser Val Val Ser Asn Gln Asn His Asn
    2405                2410                2415
Asp Gly Lys Trp Lys Ser Phe Thr Leu Ser Arg Ile Gln Lys Gln
    2420                2425                2430
Ala Asn Ile Ser Ile Val Asp Ile Asp Thr Asn Gln Glu Glu Asn
    2435                2440                2445
Ile Ala Thr Ser Ser Ser Gly Asn Asn Phe Gly Leu Asp Leu Lys
    2450                2455                2460
Ala Asp Asp Lys Ile Tyr Phe Gly Gly Leu Pro Thr Leu Arg Asn
    2465                2470                2475
Leu Arg Pro Glu Val Asn Leu Lys Lys Tyr Ser Gly Cys Leu Lys
    2480                2485                2490
```

-continued

```
Asp Ile Glu Ile Ser Arg Thr Pro Tyr Asn Ile Leu Ser Ser Pro
2495                2500                2505

Asp Tyr Val Gly Val Thr Lys Gly Cys Ser Leu Glu Asn Val Tyr
2510                2515                2520

Thr Val Ser Phe Pro Lys Pro Gly Phe Val Glu Leu Ser Pro Val
2525                2530                2535

Pro Ile Asp Val Gly Thr Glu Ile Asn Leu Ser Phe Ser Thr Lys
2540                2545                2550

Asn Glu Ser Gly Ile Ile Leu Leu Gly Ser Gly Gly Thr Pro Ala
2555                2560                2565

Pro Pro Arg Arg Lys Arg Arg Gln Thr Gly Gln Ala Tyr Tyr Val
2570                2575                2580

Ile Leu Leu Asn Arg Gly Arg Leu Glu Val His Leu Ser Thr Gly
2585                2590                2595

Ala Arg Thr Met Arg Lys Ile Val Ile Arg Pro Glu Pro Asn Leu
2600                2605                2610

Phe His Asp Gly Arg Glu His Ser Val His Val Glu Arg Thr Arg
2615                2620                2625

Gly Ile Phe Thr Val Gln Val Asp Glu Asn Arg Arg Tyr Met Gln
2630                2635                2640

Asn Leu Thr Val Glu Gln Pro Ile Glu Val Lys Lys Leu Phe Val
2645                2650                2655

Gly Gly Ala Pro Pro Glu Phe Gln Pro Ser Pro Leu Arg Asn Ile
2660                2665                2670

Pro Pro Phe Glu Gly Cys Ile Trp Asn Leu Val Ile Asn Ser Val
2675                2680                2685

Pro Met Asp Phe Ala Arg Pro Val Ser Phe Lys Asn Ala Asp Ile
2690                2695                2700

Gly Arg Cys Ala His Gln Lys Leu Arg Glu Asp Glu Asp Gly Ala
2705                2710                2715

Ala Pro Ala Glu Ile Val Ile Gln Pro Glu Pro Val Pro Thr Pro
2720                2725                2730

Ala Phe Pro Thr Pro Thr Pro Val Leu Thr His Gly Pro Cys Ala
2735                2740                2745

Ala Glu Ser Glu Pro Ala Leu Leu Ile Gly Ser Lys Gln Phe Gly
2750                2755                2760

Leu Ser Arg Asn Ser His Ile Ala Ile Ala Phe Asp Asp Thr Lys
2765                2770                2775

Val Lys Asn Arg Leu Thr Ile Glu Leu Glu Val Arg Thr Glu Ala
2780                2785                2790

Glu Ser Gly Leu Leu Phe Tyr Met Ala Arg Ile Asn His Ala Asp
2795                2800                2805

Phe Ala Thr Val Gln Leu Arg Asn Gly Leu Pro Tyr Phe Ser Tyr
2810                2815                2820

Asp Leu Gly Ser Gly Asp Thr His Thr Met Ile Pro Thr Lys Ile
2825                2830                2835

Asn Asp Gly Gln Trp His Lys Ile Lys Ile Met Arg Ser Lys Gln
2840                2845                2850

Glu Gly Ile Leu Tyr Val Asp Gly Ala Ser Asn Arg Thr Ile Ser
2855                2860                2865

Pro Lys Lys Ala Asp Ile Leu Asp Val Val Gly Met Leu Tyr Val
2870                2875                2880
```

Gly Gly Leu Pro Ile Asn Tyr Thr Thr Arg Arg Ile Gly Pro Val
            2885                2890                2895

Thr Tyr Ser Ile Asp Gly Cys Val Arg Asn Leu His Met Ala Glu
    2900                2905                2910

Ala Pro Ala Asp Leu Glu Gln Pro Thr Ser Ser Phe His Val Gly
    2915                2920                2925

Thr Cys Phe Ala Asn Ala Gln Arg Gly Thr Tyr Phe Asp Gly Thr
    2930                2935                2940

Gly Phe Ala Lys Ala Val Gly Gly Phe Lys Val Gly Leu Asp Leu
    2945                2950                2955

Leu Val Glu Phe Glu Phe Arg Thr Thr Thr Thr Thr Gly Val Leu
    2960                2965                2970

Leu Gly Ile Ser Ser Gln Lys Met Asp Gly Met Gly Ile Glu Met
    2975                2980                2985

Ile Asp Glu Lys Leu Met Phe His Val Asp Asn Gly Ala Gly Arg
    2990                2995                3000

Phe Thr Ala Val Tyr Asp Ala Gly Val Pro Gly His Leu Cys Asp
    3005                3010                3015

Gly Gln Trp His Lys Val Thr Ala Asn Lys Ile Lys His Arg Ile
    3020                3025                3030

Glu Leu Thr Val Asp Gly Asn Gln Val Glu Ala Gln Ser Pro Asn
    3035                3040                3045

Pro Ala Ser Thr Ser Ala Asp Thr Asn Asp Pro Val Phe Val Gly
    3050                3055                3060

Gly Phe Pro Asp Asp Leu Lys Gln Phe Gly Leu Thr Thr Ser Ile
    3065                3070                3075

Pro Phe Arg Gly Cys Ile Arg Ser Leu Lys Leu Thr Lys Gly Thr
    3080                3085                3090

Gly Lys Pro Leu Glu Val Asn Phe Ala Lys Ala Leu Glu Leu Arg
    3095                3100                3105

Gly Val Gln Pro Val Ser Cys Pro Ala Asn
    3110                3115

<210> SEQ ID NO 28
<211> LENGTH: 3333
<212> TYPE: PRT
<213> ORGANISM: Homo sapiens

<400> SEQUENCE: 28

Met Ala Ala Ala Arg Pro Arg Gly Arg Ala Leu Gly Pro Val Leu
1               5                   10                  15

Pro Pro Thr Pro Leu Leu Leu Val Leu Arg Val Leu Pro Ala Cys
                20                  25                  30

Gly Ala Thr Ala Arg Asp Pro Gly Ala Ala Gly Leu Ser Leu His
                35                  40                  45

Pro Thr Tyr Phe Asn Leu Ala Glu Ala Ala Arg Ile Trp Ala Thr Ala
                50                  55                  60

Thr Cys Gly Glu Arg Gly Pro Gly Glu Gly Arg Pro Gln Pro Glu Leu
65                  70                  75                  80

Tyr Cys Lys Leu Val Gly Gly Pro Thr Ala Pro Gly Ser Gly His Thr
                85                  90                  95

Ile Gln Gly Gln Phe Cys Asp Tyr Cys Asn Ser Glu Asp Pro Arg Lys
                100                 105                 110

Ala His Pro Val Thr Asn Ala Ile Asp Gly Ser Glu Arg Trp Trp Gln
                115                 120                 125

Ser Pro Pro Leu Ser Ser Gly Thr Gln Tyr Asn Arg Val Asn Leu Thr
130                 135                 140

Leu Asp Leu Gly Gln Leu Phe His Val Ala Tyr Ile Leu Ile Lys Phe
145                 150                 155                 160

Ala Asn Ser Pro Arg Pro Asp Leu Trp Val Leu Glu Arg Ser Val Asp
            165                 170                 175

Phe Gly Ser Thr Tyr Ser Pro Trp Gln Tyr Phe Ala His Ser Lys Val
            180                 185                 190

Asp Cys Leu Lys Glu Phe Gly Arg Glu Ala Asn Met Ala Val Thr Arg
            195                 200                 205

Asp Asp Asp Val Leu Cys Val Thr Glu Tyr Ser Arg Ile Val Pro Leu
210                 215                 220

Glu Asn Gly Glu Val Val Val Ser Leu Ile Asn Gly Arg Pro Gly Ala
225                 230                 235                 240

Lys Asn Phe Thr Phe Ser His Thr Leu Arg Glu Phe Thr Lys Ala Thr
            245                 250                 255

Asn Ile Arg Leu Arg Phe Leu Arg Thr Asn Thr Leu Leu Gly His Leu
            260                 265                 270

Ile Ser Lys Ala Gln Arg Asp Pro Thr Val Thr Arg Arg Tyr Tyr Tyr
            275                 280                 285

Ser Ile Lys Asp Ile Ser Ile Gly Gly Gln Cys Val Cys Asn Gly His
            290                 295                 300

Ala Glu Val Cys Asn Ile Asn Asn Pro Glu Lys Leu Phe Arg Cys Glu
305                 310                 315                 320

Cys Gln His His Thr Cys Gly Glu Thr Cys Asp Arg Cys Cys Thr Gly
            325                 330                 335

Tyr Asn Gln Arg Arg Trp Arg Pro Ala Ala Trp Glu Gln Ser His Glu
            340                 345                 350

Cys Glu Ala Cys Asn Cys His Gly His Ala Ser Asn Cys Tyr Tyr Asp
            355                 360                 365

Pro Asp Val Glu Arg Gln Gln Ala Ser Leu Asn Thr Gln Gly Ile Tyr
            370                 375                 380

Ala Gly Gly Gly Val Cys Ile Asn Cys Gln His Asn Thr Ala Gly Val
385                 390                 395                 400

Asn Cys Glu Gln Cys Ala Lys Gly Tyr Tyr Arg Pro Tyr Gly Val Pro
            405                 410                 415

Val Asp Ala Pro Asp Gly Cys Ile Pro Cys Ser Cys Asp Pro Glu His
            420                 425                 430

Ala Asp Gly Cys Glu Gln Gly Ser Gly Arg Cys His Cys Lys Pro Asn
            435                 440                 445

Phe His Gly Asp Asn Cys Glu Lys Cys Ala Ile Gly Tyr Tyr Asn Phe
450                 455                 460

Pro Phe Cys Leu Arg Ile Pro Ile Phe Pro Val Ser Thr Pro Ser Ser
465                 470                 475                 480

Glu Asp Pro Val Ala Gly Asp Ile Lys Gly Cys Asp Cys Asn Leu Glu
            485                 490                 495

Gly Val Leu Pro Glu Ile Cys Asp Ala His Gly Arg Cys Leu Cys Arg
            500                 505                 510

Pro Gly Val Glu Gly Pro Arg Cys Asp Thr Cys Arg Ser Gly Phe Tyr
            515                 520                 525

Ser Phe Pro Ile Cys Gln Ala Cys Trp Cys Ser Ala Leu Gly Ser Tyr
530                 535                 540

```
Gln Met Pro Cys Ser Ser Val Thr Gly Gln Cys Glu Cys Arg Pro Gly
545                 550                 555                 560

Val Thr Gly Gln Arg Cys Asp Arg Cys Leu Ser Gly Ala Tyr Asp Phe
            565                 570                 575

Pro His Cys Gln Gly Ser Ser Ala Cys Asp Pro Ala Gly Thr Ile
            580                 585                 590

Asn Ser Asn Leu Gly Tyr Cys Gln Cys Lys Leu His Val Glu Gly Pro
    595                 600                 605

Thr Cys Ser Arg Cys Lys Leu Leu Tyr Trp Asn Leu Asp Lys Glu Asn
610                 615                 620

Pro Ser Gly Cys Ser Glu Cys Lys Cys His Lys Ala Gly Thr Val Ser
625                 630                 635                 640

Gly Thr Gly Glu Cys Arg Gln Gly Asp Gly Asp Cys His Cys Lys Ser
            645                 650                 655

His Val Gly Gly Asp Ser Cys Asp Thr Cys Glu Asp Gly Tyr Phe Ala
            660                 665                 670

Leu Glu Lys Ser Asn Tyr Phe Gly Cys Gln Gly Cys Gln Cys Asp Ile
    675                 680                 685

Gly Gly Ala Leu Ser Ser Met Cys Ser Gly Pro Ser Gly Val Cys Gln
690                 695                 700

Cys Arg Glu His Val Val Gly Lys Val Cys Gln Arg Pro Glu Asn Asn
705                 710                 715                 720

Tyr Tyr Phe Pro Asp Leu His His Met Lys Tyr Glu Ile Glu Asp Gly
            725                 730                 735

Ser Thr Pro Asn Gly Arg Asp Leu Arg Phe Gly Phe Asp Pro Leu Ala
            740                 745                 750

Phe Pro Glu Phe Ser Trp Arg Gly Tyr Ala Gln Met Thr Ser Val Gln
    755                 760                 765

Asn Asp Val Arg Ile Thr Leu Asn Val Gly Lys Ser Ser Gly Ser Leu
770                 775                 780

Phe Arg Val Ile Leu Arg Tyr Val Asn Pro Gly Thr Glu Ala Val Ser
785                 790                 795                 800

Gly His Ile Thr Ile Tyr Pro Ser Trp Gly Ala Ala Gln Ser Lys Glu
            805                 810                 815

Ile Ile Phe Leu Pro Ser Lys Glu Pro Ala Phe Val Thr Val Pro Gly
            820                 825                 830

Asn Gly Phe Ala Asp Pro Phe Ser Ile Thr Pro Gly Ile Trp Val Ala
    835                 840                 845

Cys Ile Lys Ala Glu Gly Val Leu Leu Asp Tyr Leu Val Leu Leu Pro
850                 855                 860

Arg Asp Tyr Tyr Glu Ala Ser Val Leu Gln Leu Pro Val Thr Glu Pro
865                 870                 875                 880

Cys Ala Tyr Ala Gly Pro Pro Gln Glu Asn Cys Leu Leu Tyr Gln His
            885                 890                 895

Leu Pro Val Thr Arg Phe Pro Cys Thr Leu Ala Cys Glu Ala Arg His
            900                 905                 910

Phe Leu Leu Asp Gly Glu Pro Arg Pro Val Ala Val Arg Gln Pro Thr
    915                 920                 925

Pro Ala His Pro Val Met Val Asp Leu Ser Gly Arg Glu Val Glu Leu
            930                 935                 940

His Leu Arg Leu Arg Ile Pro Gln Val Gly His Tyr Val Val Val
945                 950                 955                 960

Glu Tyr Ser Thr Glu Ala Ala Gln Leu Phe Val Val Asp Val Asn Val
```

-continued

```
            965                 970                 975
Lys Ser Ser Gly Ser Val Leu Ala Gly Gln Val Asn Ile Tyr Ser Cys
            980                 985                 990
Asn Tyr Ser Val Leu Cys Arg Ser Ala Val Ile Asp His Met Ser Arg
            995                1000                1005
Ile Ala Met Tyr Glu Leu Leu Ala Asp Ala Asp Ile Gln Leu Lys
   1010                1015                1020
Gly His Met Ala Arg Phe Leu Leu His Gln Val Cys Ile Ile Pro
   1025                1030                1035
Ile Glu Glu Phe Ser Ala Glu Tyr Val Arg Pro Gln Val His Cys
   1040                1045                1050
Ile Ala Ser Tyr Gly Arg Phe Val Asn Gln Ser Ala Thr Cys Val
   1055                1060                1065
Ser Leu Ala His Glu Thr Pro Pro Thr Ala Leu Ile Leu Asp Val
   1070                1075                1080
Leu Ser Gly Arg Pro Phe Pro His Leu Pro Gln Gln Ser Ser Pro
   1085                1090                1095
Ser Val Asp Val Leu Pro Gly Val Thr Leu Lys Ala Pro Gln Asn
   1100                1105                1110
Gln Val Thr Leu Arg Gly Arg Val Pro His Leu Gly Arg Tyr Val
   1115                1120                1125
Phe Val Ile His Phe Tyr Gln Ala Ala His Pro Thr Phe Pro Ala
   1130                1135                1140
Gln Val Ser Val Asp Gly Gly Trp Pro Arg Ala Gly Ser Phe His
   1145                1150                1155
Ala Ser Phe Cys Pro His Val Leu Gly Cys Arg Asp Gln Val Ile
   1160                1165                1170
Ala Glu Gly Gln Ile Glu Phe Asp Ile Ser Glu Pro Glu Val Ala
   1175                1180                1185
Ala Thr Val Lys Val Pro Glu Gly Lys Ser Leu Val Leu Val Arg
   1190                1195                1200
Val Leu Val Val Pro Ala Glu Asn Tyr Asp Tyr Gln Ile Leu His
   1205                1210                1215
Lys Lys Ser Met Asp Lys Ser Leu Glu Phe Ile Thr Asn Cys Gly
   1220                1225                1230
Lys Asn Ser Phe Tyr Leu Asp Pro Gln Thr Ala Ser Arg Phe Cys
   1235                1240                1245
Lys Asn Ser Ala Arg Ser Leu Val Ala Phe Tyr His Lys Gly Ala
   1250                1255                1260
Leu Pro Cys Glu Cys His Pro Thr Gly Ala Thr Gly Pro His Cys
   1265                1270                1275
Ser Pro Glu Gly Gly Gln Cys Pro Cys Gln Pro Asn Val Ile Gly
   1280                1285                1290
Arg Gln Cys Thr Arg Cys Ala Thr Gly His Tyr Gly Phe Pro Arg
   1295                1300                1305
Cys Lys Pro Cys Ser Cys Gly Arg Arg Leu Cys Glu Glu Met Thr
   1310                1315                1320
Gly Gln Cys Arg Cys Pro Pro Arg Thr Val Arg Pro Gln Cys Glu
   1325                1330                1335
Val Cys Glu Thr His Ser Phe Ser Phe His Pro Met Ala Gly Cys
   1340                1345                1350
Glu Gly Cys Asn Cys Ser Arg Arg Gly Thr Ile Glu Ala Ala Met
   1355                1360                1365
```

```
Pro Glu Cys Asp Arg Asp Ser Gly Gln Cys Arg Cys Lys Pro Arg
    1370            1375                1380
Ile Thr Gly Arg Gln Cys Asp Arg Cys Ala Ser Gly Phe Tyr Arg
    1385            1390                1395
Phe Pro Glu Cys Val Pro Cys Asn Cys Asn Arg Asp Gly Thr Glu
    1400            1405                1410
Pro Gly Val Cys Asp Pro Gly Thr Gly Ala Cys Leu Cys Lys Glu
    1415            1420                1425
Asn Val Glu Gly Thr Glu Cys Asn Val Cys Arg Glu Gly Ser Phe
    1430            1435                1440
His Leu Asp Pro Ala Asn Leu Lys Gly Cys Thr Ser Cys Phe Cys
    1445            1450                1455
Phe Gly Val Asn Asn Gln Cys His Ser Ser His Lys Arg Arg Thr
    1460            1465                1470
Lys Phe Val Asp Met Leu Gly Trp His Leu Glu Thr Ala Asp Arg
    1475            1480                1485
Val Asp Ile Pro Val Ser Phe Asn Pro Gly Ser Asn Ser Met Val
    1490            1495                1500
Ala Asp Leu Gln Glu Leu Pro Ala Thr Ile His Ser Ala Ser Trp
    1505            1510                1515
Val Ala Pro Thr Ser Tyr Leu Gly Asp Lys Val Ser Ser Tyr Gly
    1520            1525                1530
Gly Tyr Leu Thr Tyr Gln Ala Lys Ser Phe Gly Leu Pro Gly Asp
    1535            1540                1545
Met Val Leu Leu Glu Lys Lys Pro Asp Val Gln Leu Thr Gly Gln
    1550            1555                1560
His Met Ser Ile Ile Tyr Glu Glu Thr Asn Thr Pro Arg Pro Asp
    1565            1570                1575
Arg Leu His His Gly Arg Val His Val Val Glu Gly Asn Phe Arg
    1580            1585                1590
His Ala Ser Ser Arg Ala Pro Val Ser Arg Glu Glu Leu Met Thr
    1595            1600                1605
Val Leu Ser Arg Leu Ala Asp Val Arg Ile Gln Gly Leu Tyr Phe
    1610            1615                1620
Thr Glu Thr Gln Arg Leu Thr Leu Ser Glu Val Gly Leu Glu Glu
    1625            1630                1635
Ala Ser Asp Thr Gly Ser Gly Arg Ile Ala Leu Ala Val Glu Ile
    1640            1645                1650
Cys Ala Cys Pro Pro Ala Tyr Ala Gly Asp Ser Cys Gln Gly Cys
    1655            1660                1665
Ser Pro Gly Tyr Tyr Arg Asp His Lys Gly Leu Tyr Thr Gly Arg
    1670            1675                1680
Cys Val Pro Cys Asn Cys Asn Gly His Ser Asn Gln Cys Gln Asp
    1685            1690                1695
Gly Ser Gly Ile Cys Val Asn Cys Gln His Asn Thr Ala Gly Glu
    1700            1705                1710
His Cys Glu Arg Cys Gln Glu Gly Tyr Tyr Gly Asn Ala Val His
    1715            1720                1725
Gly Ser Cys Arg Ala Cys Pro Cys Pro His Thr Asn Ser Phe Ala
    1730            1735                1740
Thr Gly Cys Val Val Asn Gly Gly Asp Val Arg Cys Ser Cys Lys
    1745            1750                1755
```

```
Ala Gly Tyr Thr Gly Thr Gln Cys Glu Arg Cys Ala Pro Gly Tyr
    1760                1765                1770

Phe Gly Asn Pro Gln Lys Phe Gly Gly Ser Cys Gln Pro Cys Ser
    1775                1780                1785

Cys Asn Ser Asn Gly Gln Leu Gly Ser Cys His Pro Leu Thr Gly
    1790                1795                1800

Asp Cys Ile Asn Gln Glu Pro Lys Asp Ser Ser Pro Ala Glu Glu
    1805                1810                1815

Cys Asp Asp Cys Asp Ser Cys Val Met Thr Leu Leu Asn Asp Leu
    1820                1825                1830

Ala Thr Met Gly Glu Gln Leu Arg Leu Val Lys Ser Gln Leu Gln
    1835                1840                1845

Gly Leu Ser Ala Ser Ala Gly Leu Leu Glu Gln Met Arg His Met
    1850                1855                1860

Glu Thr Gln Ala Lys Asp Leu Arg Asn Gln Leu Leu Asn Tyr Arg
    1865                1870                1875

Ser Ala Ile Ser Asn His Gly Ser Lys Ile Glu Gly Leu Glu Arg
    1880                1885                1890

Glu Leu Thr Asp Leu Asn Gln Glu Phe Glu Thr Leu Gln Glu Lys
    1895                1900                1905

Ala Gln Val Asn Ser Arg Lys Ala Gln Thr Leu Asn Asn Asn Val
    1910                1915                1920

Asn Arg Ala Thr Gln Ser Ala Lys Glu Leu Asp Val Lys Ile Lys
    1925                1930                1935

Asn Val Ile Arg Asn Val His Ile Leu Leu Lys Gln Ile Ser Gly
    1940                1945                1950

Thr Asp Gly Glu Gly Asn Asn Val Pro Ser Gly Asp Phe Ser Arg
    1955                1960                1965

Glu Trp Ala Glu Ala Gln Arg Met Met Arg Glu Leu Arg Asn Arg
    1970                1975                1980

Asn Phe Gly Lys His Leu Arg Glu Ala Glu Ala Asp Lys Arg Glu
    1985                1990                1995

Ser Gln Leu Leu Leu Asn Arg Ile Arg Thr Trp Gln Lys Thr His
    2000                2005                2010

Gln Gly Glu Asn Asn Gly Leu Ala Asn Ser Ile Arg Asp Ser Leu
    2015                2020                2025

Asn Glu Tyr Glu Ala Lys Leu Ser Asp Leu Arg Ala Arg Leu Gln
    2030                2035                2040

Glu Ala Ala Ala Gln Ala Lys Gln Ala Asn Gly Leu Asn Gln Glu
    2045                2050                2055

Asn Glu Arg Ala Leu Gly Ala Ile Gln Arg Gln Val Lys Glu Ile
    2060                2065                2070

Asn Ser Leu Gln Ser Asp Phe Thr Lys Tyr Leu Thr Thr Ala Asp
    2075                2080                2085

Ser Ser Leu Leu Gln Thr Asn Ile Ala Leu Gln Leu Met Glu Lys
    2090                2095                2100

Ser Gln Lys Glu Tyr Glu Lys Leu Ala Ala Ser Leu Asn Glu Ala
    2105                2110                2115

Arg Gln Glu Leu Ser Asp Lys Val Arg Glu Leu Ser Arg Ser Ala
    2120                2125                2130

Gly Lys Thr Ser Leu Val Glu Glu Ala Glu Lys His Ala Arg Ser
    2135                2140                2145

Leu Gln Glu Leu Ala Lys Gln Leu Glu Glu Ile Lys Arg Asn Ala
```

-continued

```
                2150                2155                2160

Ser Gly Asp Glu Leu Val Arg Cys Ala Val Asp Ala Ala Thr Ala
    2165                2170                2175

Tyr Glu Asn Ile Leu Asn Ala Ile Lys Ala Ala Glu Asp Ala Ala
    2180                2185                2190

Asn Arg Ala Ala Ser Ala Ser Glu Ser Ala Leu Gln Thr Val Ile
    2195                2200                2205

Lys Glu Asp Leu Pro Arg Lys Ala Lys Thr Leu Ser Ser Asn Ser
    2210                2215                2220

Asp Lys Leu Leu Asn Glu Ala Lys Met Thr Gln Lys Lys Leu Lys
    2225                2230                2235

Gln Glu Val Ser Pro Ala Leu Asn Asn Leu Gln Gln Thr Leu Asn
    2240                2245                2250

Ile Val Thr Val Gln Lys Glu Val Ile Asp Thr Asn Leu Thr Thr
    2255                2260                2265

Leu Arg Asp Gly Leu His Gly Ile Gln Arg Gly Asp Ile Asp Ala
    2270                2275                2280

Met Ile Ser Ser Ala Lys Ser Met Val Arg Lys Ala Asn Asp Ile
    2285                2290                2295

Thr Asp Glu Val Leu Asp Gly Leu Asn Pro Ile Gln Thr Asp Val
    2300                2305                2310

Glu Arg Ile Lys Asp Thr Tyr Gly Arg Thr Gln Asn Glu Asp Phe
    2315                2320                2325

Lys Lys Ala Leu Thr Asp Ala Asp Asn Ser Val Asn Lys Leu Thr
    2330                2335                2340

Asn Lys Leu Pro Asp Leu Trp Arg Lys Ile Glu Ser Ile Asn Gln
    2345                2350                2355

Gln Leu Leu Pro Leu Gly Asn Ile Ser Asp Asn Met Asp Arg Ile
    2360                2365                2370

Arg Glu Leu Ile Gln Gln Ala Arg Asp Ala Ala Ser Lys Val Ala
    2375                2380                2385

Val Pro Met Arg Phe Asn Gly Lys Ser Gly Val Glu Val Arg Leu
    2390                2395                2400

Pro Asn Asp Leu Glu Asp Leu Lys Gly Tyr Thr Ser Leu Ser Leu
    2405                2410                2415

Phe Leu Gln Arg Pro Asn Ser Arg Glu Asn Gly Gly Thr Glu Asn
    2420                2425                2430

Met Phe Val Met Tyr Leu Gly Asn Lys Asp Ala Ser Arg Asp Tyr
    2435                2440                2445

Ile Gly Met Ala Val Val Asp Gly Gln Leu Thr Cys Val Tyr Asn
    2450                2455                2460

Leu Gly Asp Arg Glu Ala Glu Leu Gln Val Asp Gln Ile Leu Thr
    2465                2470                2475

Lys Ser Glu Thr Lys Glu Ala Val Met Asp Arg Val Lys Phe Gln
    2480                2485                2490

Arg Ile Tyr Gln Phe Ala Arg Leu Asn Tyr Thr Lys Gly Ala Thr
    2495                2500                2505

Ser Ser Lys Pro Glu Thr Pro Gly Val Tyr Asp Met Asp Gly Arg
    2510                2515                2520

Asn Ser Asn Thr Leu Leu Asn Leu Asp Pro Glu Asn Val Val Phe
    2525                2530                2535

Tyr Val Gly Gly Tyr Pro Pro Asp Phe Lys Leu Pro Ser Arg Leu
    2540                2545                2550
```

-continued

```
Ser Phe Pro Pro Tyr Lys Gly Cys Ile Glu Leu Asp Asp Leu Asn
2555                2560                2565

Glu Asn Val Leu Ser Leu Tyr Asn Phe Lys Lys Thr Phe Asn Leu
2570                2575                2580

Asn Thr Thr Glu Val Glu Pro Cys Arg Arg Arg Lys Glu Glu Ser
2585                2590                2595

Asp Lys Asn Tyr Phe Glu Gly Thr Gly Tyr Ala Arg Val Pro Thr
2600                2605                2610

Gln Pro His Ala Pro Ile Pro Thr Phe Gly Gln Thr Ile Gln Thr
2615                2620                2625

Thr Val Asp Arg Gly Leu Leu Phe Phe Ala Glu Asn Gly Asp Arg
2630                2635                2640

Phe Ile Ser Leu Asn Ile Glu Asp Gly Lys Leu Met Val Arg Tyr
2645                2650                2655

Lys Leu Asn Ser Glu Leu Pro Lys Glu Arg Gly Val Gly Asp Ala
2660                2665                2670

Ile Asn Asn Gly Arg Asp His Ser Ile Gln Ile Lys Ile Gly Lys
2675                2680                2685

Leu Gln Lys Arg Met Trp Ile Asn Val Asp Val Gln Asn Thr Ile
2690                2695                2700

Ile Asp Gly Glu Val Phe Asp Phe Ser Thr Tyr Tyr Leu Gly Gly
2705                2710                2715

Ile Pro Ile Ala Ile Arg Glu Arg Phe Asn Ile Ser Thr Pro Ala
2720                2725                2730

Phe Arg Gly Cys Met Lys Asn Leu Lys Lys Thr Ser Gly Val Val
2735                2740                2745

Arg Leu Asn Asp Thr Val Gly Val Thr Lys Lys Cys Ser Glu Asp
2750                2755                2760

Trp Lys Leu Val Arg Ser Ala Ser Phe Ser Arg Gly Gly Gln Leu
2765                2770                2775

Ser Phe Thr Asp Leu Gly Leu Pro Pro Thr Asp His Leu Gln Ala
2780                2785                2790

Ser Phe Gly Phe Gln Thr Phe Gln Pro Ser Gly Ile Leu Leu Asp
2795                2800                2805

His Gln Thr Trp Thr Arg Asn Leu Gln Val Thr Leu Glu Asp Gly
2810                2815                2820

Tyr Ile Glu Leu Ser Thr Ser Asp Ser Gly Gly Pro Ile Phe Lys
2825                2830                2835

Ser Pro Gln Thr Tyr Met Asp Gly Leu Leu His Tyr Val Ser Val
2840                2845                2850

Ile Ser Asp Asn Ser Gly Leu Arg Leu Leu Ile Asp Asp Gln Leu
2855                2860                2865

Leu Arg Asn Ser Lys Arg Leu Lys His Ile Ser Ser Ser Arg Gln
2870                2875                2880

Ser Leu Arg Leu Gly Gly Ser Asn Phe Glu Gly Cys Ile Ser Asn
2885                2890                2895

Val Phe Val Gln Arg Leu Ser Leu Ser Pro Glu Val Leu Asp Leu
2900                2905                2910

Thr Ser Asn Ser Leu Lys Arg Asp Val Ser Leu Gly Gly Cys Ser
2915                2920                2925

Leu Asn Lys Pro Pro Phe Leu Met Leu Leu Lys Gly Ser Thr Arg
2930                2935                2940
```

```
Phe Asn Lys Thr Lys Thr Phe Arg Ile Asn Gln Leu Leu Gln Asp
2945                2950                2955

Thr Pro Val Ala Ser Pro Arg Ser Val Lys Val Trp Gln Asp Ala
2960                2965                2970

Cys Ser Pro Leu Pro Lys Thr Gln Ala Asn His Gly Ala Leu Gln
2975                2980                2985

Phe Gly Asp Ile Pro Thr Ser His Leu Leu Phe Lys Leu Pro Gln
2990                2995                3000

Glu Leu Leu Lys Pro Arg Ser Gln Phe Ala Val Asp Met Gln Thr
3005                3010                3015

Thr Ser Ser Arg Gly Leu Val Phe His Thr Gly Thr Lys Asn Ser
3020                3025                3030

Phe Met Ala Leu Tyr Leu Ser Lys Gly Arg Leu Val Phe Ala Leu
3035                3040                3045

Gly Thr Asp Gly Lys Lys Leu Arg Ile Lys Ser Lys Glu Lys Cys
3050                3055                3060

Asn Asp Gly Lys Trp His Thr Val Val Phe Gly His Asp Gly Glu
3065                3070                3075

Lys Gly Arg Leu Val Val Asp Gly Leu Arg Ala Arg Glu Gly Ser
3080                3085                3090

Leu Pro Gly Asn Ser Thr Ile Ser Ile Arg Ala Pro Val Tyr Leu
3095                3100                3105

Gly Ser Pro Pro Ser Gly Lys Pro Lys Ser Leu Pro Thr Asn Ser
3110                3115                3120

Phe Val Gly Cys Leu Lys Asn Phe Gln Leu Asp Ser Lys Pro Leu
3125                3130                3135

Tyr Thr Pro Ser Ser Phe Gly Val Ser Ser Cys Leu Gly Gly
3140                3145                3150

Pro Leu Glu Lys Gly Ile Tyr Phe Ser Glu Glu Gly Gly His Val
3155                3160                3165

Val Leu Ala His Ser Val Leu Leu Gly Pro Glu Phe Lys Leu Val
3170                3175                3180

Phe Ser Ile Arg Pro Arg Ser Leu Thr Gly Ile Leu Ile His Ile
3185                3190                3195

Gly Ser Gln Pro Gly Lys His Leu Cys Val Tyr Leu Glu Ala Gly
3200                3205                3210

Lys Val Thr Ala Ser Met Asp Ser Gly Ala Gly Gly Thr Ser Thr
3215                3220                3225

Ser Val Thr Pro Lys Gln Ser Leu Cys Asp Gly Gln Trp His Ser
3230                3235                3240

Val Ala Val Thr Ile Lys Gln His Ile Leu His Leu Glu Leu Asp
3245                3250                3255

Thr Asp Ser Ser Tyr Thr Ala Gly Gln Ile Pro Phe Pro Pro Ala
3260                3265                3270

Ser Thr Gln Glu Pro Leu His Leu Gly Gly Ala Pro Ala Asn Leu
3275                3280                3285

Thr Thr Leu Arg Ile Pro Val Trp Lys Ser Phe Phe Gly Cys Leu
3290                3295                3300

Arg Asn Ile His Val Asn His Ile Pro Val Pro Val Thr Glu Ala
3305                3310                3315

Leu Glu Val Gln Gly Pro Val Ser Leu Asn Gly Cys Pro Asp Gln
3320                3325                3330
```

<210> SEQ ID NO 29
<211> LENGTH: 1724
<212> TYPE: PRT
<213> ORGANISM: Homo sapiens

<400> SEQUENCE: 29

```
Met Pro Pro Ala Val Arg Arg Ser Ala Cys Ser Met Gly Trp Leu Trp
1               5                   10                  15

Ile Phe Gly Ala Ala Leu Gly Gln Cys Leu Gly Tyr Ser Ser Gln Gln
                20                  25                  30

Gln Arg Val Pro Phe Leu Gln Pro Pro Gly Gln Ser Gln Leu Gln Ala
            35                  40                  45

Ser Tyr Val Glu Phe Arg Pro Ser Gln Gly Cys Ser Pro Gly Tyr Tyr
    50                  55                  60

Arg Asp His Lys Gly Leu Tyr Thr Gly Arg Cys Val Pro Cys Asn Cys
65                  70                  75                  80

Asn Gly His Ser Asn Gln Cys Gln Asp Gly Ser Gly Ile Cys Val Asn
                85                  90                  95

Cys Gln His Asn Thr Ala Gly Glu His Cys Glu Arg Cys Gln Glu Gly
            100                 105                 110

Tyr Tyr Gly Asn Ala Val His Gly Ser Cys Arg Ala Cys Pro Cys Pro
        115                 120                 125

His Thr Asn Ser Phe Ala Thr Gly Cys Val Val Asn Gly Gly Asp Val
130                 135                 140

Arg Cys Ser Cys Lys Ala Gly Tyr Thr Gly Thr Gln Cys Glu Arg Cys
145                 150                 155                 160

Ala Pro Gly Tyr Phe Gly Asn Pro Gln Lys Phe Gly Gly Ser Cys Gln
                165                 170                 175

Pro Cys Ser Cys Asn Ser Asn Gly Gln Leu Gly Ser Cys His Pro Leu
            180                 185                 190

Thr Gly Asp Cys Ile Asn Gln Glu Pro Lys Asp Ser Ser Pro Ala Glu
        195                 200                 205

Glu Cys Asp Asp Cys Asp Ser Cys Val Met Thr Leu Leu Asn Asp Leu
    210                 215                 220

Ala Thr Met Gly Glu Gln Leu Arg Leu Val Lys Ser Gln Leu Gln Gly
225                 230                 235                 240

Leu Ser Ala Ser Ala Gly Leu Leu Glu Gln Met Arg His Met Glu Thr
                245                 250                 255

Gln Ala Lys Asp Leu Arg Asn Gln Leu Leu Asn Tyr Arg Ser Ala Ile
            260                 265                 270

Ser Asn His Gly Ser Lys Ile Glu Gly Leu Glu Arg Glu Leu Thr Asp
        275                 280                 285

Leu Asn Gln Glu Phe Glu Thr Leu Gln Glu Lys Ala Gln Val Asn Ser
    290                 295                 300

Arg Lys Ala Gln Thr Leu Asn Asn Asn Val Asn Arg Ala Thr Gln Ser
305                 310                 315                 320

Ala Lys Glu Leu Asp Val Lys Ile Lys Asn Val Ile Arg Asn Val His
                325                 330                 335

Ile Leu Leu Lys Gln Ile Ser Gly Thr Asp Gly Glu Gly Asn Asn Val
            340                 345                 350

Pro Ser Gly Asp Phe Ser Arg Glu Trp Ala Glu Ala Gln Arg Met Met
        355                 360                 365

Arg Glu Leu Arg Asn Arg Asn Phe Gly Lys His Leu Arg Glu Ala Glu
    370                 375                 380
```

```
Ala Asp Lys Arg Glu Ser Gln Leu Leu Asn Arg Ile Arg Thr Trp
385                 390                 395                 400

Gln Lys Thr His Gln Gly Glu Asn Asn Gly Leu Ala Asn Ser Ile Arg
            405                 410                 415

Asp Ser Leu Asn Glu Tyr Glu Ala Lys Leu Ser Asp Leu Arg Ala Arg
            420                 425                 430

Leu Gln Glu Ala Ala Ala Gln Ala Lys Gln Ala Asn Gly Leu Asn Gln
            435                 440                 445

Glu Asn Glu Arg Ala Leu Gly Ala Ile Gln Arg Gln Val Lys Glu Ile
450                 455                 460

Asn Ser Leu Gln Ser Asp Phe Thr Lys Tyr Leu Thr Thr Ala Asp Ser
465                 470                 475                 480

Ser Leu Leu Gln Thr Asn Ile Ala Leu Gln Leu Met Glu Lys Ser Gln
            485                 490                 495

Lys Glu Tyr Glu Lys Leu Ala Ala Ser Leu Asn Glu Ala Arg Gln Glu
            500                 505                 510

Leu Ser Asp Lys Val Arg Glu Leu Ser Arg Ser Ala Gly Lys Thr Ser
            515                 520                 525

Leu Val Glu Glu Ala Glu Lys His Ala Arg Ser Leu Gln Glu Leu Ala
530                 535                 540

Lys Gln Leu Glu Glu Ile Lys Arg Asn Ala Ser Gly Asp Glu Leu Val
545                 550                 555                 560

Arg Cys Ala Val Asp Ala Ala Thr Ala Tyr Glu Asn Ile Leu Asn Ala
            565                 570                 575

Ile Lys Ala Ala Glu Asp Ala Ala Asn Arg Ala Ala Ser Ala Ser Glu
            580                 585                 590

Ser Ala Leu Gln Thr Val Ile Lys Glu Asp Leu Pro Arg Lys Ala Lys
            595                 600                 605

Thr Leu Ser Ser Asn Ser Asp Lys Leu Leu Asn Glu Ala Lys Met Thr
            610                 615                 620

Gln Lys Lys Leu Lys Gln Glu Val Ser Pro Ala Leu Asn Asn Leu Gln
625                 630                 635                 640

Gln Thr Leu Asn Ile Val Thr Val Gln Lys Glu Val Ile Asp Thr Asn
            645                 650                 655

Leu Thr Thr Leu Arg Asp Gly Leu His Gly Ile Gln Arg Gly Asp Ile
            660                 665                 670

Asp Ala Met Ile Ser Ser Ala Lys Ser Met Val Arg Lys Ala Asn Asp
            675                 680                 685

Ile Thr Asp Glu Val Leu Asp Gly Leu Asn Pro Ile Gln Thr Asp Val
            690                 695                 700

Glu Arg Ile Lys Asp Thr Tyr Gly Arg Thr Gln Asn Glu Asp Phe Lys
705                 710                 715                 720

Lys Ala Leu Thr Asp Ala Asp Asn Ser Val Asn Lys Leu Thr Asn Lys
            725                 730                 735

Leu Pro Asp Leu Trp Arg Lys Ile Glu Ser Ile Asn Gln Gln Leu Leu
            740                 745                 750

Pro Leu Gly Asn Ile Ser Asp Asn Met Asp Arg Ile Arg Glu Leu Ile
            755                 760                 765

Gln Gln Ala Arg Asp Ala Ala Ser Lys Val Ala Val Pro Met Arg Phe
            770                 775                 780

Asn Gly Lys Ser Gly Val Glu Val Arg Leu Pro Asn Asp Leu Glu Asp
785                 790                 795                 800

Leu Lys Gly Tyr Thr Ser Leu Ser Leu Phe Leu Gln Arg Pro Asn Ser
```

805                 810                 815
Arg Glu Asn Gly Gly Thr Glu Asn Met Phe Val Met Tyr Leu Gly Asn
                820                 825                 830

Lys Asp Ala Ser Arg Asp Tyr Ile Gly Met Ala Val Val Asp Gly Gln
            835                 840                 845

Leu Thr Cys Val Tyr Asn Leu Gly Asp Arg Glu Ala Glu Leu Gln Val
        850                 855                 860

Asp Gln Ile Leu Thr Lys Ser Glu Thr Lys Glu Ala Val Met Asp Arg
865                 870                 875                 880

Val Lys Phe Gln Arg Ile Tyr Gln Phe Ala Arg Leu Asn Tyr Thr Lys
                885                 890                 895

Gly Ala Thr Ser Ser Lys Pro Glu Thr Pro Gly Val Tyr Asp Met Asp
            900                 905                 910

Gly Arg Asn Ser Asn Thr Leu Leu Asn Leu Asp Pro Glu Asn Val Val
        915                 920                 925

Phe Tyr Val Gly Gly Tyr Pro Pro Asp Phe Lys Leu Pro Ser Arg Leu
    930                 935                 940

Ser Phe Pro Pro Tyr Lys Gly Cys Ile Glu Leu Asp Asp Leu Asn Glu
945                 950                 955                 960

Asn Val Leu Ser Leu Tyr Asn Phe Lys Lys Thr Phe Asn Leu Asn Thr
                965                 970                 975

Thr Glu Val Glu Pro Cys Arg Arg Arg Lys Glu Glu Ser Asp Lys Asn
            980                 985                 990

Tyr Phe Glu Gly Thr Gly Tyr Ala Arg Val Pro Thr Gln Pro His Ala
        995                 1000                1005

Pro Ile Pro Thr Phe Gly Gln Thr Ile Gln Thr Thr Val Asp Arg
    1010                1015                1020

Gly Leu Leu Phe Phe Ala Glu Asn Gly Asp Arg Phe Ile Ser Leu
    1025                1030                1035

Asn Ile Glu Asp Gly Lys Leu Met Val Arg Tyr Lys Leu Asn Ser
    1040                1045                1050

Glu Leu Pro Lys Glu Arg Gly Val Gly Asp Ala Ile Asn Asn Gly
    1055                1060                1065

Arg Asp His Ser Ile Gln Ile Lys Ile Gly Lys Leu Gln Lys Arg
    1070                1075                1080

Met Trp Ile Asn Val Asp Val Gln Asn Thr Ile Ile Asp Gly Glu
    1085                1090                1095

Val Phe Asp Phe Ser Thr Tyr Tyr Leu Gly Gly Ile Pro Ile Ala
    1100                1105                1110

Ile Arg Glu Arg Phe Asn Ile Ser Thr Pro Ala Phe Arg Gly Cys
    1115                1120                1125

Met Lys Asn Leu Lys Lys Thr Ser Gly Val Val Arg Leu Asn Asp
    1130                1135                1140

Thr Val Gly Val Thr Lys Lys Cys Ser Glu Asp Trp Lys Leu Val
    1145                1150                1155

Arg Ser Ala Ser Phe Ser Arg Gly Gly Gln Leu Ser Phe Thr Asp
    1160                1165                1170

Leu Gly Leu Pro Pro Thr Asp His Leu Gln Ala Ser Phe Gly Phe
    1175                1180                1185

Gln Thr Phe Gln Pro Ser Gly Ile Leu Leu Asp His Gln Thr Trp
    1190                1195                1200

Thr Arg Asn Leu Gln Val Thr Leu Glu Asp Gly Tyr Ile Glu Leu
    1205                1210                1215

```
Ser Thr Ser Asp Ser Gly Gly Pro Ile Phe Lys Ser Pro Gln Thr
1220            1225                1230

Tyr Met Asp Gly Leu Leu His Tyr Val Ser Val Ile Ser Asp Asn
1235            1240                1245

Ser Gly Leu Arg Leu Leu Ile Asp Asp Gln Leu Leu Arg Asn Ser
1250            1255                1260

Lys Arg Leu Lys His Ile Ser Ser Ser Arg Gln Ser Leu Arg Leu
1265            1270                1275

Gly Gly Ser Asn Phe Glu Gly Cys Ile Ser Asn Val Phe Val Gln
1280            1285                1290

Arg Leu Ser Leu Ser Pro Glu Val Leu Asp Leu Thr Ser Asn Ser
1295            1300                1305

Leu Lys Arg Asp Val Ser Leu Gly Gly Cys Ser Leu Asn Lys Pro
1310            1315                1320

Pro Phe Leu Met Leu Leu Lys Gly Ser Thr Arg Phe Asn Lys Thr
1325            1330                1335

Lys Thr Phe Arg Ile Asn Gln Leu Leu Gln Asp Thr Pro Val Ala
1340            1345                1350

Ser Pro Arg Ser Val Lys Val Trp Gln Asp Ala Cys Ser Pro Leu
1355            1360                1365

Pro Lys Thr Gln Ala Asn His Gly Ala Leu Gln Phe Gly Asp Ile
1370            1375                1380

Pro Thr Ser His Leu Leu Phe Lys Leu Pro Gln Glu Leu Leu Lys
1385            1390                1395

Pro Arg Ser Gln Phe Ala Val Asp Met Gln Thr Thr Ser Ser Arg
1400            1405                1410

Gly Leu Val Phe His Thr Gly Thr Lys Asn Ser Phe Met Ala Leu
1415            1420                1425

Tyr Leu Ser Lys Gly Arg Leu Val Phe Ala Leu Gly Thr Asp Gly
1430            1435                1440

Lys Lys Leu Arg Ile Lys Ser Lys Glu Lys Cys Asn Asp Gly Lys
1445            1450                1455

Trp His Thr Val Val Phe Gly His Asp Gly Glu Lys Gly Arg Leu
1460            1465                1470

Val Val Asp Gly Leu Arg Ala Arg Glu Gly Ser Leu Pro Gly Asn
1475            1480                1485

Ser Thr Ile Ser Ile Arg Ala Pro Val Tyr Leu Gly Ser Pro Pro
1490            1495                1500

Ser Gly Lys Pro Lys Ser Leu Pro Thr Asn Ser Phe Val Gly Cys
1505            1510                1515

Leu Lys Asn Phe Gln Leu Asp Ser Lys Pro Leu Tyr Thr Pro Ser
1520            1525                1530

Ser Ser Phe Gly Val Ser Ser Cys Leu Gly Gly Pro Leu Glu Lys
1535            1540                1545

Gly Ile Tyr Phe Ser Glu Glu Gly Gly His Val Val Leu Ala His
1550            1555                1560

Ser Val Leu Leu Gly Pro Glu Phe Lys Leu Val Phe Ser Ile Arg
1565            1570                1575

Pro Arg Ser Leu Thr Gly Ile Leu Ile His Ile Gly Ser Gln Pro
1580            1585                1590

Gly Lys His Leu Cys Val Tyr Leu Glu Ala Gly Lys Val Thr Ala
1595            1600                1605
```

-continued

```
Ser Met Asp Ser Gly Ala Gly Gly Thr Ser Thr Ser Val Thr Pro
    1610                1615                1620

Lys Gln Ser Leu Cys Asp Gly Gln Trp His Ser Val Ala Val Thr
    1625                1630                1635

Ile Lys Gln His Ile Leu His Leu Glu Leu Asp Thr Asp Ser Ser
    1640                1645                1650

Tyr Thr Ala Gly Gln Ile Pro Phe Pro Pro Ala Ser Thr Gln Glu
    1655                1660                1665

Pro Leu His Leu Gly Gly Ala Pro Ala Asn Leu Thr Thr Leu Arg
    1670                1675                1680

Ile Pro Val Trp Lys Ser Phe Phe Gly Cys Leu Arg Asn Ile His
    1685                1690                1695

Val Asn His Ile Pro Val Pro Val Thr Glu Ala Leu Glu Val Gln
    1700                1705                1710

Gly Pro Val Ser Leu Asn Gly Cys Pro Asp Gln
    1715                1720

<210> SEQ ID NO 30
<211> LENGTH: 3277
<212> TYPE: PRT
<213> ORGANISM: Homo sapiens

<400> SEQUENCE: 30

Met Ala Ala Ala Arg Pro Arg Gly Arg Leu Gly Pro Val Leu
1               5                   10                  15

Pro Pro Thr Pro Leu Leu Leu Val Leu Arg Val Leu Pro Ala Cys
                20                  25                  30

Gly Ala Thr Ala Arg Asp Pro Gly Ala Ala Gly Leu Ser Leu His
            35                  40                  45

Pro Thr Tyr Phe Asn Leu Ala Glu Ala Ala Arg Ile Trp Ala Thr Ala
    50                  55                  60

Thr Cys Gly Glu Arg Gly Pro Gly Glu Gly Arg Pro Gln Pro Glu Leu
65                  70                  75                  80

Tyr Cys Lys Leu Val Gly Gly Pro Thr Ala Pro Gly Ser Gly His Thr
                85                  90                  95

Ile Gln Gly Gln Phe Cys Asp Tyr Cys Asn Ser Glu Asp Pro Arg Lys
            100                 105                 110

Ala His Pro Val Thr Asn Ala Ile Asp Gly Ser Glu Arg Trp Trp Gln
        115                 120                 125

Ser Pro Pro Leu Ser Ser Gly Thr Gln Tyr Asn Arg Val Asn Leu Thr
    130                 135                 140

Leu Asp Leu Gly Gln Leu Phe His Val Ala Tyr Ile Leu Ile Lys Phe
145                 150                 155                 160

Ala Asn Ser Pro Arg Pro Asp Leu Trp Val Leu Glu Arg Ser Val Asp
                165                 170                 175

Phe Gly Ser Thr Tyr Ser Pro Trp Gln Tyr Phe Ala His Ser Lys Val
            180                 185                 190

Asp Cys Leu Lys Glu Phe Gly Arg Glu Ala Asn Met Ala Val Thr Arg
        195                 200                 205

Asp Asp Asp Val Leu Cys Val Thr Glu Tyr Ser Arg Ile Val Pro Leu
    210                 215                 220

Glu Asn Gly Glu Val Val Val Ser Leu Ile Asn Gly Arg Pro Gly Ala
225                 230                 235                 240

Lys Asn Phe Thr Phe Ser His Thr Leu Arg Glu Phe Thr Lys Ala Thr
                245                 250                 255
```

```
Asn Ile Arg Leu Arg Phe Leu Arg Thr Asn Thr Leu Leu Gly His Leu
            260                 265                 270

Ile Ser Lys Ala Gln Arg Asp Pro Thr Val Thr Arg Tyr Tyr Tyr
        275                 280                 285

Ser Ile Lys Asp Ile Ser Ile Gly Gly Gln Cys Val Cys Asn Gly His
        290                 295                 300

Ala Glu Val Cys Asn Ile Asn Asn Pro Glu Lys Leu Phe Arg Cys Glu
305                 310                 315                 320

Cys Gln His His Thr Cys Gly Glu Thr Cys Asp Arg Cys Cys Thr Gly
                325                 330                 335

Tyr Asn Gln Arg Arg Trp Arg Pro Ala Ala Trp Glu Gln Ser His Glu
            340                 345                 350

Cys Glu Ala Cys Asn Cys His Gly His Ala Ser Asn Cys Tyr Tyr Asp
                355                 360                 365

Pro Asp Val Glu Arg Gln Gln Ala Ser Leu Asn Thr Gln Gly Ile Tyr
        370                 375                 380

Ala Gly Gly Gly Val Cys Ile Asn Cys Gln His Asn Thr Ala Gly Val
385                 390                 395                 400

Asn Cys Glu Gln Cys Ala Lys Gly Tyr Tyr Arg Pro Tyr Gly Val Pro
                405                 410                 415

Val Asp Ala Pro Asp Gly Cys Ile Pro Cys Ser Cys Asp Pro Glu His
            420                 425                 430

Ala Asp Gly Cys Glu Gln Gly Ser Gly Arg Cys His Cys Lys Pro Asn
            435                 440                 445

Phe His Gly Asp Asn Cys Glu Lys Cys Ala Ile Gly Tyr Tyr Asn Phe
        450                 455                 460

Pro Phe Cys Leu Arg Ile Pro Ile Phe Pro Val Ser Thr Pro Ser Ser
465                 470                 475                 480

Glu Asp Pro Val Ala Gly Asp Ile Lys Gly Cys Asp Cys Asn Leu Glu
            485                 490                 495

Gly Val Leu Pro Glu Ile Cys Asp Ala His Gly Arg Cys Leu Cys Arg
            500                 505                 510

Pro Gly Val Glu Gly Pro Arg Cys Asp Thr Cys Arg Ser Gly Phe Tyr
            515                 520                 525

Ser Phe Pro Ile Cys Gln Ala Cys Trp Cys Ser Ala Leu Gly Ser Tyr
        530                 535                 540

Gln Met Pro Cys Ser Ser Val Thr Gly Gln Cys Glu Cys Arg Pro Gly
545                 550                 555                 560

Val Thr Gly Gln Arg Cys Asp Arg Cys Leu Ser Gly Ala Tyr Asp Phe
            565                 570                 575

Pro His Cys Gln Gly Ser Ser Ser Ala Cys Asp Pro Ala Gly Thr Ile
            580                 585                 590

Asn Ser Asn Leu Gly Tyr Cys Gln Cys Lys Leu His Val Glu Gly Pro
        595                 600                 605

Thr Cys Ser Arg Cys Lys Leu Leu Tyr Trp Asn Leu Asp Lys Glu Asn
        610                 615                 620

Pro Ser Gly Cys Ser Glu Cys Lys Cys His Lys Ala Gly Thr Val Ser
625                 630                 635                 640

Gly Thr Gly Glu Cys Arg Gln Gly Asp Gly Asp Cys His Cys Lys Ser
            645                 650                 655

His Val Gly Gly Asp Ser Cys Asp Thr Cys Glu Asp Gly Tyr Phe Ala
            660                 665                 670
```

```
Leu Glu Lys Ser Asn Tyr Phe Gly Cys Gln Gly Cys Gln Cys Asp Ile
            675                 680                 685

Gly Gly Ala Leu Ser Ser Met Cys Ser Gly Pro Ser Gly Val Cys Gln
690                 695                 700

Cys Arg Glu His Val Val Gly Lys Val Cys Gln Arg Pro Glu Asn Asn
705                 710                 715                 720

Tyr Tyr Phe Pro Asp Leu His His Met Lys Tyr Glu Ile Glu Asp Gly
            725                 730                 735

Ser Thr Pro Asn Gly Arg Asp Leu Arg Phe Gly Phe Asp Pro Leu Ala
            740                 745                 750

Phe Pro Glu Phe Ser Trp Arg Gly Tyr Ala Gln Met Thr Ser Val Gln
            755                 760                 765

Asn Asp Val Arg Ile Thr Leu Asn Val Gly Lys Ser Ser Gly Ser Leu
            770                 775                 780

Phe Arg Val Ile Leu Arg Tyr Val Asn Pro Gly Thr Glu Ala Val Ser
785                 790                 795                 800

Gly His Ile Thr Ile Tyr Pro Ser Trp Gly Ala Ala Gln Ser Lys Glu
            805                 810                 815

Ile Ile Phe Leu Pro Ser Lys Glu Pro Ala Phe Val Thr Val Pro Gly
            820                 825                 830

Asn Gly Phe Ala Asp Pro Phe Ser Ile Thr Pro Gly Ile Trp Val Ala
            835                 840                 845

Cys Ile Lys Ala Glu Gly Val Leu Leu Asp Tyr Leu Val Leu Leu Pro
            850                 855                 860

Arg Asp Tyr Tyr Glu Ala Ser Val Leu Gln Leu Pro Val Thr Glu Pro
865                 870                 875                 880

Cys Ala Tyr Ala Gly Pro Pro Gln Glu Asn Cys Leu Leu Tyr Gln His
            885                 890                 895

Leu Pro Val Thr Arg Phe Pro Cys Thr Leu Ala Cys Glu Ala Arg His
            900                 905                 910

Phe Leu Leu Asp Gly Glu Pro Arg Pro Val Ala Val Arg Gln Pro Thr
            915                 920                 925

Pro Ala His Pro Val Met Val Asp Leu Ser Gly Arg Glu Val Glu Leu
            930                 935                 940

His Leu Arg Leu Arg Ile Pro Gln Val Gly His Tyr Val Val Val
945                 950                 955                 960

Glu Tyr Ser Thr Glu Ala Ala Gln Leu Phe Val Val Asp Val Asn Val
            965                 970                 975

Lys Ser Ser Gly Ser Val Leu Ala Gly Gln Val Asn Ile Tyr Ser Cys
            980                 985                 990

Asn Tyr Ser Val Leu Cys Arg Ser Ala Val Ile Asp His Met Ser Arg
            995                1000                1005

Ile Ala Met Tyr Glu Leu Leu Ala Asp Ala Asp Ile Gln Leu Lys
            1010                1015                1020

Gly His Met Ala Arg Phe Leu Leu His Gln Val Cys Ile Ile Pro
            1025                1030                1035

Ile Glu Glu Phe Ser Ala Glu Tyr Val Arg Pro Gln Val His Cys
            1040                1045                1050

Ile Ala Ser Tyr Gly Arg Phe Val Asn Gln Ser Ala Thr Cys Val
            1055                1060                1065

Ser Leu Ala His Glu Thr Pro Pro Thr Ala Leu Ile Leu Asp Val
            1070                1075                1080

Leu Ser Gly Arg Pro Phe Pro His Leu Pro Gln Gln Ser Ser Pro
```

```
                  1085            1090            1095
Ser Val Asp Val Leu Pro Gly Val Thr Leu Lys Ala Pro Gln Asn
    1100            1105            1110

Gln Val Thr Leu Arg Gly Arg Val Pro His Leu Gly Arg Tyr Val
    1115            1120            1125

Phe Val Ile His Phe Tyr Gln Ala Ala His Pro Thr Phe Pro Ala
    1130            1135            1140

Gln Val Ser Val Asp Gly Gly Trp Pro Arg Ala Gly Ser Phe His
    1145            1150            1155

Ala Ser Phe Cys Pro His Val Leu Gly Cys Arg Asp Gln Val Ile
    1160            1165            1170

Ala Glu Gly Gln Ile Glu Phe Asp Ile Ser Glu Pro Glu Val Ala
    1175            1180            1185

Ala Thr Val Lys Val Pro Glu Gly Lys Ser Leu Val Leu Val Arg
    1190            1195            1200

Val Leu Val Val Pro Ala Glu Asn Tyr Asp Tyr Gln Ile Leu His
    1205            1210            1215

Lys Lys Ser Met Asp Lys Ser Leu Glu Phe Ile Thr Asn Cys Gly
    1220            1225            1230

Lys Asn Ser Phe Tyr Leu Asp Pro Gln Thr Ala Ser Arg Phe Cys
    1235            1240            1245

Lys Asn Ser Ala Arg Ser Leu Val Ala Phe Tyr His Lys Gly Ala
    1250            1255            1260

Leu Pro Cys Glu Cys His Pro Thr Gly Ala Thr Gly Pro His Cys
    1265            1270            1275

Ser Pro Glu Gly Gly Gln Cys Pro Cys Gln Pro Asn Val Ile Gly
    1280            1285            1290

Arg Gln Cys Thr Arg Cys Ala Thr Gly His Tyr Gly Phe Pro Arg
    1295            1300            1305

Cys Lys Pro Cys Ser Cys Gly Arg Arg Leu Cys Glu Glu Met Thr
    1310            1315            1320

Gly Gln Cys Arg Cys Pro Pro Arg Thr Val Arg Pro Gln Cys Glu
    1325            1330            1335

Val Cys Glu Thr His Ser Phe Ser Phe His Pro Met Ala Gly Cys
    1340            1345            1350

Glu Gly Cys Asn Cys Ser Arg Arg Gly Thr Ile Glu Ala Ala Met
    1355            1360            1365

Pro Glu Cys Asp Arg Asp Ser Gly Gln Cys Arg Cys Lys Pro Arg
    1370            1375            1380

Ile Thr Gly Arg Gln Cys Asp Arg Cys Ala Ser Gly Phe Tyr Arg
    1385            1390            1395

Phe Pro Glu Cys Val Pro Cys Asn Cys Asn Arg Asp Gly Thr Glu
    1400            1405            1410

Pro Gly Val Cys Asp Pro Gly Thr Gly Ala Cys Leu Cys Lys Glu
    1415            1420            1425

Asn Val Glu Gly Thr Glu Cys Asn Val Cys Arg Glu Gly Ser Phe
    1430            1435            1440

His Leu Asp Pro Ala Asn Leu Lys Gly Cys Thr Ser Cys Phe Cys
    1445            1450            1455

Phe Gly Val Asn Asn Gln Cys His Ser Ser His Lys Arg Arg Thr
    1460            1465            1470

Lys Phe Val Asp Met Leu Gly Trp His Leu Glu Thr Ala Asp Arg
    1475            1480            1485
```

-continued

```
Val Asp Ile Pro Val Ser Phe Asn Pro Gly Ser Asn Ser Met Val
    1490             1495                 1500

Ala Asp Leu Gln Glu Leu Pro Ala Thr Ile His Ser Ala Ser Trp
    1505             1510                 1515

Val Ala Pro Thr Ser Tyr Leu Gly Asp Lys Val Ser Ser Tyr Gly
    1520             1525                 1530

Gly Tyr Leu Thr Tyr Gln Ala Lys Ser Phe Gly Leu Pro Gly Asp
    1535             1540                 1545

Met Val Leu Leu Glu Lys Lys Pro Asp Val Gln Leu Thr Gly Gln
    1550             1555                 1560

His Met Ser Ile Ile Tyr Glu Glu Thr Asn Thr Pro Arg Pro Asp
    1565             1570                 1575

Arg Leu His His Gly Arg Val His Val Val Glu Gly Asn Phe Arg
    1580             1585                 1590

His Ala Ser Ser Arg Ala Pro Val Ser Arg Glu Glu Leu Met Thr
    1595             1600                 1605

Val Leu Ser Arg Leu Ala Asp Val Arg Ile Gln Gly Leu Tyr Phe
    1610             1615                 1620

Thr Glu Thr Gln Arg Leu Thr Leu Ser Glu Val Gly Leu Glu Glu
    1625             1630                 1635

Ala Ser Asp Thr Gly Ser Gly Arg Ile Ala Leu Ala Val Glu Ile
    1640             1645                 1650

Cys Ala Cys Pro Pro Ala Tyr Ala Gly Asp Ser Cys Gln Gly Cys
    1655             1660                 1665

Ser Pro Gly Tyr Tyr Arg Asp His Lys Gly Leu Tyr Thr Gly Arg
    1670             1675                 1680

Cys Val Pro Cys Asn Cys Asn Gly His Ser Asn Gln Cys Gln Asp
    1685             1690                 1695

Gly Ser Gly Ile Cys Val Asn Cys Gln His Asn Thr Ala Gly Glu
    1700             1705                 1710

His Cys Glu Arg Cys Gln Glu Gly Tyr Tyr Gly Asn Ala Val His
    1715             1720                 1725

Gly Ser Cys Arg Ala Cys Pro Cys Pro His Thr Asn Ser Phe Ala
    1730             1735                 1740

Thr Gly Cys Val Val Asn Gly Gly Asp Val Arg Cys Ser Cys Lys
    1745             1750                 1755

Ala Gly Tyr Thr Gly Thr Gln Cys Glu Arg Cys Ala Pro Gly Tyr
    1760             1765                 1770

Phe Gly Asn Pro Gln Lys Phe Gly Gly Ser Cys Gln Pro Cys Ser
    1775             1780                 1785

Cys Asn Ser Asn Gly Gln Leu Gly Ser Cys His Pro Leu Thr Gly
    1790             1795                 1800

Asp Cys Ile Asn Gln Glu Pro Lys Asp Ser Ser Pro Ala Glu Glu
    1805             1810                 1815

Cys Asp Asp Cys Asp Ser Cys Val Met Thr Leu Leu Asn Asp Leu
    1820             1825                 1830

Ala Thr Met Gly Glu Gln Leu Arg Leu Val Lys Ser Gln Leu Gln
    1835             1840                 1845

Gly Leu Ser Ala Ser Ala Gly Leu Leu Glu Gln Met Arg His Met
    1850             1855                 1860

Glu Thr Gln Ala Lys Asp Leu Arg Asn Gln Leu Leu Asn Tyr Arg
    1865             1870                 1875
```

```
Ser Ala Ile Ser Asn His Gly Ser Lys Ile Glu Gly Leu Glu Arg
    1880                1885                1890

Glu Leu Thr Asp Leu Asn Gln Glu Phe Glu Thr Leu Gln Glu Lys
    1895                1900                1905

Ala Gln Val Asn Ser Arg Lys Ala Gln Thr Leu Asn Asn Asn Val
    1910                1915                1920

Asn Arg Ala Thr Gln Ser Ala Lys Glu Leu Asp Val Lys Ile Lys
    1925                1930                1935

Asn Val Ile Arg Asn Val His Met Leu Asn Arg Ile Arg Thr Trp
    1940                1945                1950

Gln Lys Thr His Gln Gly Glu Asn Asn Gly Leu Ala Asn Ser Ile
    1955                1960                1965

Arg Asp Ser Leu Asn Glu Tyr Glu Ala Lys Leu Ser Asp Leu Arg
    1970                1975                1980

Ala Arg Leu Gln Glu Ala Ala Gln Ala Lys Gln Ala Asn Gly
    1985                1990                1995

Leu Asn Gln Glu Asn Glu Arg Ala Leu Gly Ala Ile Gln Arg Gln
    2000                2005                2010

Val Lys Glu Ile Asn Ser Leu Gln Ser Asp Phe Thr Lys Tyr Leu
    2015                2020                2025

Thr Thr Ala Asp Ser Ser Leu Leu Gln Thr Asn Ile Ala Leu Gln
    2030                2035                2040

Leu Met Glu Lys Ser Gln Lys Glu Tyr Glu Lys Leu Ala Ala Ser
    2045                2050                2055

Leu Asn Glu Ala Arg Gln Glu Leu Ser Asp Lys Val Arg Glu Leu
    2060                2065                2070

Ser Arg Ser Ala Gly Lys Thr Ser Leu Val Glu Glu Ala Glu Lys
    2075                2080                2085

His Ala Arg Ser Leu Gln Glu Leu Ala Lys Gln Leu Glu Glu Ile
    2090                2095                2100

Lys Arg Asn Ala Ser Gly Asp Glu Leu Val Arg Cys Ala Val Asp
    2105                2110                2115

Ala Ala Thr Ala Tyr Glu Asn Ile Leu Asn Ala Ile Lys Ala Ala
    2120                2125                2130

Glu Asp Ala Ala Asn Arg Ala Ala Ser Ala Ser Glu Ser Ala Leu
    2135                2140                2145

Gln Thr Val Ile Lys Glu Asp Leu Pro Arg Lys Ala Lys Thr Leu
    2150                2155                2160

Ser Ser Asn Ser Asp Lys Leu Leu Asn Glu Ala Lys Met Thr Gln
    2165                2170                2175

Lys Lys Leu Lys Gln Glu Val Ser Pro Ala Leu Asn Asn Leu Gln
    2180                2185                2190

Gln Thr Leu Asn Ile Val Thr Val Gln Lys Glu Val Ile Asp Thr
    2195                2200                2205

Asn Leu Thr Thr Leu Arg Asp Gly Leu His Gly Ile Gln Arg Gly
    2210                2215                2220

Asp Ile Asp Ala Met Ile Ser Ser Ala Lys Ser Met Val Arg Lys
    2225                2230                2235

Ala Asn Asp Ile Thr Asp Glu Val Leu Asp Gly Leu Asn Pro Ile
    2240                2245                2250

Gln Thr Asp Val Glu Arg Ile Lys Asp Thr Tyr Gly Arg Thr Gln
    2255                2260                2265

Asn Glu Asp Phe Lys Lys Ala Leu Thr Asp Ala Asp Asn Ser Val
```

```
                    2270                2275                2280
Asn Lys Leu Thr Asn Lys Leu Pro Asp Leu Trp Arg Lys Ile Glu
        2285                2290                2295
Ser Ile Asn Gln Gln Leu Leu Pro Leu Gly Asn Ile Ser Asp Asn
        2300                2305                2310
Met Asp Arg Ile Arg Glu Leu Ile Gln Gln Ala Arg Asp Ala Ala
        2315                2320                2325
Ser Lys Val Ala Val Pro Met Arg Phe Asn Gly Lys Ser Gly Val
        2330                2335                2340
Glu Val Arg Leu Pro Asn Asp Leu Glu Asp Leu Lys Gly Tyr Thr
        2345                2350                2355
Ser Leu Ser Leu Phe Leu Gln Arg Pro Asn Ser Arg Glu Asn Gly
        2360                2365                2370
Gly Thr Glu Asn Met Phe Val Met Tyr Leu Gly Asn Lys Asp Ala
        2375                2380                2385
Ser Arg Asp Tyr Ile Gly Met Ala Val Val Asp Gly Gln Leu Thr
        2390                2395                2400
Cys Val Tyr Asn Leu Gly Asp Arg Glu Ala Glu Leu Gln Val Asp
        2405                2410                2415
Gln Ile Leu Thr Lys Ser Glu Thr Lys Glu Ala Val Met Asp Arg
        2420                2425                2430
Val Lys Phe Gln Arg Ile Tyr Gln Phe Ala Arg Leu Asn Tyr Thr
        2435                2440                2445
Lys Gly Ala Thr Ser Ser Lys Pro Glu Thr Pro Gly Val Tyr Asp
        2450                2455                2460
Met Asp Gly Arg Asn Ser Asn Thr Leu Leu Asn Leu Asp Pro Glu
        2465                2470                2475
Asn Val Val Phe Tyr Val Gly Gly Tyr Pro Pro Asp Phe Lys Leu
        2480                2485                2490
Pro Ser Arg Leu Ser Phe Pro Pro Tyr Lys Gly Cys Ile Glu Leu
        2495                2500                2505
Asp Asp Leu Asn Glu Asn Val Leu Ser Leu Tyr Asn Phe Lys Lys
        2510                2515                2520
Thr Phe Asn Leu Asn Thr Thr Glu Val Glu Pro Cys Arg Arg Arg
        2525                2530                2535
Lys Glu Glu Ser Asp Lys Asn Tyr Phe Glu Gly Thr Gly Tyr Ala
        2540                2545                2550
Arg Val Pro Thr Gln Pro His Ala Pro Ile Pro Thr Phe Gly Gln
        2555                2560                2565
Thr Ile Gln Thr Thr Val Asp Arg Gly Leu Leu Phe Phe Ala Glu
        2570                2575                2580
Asn Gly Asp Arg Phe Ile Ser Leu Asn Ile Glu Asp Gly Lys Leu
        2585                2590                2595
Met Val Arg Tyr Lys Leu Asn Ser Glu Leu Pro Lys Glu Arg Gly
        2600                2605                2610
Val Gly Asp Ala Ile Asn Asn Gly Arg Asp His Ser Ile Gln Ile
        2615                2620                2625
Lys Ile Gly Lys Leu Gln Lys Arg Met Trp Ile Asn Val Asp Val
        2630                2635                2640
Gln Asn Thr Ile Ile Asp Gly Glu Val Phe Asp Phe Ser Thr Tyr
        2645                2650                2655
Tyr Leu Gly Gly Ile Pro Ile Ala Ile Arg Glu Arg Phe Asn Ile
        2660                2665                2670
```

```
Ser Thr Pro Ala Phe Arg Gly Cys Met Lys Asn Leu Lys Lys Thr
2675                2680                2685

Ser Gly Val Val Arg Leu Asn Asp Thr Val Gly Val Thr Lys Lys
2690                2695                2700

Cys Ser Glu Asp Trp Lys Leu Val Arg Ser Ala Ser Phe Ser Arg
2705                2710                2715

Gly Gly Gln Leu Ser Phe Thr Asp Leu Gly Leu Pro Pro Thr Asp
2720                2725                2730

His Leu Gln Ala Ser Phe Gly Phe Gln Thr Phe Gln Pro Ser Gly
2735                2740                2745

Ile Leu Leu Asp His Gln Thr Trp Thr Arg Asn Leu Gln Val Thr
2750                2755                2760

Leu Glu Asp Gly Tyr Ile Glu Leu Ser Thr Ser Asp Ser Gly Gly
2765                2770                2775

Pro Ile Phe Lys Ser Pro Gln Thr Tyr Met Asp Gly Leu Leu His
2780                2785                2790

Tyr Val Ser Val Ile Ser Asp Asn Ser Gly Leu Arg Leu Leu Ile
2795                2800                2805

Asp Asp Gln Leu Leu Arg Asn Ser Lys Arg Leu Lys His Ile Ser
2810                2815                2820

Ser Ser Arg Gln Ser Leu Arg Leu Gly Gly Ser Asn Phe Glu Gly
2825                2830                2835

Cys Ile Ser Asn Val Phe Val Gln Arg Leu Ser Leu Ser Pro Glu
2840                2845                2850

Val Leu Asp Leu Thr Ser Asn Ser Leu Lys Arg Asp Val Ser Leu
2855                2860                2865

Gly Gly Cys Ser Leu Asn Lys Pro Pro Phe Leu Met Leu Leu Lys
2870                2875                2880

Gly Ser Thr Arg Phe Asn Lys Thr Lys Thr Phe Arg Ile Asn Gln
2885                2890                2895

Leu Leu Gln Asp Thr Pro Val Ala Ser Pro Arg Ser Val Lys Val
2900                2905                2910

Trp Gln Asp Ala Cys Ser Pro Leu Pro Lys Thr Gln Ala Asn His
2915                2920                2925

Gly Ala Leu Gln Phe Gly Asp Ile Pro Thr Ser His Leu Leu Phe
2930                2935                2940

Lys Leu Pro Gln Glu Leu Leu Lys Pro Arg Ser Gln Phe Ala Val
2945                2950                2955

Asp Met Gln Thr Thr Ser Ser Arg Gly Leu Val Phe His Thr Gly
2960                2965                2970

Thr Lys Asn Ser Phe Met Ala Leu Tyr Leu Ser Lys Gly Arg Leu
2975                2980                2985

Val Phe Ala Leu Gly Thr Asp Gly Lys Lys Leu Arg Ile Lys Ser
2990                2995                3000

Lys Glu Lys Cys Asn Asp Gly Lys Trp His Thr Val Val Phe Gly
3005                3010                3015

His Asp Gly Glu Lys Gly Arg Leu Val Val Asp Gly Leu Arg Ala
3020                3025                3030

Arg Glu Gly Ser Leu Pro Gly Asn Ser Thr Ile Ser Ile Arg Ala
3035                3040                3045

Pro Val Tyr Leu Gly Ser Pro Pro Ser Gly Lys Pro Lys Ser Leu
3050                3055                3060
```

```
Pro Thr Asn Ser Phe Val Gly Cys Leu Lys Asn Phe Gln Leu Asp
    3065                3070                3075

Ser Lys Pro Leu Tyr Thr Pro Ser Ser Ser Phe Gly Val Ser Ser
    3080                3085                3090

Cys Leu Gly Gly Pro Leu Glu Lys Gly Ile Tyr Phe Ser Glu Glu
    3095                3100                3105

Gly Gly His Val Val Leu Ala His Ser Val Leu Leu Gly Pro Glu
    3110                3115                3120

Phe Lys Leu Val Phe Ser Ile Arg Pro Arg Ser Leu Thr Gly Ile
    3125                3130                3135

Leu Ile His Ile Gly Ser Gln Pro Gly Lys His Leu Cys Val Tyr
    3140                3145                3150

Leu Glu Ala Gly Lys Val Thr Ala Ser Met Asp Ser Gly Ala Gly
    3155                3160                3165

Gly Thr Ser Thr Ser Val Thr Pro Lys Gln Ser Leu Cys Asp Gly
    3170                3175                3180

Gln Trp His Ser Val Ala Val Thr Ile Lys Gln His Ile Leu His
    3185                3190                3195

Leu Glu Leu Asp Thr Asp Ser Ser Tyr Thr Ala Gly Gln Ile Pro
    3200                3205                3210

Phe Pro Pro Ala Ser Thr Gln Glu Pro Leu His Leu Gly Gly Ala
    3215                3220                3225

Pro Ala Asn Leu Thr Thr Leu Arg Ile Pro Val Trp Lys Ser Phe
    3230                3235                3240

Phe Gly Cys Leu Arg Asn Ile His Val Asn His Ile Pro Val Pro
    3245                3250                3255

Val Thr Glu Ala Leu Glu Val Gln Gly Pro Val Ser Leu Asn Gly
    3260                3265                3270

Cys Pro Asp Gln
    3275

<210> SEQ ID NO 31
<211> LENGTH: 1668
<212> TYPE: PRT
<213> ORGANISM: Homo sapiens

<400> SEQUENCE: 31

Met Pro Pro Ala Val Arg Arg Ser Ala Cys Ser Met Gly Trp Leu Trp
1               5                   10                  15

Ile Phe Gly Ala Ala Leu Gly Gln Cys Leu Gly Tyr Ser Ser Gln Gln
                20                  25                  30

Gln Arg Val Pro Phe Leu Gln Pro Pro Gly Gln Ser Gln Leu Gln Ala
            35                  40                  45

Ser Tyr Val Glu Phe Arg Pro Ser Gln Gly Cys Ser Pro Gly Tyr Tyr
        50                  55                  60

Arg Asp His Lys Gly Leu Tyr Thr Gly Arg Cys Val Pro Cys Asn Cys
65                  70                  75                  80

Asn Gly His Ser Asn Gln Cys Gln Asp Gly Ser Gly Ile Cys Val Asn
                85                  90                  95

Cys Gln His Asn Thr Ala Gly Glu His Cys Glu Arg Cys Gln Glu Gly
                100                 105                 110

Tyr Tyr Gly Asn Ala Val His Gly Ser Cys Arg Ala Cys Pro Cys Pro
            115                 120                 125

His Thr Asn Ser Phe Ala Thr Gly Cys Val Val Asn Gly Gly Asp Val
        130                 135                 140
```

-continued

Arg Cys Ser Cys Lys Ala Gly Tyr Thr Gly Thr Gln Cys Glu Arg Cys
145                 150                 155                 160

Ala Pro Gly Tyr Phe Gly Asn Pro Gln Lys Phe Gly Ser Cys Gln
            165                 170                 175

Pro Cys Ser Cys Asn Ser Asn Gly Gln Leu Gly Ser Cys His Pro Leu
            180                 185                 190

Thr Gly Asp Cys Ile Asn Gln Glu Pro Lys Asp Ser Pro Ala Glu
            195                 200                 205

Glu Cys Asp Asp Cys Asp Ser Cys Val Met Thr Leu Leu Asn Asp Leu
210                 215                 220

Ala Thr Met Gly Glu Gln Leu Arg Leu Val Lys Ser Gln Leu Gln Gly
225                 230                 235                 240

Leu Ser Ala Ser Ala Gly Leu Leu Glu Gln Met Arg His Met Glu Thr
            245                 250                 255

Gln Ala Lys Asp Leu Arg Asn Gln Leu Leu Asn Tyr Arg Ser Ala Ile
            260                 265                 270

Ser Asn His Gly Ser Lys Ile Glu Gly Leu Glu Arg Glu Leu Thr Asp
            275                 280                 285

Leu Asn Gln Glu Phe Glu Thr Leu Gln Glu Lys Ala Gln Val Asn Ser
            290                 295                 300

Arg Lys Ala Gln Thr Leu Asn Asn Asn Val Asn Arg Ala Thr Gln Ser
305                 310                 315                 320

Ala Lys Glu Leu Asp Val Lys Ile Lys Asn Val Ile Arg Asn Val His
            325                 330                 335

Met Leu Asn Arg Ile Arg Thr Trp Gln Lys Thr His Gln Gly Glu Asn
            340                 345                 350

Asn Gly Leu Ala Asn Ser Ile Arg Asp Ser Leu Asn Glu Tyr Glu Ala
            355                 360                 365

Lys Leu Ser Asp Leu Arg Ala Arg Leu Gln Glu Ala Ala Gln Ala
370                 375                 380

Lys Gln Ala Asn Gly Leu Asn Gln Glu Asn Glu Arg Ala Leu Gly Ala
385                 390                 395                 400

Ile Gln Arg Gln Val Lys Glu Ile Asn Ser Leu Gln Ser Asp Phe Thr
            405                 410                 415

Lys Tyr Leu Thr Thr Ala Asp Ser Ser Leu Leu Gln Thr Asn Ile Ala
            420                 425                 430

Leu Gln Leu Met Glu Lys Ser Gln Lys Glu Tyr Glu Lys Leu Ala Ala
            435                 440                 445

Ser Leu Asn Glu Ala Arg Gln Glu Leu Ser Asp Lys Val Arg Glu Leu
            450                 455                 460

Ser Arg Ser Ala Gly Lys Thr Ser Leu Val Glu Glu Ala Glu Lys His
465                 470                 475                 480

Ala Arg Ser Leu Gln Glu Leu Ala Lys Gln Leu Glu Glu Ile Lys Arg
            485                 490                 495

Asn Ala Ser Gly Asp Glu Leu Val Arg Cys Ala Val Asp Ala Ala Thr
            500                 505                 510

Ala Tyr Glu Asn Ile Leu Asn Ala Ile Lys Ala Glu Asp Ala Ala
            515                 520                 525

Asn Arg Ala Ala Ser Ala Ser Glu Ser Ala Leu Gln Thr Val Ile Lys
            530                 535                 540

Glu Asp Leu Pro Arg Lys Ala Lys Thr Leu Ser Ser Asn Ser Asp Lys
545                 550                 555                 560

-continued

```
Leu Leu Asn Glu Ala Lys Met Thr Gln Lys Lys Leu Lys Gln Glu Val
            565                 570                 575
Ser Pro Ala Leu Asn Asn Leu Gln Gln Thr Leu Asn Ile Val Thr Val
            580                 585                 590
Gln Lys Glu Val Ile Asp Thr Asn Leu Thr Thr Leu Arg Asp Gly Leu
            595                 600                 605
His Gly Ile Gln Arg Gly Asp Ile Asp Ala Met Ile Ser Ser Ala Lys
            610                 615                 620
Ser Met Val Arg Lys Ala Asn Asp Ile Thr Asp Glu Val Leu Asp Gly
625                 630                 635                 640
Leu Asn Pro Ile Gln Thr Asp Val Glu Arg Ile Lys Asp Thr Tyr Gly
            645                 650                 655
Arg Thr Gln Asn Glu Asp Phe Lys Lys Ala Leu Thr Asp Ala Asp Asn
            660                 665                 670
Ser Val Asn Lys Leu Thr Asn Lys Leu Pro Asp Leu Trp Arg Lys Ile
            675                 680                 685
Glu Ser Ile Asn Gln Gln Leu Leu Pro Leu Gly Asn Ile Ser Asp Asn
            690                 695                 700
Met Asp Arg Ile Arg Glu Leu Ile Gln Gln Ala Arg Asp Ala Ala Ser
705                 710                 715                 720
Lys Val Ala Val Pro Met Arg Phe Asn Gly Lys Ser Gly Val Glu Val
            725                 730                 735
Arg Leu Pro Asn Asp Leu Glu Asp Leu Lys Gly Tyr Thr Ser Leu Ser
            740                 745                 750
Leu Phe Leu Gln Arg Pro Asn Ser Arg Glu Asn Gly Thr Glu Asn
            755                 760                 765
Met Phe Val Met Tyr Leu Gly Asn Lys Asp Ala Ser Arg Asp Tyr Ile
770                 775                 780
Gly Met Ala Val Val Asp Gly Gln Leu Thr Cys Val Tyr Asn Leu Gly
785                 790                 795                 800
Asp Arg Glu Ala Glu Leu Gln Val Asp Gln Ile Leu Thr Lys Ser Glu
            805                 810                 815
Thr Lys Glu Ala Val Met Asp Arg Val Lys Phe Gln Arg Ile Tyr Gln
            820                 825                 830
Phe Ala Arg Leu Asn Tyr Thr Lys Gly Ala Thr Ser Ser Lys Pro Glu
            835                 840                 845
Thr Pro Gly Val Tyr Asp Met Asp Gly Arg Asn Ser Asn Thr Leu Leu
            850                 855                 860
Asn Leu Asp Pro Glu Asn Val Val Phe Tyr Val Gly Gly Tyr Pro Pro
865                 870                 875                 880
Asp Phe Lys Leu Pro Ser Arg Leu Ser Phe Pro Pro Tyr Lys Gly Cys
            885                 890                 895
Ile Glu Leu Asp Asp Leu Asn Glu Asn Val Leu Ser Leu Tyr Asn Phe
            900                 905                 910
Lys Lys Thr Phe Asn Leu Asn Thr Thr Glu Val Glu Pro Cys Arg Arg
            915                 920                 925
Arg Lys Glu Glu Ser Asp Lys Asn Tyr Phe Glu Gly Thr Gly Tyr Ala
930                 935                 940
Arg Val Pro Thr Gln Pro His Ala Pro Ile Pro Thr Phe Gly Gln Thr
945                 950                 955                 960
Ile Gln Thr Thr Val Asp Arg Gly Leu Leu Phe Phe Ala Glu Asn Gly
            965                 970                 975
Asp Arg Phe Ile Ser Leu Asn Ile Glu Asp Gly Lys Leu Met Val Arg
```

-continued

Tyr Lys Leu Asn Ser Glu Leu Pro Lys Glu Arg Gly Val Gly Asp Ala
    980                 985                 990
                995                 1000                1005

Ile Asn Asn Gly Arg Asp His Ser Ile Gln Ile Lys Ile Gly Lys
    1010                1015                1020

Leu Gln Lys Arg Met Trp Ile Asn Val Asp Val Gln Asn Thr Ile
    1025                1030                1035

Ile Asp Gly Glu Val Phe Asp Phe Ser Thr Tyr Tyr Leu Gly Gly
    1040                1045                1050

Ile Pro Ile Ala Ile Arg Glu Arg Phe Asn Ile Ser Thr Pro Ala
    1055                1060                1065

Phe Arg Gly Cys Met Lys Asn Leu Lys Lys Thr Ser Gly Val Val
    1070                1075                1080

Arg Leu Asn Asp Thr Val Gly Val Thr Lys Lys Cys Ser Glu Asp
    1085                1090                1095

Trp Lys Leu Val Arg Ser Ala Ser Phe Ser Arg Gly Gly Gln Leu
    1100                1105                1110

Ser Phe Thr Asp Leu Gly Leu Pro Pro Thr Asp His Leu Gln Ala
    1115                1120                1125

Ser Phe Gly Phe Gln Thr Phe Gln Pro Ser Gly Ile Leu Leu Asp
    1130                1135                1140

His Gln Thr Trp Thr Arg Asn Leu Gln Val Thr Leu Glu Asp Gly
    1145                1150                1155

Tyr Ile Glu Leu Ser Thr Ser Asp Ser Gly Gly Pro Ile Phe Lys
    1160                1165                1170

Ser Pro Gln Thr Tyr Met Asp Gly Leu Leu His Tyr Val Ser Val
    1175                1180                1185

Ile Ser Asp Asn Ser Gly Leu Arg Leu Leu Ile Asp Asp Gln Leu
    1190                1195                1200

Leu Arg Asn Ser Lys Arg Leu Lys His Ile Ser Ser Ser Arg Gln
    1205                1210                1215

Ser Leu Arg Leu Gly Gly Ser Asn Phe Glu Gly Cys Ile Ser Asn
    1220                1225                1230

Val Phe Val Gln Arg Leu Ser Leu Ser Pro Glu Val Leu Asp Leu
    1235                1240                1245

Thr Ser Asn Ser Leu Lys Arg Asp Val Ser Leu Gly Gly Cys Ser
    1250                1255                1260

Leu Asn Lys Pro Pro Phe Leu Met Leu Leu Lys Gly Ser Thr Arg
    1265                1270                1275

Phe Asn Lys Thr Lys Thr Phe Arg Ile Asn Gln Leu Leu Gln Asp
    1280                1285                1290

Thr Pro Val Ala Ser Pro Arg Ser Val Lys Val Trp Gln Asp Ala
    1295                1300                1305

Cys Ser Pro Leu Pro Lys Thr Gln Ala Asn His Gly Ala Leu Gln
    1310                1315                1320

Phe Gly Asp Ile Pro Thr Ser His Leu Leu Phe Lys Leu Pro Gln
    1325                1330                1335

Glu Leu Leu Lys Pro Arg Ser Gln Phe Ala Val Asp Met Gln Thr
    1340                1345                1350

Thr Ser Ser Arg Gly Leu Val Phe His Thr Gly Thr Lys Asn Ser
    1355                1360                1365

Phe Met Ala Leu Tyr Leu Ser Lys Gly Arg Leu Val Phe Ala Leu
    1370                1375                1380

Gly Thr Asp Gly Lys Lys Leu Arg Ile Lys Ser Lys Glu Lys Cys
            1385                1390                1395

Asn Asp Gly Lys Trp His Thr Val Val Phe Gly His Asp Gly Glu
    1400                1405                1410

Lys Gly Arg Leu Val Val Asp Gly Leu Arg Ala Arg Glu Gly Ser
    1415                1420                1425

Leu Pro Gly Asn Ser Thr Ile Ser Ile Arg Ala Pro Val Tyr Leu
    1430                1435                1440

Gly Ser Pro Pro Ser Gly Lys Pro Lys Ser Leu Pro Thr Asn Ser
    1445                1450                1455

Phe Val Gly Cys Leu Lys Asn Phe Gln Leu Asp Ser Lys Pro Leu
    1460                1465                1470

Tyr Thr Pro Ser Ser Ser Phe Gly Val Ser Ser Cys Leu Gly Gly
    1475                1480                1485

Pro Leu Glu Lys Gly Ile Tyr Phe Ser Glu Gly Gly His Val
    1490                1495                1500

Val Leu Ala His Ser Val Leu Leu Gly Pro Glu Phe Lys Leu Val
    1505                1510                1515

Phe Ser Ile Arg Pro Arg Ser Leu Thr Gly Ile Leu Ile His Ile
    1520                1525                1530

Gly Ser Gln Pro Gly Lys His Leu Cys Val Tyr Leu Glu Ala Gly
    1535                1540                1545

Lys Val Thr Ala Ser Met Asp Ser Gly Ala Gly Thr Ser Thr
    1550                1555                1560

Ser Val Thr Pro Lys Gln Ser Leu Cys Asp Gly Gln Trp His Ser
    1565                1570                1575

Val Ala Val Thr Ile Lys Gln His Ile Leu His Leu Glu Leu Asp
    1580                1585                1590

Thr Asp Ser Ser Tyr Thr Ala Gly Gln Ile Pro Phe Pro Pro Ala
    1595                1600                1605

Ser Thr Gln Glu Pro Leu His Leu Gly Gly Ala Pro Ala Asn Leu
    1610                1615                1620

Thr Thr Leu Arg Ile Pro Val Trp Lys Ser Phe Phe Gly Cys Leu
    1625                1630                1635

Arg Asn Ile His Val Asn His His Ile Pro Val Pro Thr Glu Ala
    1640                1645                1650

Leu Glu Val Gln Gly Pro Val Ser Leu Asn Gly Cys Pro Asp Gln
    1655                1660                1665

<210> SEQ ID NO 32
<211> LENGTH: 488
<212> TYPE: PRT
<213> ORGANISM: Homo sapiens

<400> SEQUENCE: 32

Met Ala Ala Ala Ala Arg Pro Arg Gly Arg Ala Leu Gly Pro Val Leu
1               5                   10                  15

Pro Pro Thr Pro Leu Leu Leu Leu Val Leu Arg Val Leu Pro Ala Cys
                20                  25                  30

Gly Ala Thr Ala Arg Asp Pro Gly Ala Ala Ala Gly Leu Ser Leu His
            35                  40                  45

Pro Thr Tyr Phe Asn Leu Ala Glu Ala Ala Arg Ile Trp Ala Thr Ala
        50                  55                  60

Thr Cys Gly Glu Arg Gly Pro Gly Glu Gly Arg Pro Gln Pro Glu Leu

```
            65                  70                  75                  80
Tyr Cys Lys Leu Val Gly Gly Pro Thr Ala Pro Gly Ser Gly His Thr
                    85                  90                  95
Ile Gln Gly Gln Phe Cys Asp Tyr Cys Asn Ser Glu Asp Pro Arg Lys
                    100                 105                 110
Ala His Pro Val Thr Asn Ala Ile Asp Gly Ser Glu Arg Trp Trp Gln
                    115                 120                 125
Ser Pro Pro Leu Ser Ser Gly Thr Gln Tyr Asn Arg Val Asn Leu Thr
        130                 135                 140
Leu Asp Leu Gly Gln Leu Phe His Val Ala Tyr Ile Leu Ile Lys Phe
145                 150                 155                 160
Ala Asn Ser Pro Arg Pro Asp Leu Trp Val Leu Glu Arg Ser Val Asp
                    165                 170                 175
Phe Gly Ser Thr Tyr Ser Pro Trp Gln Tyr Phe Ala His Ser Lys Val
                    180                 185                 190
Asp Cys Leu Lys Glu Phe Gly Arg Glu Ala Asn Met Ala Val Thr Arg
            195                 200                 205
Asp Asp Asp Val Leu Cys Val Thr Glu Tyr Ser Arg Ile Val Pro Leu
        210                 215                 220
Glu Asn Gly Glu Val Val Val Ser Leu Ile Asn Gly Arg Pro Gly Ala
225                 230                 235                 240
Lys Asn Phe Thr Phe Ser His Thr Leu Arg Glu Phe Thr Lys Ala Thr
                245                 250                 255
Asn Ile Arg Leu Arg Phe Leu Arg Thr Asn Thr Leu Leu Gly His Leu
                260                 265                 270
Ile Ser Lys Ala Gln Arg Asp Pro Thr Val Thr Arg Arg Tyr Tyr Tyr
            275                 280                 285
Ser Ile Lys Asp Ile Ser Ile Gly Gly Gln Cys Val Cys Asn Gly His
        290                 295                 300
Ala Glu Val Cys Asn Ile Asn Asn Pro Glu Lys Leu Phe Arg Cys Glu
305                 310                 315                 320
Cys Gln His His Thr Cys Gly Glu Thr Cys Asp Arg Cys Cys Thr Gly
                325                 330                 335
Tyr Asn Gln Arg Arg Trp Arg Pro Ala Ala Trp Glu Gln Ser His Glu
                340                 345                 350
Cys Glu Ala Cys Asn Cys His Gly His Ala Ser Asn Cys Tyr Tyr Asp
            355                 360                 365
Pro Asp Val Glu Arg Gln Gln Ala Ser Leu Asn Thr Gln Gly Ile Tyr
        370                 375                 380
Ala Gly Gly Gly Val Cys Ile Asn Cys Gln His Asn Thr Ala Gly Val
385                 390                 395                 400
Asn Cys Glu Gln Cys Ala Lys Gly Tyr Tyr Arg Pro Tyr Gly Val Pro
                405                 410                 415
Val Asp Ala Pro Asp Gly Cys Ile Arg Lys Phe His Phe Lys Leu Val
            420                 425                 430
Tyr Leu Ser Leu Cys Val Leu Pro Gln Arg Ser His Gln Ala Asn Phe
        435                 440                 445
Gly Ser Val Asn Asn Phe Leu His Ala Leu Ser Leu Gln Ser Ile Ser
450                 455                 460
Cys Ala Arg Tyr Val Thr Ser Val Thr Tyr Thr Val Ser Leu Asn Phe
465                 470                 475                 480
Gly Phe Ile Ala Cys Lys Trp Lys
                485
```

<210> SEQ ID NO 33
<211> LENGTH: 1823
<212> TYPE: PRT
<213> ORGANISM: Homo sapiens

<400> SEQUENCE: 33

```
Met Ala Leu Ser Ser Ala Trp Arg Ser Val Leu Pro Leu Trp Leu Leu
1               5                   10                  15

Trp Ser Ala Ala Cys Ser Arg Ala Ala Ser Gly Asp Asp Asn Ala Phe
            20                  25                  30

Pro Phe Asp Ile Glu Gly Ser Ser Ala Val Gly Arg Gln Asp Pro Pro
        35                  40                  45

Glu Thr Ser Glu Pro Arg Val Ala Leu Gly Arg Leu Pro Pro Ala Ala
50                  55                  60

Glu Lys Cys Asn Ala Gly Phe Phe His Thr Leu Ser Gly Glu Cys Val
65                  70                  75                  80

Pro Cys Asp Cys Asn Gly Asn Ser Asn Glu Cys Leu Asp Gly Ser Gly
                85                  90                  95

Tyr Cys Val His Cys Gln Arg Asn Thr Thr Gly Glu His Cys Glu Lys
            100                 105                 110

Cys Leu Asp Gly Tyr Ile Gly Asp Ser Ile Arg Gly Ala Pro Gln Phe
        115                 120                 125

Cys Gln Pro Cys Pro Cys Pro Leu Pro His Leu Ala Asn Phe Ala Glu
    130                 135                 140

Ser Cys Tyr Arg Lys Asn Gly Ala Val Arg Cys Ile Cys Asn Glu Asn
145                 150                 155                 160

Tyr Ala Gly Pro Asn Cys Glu Arg Cys Ala Pro Gly Tyr Tyr Gly Asn
                165                 170                 175

Pro Leu Leu Ile Gly Ser Thr Cys Lys Lys Cys Asp Cys Ser Gly Asn
            180                 185                 190

Ser Asp Pro Asn Leu Ile Phe Glu Asp Cys Asp Glu Val Thr Gly Gln
        195                 200                 205

Cys Arg Asn Cys Leu Arg Asn Thr Thr Gly Phe Lys Cys Glu Arg Cys
    210                 215                 220

Ala Pro Gly Tyr Tyr Gly Asp Ala Arg Ile Ala Lys Asn Cys Ala Val
225                 230                 235                 240

Cys Asn Cys Gly Gly Gly Pro Cys Asp Ser Val Thr Gly Glu Cys Leu
                245                 250                 255

Glu Glu Gly Phe Glu Pro Pro Thr Gly Met Asp Cys Pro Thr Ile Ser
            260                 265                 270

Cys Asp Lys Cys Val Trp Asp Leu Thr Asp Asp Leu Arg Leu Ala Ala
        275                 280                 285

Leu Ser Ile Glu Glu Gly Lys Ser Gly Val Leu Ser Val Ser Ser Gly
    290                 295                 300

Ala Ala Ala His Arg His Val Asn Glu Ile Asn Ala Thr Ile Tyr Leu
305                 310                 315                 320

Leu Lys Thr Lys Leu Ser Glu Arg Glu Asn Gln Tyr Ala Leu Arg Lys
                325                 330                 335

Ile Gln Ile Asn Asn Ala Glu Asn Thr Met Lys Ser Leu Leu Ser Asp
            340                 345                 350

Val Glu Glu Leu Val Glu Lys Glu Asn Gln Ala Ser Arg Lys Gly Gln
        355                 360                 365

Leu Val Gln Lys Glu Ser Met Asp Thr Ile Asn His Ala Ser Gln Leu
```

```
                370                 375                 380
Val Glu Gln Ala His Asp Met Arg Asp Lys Ile Gln Glu Ile Asn Asn
385                 390                 395                 400

Lys Met Leu Tyr Tyr Gly Glu His Glu Leu Ser Pro Lys Glu Ile
            405                 410                 415

Ser Glu Lys Leu Val Leu Ala Gln Lys Met Leu Glu Ile Arg Ser
                420                 425                 430

Arg Gln Pro Phe Phe Thr Gln Arg Glu Leu Val Asp Glu Ala Asp
            435                 440                 445

Glu Ala Tyr Glu Leu Leu Ser Gln Ala Glu Ser Trp Gln Arg Leu His
        450                 455                 460

Asn Glu Thr Arg Thr Leu Phe Pro Val Val Leu Gln Leu Asp Asp
465                 470                 475                 480

Tyr Asn Ala Lys Leu Ser Asp Leu Gln Glu Ala Leu Asp Gln Ala Leu
                485                 490                 495

Asn Tyr Val Arg Asp Ala Glu Asp Met Asn Arg Ala Thr Ala Ala Arg
            500                 505                 510

Gln Arg Asp His Glu Lys Gln Gln Glu Arg Val Arg Glu Gln Met Glu
        515                 520                 525

Val Val Asn Met Ser Leu Ser Thr Ser Ala Asp Ser Leu Thr Thr Pro
530                 535                 540

Arg Leu Thr Leu Ser Glu Leu Asp Asp Ile Ile Lys Asn Ala Ser Gly
545                 550                 555                 560

Ile Tyr Ala Glu Ile Asp Gly Ala Lys Ser Glu Leu Gln Val Lys Leu
                565                 570                 575

Ser Asn Leu Ser Asn Leu Ser His Asp Leu Val Gln Glu Ala Ile Asp
            580                 585                 590

His Ala Gln Asp Leu Gln Gln Glu Ala Asn Glu Leu Ser Arg Lys Leu
        595                 600                 605

His Ser Ser Asp Met Asn Gly Leu Val Gln Lys Ala Leu Asp Ala Ser
610                 615                 620

Asn Val Tyr Glu Asn Ile Val Asn Tyr Val Ser Glu Ala Asn Glu Thr
625                 630                 635                 640

Ala Glu Phe Ala Leu Asn Thr Thr Asp Arg Ile Tyr Asp Ala Val Ser
                645                 650                 655

Gly Ile Asp Thr Gln Ile Ile Tyr His Lys Asp Glu Ser Glu Asn Leu
            660                 665                 670

Leu Asn Gln Ala Arg Glu Leu Gln Ala Lys Ala Glu Ser Ser Ser Asp
        675                 680                 685

Glu Ala Val Ala Asp Thr Ser Arg Arg Val Gly Gly Ala Leu Ala Arg
690                 695                 700

Lys Ser Ala Leu Lys Thr Arg Leu Ser Asp Ala Val Lys Gln Leu Gln
705                 710                 715                 720

Ala Ala Glu Arg Gly Asp Ala Gln Gln Arg Leu Gly Gln Ser Arg Leu
                725                 730                 735

Ile Thr Glu Glu Ala Asn Arg Thr Thr Met Glu Val Gln Gln Ala Thr
            740                 745                 750

Ala Pro Met Ala Asn Asn Leu Thr Asn Trp Ser Gln Asn Leu Gln His
        755                 760                 765

Phe Asp Ser Ser Ala Tyr Asn Thr Ala Val Asn Ser Ala Arg Asp Ala
770                 775                 780

Val Arg Asn Leu Thr Glu Val Val Pro Gln Leu Leu Asp Gln Leu Arg
785                 790                 795                 800
```

Thr Val Glu Gln Lys Arg Pro Ala Ser Asn Val Ser Ala Ser Ile Gln
                    805                 810                 815

Arg Ile Arg Glu Leu Ile Ala Gln Thr Arg Ser Val Ala Ser Lys Ile
                    820                 825                 830

Gln Val Ser Met Met Phe Asp Gly Gln Ser Ala Val Glu Val His Ser
                    835                 840                 845

Arg Thr Ser Met Asp Asp Leu Lys Ala Phe Thr Ser Leu Ser Leu Tyr
850                 855                 860

Met Lys Pro Pro Val Lys Arg Pro Glu Leu Thr Glu Thr Ala Asp Gln
865                 870                 875                 880

Phe Ile Leu Tyr Leu Gly Ser Lys Asn Ala Lys Lys Glu Tyr Met Gly
                    885                 890                 895

Leu Ala Ile Lys Asn Asp Asn Leu Val Tyr Val Tyr Asn Leu Gly Thr
                    900                 905                 910

Lys Asp Val Glu Ile Pro Leu Asp Ser Lys Pro Val Ser Ser Trp Pro
                    915                 920                 925

Ala Tyr Phe Ser Ile Val Lys Ile Glu Arg Val Gly Lys His Gly Lys
                    930                 935                 940

Val Phe Leu Thr Val Pro Ser Leu Ser Ser Thr Ala Glu Glu Lys Phe
945                 950                 955                 960

Ile Lys Lys Gly Glu Phe Ser Gly Asp Asp Ser Leu Leu Asp Leu Asp
                    965                 970                 975

Pro Glu Asp Thr Val Phe Tyr Val Gly Gly Val Pro Ser Asn Phe Lys
                    980                 985                 990

Leu Pro Thr Ser Leu Asn Leu Pro Gly Phe Val Gly Cys Leu Glu Leu
                    995                 1000                1005

Ala Thr Leu Asn Asn Asp Val Ile Ser Leu Tyr Asn Phe Lys His
                    1010                1015                1020

Ile Tyr Asn Met Asp Pro Ser Thr Ser Val Pro Cys Ala Arg Asp
                    1025                1030                1035

Lys Leu Ala Phe Thr Gln Ser Arg Ala Ala Ser Tyr Phe Phe Asp
                    1040                1045                1050

Gly Ser Gly Tyr Ala Val Val Arg Asp Ile Thr Arg Arg Gly Lys
                    1055                1060                1065

Phe Gly Gln Val Thr Arg Phe Asp Ile Glu Val Arg Thr Pro Ala
                    1070                1075                1080

Asp Asn Gly Leu Ile Leu Leu Met Val Asn Gly Ser Met Phe Phe
                    1085                1090                1095

Arg Leu Glu Met Arg Asn Gly Tyr Leu His Val Phe Tyr Asp Phe
                    1100                1105                1110

Gly Phe Ser Gly Gly Pro Val His Leu Glu Asp Thr Leu Lys Lys
                    1115                1120                1125

Ala Gln Ile Asn Asp Ala Lys Tyr His Glu Ile Ser Ile Ile Tyr
                    1130                1135                1140

His Asn Asp Lys Lys Met Ile Leu Val Val Asp Arg Arg His Val
                    1145                1150                1155

Lys Ser Met Asp Asn Glu Lys Met Lys Ile Pro Phe Thr Asp Ile
                    1160                1165                1170

Tyr Ile Gly Gly Ala Pro Pro Glu Ile Leu Gln Ser Arg Ala Leu
                    1175                1180                1185

Arg Ala His Leu Pro Leu Asp Ile Asn Phe Arg Gly Cys Met Lys
                    1190                1195                1200

```
Gly Phe Gln Phe Gln Lys Lys Asp Phe Asn Leu Leu Glu Gln Thr
    1205                1210                1215
Glu Thr Leu Gly Val Gly Tyr Gly Cys Pro Glu Asp Ser Leu Ile
    1220                1225                1230
Ser Arg Arg Ala Tyr Phe Asn Gly Gln Ser Phe Ile Ala Ser Ile
    1235                1240                1245
Gln Lys Ile Ser Phe Phe Asp Gly Phe Glu Gly Gly Phe Asn Phe
    1250                1255                1260
Arg Thr Leu Gln Pro Asn Gly Leu Leu Phe Tyr Tyr Ala Ser Gly
    1265                1270                1275
Ser Asp Val Phe Ser Ile Ser Leu Asp Asn Gly Thr Val Ile Met
    1280                1285                1290
Asp Val Lys Gly Ile Lys Val Gln Ser Val Asp Lys Gln Tyr Asn
    1295                1300                1305
Asp Gly Leu Ser His Phe Val Ile Ser Ser Val Ser Pro Thr Arg
    1310                1315                1320
Tyr Glu Leu Ile Val Asp Lys Ser Arg Val Gly Ser Lys Asn Pro
    1325                1330                1335
Thr Lys Gly Lys Ile Glu Gln Thr Gln Ala Ser Glu Lys Lys Phe
    1340                1345                1350
Tyr Phe Gly Gly Ser Pro Ile Ser Ala Gln Tyr Ala Asn Phe Thr
    1355                1360                1365
Gly Cys Ile Ser Asn Ala Tyr Phe Thr Arg Val Asp Arg Asp Val
    1370                1375                1380
Glu Val Glu Asp Phe Gln Arg Tyr Thr Glu Lys Val His Thr Ser
    1385                1390                1395
Leu Tyr Glu Cys Pro Ile Glu Ser Ser Pro Leu Phe Leu Leu His
    1400                1405                1410
Lys Lys Gly Lys Asn Leu Ser Lys Pro Lys Ala Ser Gln Asn Lys
    1415                1420                1425
Lys Gly Gly Lys Ser Lys Asp Ala Pro Ser Trp Asp Pro Val Ala
    1430                1435                1440
Leu Lys Leu Pro Glu Arg Asn Thr Pro Arg Asn Ser His Cys His
    1445                1450                1455
Leu Ser Asn Ser Pro Arg Ala Ile Glu His Ala Tyr Gln Tyr Gly
    1460                1465                1470
Gly Thr Ala Asn Ser Arg Gln Glu Phe Glu His Leu Lys Gly Asp
    1475                1480                1485
Phe Gly Ala Lys Ser Gln Phe Ser Ile Arg Leu Arg Thr Arg Ser
    1490                1495                1500
Ser His Gly Met Ile Phe Tyr Val Ser Asp Gln Glu Glu Asn Asp
    1505                1510                1515
Phe Met Thr Leu Phe Leu Ala His Gly Arg Leu Val Tyr Met Phe
    1520                1525                1530
Asn Val Gly His Lys Lys Leu Lys Ile Arg Ser Gln Glu Lys Tyr
    1535                1540                1545
Asn Asp Gly Leu Trp His Asp Val Ile Phe Ile Arg Glu Arg Ser
    1550                1555                1560
Ser Gly Arg Leu Val Ile Asp Gly Leu Arg Val Leu Glu Glu Ser
    1565                1570                1575
Leu Pro Pro Thr Glu Ala Thr Trp Lys Ile Lys Gly Pro Ile Tyr
    1580                1585                1590
Leu Gly Gly Val Ala Pro Gly Lys Ala Val Lys Asn Val Gln Ile
```

```
                1595                1600                1605

Asn Ser Ile Tyr Ser Phe Ser Gly Cys Leu Ser Asn Leu Gln Leu
    1610                1615                1620

Asn Gly Ala Ser Ile Thr Ser Ala Ser Gln Thr Phe Ser Val Thr
    1625                1630                1635

Pro Cys Phe Glu Gly Pro Met Glu Thr Gly Thr Tyr Phe Ser Thr
    1640                1645                1650

Glu Gly Gly Tyr Val Val Leu Asp Glu Ser Phe Asn Ile Gly Leu
    1655                1660                1665

Lys Phe Glu Ile Ala Phe Glu Val Arg Pro Arg Ser Ser Ser Gly
    1670                1675                1680

Thr Leu Val His Gly His Ser Val Asn Gly Glu Tyr Leu Asn Val
    1685                1690                1695

His Met Lys Asn Gly Gln Val Ile Val Lys Val Asn Asn Gly Ile
    1700                1705                1710

Arg Asp Phe Ser Thr Ser Val Thr Pro Lys Gln Ser Leu Cys Asp
    1715                1720                1725

Gly Arg Trp His Arg Ile Thr Val Ile Arg Asp Ser Asn Val Val
    1730                1735                1740

Gln Leu Asp Val Asp Ser Glu Val Asn His Val Val Gly Pro Leu
    1745                1750                1755

Asn Pro Lys Pro Ile Asp His Arg Glu Pro Val Phe Val Gly Gly
    1760                1765                1770

Val Pro Glu Ser Leu Leu Thr Pro Arg Leu Ala Pro Ser Lys Pro
    1775                1780                1785

Phe Thr Gly Cys Ile Arg His Phe Val Ile Asp Gly His Pro Val
    1790                1795                1800

Ser Phe Ser Lys Ala Ala Leu Val Ser Gly Ala Val Ser Ile Asn
    1805                1810                1815

Ser Cys Pro Ala Ala
    1820

<210> SEQ ID NO 34
<211> LENGTH: 1816
<212> TYPE: PRT
<213> ORGANISM: Homo sapiens

<400> SEQUENCE: 34

Met Ala Leu Ser Ser Ala Trp Arg Ser Val Leu Pro Leu Trp Leu Leu
1               5                   10                  15

Trp Ser Ala Ala Cys Ser Arg Ala Ala Ser Gly Asp Asp Asn Ala Phe
                20                  25                  30

Pro Phe Asp Ile Glu Gly Ser Ser Ala Val Gly Arg Gln Asp Pro Pro
            35                  40                  45

Glu Thr Ser Glu Pro Arg Val Ala Leu Gly Arg Leu Pro Pro Ala Ala
        50                  55                  60

Glu Lys Cys Asn Ala Gly Phe Phe His Thr Leu Ser Gly Glu Cys Val
65                  70                  75                  80

Pro Cys Asp Cys Asn Gly Asn Ser Asn Glu Cys Leu Asp Gly Ser Gly
                85                  90                  95

Tyr Cys Val His Cys Gln Arg Asn Thr Thr Gly Glu His Cys Glu Lys
            100                 105                 110

Cys Leu Asp Gly Tyr Ile Gly Asp Ser Ile Arg Gly Ala Pro Gln Phe
        115                 120                 125
```

```
Cys Gln Pro Cys Pro Cys Pro Leu Pro His Leu Ala Asn Phe Ala Glu
    130                 135                 140

Ser Cys Tyr Arg Lys Asn Gly Ala Val Arg Cys Ile Cys Asn Glu Asn
145                 150                 155                 160

Tyr Ala Gly Pro Asn Cys Glu Arg Cys Ala Pro Gly Tyr Tyr Gly Asn
                165                 170                 175

Pro Leu Leu Ile Gly Ser Thr Cys Lys Lys Cys Asp Cys Ser Gly Asn
            180                 185                 190

Ser Asp Pro Asn Leu Ile Phe Glu Asp Cys Asp Glu Val Thr Gly Gln
        195                 200                 205

Cys Arg Asn Cys Leu Arg Asn Thr Thr Gly Phe Lys Cys Glu Arg Cys
    210                 215                 220

Ala Pro Gly Tyr Tyr Gly Asp Ala Arg Ile Ala Lys Asn Cys Ala Val
225                 230                 235                 240

Cys Asn Cys Gly Gly Gly Pro Cys Asp Ser Val Thr Gly Glu Cys Leu
                245                 250                 255

Glu Glu Gly Phe Glu Pro Pro Thr Gly Cys Asp Lys Cys Val Trp Asp
            260                 265                 270

Leu Thr Asp Asp Leu Arg Leu Ala Ala Leu Ser Ile Glu Glu Gly Lys
        275                 280                 285

Ser Gly Val Leu Ser Val Ser Ser Gly Ala Ala Ala His Arg His Val
    290                 295                 300

Asn Glu Ile Asn Ala Thr Ile Tyr Leu Leu Lys Thr Lys Leu Ser Glu
305                 310                 315                 320

Arg Glu Asn Gln Tyr Ala Leu Arg Lys Ile Gln Ile Asn Asn Ala Glu
                325                 330                 335

Asn Thr Met Lys Ser Leu Leu Ser Asp Val Glu Glu Leu Val Glu Lys
            340                 345                 350

Glu Asn Gln Ala Ser Arg Lys Gly Gln Leu Val Gln Lys Glu Ser Met
        355                 360                 365

Asp Thr Ile Asn His Ala Ser Gln Leu Val Glu Gln Ala His Asp Met
    370                 375                 380

Arg Asp Lys Ile Gln Glu Ile Asn Asn Lys Met Leu Tyr Tyr Gly Glu
385                 390                 395                 400

Glu His Glu Leu Ser Pro Lys Glu Ile Ser Glu Lys Leu Val Leu Ala
                405                 410                 415

Gln Lys Met Leu Glu Glu Ile Arg Ser Arg Gln Pro Phe Phe Thr Gln
            420                 425                 430

Arg Glu Leu Val Asp Glu Glu Ala Asp Glu Ala Tyr Glu Leu Leu Ser
        435                 440                 445

Gln Ala Glu Ser Trp Gln Arg Leu His Asn Glu Thr Arg Thr Leu Phe
    450                 455                 460

Pro Val Val Leu Glu Gln Leu Asp Asp Tyr Asn Ala Lys Leu Ser Asp
465                 470                 475                 480

Leu Gln Glu Ala Leu Asp Gln Ala Leu Asn Tyr Val Arg Asp Ala Glu
                485                 490                 495

Asp Met Asn Arg Ala Thr Ala Ala Arg Gln Arg Asp His Glu Lys Gln
            500                 505                 510

Gln Glu Arg Val Arg Glu Gln Met Glu Val Val Asn Met Ser Leu Ser
        515                 520                 525

Thr Ser Ala Asp Ser Leu Thr Thr Pro Arg Leu Thr Leu Ser Glu Leu
    530                 535                 540

Asp Asp Ile Ile Lys Asn Ala Ser Gly Ile Tyr Ala Glu Ile Asp Gly
```

```
            545                 550                 555                 560
        Ala Lys Ser Glu Leu Gln Val Lys Leu Ser Asn Leu Ser Asn Leu Ser
                        565                 570                 575

His Asp Leu Val Gln Glu Ala Ile Asp His Ala Gln Asp Leu Gln Gln
                        580                 585                 590

Glu Ala Asn Glu Leu Ser Arg Lys Leu His Ser Ser Asp Met Asn Gly
                        595                 600                 605

Leu Val Gln Lys Ala Leu Asp Ala Ser Asn Val Tyr Glu Asn Ile Val
                        610                 615                 620

Asn Tyr Val Ser Glu Ala Asn Glu Thr Ala Glu Phe Ala Leu Asn Thr
        625                 630                 635                 640

Thr Asp Arg Ile Tyr Asp Ala Val Ser Gly Ile Asp Thr Gln Ile Ile
                        645                 650                 655

Tyr His Lys Asp Glu Ser Glu Asn Leu Leu Asn Gln Ala Arg Glu Leu
                        660                 665                 670

Gln Ala Lys Ala Glu Ser Ser Ser Asp Glu Ala Val Ala Asp Thr Ser
                        675                 680                 685

Arg Arg Val Gly Gly Ala Leu Ala Arg Lys Ser Ala Leu Lys Thr Arg
        690                 695                 700

Leu Ser Asp Ala Val Lys Gln Leu Gln Ala Ala Glu Arg Gly Asp Ala
        705                 710                 715                 720

Gln Gln Arg Leu Gly Gln Ser Arg Leu Ile Thr Glu Glu Ala Asn Arg
                        725                 730                 735

Thr Thr Met Glu Val Gln Gln Ala Thr Ala Pro Met Ala Asn Asn Leu
                        740                 745                 750

Thr Asn Trp Ser Gln Asn Leu Gln His Phe Asp Ser Ser Ala Tyr Asn
                        755                 760                 765

Thr Ala Val Asn Ser Ala Arg Asp Ala Val Arg Asn Leu Thr Glu Val
                        770                 775                 780

Val Pro Gln Leu Leu Asp Gln Leu Arg Thr Val Glu Gln Lys Arg Pro
        785                 790                 795                 800

Ala Ser Asn Val Ser Ala Ser Ile Gln Arg Ile Arg Glu Leu Ile Ala
                        805                 810                 815

Gln Thr Arg Ser Val Ala Ser Lys Ile Gln Val Ser Met Met Phe Asp
                        820                 825                 830

Gly Gln Ser Ala Val Glu Val His Ser Arg Thr Ser Met Asp Asp Leu
                        835                 840                 845

Lys Ala Phe Thr Ser Leu Ser Leu Tyr Met Lys Pro Pro Val Lys Arg
                        850                 855                 860

Pro Glu Leu Thr Glu Thr Ala Asp Gln Phe Ile Leu Tyr Leu Gly Ser
        865                 870                 875                 880

Lys Asn Ala Lys Lys Glu Tyr Met Gly Leu Ala Ile Lys Asn Asp Asn
                        885                 890                 895

Leu Val Tyr Val Tyr Asn Leu Gly Thr Lys Asp Val Glu Ile Pro Leu
                        900                 905                 910

Asp Ser Lys Pro Val Ser Ser Trp Pro Ala Tyr Phe Ser Ile Val Lys
                        915                 920                 925

Ile Glu Arg Val Gly Lys His Gly Lys Val Phe Leu Thr Val Pro Ser
                        930                 935                 940

Leu Ser Ser Thr Ala Glu Glu Lys Phe Ile Lys Lys Gly Glu Phe Ser
        945                 950                 955                 960

Gly Asp Asp Ser Leu Leu Asp Leu Asp Pro Glu Asp Thr Val Phe Tyr
                        965                 970                 975
```

-continued

```
Val Gly Gly Val Pro Ser Asn Phe Lys Leu Pro Thr Ser Leu Asn Leu
            980                 985                 990

Pro Gly Phe Val Gly Cys Leu Glu Leu Ala Thr Leu Asn Asn Asp Val
        995                1000                1005

Ile Ser Leu Tyr Asn Phe Lys His Ile Tyr Asn Met Asp Pro Ser
    1010                1015                1020

Thr Ser Val Pro Cys Ala Arg Asp Lys Leu Ala Phe Thr Gln Ser
    1025                1030                1035

Arg Ala Ala Ser Tyr Phe Phe Asp Gly Ser Gly Tyr Ala Val Val
    1040                1045                1050

Arg Asp Ile Thr Arg Arg Gly Lys Phe Gly Gln Val Thr Arg Phe
    1055                1060                1065

Asp Ile Glu Val Arg Thr Pro Ala Asp Asn Gly Leu Ile Leu Leu
    1070                1075                1080

Met Val Asn Gly Ser Met Phe Phe Arg Leu Glu Met Arg Asn Gly
    1085                1090                1095

Tyr Leu His Val Phe Tyr Asp Phe Gly Phe Ser Gly Gly Pro Val
    1100                1105                1110

His Leu Glu Asp Thr Leu Lys Lys Ala Gln Ile Asn Asp Ala Lys
    1115                1120                1125

Tyr His Glu Ile Ser Ile Ile Tyr His Asn Asp Lys Lys Met Ile
    1130                1135                1140

Leu Val Val Asp Arg Arg His Val Lys Ser Met Asp Asn Glu Lys
    1145                1150                1155

Met Lys Ile Pro Phe Thr Asp Ile Tyr Ile Gly Gly Ala Pro Pro
    1160                1165                1170

Glu Ile Leu Gln Ser Arg Ala Leu Arg Ala His Leu Pro Leu Asp
    1175                1180                1185

Ile Asn Phe Arg Gly Cys Met Lys Gly Phe Gln Phe Gln Lys Lys
    1190                1195                1200

Asp Phe Asn Leu Leu Glu Gln Thr Glu Thr Leu Gly Val Gly Tyr
    1205                1210                1215

Gly Cys Pro Glu Asp Ser Leu Ile Ser Arg Arg Ala Tyr Phe Asn
    1220                1225                1230

Gly Gln Ser Phe Ile Ala Ser Ile Gln Lys Ile Ser Phe Phe Asp
    1235                1240                1245

Gly Phe Glu Gly Gly Phe Asn Phe Arg Thr Leu Gln Pro Asn Gly
    1250                1255                1260

Leu Leu Phe Tyr Tyr Ala Ser Gly Ser Asp Val Phe Ser Ile Ser
    1265                1270                1275

Leu Asp Asn Gly Thr Val Ile Met Asp Val Lys Gly Ile Lys Val
    1280                1285                1290

Gln Ser Val Asp Lys Gln Tyr Asn Asp Gly Leu Ser His Phe Val
    1295                1300                1305

Ile Ser Ser Val Ser Pro Thr Arg Tyr Glu Leu Ile Val Asp Lys
    1310                1315                1320

Ser Arg Val Gly Ser Lys Asn Pro Thr Lys Gly Lys Ile Glu Gln
    1325                1330                1335

Thr Gln Ala Ser Glu Lys Lys Phe Tyr Phe Gly Gly Ser Pro Ile
    1340                1345                1350

Ser Ala Gln Tyr Ala Asn Phe Thr Gly Cys Ile Ser Asn Ala Tyr
    1355                1360                1365
```

```
Phe Thr Arg Val Asp Arg Asp Val Glu Val Glu Asp Phe Gln Arg
1370                 1375                1380

Tyr Thr Glu Lys Val His Thr Ser Leu Tyr Glu Cys Pro Ile Glu
1385                 1390                1395

Ser Ser Pro Leu Phe Leu Leu His Lys Lys Gly Lys Asn Leu Ser
1400                 1405                1410

Lys Pro Lys Ala Ser Gln Asn Lys Lys Gly Gly Lys Ser Lys Asp
1415                 1420                1425

Ala Pro Ser Trp Asp Pro Val Ala Leu Lys Leu Pro Glu Arg Asn
1430                 1435                1440

Thr Pro Arg Asn Ser His Cys His Leu Ser Asn Ser Pro Arg Ala
1445                 1450                1455

Ile Glu His Ala Tyr Gln Tyr Gly Gly Thr Ala Asn Ser Arg Gln
1460                 1465                1470

Glu Phe Glu His Leu Lys Gly Asp Phe Gly Ala Lys Ser Gln Phe
1475                 1480                1485

Ser Ile Arg Leu Arg Thr Arg Ser Ser His Gly Met Ile Phe Tyr
1490                 1495                1500

Val Ser Asp Gln Glu Glu Asn Asp Phe Met Thr Leu Phe Leu Ala
1505                 1510                1515

His Gly Arg Leu Val Tyr Met Phe Asn Val Gly His Lys Lys Leu
1520                 1525                1530

Lys Ile Arg Ser Gln Glu Lys Tyr Asn Asp Gly Leu Trp His Asp
1535                 1540                1545

Val Ile Phe Ile Arg Glu Arg Ser Ser Gly Arg Leu Val Ile Asp
1550                 1555                1560

Gly Leu Arg Val Leu Glu Glu Ser Leu Pro Pro Thr Glu Ala Thr
1565                 1570                1575

Trp Lys Ile Lys Gly Pro Ile Tyr Leu Gly Gly Val Ala Pro Gly
1580                 1585                1590

Lys Ala Val Lys Asn Val Gln Ile Asn Ser Ile Tyr Ser Phe Ser
1595                 1600                1605

Gly Cys Leu Ser Asn Leu Gln Leu Asn Gly Ala Ser Ile Thr Ser
1610                 1615                1620

Ala Ser Gln Thr Phe Ser Val Thr Pro Cys Phe Glu Gly Pro Met
1625                 1630                1635

Glu Thr Gly Thr Tyr Phe Ser Thr Glu Gly Gly Tyr Val Val Leu
1640                 1645                1650

Asp Glu Ser Phe Asn Ile Gly Leu Lys Phe Glu Ile Ala Phe Glu
1655                 1660                1665

Val Arg Pro Arg Ser Ser Ser Gly Thr Leu Val His Gly His Ser
1670                 1675                1680

Val Asn Gly Glu Tyr Leu Asn Val His Met Lys Asn Gly Gln Val
1685                 1690                1695

Ile Val Lys Val Asn Asn Gly Ile Arg Asp Phe Ser Thr Ser Val
1700                 1705                1710

Thr Pro Lys Gln Ser Leu Cys Asp Gly Arg Trp His Arg Ile Thr
1715                 1720                1725

Val Ile Arg Asp Ser Asn Val Val Gln Leu Asp Val Asp Ser Glu
1730                 1735                1740

Val Asn His Val Val Gly Pro Leu Asn Pro Lys Pro Ile Asp His
1745                 1750                1755

Arg Glu Pro Val Phe Val Gly Gly Val Pro Glu Ser Leu Leu Thr
```

-continued

```
              1760                1765                1770

Pro Arg Leu Ala Pro Ser Lys Pro Phe Thr Gly Cys Ile Arg His
        1775                1780                1785

Phe Val Ile Asp Gly His Pro Val Ser Phe Ser Lys Ala Ala Leu
        1790                1795                1800

Val Ser Gly Ala Val Ser Ile Asn Ser Cys Pro Ala Ala
        1805                1810                1815

<210> SEQ ID NO 35
<211> LENGTH: 120
<212> TYPE: PRT
<213> ORGANISM: Homo sapiens

<400> SEQUENCE: 35

Met Ala Leu Ser Ser Ala Trp Arg Ser Val Leu Pro Leu Trp Leu
1               5                   10                  15

Trp Ser Ala Ala Cys Ser Arg Ala Ala Ser Gly Asp Asp Asn Ala Phe
                20                  25                  30

Pro Phe Asp Ile Glu Gly Ser Ser Ala Val Gly Arg Gln Asp Pro Pro
            35                  40                  45

Glu Thr Ser Glu Pro Arg Val Ala Leu Gly Arg Leu Pro Pro Ala Ala
    50                  55                  60

Glu Val Gln Cys Pro Cys His Cys His Pro Ala Gly Ala Pro Ala Pro
65                  70                  75                  80

Pro Arg Ala Val Pro His Ser Ser Phe Ser Leu Ser Pro Pro Leu Ser
                85                  90                  95

Ser Pro Gln Cys Leu Glu Ser Phe Thr Trp Ala Arg Ser Val Arg Lys
            100                 105                 110

Leu Glu Ile Lys Ser Phe Pro Leu
        115                 120

<210> SEQ ID NO 36
<211> LENGTH: 3695
<212> TYPE: PRT
<213> ORGANISM: Homo sapiens

<400> SEQUENCE: 36

Met Ala Lys Arg Leu Cys Ala Gly Ser Ala Leu Cys Val Arg Gly Pro
1               5                   10                  15

Arg Gly Pro Ala Pro Leu Leu Leu Val Gly Leu Ala Leu Leu Gly Ala
                20                  25                  30

Ala Arg Ala Arg Glu Glu Ala Gly Gly Gly Phe Ser Leu His Pro Pro
            35                  40                  45

Tyr Phe Asn Leu Ala Glu Gly Ala Arg Ile Ala Ala Ser Ala Thr Cys
    50                  55                  60

Gly Glu Glu Ala Pro Ala Arg Gly Ser Pro Arg Pro Thr Glu Asp Leu
65                  70                  75                  80

Tyr Cys Lys Leu Val Gly Gly Pro Val Ala Gly Asp Pro Asn Gln
                85                  90                  95

Thr Ile Arg Gly Gln Tyr Cys Asp Ile Cys Thr Ala Ala Asn Ser Asn
            100                 105                 110

Lys Ala His Pro Ala Ser Asn Ala Ile Asp Gly Thr Glu Arg Trp Trp
        115                 120                 125

Gln Ser Pro Pro Leu Ser Arg Gly Leu Glu Tyr Asn Glu Val Asn Val
    130                 135                 140

Thr Leu Asp Leu Gly Gln Val Phe His Val Ala Tyr Val Leu Ile Lys
```

```
            145                 150                 155                 160
        Phe Ala Asn Ser Pro Arg Pro Asp Leu Trp Val Leu Glu Arg Ser Met
                        165                 170                 175
        Asp Phe Gly Arg Thr Tyr Gln Pro Trp Gln Phe Phe Ala Ser Ser Lys
                        180                 185                 190
        Arg Asp Cys Leu Glu Arg Phe Gly Pro Gln Thr Leu Glu Arg Ile Thr
                        195                 200                 205
        Arg Asp Asp Ala Ala Ile Cys Thr Thr Glu Tyr Ser Arg Ile Val Pro
                        210                 215                 220
        Leu Glu Asn Gly Glu Ile Val Val Ser Leu Val Asn Gly Arg Pro Gly
        225                 230                 235                 240
        Ala Met Asn Phe Ser Tyr Ser Pro Leu Leu Arg Glu Phe Thr Lys Ala
                        245                 250                 255
        Thr Asn Val Arg Leu Arg Phe Leu Arg Thr Asn Thr Leu Leu Gly His
                        260                 265                 270
        Leu Met Gly Lys Ala Leu Arg Asp Pro Thr Val Thr Arg Arg Tyr Tyr
                        275                 280                 285
        Tyr Ser Ile Lys Asp Ile Ser Ile Gly Gly Arg Cys Val Cys His Gly
                        290                 295                 300
        His Ala Asp Ala Cys Asp Ala Lys Asp Pro Thr Asp Pro Phe Arg Leu
        305                 310                 315                 320
        Gln Cys Thr Cys Gln His Asn Thr Cys Gly Gly Thr Cys Asp Arg Cys
                        325                 330                 335
        Cys Pro Gly Phe Asn Gln Gln Pro Trp Lys Pro Ala Thr Ala Asn Ser
                        340                 345                 350
        Ala Asn Glu Cys Gln Ser Cys Asn Cys Tyr Gly His Ala Thr Asp Cys
                        355                 360                 365
        Tyr Tyr Asp Pro Glu Val Asp Arg Arg Arg Ala Ser Gln Ser Leu Asp
                        370                 375                 380
        Gly Thr Tyr Gln Gly Gly Gly Val Cys Ile Asp Cys Gln His His Thr
        385                 390                 395                 400
        Thr Gly Val Asn Cys Glu Arg Cys Leu Pro Gly Phe Tyr Arg Ser Pro
                        405                 410                 415
        Asn His Pro Leu Asp Ser Pro His Val Cys Arg Arg Cys Asn Cys Glu
                        420                 425                 430
        Ser Asp Phe Thr Asp Gly Thr Cys Glu Asp Leu Thr Gly Arg Cys Tyr
                        435                 440                 445
        Cys Arg Pro Asn Phe Ser Gly Glu Arg Cys Asp Val Cys Ala Glu Gly
                        450                 455                 460
        Phe Thr Gly Phe Pro Ser Cys Tyr Pro Thr Pro Ser Ser Ser Asn Asp
        465                 470                 475                 480
        Thr Arg Glu Gln Val Leu Pro Ala Gly Gln Ile Val Asn Cys Asp Cys
                        485                 490                 495
        Ser Ala Ala Gly Thr Gln Gly Asn Ala Cys Arg Lys Asp Pro Arg Val
                        500                 505                 510
        Gly Arg Cys Leu Cys Lys Pro Asn Phe Gln Gly Thr His Cys Glu Leu
                        515                 520                 525
        Cys Ala Pro Gly Phe Tyr Gly Pro Gly Cys Gln Pro Cys Gln Cys Ser
                        530                 535                 540
        Ser Pro Gly Val Ala Asp Asp Arg Cys Asp Pro Asp Thr Gly Gln Cys
        545                 550                 555                 560
        Arg Cys Arg Val Gly Phe Glu Gly Ala Thr Cys Asp Arg Cys Ala Pro
                        565                 570                 575
```

```
Gly Tyr Phe His Phe Pro Leu Cys Gln Leu Cys Gly Cys Ser Pro Ala
            580                 585                 590

Gly Thr Leu Pro Glu Gly Cys Asp Glu Ala Gly Arg Cys Leu Cys Gln
            595                 600                 605

Pro Glu Phe Ala Gly Pro His Cys Asp Arg Cys Arg Pro Gly Tyr His
            610                 615                 620

Gly Phe Pro Asn Cys Gln Ala Cys Thr Cys Asp Pro Arg Gly Ala Leu
625                 630                 635                 640

Asp Gln Leu Cys Gly Ala Gly Gly Leu Cys Arg Cys Arg Pro Gly Tyr
                645                 650                 655

Thr Gly Thr Ala Cys Gln Glu Cys Ser Pro Gly Phe His Gly Phe Pro
            660                 665                 670

Ser Cys Val Pro Cys His Cys Ser Ala Glu Gly Ser Leu His Ala Ala
            675                 680                 685

Cys Asp Pro Arg Ser Gly Gln Cys Ser Cys Arg Pro Arg Val Thr Gly
            690                 695                 700

Leu Arg Cys Asp Thr Cys Val Pro Gly Ala Tyr Asn Phe Pro Tyr Cys
705                 710                 715                 720

Glu Ala Gly Ser Cys His Pro Ala Gly Leu Ala Pro Val Asp Pro Ala
                725                 730                 735

Leu Pro Glu Ala Gln Val Pro Cys Met Cys Arg Ala His Val Glu Gly
            740                 745                 750

Pro Ser Cys Asp Arg Cys Lys Pro Gly Phe Trp Gly Leu Ser Pro Ser
            755                 760                 765

Asn Pro Glu Gly Cys Thr Arg Cys Ser Cys Asp Leu Arg Gly Thr Leu
            770                 775                 780

Gly Gly Val Ala Glu Cys Gln Pro Gly Thr Gly Gln Cys Phe Cys Lys
785                 790                 795                 800

Pro His Val Cys Gly Gln Ala Cys Ala Ser Cys Lys Asp Gly Phe Phe
                805                 810                 815

Gly Leu Asp Gln Ala Asp Tyr Phe Gly Cys Arg Ser Cys Arg Cys Asp
            820                 825                 830

Ile Gly Gly Ala Leu Gly Gln Ser Cys Glu Pro Arg Thr Gly Val Cys
            835                 840                 845

Arg Cys Arg Pro Asn Thr Gln Gly Pro Thr Cys Ser Glu Pro Ala Arg
850                 855                 860

Asp His Tyr Leu Pro Asp Leu His His Leu Arg Leu Glu Leu Glu Glu
865                 870                 875                 880

Ala Ala Thr Pro Glu Gly His Ala Val Arg Phe Gly Phe Asn Pro Leu
                885                 890                 895

Glu Phe Glu Asn Phe Ser Trp Arg Gly Tyr Ala Gln Met Ala Pro Val
            900                 905                 910

Gln Pro Arg Ile Val Ala Arg Leu Asn Leu Thr Ser Pro Asp Leu Phe
            915                 920                 925

Trp Leu Val Phe Arg Tyr Val Asn Arg Gly Ala Met Ser Val Ser Gly
            930                 935                 940

Arg Val Ser Val Arg Glu Glu Gly Arg Ser Ala Thr Cys Ala Asn Cys
945                 950                 955                 960

Thr Ala Gln Ser Gln Pro Val Ala Phe Pro Pro Ser Thr Glu Pro Ala
                965                 970                 975

Phe Ile Thr Val Pro Gln Arg Gly Phe Gly Glu Pro Phe Val Leu Asn
            980                 985                 990
```

```
Pro Gly Thr Trp Ala Leu Arg Val  Glu Ala Glu Gly Val  Leu Leu Asp
        995                 1000                 1005

Tyr Val  Val Leu Leu Pro Ser  Ala Tyr Tyr Glu Ala  Ala Leu Leu
    1010             1015                 1020

Gln Leu  Arg Val Thr Glu Ala  Cys Thr Tyr Arg Pro  Ser Ala Gln
    1025             1030                 1035

Gln Ser  Gly Asp Asn Cys Leu  Leu Tyr Thr His Leu  Pro Leu Asp
    1040             1045                 1050

Gly Phe  Pro Ser Ala Ala Gly  Leu Glu Ala Leu Cys  Arg Gln Asp
    1055             1060                 1065

Asn Ser  Leu Pro Arg Pro Cys  Pro Thr Glu Gln Leu  Ser Pro Ser
    1070             1075                 1080

His Pro  Pro Leu Ile Thr Cys  Thr Gly Ser Asp Val  Asp Val Gln
    1085             1090                 1095

Leu Gln  Val Ala Val Pro Gln  Pro Gly Arg Tyr Ala  Leu Val Val
    1100             1105                 1110

Glu Tyr  Ala Asn Glu Asp Ala  Arg Gln Glu Val Gly  Val Ala Val
    1115             1120                 1125

His Thr  Pro Gln Arg Ala Pro  Gln Gln Gly Leu Leu  Ser Leu His
    1130             1135                 1140

Pro Cys  Leu Tyr Ser Thr Leu  Cys Arg Gly Thr Ala  Arg Asp Thr
    1145             1150                 1155

Gln Asp  His Leu Ala Val Phe  His Leu Asp Ser Glu  Ala Ser Val
    1160             1165                 1170

Arg Leu  Thr Ala Glu Gln Ala  Arg Phe Phe Leu His  Gly Val Thr
    1175             1180                 1185

Leu Val  Pro Ile Glu Glu Phe  Ser Pro Glu Phe Val  Glu Pro Arg
    1190             1195                 1200

Val Ser  Cys Ile Ser Ser His  Gly Ala Phe Gly Pro  Asn Ser Ala
    1205             1210                 1215

Ala Cys  Leu Pro Ser Arg Phe  Pro Lys Pro Pro Gln  Pro Ile Ile
    1220             1225                 1230

Leu Arg  Asp Cys Gln Val Ile  Pro Leu Pro Pro Gly  Leu Pro Leu
    1235             1240                 1245

Thr His  Ala Gln Asp Leu Thr  Pro Ala Met Ser Pro  Ala Gly Pro
    1250             1255                 1260

Arg Pro  Arg Pro Pro Thr Ala  Val Asp Pro Asp Ala  Glu Pro Thr
    1265             1270                 1275

Leu Leu  Arg Glu Pro Gln Ala  Thr Val Val Phe Thr  Thr His Val
    1280             1285                 1290

Pro Thr  Leu Gly Arg Tyr Ala  Phe Leu Leu His Gly  Tyr Gln Pro
    1295             1300                 1305

Ala His  Pro Thr Phe Pro Val  Glu Val Leu Ile Asn  Ala Gly Arg
    1310             1315                 1320

Val Trp  Gln Gly His Ala Asn  Ala Ser Phe Cys Pro  His Gly Tyr
    1325             1330                 1335

Gly Cys  Arg Thr Leu Val Val  Cys Glu Gly Gln Ala  Leu Leu Asp
    1340             1345                 1350

Val Thr  His Ser Glu Leu Thr  Val Thr Val Arg Val  Pro Lys Gly
    1355             1360                 1365

Arg Trp  Leu Trp Leu Asp Tyr  Val Leu Val Val Pro  Glu Asn Val
    1370             1375                 1380

Tyr Ser  Phe Gly Tyr Leu Arg  Glu Glu Pro Leu Asp  Lys Ser Tyr
```

```
            1385                1390                1395

Asp Phe Ile Ser His Cys Ala Ala Gln Gly Tyr His Ile Ser Pro
    1400                1405                1410

Ser Ser Ser Ser Leu Phe Cys Arg Asn Ala Ala Ala Ser Leu Ser
    1415                1420                1425

Leu Phe Tyr Asn Asn Gly Ala Arg Pro Cys Gly Cys His Glu Val
    1430                1435                1440

Gly Ala Thr Gly Pro Thr Cys Glu Pro Phe Gly Gly Gln Cys Pro
    1445                1450                1455

Cys His Ala His Val Ile Gly Arg Asp Cys Ser Arg Cys Ala Thr
    1460                1465                1470

Gly Tyr Trp Gly Phe Pro Asn Cys Arg Pro Cys Asp Cys Gly Ala
    1475                1480                1485

Arg Leu Cys Asp Glu Leu Thr Gly Gln Cys Ile Cys Pro Pro Arg
    1490                1495                1500

Thr Ile Pro Pro Asp Cys Leu Leu Cys Gln Pro Gln Thr Phe Gly
    1505                1510                1515

Cys His Pro Leu Val Gly Cys Glu Glu Cys Asn Cys Ser Gly Pro
    1520                1525                1530

Gly Ile Gln Glu Leu Thr Asp Pro Thr Cys Asp Thr Asp Ser Gly
    1535                1540                1545

Gln Cys Lys Cys Arg Pro Asn Val Thr Gly Arg Arg Cys Asp Thr
    1550                1555                1560

Cys Ser Pro Gly Phe His Gly Tyr Pro Arg Cys Arg Pro Cys Asp
    1565                1570                1575

Cys His Glu Ala Gly Thr Ala Pro Gly Val Cys Asp Pro Leu Thr
    1580                1585                1590

Gly Gln Cys Tyr Cys Lys Glu Asn Val Gln Gly Pro Lys Cys Asp
    1595                1600                1605

Gln Cys Ser Leu Gly Thr Phe Ser Leu Asp Ala Ala Asn Pro Lys
    1610                1615                1620

Gly Cys Thr Arg Cys Phe Cys Phe Gly Ala Thr Glu Arg Cys Arg
    1625                1630                1635

Ser Ser Ser Tyr Thr Arg Gln Glu Phe Val Asp Met Glu Gly Trp
    1640                1645                1650

Val Leu Leu Ser Thr Asp Arg Gln Val Val Pro His Glu Arg Gln
    1655                1660                1665

Pro Gly Thr Glu Met Leu Arg Ala Asp Leu Arg His Val Pro Glu
    1670                1675                1680

Ala Val Pro Glu Ala Phe Pro Glu Leu Tyr Trp Gln Ala Pro Pro
    1685                1690                1695

Ser Tyr Leu Gly Asp Arg Val Ser Ser Tyr Gly Gly Thr Leu Arg
    1700                1705                1710

Tyr Glu Leu His Ser Glu Thr Gln Arg Gly Asp Val Phe Val Pro
    1715                1720                1725

Met Glu Ser Arg Pro Asp Val Val Leu Gln Gly Asn Gln Met Ser
    1730                1735                1740

Ile Thr Phe Leu Glu Pro Ala Tyr Pro Thr Pro Gly His Val His
    1745                1750                1755

Arg Gly Gln Leu Gln Leu Val Glu Gly Asn Phe Arg His Thr Glu
    1760                1765                1770

Thr Arg Asn Thr Val Ser Arg Glu Glu Leu Met Met Val Leu Ala
    1775                1780                1785
```

```
Ser Leu Glu Gln Leu Gln Ile Arg Ala Leu Phe Ser Gln Ile Ser
    1790                1795                1800
Ser Ala Val Phe Leu Arg Arg Val Ala Leu Glu Val Ala Ser Pro
    1805                1810                1815
Ala Gly Gln Gly Ala Leu Ala Ser Asn Val Glu Leu Cys Leu Cys
    1820                1825                1830
Pro Ala Ser Tyr Arg Gly Asp Ser Cys Gln Glu Cys Ala Pro Gly
    1835                1840                1845
Phe Tyr Arg Asp Val Lys Gly Leu Phe Leu Gly Arg Cys Val Pro
    1850                1855                1860
Cys Gln Cys His Gly His Ser Asp Arg Cys Leu Pro Gly Ser Gly
    1865                1870                1875
Val Cys Val Asp Cys Gln His Asn Thr Glu Gly Ala His Cys Glu
    1880                1885                1890
Arg Cys Gln Ala Gly Phe Val Ser Ser Arg Asp Asp Pro Ser Ala
    1895                1900                1905
Pro Cys Val Ser Cys Pro Cys Pro Leu Ser Val Pro Ser Asn Asn
    1910                1915                1920
Phe Ala Glu Gly Cys Val Leu Arg Gly Gly Arg Thr Gln Cys Leu
    1925                1930                1935
Cys Lys Pro Gly Tyr Ala Gly Ala Ser Cys Glu Arg Cys Ala Pro
    1940                1945                1950
Gly Phe Phe Gly Asn Pro Leu Val Leu Gly Ser Ser Cys Gln Pro
    1955                1960                1965
Cys Asp Cys Ser Gly Asn Gly Asp Pro Asn Leu Leu Phe Ser Asp
    1970                1975                1980
Cys Asp Pro Leu Thr Gly Ala Cys Arg Gly Cys Leu Arg His Thr
    1985                1990                1995
Thr Gly Pro Arg Cys Glu Ile Cys Ala Pro Gly Phe Tyr Gly Asn
    2000                2005                2010
Ala Leu Leu Pro Gly Asn Cys Thr Arg Cys Asp Cys Thr Pro Cys
    2015                2020                2025
Gly Thr Glu Ala Cys Asp Pro His Ser Gly His Cys Leu Cys Lys
    2030                2035                2040
Ala Gly Val Thr Gly Arg Arg Cys Asp Arg Cys Gln Glu Gly His
    2045                2050                2055
Phe Gly Phe Asp Gly Cys Gly Gly Cys Arg Pro Cys Ala Cys Gly
    2060                2065                2070
Pro Ala Ala Glu Gly Ser Glu Cys His Pro Gln Ser Gly Gln Cys
    2075                2080                2085
His Cys Arg Pro Gly Thr Met Gly Pro Gln Cys Arg Glu Cys Ala
    2090                2095                2100
Pro Gly Tyr Trp Gly Leu Pro Glu Gln Gly Cys Arg Arg Cys Gln
    2105                2110                2115
Cys Pro Gly Gly Arg Cys Asp Pro His Thr Gly Arg Cys Asn Cys
    2120                2125                2130
Pro Pro Gly Leu Ser Gly Glu Arg Cys Asp Thr Cys Ser Gln Gln
    2135                2140                2145
His Gln Val Pro Val Pro Gly Gly Pro Val Gly His Ser Ile His
    2150                2155                2160
Cys Glu Val Cys Asp His Cys Val Val Leu Leu Leu Asp Asp Leu
    2165                2170                2175
```

```
Glu Arg Ala Gly Ala Leu Leu Pro Ala Ile His Glu Gln Leu Arg
    2180                2185                2190

Gly Ile Asn Ala Ser Ser Met Ala Trp Ala Arg Leu His Arg Leu
    2195                2200                2205

Asn Ala Ser Ile Ala Asp Leu Gln Ser Gln Leu Arg Ser Pro Leu
    2210                2215                2220

Gly Pro Arg His Glu Thr Ala Gln Gln Leu Glu Val Leu Glu Gln
    2225                2230                2235

Gln Ser Thr Ser Leu Gly Gln Asp Ala Arg Arg Leu Gly Gly Gln
    2240                2245                2250

Ala Val Gly Thr Arg Asp Gln Ala Ser Gln Leu Leu Ala Gly Thr
    2255                2260                2265

Glu Ala Thr Leu Gly His Ala Lys Thr Leu Leu Ala Ala Ile Arg
    2270                2275                2280

Ala Val Asp Arg Thr Leu Ser Glu Leu Met Ser Gln Thr Gly His
    2285                2290                2295

Leu Gly Leu Ala Asn Ala Ser Ala Pro Ser Gly Glu Gln Leu Leu
    2300                2305                2310

Arg Thr Leu Ala Glu Val Glu Arg Leu Leu Trp Glu Met Arg Ala
    2315                2320                2325

Arg Asp Leu Gly Ala Pro Gln Ala Ala Glu Ala Glu Leu Ala
    2330                2335                2340

Ala Ala Gln Arg Leu Leu Ala Arg Val Gln Glu Gln Leu Ser Ser
    2345                2350                2355

Leu Trp Glu Glu Asn Gln Ala Leu Ala Thr Gln Thr Arg Asp Arg
    2360                2365                2370

Leu Ala Gln His Glu Ala Gly Leu Met Asp Leu Arg Glu Ala Leu
    2375                2380                2385

Asn Arg Ala Val Asp Ala Thr Arg Glu Ala Gln Glu Leu Asn Ser
    2390                2395                2400

Arg Asn Gln Glu Arg Leu Glu Glu Ala Leu Gln Arg Lys Gln Glu
    2405                2410                2415

Leu Ser Arg Asp Asn Ala Thr Leu Gln Ala Thr Leu His Ala Ala
    2420                2425                2430

Arg Asp Thr Leu Ala Ser Val Phe Arg Leu Leu His Ser Leu Asp
    2435                2440                2445

Gln Ala Lys Glu Glu Leu Glu Arg Leu Ala Ala Ser Leu Asp Gly
    2450                2455                2460

Ala Arg Thr Pro Leu Leu Gln Arg Met Gln Thr Phe Ser Pro Ala
    2465                2470                2475

Gly Ser Lys Leu Arg Leu Val Glu Ala Ala Glu Ala His Ala Gln
    2480                2485                2490

Gln Leu Gly Gln Leu Ala Leu Asn Leu Ser Ser Ile Ile Leu Asp
    2495                2500                2505

Val Asn Gln Asp Arg Leu Thr Gln Arg Ala Ile Glu Ala Ser Asn
    2510                2515                2520

Ala Tyr Ser Arg Ile Leu Gln Ala Val Gln Ala Ala Glu Asp Ala
    2525                2530                2535

Ala Gly Gln Ala Leu Gln Gln Ala Asp His Thr Trp Ala Thr Val
    2540                2545                2550

Val Arg Gln Gly Leu Val Asp Arg Ala Gln Gln Leu Leu Ala Asn
    2555                2560                2565

Ser Thr Ala Leu Glu Glu Ala Met Leu Gln Glu Gln Gln Arg Leu
```

-continued

```
            2570                2575                2580

Gly Leu Val Trp Ala Ala Leu Gln Gly Ala Arg Thr  Gln Leu Arg
        2585                2590                2595

Asp Val Arg Ala Lys Lys Asp Gln Leu Glu Ala His  Ile Gln Ala
    2600                2605                2610

Ala Gln Ala Met Leu Ala Met Asp Thr Asp Glu Thr  Ser Lys Lys
    2615                2620                2625

Ile Ala His Ala Lys Ala Val Ala Ala Glu Ala Gln  Asp Thr Ala
    2630                2635                2640

Thr Arg Val Gln Ser Gln Leu Gln Ala Met Gln Glu  Asn Val Glu
    2645                2650                2655

Arg Trp Gln Gly Gln Tyr Glu Gly Leu Arg Gly Gln  Asp Leu Gly
    2660                2665                2670

Gln Ala Val Leu Asp Ala Gly His Ser Val Ser Thr  Leu Glu Lys
    2675                2680                2685

Thr Leu Pro Gln Leu Leu Ala Lys Leu Ser Ile Leu  Glu Asn Arg
    2690                2695                2700

Gly Val His Asn Ala Ser Leu Ala Leu Ser Ala Ser  Ile Gly Arg
    2705                2710                2715

Val Arg Glu Leu Ile Ala Gln Ala Arg Gly Ala Ala  Ser Lys Val
    2720                2725                2730

Lys Val Pro Met Lys Phe Asn Gly Arg Ser Gly Val  Gln Leu Arg
    2735                2740                2745

Thr Pro Arg Asp Leu Ala Asp Leu Ala Ala Tyr Thr  Ala Leu Lys
    2750                2755                2760

Phe Tyr Leu Gln Gly Pro Glu Pro Glu Pro Gln Gly  Gly Thr Glu
    2765                2770                2775

Asp Arg Phe Val Met Tyr Met Gly Ser Arg Gln Ala  Thr Gly Asp
    2780                2785                2790

Tyr Met Gly Val Ser Leu Arg Asp Lys Lys Val His  Trp Val Tyr
    2795                2800                2805

Gln Leu Gly Glu Ala Gly Pro Ala Val Leu Ser Ile  Asp Glu Asp
    2810                2815                2820

Ile Gly Glu Gln Phe Ala Ala Val Ser Leu Asp Arg  Thr Leu Gln
    2825                2830                2835

Phe Gly His Met Ser Val Thr Val Glu Arg Gln Met  Ile Gln Glu
    2840                2845                2850

Thr Lys Gly Asp Thr Val Ala Pro Gly Ala Glu Gly  Leu Leu Asn
    2855                2860                2865

Leu Arg Pro Asp Asp Phe Val Phe Tyr Val Gly Gly  Tyr Pro Ser
    2870                2875                2880

Thr Phe Thr Pro Pro Leu Leu Arg Phe Pro Gly Tyr  Arg Gly
    2885                2890                2895

Cys Ile Glu Met Asp Thr Leu Asn Glu Glu Val Val  Ser Leu Tyr
    2900                2905                2910

Asn Phe Glu Arg Thr Phe Gln Leu Asp Thr Ala Val  Asp Arg Pro
    2915                2920                2925

Cys Ala Arg Ser Lys Ser Thr Gly Asp Pro Trp Leu  Thr Asp Gly
    2930                2935                2940

Ser Tyr Leu Asp Gly Thr Gly Phe Ala Arg Ile Ser  Phe Asp Ser
    2945                2950                2955

Gln Ile Ser Thr Thr Lys Arg Phe Glu Gln Glu Leu  Arg Leu Val
    2960                2965                2970
```

```
Ser Tyr Ser Gly Val Leu Phe Phe Leu Lys Gln Gln Ser Gln Phe
    2975                2980                2985

Leu Cys Leu Ala Val Gln Glu Gly Ser Leu Val Leu Leu Tyr Asp
    2990                2995                3000

Phe Gly Ala Gly Leu Lys Lys Ala Val Pro Leu Gln Pro Pro Pro
    3005                3010                3015

Pro Leu Thr Ser Ala Ser Lys Ala Ile Gln Val Phe Leu Leu Gly
    3020                3025                3030

Gly Ser Arg Lys Arg Val Leu Val Arg Val Glu Arg Ala Thr Val
    3035                3040                3045

Tyr Ser Val Glu Gln Asp Asn Asp Leu Glu Leu Ala Asp Ala Tyr
    3050                3055                3060

Tyr Leu Gly Gly Val Pro Pro Asp Gln Leu Pro Pro Ser Leu Arg
    3065                3070                3075

Arg Leu Phe Pro Thr Gly Gly Ser Val Arg Gly Cys Val Lys Gly
    3080                3085                3090

Ile Lys Ala Leu Gly Lys Tyr Val Asp Leu Lys Arg Leu Asn Thr
    3095                3100                3105

Thr Gly Val Ser Ala Gly Cys Thr Ala Asp Leu Leu Val Gly Arg
    3110                3115                3120

Ala Met Thr Phe His Gly His Gly Phe Leu Arg Leu Ala Leu Ser
    3125                3130                3135

Asn Val Ala Pro Leu Thr Gly Asn Val Tyr Ser Gly Phe Gly Phe
    3140                3145                3150

His Ser Ala Gln Asp Ser Ala Leu Leu Tyr Tyr Arg Ala Ser Pro
    3155                3160                3165

Asp Gly Leu Cys Gln Val Ser Leu Gln Gln Gly Arg Val Ser Leu
    3170                3175                3180

Gln Leu Leu Arg Thr Glu Val Lys Thr Gln Ala Gly Phe Ala Asp
    3185                3190                3195

Gly Ala Pro His Tyr Val Ala Phe Tyr Ser Asn Ala Thr Gly Val
    3200                3205                3210

Trp Leu Tyr Val Asp Asp Gln Leu Gln Gln Met Lys Pro His Arg
    3215                3220                3225

Gly Pro Pro Pro Glu Leu Gln Pro Gln Pro Gly Pro Pro Arg
    3230                3235                3240

Leu Leu Leu Gly Gly Leu Pro Glu Ser Gly Thr Ile Tyr Asn Phe
    3245                3250                3255

Ser Gly Cys Ile Ser Asn Val Phe Val Gln Arg Leu Leu Gly Pro
    3260                3265                3270

Gln Arg Val Phe Asp Leu Gln Gln Asn Leu Gly Ser Val Asn Val
    3275                3280                3285

Ser Thr Gly Cys Ala Pro Ala Leu Gln Ala Gln Thr Pro Gly Leu
    3290                3295                3300

Gly Pro Arg Gly Leu Gln Ala Thr Ala Arg Lys Ala Ser Arg Arg
    3305                3310                3315

Ser Arg Gln Pro Ala Arg His Pro Ala Cys Met Leu Pro Pro His
    3320                3325                3330

Leu Arg Thr Thr Arg Asp Ser Tyr Gln Phe Gly Gly Ser Leu Ser
    3335                3340                3345

Ser His Leu Glu Phe Val Gly Ile Leu Ala Arg His Arg Asn Trp
    3350                3355                3360
```

Pro Ser Leu Ser Met His Val Leu Pro Arg Ser Ser Arg Gly Leu
    3365                3370                3375

Leu Leu Phe Thr Ala Arg Leu Arg Pro Gly Ser Pro Ser Leu Ala
    3380                3385                3390

Leu Phe Leu Ser Asn Gly His Phe Val Ala Gln Met Glu Gly Leu
    3395                3400                3405

Gly Thr Arg Leu Arg Ala Gln Ser Arg Gln Arg Ser Arg Pro Gly
    3410                3415                3420

Arg Trp His Lys Val Ser Val Arg Trp Glu Lys Asn Arg Ile Leu
    3425                3430                3435

Leu Val Thr Asp Gly Ala Arg Ala Trp Ser Gln Glu Gly Pro His
    3440                3445                3450

Arg Gln His Gln Gly Ala Glu His Pro Gln Pro His Thr Leu Phe
    3455                3460                3465

Val Gly Gly Leu Pro Ala Ser Ser His Ser Ser Lys Leu Pro Val
    3470                3475                3480

Thr Val Gly Phe Ser Gly Cys Val Lys Arg Leu Arg Leu His Gly
    3485                3490                3495

Arg Pro Leu Gly Ala Pro Thr Arg Met Ala Gly Val Thr Pro Cys
    3500                3505                3510

Ile Leu Gly Pro Leu Glu Ala Gly Leu Phe Phe Pro Gly Ser Gly
    3515                3520                3525

Gly Val Ile Thr Leu Asp Leu Pro Gly Ala Thr Leu Pro Asp Val
    3530                3535                3540

Gly Leu Glu Leu Glu Val Arg Pro Leu Ala Val Thr Gly Leu Ile
    3545                3550                3555

Phe His Leu Gly Gln Ala Arg Thr Pro Pro Tyr Leu Gln Leu Gln
    3560                3565                3570

Val Thr Glu Lys Gln Val Leu Leu Arg Ala Asp Asp Gly Ala Gly
    3575                3580                3585

Glu Phe Ser Thr Ser Val Thr Arg Pro Ser Val Leu Cys Asp Gly
    3590                3595                3600

Gln Trp His Arg Leu Ala Val Met Lys Ser Gly Asn Val Leu Arg
    3605                3610                3615

Leu Glu Val Asp Ala Gln Ser Asn His Thr Val Gly Pro Leu Leu
    3620                3625                3630

Ala Ala Ala Ala Gly Ala Pro Ala Pro Leu Tyr Leu Gly Gly Leu
    3635                3640                3645

Pro Glu Pro Met Ala Val Gln Pro Trp Pro Ala Tyr Cys Gly
    3650                3655                3660

Cys Met Arg Arg Leu Ala Val Asn Arg Ser Pro Val Ala Met Thr
    3665                3670                3675

Arg Ser Val Glu Val His Gly Ala Val Gly Ala Ser Gly Cys Pro
    3680                3685                3690

Ala Ala
    3695

<210> SEQ ID NO 37
<211> LENGTH: 1786
<212> TYPE: PRT
<213> ORGANISM: Homo sapiens

<400> SEQUENCE: 37

Met Gly Leu Leu Gln Leu Leu Ala Phe Ser Phe Leu Ala Leu Cys Arg
1               5                   10                  15

Ala Arg Val Arg Ala Gln Glu Pro Glu Phe Ser Tyr Gly Cys Ala Glu
            20                  25                  30

Gly Ser Cys Tyr Pro Ala Thr Gly Asp Leu Leu Ile Gly Arg Ala Gln
        35                  40                  45

Lys Leu Ser Val Thr Ser Thr Cys Gly Leu His Lys Pro Glu Pro Tyr
50                  55                  60

Cys Ile Val Ser His Leu Gln Glu Asp Lys Lys Cys Phe Ile Cys Asn
65                  70                  75                  80

Ser Gln Asp Pro Tyr His Glu Thr Leu Asn Pro Asp Ser His Leu Ile
                85                  90                  95

Glu Asn Val Val Thr Thr Phe Ala Pro Asn Arg Leu Lys Ile Trp Trp
            100                 105                 110

Gln Ser Glu Asn Gly Val Glu Asn Val Thr Ile Gln Leu Asp Leu Glu
        115                 120                 125

Ala Glu Phe His Phe Thr His Leu Ile Met Thr Phe Lys Thr Phe Arg
130                 135                 140

Pro Ala Ala Met Leu Ile Glu Arg Ser Ser Asp Phe Gly Lys Thr Trp
145                 150                 155                 160

Gly Val Tyr Arg Tyr Phe Ala Tyr Asp Cys Glu Ala Ser Phe Pro Gly
                165                 170                 175

Ile Ser Thr Gly Pro Met Lys Lys Val Asp Asp Ile Ile Cys Asp Ser
            180                 185                 190

Arg Tyr Ser Asp Ile Glu Pro Ser Thr Glu Gly Glu Val Ile Phe Arg
        195                 200                 205

Ala Leu Asp Pro Ala Phe Lys Ile Glu Asp Pro Tyr Ser Pro Arg Ile
210                 215                 220

Gln Asn Leu Leu Lys Ile Thr Asn Leu Arg Ile Lys Phe Val Lys Leu
225                 230                 235                 240

His Thr Leu Gly Asp Asn Leu Leu Asp Ser Arg Met Glu Ile Arg Glu
                245                 250                 255

Lys Tyr Tyr Tyr Ala Val Tyr Asp Met Val Val Arg Gly Asn Cys Phe
            260                 265                 270

Cys Tyr Gly His Ala Ser Glu Cys Ala Pro Val Asp Gly Phe Asn Glu
        275                 280                 285

Glu Val Glu Gly Met Val His Gly His Cys Met Cys Arg His Asn Thr
290                 295                 300

Lys Gly Leu Asn Cys Glu Leu Cys Met Asp Phe Tyr His Asp Leu Pro
305                 310                 315                 320

Trp Arg Pro Ala Glu Gly Arg Asn Ser Asn Ala Cys Lys Lys Cys Asn
                325                 330                 335

Cys Asn Glu His Ser Ile Ser Cys His Phe Asp Met Ala Val Tyr Leu
            340                 345                 350

Ala Thr Gly Asn Val Ser Gly Gly Val Cys Asp Asp Cys Gln His Asn
        355                 360                 365

Thr Met Gly Arg Asn Cys Glu Gln Cys Lys Pro Phe Tyr Tyr Gln His
370                 375                 380

Pro Glu Arg Asp Ile Arg Asp Pro Asn Phe Cys Glu Arg Cys Thr Cys
385                 390                 395                 400

Asp Pro Ala Gly Ser Gln Asn Glu Gly Ile Cys Asp Ser Tyr Thr Asp
                405                 410                 415

Phe Ser Thr Gly Leu Ile Ala Gly Gln Cys Arg Cys Lys Leu Asn Val
            420                 425                 430

-continued

Glu Gly Glu His Cys Asp Val Cys Lys Glu Gly Phe Tyr Asp Leu Ser
    435                 440                 445

Ser Glu Asp Pro Phe Gly Cys Lys Ser Ala Cys Asn Pro Leu Gly
450                 455                 460

Thr Ile Pro Gly Gly Asn Pro Cys Asp Ser Glu Thr Gly His Cys Tyr
465                 470                 475                 480

Cys Lys Arg Leu Val Thr Gly Gln His Cys Asp Gln Cys Leu Pro Glu
                485                 490                 495

His Trp Gly Leu Ser Asn Asp Leu Asp Gly Cys Arg Pro Cys Asp Cys
            500                 505                 510

Asp Leu Gly Gly Ala Leu Asn Asn Ser Cys Phe Ala Glu Ser Gly Gln
            515                 520                 525

Cys Ser Cys Arg Pro His Met Ile Gly Arg Gln Cys Asn Glu Val Glu
            530                 535                 540

Pro Gly Tyr Tyr Phe Ala Thr Leu Asp His Tyr Leu Tyr Glu Ala Glu
545                 550                 555                 560

Glu Ala Asn Leu Gly Pro Gly Val Ser Ile Val Glu Arg Gln Tyr Ile
                565                 570                 575

Gln Asp Arg Ile Pro Ser Trp Thr Gly Ala Gly Phe Val Arg Val Pro
            580                 585                 590

Glu Gly Ala Tyr Leu Glu Phe Phe Ile Asp Asn Ile Pro Tyr Ser Met
            595                 600                 605

Glu Tyr Asp Ile Leu Ile Arg Tyr Glu Pro Gln Leu Pro Asp His Trp
            610                 615                 620

Glu Lys Ala Val Ile Thr Val Gln Arg Pro Gly Arg Ile Pro Thr Ser
625                 630                 635                 640

Ser Arg Cys Gly Asn Thr Ile Pro Asp Asp Asn Gln Val Val Ser
                645                 650                 655

Leu Ser Pro Gly Ser Arg Tyr Val Val Leu Pro Arg Pro Val Cys Phe
                660                 665                 670

Glu Lys Gly Thr Asn Tyr Thr Val Arg Leu Glu Leu Pro Gln Tyr Thr
            675                 680                 685

Ser Ser Asp Ser Asp Val Glu Ser Pro Tyr Thr Leu Ile Asp Ser Leu
690                 695                 700

Val Leu Met Pro Tyr Cys Lys Ser Leu Asp Ile Phe Thr Val Gly Gly
705                 710                 715                 720

Ser Gly Asp Gly Val Val Thr Asn Ser Ala Trp Glu Thr Phe Gln Arg
                725                 730                 735

Tyr Arg Cys Leu Glu Asn Ser Arg Ser Val Val Lys Thr Pro Met Thr
            740                 745                 750

Asp Val Cys Arg Asn Ile Ile Phe Ser Ile Ser Ala Leu Leu His Gln
            755                 760                 765

Thr Gly Leu Ala Cys Glu Cys Asp Pro Gln Gly Ser Leu Ser Ser Val
770                 775                 780

Cys Asp Pro Asn Gly Gly Gln Cys Gln Cys Arg Pro Asn Val Val Gly
785                 790                 795                 800

Arg Thr Cys Asn Arg Cys Ala Pro Gly Thr Phe Gly Phe Gly Pro Ser
                805                 810                 815

Gly Cys Lys Pro Cys Glu Cys His Leu Gln Gly Ser Val Asn Ala Phe
            820                 825                 830

Cys Asn Pro Val Thr Gly Gln Cys His Cys Phe Gln Gly Val Tyr Ala
            835                 840                 845

Arg Gln Cys Asp Arg Cys Leu Pro Gly His Trp Gly Phe Pro Ser Cys

```
                850             855             860
Gln Pro Cys Gln Cys Asn Gly His Ala Asp Asp Cys Asp Pro Val Thr
865                 870             875             880
Gly Glu Cys Leu Asn Cys Gln Asp Tyr Thr Met Gly His Asn Cys Glu
                885             890             895
Arg Cys Leu Ala Gly Tyr Tyr Gly Asp Pro Ile Ile Gly Ser Gly Asp
            900             905             910
His Cys Arg Pro Cys Pro Cys Pro Asp Gly Pro Asp Ser Gly Arg Gln
            915             920             925
Phe Ala Arg Ser Cys Tyr Gln Asp Pro Val Thr Leu Gln Leu Ala Cys
            930             935             940
Val Cys Asp Pro Gly Tyr Ile Gly Ser Arg Cys Asp Cys Ala Ser
945             950             955             960
Gly Tyr Phe Gly Asn Pro Ser Glu Val Gly Ser Cys Gln Pro Cys
            965             970             975
Gln Cys His Asn Asn Ile Asp Thr Thr Asp Pro Glu Ala Cys Asp Lys
            980             985             990
Glu Thr Gly Arg Cys Leu Lys Cys Leu Tyr His Thr Glu Gly Glu His
        995             1000            1005
Cys Gln Phe Cys Arg Phe Gly Tyr Tyr Gly Asp Ala Leu Gln Gln
    1010            1015            1020
Asp Cys Arg Lys Cys Val Cys Asn Tyr Leu Gly Thr Val Gln Glu
    1025            1030            1035
His Cys Asn Gly Ser Asp Cys Gln Cys Asp Lys Ala Thr Gly Gln
    1040            1045            1050
Cys Leu Cys Leu Pro Asn Val Ile Gly Gln Asn Cys Asp Arg Cys
    1055            1060            1065
Ala Pro Asn Thr Trp Gln Leu Ala Ser Gly Thr Gly Cys Asp Pro
    1070            1075            1080
Cys Asn Cys Asn Ala Ala His Ser Phe Gly Pro Ser Cys Asn Glu
    1085            1090            1095
Phe Thr Gly Gln Cys Gln Cys Met Pro Gly Phe Gly Gly Arg Thr
    1100            1105            1110
Cys Ser Glu Cys Gln Glu Leu Phe Trp Gly Asp Pro Asp Val Glu
    1115            1120            1125
Cys Arg Ala Cys Asp Cys Asp Pro Arg Gly Ile Glu Thr Pro Gln
    1130            1135            1140
Cys Asp Gln Ser Thr Gly Gln Cys Val Cys Val Glu Gly Val Glu
    1145            1150            1155
Gly Pro Arg Cys Asp Lys Cys Thr Arg Gly Tyr Ser Gly Val Phe
    1160            1165            1170
Pro Asp Cys Thr Pro Cys His Gln Cys Phe Ala Leu Trp Asp Val
    1175            1180            1185
Ile Ile Ala Glu Leu Thr Asn Arg Thr His Arg Phe Leu Glu Lys
    1190            1195            1200
Ala Lys Ala Leu Lys Ile Ser Gly Val Ile Gly Pro Tyr Arg Glu
    1205            1210            1215
Thr Val Asp Ser Val Glu Arg Lys Val Ser Glu Ile Lys Asp Ile
    1220            1225            1230
Leu Ala Gln Ser Pro Ala Ala Glu Pro Leu Lys Asn Ile Gly Asn
    1235            1240            1245
Leu Phe Glu Glu Ala Glu Lys Leu Ile Lys Asp Val Thr Glu Met
    1250            1255            1260
```

```
Met Ala Gln Val Glu Val Lys Leu Ser Asp Thr Thr Ser Gln Ser
    1265              1270                  1275

Asn Ser Thr Ala Lys Glu Leu Asp Ser Leu Gln Thr Glu Ala Glu
    1280              1285                  1290

Ser Leu Asp Asn Thr Val Lys Glu Leu Ala Glu Gln Leu Glu Phe
    1295              1300                  1305

Ile Lys Asn Ser Asp Ile Arg Gly Ala Leu Asp Ser Ile Thr Lys
    1310              1315                  1320

Tyr Phe Gln Met Ser Leu Glu Ala Glu Arg Val Asn Ala Ser
    1325              1330                  1335

Thr Thr Glu Pro Asn Ser Thr Val Glu Gln Ser Ala Leu Met Arg
    1340              1345                  1350

Asp Arg Val Glu Asp Val Met Met Glu Arg Glu Ser Gln Phe Lys
    1355              1360                  1365

Glu Lys Gln Glu Glu Gln Ala Arg Leu Leu Asp Glu Leu Ala Gly
    1370              1375                  1380

Lys Leu Gln Ser Leu Asp Leu Ser Ala Ala Ala Glu Met Thr Cys
    1385              1390                  1395

Gly Thr Pro Pro Gly Ala Ser Cys Ser Glu Thr Glu Cys Gly Gly
    1400              1405                  1410

Pro Asn Cys Arg Thr Asp Glu Gly Glu Arg Lys Cys Gly Gly Pro
    1415              1420                  1425

Gly Cys Gly Gly Leu Val Thr Val Ala His Asn Ala Trp Gln Lys
    1430              1435                  1440

Ala Met Asp Leu Asp Gln Asp Val Leu Ser Ala Leu Ala Glu Val
    1445              1450                  1455

Glu Gln Leu Ser Lys Met Val Ser Glu Ala Lys Leu Arg Ala Asp
    1460              1465                  1470

Glu Ala Lys Gln Ser Ala Glu Asp Ile Leu Leu Lys Thr Asn Ala
    1475              1480                  1485

Thr Lys Glu Lys Met Asp Lys Ser Asn Glu Glu Leu Arg Asn Leu
    1490              1495                  1500

Ile Lys Gln Ile Arg Asn Phe Leu Thr Gln Asp Ser Ala Asp Leu
    1505              1510                  1515

Asp Ser Ile Glu Ala Val Ala Asn Glu Val Leu Lys Met Glu Met
    1520              1525                  1530

Pro Ser Thr Pro Gln Gln Leu Gln Asn Leu Thr Glu Asp Ile Arg
    1535              1540                  1545

Glu Arg Val Glu Ser Leu Ser Gln Val Glu Val Ile Leu Gln His
    1550              1555                  1560

Ser Ala Ala Asp Ile Ala Arg Ala Glu Met Leu Leu Glu Glu Ala
    1565              1570                  1575

Lys Arg Ala Ser Lys Ser Ala Thr Asp Val Lys Val Thr Ala Asp
    1580              1585                  1590

Met Val Lys Glu Ala Leu Glu Glu Ala Glu Lys Ala Gln Val Ala
    1595              1600                  1605

Ala Glu Lys Ala Ile Lys Gln Ala Asp Glu Asp Ile Gln Gly Thr
    1610              1615                  1620

Gln Asn Leu Leu Thr Ser Ile Glu Ser Glu Thr Ala Ala Ser Glu
    1625              1630                  1635

Glu Thr Leu Phe Asn Ala Ser Gln Arg Ile Ser Glu Leu Glu Arg
    1640              1645                  1650
```

```
Asn Val Glu Glu Leu Lys Arg Lys Ala Ala Gln Asn Ser Gly Glu
    1655                1660                1665

Ala Glu Tyr Ile Glu Lys Val Val Tyr Thr Val Lys Gln Ser Ala
    1670                1675                1680

Glu Asp Val Lys Lys Thr Leu Asp Gly Glu Leu Asp Glu Lys Tyr
    1685                1690                1695

Lys Lys Val Glu Asn Leu Ile Ala Lys Lys Thr Glu Glu Ser Ala
    1700                1705                1710

Asp Ala Arg Arg Lys Ala Glu Met Leu Gln Asn Glu Ala Lys Thr
    1715                1720                1725

Leu Leu Ala Gln Ala Asn Ser Lys Leu Gln Leu Leu Lys Asp Leu
    1730                1735                1740

Glu Arg Lys Tyr Glu Asp Asn Gln Arg Tyr Leu Glu Asp Lys Ala
    1745                1750                1755

Gln Glu Leu Ala Arg Leu Glu Gly Glu Val Arg Ser Leu Leu Lys
    1760                1765                1770

Asp Ile Ser Gln Lys Val Ala Val Tyr Ser Thr Cys Leu
    1775                1780                1785

<210> SEQ ID NO 38
<211> LENGTH: 1798
<212> TYPE: PRT
<213> ORGANISM: Homo sapiens

<400> SEQUENCE: 38

Met Glu Leu Thr Ser Arg Glu Arg Gly Arg Gly Gln Pro Leu Pro Trp
1               5                   10                  15

Glu Leu Arg Leu Gly Leu Leu Leu Ser Val Leu Ala Ala Thr Leu Ala
                20                  25                  30

Gln Ala Pro Ala Pro Asp Val Pro Gly Cys Ser Arg Gly Ser Cys Tyr
            35                  40                  45

Pro Ala Thr Gly Asp Leu Leu Val Gly Arg Ala Asp Arg Leu Thr Ala
        50                  55                  60

Ser Ser Thr Cys Gly Leu Asn Gly Pro Gln Pro Tyr Cys Ile Val Ser
65                  70                  75                  80

His Leu Gln Asp Glu Lys Lys Cys Phe Leu Cys Asp Ser Arg Arg Pro
                85                  90                  95

Phe Ser Ala Arg Asp Asn Pro His Ser His Arg Ile Gln Asn Val Val
            100                 105                 110

Thr Ser Phe Ala Pro Gln Arg Arg Ala Ala Trp Trp Gln Ser Glu Asn
        115                 120                 125

Gly Ile Pro Ala Val Thr Ile Gln Leu Asp Leu Glu Ala Glu Phe His
    130                 135                 140

Phe Thr His Leu Ile Met Thr Phe Lys Thr Phe Arg Pro Ala Ala Met
145                 150                 155                 160

Leu Val Glu Arg Ser Ala Asp Phe Gly Arg Thr Trp His Val Tyr Arg
                165                 170                 175

Tyr Phe Ser Tyr Asp Cys Gly Ala Asp Phe Pro Gly Val Pro Leu Ala
            180                 185                 190

Pro Pro Arg His Trp Asp Asp Val Val Cys Glu Ser Arg Tyr Ser Glu
        195                 200                 205

Ile Glu Pro Ser Thr Glu Gly Glu Val Ile Tyr Arg Val Leu Asp Pro
    210                 215                 220

Ala Ile Pro Ile Pro Asp Pro Tyr Ser Ser Arg Ile Gln Asn Leu Leu
225                 230                 235                 240
```

```
Lys Ile Thr Asn Leu Arg Val Asn Leu Thr Arg Leu His Thr Leu Gly
                245                 250                 255

Asp Asn Leu Leu Asp Pro Arg Arg Glu Ile Arg Glu Lys Tyr Tyr Tyr
            260                 265                 270

Ala Leu Tyr Glu Leu Val Val Arg Gly Asn Cys Phe Cys Tyr Gly His
        275                 280                 285

Ala Ser Glu Cys Ala Pro Ala Pro Gly Ala Pro Ala His Ala Glu Gly
    290                 295                 300

Met Val His Gly Ala Cys Ile Cys Lys His Asn Thr Arg Gly Leu Asn
305                 310                 315                 320

Cys Glu Gln Cys Gln Asp Phe Tyr Arg Asp Leu Pro Trp Arg Pro Ala
                325                 330                 335

Glu Asp Gly His Ser His Ala Cys Arg Lys Cys Glu Cys His Gly His
            340                 345                 350

Thr His Ser Cys His Phe Asp Met Ala Val Tyr Leu Ala Ser Gly Asn
        355                 360                 365

Val Ser Gly Gly Val Cys Asp Gly Cys Gln His Asn Thr Ala Gly Arg
    370                 375                 380

His Cys Glu Leu Cys Arg Pro Phe Phe Tyr Arg Asp Pro Thr Lys Asp
385                 390                 395                 400

Leu Arg Asp Pro Ala Val Cys Arg Ser Cys Asp Cys Asp Pro Met Gly
                405                 410                 415

Ser Gln Asp Gly Gly Arg Cys Asp Ser His Asp Asp Pro Ala Leu Gly
            420                 425                 430

Leu Val Ser Gly Gln Cys Arg Cys Lys Glu His Val Val Gly Thr Arg
    435                 440                 445

Cys Gln Gln Cys Arg Asp Gly Phe Phe Gly Leu Ser Ile Ser Asp Arg
450                 455                 460

Leu Gly Cys Arg Arg Cys Gln Cys Asn Ala Arg Gly Thr Val Pro Gly
465                 470                 475                 480

Ser Thr Pro Cys Asp Pro Asn Ser Gly Ser Cys Tyr Cys Lys Arg Leu
                485                 490                 495

Val Thr Gly Arg Gly Cys Asp Arg Cys Leu Pro Gly His Trp Gly Leu
            500                 505                 510

Ser His Asp Leu Leu Gly Cys Arg Pro Cys Asp Cys Asp Val Gly Gly
    515                 520                 525

Ala Leu Asp Pro Gln Cys Asp Glu Gly Thr Gly Gln Cys His Cys Arg
530                 535                 540

Gln His Met Val Gly Arg Arg Cys Glu Gln Val Gln Pro Gly Tyr Phe
545                 550                 555                 560

Arg Pro Phe Leu Asp His Leu Ile Trp Glu Ala Glu Asp Thr Arg Gly
                565                 570                 575

Gln Val Leu Asp Val Val Glu Arg Leu Val Thr Pro Gly Glu Thr Pro
            580                 585                 590

Ser Trp Thr Gly Ser Gly Phe Val Arg Leu Gln Glu Gly Gln Thr Leu
    595                 600                 605

Glu Phe Leu Val Ala Ser Val Pro Lys Ala Met Asp Tyr Asp Leu Leu
610                 615                 620

Leu Arg Leu Glu Pro Gln Val Pro Glu Gln Trp Ala Glu Leu Glu Leu
625                 630                 635                 640

Ile Val Gln Arg Pro Gly Pro Val Pro Ala His Ser Leu Cys Gly His
                645                 650                 655
```

-continued

Leu Val Pro Lys Asp Asp Arg Ile Gln Gly Thr Leu Gln Pro His Ala
            660                 665                 670

Arg Tyr Leu Ile Phe Pro Asn Pro Val Cys Leu Glu Pro Gly Ile Ser
            675                 680                 685

Tyr Lys Leu His Leu Lys Leu Val Arg Thr Gly Gly Ser Ala Gln Pro
            690                 695                 700

Glu Thr Pro Tyr Ser Gly Pro Gly Leu Leu Ile Asp Ser Leu Val Leu
705                     710                 715                 720

Leu Pro Arg Val Leu Val Leu Glu Met Phe Ser Gly Gly Asp Ala Ala
                    725                 730                 735

Ala Leu Glu Arg Gln Ala Thr Phe Glu Arg Tyr Gln Cys His Glu Glu
            740                 745                 750

Gly Leu Val Pro Ser Lys Thr Ser Pro Ser Glu Ala Cys Ala Pro Leu
            755                 760                 765

Leu Ile Ser Leu Ser Thr Leu Ile Tyr Asn Gly Ala Leu Pro Cys Gln
            770                 775                 780

Cys Asn Pro Gln Gly Ser Leu Ser Ser Glu Cys Asn Pro His Gly Gly
785                 790                 795                 800

Gln Cys Leu Cys Lys Pro Gly Val Val Gly Arg Arg Cys Asp Leu Cys
            805                 810                 815

Ala Pro Gly Tyr Tyr Gly Phe Gly Pro Thr Gly Cys Gln Ala Cys Gln
            820                 825                 830

Cys Ser His Glu Gly Ala Leu Ser Ser Leu Cys Glu Lys Thr Ser Gly
            835                 840                 845

Gln Cys Leu Cys Arg Thr Gly Ala Phe Gly Leu Arg Cys Asp Arg Cys
850                 855                 860

Gln Arg Gly Gln Trp Gly Phe Pro Ser Cys Arg Pro Cys Val Cys Asn
865                 870                 875                 880

Gly His Ala Asp Glu Cys Asn Thr His Thr Gly Ala Cys Leu Gly Cys
                    885                 890                 895

Arg Asp His Thr Gly Gly Glu His Cys Glu Arg Cys Ile Ala Gly Phe
            900                 905                 910

His Gly Asp Pro Arg Leu Pro Tyr Gly Gly Gln Cys Arg Pro Cys Pro
            915                 920                 925

Cys Pro Glu Gly Pro Gly Ser Gln Arg His Phe Ala Thr Ser Cys His
930                 935                 940

Gln Asp Glu Tyr Ser Gln Gln Ile Val Cys His Cys Arg Ala Gly Tyr
945                 950                 955                 960

Thr Gly Leu Arg Cys Glu Ala Cys Ala Pro Gly His Phe Gly Asp Pro
            965                 970                 975

Ser Arg Pro Gly Gly Arg Cys Gln Leu Cys Glu Cys Ser Gly Asn Ile
            980                 985                 990

Asp Pro Met Asp Pro Asp Ala Cys Asp Pro His Thr Gly Gln Cys Leu
            995                 1000                1005

Arg Cys Leu His His Thr Glu Gly Pro His Cys Ala His Cys Lys
        1010                1015                1020

Pro Gly Phe His Gly Gln Ala Ala Arg Gln Ser Cys His Arg Cys
        1025                1030                1035

Thr Cys Asn Leu Leu Gly Thr Asn Pro Gln Gln Cys Pro Ser Pro
        1040                1045                1050

Asp Gln Cys His Cys Asp Pro Ser Ser Gly Gln Cys Pro Cys Leu
        1055                1060                1065

Pro Asn Val Gln Gly Pro Ser Cys Asp Arg Cys Ala Pro Asn Phe

```
                1070                1075                1080
Trp Asn Leu Thr Ser Gly His Gly Cys Gln Pro Cys Ala Cys His
    1085                1090                1095

Pro Ser Arg Ala Arg Gly Pro Thr Cys Asn Glu Phe Thr Gly Gln
    1100                1105                1110

Cys His Cys Arg Ala Gly Phe Gly Gly Arg Thr Cys Ser Glu Cys
    1115                1120                1125

Gln Glu Leu His Trp Gly Asp Pro Gly Leu Gln Cys His Ala Cys
    1130                1135                1140

Asp Cys Asp Ser Arg Gly Ile Asp Thr Pro Gln Cys His Arg Phe
    1145                1150                1155

Thr Gly His Cys Ser Cys Arg Pro Gly Val Ser Gly Val Arg Cys
    1160                1165                1170

Asp Gln Cys Ala Arg Gly Phe Ser Gly Ile Phe Pro Ala Cys His
    1175                1180                1185

Pro Cys His Ala Cys Phe Gly Asp Trp Asp Arg Val Val Gln Asp
    1190                1195                1200

Leu Ala Ala Arg Thr Gln Arg Leu Glu Gln Arg Ala Gln Glu Leu
    1205                1210                1215

Gln Gln Thr Gly Val Leu Gly Ala Phe Glu Ser Ser Phe Trp His
    1220                1225                1230

Met Gln Glu Lys Leu Gly Ile Val Gln Gly Ile Val Gly Ala Arg
    1235                1240                1245

Asn Thr Ser Ala Ala Ser Thr Ala Gln Leu Val Glu Ala Thr Glu
    1250                1255                1260

Glu Leu Arg Arg Glu Ile Gly Glu Ala Thr Glu His Leu Thr Gln
    1265                1270                1275

Leu Glu Ala Asp Leu Thr Asp Val Gln Asp Glu Asn Phe Asn Ala
    1280                1285                1290

Asn His Ala Leu Ser Gly Leu Glu Arg Asp Arg Leu Ala Leu Asn
    1295                1300                1305

Leu Thr Leu Arg Gln Leu Asp Gln His Leu Asp Leu Leu Lys His
    1310                1315                1320

Ser Asn Phe Leu Gly Ala Tyr Asp Ser Ile Arg His Ala His Ser
    1325                1330                1335

Gln Ser Ala Glu Ala Glu Arg Arg Ala Asn Thr Ser Ala Leu Ala
    1340                1345                1350

Val Pro Ser Pro Val Ser Asn Ser Ala Ser Ala Arg His Arg Thr
    1355                1360                1365

Glu Ala Leu Met Asp Ala Gln Lys Glu Asp Phe Asn Ser Lys His
    1370                1375                1380

Met Ala Asn Gln Arg Ala Leu Gly Lys Leu Ser Ala His Thr His
    1385                1390                1395

Thr Leu Ser Leu Thr Asp Ile Asn Glu Leu Val Cys Gly Ala Pro
    1400                1405                1410

Gly Asp Ala Pro Cys Ala Thr Ser Pro Cys Gly Gly Ala Gly Cys
    1415                1420                1425

Arg Asp Glu Asp Gly Gln Pro Arg Cys Gly Gly Leu Ser Cys Asn
    1430                1435                1440

Gly Ala Ala Ala Thr Ala Asp Leu Ala Leu Gly Arg Ala Arg His
    1445                1450                1455

Thr Gln Ala Glu Leu Gln Arg Ala Leu Ala Glu Gly Gly Ser Ile
    1460                1465                1470
```

```
Leu Ser Arg Val Ala Glu Thr Arg Arg Gln Ala Ser Glu Ala Gln
    1475                1480                1485

Gln Arg Ala Gln Ala Ala Leu Asp Lys Ala Asn Ala Ser Arg Gly
    1490                1495                1500

Gln Val Glu Gln Ala Asn Gln Glu Leu Gln Glu Leu Ile Gln Ser
    1505                1510                1515

Val Lys Asp Phe Leu Asn Gln Glu Gly Ala Asp Pro Asp Ser Ile
    1520                1525                1530

Glu Met Val Ala Thr Arg Val Leu Glu Leu Ser Ile Pro Ala Ser
    1535                1540                1545

Ala Glu Gln Ile Gln His Leu Ala Gly Ala Ile Ala Glu Arg Val
    1550                1555                1560

Arg Ser Leu Ala Asp Val Asp Ala Ile Leu Ala Arg Thr Val Gly
    1565                1570                1575

Asp Val Arg Arg Ala Glu Gln Leu Leu Gln Asp Ala Arg Arg Ala
    1580                1585                1590

Arg Ser Trp Ala Glu Asp Glu Lys Gln Lys Ala Glu Thr Val Gln
    1595                1600                1605

Ala Ala Leu Glu Glu Ala Gln Arg Ala Gln Gly Ile Ala Gln Gly
    1610                1615                1620

Ala Ile Arg Gly Ala Val Ala Asp Thr Arg Asp Thr Glu Gln Thr
    1625                1630                1635

Leu Tyr Gln Val Gln Glu Arg Met Ala Gly Ala Glu Arg Ala Leu
    1640                1645                1650

Ser Ser Ala Gly Glu Arg Ala Arg Gln Leu Asp Ala Leu Leu Glu
    1655                1660                1665

Ala Leu Lys Leu Lys Arg Ala Gly Asn Ser Leu Ala Ala Ser Thr
    1670                1675                1680

Ala Glu Glu Thr Ala Gly Ser Ala Gln Gly Arg Ala Gln Glu Ala
    1685                1690                1695

Glu Gln Leu Leu Arg Gly Pro Leu Gly Asp Gln Tyr Gln Thr Val
    1700                1705                1710

Lys Ala Leu Ala Glu Arg Lys Ala Gln Gly Val Leu Ala Ala Gln
    1715                1720                1725

Ala Arg Ala Glu Gln Leu Arg Asp Glu Ala Arg Asp Leu Leu Gln
    1730                1735                1740

Ala Ala Gln Asp Lys Leu Gln Arg Leu Gln Glu Leu Glu Gly Thr
    1745                1750                1755

Tyr Glu Glu Asn Glu Arg Ala Leu Glu Ser Lys Ala Ala Gln Leu
    1760                1765                1770

Asp Gly Leu Glu Ala Arg Met Arg Ser Val Leu Gln Ala Ile Asn
    1775                1780                1785

Leu Gln Val Gln Ile Tyr Asn Thr Cys Gln
    1790                1795

<210> SEQ ID NO 39
<211> LENGTH: 1172
<212> TYPE: PRT
<213> ORGANISM: Homo sapiens

<400> SEQUENCE: 39

Met Arg Pro Phe Phe Leu Leu Cys Phe Ala Leu Pro Gly Leu Leu His
1               5                   10                  15

Ala Gln Gln Ala Cys Ser Arg Gly Ala Cys Tyr Pro Pro Val Gly Asp
```

```
                20                  25                  30
Leu Leu Val Gly Arg Thr Arg Phe Leu Arg Ala Ser Ser Thr Cys Gly
            35                  40                  45
Leu Thr Lys Pro Glu Thr Tyr Cys Thr Gln Tyr Gly Glu Trp Gln Met
        50                  55                  60
Lys Cys Cys Lys Cys Asp Ser Arg Gln Pro His Asn Tyr Tyr Ser His
65                  70                  75                  80
Arg Val Glu Asn Val Ala Ser Ser Gly Pro Met Arg Trp Trp Gln
                85                  90                  95
Ser Gln Asn Asp Val Asn Pro Val Ser Leu Gln Leu Asp Leu Asp Arg
            100                 105                 110
Arg Phe Gln Leu Gln Glu Val Met Met Glu Phe Gln Gly Pro Met Pro
        115                 120                 125
Ala Gly Met Leu Ile Glu Arg Ser Ser Asp Phe Gly Lys Thr Trp Arg
        130                 135                 140
Val Tyr Gln Tyr Leu Ala Ala Asp Cys Thr Ser Thr Phe Pro Arg Val
145                 150                 155                 160
Arg Gln Gly Arg Pro Gln Ser Trp Gln Asp Val Arg Cys Gln Ser Leu
                165                 170                 175
Pro Gln Arg Pro Asn Ala Arg Leu Asn Gly Gly Lys Val Gln Leu Asn
            180                 185                 190
Leu Met Asp Leu Val Ser Gly Ile Pro Ala Thr Gln Ser Gln Lys Ile
        195                 200                 205
Gln Glu Val Gly Glu Ile Thr Asn Leu Arg Val Asn Phe Thr Arg Leu
        210                 215                 220
Ala Pro Val Pro Gln Arg Gly Tyr His Pro Pro Ser Ala Tyr Tyr Ala
225                 230                 235                 240
Val Ser Gln Leu Arg Leu Gln Gly Ser Cys Phe Cys His Gly His Ala
                245                 250                 255
Asp Arg Cys Ala Pro Lys Pro Gly Ala Ser Ala Gly Pro Ser Thr Ala
            260                 265                 270
Val Gln Val His Asp Val Cys Val Cys Gln His Asn Thr Ala Gly Pro
        275                 280                 285
Asn Cys Glu Arg Cys Ala Pro Phe Tyr Asn Asn Arg Pro Trp Arg Pro
        290                 295                 300
Ala Glu Gly Gln Asp Ala His Glu Cys Gln Arg Cys Asp Cys Asn Gly
305                 310                 315                 320
His Ser Glu Thr Cys His Phe Asp Pro Ala Val Phe Ala Ala Ser Gln
                325                 330                 335
Gly Ala Tyr Gly Gly Val Cys Asp Asn Cys Arg Asp His Thr Glu Gly
            340                 345                 350
Lys Asn Cys Glu Arg Cys Gln Leu His Tyr Phe Arg Asn Arg Arg Pro
        355                 360                 365
Gly Ala Ser Ile Gln Glu Thr Cys Ile Ser Cys Glu Cys Asp Pro Asp
        370                 375                 380
Gly Ala Val Pro Gly Ala Pro Cys Asp Pro Val Thr Gly Gln Cys Val
385                 390                 395                 400
Cys Lys Glu His Val Gln Gly Glu Arg Cys Asp Leu Cys Lys Pro Gly
                405                 410                 415
Phe Thr Gly Leu Thr Tyr Ala Asn Pro Gln Gly Cys His Arg Cys Asp
            420                 425                 430
Cys Asn Ile Leu Gly Ser Arg Arg Asp Met Pro Cys Asp Glu Glu Ser
        435                 440                 445
```

Gly Arg Cys Leu Cys Leu Pro Asn Val Val Gly Pro Lys Cys Asp Gln
            450                 455                 460

Cys Ala Pro Tyr His Trp Lys Leu Ala Ser Gly Gln Gly Cys Glu Pro
465                 470                 475                 480

Cys Ala Cys Asp Pro His Asn Ser Leu Ser Pro Gln Cys Asn Gln Phe
                485                 490                 495

Thr Gly Gln Cys Pro Cys Arg Glu Gly Phe Gly Gly Leu Met Cys Ser
            500                 505                 510

Ala Ala Ala Ile Arg Gln Cys Pro Asp Arg Thr Tyr Gly Asp Val Ala
            515                 520                 525

Thr Gly Cys Arg Ala Cys Asp Cys Asp Phe Arg Gly Thr Glu Gly Pro
            530                 535                 540

Gly Cys Asp Lys Ala Ser Gly Arg Cys Leu Cys Arg Pro Gly Leu Thr
545                 550                 555                 560

Gly Pro Arg Cys Asp Gln Cys Gln Arg Gly Tyr Cys Asn Arg Tyr Pro
                565                 570                 575

Val Cys Val Ala Cys His Pro Cys Phe Gln Thr Tyr Asp Ala Asp Leu
            580                 585                 590

Arg Glu Gln Ala Leu Arg Phe Gly Arg Leu Arg Asn Ala Thr Ala Ser
            595                 600                 605

Leu Trp Ser Gly Pro Gly Leu Glu Asp Arg Gly Leu Ala Ser Arg Ile
610                 615                 620

Leu Asp Ala Lys Ser Lys Ile Glu Gln Ile Arg Ala Val Leu Ser Ser
625                 630                 635                 640

Pro Ala Val Thr Glu Gln Glu Val Ala Gln Val Ala Ser Ala Ile Leu
            645                 650                 655

Ser Leu Arg Arg Thr Leu Gln Gly Leu Gln Leu Asp Leu Pro Leu Glu
            660                 665                 670

Glu Glu Thr Leu Ser Leu Pro Arg Asp Leu Glu Ser Leu Asp Arg Ser
            675                 680                 685

Phe Asn Gly Leu Leu Thr Met Tyr Gln Arg Lys Arg Glu Gln Phe Glu
690                 695                 700

Lys Ile Ser Ser Ala Asp Pro Ser Gly Ala Phe Arg Met Leu Ser Thr
705                 710                 715                 720

Ala Tyr Glu Gln Ser Ala Gln Ala Ala Gln Gln Val Ser Asp Ser Ser
            725                 730                 735

Arg Leu Leu Asp Gln Leu Arg Asp Ser Arg Arg Glu Ala Glu Arg Leu
            740                 745                 750

Val Arg Gln Ala Gly Gly Gly Gly Thr Gly Ser Pro Lys Leu Val
            755                 760                 765

Ala Leu Arg Leu Glu Met Ser Ser Leu Pro Asp Leu Thr Pro Thr Phe
770                 775                 780

Asn Lys Leu Cys Gly Asn Ser Arg Gln Met Ala Cys Thr Pro Ile Ser
785                 790                 795                 800

Cys Pro Gly Glu Leu Cys Pro Gln Asp Asn Gly Thr Ala Cys Gly Ser
            805                 810                 815

Arg Cys Arg Gly Val Leu Pro Arg Ala Gly Gly Ala Phe Leu Met Ala
            820                 825                 830

Gly Gln Val Ala Glu Gln Leu Arg Gly Phe Asn Ala Gln Leu Gln Arg
            835                 840                 845

Thr Arg Gln Met Ile Arg Ala Ala Glu Glu Ser Ala Ser Gln Ile Gln
            850                 855                 860

```
Ser Ser Ala Gln Arg Leu Glu Thr Gln Val Ser Ala Arg Ser Gln
865                 870                 875                 880

Met Glu Glu Asp Val Arg Arg Thr Arg Leu Leu Ile Gln Gln Val Arg
                885                 890                 895

Asp Phe Leu Thr Asp Pro Asp Thr Asp Ala Ala Thr Ile Gln Glu Val
            900                 905                 910

Ser Glu Ala Val Leu Ala Leu Trp Leu Pro Thr Asp Ser Ala Thr Val
        915                 920                 925

Leu Gln Lys Met Asn Glu Ile Gln Ala Ile Ala Ala Arg Leu Pro Asn
    930                 935                 940

Val Asp Leu Val Leu Ser Gln Thr Lys Gln Asp Ile Ala Arg Ala Arg
945                 950                 955                 960

Arg Leu Gln Ala Glu Ala Glu Glu Ala Arg Ser Arg Ala His Ala Val
                965                 970                 975

Glu Gly Gln Val Glu Asp Val Val Gly Asn Leu Arg Gln Gly Thr Val
            980                 985                 990

Ala Leu Gln Glu Ala Gln Asp Thr Met Gln Gly Thr Ser Arg Ser Leu
        995                 1000                1005

Arg Leu Ile Gln Asp Arg Val Ala Glu Val Gln Gln Val Leu Arg
    1010                1015                1020

Pro Ala Glu Lys Leu Val Thr Ser Met Thr Lys Gln Leu Gly Asp
    1025                1030                1035

Phe Trp Thr Arg Met Glu Glu Leu Arg His Gln Ala Arg Gln Gln
    1040                1045                1050

Gly Ala Glu Ala Val Gln Ala Gln Gln Leu Ala Glu Gly Ala Ser
    1055                1060                1065

Glu Gln Ala Leu Ser Ala Gln Glu Gly Phe Glu Arg Ile Lys Gln
    1070                1075                1080

Lys Tyr Ala Glu Leu Lys Asp Arg Leu Gly Gln Ser Ser Met Leu
    1085                1090                1095

Gly Glu Gln Gly Ala Arg Ile Gln Ser Val Lys Thr Glu Ala Glu
    1100                1105                1110

Glu Leu Phe Gly Glu Thr Met Glu Met Met Asp Arg Met Lys Asp
    1115                1120                1125

Met Glu Leu Glu Leu Leu Arg Gly Ser Gln Ala Ile Met Leu Arg
    1130                1135                1140

Ser Ala Asp Leu Thr Gly Leu Glu Lys Arg Val Glu Gln Ile Arg
    1145                1150                1155

Asp His Ile Asn Gly Arg Val Leu Tyr Tyr Ala Thr Cys Lys
    1160                1165                1170

<210> SEQ ID NO 40
<211> LENGTH: 1761
<212> TYPE: PRT
<213> ORGANISM: Homo sapiens

<400> SEQUENCE: 40

Met Gln Phe Gln Leu Thr Leu Phe Leu His Leu Gly Trp Leu Ser Tyr
1               5                   10                  15

Ser Lys Ala Gln Asp Asp Cys Asn Arg Gly Ala Cys His Pro Thr Thr
            20                  25                  30

Gly Asp Leu Leu Val Gly Arg Asn Thr Gln Leu Met Ala Ser Ser Thr
        35                  40                  45

Cys Gly Leu Ser Arg Ala Gln Lys Tyr Cys Ile Leu Ser Tyr Leu Glu
    50                  55                  60
```

-continued

Gly Glu Gln Lys Cys Phe Ile Cys Asp Ser Arg Phe Pro Tyr Asp Pro
65                  70                  75                  80

Tyr Asp Gln Pro Asn Ser His Thr Ile Glu Asn Val Ile Val Ser Phe
            85                  90                  95

Glu Pro Asp Arg Glu Lys Lys Trp Trp Gln Ser Glu Asn Gly Leu Asp
            100                 105                 110

His Val Ser Ile Arg Leu Asp Leu Glu Ala Leu Phe Arg Phe Ser His
            115                 120                 125

Leu Ile Leu Thr Phe Lys Thr Phe Arg Pro Ala Ala Met Leu Val Glu
130                 135                 140

Arg Ser Thr Asp Tyr Gly His Asn Trp Lys Val Phe Lys Tyr Phe Ala
145                 150                 155                 160

Lys Asp Cys Ala Thr Ser Phe Pro Asn Ile Thr Ser Gly Gln Ala Gln
                165                 170                 175

Gly Val Gly Asp Ile Val Cys Asp Ser Lys Tyr Ser Asp Ile Glu Pro
            180                 185                 190

Ser Thr Gly Gly Glu Val Val Leu Lys Val Leu Asp Pro Ser Phe Glu
            195                 200                 205

Ile Glu Asn Pro Tyr Ser Pro Tyr Ile Gln Asp Leu Val Thr Leu Thr
210                 215                 220

Asn Leu Arg Ile Asn Phe Thr Lys Leu His Thr Leu Gly Asp Ala Leu
225                 230                 235                 240

Leu Gly Arg Arg Gln Asn Asp Ser Leu Asp Lys Tyr Tyr Tyr Ala Leu
            245                 250                 255

Tyr Glu Met Ile Val Arg Gly Ser Cys Phe Cys Asn Gly His Ala Ser
            260                 265                 270

Glu Cys Arg Pro Met Gln Lys Met Arg Gly Asp Val Phe Ser Pro Pro
            275                 280                 285

Gly Met Val His Gly Gln Cys Val Cys Gln His Asn Thr Asp Gly Pro
290                 295                 300

Asn Cys Glu Arg Cys Lys Asp Phe Phe Gln Asp Ala Pro Trp Arg Pro
305                 310                 315                 320

Ala Ala Asp Leu Gln Asp Asn Ala Cys Arg Ser Cys Ser Cys Asn Ser
            325                 330                 335

His Ser Ser Arg Cys His Phe Asp Met Thr Thr Tyr Leu Ala Ser Gly
            340                 345                 350

Gly Leu Ser Gly Gly Val Cys Glu Asp Cys Gln His Asn Thr Glu Gly
            355                 360                 365

Gln His Cys Asp Arg Cys Arg Pro Leu Phe Tyr Arg Asp Pro Leu Lys
            370                 375                 380

Thr Ile Ser Asp Pro Tyr Ala Cys Ile Pro Cys Glu Cys Asp Pro Asp
385                 390                 395                 400

Gly Thr Ile Ser Gly Gly Ile Cys Val Ser His Ser Asp Pro Ala Leu
            405                 410                 415

Gly Ser Val Ala Gly Gln Cys Leu Cys Lys Glu Asn Val Glu Gly Ala
            420                 425                 430

Lys Cys Asp Gln Cys Lys Pro Asn His Tyr Gly Leu Ser Ala Thr Asp
            435                 440                 445

Pro Leu Gly Cys Gln Pro Cys Asp Cys Asn Pro Leu Gly Ser Leu Pro
            450                 455                 460

Phe Leu Thr Cys Asp Val Asp Thr Gly Gln Cys Leu Cys Leu Ser Tyr
465                 470                 475                 480

Val Thr Gly Ala His Cys Glu Glu Cys Thr Val Gly Tyr Trp Gly Leu
            485                 490                 495

Gly Asn His Leu His Gly Cys Ser Pro Cys Asp Cys Asp Ile Gly Gly
        500                 505                 510

Ala Tyr Ser Asn Val Cys Ser Pro Lys Asn Gly Gln Cys Glu Cys Arg
        515                 520                 525

Pro His Val Thr Gly Arg Ser Cys Ser Glu Pro Ala Pro Gly Tyr Phe
    530                 535                 540

Phe Ala Pro Leu Asn Phe Tyr Leu Tyr Glu Ala Glu Ala Thr Thr
545                 550                 555                 560

Leu Gln Gly Leu Ala Pro Leu Gly Ser Glu Thr Phe Gly Gln Ser Pro
                565                 570                 575

Ala Val His Val Val Leu Gly Glu Pro Val Pro Gly Asn Pro Val Thr
            580                 585                 590

Trp Thr Gly Pro Gly Phe Ala Arg Val Leu Pro Gly Ala Gly Leu Arg
            595                 600                 605

Phe Ala Val Asn Asn Ile Pro Phe Pro Val Asp Phe Thr Ile Ala Ile
    610                 615                 620

His Tyr Glu Thr Gln Ser Ala Ala Asp Trp Thr Val Gln Ile Val Val
625                 630                 635                 640

Asn Pro Pro Gly Gly Ser Glu His Cys Ile Pro Lys Thr Leu Gln Ser
                645                 650                 655

Lys Pro Gln Ser Phe Ala Leu Pro Ala Ala Thr Arg Ile Met Leu Leu
                660                 665                 670

Pro Thr Pro Ile Cys Leu Glu Pro Asp Val Gln Tyr Ser Ile Asp Val
            675                 680                 685

Tyr Phe Ser Gln Pro Leu Gln Gly Glu Ser His Ala His Ser His Val
    690                 695                 700

Leu Val Asp Ser Leu Gly Leu Ile Pro Gln Ile Asn Ser Leu Glu Asn
705                 710                 715                 720

Phe Cys Ser Lys Gln Asp Leu Asp Glu Tyr Gln Leu His Asn Cys Val
                725                 730                 735

Glu Ile Ala Ser Ala Met Gly Pro Gln Val Leu Pro Gly Ala Cys Glu
            740                 745                 750

Arg Leu Ile Ile Ser Met Ser Ala Lys Leu His Asp Gly Ala Val Ala
            755                 760                 765

Cys Lys Cys His Pro Gln Gly Ser Val Gly Ser Ser Cys Ser Arg Leu
    770                 775                 780

Gly Gly Gln Cys Gln Cys Lys Pro Leu Val Val Gly Arg Cys Cys Asp
785                 790                 795                 800

Arg Cys Ser Thr Gly Ser Tyr Asp Leu Gly His His Gly Cys His Pro
            805                 810                 815

Cys His Cys His Pro Gln Gly Ser Lys Asp Thr Val Cys Asp Gln Val
            820                 825                 830

Thr Gly Gln Cys Pro Cys His Gly Glu Val Ser Gly Arg Arg Cys Asp
            835                 840                 845

Arg Cys Leu Ala Gly Tyr Phe Gly Phe Pro Ser Cys His Pro Cys Pro
    850                 855                 860

Cys Asn Arg Phe Ala Glu Leu Cys Asp Pro Glu Thr Gly Ser Cys Phe
865                 870                 875                 880

Asn Cys Gly Gly Phe Thr Thr Gly Arg Asn Cys Glu Arg Cys Ile Asp
                885                 890                 895

Gly Tyr Tyr Gly Asn Pro Ser Ser Gly Gln Pro Cys Arg Pro Cys Leu

```
            900             905             910
Cys Pro Asp Asp Pro Ser Ser Asn Gln Tyr Phe Ala His Ser Cys Tyr
            915             920             925
Gln Asn Leu Trp Ser Ser Asp Val Ile Cys Asn Cys Leu Gln Gly Tyr
            930             935             940
Thr Gly Thr Gln Cys Gly Glu Cys Ser Thr Gly Phe Tyr Gly Asn Pro
945             950             955             960
Arg Ile Ser Gly Ala Pro Cys Gln Pro Cys Ala Cys Asn Asn Asn Ile
            965             970             975
Asp Val Thr Asp Pro Glu Ser Cys Ser Arg Val Thr Gly Glu Cys Leu
            980             985             990
Arg Cys Leu His Asn Thr Gln Gly Ala Asn Cys Gln Leu Cys Lys Pro
            995             1000            1005
Gly His Tyr Gly Ser Ala Leu Asn Gln Thr Cys Arg Arg Cys Ser
            1010            1015            1020
Cys His Ala Ser Gly Val Ser Pro Met Glu Cys Pro Pro Gly Gly
            1025            1030            1035
Gly Ala Cys Leu Cys Asp Pro Val Thr Gly Ala Cys Pro Cys Leu
            1040            1045            1050
Pro Asn Val Thr Gly Leu Ala Cys Asp Arg Cys Ala Asp Gly Tyr
            1055            1060            1065
Trp Asn Leu Val Pro Gly Arg Gly Cys Gln Ser Cys Asp Cys Asp
            1070            1075            1080
Pro Arg Thr Ser Gln Ser Ser His Cys Asp Gln Leu Thr Gly Gln
            1085            1090            1095
Cys Pro Cys Lys Leu Gly Tyr Gly Gly Lys Arg Cys Ser Glu Cys
            1100            1105            1110
Gln Glu Asn Tyr Tyr Gly Asp Pro Pro Gly Arg Cys Ile Pro Cys
            1115            1120            1125
Asp Cys Asn Arg Ala Gly Thr Gln Lys Pro Ile Cys Asp Pro Asp
            1130            1135            1140
Thr Gly Met Cys Arg Cys Arg Glu Gly Val Ser Gly Gln Arg Cys
            1145            1150            1155
Asp Arg Cys Ala Arg Gly His Ser Gln Glu Phe Pro Thr Cys Leu
            1160            1165            1170
Gln Cys His Leu Cys Phe Asp Gln Trp Asp His Thr Ile Ser Ser
            1175            1180            1185
Leu Ser Lys Ala Val Gln Gly Leu Met Arg Leu Ala Ala Asn Met
            1190            1195            1200
Glu Asp Lys Arg Glu Thr Leu Pro Val Cys Glu Ala Asp Phe Lys
            1205            1210            1215
Asp Leu Arg Gly Asn Val Ser Glu Ile Glu Arg Ile Leu Lys His
            1220            1225            1230
Pro Val Phe Pro Ser Gly Lys Phe Leu Lys Val Lys Asp Tyr His
            1235            1240            1245
Asp Ser Val Arg Arg Gln Ile Met Gln Leu Asn Glu Gln Leu Lys
            1250            1255            1260
Ala Val Tyr Glu Phe Gln Asp Leu Lys Asp Thr Ile Glu Arg Ala
            1265            1270            1275
Lys Asn Glu Ala Asp Leu Leu Leu Glu Asp Leu Gln Glu Glu Ile
            1280            1285            1290
Asp Leu Gln Ser Ser Val Leu Asn Ala Ser Ile Ala Asp Ser Ser
            1295            1300            1305
```

```
Glu Asn Ile Lys Lys Tyr Tyr His Ile Ser Ser Ser Ala Glu Lys
    1310                1315                1320

Lys Ile Asn Glu Thr Ser Ser Thr Ile Asn Thr Ser Ala Asn Thr
    1325                1330                1335

Arg Asn Asp Leu Leu Thr Ile Leu Asp Thr Leu Thr Ser Lys Gly
    1340                1345                1350

Asn Leu Ser Leu Glu Arg Leu Lys Gln Ile Lys Ile Pro Asp Ile
    1355                1360                1365

Gln Ile Leu Asn Glu Lys Val Cys Gly Asp Pro Gly Asn Val Pro
    1370                1375                1380

Cys Val Pro Leu Pro Cys Gly Gly Ala Leu Cys Thr Gly Arg Lys
    1385                1390                1395

Gly His Arg Lys Cys Arg Gly Pro Gly Cys His Gly Ser Leu Thr
    1400                1405                1410

Leu Ser Thr Asn Ala Leu Gln Lys Ala Gln Glu Ala Lys Ser Ile
    1415                1420                1425

Ile Arg Asn Leu Asp Lys Gln Val Arg Gly Leu Lys Asn Gln Ile
    1430                1435                1440

Glu Ser Ile Ser Glu Gln Ala Glu Val Ser Lys Asn Asn Ala Leu
    1445                1450                1455

Gln Leu Arg Glu Lys Leu Gly Asn Ile Arg Asn Gln Ser Asp Ser
    1460                1465                1470

Glu Glu Glu Asn Ile Asn Leu Phe Ile Lys Lys Val Lys Asn Phe
    1475                1480                1485

Leu Leu Glu Glu Asn Val Pro Pro Glu Asp Ile Glu Lys Val Ala
    1490                1495                1500

Asn Gly Val Leu Asp Ile His Leu Pro Ile Pro Ser Gln Asn Leu
    1505                1510                1515

Thr Asp Glu Leu Val Lys Ile Gln Lys His Met Gln Leu Cys Glu
    1520                1525                1530

Asp Tyr Arg Thr Asp Glu Asn Arg Leu Asn Glu Glu Ala Asp Gly
    1535                1540                1545

Ala Gln Lys Leu Leu Val Lys Ala Lys Ala Ala Glu Lys Ala Ala
    1550                1555                1560

Asn Ile Leu Leu Asn Leu Asp Lys Thr Leu Asn Gln Leu Gln Gln
    1565                1570                1575

Ala Gln Ile Thr Gln Gly Arg Ala Asn Ser Thr Ile Thr Gln Leu
    1580                1585                1590

Thr Ala Asn Ile Thr Lys Ile Lys Lys Asn Val Leu Gln Ala Glu
    1595                1600                1605

Asn Gln Thr Arg Glu Met Lys Ser Glu Leu Glu Leu Ala Lys Gln
    1610                1615                1620

Arg Ser Gly Leu Glu Asp Gly Leu Ser Leu Leu Gln Thr Lys Leu
    1625                1630                1635

Gln Arg His Gln Asp His Ala Val Asn Ala Lys Val Gln Ala Glu
    1640                1645                1650

Ser Ala Gln His Gln Ala Gly Ser Leu Glu Lys Glu Phe Val Glu
    1655                1660                1665

Leu Lys Lys Gln Tyr Ala Ile Leu Gln Arg Lys Thr Ser Thr Thr
    1670                1675                1680

Gly Leu Thr Lys Glu Thr Leu Gly Lys Val Lys Gln Leu Lys Asp
    1685                1690                1695
```

```
Ala Ala Glu Lys Leu Ala Gly Asp Thr Glu Ala Lys Ile Arg Arg
    1700                1705                1710

Ile Thr Asp Leu Glu Arg Lys Ile Gln Asp Leu Asn Leu Ser Arg
    1715                1720                1725

Gln Ala Lys Ala Asp Gln Leu Arg Ile Leu Glu Asp Gln Val Val
    1730                1735                1740

Ala Ile Lys Asn Glu Ile Val Glu Gln Glu Lys Lys Tyr Ala Arg
    1745                1750                1755

Cys Tyr Ser
    1760

<210> SEQ ID NO 41
<211> LENGTH: 1101
<212> TYPE: PRT
<213> ORGANISM: Homo sapiens

<400> SEQUENCE: 41

Met Gln Phe Gln Leu Thr Leu Phe Leu His Leu Gly Trp Leu Ser Tyr
1               5                   10                  15

Ser Lys Ala Gln Asp Asp Cys Asn Arg Gly Ala Cys His Pro Thr Thr
            20                  25                  30

Gly Asp Leu Leu Val Gly Arg Asn Thr Gln Leu Met Ala Ser Ser Thr
        35                  40                  45

Cys Gly Leu Ser Arg Ala Gln Lys Tyr Cys Ile Leu Ser Tyr Leu Glu
    50                  55                  60

Gly Glu Gln Lys Cys Phe Ile Cys Asp Ser Arg Phe Pro Tyr Asp Pro
65                  70                  75                  80

Tyr Asp Gln Pro Asn Ser His Thr Ile Glu Asn Val Ile Val Ser Phe
                85                  90                  95

Glu Pro Asp Arg Glu Lys Lys Trp Trp Gln Ser Glu Asn Gly Leu Asp
            100                 105                 110

His Val Ser Ile Arg Leu Asp Leu Glu Ala Leu Phe Arg Phe Ser His
        115                 120                 125

Leu Ile Leu Thr Phe Lys Thr Phe Arg Pro Ala Ala Met Leu Val Glu
    130                 135                 140

Arg Ser Thr Asp Tyr Gly His Asn Trp Lys Val Phe Lys Tyr Phe Ala
145                 150                 155                 160

Lys Asp Cys Ala Thr Ser Phe Pro Asn Ile Thr Ser Gly Gln Ala Gln
                165                 170                 175

Gly Val Gly Asp Ile Val Cys Asp Ser Lys Tyr Ser Asp Ile Glu Pro
            180                 185                 190

Ser Thr Gly Gly Glu Val Val Leu Lys Val Leu Asp Pro Ser Phe Glu
        195                 200                 205

Ile Glu Asn Pro Tyr Ser Pro Tyr Ile Gln Asp Leu Val Thr Leu Thr
    210                 215                 220

Asn Leu Arg Ile Asn Phe Thr Lys Leu His Thr Leu Gly Asp Ala Leu
225                 230                 235                 240

Leu Gly Arg Arg Gln Asn Asp Ser Leu Asp Lys Tyr Tyr Tyr Ala Leu
                245                 250                 255

Tyr Glu Met Ile Val Arg Gly Ser Cys Phe Cys Asn Gly His Ala Ser
            260                 265                 270

Glu Cys Arg Pro Met Gln Lys Met Arg Gly Asp Val Phe Ser Pro Pro
        275                 280                 285

Gly Met Val His Gly Gln Cys Val Cys Gln His Asn Thr Asp Gly Pro
    290                 295                 300
```

-continued

```
Asn Cys Glu Arg Cys Lys Asp Phe Phe Gln Asp Ala Pro Trp Arg Pro
305                 310                 315                 320

Ala Ala Asp Leu Gln Asp Asn Ala Cys Arg Ser Cys Ser Cys Asn Ser
            325                 330                 335

His Ser Ser Arg Cys His Phe Asp Met Thr Thr Tyr Leu Ala Ser Gly
        340                 345                 350

Gly Leu Ser Gly Gly Val Cys Glu Asp Cys Gln His Asn Thr Glu Gly
    355                 360                 365

Gln His Cys Asp Arg Cys Arg Pro Leu Phe Tyr Arg Asp Pro Leu Lys
370                 375                 380

Thr Ile Ser Asp Pro Tyr Ala Cys Ile Pro Cys Glu Cys Asp Pro Asp
385                 390                 395                 400

Gly Thr Ile Ser Gly Gly Ile Cys Val Ser His Ser Asp Pro Ala Leu
            405                 410                 415

Gly Ser Val Ala Gly Gln Cys Leu Cys Lys Glu Asn Val Glu Gly Ala
        420                 425                 430

Lys Cys Asp Gln Cys Lys Pro Asn His Tyr Gly Leu Ser Ala Thr Asp
    435                 440                 445

Pro Leu Gly Cys Gln Pro Cys Asp Cys Asn Pro Leu Gly Ser Leu Pro
450                 455                 460

Phe Leu Thr Cys Asp Val Asp Thr Gly Gln Cys Leu Cys Leu Ser Tyr
465                 470                 475                 480

Val Thr Gly Ala His Cys Glu Glu Cys Thr Val Gly Tyr Trp Gly Leu
            485                 490                 495

Gly Asn His Leu His Gly Cys Ser Pro Cys Asp Cys Asp Ile Gly Gly
        500                 505                 510

Ala Tyr Ser Asn Val Cys Ser Pro Lys Asn Gly Gln Cys Glu Cys Arg
    515                 520                 525

Pro His Val Thr Gly Arg Ser Cys Ser Glu Pro Ala Pro Gly Tyr Phe
530                 535                 540

Phe Ala Pro Leu Asn Phe Tyr Leu Tyr Glu Ala Glu Glu Ala Thr Thr
545                 550                 555                 560

Leu Gln Gly Leu Ala Pro Leu Gly Ser Glu Thr Phe Gly Gln Ser Pro
            565                 570                 575

Ala Val His Val Val Leu Gly Glu Pro Val Pro Gly Asn Pro Val Thr
        580                 585                 590

Trp Thr Gly Pro Gly Phe Ala Arg Val Leu Pro Gly Ala Gly Leu Arg
    595                 600                 605

Phe Ala Val Asn Asn Ile Pro Phe Pro Val Asp Phe Thr Ile Ala Ile
610                 615                 620

His Tyr Glu Thr Gln Ser Ala Ala Asp Trp Thr Val Gln Ile Val Val
625                 630                 635                 640

Asn Pro Pro Gly Gly Ser Glu His Cys Ile Pro Lys Thr Leu Gln Ser
            645                 650                 655

Lys Pro Gln Ser Phe Ala Leu Pro Ala Ala Thr Arg Ile Met Leu Leu
        660                 665                 670

Pro Thr Pro Ile Cys Leu Glu Pro Asp Val Gln Tyr Ser Ile Asp Val
    675                 680                 685

Tyr Phe Ser Gln Pro Leu Gln Gly Glu Ser His Ala His Ser His Val
690                 695                 700

Leu Val Asp Ser Leu Gly Leu Ile Pro Gln Ile Asn Ser Leu Glu Asn
705                 710                 715                 720
```

```
Phe Cys Ser Lys Gln Asp Leu Asp Glu Tyr Gln Leu His Asn Cys Val
                725                 730                 735

Glu Ile Ala Ser Ala Met Gly Pro Gln Val Leu Pro Gly Ala Cys Glu
            740                 745                 750

Arg Leu Ile Ile Ser Met Ser Ala Lys Leu His Asp Gly Ala Val Ala
        755                 760                 765

Cys Lys Cys His Pro Gln Gly Ser Val Gly Ser Ser Cys Ser Arg Leu
    770                 775                 780

Gly Gly Gln Cys Gln Cys Lys Pro Leu Val Val Gly Arg Cys Cys Asp
785                 790                 795                 800

Arg Cys Ser Thr Gly Ser Tyr Asp Leu Gly His His Gly Cys His Pro
                805                 810                 815

Cys His Cys His Pro Gln Gly Ser Lys Asp Thr Val Cys Asp Gln Val
            820                 825                 830

Thr Gly Gln Cys Pro Cys His Gly Glu Val Ser Gly Arg Arg Cys Asp
        835                 840                 845

Arg Cys Leu Ala Gly Tyr Phe Gly Phe Pro Ser Cys His Pro Cys Pro
    850                 855                 860

Cys Asn Arg Phe Ala Glu Leu Cys Asp Pro Glu Thr Gly Ser Cys Phe
865                 870                 875                 880

Asn Cys Gly Gly Phe Thr Thr Gly Arg Asn Cys Glu Arg Cys Ile Asp
                885                 890                 895

Gly Tyr Tyr Gly Asn Pro Ser Ser Gly Gln Pro Cys Arg Pro Cys Leu
            900                 905                 910

Cys Pro Asp Asp Pro Ser Ser Asn Gln Tyr Phe Ala His Ser Cys Tyr
        915                 920                 925

Gln Asn Leu Trp Ser Ser Asp Val Ile Cys Asn Cys Leu Gln Gly Tyr
    930                 935                 940

Thr Gly Thr Gln Cys Gly Glu Cys Ser Thr Gly Phe Tyr Gly Asn Pro
945                 950                 955                 960

Arg Ile Ser Gly Ala Pro Cys Gln Pro Cys Ala Cys Asn Asn Asn Ile
                965                 970                 975

Asp Val Thr Asp Pro Glu Ser Cys Ser Arg Val Thr Gly Glu Cys Leu
            980                 985                 990

Arg Cys Leu His Asn Thr Gln Gly Ala Asn Cys Gln Leu Cys Lys Pro
        995                 1000                1005

Gly His Tyr Gly Ser Ala Leu Asn Gln Thr Cys Arg Arg Cys Ser
    1010                1015                1020

Cys His Ala Ser Gly Val Ser Pro Met Glu Cys Pro Pro Gly Gly
    1025                1030                1035

Gly Ala Cys Leu Cys Asp Pro Val Thr Gly Ala Cys Pro Cys Leu
    1040                1045                1050

Pro Asn Val Thr Gly Leu Ala Cys Asp Arg Cys Ala Asp Gly Tyr
    1055                1060                1065

Trp Asn Leu Val Pro Gly Arg Gly Cys Gln Ser Cys Asp Cys Asp
    1070                1075                1080

Pro Arg Thr Ser Gln Ser Ser His Cys Asp Gln Ala Arg Tyr Phe
    1085                1090                1095

Lys Ala Tyr
    1100

<210> SEQ ID NO 42
<211> LENGTH: 772
<212> TYPE: PRT
```

<213> ORGANISM: Homo sapiens

<400> SEQUENCE: 42

| Met | Gln | Phe | Gln | Leu | Thr | Leu | Phe | Leu | His | Leu | Gly | Trp | Leu | Ser | Tyr |
|---|---|---|---|---|---|---|---|---|---|---|---|---|---|---|---|
| 1 | | | | 5 | | | | | 10 | | | | | 15 | |

| Ser | Lys | Ala | Gln | Asp | Asp | Cys | Asn | Arg | Gly | Ala | Cys | His | Pro | Thr | Thr |
|---|---|---|---|---|---|---|---|---|---|---|---|---|---|---|---|
| | | | 20 | | | | | 25 | | | | | 30 | | |

| Gly | Asp | Leu | Leu | Val | Gly | Arg | Asn | Thr | Gln | Leu | Met | Ala | Ser | Ser | Thr |
|---|---|---|---|---|---|---|---|---|---|---|---|---|---|---|---|
| | | 35 | | | | | 40 | | | | | 45 | | | |

| Cys | Gly | Leu | Ser | Arg | Ala | Gln | Lys | Tyr | Cys | Ile | Leu | Ser | Tyr | Leu | Glu |
|---|---|---|---|---|---|---|---|---|---|---|---|---|---|---|---|
| 50 | | | | | 55 | | | | | 60 | | | | | |

| Gly | Glu | Gln | Lys | Cys | Phe | Ile | Cys | Asp | Ser | Arg | Phe | Pro | Tyr | Asp | Pro |
|---|---|---|---|---|---|---|---|---|---|---|---|---|---|---|---|
| 65 | | | | | 70 | | | | | 75 | | | | | 80 |

| Tyr | Asp | Gln | Pro | Asn | Ser | His | Thr | Ile | Glu | Asn | Val | Ile | Val | Ser | Phe |
|---|---|---|---|---|---|---|---|---|---|---|---|---|---|---|---|
| | | | | 85 | | | | | 90 | | | | | 95 | |

| Glu | Pro | Asp | Arg | Glu | Lys | Lys | Trp | Trp | Gln | Ser | Glu | Asn | Gly | Leu | Asp |
|---|---|---|---|---|---|---|---|---|---|---|---|---|---|---|---|
| | | | 100 | | | | | 105 | | | | | 110 | | |

| His | Val | Ser | Ile | Arg | Leu | Asp | Leu | Glu | Ala | Leu | Phe | Arg | Phe | Ser | His |
|---|---|---|---|---|---|---|---|---|---|---|---|---|---|---|---|
| | | 115 | | | | | 120 | | | | | 125 | | | |

| Leu | Ile | Leu | Thr | Phe | Lys | Thr | Phe | Arg | Pro | Ala | Ala | Met | Leu | Val | Glu |
|---|---|---|---|---|---|---|---|---|---|---|---|---|---|---|---|
| 130 | | | | | 135 | | | | | 140 | | | | | |

| Arg | Ser | Thr | Asp | Tyr | Gly | His | Asn | Trp | Lys | Val | Phe | Lys | Tyr | Phe | Ala |
|---|---|---|---|---|---|---|---|---|---|---|---|---|---|---|---|
| 145 | | | | | 150 | | | | | 155 | | | | | 160 |

| Lys | Asp | Cys | Ala | Thr | Ser | Phe | Pro | Asn | Ile | Thr | Ser | Gly | Gln | Ala | Gln |
|---|---|---|---|---|---|---|---|---|---|---|---|---|---|---|---|
| | | | | 165 | | | | | 170 | | | | | 175 | |

| Gly | Val | Gly | Asp | Ile | Val | Cys | Asp | Ser | Lys | Tyr | Ser | Asp | Ile | Glu | Pro |
|---|---|---|---|---|---|---|---|---|---|---|---|---|---|---|---|
| | | | 180 | | | | | 185 | | | | | 190 | | |

| Ser | Thr | Gly | Gly | Glu | Val | Val | Leu | Lys | Val | Leu | Asp | Pro | Ser | Phe | Glu |
|---|---|---|---|---|---|---|---|---|---|---|---|---|---|---|---|
| | | 195 | | | | | 200 | | | | | 205 | | | |

| Ile | Glu | Asn | Pro | Tyr | Ser | Pro | Tyr | Ile | Gln | Asp | Leu | Val | Thr | Leu | Thr |
|---|---|---|---|---|---|---|---|---|---|---|---|---|---|---|---|
| | 210 | | | | | 215 | | | | | 220 | | | | |

| Asn | Leu | Arg | Ile | Asn | Phe | Thr | Lys | Leu | His | Thr | Leu | Gly | Asp | Ala | Leu |
|---|---|---|---|---|---|---|---|---|---|---|---|---|---|---|---|
| 225 | | | | | 230 | | | | | 235 | | | | | 240 |

| Leu | Gly | Arg | Arg | Gln | Asn | Asp | Ser | Leu | Asp | Lys | Tyr | Tyr | Tyr | Ala | Leu |
|---|---|---|---|---|---|---|---|---|---|---|---|---|---|---|---|
| | | | | 245 | | | | | 250 | | | | | 255 | |

| Tyr | Glu | Met | Ile | Val | Arg | Gly | Ser | Cys | Phe | Cys | Asn | Gly | His | Ala | Ser |
|---|---|---|---|---|---|---|---|---|---|---|---|---|---|---|---|
| | | | 260 | | | | | 265 | | | | | 270 | | |

| Glu | Cys | Arg | Pro | Met | Gln | Lys | Met | Arg | Gly | Asp | Val | Phe | Ser | Pro | Pro |
|---|---|---|---|---|---|---|---|---|---|---|---|---|---|---|---|
| | | 275 | | | | | 280 | | | | | 285 | | | |

| Gly | Met | Val | His | Gly | Gln | Cys | Val | Cys | Gln | His | Asn | Thr | Asp | Gly | Pro |
|---|---|---|---|---|---|---|---|---|---|---|---|---|---|---|---|
| | 290 | | | | | 295 | | | | | 300 | | | | |

| Asn | Cys | Glu | Arg | Cys | Lys | Asp | Phe | Phe | Gln | Asp | Ala | Pro | Trp | Arg | Pro |
|---|---|---|---|---|---|---|---|---|---|---|---|---|---|---|---|
| 305 | | | | | 310 | | | | | 315 | | | | | 320 |

| Ala | Ala | Asp | Leu | Gln | Asp | Asn | Ala | Cys | Arg | Ser | Cys | Ser | Cys | Asn | Ser |
|---|---|---|---|---|---|---|---|---|---|---|---|---|---|---|---|
| | | | | 325 | | | | | 330 | | | | | 335 | |

| His | Ser | Ser | Arg | Cys | His | Phe | Asp | Met | Thr | Thr | Tyr | Leu | Ala | Ser | Gly |
|---|---|---|---|---|---|---|---|---|---|---|---|---|---|---|---|
| | | | 340 | | | | | 345 | | | | | 350 | | |

| Gly | Leu | Ser | Gly | Gly | Val | Cys | Glu | Asp | Cys | Gln | His | Asn | Thr | Glu | Gly |
|---|---|---|---|---|---|---|---|---|---|---|---|---|---|---|---|
| | | 355 | | | | | 360 | | | | | 365 | | | |

| Gln | His | Cys | Asp | Arg | Cys | Arg | Pro | Leu | Phe | Tyr | Arg | Asp | Pro | Leu | Lys |
|---|---|---|---|---|---|---|---|---|---|---|---|---|---|---|---|
| 370 | | | | | 375 | | | | | 380 | | | | | |

| Thr | Ile | Ser | Asp | Pro | Tyr | Ala | Cys | Ile | Pro | Cys | Glu | Cys | Asp | Pro | Asp |
|---|---|---|---|---|---|---|---|---|---|---|---|---|---|---|---|
| 385 | | | | | 390 | | | | | 395 | | | | | 400 |

```
Gly Thr Ile Ser Gly Gly Ile Cys Val Ser His Ser Asp Pro Ala Leu
                405                 410                 415

Gly Ser Val Ala Gly Gln Cys Leu Cys Lys Glu Asn Val Glu Gly Ala
            420                 425                 430

Lys Cys Asp Gln Cys Lys Pro Asn His Tyr Gly Leu Ser Ala Thr Asp
        435                 440                 445

Pro Leu Gly Cys Gln Pro Cys Asp Cys Asn Pro Leu Gly Ser Leu Pro
    450                 455                 460

Phe Leu Thr Cys Asp Val Asp Thr Gly Gln Cys Leu Cys Leu Ser Tyr
465                 470                 475                 480

Val Thr Gly Ala His Cys Glu Glu Cys Thr Val Gly Tyr Trp Gly Leu
                485                 490                 495

Gly Asn His Leu His Gly Cys Ser Pro Cys Asp Cys Asp Ile Gly Gly
            500                 505                 510

Ala Tyr Ser Asn Val Cys Ser Pro Lys Asn Gly Gln Cys Glu Cys Arg
        515                 520                 525

Pro His Val Thr Gly Arg Ser Cys Ser Glu Pro Ala Pro Gly Tyr Phe
    530                 535                 540

Phe Ala Pro Leu Asn Phe Tyr Leu Tyr Glu Ala Glu Glu Ala Thr Thr
545                 550                 555                 560

Leu Gln Gly Leu Ala Pro Leu Gly Ser Glu Thr Phe Gly Gln Ser Pro
                565                 570                 575

Ala Val His Val Val Leu Gly Glu Pro Val Pro Gly Asn Pro Val Thr
            580                 585                 590

Trp Thr Gly Pro Gly Phe Ala Arg Val Leu Pro Gly Ala Gly Leu Arg
        595                 600                 605

Phe Ala Val Asn Asn Ile Pro Phe Pro Val Asp Phe Thr Ile Ala Ile
    610                 615                 620

His Tyr Glu Thr Gln Ser Ala Ala Asp Trp Thr Val Gln Ile Val Val
625                 630                 635                 640

Asn Pro Pro Gly Gly Ser Glu His Cys Ile Pro Lys Thr Leu Gln Ser
                645                 650                 655

Lys Pro Gln Ser Phe Ala Leu Pro Ala Ala Thr Arg Ile Met Leu Leu
            660                 665                 670

Pro Thr Pro Ile Cys Leu Glu Pro Asp Val Gln Tyr Ser Ile Asp Val
        675                 680                 685

Tyr Phe Ser Gln Pro Leu Gln Gly Glu Ser His Ala His Ser His Val
    690                 695                 700

Leu Val Asp Ser Ala Ala Val Gln Trp His Asn Leu Gly Ser Leu Gln
705                 710                 715                 720

Pro Pro Pro Pro Glu Cys Lys Gln Phe Ser Cys Phe Ser Phe Pro Ser
                725                 730                 735

Ser Trp Asp Tyr Arg His Pro Pro His Leu Ala Asn Phe Cys Ile
            740                 745                 750

Phe Ser Arg Asp Gly Val Ser Pro His Trp Pro Gly Trp Ser Gln Thr
        755                 760                 765

Pro Asp Leu Arg
    770

<210> SEQ ID NO 43
<211> LENGTH: 1609
<212> TYPE: PRT
<213> ORGANISM: Homo sapiens

<400> SEQUENCE: 43
```

```
Met Arg Gly Ser His Arg Ala Ala Pro Ala Leu Arg Pro Arg Gly Arg
1               5                   10                  15

Leu Trp Pro Val Leu Ala Val Leu Ala Ala Ala Ala Ala Gly Cys
            20                  25                  30

Ala Gln Ala Ala Met Asp Glu Cys Thr Asp Glu Gly Gly Arg Pro Gln
        35                  40                  45

Arg Cys Met Pro Glu Phe Val Asn Ala Ala Phe Asn Val Thr Val Val
    50                  55                  60

Ala Thr Asn Thr Cys Gly Thr Pro Pro Glu Glu Tyr Cys Val Gln Thr
65                  70                  75                  80

Gly Val Thr Gly Val Thr Lys Ser Cys His Leu Cys Asp Ala Gly Gln
                85                  90                  95

Pro His Leu Gln His Gly Ala Ala Phe Leu Thr Asp Tyr Asn Asn Gln
            100                 105                 110

Ala Asp Thr Thr Trp Trp Gln Ser Gln Thr Met Leu Ala Gly Val Gln
        115                 120                 125

Tyr Pro Ser Ser Ile Asn Leu Thr Leu His Leu Gly Lys Ala Phe Asp
    130                 135                 140

Ile Thr Tyr Val Arg Leu Lys Phe His Thr Ser Arg Pro Glu Ser Phe
145                 150                 155                 160

Ala Ile Tyr Lys Arg Thr Arg Glu Asp Gly Pro Trp Ile Pro Tyr Gln
                165                 170                 175

Tyr Tyr Ser Gly Ser Cys Glu Asn Thr Tyr Ser Lys Ala Asn Arg Gly
            180                 185                 190

Phe Ile Arg Thr Gly Gly Asp Glu Gln Gln Ala Leu Cys Thr Asp Glu
        195                 200                 205

Phe Ser Asp Ile Ser Pro Leu Thr Gly Gly Asn Val Ala Phe Ser Thr
    210                 215                 220

Leu Glu Gly Arg Pro Ser Ala Tyr Asn Phe Asp Asn Ser Pro Val Leu
225                 230                 235                 240

Gln Glu Trp Val Thr Ala Thr Asp Ile Arg Val Thr Leu Asn Arg Leu
                245                 250                 255

Asn Thr Phe Gly Asp Glu Val Phe Asn Asp Pro Lys Val Leu Lys Ser
            260                 265                 270

Tyr Tyr Tyr Ala Ile Ser Asp Phe Ala Val Gly Gly Arg Cys Lys Cys
        275                 280                 285

Asn Gly His Ala Ser Glu Cys Met Lys Asn Glu Phe Asp Lys Leu Val
    290                 295                 300

Cys Asn Cys Lys His Asn Thr Tyr Gly Val Asp Cys Glu Lys Cys Leu
305                 310                 315                 320

Pro Phe Phe Asn Asp Arg Pro Trp Arg Arg Ala Thr Ala Glu Ser Ala
                325                 330                 335

Ser Glu Cys Leu Pro Cys Asp Cys Asn Gly Arg Ser Gln Glu Cys Tyr
            340                 345                 350

Phe Asp Pro Glu Leu Tyr Arg Ser Thr Gly His Gly Gly His Cys Thr
        355                 360                 365

Asn Cys Gln Asp Asn Thr Asp Gly Ala His Cys Glu Arg Cys Arg Glu
    370                 375                 380

Asn Phe Phe Arg Leu Gly Asn Asn Glu Ala Cys Ser Ser Cys His Cys
385                 390                 395                 400

Ser Pro Val Gly Ser Leu Ser Thr Gln Cys Asp Ser Tyr Gly Arg Cys
                405                 410                 415
```

-continued

Ser Cys Lys Pro Gly Val Met Gly Asp Lys Cys Asp Arg Cys Gln Pro
            420                 425                 430

Gly Phe His Ser Leu Thr Glu Ala Gly Cys Arg Pro Cys Ser Cys Asp
        435                 440                 445

Pro Ser Gly Ser Ile Asp Glu Cys Asn Ile Glu Thr Gly Arg Cys Val
    450                 455                 460

Cys Lys Asp Asn Val Glu Gly Phe Asn Cys Glu Arg Cys Lys Pro Gly
465                 470                 475                 480

Phe Phe Asn Leu Glu Ser Ser Asn Pro Arg Gly Cys Thr Pro Cys Phe
                485                 490                 495

Cys Phe Gly His Ser Ser Val Cys Thr Asn Ala Val Gly Tyr Ser Val
            500                 505                 510

Tyr Ser Ile Ser Ser Thr Phe Gln Ile Asp Glu Asp Gly Trp Arg Ala
        515                 520                 525

Glu Gln Arg Asp Gly Ser Glu Ala Ser Leu Glu Trp Ser Ser Glu Arg
    530                 535                 540

Gln Asp Ile Ala Val Ile Ser Asp Ser Tyr Phe Pro Arg Tyr Phe Ile
545                 550                 555                 560

Ala Pro Ala Lys Phe Leu Gly Lys Gln Val Leu Ser Tyr Gly Gln Asn
                565                 570                 575

Leu Ser Phe Ser Phe Arg Val Asp Arg Arg Asp Thr Arg Leu Ser Ala
            580                 585                 590

Glu Asp Leu Val Leu Glu Gly Ala Gly Leu Arg Val Ser Val Pro Leu
        595                 600                 605

Ile Ala Gln Gly Asn Ser Tyr Pro Ser Glu Thr Thr Val Lys Tyr Val
    610                 615                 620

Phe Arg Leu His Glu Ala Thr Asp Tyr Pro Trp Arg Pro Ala Leu Thr
625                 630                 635                 640

Pro Phe Glu Phe Gln Lys Leu Leu Asn Asn Leu Thr Ser Ile Lys Ile
                645                 650                 655

Arg Gly Thr Tyr Ser Glu Arg Ser Ala Gly Tyr Leu Asp Asp Val Thr
            660                 665                 670

Leu Ala Ser Ala Arg Pro Gly Pro Gly Val Pro Ala Thr Trp Val Glu
        675                 680                 685

Ser Cys Thr Cys Pro Val Gly Tyr Gly Gly Gln Phe Cys Glu Met Cys
    690                 695                 700

Leu Ser Gly Tyr Arg Arg Glu Thr Pro Asn Leu Gly Pro Tyr Ser Pro
705                 710                 715                 720

Cys Val Leu Cys Ala Cys Asn Gly His Ser Glu Thr Cys Asp Pro Glu
                725                 730                 735

Thr Gly Val Cys Asn Cys Arg Asp Asn Thr Ala Gly Pro His Cys Glu
            740                 745                 750

Lys Cys Ser Asp Gly Tyr Tyr Gly Asp Ser Thr Ala Gly Thr Ser Ser
        755                 760                 765

Asp Cys Gln Pro Cys Pro Cys Pro Gly Gly Ser Ser Cys Ala Val Val
    770                 775                 780

Pro Lys Thr Lys Glu Val Val Cys Thr Asn Cys Pro Thr Gly Thr Thr
785                 790                 795                 800

Gly Lys Arg Cys Glu Leu Cys Asp Asp Gly Tyr Phe Gly Asp Pro Leu
                805                 810                 815

Gly Arg Asn Gly Pro Val Arg Leu Cys Arg Leu Cys Gln Cys Ser Asp
            820                 825                 830

Asn Ile Asp Pro Asn Ala Val Gly Asn Cys Asn Arg Leu Thr Gly Glu

```
                835                 840                 845
Cys Leu Lys Cys Ile Tyr Asn Thr Ala Gly Phe Tyr Cys Asp Arg Cys
    850                 855                 860

Lys Asp Gly Phe Phe Gly Asn Pro Leu Ala Pro Asn Pro Ala Asp Lys
865                 870                 875                 880

Cys Lys Ala Cys Asn Cys Asn Leu Tyr Gly Thr Met Lys Gln Gln Ser
                885                 890                 895

Ser Cys Asn Pro Val Thr Gly Gln Cys Glu Cys Leu Pro His Val Thr
            900                 905                 910

Gly Gln Asp Cys Gly Ala Cys Asp Pro Gly Phe Tyr Asn Leu Gln Ser
        915                 920                 925

Gly Gln Gly Cys Glu Arg Cys Asp Cys His Ala Leu Gly Ser Thr Asn
    930                 935                 940

Gly Gln Cys Asp Ile Arg Thr Gly Gln Cys Glu Cys Gln Pro Gly Ile
945                 950                 955                 960

Thr Gly Gln His Cys Glu Arg Cys Glu Val Asn His Phe Gly Phe Gly
                965                 970                 975

Pro Glu Gly Cys Lys Pro Cys Asp Cys His Pro Glu Gly Ser Leu Ser
            980                 985                 990

Leu Gln Cys Lys Asp Asp Gly Arg Cys Glu Cys Arg Glu Gly Phe Val
        995                 1000                1005

Gly Asn Arg Cys Asp Gln Cys Glu Glu Asn Tyr Phe Tyr Asn Arg
    1010                1015                1020

Ser Trp Pro Gly Cys Gln Glu Cys Pro Ala Cys Tyr Arg Leu Val
    1025                1030                1035

Lys Asp Lys Val Ala Asp His Arg Val Lys Leu Gln Glu Leu Glu
    1040                1045                1050

Ser Leu Ile Ala Asn Leu Gly Thr Gly Asp Glu Met Val Thr Asp
    1055                1060                1065

Gln Ala Phe Glu Asp Arg Leu Lys Glu Ala Glu Arg Glu Val Met
    1070                1075                1080

Asp Leu Leu Arg Glu Ala Gln Asp Val Lys Asp Val Asp Gln Asn
    1085                1090                1095

Leu Met Asp Arg Leu Gln Arg Val Asn Asn Thr Leu Ser Ser Gln
    1100                1105                1110

Ile Ser Arg Leu Gln Asn Ile Arg Asn Thr Ile Glu Glu Thr Gly
    1115                1120                1125

Asn Leu Ala Glu Gln Ala Arg Ala His Val Glu Asn Thr Glu Arg
    1130                1135                1140

Leu Ile Glu Ile Ala Ser Arg Glu Leu Glu Lys Ala Lys Val Ala
    1145                1150                1155

Ala Ala Asn Val Ser Val Thr Gln Pro Glu Ser Thr Gly Asp Pro
    1160                1165                1170

Asn Asn Met Thr Leu Leu Ala Glu Glu Ala Arg Lys Leu Ala Glu
    1175                1180                1185

Arg His Lys Gln Glu Ala Asp Asp Ile Val Arg Val Ala Lys Thr
    1190                1195                1200

Ala Asn Asp Thr Ser Thr Glu Ala Tyr Asn Leu Leu Leu Arg Thr
    1205                1210                1215

Leu Ala Gly Glu Asn Gln Thr Ala Phe Glu Ile Glu Glu Leu Asn
    1220                1225                1230

Arg Lys Tyr Glu Gln Ala Lys Asn Ile Ser Gln Asp Leu Glu Lys
    1235                1240                1245
```

```
Gln Ala Ala Arg Val His Glu Glu Ala Lys Arg Ala Gly Asp Lys
    1250                1255                1260

Ala Val Glu Ile Tyr Ala Ser Val Ala Gln Leu Ser Pro Leu Asp
    1265                1270                1275

Ser Glu Thr Leu Glu Asn Glu Ala Asn Asn Ile Lys Met Glu Ala
    1280                1285                1290

Glu Asn Leu Glu Gln Leu Ile Asp Gln Lys Leu Lys Asp Tyr Glu
    1295                1300                1305

Asp Leu Arg Glu Asp Met Arg Gly Lys Glu Leu Glu Val Lys Asn
    1310                1315                1320

Leu Leu Glu Lys Gly Lys Thr Glu Gln Gln Thr Ala Asp Gln Leu
    1325                1330                1335

Leu Ala Arg Ala Asp Ala Ala Lys Ala Leu Ala Glu Glu Ala Ala
    1340                1345                1350

Lys Lys Gly Arg Asp Thr Leu Gln Glu Ala Asn Asp Ile Leu Asn
    1355                1360                1365

Asn Leu Lys Asp Phe Asp Arg Arg Val Asn Asp Asn Lys Thr Ala
    1370                1375                1380

Ala Glu Glu Ala Leu Arg Lys Ile Pro Ala Ile Asn Gln Thr Ile
    1385                1390                1395

Thr Glu Ala Asn Glu Lys Thr Arg Glu Ala Gln Gln Ala Leu Gly
    1400                1405                1410

Ser Ala Ala Ala Asp Ala Thr Glu Ala Lys Asn Lys Ala His Glu
    1415                1420                1425

Ala Glu Arg Ile Ala Ser Ala Val Gln Lys Asn Ala Thr Ser Thr
    1430                1435                1440

Lys Ala Glu Ala Glu Arg Thr Phe Ala Glu Val Thr Asp Leu Asp
    1445                1450                1455

Asn Glu Val Asn Asn Met Leu Lys Gln Leu Gln Glu Ala Glu Lys
    1460                1465                1470

Glu Leu Lys Arg Lys Gln Asp Asp Ala Asp Gln Asp Met Met Met
    1475                1480                1485

Ala Gly Met Ala Ser Gln Ala Ala Gln Glu Ala Glu Ile Asn Ala
    1490                1495                1500

Arg Lys Ala Lys Asn Ser Val Thr Ser Leu Leu Ser Ile Ile Asn
    1505                1510                1515

Asp Leu Leu Glu Gln Leu Gly Gln Leu Asp Thr Val Asp Leu Asn
    1520                1525                1530

Lys Leu Asn Glu Ile Glu Gly Thr Leu Asn Lys Ala Lys Asp Glu
    1535                1540                1545

Met Lys Val Ser Asp Leu Asp Arg Lys Val Ser Asp Leu Glu Asn
    1550                1555                1560

Glu Ala Lys Lys Gln Glu Ala Ala Ile Met Asp Tyr Asn Arg Asp
    1565                1570                1575

Ile Glu Glu Ile Met Lys Asp Ile Arg Asn Leu Glu Asp Ile Arg
    1580                1585                1590

Lys Thr Leu Pro Ser Gly Cys Phe Asn Thr Pro Ser Ile Glu Lys
    1595                1600                1605

Pro

<210> SEQ ID NO 44
<211> LENGTH: 1193
<212> TYPE: PRT
```

<213> ORGANISM: Homo sapiens

<400> SEQUENCE: 44

```
Met Pro Ala Leu Trp Leu Gly Cys Cys Leu Cys Phe Ser Leu Leu Leu
1               5                   10                  15
Pro Ala Ala Arg Ala Thr Ser Arg Arg Glu Val Cys Asp Cys Asn Gly
            20                  25                  30
Lys Ser Arg Gln Cys Ile Phe Asp Arg Glu Leu His Arg Gln Thr Gly
        35                  40                  45
Asn Gly Phe Arg Cys Leu Asn Cys Asn Asp Asn Thr Asp Gly Ile His
    50                  55                  60
Cys Glu Lys Cys Lys Asn Gly Phe Tyr Arg His Arg Glu Arg Asp Arg
65                  70                  75                  80
Cys Leu Pro Cys Asn Cys Asn Ser Lys Gly Ser Leu Ser Ala Arg Cys
                85                  90                  95
Asp Asn Ser Gly Arg Cys Ser Cys Lys Pro Gly Val Thr Gly Ala Arg
            100                 105                 110
Cys Asp Arg Cys Leu Pro Gly Phe His Met Leu Thr Asp Ala Gly Cys
        115                 120                 125
Thr Gln Asp Gln Arg Leu Leu Asp Ser Lys Cys Asp Cys Asp Pro Ala
    130                 135                 140
Gly Ile Ala Gly Pro Cys Asp Ala Gly Arg Cys Val Cys Lys Pro Ala
145                 150                 155                 160
Val Thr Gly Glu Arg Cys Asp Arg Cys Arg Ser Gly Tyr Tyr Asn Leu
                165                 170                 175
Asp Gly Gly Asn Pro Glu Gly Cys Thr Gln Cys Phe Cys Tyr Gly His
            180                 185                 190
Ser Ala Ser Cys Arg Ser Ser Ala Glu Tyr Ser Val His Lys Ile Thr
        195                 200                 205
Ser Thr Phe His Gln Asp Val Asp Gly Trp Lys Ala Val Gln Arg Asn
    210                 215                 220
Gly Ser Pro Ala Lys Leu Gln Trp Ser Gln Arg His Gln Asp Val Phe
225                 230                 235                 240
Ser Ser Ala Gln Arg Leu Asp Pro Val Tyr Phe Val Ala Pro Ala Lys
                245                 250                 255
Phe Leu Gly Asn Gln Gln Val Ser Tyr Gly Gln Ser Leu Ser Phe Asp
            260                 265                 270
Tyr Arg Val Asp Arg Gly Gly Arg His Pro Ser Ala His Asp Val Ile
        275                 280                 285
Leu Glu Gly Ala Gly Leu Arg Ile Thr Ala Pro Leu Met Pro Leu Gly
    290                 295                 300
Lys Thr Leu Pro Cys Gly Leu Thr Lys Thr Tyr Thr Phe Arg Leu Asn
305                 310                 315                 320
Glu His Pro Ser Asn Asn Trp Ser Pro Gln Leu Ser Tyr Phe Glu Tyr
                325                 330                 335
Arg Arg Leu Leu Arg Asn Leu Thr Ala Leu Arg Ile Arg Ala Thr Tyr
            340                 345                 350
Gly Glu Tyr Ser Thr Gly Tyr Ile Asp Asn Val Thr Leu Ile Ser Ala
        355                 360                 365
Arg Pro Val Ser Gly Ala Pro Ala Pro Trp Val Glu Gln Cys Ile Cys
    370                 375                 380
Pro Val Gly Tyr Lys Gly Gln Phe Cys Gln Asp Cys Ala Ser Gly Tyr
385                 390                 395                 400
```

-continued

```
Lys Arg Asp Ser Ala Arg Leu Gly Pro Phe Gly Thr Cys Ile Pro Cys
                405                 410                 415
Asn Cys Gln Gly Gly Ala Cys Asp Pro Asp Thr Gly Asp Cys Tyr
            420                 425                 430
Ser Gly Asp Glu Asn Pro Asp Ile Glu Cys Ala Asp Cys Pro Leu Gly
            435                 440                 445
Phe Tyr Asn Asp Pro His Asp Pro Arg Ser Cys Lys Pro Cys Pro Cys
450                 455                 460
His Asn Gly Phe Ser Cys Ser Val Met Pro Glu Thr Glu Val Val
465                 470                 475                 480
Cys Asn Asn Cys Pro Pro Gly Val Thr Gly Ala Arg Cys Glu Leu Cys
                485                 490                 495
Ala Asp Gly Tyr Phe Gly Asp Pro Phe Gly Glu His Gly Pro Val Arg
            500                 505                 510
Pro Cys Gln Pro Cys Gln Cys Asn Asn Val Asp Pro Ser Ala Ser
            515                 520                 525
Gly Asn Cys Asp Arg Leu Thr Gly Arg Cys Leu Lys Cys Ile His Asn
            530                 535                 540
Thr Ala Gly Ile Tyr Cys Asp Gln Cys Lys Ala Gly Tyr Phe Gly Asp
545                 550                 555                 560
Pro Leu Ala Pro Asn Pro Ala Asp Lys Cys Arg Ala Cys Asn Cys Asn
                565                 570                 575
Pro Met Gly Ser Glu Pro Val Gly Cys Arg Ser Asp Gly Thr Cys Val
            580                 585                 590
Cys Lys Pro Gly Phe Gly Gly Pro Asn Cys Glu His Gly Ala Phe Ser
            595                 600                 605
Cys Pro Ala Cys Tyr Asn Gln Val Lys Ile Gln Met Asp Gln Phe Met
            610                 615                 620
Gln Gln Leu Gln Arg Met Glu Ala Leu Ile Ser Lys Ala Gln Gly Gly
625                 630                 635                 640
Asp Gly Val Val Pro Asp Thr Glu Leu Glu Gly Arg Met Gln Gln Ala
                645                 650                 655
Glu Gln Ala Leu Gln Asp Ile Leu Arg Asp Ala Gln Ile Ser Glu Gly
            660                 665                 670
Ala Ser Arg Ser Leu Gly Leu Gln Leu Ala Lys Val Arg Ser Gln Glu
            675                 680                 685
Asn Ser Tyr Gln Ser Arg Leu Asp Asp Leu Lys Met Thr Val Glu Arg
            690                 695                 700
Val Arg Ala Leu Gly Ser Gln Tyr Gln Asn Arg Val Arg Asp Thr His
705                 710                 715                 720
Arg Leu Ile Thr Gln Met Gln Leu Ser Leu Ala Glu Ser Glu Ala Ser
                725                 730                 735
Leu Gly Asn Thr Asn Ile Pro Ala Ser Asp His Tyr Val Gly Pro Asn
            740                 745                 750
Gly Phe Lys Ser Leu Ala Gln Glu Ala Thr Arg Leu Ala Glu Ser His
            755                 760                 765
Val Glu Ser Ala Ser Asn Met Glu Gln Leu Thr Arg Glu Thr Glu Asp
            770                 775                 780
Tyr Ser Lys Gln Ala Leu Ser Leu Val Arg Lys Ala Leu His Glu Gly
785                 790                 795                 800
Val Gly Ser Gly Ser Gly Ser Pro Asp Gly Ala Val Val Gln Gly Leu
                805                 810                 815
Val Glu Lys Leu Glu Lys Thr Lys Ser Leu Ala Gln Gln Leu Thr Arg
```

```
                820              825              830
Glu Ala Thr Gln Ala Glu Ile Glu Ala Asp Arg Ser Tyr Gln His Ser
            835              840              845
Leu Arg Leu Leu Asp Ser Val Ser Arg Leu Gln Gly Val Ser Asp Gln
            850              855              860
Ser Phe Gln Val Glu Glu Ala Lys Arg Ile Lys Gln Lys Ala Asp Ser
865              870              875              880
Leu Ser Ser Leu Val Thr Arg His Met Asp Glu Phe Lys Arg Thr Gln
                885              890              895
Lys Asn Leu Gly Asn Trp Lys Glu Glu Ala Gln Gln Leu Leu Gln Asn
            900              905              910
Gly Lys Ser Gly Arg Glu Lys Ser Asp Gln Leu Leu Ser Arg Ala Asn
            915              920              925
Leu Ala Lys Ser Arg Ala Gln Glu Ala Leu Ser Met Gly Asn Ala Thr
            930              935              940
Phe Tyr Glu Val Glu Ser Ile Leu Lys Asn Leu Arg Glu Phe Asp Leu
945              950              955              960
Gln Val Asp Asn Arg Lys Ala Glu Ala Glu Glu Ala Met Lys Arg Leu
                965              970              975
Ser Tyr Ile Ser Gln Lys Val Ser Asp Ala Ser Asp Lys Thr Gln Gln
            980              985              990
Ala Glu Arg Ala Leu Gly Ser Ala Ala Ala Asp Ala Gln Arg Ala Lys
            995             1000             1005
Asn Gly Ala Gly Glu Ala Leu Glu Ile Ser Ser Glu Ile Glu Gln
           1010             1015             1020
Glu Ile Gly Ser Leu Asn Leu Glu Ala Asn Val Thr Ala Asp Gly
           1025             1030             1035
Ala Leu Ala Met Glu Lys Gly Leu Ala Ser Leu Lys Ser Glu Met
           1040             1045             1050
Arg Glu Val Glu Gly Glu Leu Glu Arg Lys Glu Leu Glu Phe Asp
           1055             1060             1065
Thr Asn Met Asp Ala Val Gln Met Val Ile Thr Glu Ala Gln Lys
           1070             1075             1080
Val Asp Thr Arg Ala Lys Asn Ala Gly Val Thr Ile Gln Asp Thr
           1085             1090             1095
Leu Asn Thr Leu Asp Gly Leu His Leu Met Asp Gln Pro Leu
           1100             1105             1110
Ser Val Asp Glu Glu Gly Leu Val Leu Glu Gln Lys Leu Ser
           1115             1120             1125
Arg Ala Lys Thr Gln Ile Asn Ser Gln Leu Arg Pro Met Met Ser
           1130             1135             1140
Glu Leu Glu Glu Arg Ala Arg Gln Gln Arg Gly His Leu His Leu
           1145             1150             1155
Leu Glu Thr Ser Ile Asp Gly Ile Leu Ala Asp Val Lys Asn Leu
           1160             1165             1170
Glu Asn Ile Arg Asp Asn Leu Pro Pro Gly Cys Tyr Asn Thr Gln
           1175             1180             1185
Ala Leu Glu Gln Gln
           1190

<210> SEQ ID NO 45
<211> LENGTH: 1111
<212> TYPE: PRT
<213> ORGANISM: Homo sapiens
```

```
<400> SEQUENCE: 45

Met Pro Ala Leu Trp Leu Gly Cys Cys Leu Cys Phe Ser Leu Leu Leu
1               5                   10                  15

Pro Ala Ala Arg Ala Thr Ser Arg Arg Glu Val Cys Asp Cys Asn Gly
                20                  25                  30

Lys Ser Arg Gln Cys Ile Phe Asp Arg Glu Leu His Arg Gln Thr Gly
            35                  40                  45

Asn Gly Phe Arg Cys Leu Asn Cys Asn Asp Asn Thr Asp Gly Ile His
        50                  55                  60

Cys Glu Lys Cys Lys Asn Gly Phe Tyr Arg His Arg Glu Arg Asp Arg
65                  70                  75                  80

Cys Leu Pro Cys Asn Cys Asn Ser Lys Gly Ser Leu Ser Ala Arg Cys
                85                  90                  95

Asp Asn Ser Gly Arg Cys Ser Cys Lys Pro Gly Val Thr Gly Ala Arg
                100                 105                 110

Cys Asp Arg Cys Leu Pro Gly Phe His Met Leu Thr Asp Ala Gly Cys
            115                 120                 125

Thr Gln Asp Gln Arg Leu Leu Asp Ser Lys Cys Asp Cys Asp Pro Ala
        130                 135                 140

Gly Ile Ala Gly Pro Cys Asp Ala Gly Arg Cys Val Cys Lys Pro Ala
145                 150                 155                 160

Val Thr Gly Glu Arg Cys Asp Arg Cys Arg Ser Gly Tyr Tyr Asn Leu
                165                 170                 175

Asp Gly Gly Asn Pro Glu Gly Cys Thr Gln Cys Phe Cys Tyr Gly His
                180                 185                 190

Ser Ala Ser Cys Arg Ser Ser Ala Glu Tyr Ser Val His Lys Ile Thr
            195                 200                 205

Ser Thr Phe His Gln Asp Val Asp Gly Trp Lys Ala Val Gln Arg Asn
        210                 215                 220

Gly Ser Pro Ala Lys Leu Gln Trp Ser Gln Arg His Gln Asp Val Phe
225                 230                 235                 240

Ser Ser Ala Gln Arg Leu Asp Pro Val Tyr Phe Val Ala Pro Ala Lys
                245                 250                 255

Phe Leu Gly Asn Gln Gln Val Ser Tyr Gly Gln Ser Leu Ser Phe Asp
                260                 265                 270

Tyr Arg Val Asp Arg Gly Gly Arg His Pro Ser Ala His Asp Val Ile
            275                 280                 285

Leu Glu Gly Ala Gly Leu Arg Ile Thr Ala Pro Leu Met Pro Leu Gly
        290                 295                 300

Lys Thr Leu Pro Cys Gly Leu Thr Lys Thr Tyr Thr Phe Arg Leu Asn
305                 310                 315                 320

Glu His Pro Ser Asn Asn Trp Ser Pro Gln Leu Ser Tyr Phe Glu Tyr
                325                 330                 335

Arg Arg Leu Leu Arg Asn Leu Thr Ala Leu Arg Ile Arg Ala Thr Tyr
            340                 345                 350

Gly Glu Tyr Ser Thr Gly Tyr Ile Asp Asn Val Thr Leu Ile Ser Ala
        355                 360                 365

Arg Pro Val Ser Gly Ala Pro Ala Pro Trp Val Glu Gln Cys Ile Cys
        370                 375                 380

Pro Val Gly Tyr Lys Gly Gln Phe Cys Gln Asp Cys Ala Ser Gly Tyr
385                 390                 395                 400

Lys Arg Asp Ser Ala Arg Leu Gly Pro Phe Gly Thr Cys Ile Pro Cys
```

-continued

```
            405                 410                 415
Asn Cys Gln Gly Gly Gly Ala Cys Asp Pro Asp Thr Gly Asp Cys Tyr
                420                 425                 430
Ser Gly Asp Glu Asn Pro Asp Ile Glu Cys Ala Asp Cys Pro Leu Gly
                435                 440                 445
Phe Tyr Asn Asp Pro His Asp Pro Arg Ser Cys Lys Pro Cys Pro Cys
    450                 455                 460
His Asn Gly Phe Ser Cys Ser Val Met Pro Glu Thr Glu Glu Val Val
465                 470                 475                 480
Cys Asn Asn Cys Pro Pro Gly Val Thr Gly Ala Arg Cys Glu Leu Cys
                485                 490                 495
Ala Asp Gly Tyr Phe Gly Asp Pro Phe Gly Glu His Gly Pro Val Arg
                500                 505                 510
Pro Cys Gln Pro Cys Gln Cys Asn Asn Asn Val Asp Pro Ser Ala Ser
            515                 520                 525
Gly Asn Cys Asp Arg Leu Thr Gly Arg Cys Leu Lys Cys Ile His Asn
        530                 535                 540
Thr Ala Gly Ile Tyr Cys Asp Gln Cys Lys Ala Gly Tyr Phe Gly Asp
545                 550                 555                 560
Pro Leu Ala Pro Asn Pro Ala Asp Lys Cys Arg Ala Cys Asn Cys Asn
                565                 570                 575
Pro Met Gly Ser Glu Pro Val Gly Cys Arg Ser Asp Gly Thr Cys Val
                580                 585                 590
Cys Lys Pro Gly Phe Gly Gly Pro Asn Cys Glu His Gly Ala Phe Ser
            595                 600                 605
Cys Pro Ala Cys Tyr Asn Gln Val Lys Ile Gln Met Asp Gln Phe Met
        610                 615                 620
Gln Gln Leu Gln Arg Met Glu Ala Leu Ile Ser Lys Ala Gln Gly Gly
625                 630                 635                 640
Asp Gly Val Val Pro Asp Thr Glu Leu Glu Gly Arg Met Gln Gln Ala
                645                 650                 655
Glu Gln Ala Leu Gln Asp Ile Leu Arg Asp Ala Gln Ile Ser Glu Gly
                660                 665                 670
Ala Ser Arg Ser Leu Gly Leu Gln Leu Ala Lys Val Arg Ser Gln Glu
            675                 680                 685
Asn Ser Tyr Gln Ser Arg Leu Asp Asp Leu Lys Met Thr Val Glu Arg
        690                 695                 700
Val Arg Ala Leu Gly Ser Gln Tyr Gln Asn Arg Val Arg Asp Thr His
705                 710                 715                 720
Arg Leu Ile Thr Gln Met Gln Leu Ser Leu Ala Glu Ser Glu Ala Ser
                725                 730                 735
Leu Gly Asn Thr Asn Ile Pro Ala Ser Asp His Tyr Val Gly Pro Asn
                740                 745                 750
Gly Phe Lys Ser Leu Ala Gln Glu Ala Thr Arg Leu Ala Glu Ser His
            755                 760                 765
Val Glu Ser Ala Ser Asn Met Glu Gln Leu Thr Arg Glu Thr Glu Asp
        770                 775                 780
Tyr Ser Lys Gln Ala Leu Ser Leu Val Arg Lys Ala Leu His Glu Gly
785                 790                 795                 800
Val Gly Ser Gly Ser Gly Ser Pro Asp Gly Ala Val Val Gln Gly Leu
                805                 810                 815
Val Glu Lys Leu Glu Lys Thr Lys Ser Leu Ala Gln Gln Leu Thr Arg
            820                 825                 830
```

Glu Ala Thr Gln Ala Glu Ile Glu Ala Asp Arg Ser Tyr Gln His Ser
            835                 840                 845

Leu Arg Leu Leu Asp Ser Val Ser Arg Leu Gln Gly Val Ser Asp Gln
    850                 855                 860

Ser Phe Gln Val Glu Ala Lys Arg Ile Lys Gln Lys Ala Asp Ser
865                 870                 875                 880

Leu Ser Ser Leu Val Thr Arg His Met Asp Glu Phe Lys Arg Thr Gln
                885                 890                 895

Lys Asn Leu Gly Asn Trp Lys Glu Ala Gln Gln Leu Leu Gln Asn
            900                 905                 910

Gly Lys Ser Gly Arg Glu Lys Ser Asp Gln Leu Leu Ser Arg Ala Asn
            915                 920                 925

Leu Ala Lys Ser Arg Ala Gln Glu Ala Leu Ser Met Gly Asn Ala Thr
    930                 935                 940

Phe Tyr Glu Val Glu Ser Ile Leu Lys Asn Leu Arg Glu Phe Asp Leu
945                 950                 955                 960

Gln Val Asp Asn Arg Lys Ala Glu Ala Glu Ala Met Lys Arg Leu
                965                 970                 975

Ser Tyr Ile Ser Gln Lys Val Ser Asp Ala Ser Asp Lys Thr Gln Gln
            980                 985                 990

Ala Glu Arg Ala Leu Gly Ser Ala  Ala Ala Asp Ala Gln  Arg Ala Lys
            995                 1000                1005

Asn Gly  Ala Gly Glu Ala Leu  Glu Ile Ser Ser Glu  Ile Glu Gln
    1010                1015                1020

Glu Ile  Gly Ser Leu Asn Leu  Glu Ala Asn Val Thr  Ala Asp Gly
    1025                1030                1035

Ala Leu  Ala Met Glu Lys Gly  Leu Ala Ser Leu Lys  Ser Glu Met
    1040                1045                1050

Arg Glu  Val Glu Gly Glu Leu  Glu Arg Lys Glu Leu  Glu Phe Asp
    1055                1060                1065

Thr Asn  Met Asp Ala Val Gln  Met Val Ile Thr Glu  Ala Gln Lys
    1070                1075                1080

Val Asp  Thr Arg Ala Lys Asn  Ala Gly Val Thr Ile  Gln Asp Thr
    1085                1090                1095

Leu Asn  Thr Leu Asp Gly Leu  Leu His Leu Met Gly  Met
    1100                1105                1110

<210> SEQ ID NO 46
<211> LENGTH: 1575
<212> TYPE: PRT
<213> ORGANISM: Homo sapiens

<400> SEQUENCE: 46

Met Ala Ala Ala Ala Leu Leu Leu Gly Leu Ala Leu Leu Ala Pro Arg
1               5                   10                  15

Ala Ala Gly Ala Gly Met Gly Ala Cys Tyr Asp Gly Ala Gly Arg Pro
            20                  25                  30

Gln Arg Cys Leu Pro Val Phe Glu Asn Ala Ala Phe Gly Arg Leu Ala
        35                  40                  45

Gln Ala Ser His Thr Cys Gly Ser Pro Pro Glu Asp Phe Cys Pro His
    50                  55                  60

Val Gly Ala Ala Gly Ala Gly Ala His Cys Gln Arg Cys Asp Ala Ala
65                  70                  75                  80

Asp Pro Gln Arg His His Asn Ala Ser Tyr Leu Thr Asp Phe His Ser

-continued

```
                85                  90                  95
Gln Asp Glu Ser Thr Trp Trp Gln Ser Pro Ser Met Ala Phe Gly Val
            100                 105                 110

Gln Tyr Pro Thr Ser Val Asn Ile Thr Leu Arg Leu Gly Lys Ala Tyr
            115                 120                 125

Glu Ile Thr Tyr Val Arg Leu Lys Phe His Thr Ser Arg Pro Glu Ser
130                 135                 140

Phe Ala Ile Tyr Lys Arg Ser Arg Ala Asp Gly Pro Trp Glu Pro Tyr
145                 150                 155                 160

Gln Phe Tyr Ser Ala Ser Cys Gln Lys Thr Tyr Gly Arg Pro Glu Gly
            165                 170                 175

Gln Tyr Leu Arg Pro Gly Glu Asp Glu Arg Val Ala Phe Cys Thr Ser
            180                 185                 190

Glu Phe Ser Asp Ile Ser Pro Leu Ser Gly Gly Asn Val Ala Phe Ser
            195                 200                 205

Thr Leu Glu Gly Arg Pro Ser Ala Tyr Asn Phe Glu Glu Ser Pro Gly
            210                 215                 220

Leu Gln Glu Trp Val Thr Ser Thr Glu Leu Leu Ile Ser Leu Asp Arg
225                 230                 235                 240

Leu Asn Thr Phe Gly Asp Asp Ile Phe Lys Asp Pro Lys Val Leu Gln
            245                 250                 255

Ser Tyr Tyr Tyr Ala Val Ser Asp Phe Ser Val Gly Gly Arg Cys Lys
            260                 265                 270

Cys Asn Gly His Ala Ser Glu Cys Gly Pro Asp Val Ala Gly Gln Leu
            275                 280                 285

Ala Cys Arg Cys Gln His Asn Thr Thr Gly Thr Asp Cys Glu Arg Cys
            290                 295                 300

Leu Pro Phe Phe Gln Asp Arg Pro Trp Ala Arg Gly Thr Ala Glu Ala
305                 310                 315                 320

Ala His Glu Cys Leu Pro Cys Asn Cys Ser Gly Arg Ser Glu Glu Cys
            325                 330                 335

Thr Phe Asp Arg Glu Leu Phe Arg Ser Thr Gly His Gly Gly Arg Cys
            340                 345                 350

His His Cys Arg Asp His Thr Ala Gly Pro His Cys Glu Arg Cys Gln
            355                 360                 365

Glu Asn Phe Tyr His Trp Asp Pro Arg Met Pro Cys Gln Pro Cys Asp
            370                 375                 380

Cys Gln Ser Ala Gly Ser Leu His Leu Gln Cys Asp Asp Thr Gly Thr
385                 390                 395                 400

Cys Ala Cys Lys Pro Thr Val Thr Gly Trp Lys Cys Asp Arg Cys Leu
            405                 410                 415

Pro Gly Phe His Ser Leu Ser Glu Gly Gly Cys Arg Pro Cys Thr Cys
            420                 425                 430

Asn Pro Ala Gly Ser Leu Asp Thr Cys Asp Pro Arg Ser Gly Arg Cys
            435                 440                 445

Pro Cys Lys Glu Asn Val Glu Gly Asn Leu Cys Asp Arg Cys Arg Pro
450                 455                 460

Gly Thr Phe Asn Leu Gln Pro His Asn Pro Ala Gly Cys Ser Ser Cys
465                 470                 475                 480

Phe Cys Tyr Gly His Ser Lys Val Cys Ala Ser Thr Ala Gln Phe Gln
            485                 490                 495

Val His His Ile Leu Ser Asp Phe His Gln Gly Ala Glu Gly Trp Trp
            500                 505                 510
```

```
Ala Arg Ser Val Gly Gly Ser Glu His Pro Pro Gln Trp Ser Pro Asn
        515                 520                 525

Gly Val Leu Leu Ser Pro Glu Asp Glu Glu Leu Thr Ala Pro Glu
    530                 535                 540

Lys Phe Leu Gly Asp Gln Arg Phe Ser Tyr Gly Gln Pro Leu Ile Leu
545                 550                 555                 560

Thr Phe Arg Val Pro Pro Gly Asp Ser Pro Leu Pro Val Gln Leu Arg
                565                 570                 575

Leu Glu Gly Thr Gly Leu Ala Leu Ser Leu Arg His Ser Ser Leu Ser
            580                 585                 590

Gly Pro Gln Asp Ala Gly His Pro Arg Glu Val Glu Leu Arg Phe His
        595                 600                 605

Leu Gln Glu Thr Ser Glu Asp Val Ala Pro Pro Leu Pro Pro Phe His
    610                 615                 620

Phe Gln Arg Leu Leu Ala Asn Leu Thr Ser Leu Arg Leu Arg Val Ser
625                 630                 635                 640

Pro Gly Pro Ser Pro Ala Gly Pro Val Phe Leu Thr Glu Val Arg Leu
                645                 650                 655

Thr Ser Ala Arg Pro Gly Leu Ser Pro Pro Ala Ser Trp Val Glu Ile
            660                 665                 670

Cys Ser Cys Pro Thr Gly Tyr Thr Gly Gln Phe Cys Glu Ser Cys Ala
        675                 680                 685

Pro Gly Tyr Lys Arg Glu Met Pro Gln Gly Gly Pro Tyr Ala Ser Cys
    690                 695                 700

Val Pro Cys Thr Cys Asn Gln His Gly Thr Cys Asp Pro Asn Thr Gly
705                 710                 715                 720

Ile Cys Val Cys Ser His His Thr Glu Gly Pro Ser Cys Glu Arg Cys
                725                 730                 735

Leu Pro Gly Phe Tyr Gly Asn Pro Phe Ala Gly Gln Ala Asp Asp Cys
            740                 745                 750

Gln Pro Cys Pro Cys Pro Gly Gln Ser Ala Cys Thr Thr Ile Pro Glu
        755                 760                 765

Ser Arg Glu Val Val Cys Thr His Cys Pro Pro Gly Gln Arg Gly Arg
    770                 775                 780

Arg Cys Glu Val Cys Asp Asp Gly Phe Phe Gly Asp Pro Leu Gly Leu
785                 790                 795                 800

Phe Gly His Pro Gln Pro Cys His Gln Cys Gln Cys Ser Gly Asn Val
                805                 810                 815

Asp Pro Asn Ala Val Gly Asn Cys Asp Pro Leu Ser Gly His Cys Leu
            820                 825                 830

Arg Cys Leu His Asn Thr Thr Gly Asp His Cys Glu His Cys Gln Glu
        835                 840                 845

Gly Phe Tyr Gly Ser Ala Leu Ala Pro Arg Pro Ala Asp Lys Cys Met
    850                 855                 860

Pro Cys Ser Cys His Pro Gln Gly Ser Val Ser Glu Gln Met Pro Cys
865                 870                 875                 880

Asp Pro Val Thr Gly Gln Cys Ser Cys Leu Pro His Val Thr Ala Arg
                885                 890                 895

Asp Cys Ser Arg Cys Tyr Pro Gly Phe Phe Asp Leu Gln Pro Gly Arg
            900                 905                 910

Gly Cys Arg Ser Cys Lys Cys His Pro Leu Gly Ser Gln Glu Asp Gln
        915                 920                 925
```

-continued

```
Cys His Pro Lys Thr Gly Gln Cys Thr Cys Arg Pro Gly Val Thr Gly
    930             935                 940

Gln Ala Cys Asp Arg Cys Gln Leu Gly Phe Phe Gly Phe Ser Ile Lys
945                 950                 955                 960

Gly Cys Arg Ala Cys Arg Cys Ser Pro Leu Gly Ala Ala Ser Ala Gln
                965                 970                 975

Cys His Glu Asn Gly Thr Cys Val Cys Arg Pro Gly Phe Glu Gly Tyr
            980                 985                 990

Lys Cys Asp Arg Cys His Asp Asn Phe Phe Leu Thr Ala Asp Gly Thr
        995                 1000                1005

His Cys Gln Gln Cys Pro Ser Cys Tyr Ala Leu Val Lys Glu Glu
    1010                1015                1020

Ala Ala Lys Leu Lys Ala Arg Leu Thr Leu Thr Glu Gly Trp Leu
    1025                1030                1035

Gln Gly Ser Asp Cys Gly Ser Pro Trp Gly Pro Leu Asp Ile Leu
    1040                1045                1050

Leu Gly Glu Ala Pro Arg Gly Asp Val Tyr Gln Gly His His Leu
    1055                1060                1065

Leu Pro Gly Ala Arg Glu Ala Phe Leu Glu Gln Met Met Ser Leu
    1070                1075                1080

Glu Gly Ala Val Lys Ala Ala Arg Glu Gln Leu Gln Arg Leu Asn
    1085                1090                1095

Lys Gly Ala Arg Cys Ala Gln Ala Gly Ser Gln Lys Thr Cys Thr
    1100                1105                1110

Gln Leu Ala Asp Leu Glu Ala Val Leu Glu Ser Ser Glu Glu Glu
    1115                1120                1125

Ile Leu His Ala Ala Ala Ile Leu Ala Ser Leu Glu Ile Pro Gln
    1130                1135                1140

Glu Gly Pro Ser Gln Pro Thr Lys Trp Ser His Leu Ala Thr Glu
    1145                1150                1155

Ala Arg Ala Leu Ala Arg Ser His Arg Asp Thr Ala Thr Lys Ile
    1160                1165                1170

Ala Ala Thr Ala Trp Arg Ala Leu Leu Ala Ser Asn Thr Ser Tyr
    1175                1180                1185

Ala Leu Leu Trp Asn Leu Leu Glu Gly Arg Val Ala Leu Glu Thr
    1190                1195                1200

Gln Arg Asp Leu Glu Asp Arg Tyr Gln Glu Val Gln Ala Ala Gln
    1205                1210                1215

Lys Ala Leu Arg Thr Ala Val Ala Glu Val Leu Pro Glu Ala Glu
    1220                1225                1230

Ser Val Leu Ala Thr Val Gln Gln Val Gly Ala Asp Thr Ala Pro
    1235                1240                1245

Tyr Leu Ala Leu Leu Ala Ser Pro Gly Ala Leu Pro Gln Lys Ser
    1250                1255                1260

Arg Ala Glu Asp Leu Gly Leu Lys Ala Lys Ala Leu Glu Lys Thr
    1265                1270                1275

Val Ala Ser Trp Gln His Met Ala Thr Glu Ala Ala Arg Thr Leu
    1280                1285                1290

Gln Thr Ala Ala Gln Ala Thr Leu Arg Gln Thr Glu Pro Leu Thr
    1295                1300                1305

Lys Leu His Gln Glu Ala Arg Ala Ala Leu Thr Gln Ala Ser Ser
    1310                1315                1320

Ser Val Gln Ala Ala Thr Val Thr Val Met Gly Ala Arg Thr Leu
```

```
                1325                1330                1335
Leu Ala  Asp Leu Glu Gly Met  Lys Leu Gln Phe Pro  Arg Pro Lys
    1340                1345                1350

Asp Gln  Ala Ala Leu Gln Arg  Lys Ala Asp Ser Val  Ser Asp Arg
    1355                1360                1365

Leu Leu  Ala Asp Thr Arg Lys  Lys Thr Lys Gln Ala  Glu Arg Met
    1370                1375                1380

Leu Gly  Asn Ala Ala Pro Leu  Ser Ser Ser Ala Lys  Lys Lys Gly
    1385                1390                1395

Arg Glu  Ala Glu Val Leu Ala  Lys Asp Ser Ala Lys  Leu Ala Lys
    1400                1405                1410

Ala Leu  Leu Arg Glu Arg Lys  Gln Ala His Arg Arg  Ala Ser Arg
    1415                1420                1425

Leu Thr  Ser Gln Thr Gln Ala  Thr Leu Gln Gln Ala  Ser Gln Gln
    1430                1435                1440

Val Leu  Ala Ser Glu Ala Arg  Arg Gln Glu Leu Glu  Glu Ala Glu
    1445                1450                1455

Arg Val  Gly Ala Gly Leu Ser  Glu Met Glu Gln Gln  Ile Arg Glu
    1460                1465                1470

Ser Arg  Ile Ser Leu Glu Lys  Asp Ile Glu Thr Leu  Ser Glu Leu
    1475                1480                1485

Leu Ala  Arg Leu Gly Ser Leu  Asp Thr His Gln Ala  Pro Ala Gln
    1490                1495                1500

Ala Leu  Asn Glu Thr Gln Trp  Ala Leu Glu Arg Leu  Arg Leu Gln
    1505                1510                1515

Leu Gly  Ser Pro Gly Ser Leu  Gln Arg Lys Leu Ser  Leu Leu Glu
    1520                1525                1530

Gln Glu  Ser Gln Gln Gln Glu  Leu Gln Ile Gln Gly  Phe Glu Ser
    1535                1540                1545

Asp Leu  Ala Glu Ile Arg Ala  Asp Lys Gln Asn Leu  Glu Ala Ile
    1550                1555                1560

Leu His  Ser Leu Pro Glu Asn  Cys Ala Ser Trp Gln
    1565                1570                1575

<210> SEQ ID NO 47
<211> LENGTH: 196
<212> TYPE: PRT
<213> ORGANISM: Unknown
<220> FEATURE:
<221> NAME/KEY: source
<223> OTHER INFORMATION: /note="Description of Unknown:
      vWF A3 domain"

<400> SEQUENCE: 47

Cys Ser Gln Pro Leu Asp Val Ile Leu Leu Leu Asp Gly Ser Ser Ser
1               5                   10                  15

Phe Pro Ala Ser Tyr Phe Asp Glu Met Lys Ser Phe Ala Lys Ala Phe
            20                  25                  30

Ile Ser Lys Ala Asn Ile Gly Pro Arg Leu Thr Gln Val Ser Val Leu
        35                  40                  45

Gln Tyr Gly Ser Ile Thr Thr Ile Asp Val Pro Trp Asn Val Val Pro
    50                  55                  60

Glu Lys Ala His Leu Leu Ser Leu Val Asp Val Met Gln Arg Glu Gly
65                  70                  75                  80

Gly Pro Ser Gln Ile Gly Asp Ala Leu Gly Phe Ala Val Arg Tyr Leu
                85                  90                  95
```

```
Thr Ser Glu Met His Gly Ala Arg Pro Gly Ala Ser Lys Ala Val Val
                100                 105                 110

Ile Leu Val Thr Asp Val Ser Val Asp Ser Val Asp Ala Ala Ala Asp
            115                 120                 125

Ala Ala Arg Ser Asn Arg Val Thr Val Phe Pro Ile Gly Ile Gly Asp
        130                 135                 140

Arg Tyr Asp Ala Ala Gln Leu Arg Ile Leu Ala Gly Pro Ala Gly Asp
145                 150                 155                 160

Ser Asn Val Val Lys Leu Gln Arg Ile Glu Asp Leu Pro Thr Met Val
                165                 170                 175

Thr Leu Gly Asn Ser Phe Leu His Lys Leu Cys Ser Gly Phe Val Arg
            180                 185                 190

Ile Cys Thr Gly
        195
```

<210> SEQ ID NO 48
<211> LENGTH: 344
<212> TYPE: PRT
<213> ORGANISM: Unknown
<220> FEATURE:
<221> NAME/KEY: source
<223> OTHER INFORMATION: /note="Description of Unknown: Decorin sequence"

<400> SEQUENCE: 48

```
Cys Gly Pro Phe Gln Gln Arg Gly Leu Phe Asp Phe Met Leu Glu Asp
1               5                   10                  15

Glu Ala Ser Gly Ile Gly Pro Glu Val Pro Asp Asp Arg Asp Phe Glu
                20                  25                  30

Pro Ser Leu Gly Pro Val Cys Pro Phe Arg Cys Gln Cys His Leu Arg
            35                  40                  45

Val Val Gln Cys Ser Asp Leu Gly Leu Asp Lys Val Pro Lys Asp Leu
        50                  55                  60

Pro Pro Asp Thr Thr Leu Leu Asp Leu Gln Asn Asn Lys Ile Thr Glu
65                  70                  75                  80

Ile Lys Asp Gly Asp Phe Lys Asn Leu Lys Asn Leu His Ala Leu Ile
                85                  90                  95

Leu Val Asn Asn Lys Ile Ser Lys Val Ser Pro Gly Ala Phe Thr Pro
                100                 105                 110

Leu Val Lys Leu Glu Arg Leu Tyr Leu Ser Lys Asn Gln Leu Lys Glu
            115                 120                 125

Leu Pro Glu Lys Met Pro Lys Thr Leu Gln Glu Leu Arg Ala His Glu
        130                 135                 140

Asn Glu Ile Thr Lys Val Arg Lys Val Thr Phe Asn Gly Leu Asn Gln
145                 150                 155                 160

Met Ile Val Ile Glu Leu Gly Thr Asn Pro Leu Lys Ser Ser Gly Ile
                165                 170                 175

Glu Asn Gly Ala Phe Gln Gly Met Lys Lys Leu Ser Tyr Ile Arg Ile
            180                 185                 190

Ala Asp Thr Asn Ile Thr Ser Ile Pro Gln Gly Leu Pro Pro Ser Leu
        195                 200                 205

Thr Glu Leu His Leu Asp Gly Asn Lys Ile Ser Arg Val Asp Ala Ala
    210                 215                 220

Ser Leu Lys Gly Leu Asn Asn Leu Ala Lys Leu Gly Leu Ser Phe Asn
225                 230                 235                 240
```

```
Ser Ile Ser Ala Val Asp Asn Gly Ser Leu Ala Asn Thr Pro His Leu
                245                 250                 255

Arg Glu Leu His Leu Asp Asn Asn Lys Leu Thr Arg Val Pro Gly Gly
            260                 265                 270

Leu Ala Glu His Lys Tyr Ile Gln Val Val Tyr Leu His Asn Asn Asn
        275                 280                 285

Ile Ser Val Val Gly Ser Ser Asp Phe Cys Pro Pro Gly His Asn Thr
    290                 295                 300

Lys Lys Ala Ser Tyr Ser Gly Val Ser Leu Phe Ser Asn Pro Val Gln
305                 310                 315                 320

Tyr Trp Glu Ile Gln Pro Ser Thr Phe Arg Cys Val Tyr Val Arg Ser
                325                 330                 335

Ala Ile Gln Leu Gly Asn Tyr Lys
            340
```

<210> SEQ ID NO 49
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

```
Tyr Ile Gly Leu Lys Asp Arg Lys Arg Pro Ser Glu Leu Arg Arg Ile
1               5                   10                  15

Ala Ser Gln Val Lys Tyr Ala Cys
            20
```

<210> SEQ ID NO 50
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

```
Tyr Ile Gly Leu Lys Asp Arg Lys Arg Pro Ser Glu Leu Arg Arg Ile
1               5                   10                  15

Ala Ser Gln Val Lys Tyr Ala
            20
```

<210> SEQ ID NO 51
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

```
Asn Gln Glu Gln Val Ser Pro Leu Tyr Ile Gly Leu Lys Asp Arg Lys
1               5                   10                  15

Arg Pro Ser Glu Leu Arg Arg Ile Ala Ser Gln Val Lys Tyr Ala
            20                  25                  30
```

<210> SEQ ID NO 52
<211> LENGTH: 24
<212> TYPE: PRT

<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Leu Tyr Cys Glu Ile Ala Arg Gly Tyr Ser Leu Lys Arg Lys Val Pro
1               5                   10                  15

Asp Gln Ile Arg Ser Arg Lys Ala
            20

<210> SEQ ID NO 53
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Tyr Ile Gly Leu Lys Asp Ser Lys Ser Pro Ser Glu Leu Ser Ser Ile
1               5                   10                  15

Ala Ser Gln Val Lys Tyr Ala Cys
            20

<210> SEQ ID NO 54
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Tyr Ile Gly Leu Lys Asp Arg Lys Arg Pro Ser Glu Leu Arg Arg Ile
1               5                   10                  15

Ala Ser Gln Val Lys Tyr Ala
            20

<210> SEQ ID NO 55
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Tyr Ile Gly Leu Lys Asp Arg Lys Arg Pro Ser Glu Leu Leu Arg Ile
1               5                   10                  15

Ala Ser Gln Val Lys Tyr Ala
            20

<210> SEQ ID NO 56
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Tyr Ile Gly Leu Lys Asp Arg Lys Arg Pro Ser Glu Leu Pro Arg Ile
1               5                   10                  15

Ala Ser Gln Val Lys Tyr Ala
            20

<210> SEQ ID NO 57
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Tyr Ile Gly Leu Lys Asp Arg Lys Arg Pro Ser Glu Leu Gln Arg Ile
1               5                   10                  15

Ala Ser Gln Val Lys Tyr Ala
            20

<210> SEQ ID NO 58
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Tyr Ile Gly Leu Lys Asp Arg Lys Arg Pro Ser Glu Leu Trp Arg Ile
1               5                   10                  15

Ala Ser Gln Val Lys Tyr Ala
            20

<210> SEQ ID NO 59
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Tyr Ile Gly Leu Lys Asp Arg Lys Arg Pro Ser Glu Leu Ser Arg Ile
1               5                   10                  15

Ala Ser Gln Val Lys Tyr Ala
            20

<210> SEQ ID NO 60
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: SITE
<222> LOCATION: (1)..(24)
<223> OTHER INFORMATION: /note="This sequence may encompass 1-6 'Gly Ser
      Gly Gly' repeating units"

<400> SEQUENCE: 60

Gly Ser Gly Gly Gly Ser Gly Gly Gly Ser Gly Gly Gly Ser Gly Gly

```
                1               5                  10                15
Gly Ser Gly Gly Gly Ser Gly Gly
            20

<210> SEQ ID NO 61
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Gly Ser Gly Gly Gly Ser Gly Gly
1               5

<210> SEQ ID NO 62
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 62

Glu Ile Val Leu Thr Gln Ser Pro Gly Thr Leu Ser Leu Ser Pro Gly
1               5                  10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ala Ile Gly Phe Pro
                85                  90                  95

Gln Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 63
<211> LENGTH: 108
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 63

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ala Ile Gly Phe Pro
                85                  90                  95

Gln Thr Phe Gly Gln Gly Thr Lys Val Glu Ile Lys
            100                 105

<210> SEQ ID NO 64
<211> LENGTH: 221
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 64

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Gln Val
        35                  40                  45

Ser Ala Ile Ser Gly Ser Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Leu Ala Ala Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205
```

Lys Val Asp Lys Arg Val Glu Pro Lys Ser Cys Gly Ser
    210                 215                 220

<210> SEQ ID NO 65
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 65

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Gln Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Leu Ala Ala Phe Asp Tyr Trp Gly Gln Gly Thr Leu Val
            100                 105                 110

Thr Val

<210> SEQ ID NO 66
<211> LENGTH: 39
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 66

Gly Cys Gly Gly Ser Leu Arg Pro Ala Pro Pro Ile Ser Gly Gly
1               5                   10                  15

Gly Tyr Arg Ala Arg Pro Ala Lys Ala Ala Ala Thr Gln Lys Lys Val
            20                  25                  30

Glu Arg Lys Ala Pro Asp Ala
        35

<210> SEQ ID NO 67
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 67

Ser Leu Arg Pro Ala Pro Pro Ile Ser Gly Gly Gly Tyr Arg Ala
1               5                   10                  15

Arg Pro Ala Lys Ala Ala Ala Thr Gln Lys Lys Val Glu Arg Lys Ala
            20                  25                  30

Pro Asp Ala
        35

<210> SEQ ID NO 68
<211> LENGTH: 225
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 68

Ser Leu Asn Lys Pro Pro Phe Leu Met Leu Leu Lys Gly Ser Thr Arg
1               5                   10                  15

Phe Asn Lys Thr Lys Thr Phe Arg Ile Asn Gln Leu Leu Gln Asp Thr
            20                  25                  30

Pro Val Ala Ser Pro Arg Ser Val Lys Val Trp Gln Asp Ala Cys Ser
        35                  40                  45

Pro Leu Pro Lys Thr Gln Ala Asn His Gly Ala Leu Gln Phe Gly Asp
    50                  55                  60

Ile Pro Thr Ser His Leu Leu Phe Lys Leu Pro Gln Glu Leu Leu Lys
65                  70                  75                  80

Pro Arg Ser Gln Phe Ala Val Asp Met Gln Thr Thr Ser Ser Arg Gly
                85                  90                  95

Leu Val Phe His Thr Gly Thr Lys Asn Ser Phe Met Ala Leu Tyr Leu
            100                 105                 110

Ser Lys Gly Arg Leu Val Phe Ala Leu Gly Thr Asp Gly Lys Lys Leu
        115                 120                 125

Arg Ile Lys Ser Lys Glu Lys Cys Asn Asp Gly Lys Trp His Thr Val
    130                 135                 140

Val Phe Gly His Asp Gly Glu Lys Gly Arg Leu Val Val Asp Gly Leu
145                 150                 155                 160

Arg Ala Arg Glu Gly Ser Leu Pro Gly Asn Ser Thr Ile Ser Ile Arg
                165                 170                 175

Ala Pro Val Tyr Leu Gly Ser Pro Pro Ser Gly Lys Pro Lys Ser Leu
            180                 185                 190

Pro Thr Asn Ser Phe Val Gly Cys Leu Lys Asn Phe Gln Leu Asp Ser
        195                 200                 205

Lys Pro Leu Tyr Thr Pro Ser Ser Ser Phe Gly Val Ser Ser Cys Thr
    210                 215                 220

Gly
225

<210> SEQ ID NO 69
<211> LENGTH: 168
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 69

Gly His Arg Pro Leu Asp Lys Lys Arg Glu Glu Ala Pro Ser Leu Arg
1               5                   10                  15

Pro Ala Pro Pro Pro Ile Ser Gly Gly Gly Tyr Arg Ala Arg Pro Ala
            20                  25                  30

Lys Ala Ala Ala Thr Gln Lys Lys Val Glu Arg Lys Ala Pro Asp Ala
        35                  40                  45

```
Gly Gly Gly Ser Gly Gly Gly Ser Gly Gly Gly His Arg Pro Leu Asp
        50                  55                  60

Lys Lys Arg Glu Glu Ala Pro Ser Leu Arg Pro Ala Pro Pro Ile
65                  70                  75                  80

Ser Gly Gly Gly Tyr Arg Ala Arg Pro Ala Lys Ala Ala Thr Gln
                85                  90                  95

Lys Lys Val Glu Arg Lys Ala Pro Asp Ala Gly Gly Ser Gly Gly
                100                 105                 110

Gly Ser Gly Gly Gly His Arg Pro Leu Asp Lys Lys Arg Glu Glu Ala
                115                 120                 125

Pro Ser Leu Arg Pro Ala Pro Pro Ile Ser Gly Gly Gly Tyr Arg
        130                 135                 140

Ala Arg Pro Ala Lys Ala Ala Thr Gln Lys Lys Val Glu Arg Lys
145                 150                 155                 160

Ala Pro Asp Ala Gly Gly Gly Thr
                165
```

<210> SEQ ID NO 70
<211> LENGTH: 168
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 70

```
Gly His Arg Pro Leu Asp Lys Lys Arg Glu Glu Ala Pro Ser Leu Arg
1               5                   10                  15

Pro Ala Pro Pro Ile Ser Gly Gly Gly Tyr Arg Ala Arg Pro Ala
                20                  25                  30

Lys Ala Ala Thr Gln Lys Lys Val Glu Arg Lys Ala Pro Asp Ala
                35                  40                  45

Gly Gly Gly Ser Gly Gly Gly Ser Gly Gly Gly His Arg Pro Leu Asp
        50                  55                  60

Lys Lys Arg Glu Glu Ala Pro Ser Leu Arg Pro Ala Pro Pro Ile
65                  70                  75                  80

Ser Gly Gly Gly Tyr Arg Ala Arg Pro Ala Lys Ala Ala Thr Gln
                85                  90                  95

Lys Lys Val Glu Arg Lys Ala Pro Asp Ala Gly Gly Ser Gly Gly
                100                 105                 110

Gly Ser Gly Gly Gly His Arg Pro Leu Asp Lys Lys Arg Glu Glu Ala
                115                 120                 125

Pro Ser Leu Arg Pro Ala Pro Pro Ile Ser Gly Gly Gly Tyr Arg
        130                 135                 140

Ala Arg Pro Ala Lys Ala Ala Thr Gln Lys Lys Val Glu Arg Lys
145                 150                 155                 160

Ala Pro Asp Ala Gly Gly Thr Gly
                165
```

<210> SEQ ID NO 71
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 71

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Gln Val
        35                  40                  45
Ser Ala Ile Ser Gly Ser Gly Gly Ser Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Thr Leu Ala Ala Phe Asp Tyr Trp Gly Gln Gly Thr Leu Val
            100                 105                 110
Thr Val Ser Ser Ala Ser Thr Lys Gly Pro Ser Val Phe Pro Leu Ala
        115                 120                 125
Pro Ser Ser Lys Ser Thr Ser Gly Gly Thr Ala Ala Leu Gly Cys Leu
    130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
            180                 185                 190
Gly Thr Gln Thr Tyr Ile Cys Asn Val Asn His Lys Pro Ser Asn Thr
        195                 200                 205
Lys Val Asp Lys Arg Val Glu Pro Lys Ser Cys Gly Ser Gly Gly Gly
    210                 215                 220
Ser Gly Gly Ser Leu Asn Lys Pro Pro Phe Leu Met Leu Leu Lys Gly
225                 230                 235                 240
Ser Thr Arg Phe Asn Lys Thr Lys Thr Phe Arg Ile Asn Gln Leu Leu
                245                 250                 255
Gln Asp Thr Pro Val Ala Ser Pro Arg Ser Val Lys Val Trp Gln Asp
            260                 265                 270
Ala Cys Ser Pro Leu Pro Lys Thr Gln Ala Asn His Gly Ala Leu Gln
        275                 280                 285
Phe Gly Asp Ile Pro Thr Ser His Leu Leu Phe Lys Leu Pro Gln Glu
    290                 295                 300
Leu Leu Lys Pro Arg Ser Gln Phe Ala Val Asp Met Gln Thr Thr Ser
305                 310                 315                 320
Ser Arg Gly Leu Val Phe His Thr Gly Thr Lys Asn Ser Phe Met Ala
                325                 330                 335
Leu Tyr Leu Ser Lys Gly Arg Leu Val Phe Ala Leu Gly Thr Asp Gly
            340                 345                 350
Lys Lys Leu Arg Ile Lys Ser Lys Glu Lys Cys Asn Asp Gly Lys Trp
        355                 360                 365
His Thr Val Val Phe Gly His Asp Gly Glu Lys Gly Arg Leu Val Val
    370                 375                 380
Asp Gly Leu Arg Ala Arg Glu Gly Ser Leu Pro Gly Asn Ser Thr Ile
385                 390                 395                 400
Ser Ile Arg Ala Pro Val Tyr Leu Gly Ser Pro Ser Gly Lys Pro
                405                 410                 415
```

```
Lys Ser Leu Pro Thr Asn Ser Phe Val Gly Cys Leu Lys Asn Phe Gln
            420                 425                 430

Leu Asp Ser Lys Pro Leu Tyr Thr Pro Ser Ser Ser Phe Gly Val Ser
            435                 440                 445

Ser Cys Thr Gly
        450

<210> SEQ ID NO 72
<211> LENGTH: 391
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 72

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ala Ile Gly Phe Pro
                85                  90                  95

Gln Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Gly Ala Gly Gly Ser Gly Gly Gly
    210                 215                 220

His Arg Pro Leu Asp Lys Lys Arg Glu Glu Ala Pro Ser Leu Arg Pro
225                 230                 235                 240

Ala Pro Pro Pro Ile Ser Gly Gly Gly Tyr Arg Ala Arg Pro Ala Lys
                245                 250                 255

Ala Ala Ala Thr Gln Lys Lys Val Glu Arg Lys Ala Pro Asp Ala Gly
            260                 265                 270

Gly Gly Ser Gly Gly Gly Ser Gly Gly Gly His Arg Pro Leu Asp Lys
        275                 280                 285

Lys Arg Glu Glu Ala Pro Ser Leu Arg Pro Ala Pro Pro Pro Ile Ser
    290                 295                 300
```

```
Gly Gly Gly Tyr Arg Ala Arg Pro Ala Lys Ala Ala Thr Gln Lys
305                 310                 315                 320

Lys Val Glu Arg Lys Ala Pro Asp Ala Gly Gly Ser Gly Gly Gly
            325                 330                 335

Ser Gly Gly Gly His Arg Pro Leu Asp Lys Lys Arg Glu Glu Ala Pro
        340                 345                 350

Ser Leu Arg Pro Ala Pro Pro Ile Ser Gly Gly Gly Tyr Arg Ala
        355                 360                 365

Arg Pro Ala Lys Ala Ala Ala Thr Gln Lys Lys Val Glu Arg Lys Ala
    370                 375                 380

Pro Asp Ala Gly Gly Gly Thr
385                 390

<210> SEQ ID NO 73
<211> LENGTH: 395
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 73

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Gln Val
        35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Leu Ala Ala Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Gly Ser Gly Gly Gly
    210                 215                 220

Ser Gly Gly Gly His Arg Pro Leu Asp Lys Lys Arg Glu Glu Ala Pro
225                 230                 235                 240

Ser Leu Arg Pro Ala Pro Pro Ile Ser Gly Gly Gly Tyr Arg Ala
                245                 250                 255

Arg Pro Ala Lys Ala Ala Ala Thr Gln Lys Lys Val Glu Arg Lys Ala
```

```
                260                 265                 270
Pro Asp Ala Gly Gly Ser Gly Gly Ser Gly Gly His Arg
        275                 280                 285

Pro Leu Asp Lys Lys Arg Glu Glu Ala Pro Ser Leu Arg Pro Ala Pro
        290                 295                 300

Pro Pro Ile Ser Gly Gly Tyr Arg Ala Arg Pro Ala Lys Ala Ala
305                 310                 315                 320

Ala Thr Gln Lys Lys Val Glu Arg Lys Ala Pro Asp Ala Gly Gly
                325                 330                 335

Ser Gly Gly Gly Ser Gly Gly Gly His Arg Pro Leu Asp Lys Arg
        340                 345                 350

Glu Glu Ala Pro Ser Leu Arg Pro Ala Pro Pro Ile Ser Gly Gly
        355                 360                 365

Gly Tyr Arg Ala Arg Pro Ala Lys Ala Ala Thr Gln Lys Lys Val
        370                 375                 380

Glu Arg Lys Ala Pro Asp Ala Gly Gly Thr Gly
385                 390                 395

<210> SEQ ID NO 74
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 74

Arg Leu Val Lys Ala Leu Lys Thr Asp Lys Phe Leu Gly Arg Ile Gly
1               5                   10                  15

Ser Glu Lys Cys Asn Asp Lys Gly Lys
            20                  25

<210> SEQ ID NO 75
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

Arg Lys Thr Asp Ala Leu Glu Leu Val Phe Leu Lys Lys Gly Gly Ile
1               5                   10                  15

Gly Ser Lys Lys Cys Asn Asp Lys Arg
            20                  25

<210> SEQ ID NO 76
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76

Cys Arg Lys Lys Arg Lys Lys Lys Ala Leu Leu Leu Gly Ile Gly
1               5                   10                  15

Asp Phe Asn Ser Glu Val Thr Asp Gly
            20                  25
```

```
<210> SEQ ID NO 77
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 77

Lys Lys Arg Lys Leu Val Ala Leu Thr Asp Phe Leu Gly Ile Cys Gly
1               5                   10                  15

Ser Glu Asn Asp Gly Arg Lys Lys Lys
            20                  25

<210> SEQ ID NO 78
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 78

Leu Val Arg Ala Lys Leu Thr Asp Lys Phe Leu Gly Lys Arg Ile Gly
1               5                   10                  15

Ser Lys Glu Cys Asn Lys Asp Lys Gly
            20                  25

<210> SEQ ID NO 79
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 79

Ala Leu Leu Leu Gly Ile Gly Arg Asp Phe Asn Lys Lys Lys Arg Lys
1               5                   10                  15

Lys Lys Ser Glu Val Thr Asp Gly Cys
            20                  25

<210> SEQ ID NO 80
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 80

His His His His His His
1               5

<210> SEQ ID NO 81
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 81

Gly Gly Ser Gly
1
```